United States Patent
Kodali et al.

(10) Patent No.: US 11,814,412 B2
(45) Date of Patent: *Nov. 14, 2023

(54) ARTIFICIAL PROTEINS AND COMPOSITIONS AND METHODS THEREOF

(71) Applicant: The Trustees of the University of Pennsylvania, Philadelphia, PA (US)

(72) Inventors: Goutham Kodali, Malvern, PA (US); Molly Marie Sheehan, Philadelphia, PA (US); Joshua Mancini, Philadelphia, PA (US); Bohdana Marie Discher, Philadelphia, PA (US); Michael Magaraci, Philadelphia, PA (US); Nathan M. Ennist, Philadelphia, PA (US); Brian Chow, Cherry Hill, NJ (US); Peter Leslie Dutton, Media, PA (US); Christopher Moser, Morrisville, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/362,552

(22) Filed: Jun. 29, 2021

(65) Prior Publication Data

US 2021/0340183 A1    Nov. 4, 2021

Related U.S. Application Data

(62) Division of application No. 15/773,891, filed as application No. PCT/US2016/060677 on Nov. 4, 2016, now Pat. No. 11,084,848.

(60) Provisional application No. 62/251,171, filed on Nov. 5, 2015, provisional application No. 62/250,812, filed on Nov. 4, 2015.

(51) Int. Cl.
*C07K 14/00* (2006.01)
*G01N 33/68* (2006.01)

(52) U.S. Cl.
CPC ......... *C07K 14/001* (2013.01); *G01N 33/68* (2013.01)

(58) Field of Classification Search
CPC ....... C07K 14/001; C07K 14/00; G01N 33/68
See application file for complete search history.

(56) References Cited

U.S. PATENT DOCUMENTS

| | | | |
|---|---|---|---|
| 2006/0127997 | A1 | 6/2006 | Quaedflieg et al. |
| 2011/0052587 | A1 | 3/2011 | Hunig et al. |
| 2012/0065133 | A1 | 3/2012 | Dutton |
| 2013/0102770 | A9 | 4/2013 | Geddes |

OTHER PUBLICATIONS

Tammer A Farid, Elementary tetrahelical protein design for diverse oxidoreductase functions, Nat Chem Biol. Dec. 2013 ; 9(12): 826-833.*
International Search Report for PCT/US2016/060677; dated Apr. 28, 2017; 7 pages.
Written Opinion for PCT/US2016/060677; dated Apr. 28, 2017; 11 pages.
Accession XP_004536462; Publication [online]; Apr. 13, 2015 [retrieved Mar. 23, 2017]; Retrieved from the Internet: <URL: https://www.ncbi.nlm.nih.gov/protein/499009020?report=genbank &log$=protalign&blast_rank=1&RID=D7RN1MSY016.; pp. 1-2; p. 1.
Anderson, J. et al. "Constructing A Man-Made C-Type Cytochrome Maquette In Vivo: Electron Transfer, Oxygen Transport And Conversion To A Photoactive Light Harvesting Maquette"; Chemical Science 2014, vol. 5, No. 2, pp. 507-514; abstract, p. 6, second paragraph, DOI:10.1039/C3SC52019F; 16 pages.
K. M. Towle, Structural features of many circular and leaderless bacteriocins are similar to those in saposins and saposin-like peptides, Med. Chem. Commun., 2017, 8,276.
Park IH, et al. 2012. Nontypeable pneumococci can be divided into multiple cps types, including one type expressing the novel gene pspK. mBio 3(3):e00035-12. doi: 10.1128/mBio.00035-12.
UniProtKB—H2BJKO, pspK Organism *Streptococcus pneumoniae*, pp. 1-5, accessed on Sep. 9, 2020.

* cited by examiner

*Primary Examiner* — Julie Ha
*Assistant Examiner* — Erinne R Dabkowski
(74) *Attorney, Agent, or Firm* — Morgan, Lewis & Bockius LLP

(57) ABSTRACT

De novo artificial protein based reporters that may be expressed in eukaryotic (e.g., mammalian) cells and methods of using the same are provided herein.

7 Claims, 48 Drawing Sheets

Specification includes a Sequence Listing.

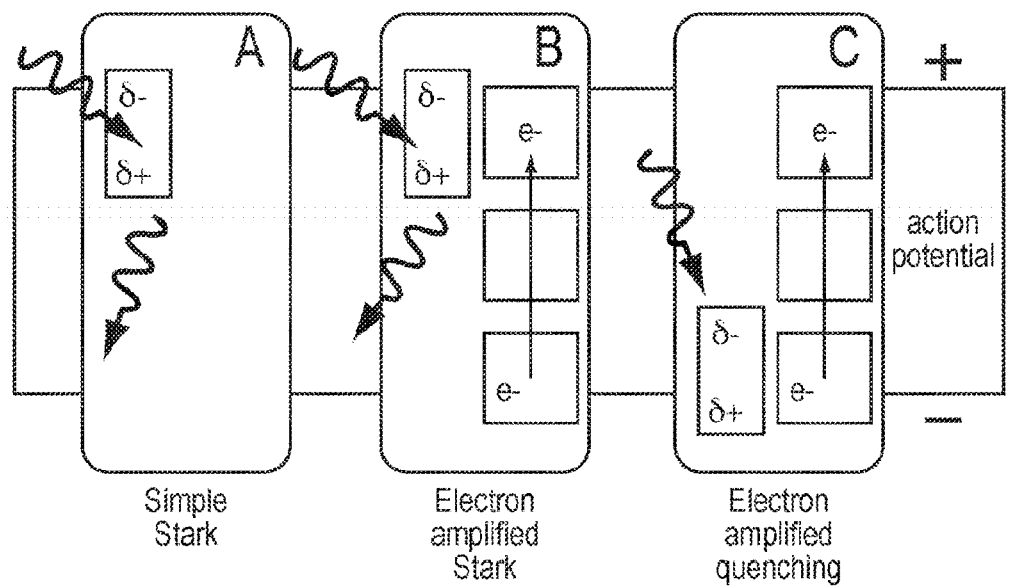
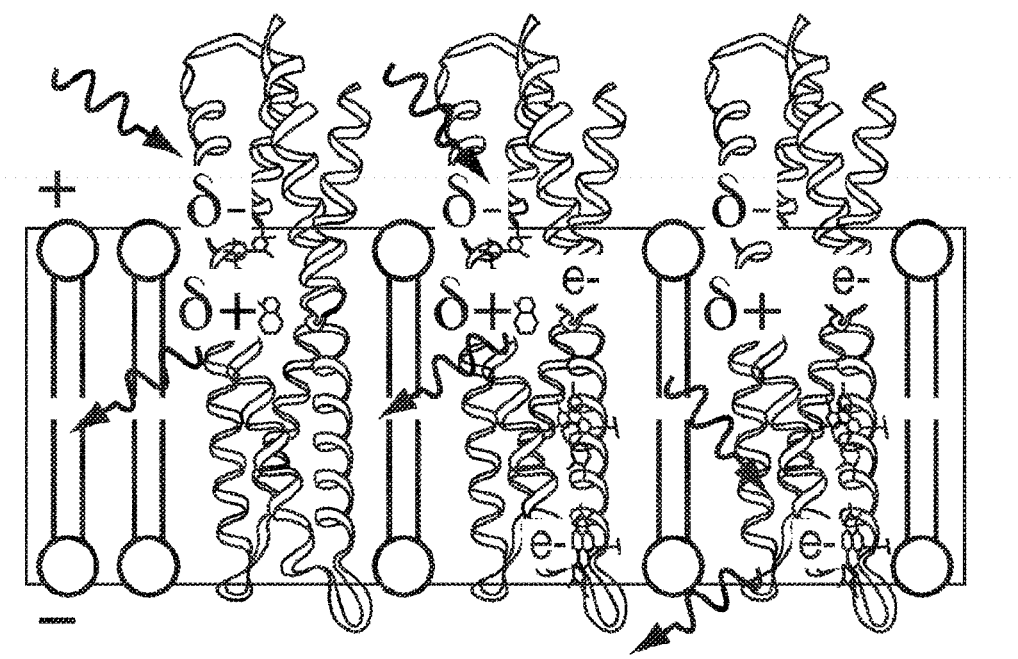
FIG. 2

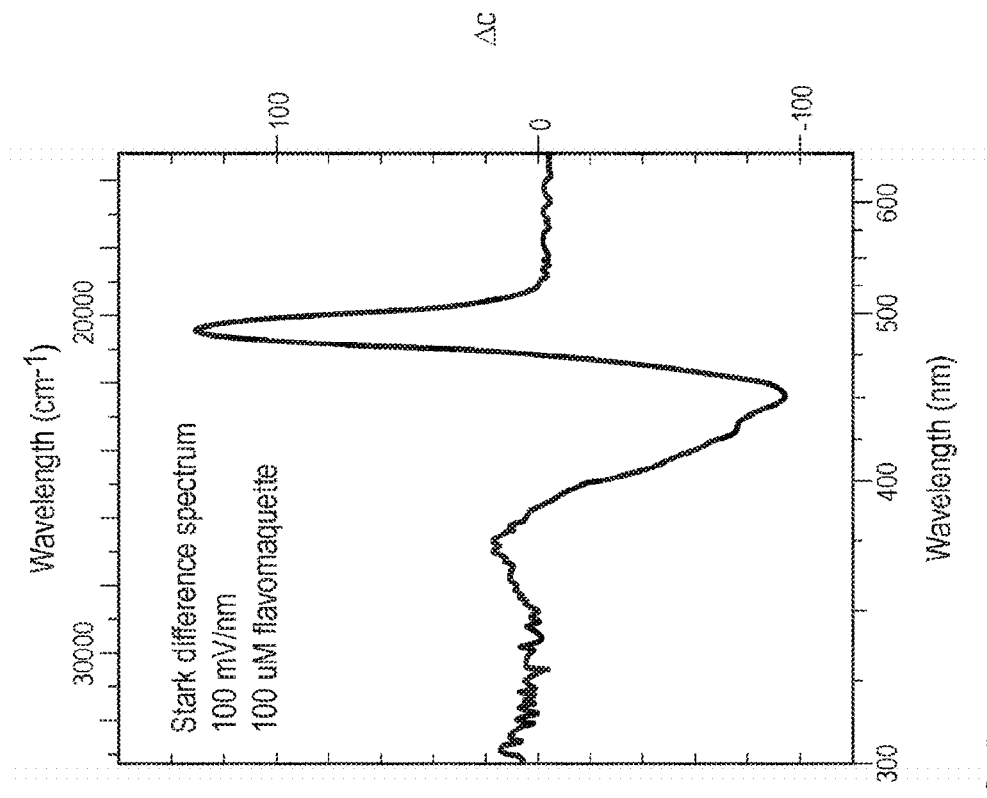
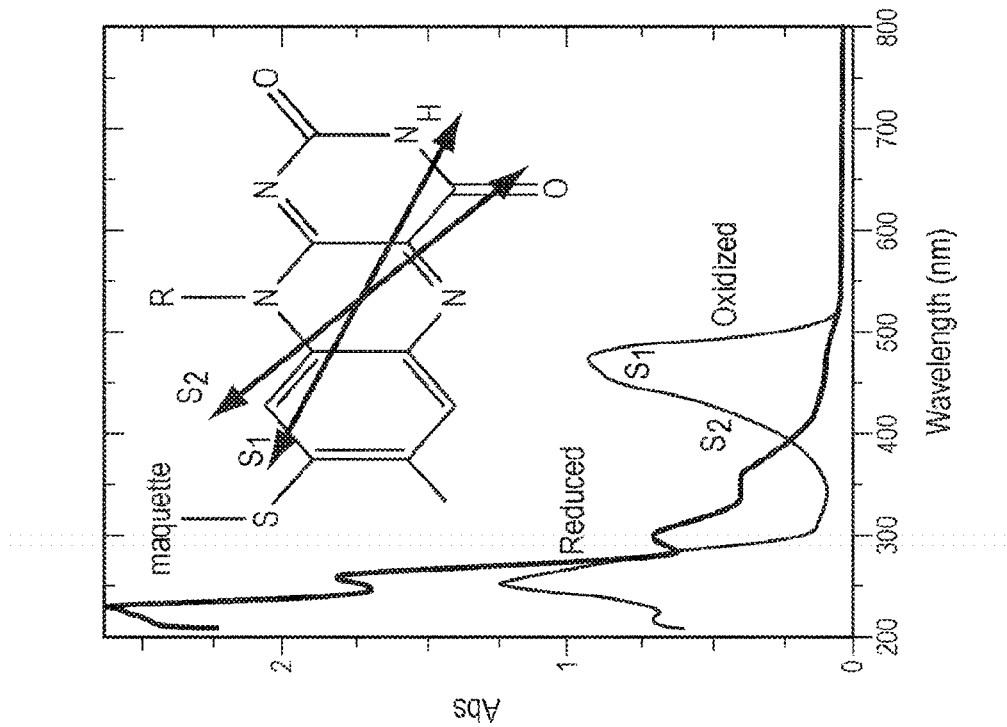
FIG. 6

Sequence 1: Rows show helical register and each of the 4 helices (loops removed) from top to bottom. X's denote wildcards in GL scaffold for mammalian trafficking.

|  | c | d | e | f | g | a | b | c | d | e | f | g | a | b | c | d | e | f | g | a | b | c | d | e | f | g |
|---|---|---|---|---|---|---|---|---|---|---|---|---|---|---|---|---|---|---|---|---|---|---|---|---|---|---|
| SEQ ID No. 1 | E | I | W | K | X | X | E | D | A | L | Q | K | F | E | X | X | L | N | Q | F | E | D | X | X | Q | L |
| SEQ ID No. 2 | E | I | K | Q | R | X | E | D | X | L | R | K | F | E | E | A | L | K | R | F | E | D | L | K | Q | K |
| SEQ ID No. 3 | R | X | W | K | X | X | E | D | A | X | Q | K | F | E | E | A | L | N | Q | F | E | D | L | K | Q | L |
| SEQ ID No. 4 | E | I | K | Q | R | X | E | D | A | L | R | K | F | E | E | A | L | K | R | X | E | D | X | X | Q | K |

Sequence 2: Sequence wildcards generalized by heptad position to show all wildcards.

| SEQ ID No. 5 | E | X | X | K | X | X | E | D | X | X | Q | K | X | E | E | X | X | N | Q | X | E | D | X | X | Q | L |
| SEQ ID No. 6 | E | X | K | Q | R | X | E | D | X | X | R | K | X | E | E | X | X | K | R | X | E | D | X | K | Q | K |
| SEQ ID No. 7 | R | X | X | K | X | X | E | D | X | X | Q | K | X | E | E | X | X | N | Q | X | E | D | X | K | Q | L |
| SEQ ID No. 8 | E | X | K | Q | R | X | E | D | X | X | R | K | X | E | E | X | X | K | R | X | E | D | X | X | Q | K |

Sequence 3: Highlighted sites of change between neutral and charged sequences.

| SEQ ID No. 9 | E | X | X | K | X | X | E | D | X | X | Q | K | X | E | E | X | X | N | Q | X | E | D | X | X | Q | L |
| SEQ ID No. 10 | E | X | K | Q | R | X | E | D | X | X | R | K | X | E | E | X | X | K | R | X | E | D | X | K | Q | K |
| SEQ ID No. 11 | R | X | X | K | X | X | E | D | X | X | Q | K | X | E | E | X | X | N | Q | X | E | D | X | K | Q | L |
| SEQ ID No. 12 | E | X | K | Q | R | X | E | D | X | X | R | K | X | E | E | X | X | K | R | X | E | D | X | X | Q | K |

Sequence 4: Highlighted generalized sites of importance for trafficking.

| SEQ ID No. 13 | E | X | X | K | X | X | E | D | X | X | Q | K | X | E | E | X | X | N | Q | X | E | D | X | X | Q | L |
| SEQ ID No. 14 | E | X | K | Q | R | X | E | D | X | X | R | K | X | E | E | X | X | K | R | X | E | D | X | K | Q | K |
| SEQ ID No. 15 | R | X | X | K | X | X | E | D | X | X | Q | K | X | E | E | X | X | N | Q | X | E | D | X | K | Q | L |
| SEQ ID No. 16 | E | X | K | Q | R | X | E | D | X | X | R | K | X | E | E | X | X | K | R | X | E | D | X | X | Q | K |

Sequence 5: Generalized sequence where - are negative residues, + are positive residues and 0 are amine residues and particularly important positions are highlighted.

| A: | - | X | X | + | X | X | - | - | X | X | 0 | + | X | - | - | X | X | 0 | 0 | X | - | - | X | X | 0 | L |
| B: | - | X | + | 0 | + | X | - | - | X | X | + | + | X | - | - | X | X | + | + | X | - | - | X | + | 0 | + |
| C: | + | X | X | + | X | X | - | - | X | X | 0 | + | X | - | - | X | X | 0 | 0 | X | - | - | X | + | 0 | L |
| D: | - | X | + | 0 | + | X | - | - | X | X | + | + | X | - | - | X | X | + | + | X | - | - | X | X | 0 | + |

| Construct | Mutation | $\lambda_{ex}$ (nm) | $\lambda_{ex}$ (nm) | QY (%) | BV Attach (%) | ε Q-band (cm$^{-1}$ M$^{-1}$) | Brightness (rel.) |
|---|---|---|---|---|---|---|---|
| (1) |  | 578 | 657 | 0.07 | * | * | * |
| (2) | S64C, K124V | 646 | 658 | 0.79 | 3.99 | 22,449 | 3.1 |
| (3) | L5S | 646 | 662 | 0.76 | 5.79 | 18,560 | 4.4 |
| (4) dFP1.0 | L75H, F120H | 648 | 662 | 1.58 | 8.91 | 17,162 | 14.1 |
| IFP1.4 |  | 648 | 662 | 1.38 | 19.21 | 23,685 | 26.5 |
| dFP1.0 [HO1] |  | 671 | 705 | 1.60 | 0.81 | 71,151 | 1.3 |
| IFP1.4 [HO1] |  | 678 | 710 | 8.06 | 1.52 | 50,856 | 12.2 |

FIG. 24 (Cont.)

g.
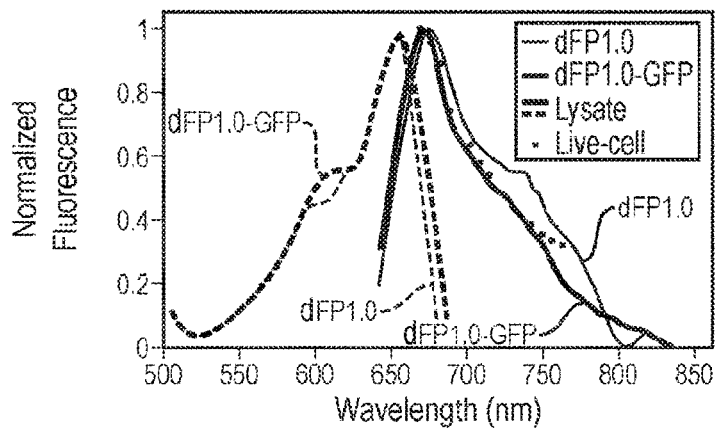
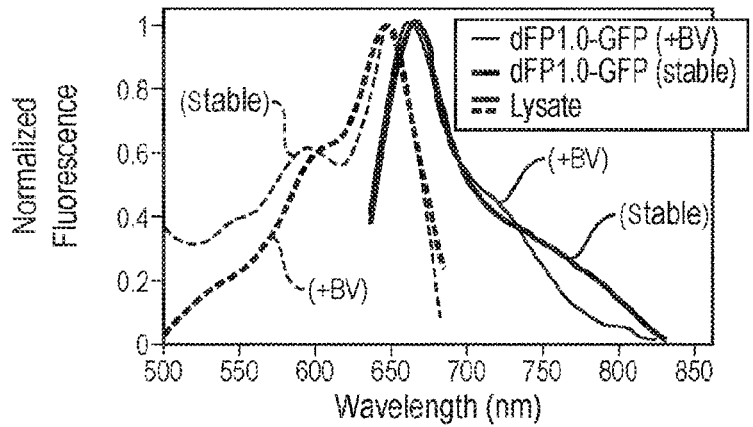
h.
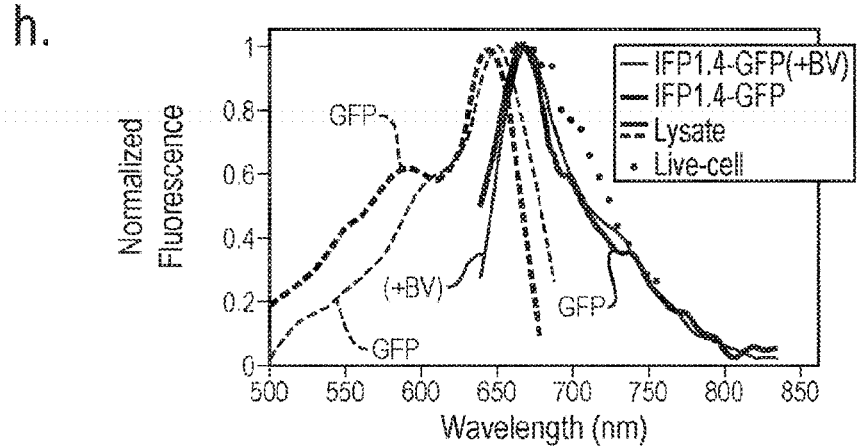
FIG. 25 (Cont.)

| | Construct | λexc (nm) | λem (nm) | QY (%) (vs. Cy5) | BV Attach (%) | ε Q-band (cm⁻¹ M⁻¹) | Brightness (rel.) |
|---|---|---|---|---|---|---|---|
| SEQ ID No. 25 | dFP1.0 [Z=-3] | 648 | 662 | 1.58 | 8.91 | 17,162 | 14.1 |
| SEQ ID No. 157 | dFP1.0 [Z=-15] | 648 | 660 | 1.57 | 3.72 | 17,786 | 5.8 |
| SEQ ID No. 120 | IFP1.4 | 648 | 662 | 1.38 | 19.21 | 23,685 | 26.5 |

ARTIFICIAL PROTEINS AND COMPOSITIONS AND METHODS THEREOF

CROSS-REFERENCE TO RELATED APPLICATION

This application is a divisional of U.S. patent application Ser. No. 15/773,891, filed May 4, 2018, which is a U.S. National Stage Patent Application of International Application No. PCT/US2016/060677, filed Nov. 4, 2016, which claims the benefit of priority to U.S. Provisional Application No. 62/250,812, filed Nov. 4, 2015, and U.S. Provisional Application No. 62/251,171, filed Nov. 5, 2015, all of which are incorporated herein by reference in their entireties.

FIELD OF THE INVENTION

The invention relates generally to artificial, de novo protein-based sensors that may be expressed in eukaryotic cells and may be configured to bind one or more cofactors to thereby exhibit variable and tunable characteristics.

BACKGROUND OF THE INVENTION

De novo proteins of human-made and computational designs are powerful tools for exploring principles and limits of protein folding, protein-protein interaction, and biochemical function without the distributed structure-function constraints imposed by natural scaffolds as starting points for protein engineering. However, despite their biomedical promise, completely non-natural proteins have not been functionally expressed in eukaryotic systems.

The invention described herein meets the needs in the field by providing artificial, de novo proteins as sensing agents that may be expressed in eukaryotic cells.

SUMMARY OF THE INVENTION

In an embodiment, the invention includes an artificial protein configured to bind one or more cofactors, wherein the artificial protein may be expressed in eukaryotic cells. In some embodiments, the artificial protein may be expressed in mammalian cells. In some embodiments, the artificial protein of the invention may be amphiphilic. In some embodiments, the artificial protein of the invention may have a cytosolic portion, a transmembrane portion, and an extracellular portion. In some embodiments, the artificial proteins of the invention may be artificial transmembrane proteins.

In some embodiments, the invention includes an artificial protein may include an amino acid sequence selected to provide at least four helices (e.g., α-helices), wherein the artificial protein may be expressible in eukaryotic cells. In some embodiments, the artificial protein may be expressible in mammalian cells. In some embodiments, such amino acid sequences of the invention may be selected to provide an amphiphilic artificial protein.

In some embodiments, the artificial protein of the invention may have a net surface charge (i.e., $Z_{net}$) of about −12 to about +8. In some embodiments, the artificial protein of the invention may have a net surface charge that is negative.

In certain embodiments, the amino acid sequence of the artificial protein may include one or more of:
−XX+XX−−XX0+X−−XX00X−−XX0L    (Generic Sequence A);
−X+0+X−−XX++X−−XX++X−−X+0+(Generic Sequence B);
+XX+XX−−XX0+X−−XX00X−−X+0L    (Generic Sequence C); and
−XX+0+−−XX++X−−XX++X−−XX0+(Generic Sequence D),
wherein (+) represents a positively charged amino acid, (−) represents a negatively charged amino acid, (0) represents an amino acid having an amide side-chain, and (X) represents any amino acid.

In certain embodiments, the amino acid sequence of the artificial protein may include one or more of: SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, and SEQ ID No: 16, or a variant thereof.

In certain embodiments, the amino acid sequence of the artificial protein may include one or more LOOPs selected from the group consisting of GGSGKGSGG (SEQ ID No. 17), GGCG (SEQ ID No: 18), GACG (SEQ ID No: 19), and GGSG (SEQ ID No. 20), or a variant thereof.

In certain embodiments, the amino acid sequence of the artificial protein may include SEQ ID NO: 25, SEQ ID NO: 30, SEQ ID NO: 31, SEQ ID NO: 51, SEQ ID NO: 54, SEQ ID NO: 63, SEQ ID NO: 64, or SEQ ID NO: 69, or a variant thereof.

In certain embodiments, the amino acid sequence of the artificial protein may include SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 141, SEQ ID NO: 142, or SEQ ID NO: 147, or a variant thereof.

In some embodiments, the invention includes a composition comprising a peptide comprising one or more amino acid sequences of a formula selected from the group consisting of:
−XX+XX−−XX0+X−−XX00X−−XX0L    (Generic Sequence A);
−X+0+X−−XX++X−−XX++X−−X+0+(Generic Sequence B);
+XX+XX−−XX0+X−−XX00X−−X+0L    (Generic Sequence C); and
−XX+0+−−XX++X−−XX++X−−XX0+(Generic Sequence D), or a variant thereof,
wherein (+) represents a positively charged amino acid, (−) represents a negatively charged amino acid, (0) represents an amino acid having an amide side-chain, and (X) represents any amino acid.

In some embodiments, the invention includes a composition comprising a peptide comprising one or more amino acid sequences selected from the group consisting of SEQ ID No: 1, SEQ ID No: 2, SEQ ID No: 3, SEQ ID No: 4, SEQ ID No: 5, SEQ ID No: 6, SEQ ID No: 7, SEQ ID No: 8, SEQ ID No: 9, SEQ ID No: 10, SEQ ID No: 11, SEQ ID No: 12, SEQ ID No: 13, SEQ ID No: 14, SEQ ID No: 15, and SEQ ID No: 16, or a variant thereof.

In some embodiments, the invention includes a composition comprising a peptide comprising an amino acid sequence selected from the group consisting of SEQ ID Nos. 25, 30, 31, 51, 54, 63, 66, and 69, or a variant thereof.

In some embodiments, the invention includes a composition comprising a peptide comprising an amino acid sequence selected from Table 2, or a variant thereof.

In some embodiments, the invention includes a composition comprising a peptide comprising an amino acid sequence selected from Table 3, or a variant thereof.

In some embodiments, the invention includes a composition comprising a peptide comprising an amino acid sequence selected from Table 4, or a variant thereof.

BRIEF DESCRIPTION OF THE DRAWINGS

The following detailed description of embodiments will be better understood when read in conjunction with the appended drawings. However, the invention is not limited to the precise arrangements and instrumentalities of the embodiments depicted in the drawings.

In the drawings:

FIG. 2 is an illustration of an artificial protein according to an embodiment of the invention that allows modular assembly of functional cofactors for field sensing. Example designs for rapid Stark cofactor field sensing in the depolarized state (hence shown as positive charge on cytoplasmic side) (Panel A) and enhanced field sensing through field stimulated electron transfer (Panel B), field stimulated redox quenching (Panel C). (Top) Scheme, (Bottom) Structural model. Systems are directional so that signal increases upon depolarization to avoid false positives from bleaching.

FIG. 6 shows the results of the Stark effect in flavin-binding maquettes. Electric field sensitive transition dipoles to S1 and S2 excited states (left, red and blue) are oriented nearly along the long axis of the flavin cofactor—thus the long flavin axis should be oriented parallel to field changes for maximum sensitivity. The Stark electric field induced absorption changes of flavomaquettes (right) follows the second derivative of the oxidized absorption spectrum (left) as expected.

FIG. 14 shows sequence listings of five sequences according to various embodiments of the invention, of increasingly greater generalization.

In FIG. 37, the artificial proteins listed include 1321 (i.e., AM-528-C4 (SEQ ID NO. 63)), 1323 (i.e., AM-1196, SEQ ID NO. 66), and 1329 (i.e., AM-528 (SEQ ID NO. 69).

DETAILED DESCRIPTION OF THE INVENTION

Figure 1:
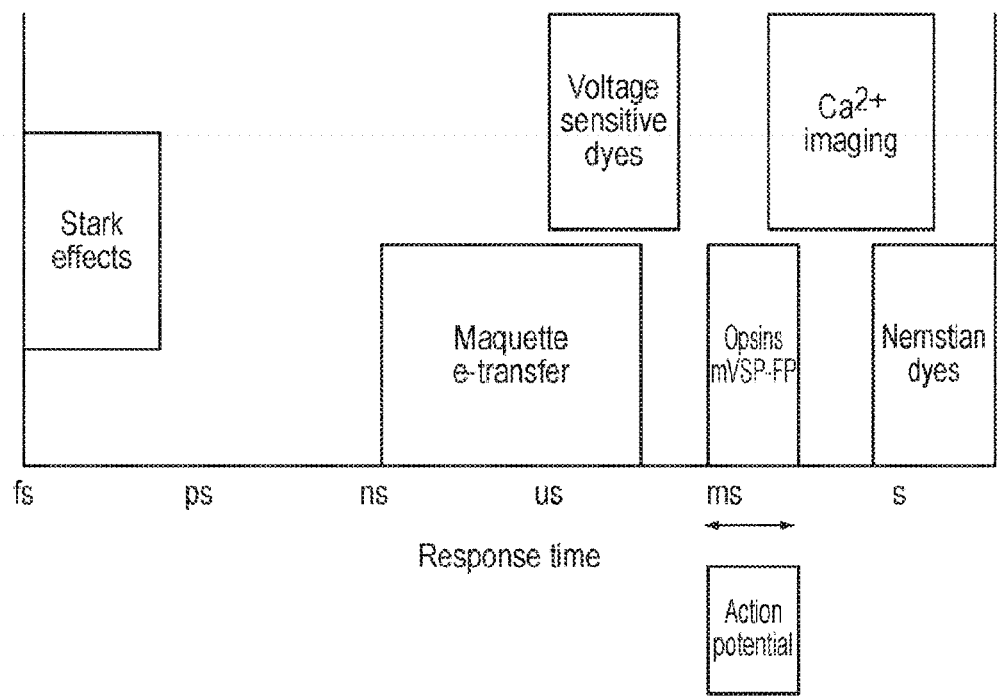
FIG. 1 is a chart showing timescales of optical voltage indicators. Stark cofactor absorbance and fluorescence effects take place at ultrafast timescales with respect to action potentials, while electron transfer mediated transmembrane field enhancement takes place on ns-to-μs timescales. Sensors based on such biophysics are intrinsically faster than state-of-the-art GEVIs that require structural rearrangements that reduce fluorescence.

In some embodiments, the invention includes artificial, de novo proteins that may function as sensors, and which may be expressed in eukaryotic cells. In some embodiments, the artificial proteins of the invention may be expressed in mammalian cells.

In some embodiments, the artificial proteins described herein may be soluble proteins and may or may not be amphiphilic. Indeed, in certain selected embodiments of the invention, the artificial proteins described herein may include (1) soluble de novo fluorescent proteins (i.e., proteins that may include a fluorophore), and/or (2) de novo fluorescent amphiphiles that may form integral membrane proteins in which the amphiphile may be a chimeric structure that includes the soluble proteins.

In some embodiments, the artificial proteins of the invention may be transmembrane proteins having a transmembrane portion, an intracellular or cytosolic portion, and an extracellular portion. For example, in some embodiments, the transmembrane portion of the artificial proteins described herein may include leucine rich sequences having a ratio of at least about of at least about 1:1 Leu to Ala, or at least about 2:1 Leu to Ala, or at least about 3:1 Leu to Ala, or at least about 4:1 Leu to Ala, or at least about 5:1 Leu to Ala. In certain embodiments, the transmembrane portion of the artificial proteins described herein may include leucine rich sequences having a ratio of about 4:1 Leu to Ala. In some embodiments, the transmembrane portion of the artificial proteins described herein may include aromatic residues providing lower insertion energies for placement at the cell membrane interface.

In some embodiments, the artificial proteins of the invention may be configured to traffic through a eukaryotic (e.g., mammalian) cell's endoplasmic reticulum and Golgi apparatus. In some methods of the invention that include the preparation of one or more of the artificial proteins described herein, such methods may include trafficking the artificial protein through a eukaryotic (e.g., mammalian) cell's endoplasmic reticulum and Golgi apparatus.

In some embodiments, the artificial protein of the invention may have a net surface charge (i.e., $Z_{net}$) of about −12 to about +8. The net surface charge of the artificial proteins of the invention may be varied or modified by adjusting the amino acid sequence of the artificial proteins described herein. In some embodiments, those artificial proteins of the invention having a net surface charge of about −12 to about +8 may be expressed in eukaryotic (e.g., mammalian) cells. In some embodiments, the net surface charge may be greater than about −12, or greater than about −11, or greater than about −10, or greater than about −9, or greater than about −8, or greater than about −7, or greater than about −6, or greater than about −5, or greater than about −4, or greater than about −3, or greater than about −2, or greater than about −1, or greater than about 0, or greater than about +1, or greater than about +2, or greater than about +3, or greater than about +4, or greater than about +5, or greater than about +6, or greater than about +7. In some embodiments, the net surface charge may be less than about +8, or less than about +7, or less than about +6, or less than about +5, or less than about +4, or less than about +3, or less than about +2, or less than about +1, or less than about 0, or less than about −1, or less than about −2, or less than about −3, or less than about −4, or less than about −5, or less than about −6, or less than about −7, or less than about −8, or less than about −9, or less than about −10, or less than about −11. In some embodiments, the artificial protein of the invention may have a net surface charge that is negative.

In some embodiments, the artificial proteins of the invention may be modified as described herein to provide a range of functions when associated with a fluorophore and/or a cofactor. For example, the artificial proteins of the invention may be modified to function as voltage sensors, MRI contrast agents, metal binding reporters, and/or cellular probes.

In some embodiments, artificial proteins described herein are artificially designed and may be rigid 2, 3, 4, 5, 6, or more-helix bundle proteins that serve as custom scaffolds for 1, 2, 3, 4, 5, 6, or more types of biological co-factors (e.g. fluorophores or redox sensors) that can each be arbitrarily or purposefully positioned within an artificial protein of the invention. In certain embodiments, the artificial proteins of the invention include 4 helical protein bundles (i.e., α-helical protein bundles).

In some embodiments, artificial proteins of the invention are compact 4-TM helix proteins that are completely modular with respect to structure and mechanism. This compactness can be advantageous in viral transgene delivery with limited genetic payloads such as with adeno-associated virus (AAV, by comparison, opsins and mFP-based systems are ~2-3 larger genes). In some embodiments, the fluorescence signal positively correlates and increases upon depolarization to avoid false positives from bleaching, and the exposed amino acid side chains in the TM region may be uncharged/non-polar, to avoid membrane capacitance alterations. In some embodiments, the artificial proteins of the invention may provide sensors with microsecond (µs)-resolution or log orders faster resolution than current state-of-the-art protein-based sensing techniques.

Figure 3:
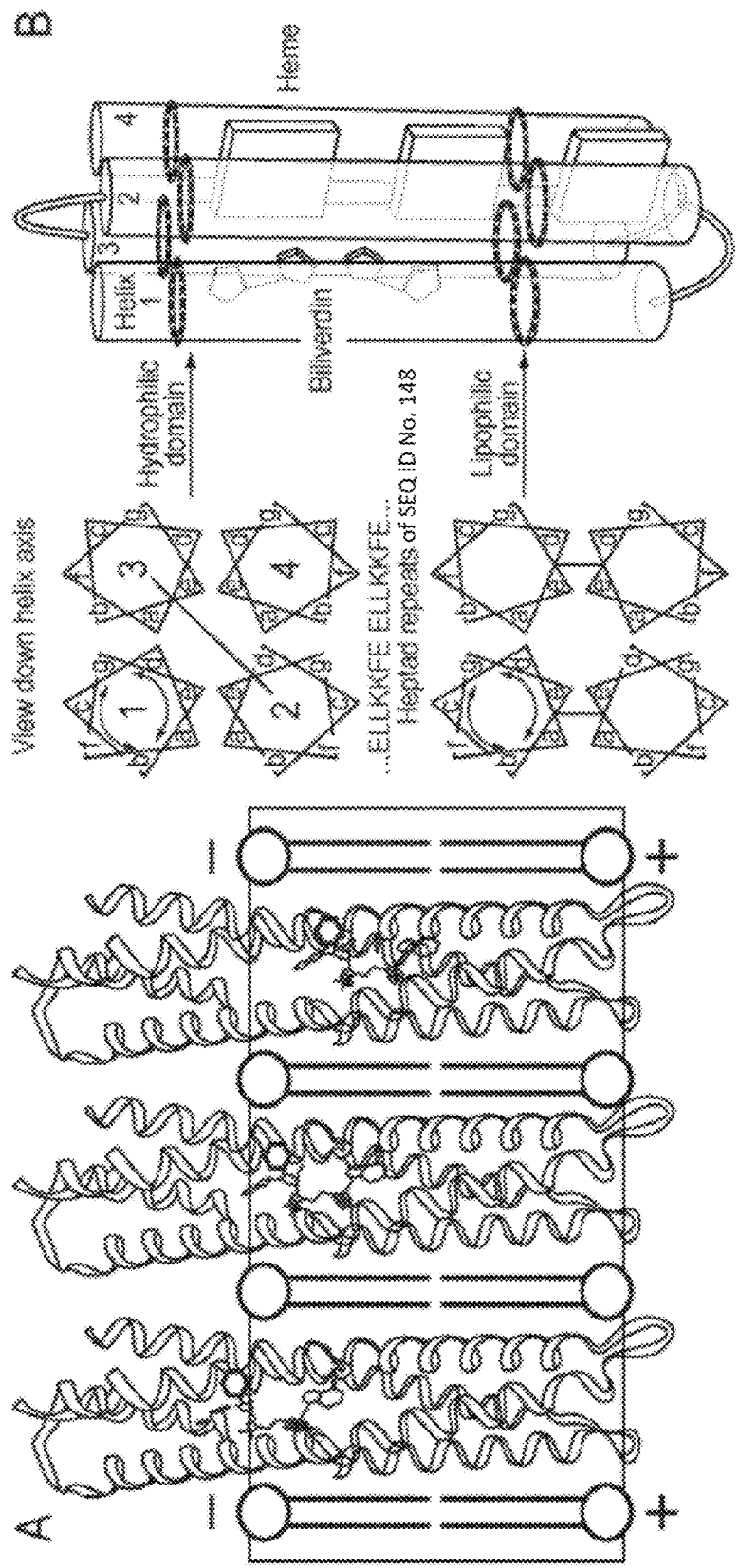
FIG. 3 is an illustration of various views of an artificial protein according to an embodiment of the invention. (Panel A) Transmembrane 4-helix bundle maquette with polar (cyan) and nonpolar regions (gray) using Cys (yellow) to anchor a field sensing biliverdin fluorophore (red). The stability and sequence tolerance of maquette first principles design permits systematic adjustment of the Cys bilin anchoring position to optimize field sensitivity. (Panel B) Sequences are based on heptad repeats that place polar groups on one face of the helix (binary patterning) so that hydrophobic forces drive 4-helix bundle assembly. Heptads are modified to be predominantly nonpolar in membrane spanning regions. Cofactors such as biliverdin, flavin, heme, and retinal are anchored with Cys, His, Thr and Lys residues at design specified sites for electron transfer and fluorescence function.

By employing fundamental rules for alpha helical protein folding and association between alpha helices, in some embodiments, artificial proteins according to the invention are stable and robust from the start. Furthermore, the simplicity and modularity of first principles design keeps the re-engineering options open and allows unprecedented adaptability to be maintained in both the number and type of cofactors that can be anchored in the artificial protein frame (FIG. 3). In natural proteins complex interdependence between structural parts accumulates during repeated cycles of mutation and natural selection; such complexity impedes or even halts re-engineering for desired function due to fragility. In contrast, the role of individual residues in structure/function relationships of artificial proteins according to some embodiments of the invention is usually isolated and identifiable. This allows for, in some embodiments, manipulation of local electric fields around cofactors or rates of electron tunneling between redox centers, in the scaffold of an artificial protein.

In some embodiments, a stripped-down protein construct exploits relatively simple, repeating, binary patterning of amino acids to create α-helices that assemble into a 4-helix bundle. In some embodiments, for the hydrophilic region extending away from the membrane, the amino acid order is selected so that polar or charged residues (positively charged Lys or Arg, negatively charged Glu or Asp) lie on one face of the helix and non-polar residues (Ala, Phe) lie on the other. Hydrophobic forces may drive the nonpolar faces together into the four-helix bundle (FIG. 3). For the lipophilic transmembrane region, one or more of the amino acids are nonpolar, with the exception of select polar amino acids that perform the task of binding cofactors between helices or making hydrogen bonds across the bundle interior from one helix to another. In some embodiments, Cys, His, and interior Lys anchor cofactors to specific locations in the helical frame.

Figure 4:
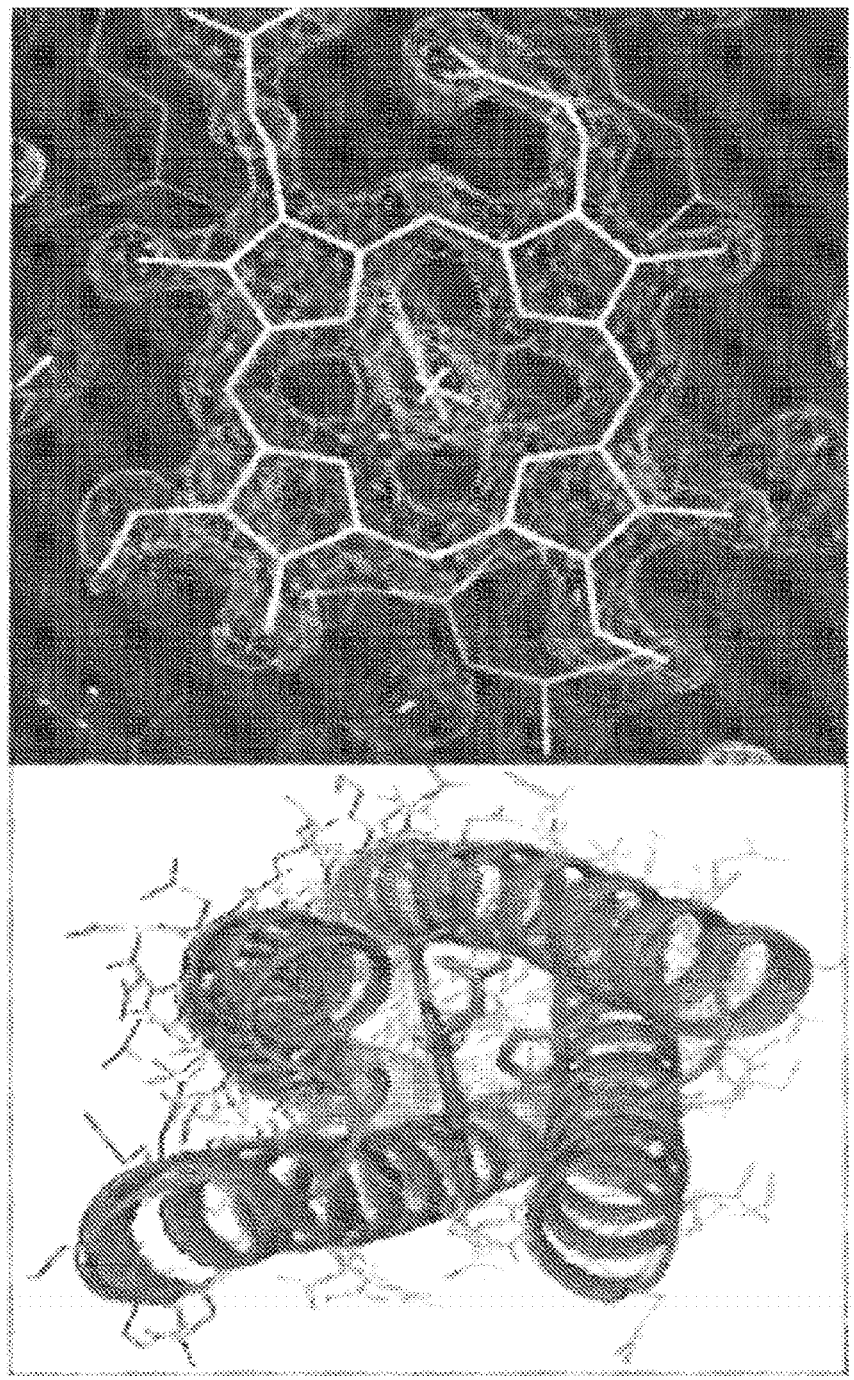
FIG. 4 is an illustration of x-ray crystal structures of an artificial protein according to an embodiment of the invention, confirming the assembly expected from simple first principles.
Figure 5:
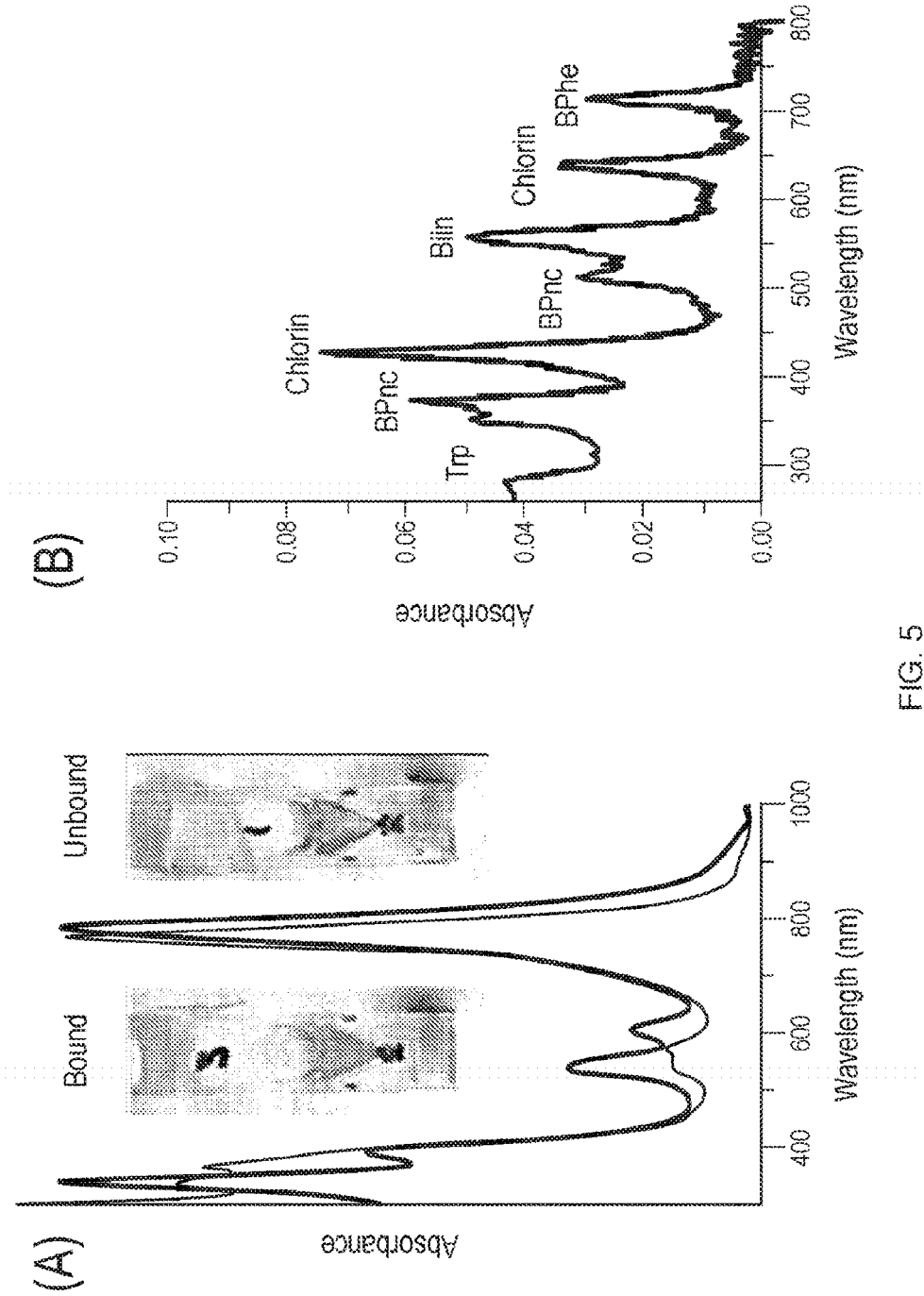
FIG. 5 shows the results of multi-chromophore binding in a single membrane artificial protein according to an embodiment of the invention. (Panel A) Local electric fields from the artificial protein environment typically change pigment color upon binding, a type of Stark effect. Here Ni bacteriochlorophyll changes from pink to blue upon binding to a transmembrane maquette. (Panel B) Maquettes bind multiple different cofactors types site-specifically within a single frame (three pigment complex: bilin and chlorin and a bacteriopheophytins).
Figure 7:
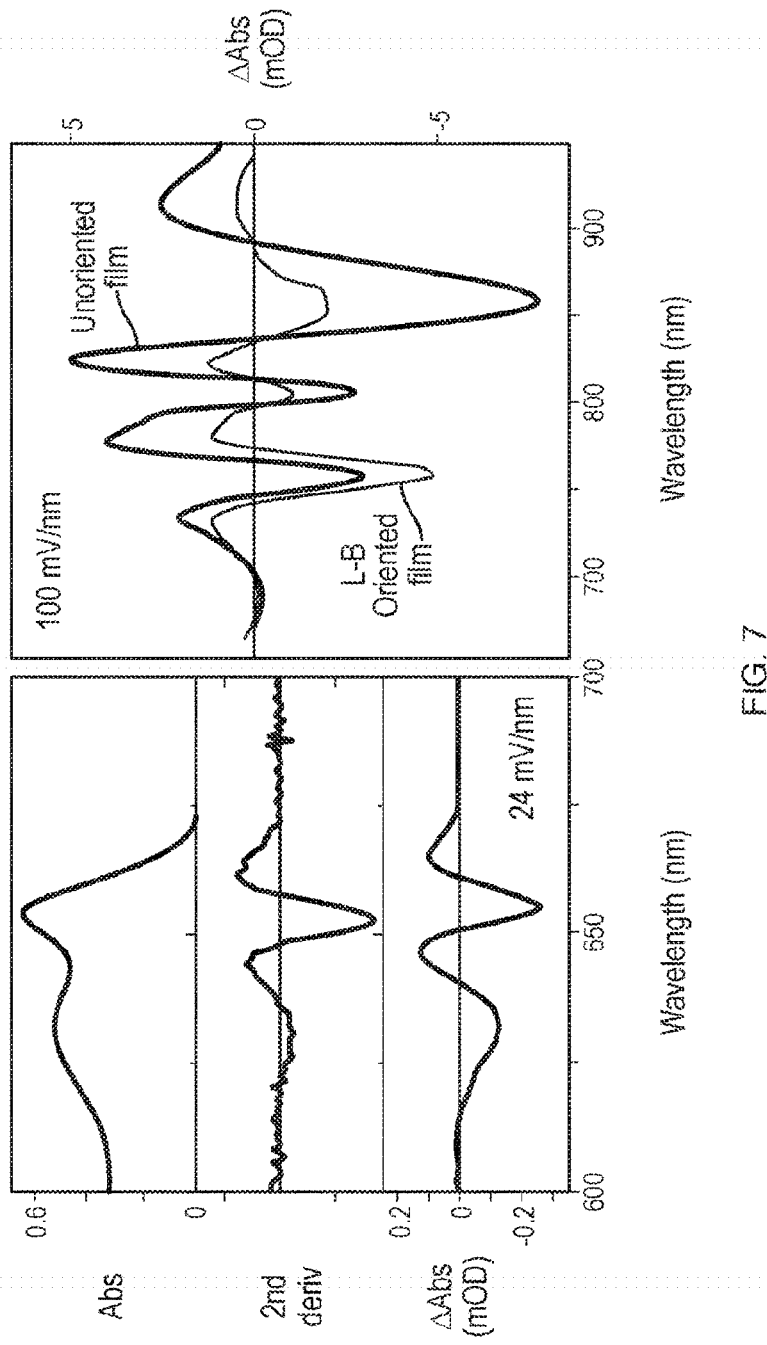
FIG. 7 shows the stark effect of bilins in natural proteins (left), which correlates with emission that are comparable to the Stark effects that have been previously measured in tetrapyrrole cofactors, the bacteriochlorophylls and bacteriopheophytins in transmembrane photosynthetic reaction centers (right). Depending on the orientation of the transition dipoles of the pigments with respect to the applied field (right, red), Stark Effects can be enhanced or depressed (right, relative amplitude of red vs blue peaks and troughs).

In some embodiments, a wide variety of natural and synthetic cofactors can be anchored to the frame at many different positions along the helices and in the connecting loops, for example, hemes and other porphyrins, flavins, various bilins, quinones, iron-sulfur clusters, carotenoids, chlorins and bacterio-chlorins (FIG. 5, see also Farid, T. A. et al., "Elementary tetrahelical protein design for diverse oxidoreductase functions" Nature Chemical Biology, 9, 826-833 (2013), hereby incorporated by reference in its entirety). In some embodiments, local electric fields from the artificial protein environment can change pigment color upon binding, a type of Stark effect (FIG. 5). X-ray crystallography up to 1.4 Å resolution and 2D-NMR can provide details of protein-cofactor interactions for iterative redesign to tune maquette physical chemical properties (FIG. 4). Because of the strong driving forces for assembly of this first principles alpha helical frame and associated high tolerance to sequence manipulation, redesign and tuning of maquette functional properties can be as simple as moving the cofactor anchoring amino acid one helical turn to adjust cofactor position. FIG. 3 illustrates three examples of Cys scanning along a single helix to anchor a field reporting cofactor at different membrane depths to optimize for maximum sensitivity.

Definitions

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

As used herein, the articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have an N-terminus and a C-terminus. The N-terminus will have an amino group, which can be free (i.e., as a $NH_2$ group) or appropriately protected (for example, with a BOC or an Fmoc group). The C-terminus will have a carboxylic group, which can be free (i.e., as a COOH group) or appropriately protected (for example, as a benzyl or a methyl ester). A cyclic peptide does not necessarily have free N- or C-termini, since they are covalently bonded through an amide bond to form the cyclic structure.

As used herein, the term "(SEQ ID NO:X)-(SEQ ID NO:Y)" indicates that SEQ ID NO:X is covalently linked to SEQ ID NO:Y by an amide bond, involving the carboxylate group on the C-terminus of SEQ ID NO:X and the amino group on the N-terminus of SEQ ID NO:Y. Accordingly, the term "(SEQ ID NO:X)-LOOP-(SEQ ID NO:Y)" indicates that SEQ ID NO:X is covalently linked to LOOP by an amide bond, involving the carboxylate group on the C-terminus of SEQ ID NO:X and an amino group in LOOP, and LOOP is covalently linked to SEQ ID NO:Y by an amide bond, involving a carboxylate group in LOOP and the amino group in the N-terminus of SEQ ID NO:Y.

As used herein, the term "LOOP" refers to a chemical linker that connects two protein segments and is able to form a loop between the two protein segments. In one embodiment, LOOP is a peptide of 4 to 8 amino acid residues, 6 to 15 amino acid residues, a hydrocarbon chain of 18 to 30 carbons, or a chain consisting of $—HN^{-1}—(CH_2CH_2O)_nCH_2C(O)—$, wherein "n" is an integer of value between 5 and 10, the group $—HN_1$ forms an amide bond with the carboxylate group at the C-terminus of one protein segment and $CH_2C(O)—$ forms an amide bond with the amino group at the N-terminus of the other protein segment. In another embodiment, LOOP is a peptide consisting of from 3 to 15 amino acids. In another embodiment, LOOP is a peptide consisting of from 4 to 8 amino acids. In yet another embodiment, LOOP is a peptide formed by amino acids selected from the group of glycine, serine and cysteine. In yet another embodiment, LOOP is a peptide of amino acid sequence selected from the group consisting of GGSGKGSGG (SEQ ID No. 17), GGCG (SEQ ID No: 18), GACG (SEQ ID No: 19), GGSG (SEQ ID No. 20).

As used herein, amino acids are represented by the full name thereof, by the three-letter code, as well as the one-letter code corresponding thereto, as indicated in the following Table 1. Additionally, as used herein "+" represents a positively charged amino acid, "−" represents a negatively charged amino acid, and "0" represents an amino acid having an amide side-chain. In some embodiments, positively charged amino acids may include acidic side-chains and may be selected from the group consisting of lysine, arginine, and histidine. In some embodiments, negatively charged amino acids may include basic side chains and may be selected from the group consisting of aspartate and glutamate. In some embodiments, amide bearing amino acids, or amino acids having an amide side-chain, (e.g., those represented by a "0") may include glutamine or asparagine. As shown in Table 1, below, "X" may represent any amino acid. The structure of amino acids and their abbreviations can also be found in the chemical literature, such as in Stryer, 1988, "Biochemistry", 3.sup.rd Ed., W. H. Freeman and Co., New York.

TABLE 1

| Full Name | Three-Letter Code | One-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methonine | Met | M |
| Phenylalanine | Phe | F |
| Proline | Pro | P |
| Serine | Ser | S |
| Threonine | Thr | T |

TABLE 1-continued

| Full Name | Three-Letter Code | One-Letter Code |
| --- | --- | --- |
| Tryptophan | Trp | W |
| Tyrosine | Tyr | Y |
| Valine | Val | V |
| Any amino acid | Xaa | X |

As used herein the term "cofactor" refers to any naturally occurring or artificial chemical group or compound that may be bound to an artificial protein of the invention.

As used herein to refer to the association between a cofactor and the peptides of the invention, the term "bound" indicates that the cofactor is coordinated to residues of the peptide, forming a complex. The complex may be more or less labile, depending on the specific nature of the cofactor and the peptide in use. In one embodiment, the complex between the cofactor and the peptides is stable enough for the complex to be useful within the needs of the invention. In another embodiment, the cofactor is covalently bound to the peptides of the invention.

As used herein, the term "fluorophore" refers to a chemical group or compound that emits light, typically ranging from the visible to near infrared regions of the electromagnetic spectrum.

As used herein, the term "electrochromic" refers to a chemical group or compound that emits light in response to an electric charge.

As used herein with respect to the compounds of the invention, "biologically active" means that the compounds elicit a biological response in a mammal that can be monitored and characterized in comparison with an untreated mammal.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, a "subject" or a "mammal" includes a human or a non-human mammal Non-human mammals include, for example, livestock and pets, such as ovine, bovine, porcine, canine, feline and murine mammals. Preferably, the subject or mammal is canine, feline or human. Most preferably, the subject or mammal is human.

The terms "sequence identity," "percent identity," and "sequence percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

Certain embodiments of the present invention comprise a variant of a peptide or polypeptide or of a nucleotide or polynucleotide of the invention. As used herein, the term "variant" encompasses but is not limited to polypeptides (or peptides) or polynucleotides (or nulcleotides) which comprise an amino acid or nucleotide sequence which differs from the amino acid or nucleotide sequence of a reference polypeptide (or peptide) or polynucleotide (or nucleotide) by way of one or more substitutions, deletions and/or additions at certain positions within or adjacent to the amino acid or nucleotide sequence of the reference polypeptide (or peptide) or polynucleotide (or nucleotide). The variant may comprise one or more conservative substitutions in its amino acid or nucleotide sequence as compared to the amino acid or nucleotide sequence of a reference polypeptide (or peptide) or polynucleotide (or nucleotide). Conservative substitutions may involve, e.g., the substitution of similarly charged or uncharged amino acids. The variant retains the ability to specifically bind to the antigen of the reference peptide or polypeptide. In certain embodiments, variants possess biological activities that are the same or similar to the sequences in question.

Artificial Proteins of the Invention

In some embodiments, artificial proteins according to the invention comprise 1, 2, 3, 4, 5, 6, or more synthetic peptides. In some embodiments, the invention includes a nucleotide sequence encoding a synthetic peptide. In an embodiment an artificial protein according to the invention comprises four (4) synthetic peptides. Each peptide may comprise an alpha helix. In some embodiments, the artificial protein has a maquette structure, i.e. comprises four (4) synthetic α-helical peptides. In some embodiments two peptides may be connected by a LOOP sequence of amino acids. In some embodiments an artificial protein comprises a first pair of peptides connected by a first LOOP sequence of amino acids and a second pair of peptides connected by a second LOOP sequence of amino acids, wherein the first and second LOOP sequences are connected by a third LOOP sequence. In some embodiments a first peptide is connected to a second peptide by a LOOP sequence, the second peptide is connected to a third peptide by a second LOOP sequence, and the third peptide is connected to a fourth peptide by a third LOOP sequence, e.g. to form a single chain artificial protein. In some embodiments, each LOOP sequence is an independently selected group of 3-15 or 4-8 amino acids.

In some embodiments, an artificial protein includes a peptide comprising any one of the amino acid sequences set forth in SEQ ID NOS: 1-16, represented below:

```
SEQ ID NO. 1:
EIWKXXEDALQKFEXXLNQFEDXXQL.
```

In some embodiments, an artificial protein includes a peptide comprising the amino acid sequence of SEQ ID NO: 2, represented below:

```
SEQ ID NO: 2:
EIKQRXEDXLRKFEEALKRFEDLKQK.
```

In some embodiments, an artificial protein includes a peptide comprising the amino acid sequence of SEQ ID NO: 3, represented below:

SEQ ID NO. 3:
RXWKXXEDAXQKFEEALNQFEDLKQL.

In some embodiments, an artificial protein includes a peptide comprising the amino acid sequence of SEQ ID NO: 4, represented below:

SEQ ID NO. 4:
EIKQRXEDALRKFEEALKRXEDXXQK.

In some embodiments, an artificial protein includes a peptide comprising one or more of an amino acid sequence selected from the group consisting of SEQ ID NO: 1, SEQ ID NO: 2, SEQ ID NO: 3, and SEQ ID NO: 4. In some embodiments an artificial protein includes a peptide comprising two or more of amino acid sequences selected from the group consisting of SEQ ID NO: 1, SEQ ID NO: 2, SEQ ID NO: 3, and SEQ ID NO: 4, wherein the two or more amino acid sequences are connected by a LOOP. A LOOP structure may comprise 3 to 15 amino acids, or preferably, 4-8 amino acids. In some embodiments a LOOP structure comprises glycine and cysteine amino acids. In some embodiments, LOOP structures are independently selected from: SEQ ID NO: 17: GGSGKGSGG, SEQ ID NO: 18: GGCG, SEQ ID NO: 19: GACG, and SEQ ID NO: 20: GGSG.

In some embodiments, an artificial protein includes a peptide comprising the amino acid sequence of (SEQ ID NO: 1)-LOOP-(SEQ ID NO: 2). In some embodiments, an artificial protein includes a peptide comprising the amino acid sequence of (SEQ ID NO: 2)-LOOP-(SEQ ID NO: 3). In some embodiments, an artificial protein includes a peptide comprising the amino acid sequence of (SEQ ID NO: 3)-LOOP-(SEQ ID NO: 4). In some embodiments, an artificial protein includes a peptide comprising the amino acid sequence of (SEQ ID NO: 1)-LOOP-(SEQ ID NO: 2)-LOOP-(SEQ ID NO: 3). In some embodiments, an artificial protein includes a peptide comprising the amino acid sequence of (SEQ ID NO: 2)-LOOP-(SEQ ID NO: 3)-LOOP-(SEQ ID NO: 4). In some embodiments, the an artificial protein includes a peptide comprising the amino acid sequence of (SEQ ID NO: 1)-LOOP-(SEQ ID NO: 2)-LOOP-(SEQ ID NO: 3)-LOOP-(SEQ ID NO: 4). In each embodiment the LOOP sequence may be as described herein.

In some embodiments, an artificial protein includes a peptide comprising the amino acid sequence of SEQ ID NO:5, represented below:

SEQ ID NO. 5:
EXXKXXEDXXQKXEEXXNQXEDXXQL.

In some embodiments, an artificial protein includes a peptide comprising the amino acid sequence of SEQ ID NO: 6, represented below:

SEQ ID NO: 6:
EXKQRXEDXXRKXEEXXKRXEDXKQK.

In some embodiments, an artificial protein includes a peptide comprising the amino acid sequence of SEQ ID NO: 7, represented below:

SEQ ID NO. 7:
RXXKXXEDXXQKXEEXXNQXEDXKQL.

In some embodiments, an artificial protein includes a peptide comprising the amino acid sequence of SEQ ID NO: 8, represented below:

SEQ ID NO. 8:
EXKQRXEDXXRKXEEXXKRXEDXXQK.

In some embodiments, an artificial protein includes a peptide comprising one or more of an amino acid sequence selected from the group consisting of SEQ ID NO: 5, SEQ ID NO: 6, SEQ ID NO: 7, and SEQ ID NO: 8. In some embodiments, an artificial protein includes a peptide comprising two or more of amino acid sequences selected from the group consisting of SEQ ID NO: 5, SEQ ID NO: 6, SEQ ID NO: 7, and SEQ ID NO: 8, wherein the two or more amino acid sequences are connected by a LOOP. A LOOP structure may comprise 3 to 15 amino acids, or preferably, 4-8 amino acids. In some embodiments, a LOOP structure comprises glycine and cysteine amino acids. In some embodiments, LOOP structures are independently selected from: SEQ ID NO: 17: GGSGKGSGG, SEQ ID NO: 18: GGCG, SEQ ID NO: 19: GACG, and SEQ ID NO: 20: GGSG.

In some embodiments, an artificial protein includes a peptide comprising the amino acid sequence of (SEQ ID NO: 5)-LOOP-(SEQ ID NO: 6). In some embodiments, an artificial protein includes a peptide comprising the amino acid sequence of (SEQ ID NO: 6)-LOOP-(SEQ ID NO: 7). In some embodiments, an artificial protein includes a peptide comprising the amino acid sequence of (SEQ ID NO: 7)-LOOP-(SEQ ID NO: 8). In some embodiments, an artificial protein includes a peptide comprising the amino acid sequence of (SEQ ID NO: 5)-LOOP-(SEQ ID NO: 6)-LOOP-(SEQ ID NO: 7). In some embodiments, an artificial protein includes a peptide comprising the amino acid sequence of (SEQ ID NO: 6)-LOOP-(SEQ ID NO: 7)-LOOP-(SEQ ID NO: 8). In some embodiments, an artificial protein includes a peptide comprising the amino acid sequence of (SEQ ID NO: 5)-LOOP-(SEQ ID NO: 6)-LOOP-(SEQ ID NO: 7)-LOOP-(SEQ ID NO: 8). In each embodiment the LOOP sequence may be as described herein.

In some embodiments, an artificial protein includes a peptide comprising the amino acid sequence of SEQ ID NO: 9, represented below:

SEQ ID NO. 9:
EXXKXXEDXXQKXEEXXNQXEDXXQL.

In some embodiments, an artificial protein includes a peptide comprising the amino acid sequence of SEQ ID NO: 10, represented below:

SEQ ID NO: 10:
EXKQRXEDXXRKXEEXXKRXEDXKQK.

In some embodiments, an artificial protein includes a peptide comprising the amino acid sequence of SEQ ID NO: 11, represented below:

SEQ ID NO. 11:
RXXKXXEDXXQKXEEXXNQXEDXKQL.

In some embodiments, an artificial protein includes a peptide comprising the amino acid sequence of SEQ ID NO: 12, represented below:

```
SEQ ID NO. 12:
EXKQRXEDXXRKXEEXXKRXEDXXQK.
```

In some embodiments, an artificial protein includes a peptide comprising one or more of an amino acid sequence selected from the group consisting of SEQ ID NO: 9, SEQ ID NO: 10, SEQ ID NO: 11, and SEQ ID NO: 12. In some embodiments an artificial protein includes a peptide comprising two or more of amino acid sequences selected from the group consisting of SEQ ID NO: 9, SEQ ID NO: 10, SEQ ID NO: 11, and SEQ ID NO: 12, wherein the two or more amino acid sequences are connected by a LOOP. A LOOP structure may comprise 3 to 15 amino acids, or preferably, 4-8 amino acids. In some embodiments a LOOP structure comprises glycine and cysteine amino acids. In some embodiments, LOOP structures are independently selected from: SEQ ID NO: 17: GGSGKGSGG, SEQ ID NO: 18: GGCG, SEQ ID NO: 19: GACG, and SEQ ID NO: 20: GGSG.

In some embodiments, an artificial protein includes a peptide comprising the amino acid sequence of (SEQ ID NO: 9)-LOOP-(SEQ ID NO: 10). In some embodiments, an artificial protein includes a peptide comprising the amino acid sequence of (SEQ ID NO: 10)-LOOP-(SEQ ID NO: 11). In some embodiments, an artificial protein includes a peptide comprising the amino acid sequence of (SEQ ID NO: 11)-LOOP-(SEQ ID NO: 12). In some embodiments, an artificial protein includes a peptide comprising the amino acid sequence of (SEQ ID NO: 9)-LOOP-(SEQ ID NO: 10)-LOOP-(SEQ ID NO: 11). In some embodiments, an artificial protein includes a peptide comprising the amino acid sequence of (SEQ ID NO: 10)-LOOP-(SEQ ID NO: 11)-LOOP-(SEQ ID NO: 12). In some embodiments, an artificial protein includes a peptide comprising the amino acid sequence of (SEQ ID NO: 9)-LOOP-(SEQ ID NO: 10)-LOOP-(SEQ ID NO: 11)-LOOP-(SEQ ID NO: 12). In each embodiment the LOOP sequence may be as described herein.

In some embodiments, an artificial protein includes a peptide comprising the amino acid sequence of SEQ ID NO: 13, represented below:

```
SEQ ID NO. 13:
EXXKXXEDXXQKXEEXXNQXEDXXQL.
```

In some embodiments, an artificial protein includes a peptide comprising the amino acid sequence of SEQ ID NO: 14, represented below:

```
SEQ ID NO: 14:
EXKQRXEDXXRKXEEXXKRXEDXKQK.
```

In some embodiments, an artificial protein includes a peptide comprising the amino acid sequence of SEQ ID NO: 15, represented below:

```
SEQ ID NO. 15:
RXXKXXEDXXQKXEEXXNQXEDXKQL.
```

In some embodiments, an artificial protein includes a peptide comprising the amino acid sequence of SEQ ID NO: 16, represented below:

```
SEQ ID NO. 16:
EXKQRXEDXXRKXEEXXKRXEDXXQK.
```

In some embodiments, an artificial protein includes a peptide comprising one or more of an amino acid sequence selected from the group consisting of SEQ ID NO: 13, SEQ ID NO: 14, SEQ ID NO: 15, and SEQ ID NO: 16. In some embodiments an artificial protein includes a peptide comprising two or more of amino acid sequences selected from the group consisting of SEQ ID NO: 13, SEQ ID NO: 14, SEQ ID NO: 15, and SEQ ID NO: 16, wherein the two or more amino acid sequences are connected by a LOOP. A LOOP structure may comprise 3 to 15 amino acids, or preferably, 4-8 amino acids. In some embodiments a LOOP structure comprises glycine and cysteine amino acids. In some embodiments, LOOP structures are independently selected from: SEQ ID NO: 17: GGSGKGSGG, SEQ ID NO: 18: GGCG, SEQ ID NO: 19: GACG, and SEQ ID NO: 20: GGSG.

In some embodiments, an artificial protein includes a peptide comprising the amino acid sequence of (SEQ ID NO: 13)-LOOP-(SEQ ID NO: 14). In some embodiments, an artificial protein includes a peptide comprising the amino acid sequence of (SEQ ID NO: 14)-LOOP-(SEQ ID NO: 15). In some embodiments, an artificial protein includes a peptide comprising the amino acid sequence of (SEQ ID NO: 15)-LOOP-(SEQ ID NO: 16). In some embodiments, an artificial protein includes a peptide comprising the amino acid sequence of (SEQ ID NO: 13)-LOOP-(SEQ ID NO: 14)-LOOP-(SEQ ID NO: 15). In some embodiments, an artificial protein includes a peptide comprising the amino acid sequence of (SEQ ID NO: 14)-LOOP-(SEQ ID NO: 15)-LOOP-(SEQ ID NO: 16). In some embodiments, an artificial protein includes a peptide comprising the amino acid sequence of (SEQ ID NO: 13)-LOOP-(SEQ ID NO: 14)-LOOP-(SEQ ID NO: 15)-LOOP-(SEQ ID NO: 16). In each embodiment the LOOP sequence may be as described herein.

In some embodiments, an artificial protein includes a peptide comprising the amino acid sequence of Generic Sequence A, represented below:

Generic Sequence A: -XX+XX--XX0+X--XX00X--XX0L

In some embodiments, an artificial protein includes a peptide comprising the amino acid sequence of Generic Sequence B, represented below:

Generic Sequence B: -X+0+X--XX++X--XX++X--X+0+

In some embodiments, an artificial protein includes a peptide comprising the amino acid sequence of Generic Sequence C, represented below:

Generic Sequence C: +XX+XX--XX0+X--XX00X--X+0L

In some embodiments, an artificial protein includes a peptide comprising the amino acid sequence of Generic Sequence D, represented below:

Generic Sequence D: -XX+0+--XX++X--XX++X--XX0+

In some embodiments, an artificial protein includes a peptide comprising one or more of an amino acid sequence selected from the group consisting of Generic Sequences A, B, C, and D. In some embodiments an artificial protein includes a peptide comprising two or more of amino acid sequences selected from the group consisting of Generic Sequences A, B, C, and D, wherein the two or more amino acid sequences are connected by a LOOP. A LOOP structure may comprise 3 to 15 amino acids, or preferably, 4-8 amino acids. In some embodiments a LOOP structure comprises glycine and cysteine amino acids. In some embodiments, LOOP structures are independently selected from: SEQ ID NO: 17: GGSGKGSGG, SEQ ID NO: 18: GGCG, SEQ ID NO: 19: GACG, and SEQ ID NO: 20: GGSG.

In some embodiments, an artificial protein includes a peptide comprising the amino acid sequence of (Generic Sequence A)-LOOP-(Generic Sequence B). In some embodiments, an artificial protein includes a peptide comprising the amino acid sequence of (Generic Sequence B)-LOOP-(Generic Sequence C). In some embodiments, an artificial protein includes a peptide comprising the amino acid sequence of (Generic Sequence C)-LOOP-(Generic Sequence D). In some embodiments, an artificial protein includes a peptide comprising the amino acid sequence of (Generic Sequence A)-LOOP-(Generic Sequence B)-LOOP-(Generic Sequence C). In some embodiments, an artificial protein includes a peptide comprising the amino acid sequence of (Generic Sequence B)-LOOP-(Generic Sequence C)-LOOP-(Generic Sequence D). In some embodiments, an artificial protein includes a peptide comprising the amino acid sequence of (Generic Sequence A)-LOOP-(Generic Sequence B)-LOOP-(Generic Sequence C)-LOOP-(Generic Sequence D). In each embodiment the LOOP sequence may be as described herein.

In some embodiments, an artificial protein includes a peptide comprising an amino acid sequence selected from the group consisting of: SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ TD NO: 40; SEQ ID NO: 41, SEQ ID NO: 42; SEQ ID NO: 43; and SEQ ID NO: 44, where SEQ TD NOS: 21-44 are as shown in Table 2.

In some embodiments, an artificial protein includes a peptide comprising an amino acid sequence as set forth in SEQ ID NO: 45, as shown in Table 2. Without being limited to any one theory of the invention, SEQ TD NO: 45 (i.e., dFP1.1) demonstrate an increase in fluorescence as compared to dFP because histidines in the 7 position of each helix, which may be due to the addition of core bulk and the ability to hydrogen bond, thereby rigidifying the core structure.

TABLE 2

| Seq ID No | Name | One Letter Sequence | |
|---|---|---|---|
| 1 | | EIWKXXEDAL QKFEXXLNQF EDXXQL | 26 |
| 2 | | EIKQRXEDXL RKFEEALKRF EDLKQK | 26 |
| 3 | | RXWKXXEDAX QKFEEALNQF EDLKQL | 26 |
| 4 | | EIKQRXEDAL RKFEEALKRX EDXXQK | 26 |
| 5 | | EXXKXXEDXX QKXEEXXNQX EDXXQL | 26 |
| 6 | | EXKQRXEDXX RKXEEXXKRX EDXXQK | 26 |
| 7 | | RXXKXXEDXX QKXEEXXNQX EDXKQL | 26 |
| 8 | | EXKQRXEDXX RKXEEXXKRX EDXXQK | 26 |
| 9 | | EXXKXXEDXX QKXEEXXNQX EDXXQL | 26 |
| 10 | | EXKQRXEDXX RKXEEXXKRX EDXKQK | 26 |
| 11 | | RXXKXXEDXX QKXEEXXNQX EDXKQL | 26 |
| 12 | | EXKQRXEDXX RKXEEXXKRX EDXXQK | 26 |
| 13 | | EXXKXXEDXX QKXEEXXNQX EDXXQL | 26 |
| 14 | | EXKQRXEDXX RKXEEXXKRX EDXKQK | 26 |
| 15 | | RXXKXXEDXX QKXEEXXNQX EDXKQL | 26 |
| 16 | | EXKQRXEDXX RKXEEXXKRX EDXXQK | 26 |
| 17 | Loop | GGSGKGSGG | 9 |
| 18 | Loop | GGCG | 4 |
| 19 | Loop | GACG | 4 |
| 20 | Loop | GGSG | 4 |
| 21 | GLSloop | EIWKQHEDAL QKFEEALNQF EDLKQLGGSG KGSGGEIKQR HEDALRKFEE ALKRFEDLKQ | 60 |
| | | KGGCGRIWKQ HEDALQKFEE ALNQFEDLKQ LGGSGKGSGG EIKQRHEDAL RKFEEALKRF | 120 |
| | | EDLKQK | 126 |
| 22 | PEB Mut B | EIWKSHEDAL QKFEEALNQF EDLKQLGGSG KGSGGEIKQR HEDALRKFEE ALKRFEDLKQ | 60 |
| | | KGACGRIWKQ HEDALQKFEE ALNQFEDLKQ LGGSGKGSGG EIKQRHEDAL RKFEEALKRF | 120 |
| | | EDRVQK | 126 |

TABLE 2-continued

| Seq ID No | Name | One Letter Sequence | |
|---|---|---|---|
| 23 | PEB Mut C | EIWKLHEDAL QKFEEALNQF EDLKQLGGSG KGSGGEIKQR HEDALRKFEE ALKRFEDLKQ | 60 |
| | | KGGCGRIWKE HEDALQKFEE ALNQFEDLKQ LGGSGKGSGG EIKQRHEDAL RKFEEALKRF | 120 |
| | | EDRVQK | 126 |
| 24 | PEB Mut D | EIWKQHEDAL QKFEEALNQF EDLKQLGGSG KGSGGEIKQR HEDALRKFEE ALKRFEDLKQ | 60 |
| | | KGGCGRIWKQ HEDALQKFEE ALNQFEDLKQ LGGSGKGSGG EIKQRHEDAL RKFEEALKRF | 120 |
| | | EDRVQK | 126 |
| 25 | dFP1.0 | EIWKSHEDAL QKFEEALNQF EDLKQLGGSG KGSGGEIKQR HEDALRKFEE ALKRFEDLKQ | 60 |
| | | KGGCGRIWKE HEDAHQKFEE ALNQFEDLKQ LGGSGKGSGG EIKQRHEDAL RKFEEALKRH | 120 |
| | | EDRVQK | 126 |
| 26 | C-His Stab CGRD | EIWKSHEDAL QKFEEALNQF EDLKQLGGSG KGSGGEIKQR HEDALRKFEE ALKRFEDLKQ | 60 |
| | | KGGCGRDWKE HEDAHQKFEE ALNQFEDLKQ LGGSGKGSGG EIKQRHEDAL RKFEEALKRH | 120 |
| | | EDRVQK | 126 |
| 27 | C41 Stab Map | EIWKLFEDAL QKFEHELNQF EDRVQLGGSG KGSGGEIKQR CADALRKFEE ALKRFEDLKQ | 60 |
| | | KGGSGEIWKL FEDALQKHEE ALNQFEDLKQ LGGSGKGSGG EIKQSHEDAL RKHEEALKRF | 120 |
| | | EDLKQK | 126 |
| 28 | C41 Stab Map CARD | EIWKLFEDAL QKFEHELNQF EDRVQLGGSG KGSGGEIKQR CARDLRKFEE ALKRFEDLKQ | 60 |
| | | KGGSGEIWKL FEDALQKHEE ALNQFEDLKQ LGGSGKGSGG EIKQSHEDAL RKHEEALKRF | 120 |
| | | EDLKQK | 126 |
| 29 | C41 Py Stab | EIWKLFEDAL QKFEEDLNQF EDRVQLGGSG KGSGGEIKQL CARDLRKFEE ALKRFEDLKQ | 60 |
| | | KGGSGEIWKL FEDALQKHEE ALNQFEDHKQ LGGSGKGSGG EIKQRSEDAL RKHEEALKRF | 120 |
| | | EDLKQK | 126 |
| 30 | 528-GL | EIWKQHEDAL QKFEEALNQF EDLKQLGGSG KGSGGEIWKQ CEDALRKFEE ALKRFEDLKQ | 61 |
| | | KGGSGEIWKQ HEDALQKFEE ALNQFEDLKQ LGGSGKGSGG EIWKQHEDAL RKFEEALKRF | 120 |
| | | EDLKQK | 126 |
| 31 | MM3 FC | ELLKKHEEAL KKFEELLKKF EEELKKGGSG SGSGGELLKK FEEALKKFEE LLKKFEEELK | 60 |
| | | KGGSGWGSGG ELLKKHEEAL KKFEELLKKF EELLKKGGSG SGSGGELLKK CEEALKKFEE | 120 |
| | | LLKKFEELLK K | 131 |
| 32 | MM3 FC H6F H76F | ELLKKFEEAL KKFEELLKKF EEELKKGGSG SGSGGELLKK FEEALKKFEE LLKKFEEELK | 60 |
| | | KGGSGWGSGG ELLKKFEEAL KKFEELLKKF EELLKKGGSG SGSGGELLKK CEEALKKFEE | 120 |
| | | LLKKFEELLK K | 131 |
| 33 | MM3 FC H6F H76F F90D | ELLKKFEEAL KKFEELLKKF EEELKKGGSG SGSGGELLKK FEEALKKFEE LLKKFEEELK | 60 |
| | | KGGSGWGSGG ELLKKFEEAL KKFEELLKKD EELLKKGGSG SGSGGELLKK CEEALKKFEE | 120 |
| | | LLKKFEELLK K | 131 |
| 34 | AM1 | EIWKQHEDAL QKFFALLLLL ALLLLLALLL HLLAFEGGSG GGSGGKFLLL LALLALLLLA | 60 |
| | | LLLHLLAFWE ALNQFEDLAK QGGSGGGSGG EIWKQHEDAL QKFFALLLLL ALLLLLALLL | 120 |
| | | HLLAFKGGSG GGSGGEFLLL LALLALLLLA LLLHLLAFWE ALNQFEDLAK Q | 171 |
| 42 | PEB Mut E | EIWKQHEDAL QKFEEALNQF EDLKQLGGSG KGSGGEIKQR HEDALRKFEE ALKRFEDLKQ | 60 |
| | | KGGCGRDWKQ HEDALQKFEE ALNQFEDLKQ LGGSGKGSGG EIKQRHEDAL RKFEEALKRF | 120 |
| | | EDLKQK | 126 |
| 43 | PEB Mut F | EIWKQHEDAL QKFEEALNQF EDLKQLGGCG EIKQRAEDAL RKFEEALKRF EDLKQKGGCG | 60 |
| | | EIWKQHEDAL QKFEEALNQF EDLKQLGGSG EIKQRHEDAL RKFEEALKRF EDLKQK | 116 |
| 44 | PEB Mut G | EIWKQHEDAL QKFEEALNQF EDLKQLGGSG KGSGGEIKQR HEDALRKFEE ALKRFEDLKQ | 60 |
| | | KGGCGREWKQ HEDALQKFEE ALNQFEDLKQ LGGSGKGSGG EIKQRHEDAL RKFEEALKRF | 120 |
| | | EDLKQK | 126 |
| 45 | dFP 1.1 | EIWKQHEDAL QKFEEALNQF EDLKQLGGSG SGSGGEIWKQ CEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 51 | Mini dfp | EIWKSHEDAL QKFEEALNQG GSGGDALRKF EEALKRFEDL KQKGGCGRIW KEHEDAHQKF | 60 |
| | | EEALNQGGSG GDALRKFEEA LKRHEDRVQK | 90 |
| 54 | Nano dfp | EIWKSHEDAL QKFEEGGSGG RFEEALKRFE DLKQKGGCGR IWKEHEDAHQ KFEEGGSGGR | 60 |
| | | FEEALKRHED RVQK | 74 |
| 63 | AM-528-C4 | EIWKQFEDAL QKFFALHLLL ALLLLLALLL FLLAFEGGSG GGSGGKFLCL LALLALLLLA | 60 |
| | | LLLFLLAFWE ALNQFEDLAK QGGSGGGSGG EIWKQFEDAL QKFFALHLLL ALLLLLALLL | 120 |
| | | FLLAFKGGSG GGSGGEFLLH LALLALLLLA LLLFLLAFWE ALNQFEDLAK Q | 171 |
| 66 | AM-1196 | EIWKSHEDAL QKFFALLLLL ALLLLLALLL HLLAFEGGSG GGSGGKFLLL LALLALLLLA | 60 |
| | | LLLHLLAFWE ALKRFEDLKQ KGGCGRIWKE HEDAHQKFFA LLLLLALLLL LALLLHLLAF | 120 |
| | | KGGSGGGSGG EFLLLLALLA LLLLALLLHL LAFWEALKRH EDRVQK | 166 |

TABLE 2-continued

| Seq ID No | Name | One Letter Sequence | |
|---|---|---|---|
| 69 | AM-528 | EIWKQFEDAL QKFFALHLLL ALLLLLALLL FLLAFEGGSG GGSGGKFLLC LALLALLLLA | 60 |
| | | LLLFLLAFWE ALNQFEDLAK QGGSGGGSGG EIWKQFEDAL QKFFALHLLL ALLLLLALLL | 120 |
| | | FLLAFKGGSG GGGGEFLLHL ALLALLLLAL LLFLLAFWEA LNQFEDLAKQ | 170 |
| 79 | 35 | EIWKQHEDAL QKFEEALNQF EDLKQLGGSG SGSGGECLRD HEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 80 | 36 | EIWKQHEDAL QKFEEALNQF EDLKQLGGSG SGSGGEICLR DEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 81 | 37 | EIWKQHEDAL QKFEEALNQF EDLKQLGGSG SGSGGEIWKQ HEDALQKFEE ALNQFEDCLR | 60 |
| | | DGGSGSGSGG EIWKQHEDAL QKFEEALNQF EDLKQLGGSG SGSGGEIWKQ HEDALQKFEE | 120 |
| | | ALNQFEDLKQ L | 131 |
| 82 | 38 | EIWKQHEDAL QKFEEALNQF EDLKQLGGSG SGSGGEIWKQ HEDALQKFEE ALNQFEDLCL | 60 |
| | | RDGSGSGSGG EIWKQHEDAL QKFEEALNQF EDLKQLGGSG SGSGGEIWKQ HEDALQKFEE | 120 |
| | | ALNQFEDLKQ L | 131 |
| 83 | 39 | EIWKQHEDAL QKFEEALNQF EDLKQLGGSG SGSGGEIWKQ HEDALQKFEE ALNQFEDLKC | 60 |
| | | LRDSGSGSGG EIWKQHEDAL QKFEEALNQF EDLKQLGGSG SGSGGEIWKQ HEDALQKFEE | 120 |
| | | ALNQFEDLKQ L | 131 |
| 84 | 61 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDLKQLGGSG SGSGGEIWKQ HEDALQKFEE | 120 |
| | | ALNQFEDLKQ L | 131 |
| 85 | 214 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDALQLGGSG SGSGEIWKQG EDALQKFEEA | 120 |
| | | LNQFEDLKQ | 129 |
| 86 | 215 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QHFEEALNQF EDALQLGGSG SGSGEIWKQG EDALQKFEEH | 120 |
| | | LNQFEDLKQL | 130 |
| 87 | 216 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKHEEALNQF EDALQKHEEA LNQFEDLKQL GGSGSGSGEI | 120 |
| | | WKQGEDALQK FEEALNQFED LKQL | 144 |
| 88 | 528 | EIWKQHEDAL QKFEEALNQF EDLKQLGGSG SGSGGEIWKQ CEDALQKFEE ALNQFEDLKQ | 60 |
| | | LGGSGSGSGG EIWKQHEDAL QHFEEALNQF EDLKQLGGSG SGSGGEIWKQ HEDALQKFEE | 120 |
| | | ALNQFEDLKQ L | 131 |
| 103 | BT6 CysAla | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDLKQLGGSG SGSGGEIWKQ AEDALQKFEE | 120 |
| | | ALNQFEDLKQ L | 131 |
| 108 | Positive | EIKRQHEDAL RKFEEALKRF EDKKQEGGSG KGSGGEIWKR HEDALRKFEE ALKRFEDKKQ | 60 |
| | | KGGSGKGSGG EIWKRHEDAL RKFEEALKRF EDKKQKGGSG KGSGGEIKQR HEDALRKFEE | 120 |
| | | ALKRFEDKKQ K | 131 |
| 112 | GLSloop Q5L | EIWKQHEDAL QKFEEALNQF EDLKQLGGSG KGSGGEIKQR HEDALRKFEE ALKRFEDLKQ | 60 |
| | | KGGSGEIWKQ HEDALQKFEE ALNQFEDLKQ LGGSGKGSGG EIKQRHEDAL RKFEEALKRF | 120 |
| | | EDRVQK | 126 |
| 113 | C L5S | EIWKSHEDAL QKFEEALNQF EDLKQLGGSG KGSGGEIKQR HEDALRKFEE ALKRFEDLKQ | 60 |
| | | KGGCGRIWKE HEDALQKFEE ALNQFEDLKQ LGGSGKGSGG EIKQRHEDAL RKFEEALKRF | 120 |
| | | EDRVQK | 126 |
| 114 | C V124K | EIWKLHEDAL QKFEEALNQF EDLKQLGGSG KGSGGEIKQR HEDALRKFEE ALKRFEDLKQ | 60 |
| | | KGGCGRIWKE HEDALQKFEE ALNQFEDLKQ LGGSGKGSGG EIKQRHEDAL RKFEEALKRF | 120 |
| | | EDRKQK | 126 |
| 117 | 1191min15 | EIWKSHEDAL QKFEEALNQF EDLKQLGGSG EGSGGEIWKQ HEDALQKFEE ALNRFEDLKQ | 60 |
| | | LGGCGRIWKE HEDAHQKFEE ALNQFEDLKQ LGGSGEGSGG EIWKQHEDAL QHFEEALNRH | 120 |
| | | EDRVQL | 126 |
| 120 | GL Van Core | ELLKQLEDLL QKLEELLNQL EDLKQLGGSG KGSGGELKQR LEDLLRELEE LLKRLEDLKQ | 60 |
| | | KGGCGRLLKE LEDLLQKLEE LLNQLEDLKQ LGGSGKGSGG ELKQRLEDLL RKFEELLKRL | 120 |
| | | EDLKQK | 126 |
| 122 | minus8 maquette | EIWKQHEDAL QKFEEALNQF EDLKQLGGSG SGSGGEIWKQ CEDALRKFEE ALKQFEDLKQ | 60 |
| | | KGGSGEIWKQ HEDALQKFEE ALNQFEDLKQ LGGSGSGSGG EIWKQHEDAL RKFEEALKQF | 120 |
| | | EDLKQK | 126 |

TABLE 2-continued

| Seq ID No | Name | One Letter Sequence | |
|---|---|---|---|
| 124 | minus12 maquette | EIWKQHEDAL QKFEEALNQF EDLKQLGGSG SGSGGEIWKQ CEDALQKFEE ALKQFEDLKQ<br>LGGSGEIWKQ HEDALQKFEE ALNQFEDLKQ LGGSGSGSGG EIWKQHEDAL QKFEEALKQF<br>EDLKQL | 60<br>120<br>126 |
| 127 | plus4 maquette | EIWKQHEDAL RKFEEALKRF EDLKQKGGSG KGSGGEIWKQ CEDALRKFEE ALKRFEDLKQ<br>KGGSGEIWKQ HEDALREFEE ALRKFEDLKQ KGGSGKGSGG EIWKQHEDAL RKFEEALKRF<br>EDLKQK | 60<br>120<br>126 |
| 130 | plus8 maquette | EIWKQHEDAL RKFEEALKRF EDKKQKGGSG KGSGGEIWKQ CEDALRKFEE ALKRFEDLKQ<br>KGGSGEIWKR HEDALRKFEE ALRKFEDKKQ KGGSGKGSGG EIWKRHEDAL RKFEEALKRF<br>EDLKQK | 60<br>120<br>126 |
| 133 | MMmin4 | ELWKKHEEAL KKFEELLKKF EEELKLGGSG EGSGGELLKK CEEALKKFEE LLKKFEEELK<br>LGGSGELLKK HEEALKKFEE LLKKFEELLK LGGSGEGSGG ELLKKHEEAL KKFEELLKKF<br>EELLKL | 60<br>120<br>126 |
| 136 | GL-MM | EIWKQHEEAL KKFEELLKQF EEELKKGGSG SGSGGEIWKQ CEEALKKFEE LLKKFEEELK<br>KGGSGEIWKQ HEEALKKFEE LLKQFEELLK KGGSGSGSGG EIWKQHEEAL KKFEELLKKF<br>EELLKK | 60<br>120<br>126 |

In some embodiments an artificial protein comprises one or more amino acid sequences as set forth in Table 3.

TABLE 3

| SEQ ID NO | Name | One Letter Sequence | |
|---|---|---|---|
| 35 | MZH3 | GSPELRQEHQ QLAQEFQQLL QEIQQLGREL LKGELQGIKQ LREASEKARN PEKKSVLQKI<br>LEDEEKHIEL LETLQQTGQE AQQLLQELQQ TGQELWQLGG SGGPELRQKH QQLAQKIQQL<br>LQKHQQLGAK ILEDEEXHIE LLETILGGSG GDELRELLKG ELQGIKQYRE LQQLGQKAQQ<br>LVQKLQQTGQ KLWQLG | 60<br>120<br>180<br>196 |
| 36 | MZH3 H138D | GSPELRQEHQ QLAQEFQQLL QEIQQLGREL LKGELQGIKQ LREASEKARN PEKKSVLQKI<br>LEDEEKHIEL LETLQQTGQE AQQLLQELQQ TGQELWQLGG SGGPELRQKH QQLAQKIQQL<br>LQKHQQLGAK ILEDEEKDIE LLETILGGSG GDELRELLKG ELQGIKQYRE LQQLGQKAQQ<br>LVQKLQQTGQ KLWQLG | 60<br>120<br>180<br>196 |
| 37 | MZH3 H138N | GSPELRQEHQ QLAQEFQQLL QEIQQLGREL LKGELQGIKQ LREASEKARN PEKKSVLQKI<br>LEDEEKHIEL LETLQQTGQE AQQLLQELQQ TGQELWQLGG SGGPELRQKH QQLAQKIQQL<br>LQKHQQLGAK ILEDEEKNIE LLETILGGSG GDELRELLKG ELQGIKQYRE LQQLGQKAQQ<br>LVQKLQQTGQ KLWQLG | 60<br>120<br>180<br>196 |
| 38 | MZH3 H67D, H138D | GSPELRQEHQ QLAQEFQQLL QEIQQLGREL LKGELQGIKQ LREASEKARN PEKKSVLQKI<br>LEDEEKDIEL LETLQQTGQE AQQLLQELQQ TGQELWQLGG SGGPELRQKH QQLAQKIQQL<br>LQKHQQLGAK ILEDEEKDIE LLETILGGSG GDELRELLKG ELQGIKQYRE LQQLGQKAQQ<br>LVQKLQQTGQ KLWQLG | 60<br>120<br>180<br>196 |
| 39 | MZH3 H67D, H138N | GSPELRQEHQ QLAQEFQQLL QEIQQLGREL LKGELQGIKQ LREASEKARN PEKKSVLQKI<br>LEDEEKDIEL LETLQQTGQE AQQLLQELQQ TGQELWQLGG SGGPELRQKH QQLAQKIQQL<br>LQKHQQLGAK ILEDEEKNIE LLETILGGSG GDELRELLKG ELQGIKQYRE LQQLGQKAQQ<br>LVQKLQQTGQ KLWQLG | 60<br>120<br>180<br>196 |
| 40 | MZH3 H67N, H138D | GSPELRQEHQ QLAQEFQQLL QEIQQLGREL LKGELQGIKQ LREASEKARN PEKKSVLQKI<br>LEDEEKNIEL LETLQQTGQE AQQLLQELQQ TGQELWQLGG SGGPELRQKH QQLAQKIQQL<br>LQKHQQLGAK ILEDEEKDIE LLETILGGSG GDELRELLKG ELQGIKQYRE LQQLGQKAQQ<br>LVQKLQQTGQ KLWQLG | 60<br>120<br>180<br>196 |
| 41 | MZH3 H67N, H138N | GSPELRQEHQ QLAQEFQQLL QEIQQLGREL LKGELQGIKQ LREASEKARN PEKKSVLQKI<br>LEDEEKNIEL LETLQQTGQE AQQLLQELQQ TGQELWQLGG SGGPELRQKH QQLAQKIQQL<br>LQKHQQLGAK ILEDEEKNIE LLETILGGSG GDELRELLKG ELQGIKQYRE LQQLGQKAQQ<br>LVQKLQQTGQ KLWQLG | 60<br>120<br>180<br>196 |
| 141 | MZH3 H67D | GSPELRQEHQ QLAQEFQQLL QEIQQLGREL LKGELQGIKQ LREASEKARN PEKKSVLQKI<br>LEDEEKDIEL LETLQQTGQE AQQLLQELQQ TGQELWQLGG SGGPELRQKH QQLAQKIQQL<br>LQKHQQLGAK ILEDEEXHIE LLETILGGSG GDELRELLKG ELQGIKQYRE LQQLGQKAQQ<br>LVQKLQQTGQ KLWQLG | 60<br>120<br>180<br>196 |
| 142 | MZH3 H67N | GSPELRQEHQ QLAQEFQQLL QEIQQLGREL LKGELQGIKQ LREASEKARN PEKKSVLQKI<br>LEDEEKNIEL LETLQQTGQE AQQLLQELQQ TGQELWQLGG SGGPELRQKH QQLAQKIQQL<br>LQKHQQLGAK ILEDEEKHIE LLETILGGSG GDELRELLKG ELQGIKQYRE LQQLGQKAQQ<br>LVQKLQQTGQ KLWQLG | 60<br>120<br>180<br>196 |

TABLE 3-continued

| SEQ ID NO | Name | One Letter Sequence | | | | | |
|---|---|---|---|---|---|---|---|
| 147 | MZH3 P3G H9A Q10D L12I A13R F16L T91R G92E L95G G100N P105T L106R R107L Q108E H110I A114G Q115R Q118R V182M Q183E L185C Q186G T188R G189A Q190M L192R W193N | GSGELRQEAD LEDEEkHIEL LQKHQQLGAK LMEkCGQRAM | QIRQELQQLL LETLQQTGQE ILEDEEkHIE KRNQLG | QEIQQLGREL AQQLLQELQQ LLETILGGSG | LKGELQGIKQ REQEGWQLGN GDELRELLKG | LREASEKARN SGGTERLEKI ELQGIKQYRE | PEKKSVLQKI QQLGRKIRQL LQQLGQKAQQ | 60 120 180 196 |

In some embodiments an artificial protein comprises one or more amino acid sequences as set forth in Table 4, or a variant thereof.

In some embodiments, the invention includes nucleotide sequences encoding any of the foregoing polypeptides. In some embodiments, the invention includes a nucleotide sequence set forth in Table 4 or a variant thereof, as would be understood by a person having ordinary skill in the art.

In some embodiments, the artificial protein of SEQ ID NO. 21 may be encoded by the nucleotide sequence of SEQ ID NO. 70 (*E. Coli*) or SEQ ID NO. 71 (FCK mammal).

In some embodiments, the artificial protein of SEQ ID NO. 25 may be encoded by the nucleotide sequence of SEQ ID NO. 46 (*E. Coli*) or SEQ ID NO. 47 (FCK mammal).

In some embodiments, the artificial protein of SEQ ID NO. 26 may be encoded by the nucleotide sequence of SEQ ID NO. 89 (*E. Coli*) or SEQ ID NO. 90 (FCK mammal).

In some embodiments, the artificial protein of SEQ ID NO. 27 may be encoded by the nucleotide sequence of SEQ ID NO. 92 (*E. Coli*) or SEQ ID NO. 93 (FCK mammal).

In some embodiments, the artificial protein of SEQ ID NO. 28 may be encoded by the nucleotide sequence of SEQ ID NO. 95 (*E. Coli*) or SEQ ID NO. 96 (FCK mammal).

In some embodiments, the artificial protein of SEQ ID NO. 29 may be encoded by the nucleotide sequence of SEQ ID NO. 98 (*E. Coli*) or SEQ ID NO. 99 (FCK mammal).

In some embodiments, the artificial protein of SEQ ID NO. 30 may be encoded by the nucleotide sequence of SEQ ID NO. 55 (*E. Coli*) or SEQ ID NO. 56 (FCK mammal).

In some embodiments, the artificial protein of SEQ ID NO. 31 may be encoded by the nucleotide sequence of SEQ ID NO. 58 (*E. Coli*) or SEQ ID NO. 59 (FCK mammal).

In some embodiments, the artificial protein of SEQ ID NO. 34 may be encoded by the nucleotide sequence of SEQ ID NO. 109 (*E. Coli*) or SEQ ID NO. 110 (FCK mammal).

In some embodiments, the artificial protein of SEQ ID NO. 35 may be encoded by the nucleotide sequence of SEQ ID NO. 137 (*E. Coli*).

In some embodiments, the artificial protein of SEQ ID NO. 51 may be encoded by the nucleotide sequence of SEQ ID NO. 49 (*E. Coli*) or SEQ ID NO. 50 (FCK mammal).

In some embodiments, the artificial protein of SEQ ID NO. 54 may be encoded by the nucleotide sequence of SEQ ID NO. 52 (*E. Coli*) or SEQ ID NO. 53 (FCK mammal).

In some embodiments, the artificial protein of SEQ ID NO. 63 may be encoded by the nucleotide sequence of SEQ ID NO. 61 (*E. Coli*) or SEQ ID NO. 62 (FCK mammal).

In some embodiments, the artificial protein of SEQ ID NO. 66 may be encoded by the nucleotide sequence of SEQ ID NO. 64 (*E. Coli*) or SEQ ID NO. 65 (FCK mammal).

In some embodiments, the artificial protein of SEQ ID NO. 69 may be encoded by the nucleotide sequence of SEQ ID NO. 67 (*E. Coli*) or SEQ ID NO. 68 (FCK mammal).

In some embodiments, the artificial protein of SEQ ID NO. 103 may be encoded by the nucleotide sequence of SEQ ID NO. 101 (*E. Coli*) or SEQ ID NO. 102 (FCK mammal).

In some embodiments, the artificial protein of SEQ ID NO. 108 may be encoded by the nucleotide sequence of SEQ ID NO. 106 (*E. Coli*) or SEQ ID NO. 107 (FCK mammal).

In some embodiments, the artificial protein of SEQ ID NO. 117 may be encoded by the nucleotide sequence of SEQ ID NO. 115 (*E. Coli*) or SEQ ID NO. 116 (FCK mammal).

In some embodiments, the artificial protein of SEQ ID NO. 120 may be encoded by the nucleotide sequence of SEQ ID NO. 118 (*E. Coli*) or SEQ ID NO. 119 (FCK mammal).

In some embodiments, the artificial protein of SEQ ID NO. 127 may be encoded by the nucleotide sequence of SEQ ID NO. 125 (*E. Coli*) or SEQ ID NO. 126 (FCK mammal).

In some embodiments, the artificial protein of SEQ ID NO. 130 may be encoded by the nucleotide sequence of SEQ ID NO. 128 (*E. Coli*) or SEQ ID NO. 129 (FCK mammal).

In some embodiments, the artificial protein of SEQ ID NO. 133 may be encoded by the nucleotide sequence of SEQ ID NO. 131 (*E. Coli*) or SEQ ID NO. 132 (FCK mammal).

In some embodiments, the artificial protein of SEQ ID NO. 136 may be encoded by the nucleotide sequence of SEQ ID NO. 134 (*E. Coli*) or SEQ ID NO. 135 (FCK mammal).

In some embodiments, the invention includes a vector comprising a nucleotide sequence encoding any of the foregoing polypeptides.

In some aspects of the invention, substantially similar artificial protein amino acid sequences (e.g., polypeptide variants) may have at least 80%, 85%, 90%, 91%, 92%, 93%, 94%, 95%, 96%, 97%, 98%, or 99% or 100% identity to an amino acid sequence described herein. Similarly, a substantially similar nucleotide sequence of the invention (e.g., polynucleotide variants) may have at least 80%, 85%, 90%, 91%, 92%, 93%, 94%, 95%, 96%, 97%, 98%, or 99% or 100% identity to a nucleotide sequence described herein.

Compositions of the Invention

The invention includes compositions comprising an artificial protein as described herein and at least one cofactor. In some embodiments the cofactor may be naturally occurring, while in other embodiments, the cofactor may be artificial. In some embodiments, compositions of the invention comprise an artificial protein as described herein and two, three, four, or more different cofactors.

In some embodiments a cofactor may be a cofactor that exhibits an electrochromic effect. In some embodiments the cofactor may exhibit an electrochromic effect in the presence of 50-100 mV voltage. In some embodiments the cofactor may exhibit an electrochromic effect in the presence of 10-1000 mV, 25-500 mV, 50-75 mV, 60-80 mV, or 80-100 mV. In some embodiments, the cofactor may be a fluorophore. In some embodiments the fluorophore may be naturally occurring in a host cell. Suitable naturally occurring fluorophores include flavins, bilins (e.g. biliverdin or bilirubin), retinals, and carotenoids. In some embodiments an electrochromic material may be used as a fluorophore. The fluorophore may be bound to the peptide through covalent or non-covalent bonds. In an embodiment, the fluorophore (e.g. a flavin) is covalently bound to a threonine residue of the peptide. In an embodiment, the fluorophore (e.g. a retinal) is covalently bound to a lysine residue. In an embodiment, the fluorophore (e.g. a bilin) is covalently bound to a cysteine residue.

In some embodiments a cofactor may be a heme. As used herein, the term "heme" refers to a prosthetic group formed of an iron atom contained in the center of a large heterocyclic organic ring called a porphyrin. Non-limiting examples of hemes are heme A, heme B, heme C, heme O, mesohemes, deuterohemes, synthetic dicyano porphyrins and symmetrical porphyrins (such as, but not limited to, protoporphyrin III). In some embodiments the heme is naturally occurring in the host cell, e.g. in a mammal. The heme may be bound to the peptide through covalent or non-covalent bonds. In an embodiment, the heme is covalently bound to a histidine residue of the peptide. In an embodiment, the heme is covalently bound to a cysteine residue of the peptide.

In some embodiments a cofactor may be a metal ion or cluster of metal ions. Non-limiting examples of useful metal ions are $Zn^{2+}$, $Fe^{2+}$, $Fe^{3+}$, $Mn^{2+}$, $Mg^{2+}$, $Cu^{2+}$, $Cu^{2+}$, $Co^{2+}$, $Co^{3+}$, $Ca^{2+}$, and $K^{+}$.

In some embodiments a cofactor may be a tetrapyrrole, for example a heme or biliverdin, though in some embodiments a cofactor may be a tetrapyrrole other than a heme or other than biliverdin. In some embodiments a cofactor may be a messenger molecule such as cAMP, ATP, a neurotransmitter, a short peptide (e.g. neuropeptide). In some embodiments a cofactor may be water. In some embodiments a cofactor may be a gas, for example oxygen. In some embodiments a cofactor may be any amphipathic molecule sized to fit within the core of an artificial protein as described herein. Suitable cofactors are also described in Solomon, L. C., et al, "Engineering the Assembly of Heme Cofactors in Man-Made Proteins" J. Am. Chem. Soc., 136, 319203199 (2014), which is hereby incorporated by reference in its entirety.

The invention also includes a preparation comprising a vesicle. The vesicle comprises an amphiphilic material, an artificial protein as described herein, and at least one cofactor. In one aspect, an artificial protein of the invention is incorporated in the walls of the vesicle, whereby the outer residues of the peptide structure contact the molecules that comprises the vesicle wall.

The amphiphilic material used in the preparation of the vesicle may be a detergent, a phospholipid or a mixture thereof. The detergent useful within the invention may be an anionic detergent, a cationic detergent, a zwitterion ionic detergent and a non-ionic detergent. Non-limiting examples of ionic detergents are perfluorooctanoate, perfluorooctanesulfonate, sodium dodecyl sulfate (SDS), ammonium lauryl sulfate, and other alkyl sulfate salts, sodium laureth sulfate, also known as sodium lauryl ether sulfate (SLES), alkyl benzene sulfonate, soaps and fatty acid salts. Non-limiting examples of cationic detergents are cetyl trimethylammonium bromide (CTAB), also known as hexadecyl trimethyl ammonium bromide, and other alkyltrimethylammonium salts, cetylpyridinium chloride (CPC), polyethoxylated tallow amine (POEA), benzalkonium chloride (BAC), and benzethonium chloride (BZT). Non-limiting examples of zwitterionic (amphoteric) detergents are dodecyl betaine, cocamidopropyl betaine and coco ampho glycinate. Non-limiting examples of non-ionic detergents are alkyl poly (ethylene oxide), alkylphenol poly(ethylene oxide), copolymers of poly(ethylene oxide) and poly(propylene oxide) (commercially called Poloxamers or Poloxamines), alkyl polyglucosides (including octyl glucoside and decyl maltoside), fatty alcohols (including cetyl alcohol and oleyl alcohol), cocamide MEA, cocamide DEA, polysorbates (such as Tween 20, Tween 80 and dodecyl dimethylamine oxide).

The phospholipid useful within the invention may be a diacylglyceride, such as phosphatidic acid (phosphatidate), phosphatidylethanolamine (cephalin), phosphatidylcholine (lecithin), phosphatidylserine, sphingomyelin or phosphoinositides. Non-limiting examples of phosphoinositides are phosphatidylinositol, phosphatidylinositol phosphate, phosphatidylinositol bisphosphate and phosphatidylinositol triphosphate.

The invention also includes a viable host cell capable of expressing an artificial protein as described herein. In an embodiment the host cell is a eukaryotic (e.g., mammalian) host cell. In an embodiment, a viable host cell is capable of expressing an artificial protein, wherein the artificial protein comprises a 1, 2, 3, 4, 5, 6, or more peptides connected by one or more LOOP amino acid sequences. In an embodiment, a viable host cell comprises four (4) peptides connected by three (3) LOOP amino acid sequences.

The invention also includes a viable host cell capable of expressing a composition as described herein. In an embodiment the host cell is a eukaryotic (e.g., mammalian) host cell. In an embodiment, a viable host cell is capable of expressing a composition comprising an artificial protein as described herein and a cofactor as described herein. In an embodiment, a viable host cell is capable of expressing an artificial protein, wherein the artificial protein comprises a 1, 2, 3, 4, 5, 6, or more peptides connected by one or more LOOP amino acid sequences. In an embodiment, a viable host cell comprises four (4) peptides connected by three (3) LOOP amino acid sequences. In some embodiments a cofactor is a heme, a fluorophore, an electrochromic material, or a metal ion. In some embodiments a viable host cell is capable of expressing a composition comprising an artificial protein as described herein and one (1), two (2), three (3), four (4), or more independently selected cofactors.

In some embodiments a viable cell does not undergo cell death for a period of 1 hour, 2 hours, 3 hours, 4 hours, 5 hours, 6 hours, 12 hours, 18 hours, 24 hours, 1 day, 2 days, 3 days, 4 days, 5 days, 6 days, 7 days, 1 week, 2 weeks, 3 weeks, 4 weeks, 1 month, 2 months, 3 months, or more. In some embodiments a viable cell line survives for greater than 10 passages, greater than 15 passages, greater than 20 passages, greater than 25 passages, greater than 30 passages, or more. In some embodiments a viable cell line survives for greater than 1 week, 2 weeks, 3 weeks, 4 weeks, 1 month, 2 months, 3 months, or more.

Delivery of proteins and/or compositions as described herein to a cell and/or expression of proteins and/or compositions as described herein in a cell can be done using delivery means known in the art.

In some embodiments of the invention an artificial protein and/or composition of the invention is included in a fusion protein. It is well known in the art how to prepare and utilize fusion proteins that comprise a polypeptide sequence. In certain embodiments of the invention, a fusion protein can be used to deliver a protein and/or composition of the invention to a cell and can also in some embodiments be used to target a protein and/or composition of the invention to specific cells or to specific cells, tissues, or regions in a subject. Targeting and suitable targeting sequences for delivery to a desired cell, tissue or region can be performed using art-known procedures.

It is an aspect of the invention to provide an artificial protein and/or composition of the invention that is non-toxic, or substantially non-toxic in cells in which it is expressed. In some embodiments, an artificial protein or composition of the invention does not significantly alter cell health or ongoing electrical activity in the cell in which it is expressed.

In some embodiments of the invention, an artificial protein and/or composition of the invention is genetically introduced into a cellular membrane, and reagents and methods are provided for genetically targeted expression of proteins and/or compositions of the invention. Genetic targeting can be used to deliver artificial proteins and/or compositions of the invention to specific cell types, to specific cell subtypes, to specific spatial regions within an organism, and to sub-cellular regions within a cell. Genetic targeting also relates to the control of the amount of artificial protein and/or compositions of the invention, and the timing of the expression.

Some embodiments of the invention include a reagent for genetically targeted expression of a deliver artificial proteins and/or compositions of the invention, wherein the reagent comprises a vector that contains the gene for the deliver artificial proteins and/or compositions of the invention.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert artificial proteins and/or compositions of the invention into dividing and non-dividing cells and can insert artificial proteins and/or compositions of the invention to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising a DNA sequence for a protein and/or composition of the invention, such as one or more sequences shown in the Appendix, or a derivative or variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a protein and/or composition of the invention in a wide variety of cell types—thus a promoter for a gene that is widely expressed in a variety of cell types, for example a "housekeeping gene" can be used to express a protein or composition of the invention in a variety of cell types. Non-limiting examples of general promoters are provided elsewhere herein and suitable alternative promoters are well known in the art. In some embodiments the promoter is CAMKII.

Specific Artificial Proteins as Cytosolic Fluorescence Reporters

In some embodiments, an artificial protein for cytosolic fluorescence reporting may include an amino acid sequence selected from the group consisting of SEQ ID NOS. 25, 30, 51, and 54.

In some embodiments, the artificial protein for cytosolic fluorescence reporting may include the amino acid sequence of SEQ ID NO. 25 (i.e., dFP1.0), and may be expressed in mammalian cells. Such an embodiment may fluoresce with a quantum yield (QY) of about 1.6% at an excitation wavelength ($\lambda_{ex}$) of 648 nm and emission wavelength ($\lambda_{em}$) of 662 nm. In some embodiments, the artificial protein for cytosolic fluorescence reporting, which includes the amino acid sequence of SEQ ID NO. 25, may include the cofactor biliverdin (BV). In certain embodiments, the biliverdin may bind in the b loop of the artificial protein that includes the amino acid sequence of SEQ ID NO. 25.

In some embodiments, the artificial protein for cytosolic fluorescence reporting may include the amino acid sequence of SEQ ID NO. 30 (i.e., 528-GL), and may be expressed in mammalian cells. Such an embodiment may fluoresce with a quantum yield (QY) of about 1.8% at an excitation wavelength ($\lambda_{ex}$) of 648 nm and emission wavelength ($\lambda_{em}$) of 662 nm. In some embodiments, the artificial protein for cytosolic fluorescence reporting, which includes the amino acid sequence of SEQ ID NO. 30, may include the cofactor biliverdin (BV). In certain embodiments, the biliverdin may bind in the core of the artificial protein that includes the amino acid sequence of SEQ ID NO. 30.

In some embodiments, the artificial protein for cytosolic fluorescence reporting may include the amino acid sequence of SEQ ID NO. 51 (i.e., minidfp), and may be expressed in mammalian cells. In some embodiments, the artificial protein that may include the amino acid sequence of SEQ ID NO. 51 may be one heptad smaller than the artificial protein for that may include SEQ ID NO. 30.

In some embodiments, the artificial protein for cytosolic fluorescence reporting may include the amino acid sequence of SEQ ID NO. 54 (i.e., nanodfp), and may be expressed in mammalian cells. In some embodiments, the artificial protein that may include the amino acid sequence of SEQ ID NO. 54 may be two heptads smaller than the artificial protein for that may include SEQ ID NO. 30.

Specific Artificial Proteins as T2 MRI Contrast Reporters

In some embodiments, an artificial protein of the invention may be a T2 MRI contrast agent and may include the amino acid sequence of SEQ ID NO. 31 (i.e., MM3 FC), and may be expressed in mammalian cells. Such an embodiment may display a T2 NMR contrast with an r2 of about 3.4 $mM^{-1}s^{-1}$. In some embodiments, the artificial protein may include a cofactor, such as Heme B.

Specific Artificial Proteins as Membrane Fluorescence Reporters

In some embodiments, an artificial protein for membrane fluorescence reporting may include an amino acid sequence selected from the group consisting of SEQ ID NOS. 63 and 66.

In some embodiments, the artificial protein for membrane fluorescence reporting may include the amino acid sequence of SEQ ID NO. 63 (i.e., AM-528-C4), and may be expressed in mammalian cells and trafficks to the membrane. In some embodiments, the artificial protein for membrane fluorescence reporting, which includes the amino acid sequence of SEQ ID NO. 63, may include the cofactor biliverdin (BV). In certain embodiments, the biliverdin may bind to the transmembrane region of the artificial protein and fluoresce.

In some embodiments the artificial protein for membrane fluorescence reporting may include the amino acid sequence of SEQ ID NO. 66 (i.e., AM-1196), and may be expressed in mammalian cells and trafficks to the membrane. In some embodiments, the artificial protein for membrane fluorescence reporting, which includes the amino acid sequence of SEQ ID NO. 66, may include the cofactor of biliverdin (BV). In certain embodiments, the biliverdin may bind to the HP region of the artificial protein and fluoresce.

Specific Artificial Proteins as Stark Effect Reporters

In some embodiments, an artificial protein for stark effect reporting may include an amino acid of SEQ ID NO. 69.

In some embodiments, the artificial protein for stark effect reporting may include the amino acid sequence of SEQ ID NO. 69 (i.e., AM-528), and may be expressed in mammalian cells and trafficks to the membrane. In some embodiments, the artificial protein for stark effect reporting, which includes the amino acid sequence of SEQ ID NO. 69, may include the cofactor biliverdin (BV). In certain embodiments, the biliverdin may bind to the transmembrane region of the artificial protein and fluoresce. Moreover, in certain embodiments, the artificial protein for stark effect reporting, which includes the amino acid sequence of SEQ ID NO. 69, may be sensitive to voltage and may demonstrate an electrochromic shift (i.e., a Stark effect).

Specific Artificial Proteins as Metal Binding Reporters

In some embodiments, an artificial protein for metal binding reporting may include an amino acid sequence selected from the group consisting of SEQ ID NOS. 35, 36, 37, 38, 39, 40, 41, 141, and 142.

In some embodiments, the artificial protein for metal binding reporting may bind a metal selected from the group consisting of $Zn^{2+}$, $Fe^{2+}$, $Fe^{3+}$, $Mn^{2+}$, $Mg^{2+}$, $Cu^{+}$, $Cu^{2+}$, $Co^{2+}$, $Co^{3+}$, $Ca^{2+}$, and $K^{+}$. In some embodiments, the artificial protein for metal binding reporting may bind $Ca^{2+}$.

In some embodiments, the artificial protein for metal binding reporting may include the amino acid sequence of SEQ ID NO. 35 (i.e., MZH3), and may be expressed in mammalian cells. Such an embodiment may bind a metal, such as $Ca^{2+}$.

In some embodiments, the artificial protein for metal binding reporting may include the amino acid sequence of SEQ ID NO. 36 (i.e., MZH3 H138D), and may be expressed in mammalian cells. Such an embodiment may bind a metal, such as $Ca^{2+}$.

In some embodiments, the artificial protein for metal binding reporting may include the amino acid sequence of SEQ ID NO. 37 (i.e., MZH3 H138N), and may be expressed in mammalian cells. Such an embodiment may bind a metal, such as $Ca^{2+}$.

In some embodiments, the artificial protein for metal binding reporting may include the amino acid sequence of SEQ ID NO. 38 (i.e., MZH3 H67D, H138D), and may be expressed in mammalian cells. Such an embodiment may bind a metal, such as $Ca^{2+}$.

In some embodiments, the artificial protein for metal binding reporting may include the amino acid sequence of SEQ ID NO. 39 (i.e., MZH3 H67D, H138N), and may be expressed in mammalian cells. Such an embodiment may bind a metal, such as $Ca^{2+}$.

In some embodiments, the artificial protein for metal binding reporting may include the amino acid sequence of SEQ ID NO. 40 (i.e., MZH3 H67N, H138D), and may be expressed in mammalian cells. Such an embodiment may bind a metal, such as $Ca^{2+}$.

In some embodiments, the artificial protein for metal binding reporting may include the amino acid sequence of SEQ ID NO. 41 (i.e., MZH3 H67N, H138N), and may be expressed in mammalian cells. Such an embodiment may bind a metal, such as $Ca^{2+}$.

In some embodiments, the artificial protein for metal binding reporting may include the amino acid sequence of SEQ ID NO. 141 (i.e., MZH3 H67D), and may be expressed in mammalian cells. Such an embodiment may bind a metal, such as $Ca^{2+}$.

In some embodiments, the artificial protein for metal binding reporting may include the amino acid sequence of SEQ ID NO. 142 (i.e., MZH3 H67N), and may be expressed in mammalian cells. Such an embodiment may bind a metal, such as $Ca^{2+}$.

In some embodiments, the artificial protein for metal binding reporting may include the amino acid sequence of SEQ ID NO. 147 (i.e., MZH3 P3G H9A Q10D L12I A13R F16L T91R G92E L95G G100N P105T L106R R107L Q108E H110I A114G Q115R Q118R V182M Q183E L185C Q186G T188R G189A Q190M L192R W193N), and may be expressed in mammalian cells.

Methods of Use

Artificial proteins described herein are well suited for transporting a cofactor to a desired location of a cell. In an embodiment, an artificial protein described herein is used to transport a cofactor to the membrane of a cell, for example, from the nucleus of the cell to the membrane of the cell. In an embodiment, a composition described herein comprising an artificial protein and a cofactor is used to transport a cofactor to the membrane of a cell, for example, from the nucleus of the cell to the membrane of the cell. In an embodiment the cofactor is electrochromic.

In some embodiments, the compositions described herein comprising an artificial protein and a cofactor that is electrochromic are well suited for detecting electrical activity of a cell. In some embodiments, a host cell can be transfected to express a composition comprising an artificial protein as described herein and a cofactor, wherein the artificial protein is configured to traffic to the cell membrane. In some embodiments the cofactor is electrochromic. In some embodiments the cofactor is a fluorophore. In some embodiments the method further comprises detecting a change in an emission of light from the cofactor. In some embodiments the emitted light may be in the visible to near infrared (IR) region of the electromagnetic spectrum. The method may further comprise correlating the light emission to an electrical activity of the cell. For example, the method may comprise correlating wavelength of the emission of light or number of photons emitted per second to an electrical activity of the cell. In some embodiments a light emission is detected at a first time and a light emission is detected at a second time. In such embodiments the method may further comprise calculating a difference between the light emission at the first time and the light emission at the second time and correlating the difference to a change in electrical activity of the cell.

In some embodiments, the compositions described herein comprising an artificial protein and a cofactor that is fluorescent may be used as optical reporters of cell physiology. In some embodiments a composition described herein comprising an artificial protein and a cofactor that is fluorescent may be used to detect changes in the concentration of a chemical, such as a metal ion or proton. For example, in an embodiment binding of a metal ion to a composition of the invention may increase the fluorescence of the cofactor by increasing the rigidity of the artificial protein. In another embodiment, an artificial protein and a cofactor that is fluorescent may be used to detect a ligand binding event. In another embodiment, an artificial protein and a cofactor that is fluorescent may be used to detect a protein binding event and/or a protein interaction event. In another embodiment, an artificial protein and a cofactor that is fluorescent may be used to detect a change in oxidative state. In some embodiments, a host cell can be transfected to express a composition comprising an artificial protein as described herein and a cofactor. In some embodiments the cofactor is a fluorophore. In some embodiments the method further comprises detecting a change in an emission of light from the cofactor. In some embodiments the emitted light may be in the visible to near infrared (IR) region of the electromagnetic spectrum. The method may further comprise correlating the light emission to an aspect of the cell's physiology, such as concentration of a chemical, such as a metal ion or proton. For example, the method may comprise correlating wavelength of the emission of light or number of photons emitted per second to an aspect of the cell's physiology, such as concentration of a chemical, such as a metal ion or proton. In some embodiments a light emission is detected at a first time and a light emission is detected at a second time. In such embodiments the method may further comprise calculating a difference between the light emission at the first time and the light emission at the second time and correlating the difference to a change in an aspect of the cell's physiology, such as concentration of a chemical, such as a metal ion or proton.

In some embodiments, the compositions described herein comprising an artificial protein and a cofactor may be used to enhance contrast of proton nuclear magnetic resonance imaging. In some embodiments, suitable compositions include a cofactor that interacts with water. In some embodiments, suitable compositions include a cofactor that is a heme. In some embodiments, suitable compositions include a cofactor that is a metal ion. In some embodiments suitable compositions include a heme and a metal ion as cofactors. In some embodiments, compositions described herein may increase T2 contrast. In some embodiments a composition described herein may be used as a genetically encoded transcriptional reporter for protein expression detection by magnetic resonance imaging. In some embodiments a composition described herein may be used as a fusion tag for protein expression detection by magnetic resonance imaging.

It will be appreciated by persons skilled in the art that numerous variations and/or modifications may be made to the invention shown in the specific embodiments without departing from the spirit and scope of the invention as broadly described. Further, each and every reference cited above is hereby incorporated by reference as if fully set forth herein.

Artificial Proteins of the Invention as Voltage Sensors

Optical transmembrane voltage sensors are of particular importance because of the ability to resolve cellular and sub-cellular activities with commercial imaging equipment for ex vivo and in vivo brain analyses. Previously reported sensors were organically synthesized amphipathic voltage sensitive dyes (VSDs) that were embedded into the plasma membrane and reported activity as Stark Effect probes, in which transmembrane potential modulates optical absorbance efficiency, wavelength and resultant emission. More recently, genetically encoded protein-based probes—i.e. optogenetic sensors or genetically encoded voltage indicators (GEVIs)—have dominated technology development efforts for their ability to isolate the activity of genetically targeted cell types when heterologously expressed under cell-type specific promoters. Previously reported GEVIs present several problems: 1) inertial and structural reorganization of previously reported sensors results in a fundamental limit to the temporal resolution such sensors can achieve; 2) natural proteins broadly impose engineering constraints (e.g. dimness of sensor); and 3) signal directionality of monomeric fluorescent protein (FP)-voltage sensor domains of membrane proteins (mVSDs) allows for bleaching to be mistaken for increased reactivity (i.e. as a false positive). There is a need for improved optical voltage sensors.

High-performance in vivo optical recording of neuronal electrical activity with the temporal and fine-feature waveform resolution on par with whole-cell patch clamp electrophysiology would permit the physiology of individual cells and cell types to be correlated to (i) neural circuit-level activity, and (ii) to the resultant activity-dependent behaviors, cognitive states, and affective states observed in the normal and diseased brain. Optical transmembrane voltage sensors are of particular importance because of the ability to resolve cellular and sub-cellular activities with commercial imaging equipment for ex vivo and in vivo brain analyses. An ideal optical reporter of electrophysiological activities would be optimized along multiple parameters:

Temporal Resolution (for Maximal Information Content): Voltage indicator response kinetics should be sub-ms timescale to reliably resolve in vivo individual action potentials, particularly during periods of high activity such as evoked responses. Microsecond-scale responses that faithfully resolve the waveforms of spikes and sub-threshold "minis" maximize information content by revealing molecular scale phenomenon such as specific ion channel/receptor contributions to spike propagation and synaptic transmission.

Safety and Genetic Targeting (for Chronic Neural Circuit Analysis): Isolating physiological activity from targeted cell types facilitates neural circuit analyses in a way that electrical recording cannot. Toxicity and exogenous chromophore supplementation impede chronic in vivo applications. Excessive membrane charge or reporter loading alters cell capacitance, and consequently, spike timing and circuit dynamics.

Signal Amplitude and Responsiveness (for Maximal Measurement Reliability): Lesser voltage-sensitivity and/or brightness reduce signal amplitude and signal-to-noise ratio (SNR), thereby making it difficult to detect sub-threshold events and "minis" that are critical to synaptic scaling and homeostatic plasticity. Lesser signal quality also indirectly reduces temporal resolution due to the requirement for increased signal integration/averaging, and increase hardware cost due to the need for sensitivity. Negative signal direction (emission decreases with depolarization) confounds reporter bleaching as false positives for neural activity.

Moreover, it is also desirable that a reporter possess:

Tunable Structure and Mechanism (for Rational Optimization): Certainty over the biophysical mechanisms augment engineering capacity for enhanced function, particularly with known first principles and molecular structures. Chromophore redshift-tuning increases light penetration, reduces background noise from endogenous proteins (including hemoglobin), and reduces scattering for better spatial contrast.

Strategic positioning of a chromophore within a transmembrane (TM) artificial protein of the invention allows for voltage sensing by the optical Stark Effect (FIG. 1), by which chromophores exhibit electric field-induced changes in absorbance on the ns timescale resulting in ultrafast changes in observed fluorescence—for example, Stark-effect dyes may exhibit ~2 μs-resolution in neurons. The voltage-dependent optical response can be molecularly amplified by introducing non-fluorescent heme co-factors to (i) tune the local electric field changes at a Stark fluorophore via electron transfer and (ii) shift the emission wavelength away from the fluorescence at neuronal resting state (FIG. 2B). In some embodiments, this combination of optical Stark Effect and local molecular amplification of field-sensitivity will be (i) ultrafast (μs resolution or ~102 enhanced vs. existing GEVIs), (ii) ultrahigh voltage-sensitive (ΔF/F of 350% per 100 mV, or ~20-fold enhanced vs. existing GEVIs).

In some embodiments, the artificial proteins of the invention that may be provided for voltage sensing and may function as Stark Effect reporters, may include an artificial protein or sequence of amino acids set forth in Table 2, or a variant thereof.

In some embodiments, the artificial proteins of the invention that may be provided for voltage sensing, and may function as Stark Effect reporters, may include an artificial protein comprising a sequence of amino acids described by one or more of Generic Sequence A, Generic Sequence B, Generic Sequence C, and Generic Sequence D.

In some embodiments, the artificial proteins of the invention that may be provided for voltage sensing, and may function as Stark Effect reporters, may include an artificial protein comprising a sequence of amino acids described by one or more of SEQ ID NOS. 1 to 16, or a variant thereof.

In some embodiments, the artificial proteins of the invention that may be provided for voltage sensing and may function as Stark Effect reporters may include an artificial protein described by one of SEQ ID NO. 21 ("GLSloop"), 22 ("PEB MUT B"), 23 ("PEB MUT C"), 24 ("PEB MUT D"), 25 ("dFP1.0"), 27 ("C41 Stab Map"), and 29 ("C41 Py Stab"), or a variant thereof.

The following examples describe the invention in further detail. These examples are provided for illustrative purposes only, and should in no way be considered as limiting the invention.

EXAMPLES

Example 1. Artificial Proteins for Cell Expression

A generalizable scaffold was found that may be expressed well in mammalian cells. Sequences were transiently transfected into HEK293t cells with lipofectamine on a plasmid backbone under a CAMKII promoter, as a fusion with EGFP. Although this transfection method was chosen, the proteins using this scaffold are only ~0.5 kbp, so are amendable to various methods of transfection and viral delivery, including AAVs with limited genetic payload. To put this into context, it is half the size of GFP. These proteins have also been expressed successfully in rat hippocampal neurons after both lipofectamine and $CaCl_2$ transfection techniques (FIG. 11) and are currently being used in a lentiviral system for viral delivery to HEK cells and hippocampal neurons.

Figure 11:
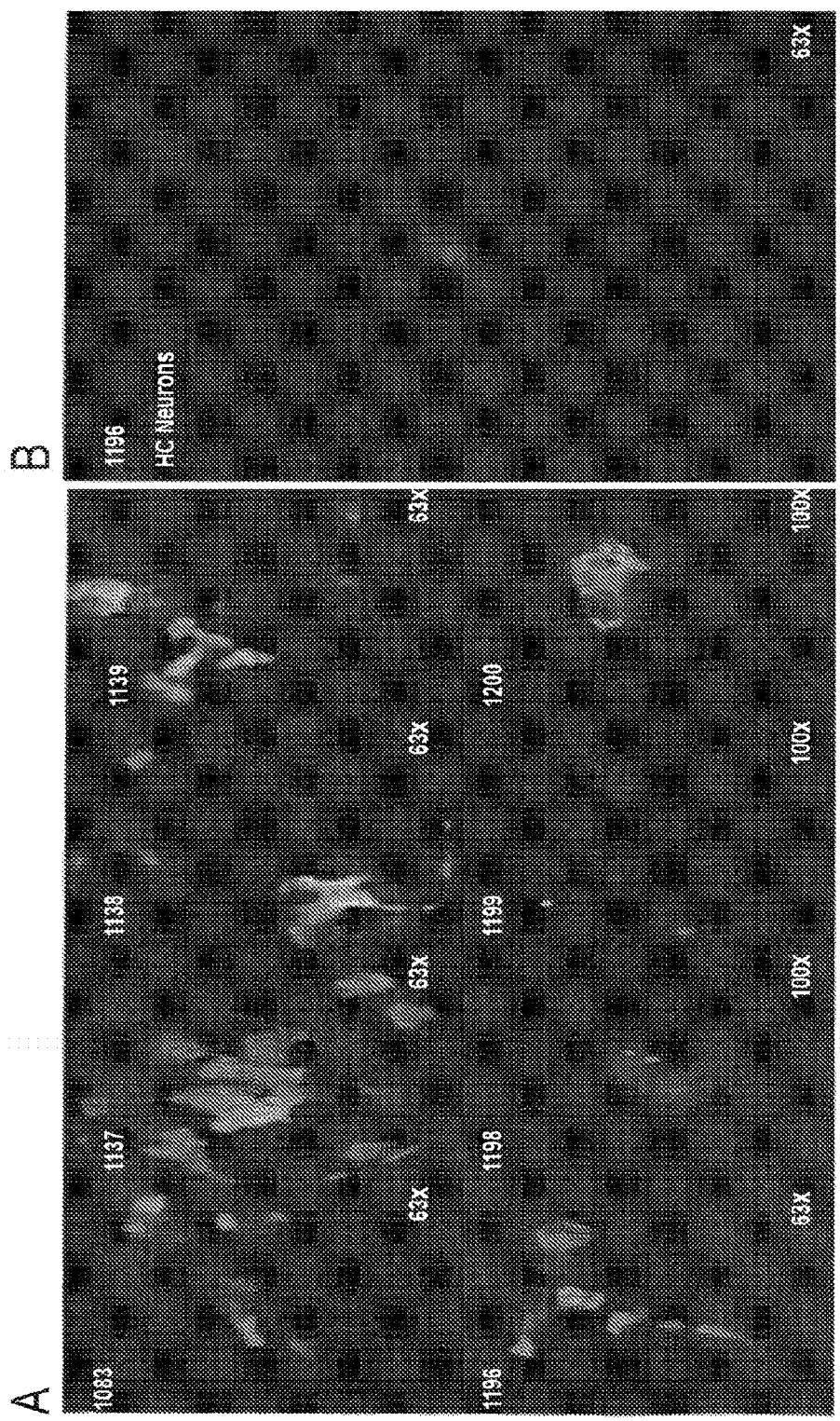
FIG. 11 shows trafficking of artificial protein variants according to embodiments of the invention. All show even cytosolic expression and BEK 293t cells (Panel A) and rat hippocampal neurons (Panel B). The artificial proteins of the invention described in FIG. 11 include 1083 (SEQ ID NO: 21), 1137 (SEQ ID NO: 22), 1138 (SEQ ID NO: 23), 1139 (SEQ ID NO: 24), 1196 (SEQ ID NO: 25), 1198 (SEQ ID NO: 27), and 1200 (SEQ ID NO:29).

Sequences of proteins from FIG. 11 show large amounts of homology, particularly in the exterior region. However, many interior mutations between them show no observable effect on cellular trafficking. X's shows sites at which there is variability between constructs in sequence 1 (see FIG. 14). It is clear from these patterns that a and d positions of the heptad repeats, which face internally to the four-helix bundle (FIG. 3) are modifiable without effect to trafficking. It also appears that e and g positions that are more interfacial (changes with register somewhat up bundle) are modifiable without effecting trafficking. From here, we can generalize more sites that should withstand variation to produce Sequence 2 shown in FIG. 14.

While there is a large amount of variability to Sequence 2 shown in FIG. 14, not all binary-charged sequences traffic well. For example, one may think that supercharged sequences should traffic the best since they are highly soluble and stable at various pHs and chemical environments.

Figure 12:
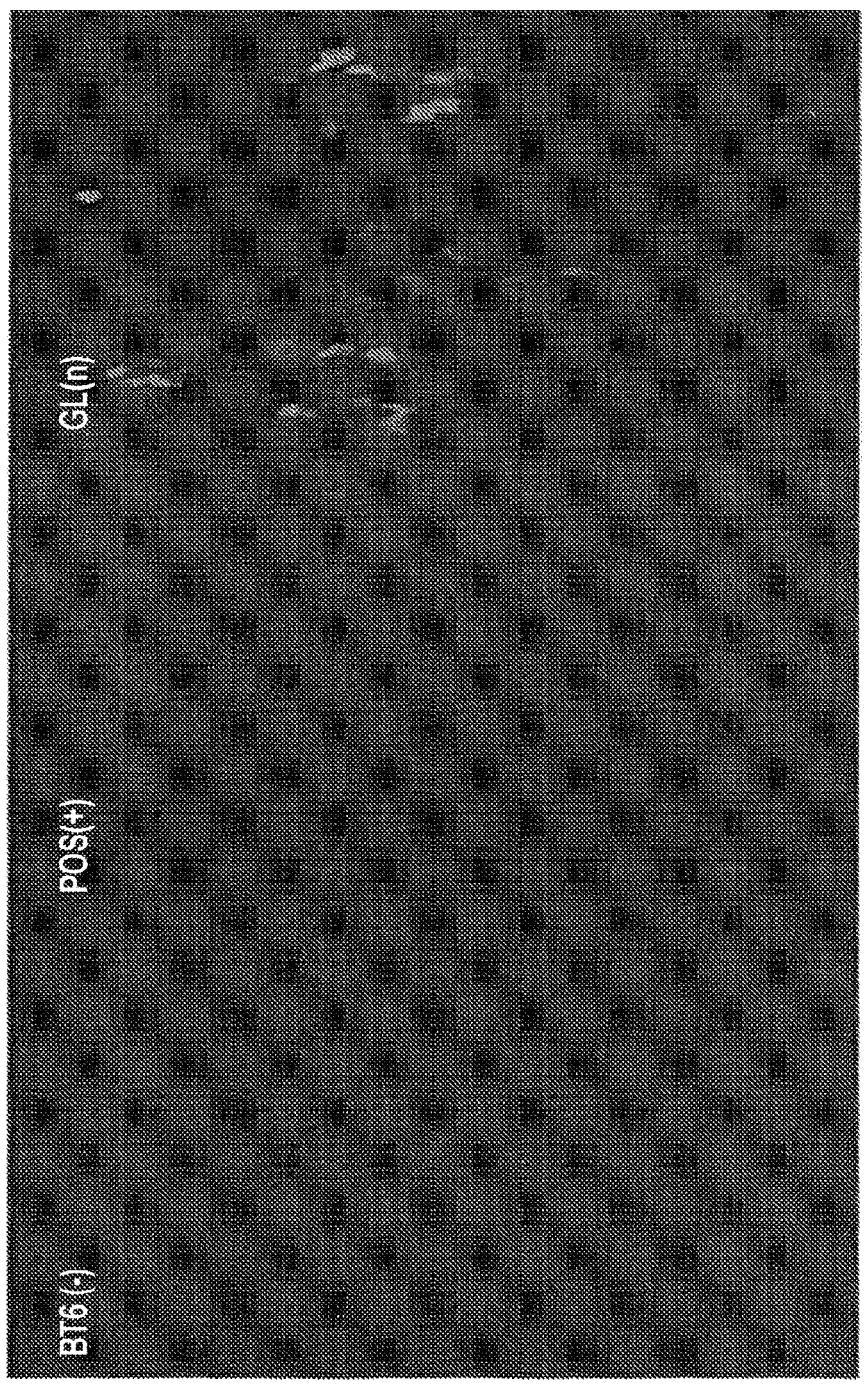
FIG. 12 shows trafficking of various scaffolds according to embodiments of the invention at 20×. GL (neutral surface), POS (positive surface, +12), and BT6 (negative surface, −14). GL both traffics well and shows even cytosolic expression. Both BT6 and POS express less effectively and show some blebbing in ER/Golgi indicating cellular stress.
Figure 13:
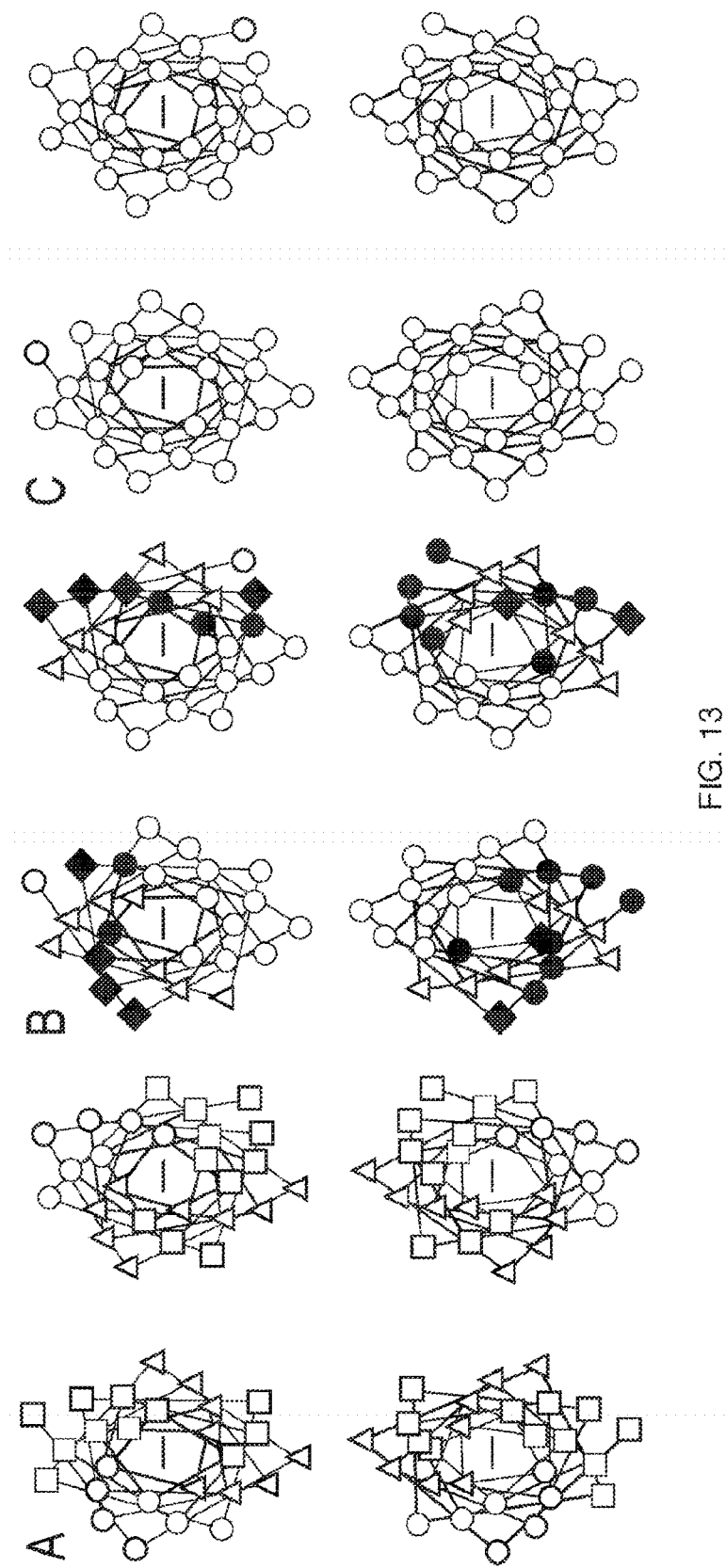
FIG. 13 shows heptad patterning of a 4-helix bundle (Panel a) and common sequence (Panel b) and generalized sequence (Panel c).

However, charged versions of this sequence may express and traffic less effectively in mammalian cells, including "BT6", a single-chain version of the protein disclosed in U.S. Pat. No. 8,846,619 (FIG. 12). When comparing these sequences, one can highlight the sites of changed for both the positively and negatively charged versions, shown in Sequence 3 of FIG. 14. Here it can be seen that f positions and non-interfacial e and g positions, when mutated across the whole protein, negatively effect cell trafficking and expression. Although not tested, it is likely analogous b and c positions (see FIG. 13) would have similar effects. Using only data-verified positions, the positions shown to be most important for trafficking in Sequence 4 shown in FIG. 14 can be highlighted. Sequence 4 shown in FIG. 14 represents a selected embodiment of a well-trafficking artificial protein for trafficking in mammalian cells. However, this sequence can likely withstand changes that preserve its charge patterning without affecting its trafficking or expression behavior. Therefore, Sequence 4 shown in FIG. 14 can be further generalized into Sequence 5 shown in FIG. 14, in which each amino acid type is specified for each position important for trafficking.

It is of note that some additional changes likely will also not effect trafficking as long as they are not so widespread throughout the sequence as to change the overall binary patterning of the helices or overall charge dramatically. That is, the sequence can withstand some additional variability (e.g., 1%, 2%, 3%, 4%, 5%, 6%, 7%, 8%, 9%, 10%, or 15% variability) so long as there is a high degree of fidelity, particularly with the generalized sequence 5 shown in FIG. 14. This is seen in SEQ ID NOS. 28 and 29.

Example 2. Exemplary Artificial Fluorescent Proteins

In this example, maquettes for genetically encoded mammalian sensors are discussed, so cofactors need to be naturally occurring in mammalian systems. While many synthetic fluorophores could be attached to maquettes, in this example those that can be incorporated in significant quantities in vivo are addressed. This list includes flavins, biliverdin (BV), bilirubin, retinals, and carotenoids. Multiple cofactors can also be bound in each scaffold, where each cofactor-binding module can be interchanged with others on each scaffold.

Figure 17:
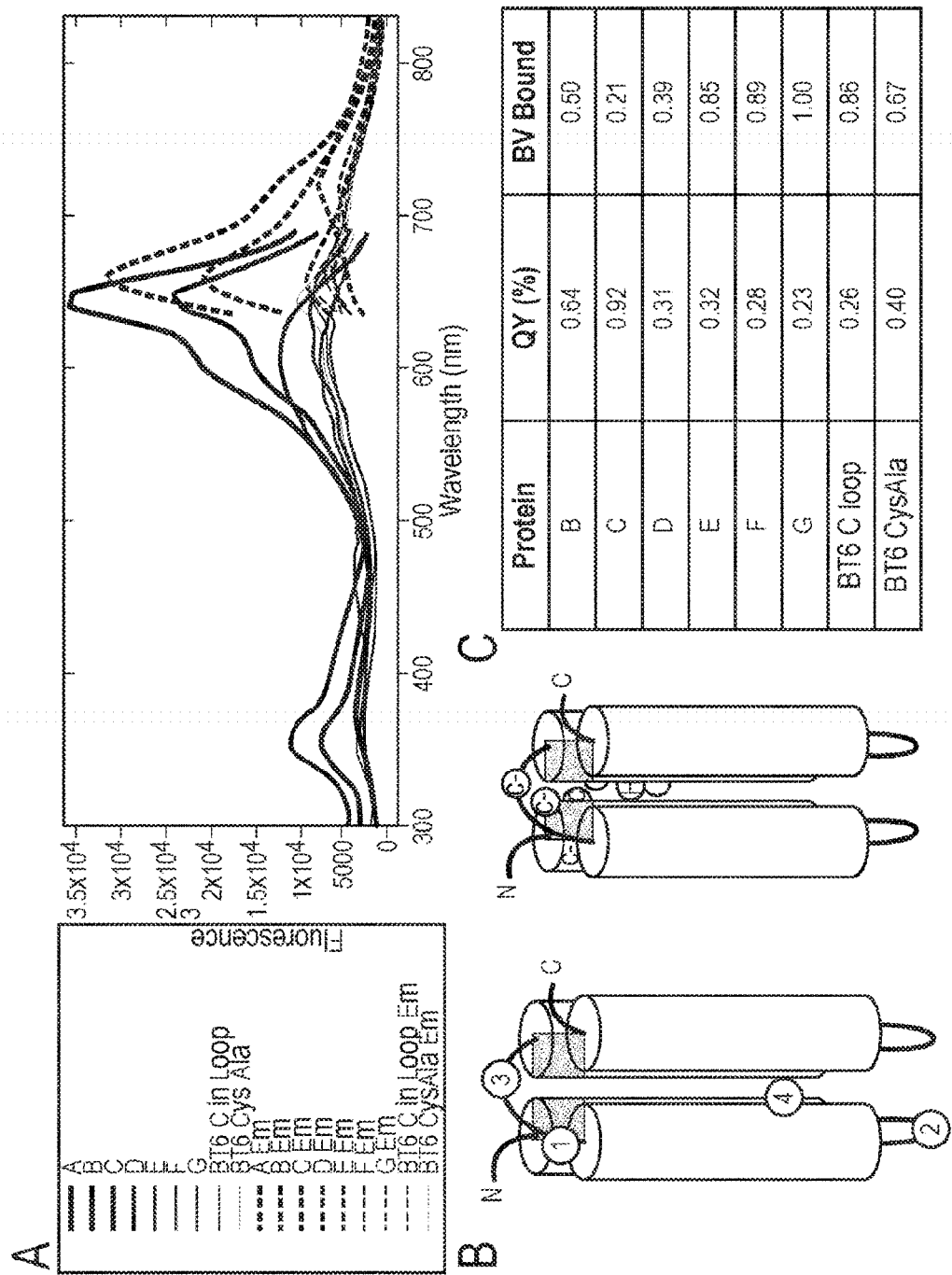
FIG. 17 shows (Panel A) Fluorescence excitation (solid) and emission (dashed) spectra normalized to absorbance at excitation wavelength 600 nm of maquette series with (Panel B) varying cysteine positions (yellow bubbles) and (Panel B) stabilizing amino acid combinations that result in (Panel C) differing quantum yields and amount of biliverdin bound in vitro.

A cytosolic rigid BV-binding protein that can be expressed in mammalian systems in scaffold "GL" is shown herein. There is a series that show both in vitro and cellular BV fluorescence. First, a series of proteins were tested with varying cofactor binding locations (depicted as yellow circles in FIG. 17, panel B) and potentially stabilizing residues in the loop cysteine-binding site. These mutants had similar excitation and emission spectra, with the exception of the two-populations seen for BT6 cys-ala, but varying quantum yields and ability to bind BV. From this cohort, it was found that BV is non-fluorescent when bound to the middle of the center loop if 8 amino acids (position 3, BT6 C in loop), binding a second non-fluorescent BV acts as a filter/quencher to the fluorescent BV (Protein F), the BV can make its way to the core if bound to a short (4 amino acid) loop (Proteins B, C, D), and that BV can be fluorescent at both positions 1 and 4 (Proteins B-G and BT6 CysAla, respectively). It was also found that fluorescence can be improved from these two positions by a series of residues depicted in FIG. 17, panel B. These include a valine to stabilize the hydrophobic pocket, an EHE modif where the glutamic acid hydrogen bonds b and c ring nitrogens and the histidine pi-stacks, and a serine that can hydrogen bond to the a-ring nitrogen. Further, it was found that the GGCGRI binding site decrease BV binding efficiency but increases fluorescence compered to GGCRD/E.

Figure 18:
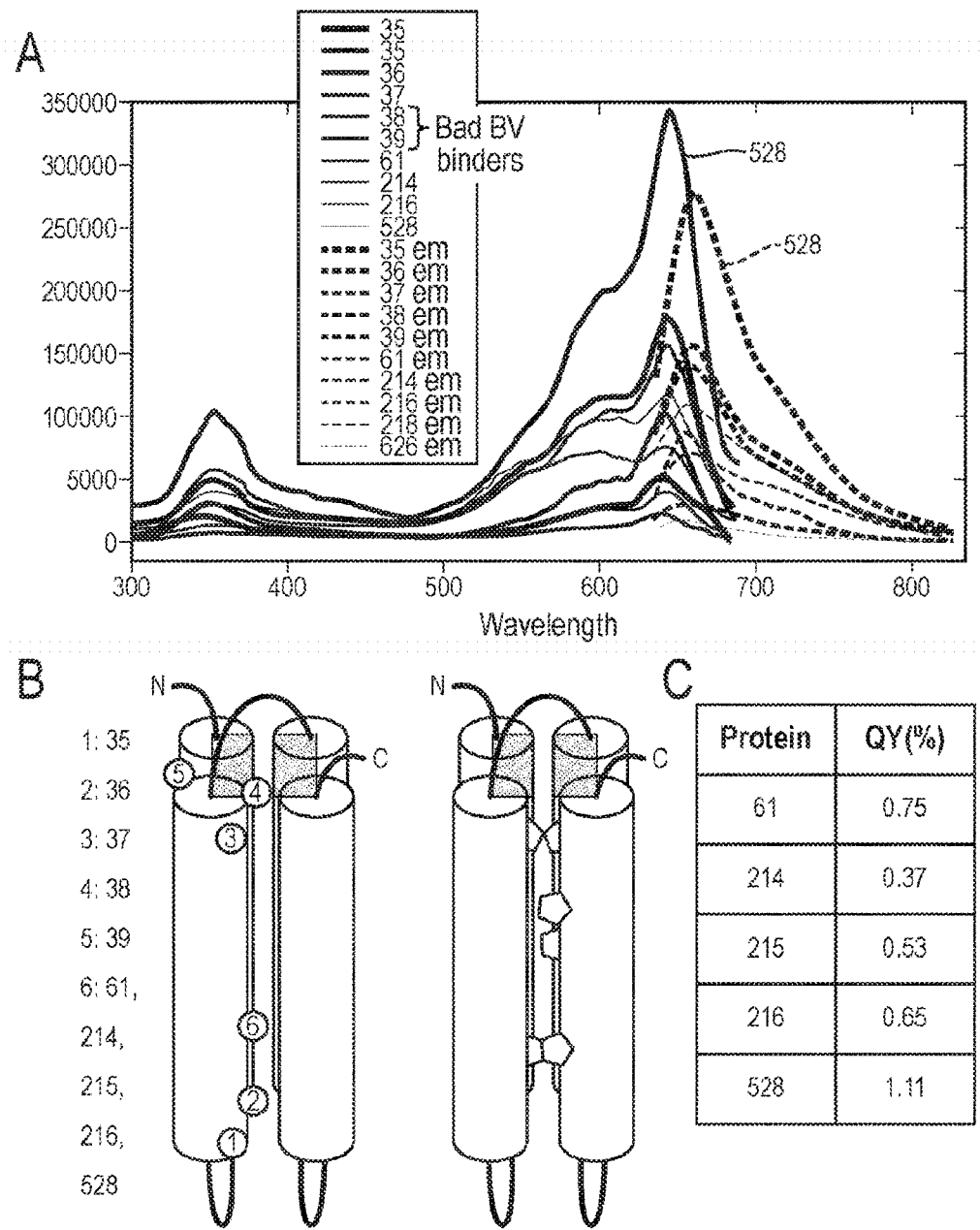
FIG. 18 shows (Panel A) Fluorescence excitation (solid) and emission (dashed) spectra normalized to absorbance at excitation wavelength 600 nm of maquette series with (Panel B) varying cysteine positions (yellow bubbles) and (Panel B) stabilizing histidine positions (green pentagons) that result in (Panel C) differing quantum yields and amount of biliverdin bound in vitro.

A second cohort was tested to further test the variability of potential BV-binding cysteine placement as well as histidines to pi-stack and further stabilize the c and d rings. From this cohort, it was found that BV only efficiently binds to the cysteine in the outside of the helix or the loop on the cross-loop section of the four-helix bundle. From these positions, the outside of the bundle does not lead to a fluorescent protein but the loop can. However, internal sites can be accessed through the other end of the bundle with internal positions binding BV at 1, 2, and 6 (FIG. 18, panel B). Further, histidine placement was found to increase BV fluorescence when placed in strategic positions near the C and D rings.

A series of proteins was designed to incorporate the stabilization factors found in the first two rounds of proteins tested. SEQ ID NO: 25 was designed to incorporate serine and histidine stabilization to SEQ ID NO: 23 (already contains EHE and V) with a CGRI binding motif SEQ ID NO: 26 contains a CGRD motif. SEQ ID NO: 27 has all of those stabilization sites mapped down into the bundle to a C41 BV-binding site using a rigid 4-helix bundle model. SEQ ID NO: 28 is similar to SEQ ID NO: 27, but has the CARD sequence of BV binding. SEQ ID NO: 29 is also mapped down like SEQ ID NO: 27 using an MD-simulation. Of these new designs, SEQ ID No. 25 performed well in vitro. It performed twice as well as its predecessor SEQ ID NO: 23. This is a selected embodiment of an artificial infrared fluorescent protein. It also trafficks well and shows good BV-fluorescence in vivo in both HEK293t cells and hippocampal neurons.

Example 3. Artificial Proteins as Stark Effect Sensors

Possible Stark sensors are proteins that include any cofactor that can be rigidly aligned within the membrane and exhibits an electrochromic effect in the presence of a 50-100 mV voltage. In order to use these sensors in the brain, they need to either cross the blood brain barrier or be genetically encoded. Since the former is unlikely to be possible for proteins, the latter is necessary so only naturally occurring cofactors may be plausible. To see a large electrochromic effect with little background, or Stark shift, these should be multi-ring fluorescent structures. Flavins and bilins are such cofactors present in high enough quantities in mammalian systems.

Figure 15:
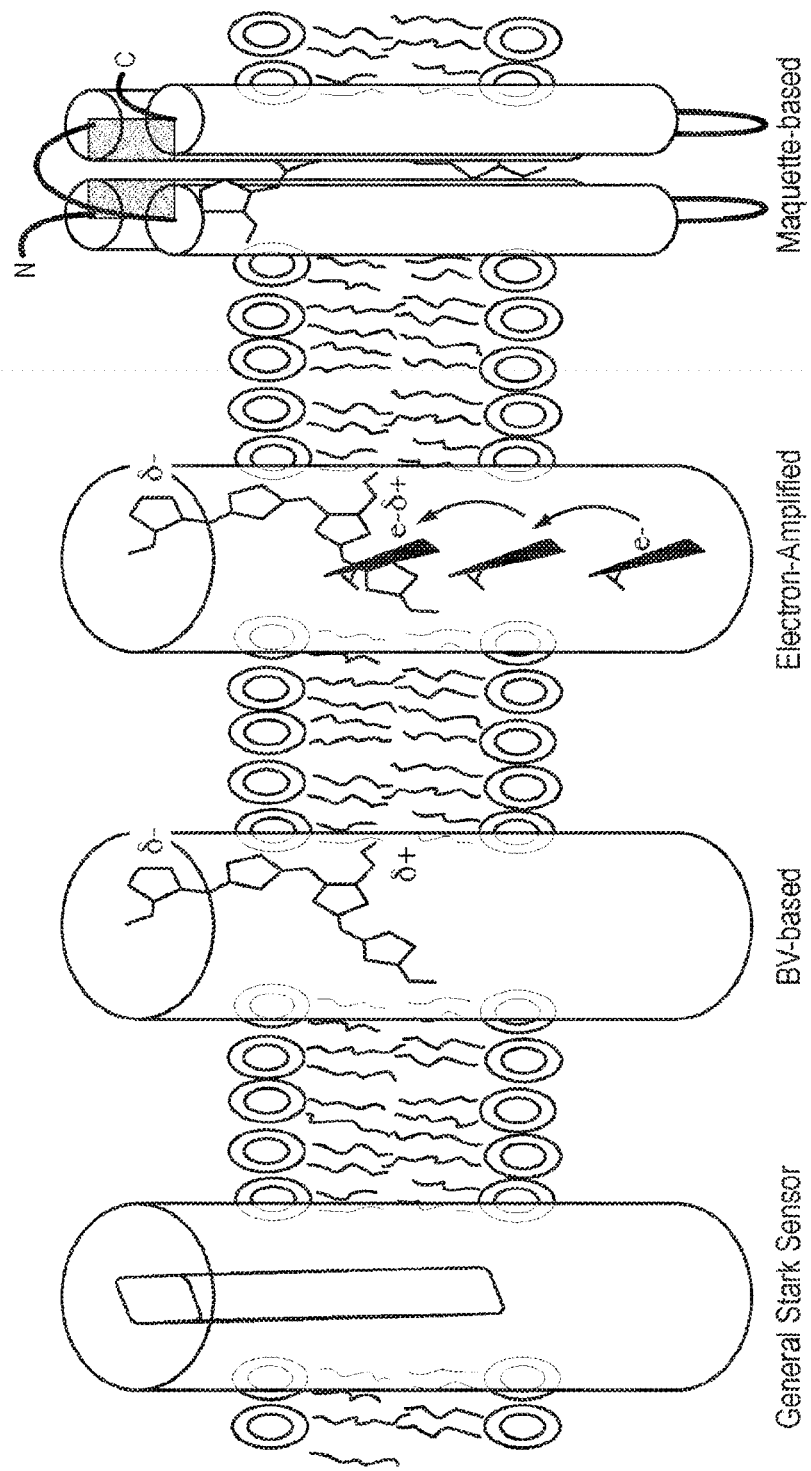
FIG. 15 shows possible Stark sensors from minimal requirements (left), to BV-based model and electron-amplified BV-based model (middle), and an artificial-protein based BV-sensor according to an embodiment of the invention (right).

Artificial proteins described herein may include transmembrane four-helix bundles that rigidly bind either a flavin or bilin along the voltage gradient, perpendicular to the membrane. The Stark effects seen by the voltage application can be further amplified through induced electron transfer between attached heme groups (FIG. 15). In a standard Stark shift system, the voltage changes the orbital energies due to the aligned dipole of the molecule. This voltage effect can be amplified greatly by that voltage inducing an electron transfer event that leads to an electric charge moving closer to the fluorescent cofactors' dipole.

Figure 16:
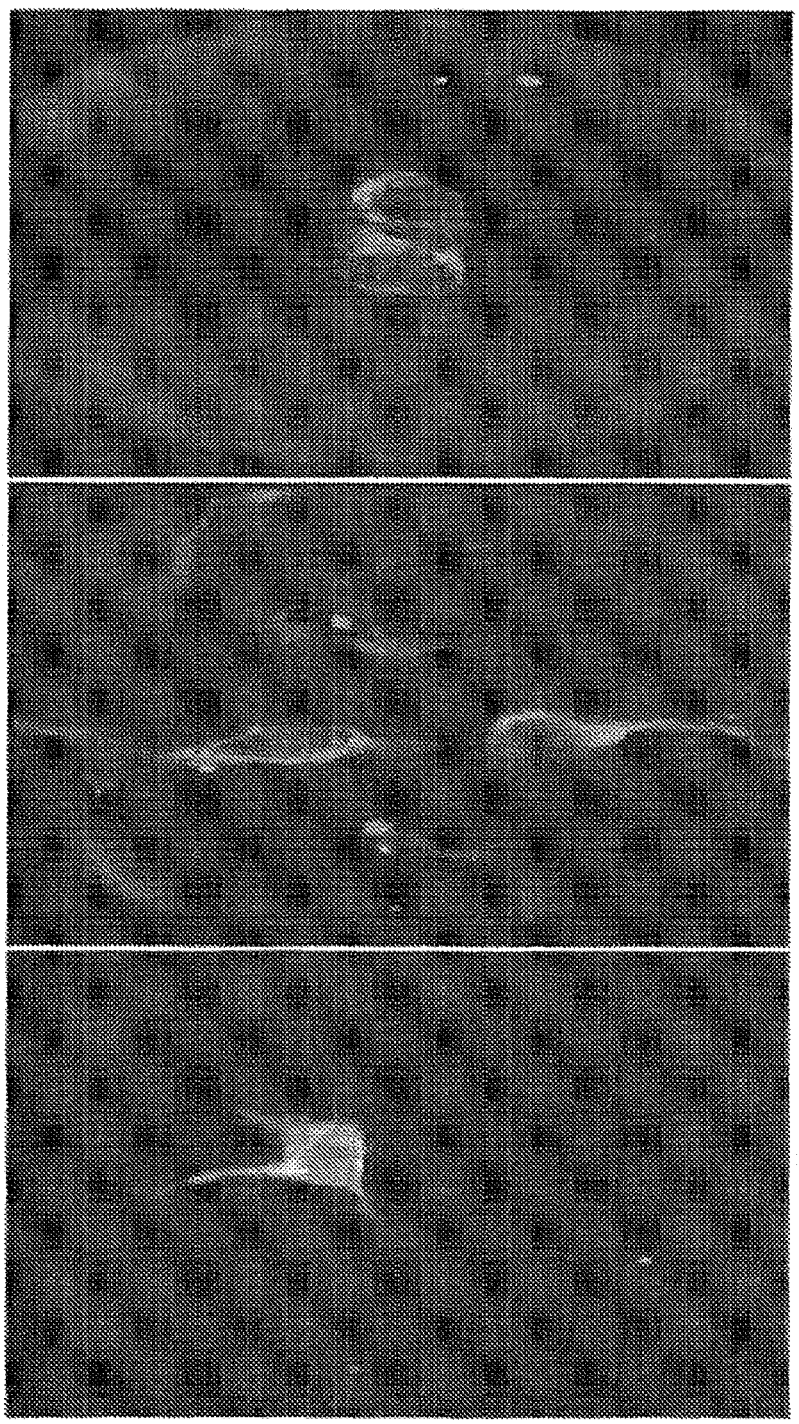
FIG. 16 shows HEK293t cells expressing a transmembrane artificial protein in accordance with an embodiment of the invention (1083 (SEQ ID NO: 21)) as a GFP fusion at 63×.

A peptide of the invention is an artificial transmembrane protein that trafficks well in mammalian (HEK293t) cells to the cellular membranes and does not cause noticeable stress or ER/Golgi aggregation (FIG. 16).

Maquette production: An experimental sequence begins with biliverdin as the Stark pigment in maquettes, but corresponding measurements apply to designs with other Stark pigments. Transmembrane (TM) versions will be expressed of already existing water-soluble bilin-binding maquettes. Leader sequences will be designed for TM insertion to vectorially orient maquettes in the membrane, with the hydrophilic extension remaining in the cytosolic as opposed to extracellular space (FIG. 3). This extension will not only keep membrane vectorial orientation high, but also provide a location for securing a second reference fluorophore that will not be influenced by transmembrane fields for potential ratiometric imaging. Bilin pigment designs exploit Cys residues for covalent anchoring to the protein frame, which will be assessed after mixing pigment with maquette by passing through a PD-10 size exclusion column under denaturing urea conditions. More precise binding yield assays will use HPLC. The bilin absorbance and fluorescence spectra and fluorescence yield of these maquettes will be characterized. For those sequences that show strong bilin binding in vitro, high yields of production (in *E. coli*) and pigment binding will be enhanced by supplying the growth medium with amino levulinic acid to boost the concentration of precursor heme. Co-expression of maquette with heme oxygenase under these conditions leads to high yields of in-cell incorporation of biliverdin. Flavin anchoring can be achieved by exploiting a natural flavin binding sequence ApbE for covalent attachment of natural flavin FMN to a Thr residue. This sequence will be spliced into transmembrane maquette designs. These sequences will be iteratively adjusted to improve the yield of in vitro and in vivo flavin binding. Retinal binding uses Lys as the covalent anchoring residue via a Schiff base. Analogous experiments apply to flavin and retinal pigment binding counterparts for all of the experiments described below.

Enhancement of dynamic range of fluorescent endogenous cofactors with polarizable amino acids to facilitate noninvasive measurements of transmembrane electrical potentials. The magnitude of fluorescence changes ΔF/F of cofactors that are endogenously present in the neuronal cells will be evaluated and the effect of protein surroundings on the ΔF/F under electric field will be investigated. The electric field within fluorescent β-barrel proteins can be one or two orders of magnitude stronger than fields generated by action potentials, varying from 10 to 100 MV/cm, and leading to very significant change in the emission of red fluorescence proteins. Iterative and/or computational design of the polarizability of the protein in the vicinity of fluorescent Stark cofactors to significantly enhance the difference in fluorescence upon applied electric field is expected.

Figure 10:
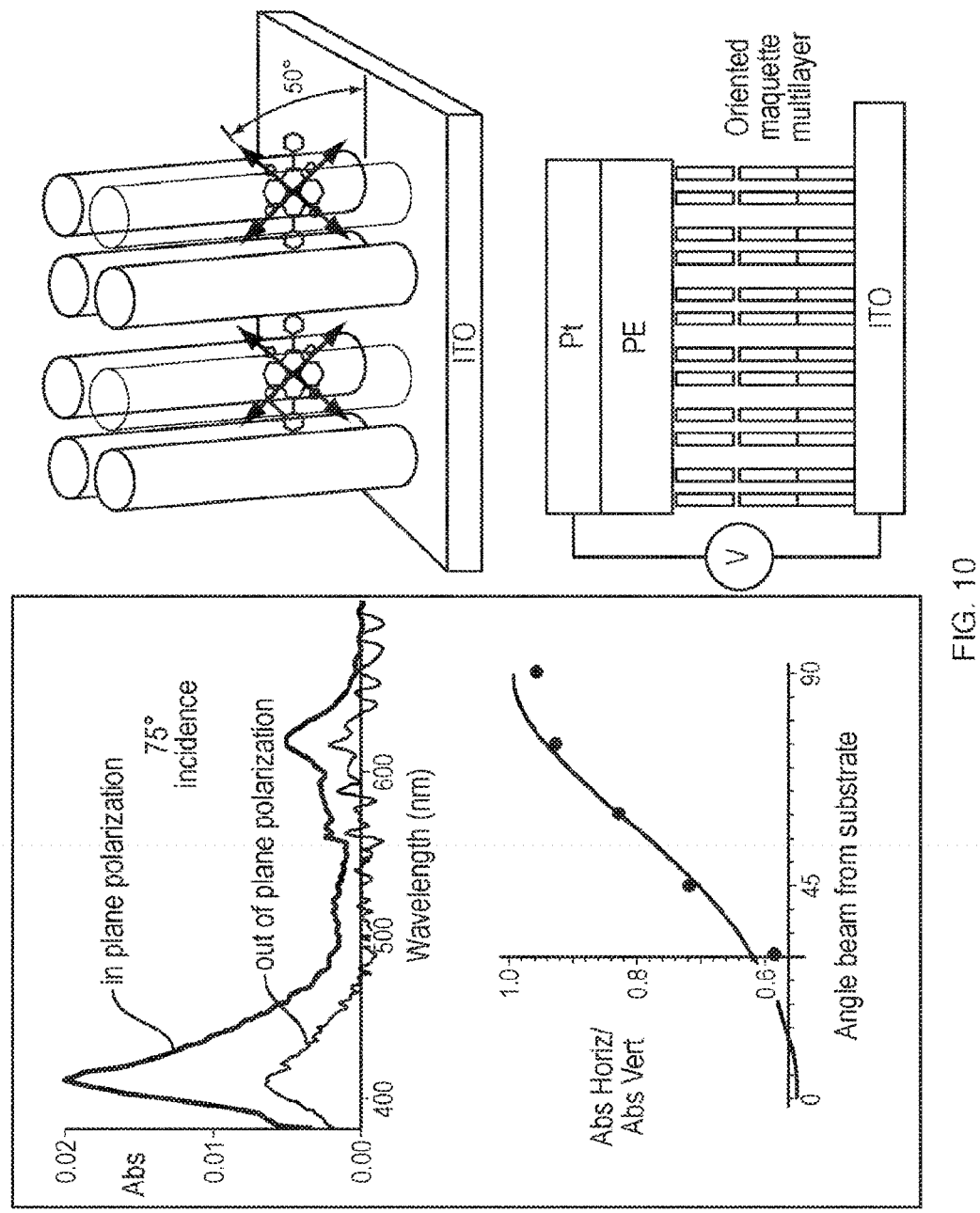
FIG. 10 shows the Stark effect measurements of purified GEVIs. Maquettes oriented at an air/water interface L-B deposited as a multilayer film on transparent ITO electrode. Linear dichroism of pigments (left) reveals pigment/protein orientation (upper right) in the final thin layer capacitor (lower right) for applied fields and Stark measurements.

The ΔF/F Stark tuning effect of bilin absorbance and emission is calibrated by creating maquette capacitors from oriented bilin maquette multilayers on transparent ITO electrodes. Using Langmuir-Blodgett technology, membrane maquettes are spread at an air-aqueous interface, compressed to orient α-helices normal to the surface with the polar extension of the membrane maquette aligning preferentially towards aqueous phase. Linear dichroic absorption with polarized light at various angles of incidence reveals the orientation of the pigment with respect to the surface (FIG. 10). A TREK×1000 voltage amplifier applies a modulated field across planar electrodes during fluorescence measurements. The most sensitive measurements use a lock-in amplifier for applying AC voltage to maquette capacitor films and photomultiplier tube (PMT) detection of fluorescence emission, using excitation and emission filters. Linear or quadratic dependence on applied field strength will be examined, a reflection of the starting electric field sensed by the chromophore by nearby residues before applying any field. The effect of nearby polar and charged amino acid on this internal field effect which can enhance Stark tuning rates will be tested. Capacitor thickness will be measured on an Alpha-step thin film profiler.

Complementary field sensitivity experiments in wet membranes will incorporate biliverdin bound transmembrane maquettes into unilamellar lipid vesicles. Fluorescence changes will be monitored upon application of a K+ pulses in the presence of a valinomycin ionophore to create calibrated transmembrane fields. Use of a classic absorbing transmembrane Stark pigment such as oxonol confirms the expected induced transmembrane electric field magnitude. Tethered monolayers between two gold electrodes (SdX Tethered Membranes) may also be formed to apply voltage pulses and measure applied field modulated fluorescence emission using a fiber-coupled laser source and PMT detector using a lock-in amplifier for greater signal to noise. These applied field assays will allow selection of the best maquette designs in terms of pigment placement and polar residues around the pigment binding site for maximal field modulation of fluorescence amplitude as well as confirming the rapid response time of the Stark effect.

Figure 8:
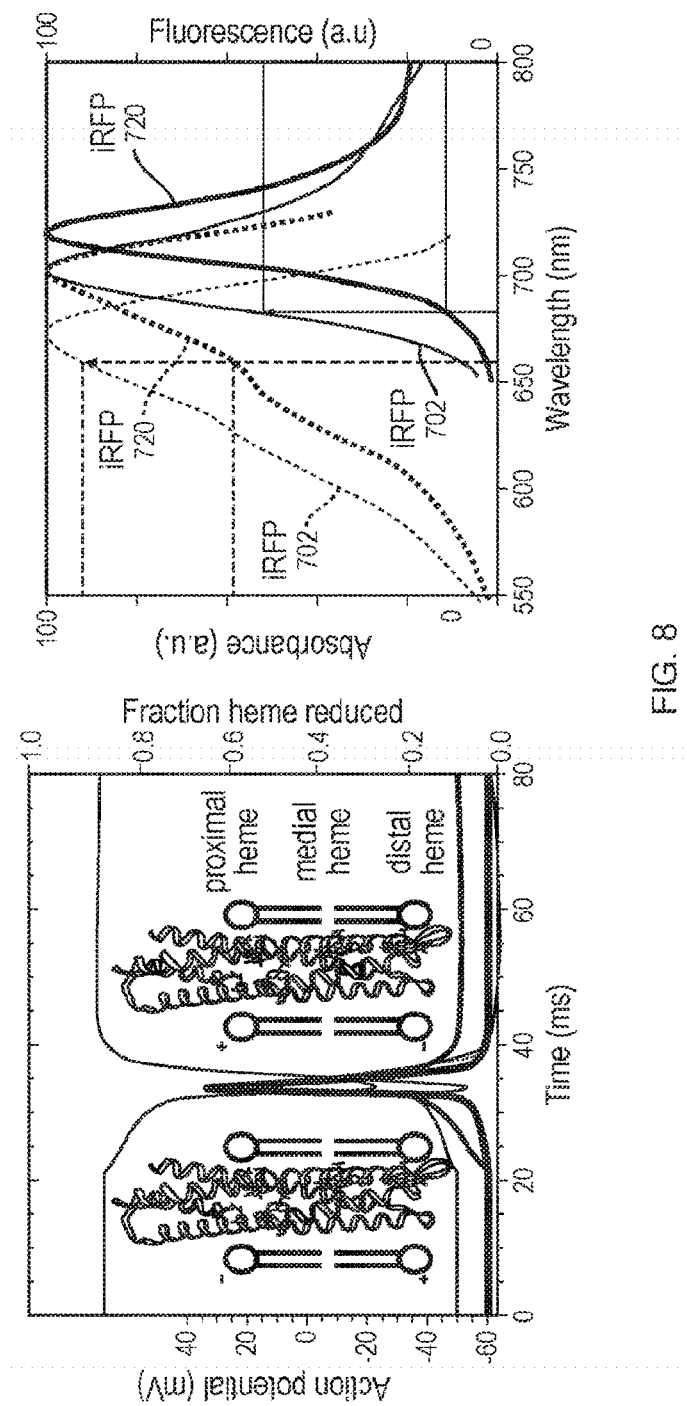
FIG. 8 shows the results of a model of high-fidelity optical recording of action potentials. Left: The action potential transmembrane field (red) moves the electron from the distal heme (green) to the proximal heme (blue) in microseconds. Proximal heme reduction is 2.2% at resting potential and 65% at peak depolarization. The charge on the reduced proximal heme creates a strong Stark field over the fluorescent bilin (red sticks). Right: A typical Stark field change of ~5 MV/cm acting on the ~5 Debye bilin difference dipole leads to a 20 nm red shift, comparable to the absorbance difference of iRFP702 (red) and iRFP720 (blue) (75). The field coupled redox change generates increased excitation absorbance at 660 nm and increased emission at 680 nm, and leads to a large $\Delta F/F$ of 350% per 100 mV.
Figure 9:
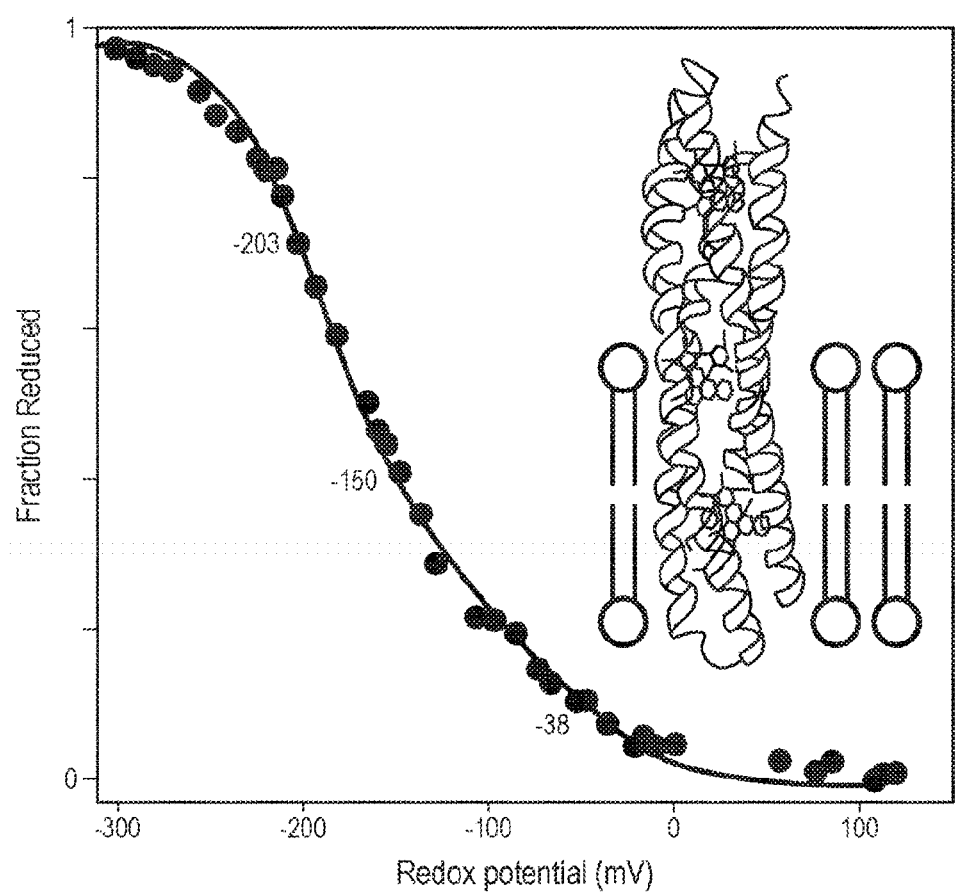
FIG. 9 shows control of heme redox potential in electron transfer chain. Equilibrium redox titrations sequentially oxidize and reduced 3 hemes with 3 different midpoint potentials in a membrane embedded maquette.

Redox chain enhancement of field sensitivity. The Stark effect can be enhanced using hemes as molecular level amplifiers of the transmembrane electric field. Both the chromophore and the hemes will sense the electric field, but the hemes will not fluoresce. Instead, voltage-dependent electron transfer between the hemes will create an additional local electric field that modulates the Stark effect chromophore (in addition to the transmembrane electric field that it would sense described above). As shown in our computational model in FIG. 8, it is anticipated that the voltage-sensitivity observed will be ΔF/F~350% per 100 mV or a log-order improved over existing GEVIs. To accomplish this, the maquette sequence of the most promising designs will be modified to include extra cofactor binding sites to construct an auxiliary transmembrane electron transfer chain. His residues at appropriate locations create three heme binding sites extending along the length of the maquette to maximize field sensitivity of intraprotein electron transfer along this heme chain. The terminal binding site will be near the level of the membrane/aqueous interface close to the Stark pigment, so that the electric field modulation by the redox changes of the heme are maximal. Equilibrium redox titrations (FIG. 9) will confirm the expected redox sensitive fluorescence changes. The heme site positioning and polar amino acids surrounding the Stark pigment will be adjusted as needed to maximize fluorescence modulation. When flavin is used as the fluorophore, redox titrations are expected to reveal modulation of the fluorescence quenching; light induced flavin photo-oxidative electron transfer quenches when the neighboring heme is reduced, while fluorescence is enhanced when the heme is oxidized.

The range of heme redox potentials in the artificial proteins of the invention (FIG. 9) is appropriate for generating mixed redox states in the natural environment of the cell. As described in the herein, the redox properties of individual hemes in the electron transfer chain can be tuned to favor oxidized or reduced states as cellular conditions indicate. Next, K+ gradient induced TM fields of maquettes in vesicles will be combined with redox poising to rapidly shift the electron along the heme chain and modulate fields around the Stark pigment, allowing for the comparison of the field induced fluorescence changes of the Stark pigment with and without electron transfer enhancement. The field induced shift will be spectrally confirmed of the redox states of the hemes from one heme type to another that is responsible for enhancing the electric field changes at the Stark pigment and also confirm the expected degree of vectorial insertion of the maquette in the artificial membranes by using spectrally distinguishable hemes in the electron transfer chain. This involves placing a covalently attached c-type heme at one end and a red shifted synthetic heme (such as diacetyl-deuteroporphyrin IX) at the b-type heme sites. When flavin is the fluorophore, field-induced relief of electron transfer fluorescence quenching will be monitored Example 4. Expression and Trafficking of Artificial Proteins and Compositions and Demonstration of Fast Optical Voltage Sensing As exogenous proteins, membrane maquette GEVIs will likely need to be engineered to safely express at high concentration in neurons. Thus, in parallel to initial biophysical studies in lipid preparations, expression of the membrane maquette scaffolds can be optimized. This decoupling between optimization experiments is possible because the rigid 4-helix scaffold itself can undergo wholesale changes without significant disruption to the pocket. In other words, the intra-bundle or co-factor binding structure optimized as described above can be mapped onto the scaffold optimized as described above, even if there is a departure in optimal scaffold design for trafficking from the scaffold. Importantly, 4-helix bundles are commonly found in mammalian plasma membrane proteins, such as the voltage-sensing domains of ion channels.

High-throughput analysis of maquette expression levels, localization, and co-factor uptake efficiency: After one-week transgene expression in hippocampal neurons, expression levels and localization will be assessed in multi-well plate format on a Leica DMI600B fluorescence microscope under Metamorph automation control. This microscope is equipped with a PCO.edge sCMOS camera and multiple LED-based illuminators with 10 kHz switching speeds that span the UV-NIR spectrum. To enhance plasma membrane signal isolation in a multiplexed screen where confocal analysis is of insufficient throughput, we can isolate the fluorescence from plasma membrane regions identified by Gaussian blur edge detection algorithms we and others have previously employed and since automated in the Metamorph environment for HEK cell lines. If needed, the system is also equipped with a digital micromirror device for spatially limit the illumination field to the Gaussian blur membrane "mask" to limit cytosolic contributions to fluorescence.

Cells will be fixed in paraformaldehyde and imaged in 1×PBS buffer, or imaged live in bicarbonate- and phenol-free media (neuron survival ~3 hours). The bilin fluorescence will be monitored, but trafficking of apo-protein can be assessed by fluorescein-labeled antibody staining against a terminal His-tag or a fused GFP. In conjunction with co-factor supplementation studies, this scheme assists in the attribution of fluorescence amplitude to expression, trafficking, or co-factor uptake. It should be noted that a fused GFP does not alter function or kinetics due to the lack of structural rearrangement in maquette GEVIs. Common techniques will be applied in optogenetic tool development. To augment expression levels, mammalian codon-optimization of the sequences is performed, but kept attuned to the possibility that high protein translation rates may impede co-factor incorporation. To test this, it is assessed whether biliverdin and heme supplementation increases fluorescence or co-factor uptake, as determined by spectroscopy (as in FIG. 5, but recorded using a Tecan M200 plate reader). To reduce ER/Golgi stress, terminal export sequences are appended from Kir2.1, which were previously utilized to create the "Jaws" reagent capable of transcranial neural silencing. Membrane-exposed residues are then mutated by standard site-directed mutagenesis or gene fragment synthesis when multiple residues are altered in parallel. If needed, directed evolution strategies are possible.

Promising candidates identified during the screening phase will be delivered via AAV virus, and the resultant expression will be assessed by high-resolution confocal microscopy after paraformaldehyde fixation. Bili-proteins are high-performance near-infrared fluorochromes in mammalian cells with minimal background fluorescence due to the long emission wavelength. This will represent a major advantage over Arch-variants in the same spectral range that require several orders of magnitude higher excitation irradiance than typical biological fluorochromes.

Optional early physiological screening by automated imaging: As preliminary high-throughput assessment of GEVI performance, high-K+ solutions may be utilized to depolarize the neurons (in the presence of NBQX, GABAzine, and TTX in order to block action potentials and synaptic inputs). As a rule of thumb, 30 mM, 50 mM, and 90 mM solutions correspond roughly to transmembrane potentials of −50, −10, and >=0 mV, respectively. $\Delta F/F$ will be measured over this range in a Tecan M200 plate reader, equipped with a fluid-delivery port to change extracellular potassium levels (and temperature and $CO_2$ control to ensure survival in clear ACSF solutions).

Rational minimization of immune response: Rational tuning of maquette properties can be extended to in vivo safety engineering. The extracellular loops play no obligate structure-functional roles, and thus can be substituted for human extracellular loops or minimized in exposure to the extracellular space to eliminate possible surface antigens (only 4 loop residues are required). All optogenetic reagents are exogenous proteins at high levels, yet safety engineering has largely been limited to appendage of terminal peptides, not rational alterations to core protein structure. The proposed degree of rational minimization of immune responses, without concern over impeding protein structure-function, is a new level of molecular precision for the field. Also maquette artificial proteins are thermostable, especially in multi co-factor systems, and thus is anticipated to be extremely robust.

Demonstrate fast optical voltage sensing in whole-cell patch clamped mouse hippocampal neurons. While K+ titrations are a facile method for depolarizing neurons, the gold standard assessment in GEVI development is whole-cell patch clamp electrophysiology and simultaneous optical recording. Multiple team members have tremendous experience performing such assays in the development of organic Stark effect probes, GEVIs, and optogenetic perturbation tools, in multiple preparations.

The electrophysiology rig matches the automated screening microscope (Leica DMI600B with PCO.edge camera and LED illuminators), except with a manual stage to reduce electrical noise. The rig is equipped with an Axopatch 200B amplifier and head stage, Sutter manipulators, and fluid delivery (bath perfusion and 8-channel picospritzer from Autom8), for simultaneous optical and electrical recording of whole-cell patch clamped neurons. Electrical recordings from cultured neurons will be obtained using standard pipette and Tyrode's bath solutions with GABAzine and NBQX synaptic blockers. The key signal-to-noise measure will be the optical change $\Delta F/F$ per 100 mV range in V-clamped neurons. To assess any potential undesired changes introduced by maquette expression, membrane resistance and capacitance (Rm and Cm) will be recorded in expressing and non-expressing pyramidal neurons (chosen to ensure uniformity in size and membrane channel repertoire). Maquette GEVIs are expected to leave these critical membrane parameters undisturbed on account of the compactness of the scaffold and lack of exposed charged residues.

After expression analysis and initial physiological screening, in order to assess temporal resolution on the sub-ms timescale, a further optimized rig will be used on an inverted microscope (Olympus) equipped with an ultra-high speed CCD camera (RedShirtImaging) for fluorescence measurements, an Axopatch-1D amplifier and patch clamp headstage for voltage control of the neuron and a micro-manipulator for accurate electrode positioning (Siskiyou). Necessary illumination intensity is obtained with a 200 mW Coherent laser of appropriate wavelength. For example, optical signals can be detected from single traces of whole-cell patch clamped hippocampal neurons having a very low $\Delta F/F$ of ~0.2% for a 100 mV depolarization (stained with the voltage-sensitive aminostyryl pyridinium dye, di-3-ANEPPDHQ, 50 μg/ml), thus establishing that very small changes in fluorescence can be recorded from these cells without, or with very modest signal averaging.

Although it has been shown that changes in fluorescence can be recorded from voltage-sensitive fluorescent protein, such as for the ArcLight variants as example GEVIs, these are orders of magnitude slower than the proposed maquettes of the invention. The action potential is complete in ~10 ms, but the resulting change in fluorescence is slower, and consequently, this particular GEVI responds quite non-linearly to subthreshold potentials and to action potentials, and is evidence for the critical nature of GEVI kinetics in resolving complex electrophysiological features. Nevertheless, it should pose no problem to record from transduced maquette proteins. Maquette GEVIs are expected to exhibit τ's that are 2-3 orders of magnitude faster, and capable of recording action potentials at frequencies greater than known to occur in brain. After establishing that action potentials from Maquette-based GEVIs expressed in hippocampal neurons can be recorded, it will then be recorded from mouse hippocampal slices, and maintained according to standard protocols.

Ex vivo validation of maquette GEVIs by simultaneous whole-cell electrophysiology and fluorescence imaging. Candidate maquette GEVIs can be evaluated by whole-cell electrophysiology in mouse tissue slices. Slice electrophysiology allows for more facile whole-cell recordings/clamping synaptic transmission studies, and optical recording than in vivo electrophysiology while still allowing for GEVI performance parameters to be assessed in intact brain tissue in which the maquette transgene has expressed long-term. Thus, slice experiments may provide the necessary characterizations for technology development, absent technical complications. Similar parameters may be measured as described above, on the high-speed imaging rig.

The transgene may be stereotactically delivered to the hippocampus with AAV virus. Possible changes in membrane capacitance and resistance may be monitored by recording maquette-expressing and wild type neurons from the same tissue slice, in order to anticipate and avoid protein designs that could alter spike timing. For initial assessments of safety in chronic in vivo use, and toxicity may also be assessed after 3 months transgene expression by immunohistochemistry in transcardial-perfused mice as previously reported in the development of microbial opsin for neural silencing (NeuN and GFAP staining, analyzed by veterinary histopathologist). Membrane localization and undesirable ER/Golgi blebbing will be assessed by confocal microscopy. Reagents with lesser performance or toxicity may be reengineered, in a critical feedback cycle that ensures in vivo utility upon distribution. In vivo whole-cell recordings are within the capabilities of a person having ordinary skill in the art.

Example 5. Development of Specific De Novo Reporters

Here, a de novo protein engineering taxonomy can be outlined and a strategy is provided by which the mammalian maquette can serve as a universal chassis for bottom-up construction of cell targetable sensors of diverse function and form (i.e. cytosolic and integral membrane) from the bottom-up through modifications in cofactor composition and stabilization by engineering the core, and cellular trafficking by engineering the exterior. Countless reporters can be created by mix-and-match of fluorescent or MR contrast "transducers" heptads modules, with ligand-binding "sensor" heptads that alter transducer output or measured signal, all within the same single-domain tetrahelical bundle of concatenated heptads. These strategies will be implemented to build the tools described hereon, and these exemplifying technologies are thematically focused on primary forms of excitability that govern fast circuit-wide dynamics, namely action potential propagation and calcium signaling.

Reporters Useful for Optogenetics

Figure 19:
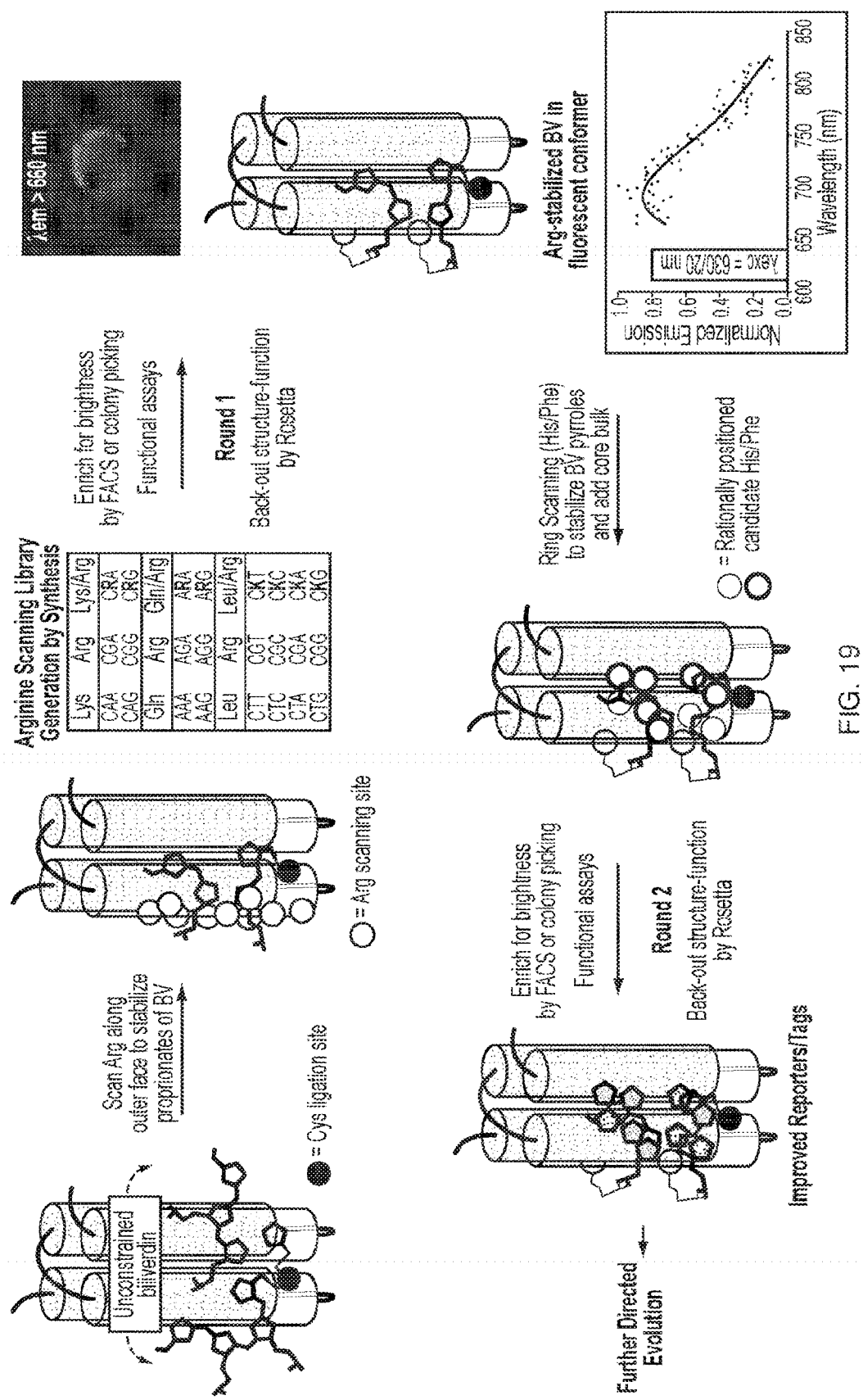
FIG. 19 illustrates the directed evolution of de novo fluorescent proteins and physiological reporters. Similar strategies apply for cytosolic dFPs or membrane proteins. Beginning with a well-placed cysteine for ligation, candidate mutation sites are identified by modeling to stabilize the propionates of BV with arginines, and to lock the bilin in its fluorescent conformer. The library is created in a single step using wildcards during chemical synthesis. Ring scanning with His/Phe stabilizes the pyrroles and adds hydrophobic core bulk to augment fluorescence. Brighter variants are candidates for experiments and subsequent rounds of computational design-guided directed evolution to stabilize the A-ring and add core bulk. Fluorescence Micrograph and Spectrum: Amphiphilic membrane protein expressed in live-cell yeast ($\lambda$em>660 nm, $\lambda$exc=630±10 nm).

Fluorescent proteins are the bedrocks of optogenetic reporters and cellular visualization. Far-red and near-infrared fluorescent proteins are especially useful for deep-tissue imaging and reducing background fluorescence from endogenous proteins. To further enhance the photophysical properties of dFPs, the power of computational protein design and directed evolution strategies that are mutually informative will be harnessed (FIG. 19). Variant dFPs can be designed with the bilin in different binding and stabilization sites using the Rosetta suite of modeling tools, and then enhanced by directed evolution in E. coli bacteria or S. cerevisiae yeast, using colony picking or fluorescence automated cell sorting (FACS) to screen for brightness and spectral properties. Beyond its utility in predictive design, Rosetta is also powerful for computationally backing out structure-function of directed evolution products to reverse-engineer them.

The general stabilization strategy described in the development of dFP1.0 will still be applied, but now with greater throughput for a larger search space. FIG. 19 shows an example scheme (drawn for a variant with a different BV attachment site). Based on modeling using structural data on maquettes bound to chemically similar heme co-factors the optimal position for the arginine residues will reside along the outer surface of the helix. Saturating all potential arginine (Arg) combinations at these residues requires ~500 candidates, and this positional scanning library can be chemically synthesized using strategic codon mixtures. Specifically, the candidate scaffold residues are all either lysine (Lys) or glutamine (Gln), which can be encoded such that a single mixed purine base (R, either A or G) in the second nucleotide position of the codon will encode for degenerate Arg/Lys or Arg/Gln. The one-pot gene synthesis pool will consist of an equal distribution of all desired combinations. Screened cells will be gated with increasing levels of stringency per induction round normalized for expression levels. The pooled plasmid library can be amplicon sequenced to get the complete sequence distribution because the maquette-encoding region is well within the amplicon-sequencing length limit. Similar approaches will follow in terms of library generation and screening for ring stabilization, where computational design will assist in defining the engineering landscapes toward specific conformers. Full photophysical properties can be measured on a plate reader using purified protein bacterially produced at extremely high yields of >100 mg/L (or even transducing cells). Later rounds will employ larger libraries created by random mutagenesis.

Reporters Described Herein May Employ Block-Like Modularity

Figure 20:
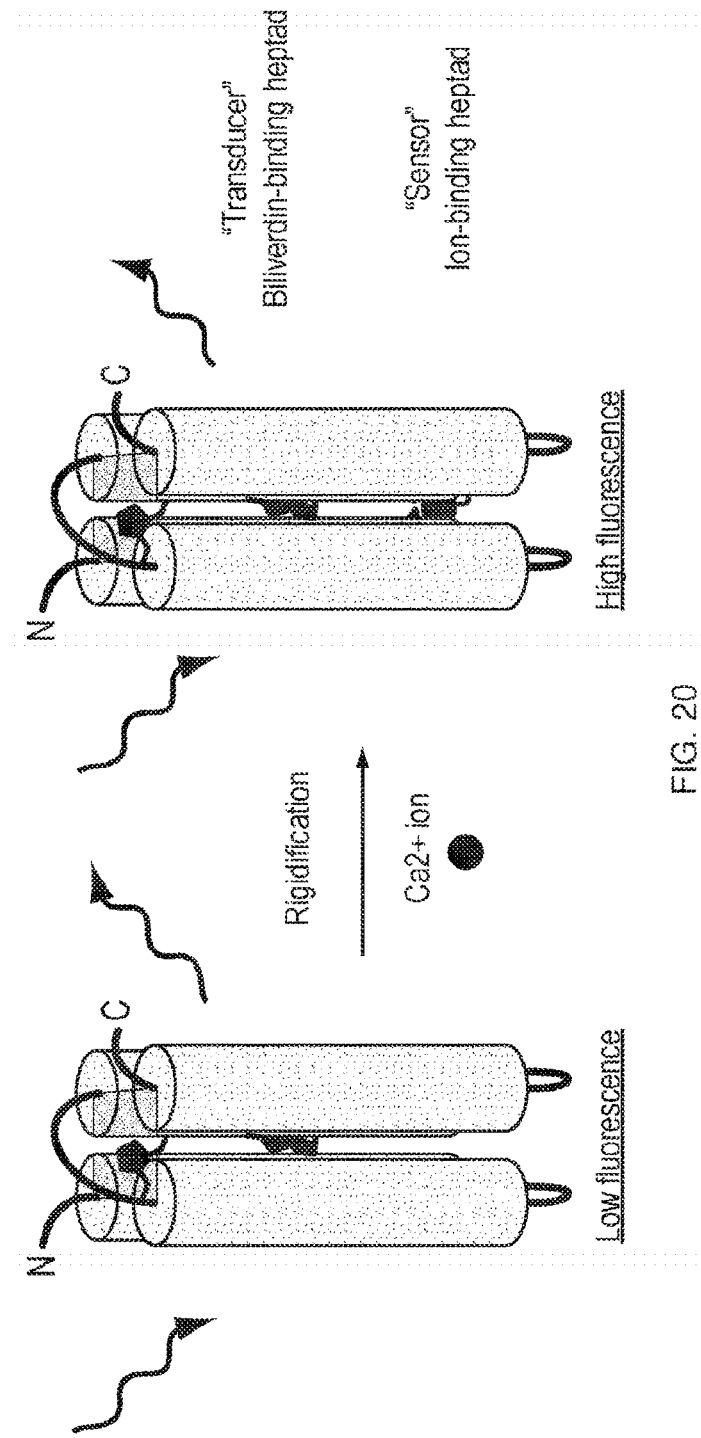
FIG. 20 illustrates single-domain IR fluorescent calcium indicators. Two modular binding sites are defined by different heptad repeats: a calcium binding sensor and a biliverdin-binding fluorescent transducer. Calcium binding rigidifies an intentionally dynamic and less fluorescent dFP (left: blurry to indicate motion), which increases fluorescence quantum yield by rigidification of the scaffold and binding pocket.

Maquettes are particularly useful for making compact reporters, which will be demonstrated by creating a 15 kD calcium indicator within a single bundle half the size of GFP (FIG. 20). A point of study includes calcium for its ubiquitous importance as a second messenger in all cell types, its ability to indirectly report neural activity, and our ongoing work in decoding the principles of calcium dependent transcription using high-sensitivity blue-light responsive optogenetic tools that are cross-activated when imaging existing red reporters. Because each heptad repeat of the bundle is theoretically a cofactor or ligand-binding module, there are intentionally two binding sites within dFP1.0, which was developed with sensing applications in mind.

Calcium binding is possible by hexavalent coordination with common metal coordination residues (histidine, glutamate, aspartate, etc.). Based on thermal melt circular dichroism, the scaffold rigidity greatly increases with each additional cofactor that is bound. To make a gain-of-fluorescence sensor, a dFP is used that is intentionally poorly fluorescent due to poor bilin stabilization and/or intentionally poor inter-helical interactions that make the protein more dynamic. Bound calcium will "clamp" the floppy structure, and consequently increase fluorescence by rigidification. An alternative but less desirable loss-of-fluorescence mode is possible if the calcium-binding site is close enough to the bilin D-ring to electronically interact with the transition dipole. Calcium-binding affinity will be evolved to a physiologically relevant dynamic range (0.01-1 µM) and maximal contrast by yeast FACS sorting in the presence of ionophores (or alternatively, with surface-displayed proteins in the absence of ionophores). The resultant product will be one quarter the size of naturally derived reporters like GCamp, and have the potential to be fast because self-assembling maquettes survey less conformational possibilities than natural proteins. Ion-binding kinetics will be assessed with purified proteins using standard stopped-flow fluorescence spectroscopy. Dynamic range and linearity will be measured by single-cell analysis of absolute calcium levels as previously done. Similar engineering principles can then be applied to further expand the toolbox to sensing other ligands.

Alternatively, a heptad repeat could be removed to evolve minimal dFPs that are only 8 kD in size and the entire bilin would still reside in the hydrophobic core. By reducing the size vs. typical fluorescent proteins by ~75%, mini dFPs may greatly improve the sensitivity of FRET-based assays by shortening the Förster distance (r) between donor and acceptor, since resonance energy transfer efficiency scales with a 1/r6 dependence. Another advantage of a mini dFP is a reduced genetic payload when used as an expression tag in AAV-mediated gene transduction/therapy, which is limited by its 5 kb payload.

Thus far, it is described how cytosolic de novo proteins can be used to create reporters analogous to GFP-based ones. De novo proteins, though, present the opportunity to create what is not possible with natural starting parts. Next, one such technology is proposed: a fluorescent integral membrane protein for ultrafast optical reporting of neural activity.

Reporters Described Herein as Biophysically Ideal Voltage Indicators

By transposing the core of cytosolic dFPs into amphiphilic scaffolds that form integral membrane proteins, an ultrafast genetically encoded voltage indicator (GEVIs) will be evaluated for optically recording the activity of excitable cells by the optical Stark effect. This biophysical sensing modality cannot be readily implemented in mammalian GEVIs built from natural starting points.

All living cells exhibit membrane potentials, and excitable cells, particularly neurons, use changes in their membrane potential (action potentials, synaptic potentials) for signaling. The ability to record the electrical activity of thousands of these neurons simultaneously is necessary to understand neural circuit-level dynamics that underlie behaviors, cognitive states, and affective states in both normal brain function and abnormal brain related pathologies. Accordingly, a critical need in neuroscience is a GEVI for reliable optical imaging of spiking activity across large populations of neurons in behaving animals. Intrinsic biophysical reasons limit existing GEVIs because they depend on protein structural rearrangements that limit temporal resolution and/or diminish fluorescence, the latter because the protein only reports voltage during a minor fraction of its cycle. Ultimately, this unavoidable consequence of using natural proteins hinders (i) the reliable detection of high frequency action potentials, (ii) the detection of sub-threshold "minis" critical to synaptic scaling and homeostatic plasticity, and (iii) the ability to resolve waveforms useful for deducing specific channel/receptor contributions to spiking and synaptic transmission.

The optical Stark effect is an ideal biophysical mechanism for reporting voltage because it is ultrafast (sub-ns or >10$^2$-fold faster than existing GEVIs) and an intrinsically voltage-sensitive phenomenon that requires no molecular motion since it is based in the field-dependence of an optical transition dipole. However, it is not readily apparent how one can create an ideal infrared Stark-based GEVI by existing approaches that use natural protein parts. An amphiphilic maquette may be prepared that orients BV within a transmembrane protein and with its dipole moment parallel to the transmembrane electric field so that it can report neural activity by the Stark effect. It may be referred to as: MASTER (Maquette Stark Effect Reporter).

Figure 21:
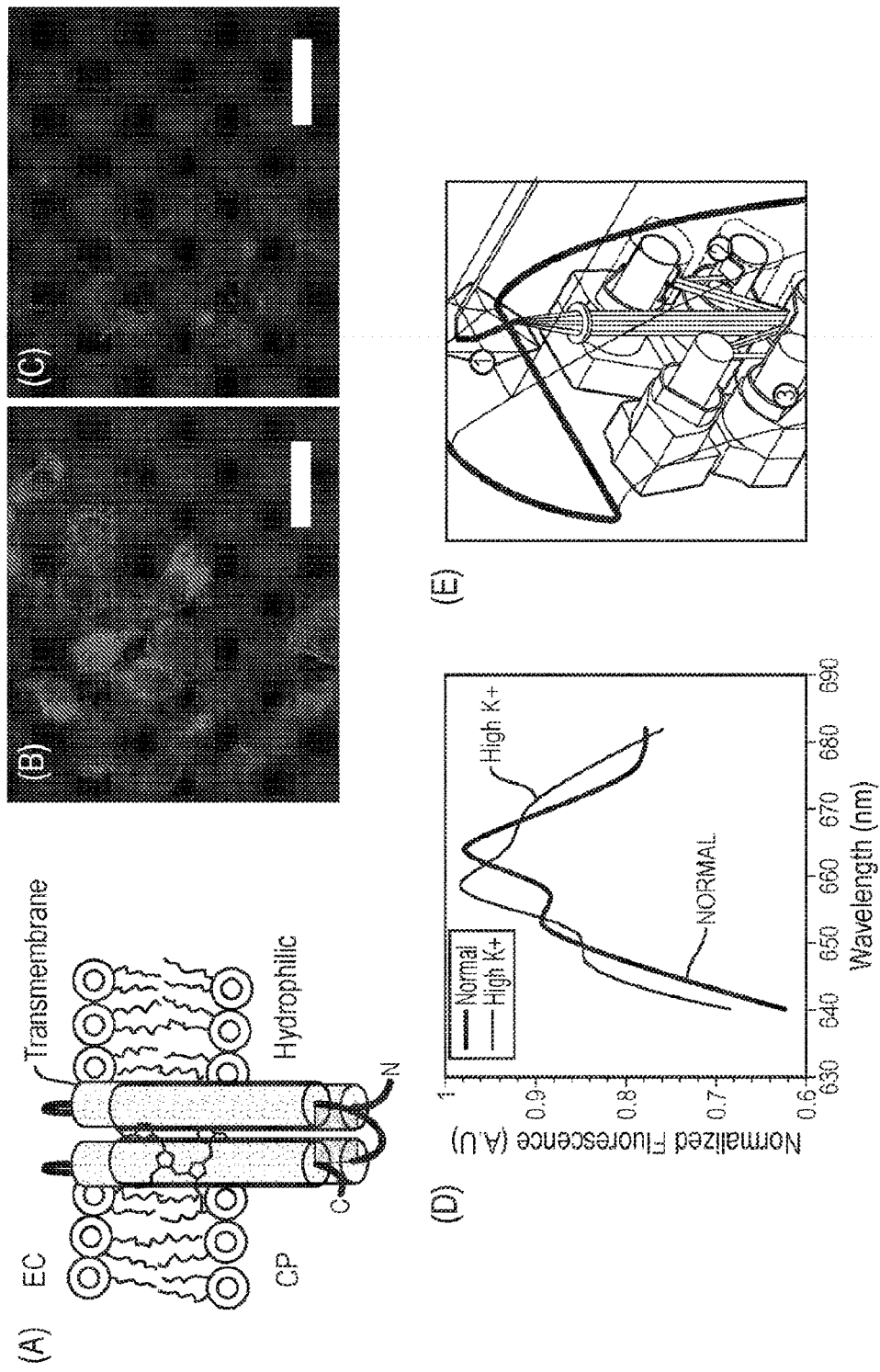
FIG. 21 illustrates de novo design of genetically encoded voltage indicator (GEVI) based on the ultrafast optical Stark Effect. (Panel A) First-generation MASTER design, which positions a field-sensing biliverdin co-factor across the plasma membrane parallel to the electric field, is composed of hydrophilic (gray) and lipophilic regions (purple). (Panels B-C) HEK293 cell line stably expressing GFPtagged MASTER created by lentiviral mediated transduction (scale=20 um, B: GFP, C: far-red, $\lambda$em>660 nm). Fluorescence decreases by ~10-15% $\Delta$F/F per 100 mV. (Panel D) Emission spectrum shifts upon high-K+ depolarization of transducing HEK293 as measured by spectral imaging. (Panel E) Spectral imaging apparatus on a Leica SP8 confocal STED microscope, in which excitation and emitted light is passed through dispersive optics for wavelength selection.

The MASTER is a chimeric maquette amphiphile comprised of a highly structured cytosolic/hydrophilic region that confers structure to a lipophilic transmembrane bundle (FIG. 21). The core structure of a dFP1.1 (which differs from dFP1.0 in that the cysteine attachment site is buried in the core as opposed to loop) is transposed into the lipophilic frame to orient the BV ring structure such that its B, C, and D rings, which together define the primary optical transition dipole, are theoretically parallel to the helices and consequently the transmembrane electric field. Live-cell spectral imaging data suggest that our first-generation MASTER reports voltage by a Stark spectral shift. An overall strategy moving forward may be to optimize MASTERs for improved plasma membrane localization and expression levels, to enhance the brightness for improved signal magnitude, and to determine the optical voltage reporting performance by simultaneous imaging and electrophysiology in cultured neurons. Localization may be enhanced by appending terminal signal peptides and/or transmembrane helices. To reduce ER/Golgi stress, export sequences may be appended. Membrane fluorescence will be quantified using Gaussian blurs as previously done.

Brighter variants may be evolved in yeast, which possess eukaryotic trafficking and secretory machinery and have long been used as an expression system for drug screening against mammalian membrane proteins and antibody discovery. MASTERs functionally express in yeast (FIG. 3) and can be selected by FACS or colony picking, and characterized by live-cell spectroscopy and spectral imaging (or purified protein spectroscopy), using similar brightness enhancement strategies described for the cytosolic variants (FIG. 19). To initially gauge Stark-dependent spectral shifts, high-K+ depolarizations may be performed (where, 30 mM, 50 mM, and 90 mM solutions correspond to transmembrane potentials ~ΔE of −50, −10, and >=0 mV, respectively). Experiments with proton ionophores will account for pH-related confounds to isolate the peak corresponding to the Stark transition. Voltage-sensitivity and temporal resolution can be assessed by simultaneous whole-cell patch clamp electrophysiology and optical imaging of MASTER-transducing excitatory hippocampal pyramidal neurons, which are abundant, easily genetically targeted, and fairly morphologically amongst neurons (purchased from the Penn School of Medicine Mahoney Institute). Spectral imaging will guide optical filter placement. Key performance parameters will be optical reporting kinetics, fluorescence voltage-sensitivity/contrast (ΔF/F per 100 mV), brightness, and unchanged membrane resistance and capacitance that would otherwise alter spike timing 19. Immune responses are not anticipated because the extracellular loops are only 4 residues each and ancillary in terms of structure-function beyond making it single-chain (i.e. modifiable if needed).

MASTERs will be ultrafast (much faster than high-speed cameras), brightly fluorescent in tissue, and extremely compact. These favorable characteristics are made possible by the Stark mechanism, which requires the cofactor to be placed across the plasma membrane in a specific conformation within a genetically encoded protein: an unlikely prospect with existing approaches but one that is possible with the mammalian maquette platform. Ultimately, MASTERs may optically recapitulate whole-cell electrophysiological recordings with no observable delay or waveform difference.

Here, it is described how dFPs can be transformed between fundamental protein types (from cytosolic to transmembrane) through rational remodeling of the exterior. Another functional diversification strategy is to remodel the core so it binds a cofactor that responds to entirely different forms of electromagnetic radiation. Next, it is describe how to bind and manipulate paramagnetic heme to build magnetic resonance (MR) contrast agents to be used as GFP-like reporters for non-invasive imaging and molecular fMRI.

Reporters Described Herein as Molecular fMRI Agents for Bridging the Translational Divide By remodeling dFP cores to bind paramagnetic heme cofactors instead of biliverdin, compact genetically encoded reporters may be prepared for non-invasive, large-scale imaging by functional magnetic resonance imaging with the biochemical precision and cell-specificity that BOLD imaging lacks (molecular fMRI).

While optogenetics has revolutionized cell-specific analyses in disease biology and cellular dynamics, large-scale imaging and direct translation of cell-expressible reporters require ones that respond to longer wavelength forms of electromagnetic radiation needed for non-invasive imaging techniques like MRI. MR contrast is typically enhanced by paramagnetic species that accelerate the relaxation time of nuclear magnetic moments of nearby water molecules through spin-lattice interactions (T1) and/or spin-spin interactions (T2). Using RF pulse sequences, an image is weighted to either T1 or T2 to enhance specific features that depend on the water properties of each tissue, and the presence of these contrast agents further accentuate anatomical features through local water interaction.

To create a de novo MR reporter, the maquette core can be designed to penta-coordinate the iron ion of heme in its high-spin state ($s=5/2$), which will affect nearby water molecules that partition into the core. Heme meets the cofactor requirements for fully genetically encoded reporters because it is endogenous to mammalian cells as the cofactor found in cytochrome P450 proteins and the biosynthetic precursor to biliverdin. A preliminary heme-bound protein does indeed exhibit contrast (FIG. 22, panels A-C) including under T2-weighted imaging conditions, which is of note because it indicates that the iron is intimately interacting with exchangeable inner sphere water molecules, unlike the more easily achieved T1 contrast that originates from less specific interactions with the outer sphere water molecules further from the paramagnet. Thus a viable starting point for a compact and de novo genetically encoded MR reporter is provided, to be further engineered to a sensitivity range within more physiologically relevant protein expression levels. It may be referred to as "3M", for mammalian maquette MR reporter.

To enhance heme-binding affinity (currently, Kd~1 uM) by directed evolution, bacterial colonies will be colormetrically selected, and heme incorporation will be confirmed by absorbance spectroscopy of purified protein, specifically the characteristic Q-band and Soret band of the iron porphyrin. Because heme partitions more easily into the core than biliverdin, the latter can be sterically occluded by constructing the cofactor binding pocket where it is known (from dFP development) that BV will not attach; indeed 3M binds heme in a 10:1 ratio vs. biliverdin by spectroscopic analysis. Next, T2 contrast will be enhanced by Rosetta-guided design for increased iron coordination to water, and then assessed by T2-weighted imaging in a 9.4 T 1H-NMR equipped with gradient coils (as used to generate FIG. 22, panel C). Beyond further proving the achievable protein engineering breadth of our de novo platform, this transformation of a fluorescent protein to a MR reporter will enable chronic and non-invasive protein tracking and quantitation in small and large mammals, useful for monitoring the pharmacokinetic distribution of gene and cellular therapies. Moreover, 3M will be a critical transducer module for molecular fMRI.

Reporters Described Herein as "Mix-and-Match" Molecular fMRI Reporters

Molecular functional magnetic resonance imaging (molecular fMRI) contrast agents are key technologies for medical imaging and translational neuroscience because they provide the dynamic molecular detail of optogenetic indicators, but at human relevant length scales and noninvasively. Importantly, existing genetically encoded agents, most notably a dopamine sensor evolved from a bacterial cytochrome P450 report biochemical levels directly through ligand-modified acceleration of water T1 relaxation times, whereas prevailing dynamic MR imaging techniques indirectly infer physiology from metabolism/blood oxygen levels (i.e. BOLD imaging) without biochemical specificity.

Figure 22:
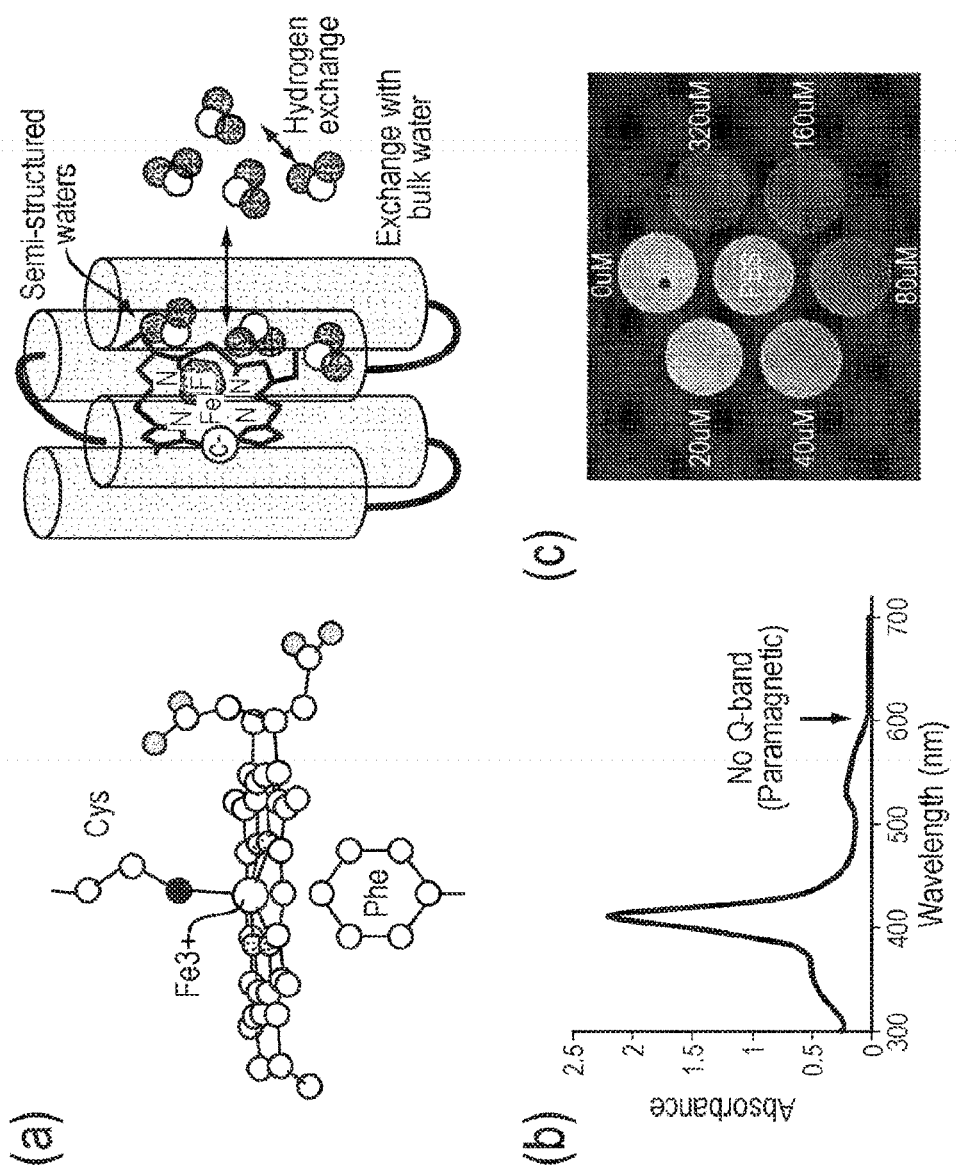
FIG. 22 illustrates de novo contrast agents for molecular fMRI. (Panel a) A hemoglobin-like pentacoordinated heme is paramagnetic and alters the T1 and T2 relaxation of local water molecules. (Panel b) Absorbance spectrum of purified 3M shows an intense Soret band and missing Q-band (arrow), indicative of paramagnetic iron porphyrins. (Panel c) T2-weighted contrast is evident by darkening in a protein concentration dependent manner (taken on a 9.4 T gradient coil H1-NMR). (Panel d) Molecular fMRI strategy by ligand-induced paramagnetic switching Ligand binding, here shown as calcium, rotates a Phe residue into the axial site of a fully coordinated diamagnetic heme, displacing water in the process. The now high-spin iron accelerates water T2 relaxation for MR contrast.
Figure 22:
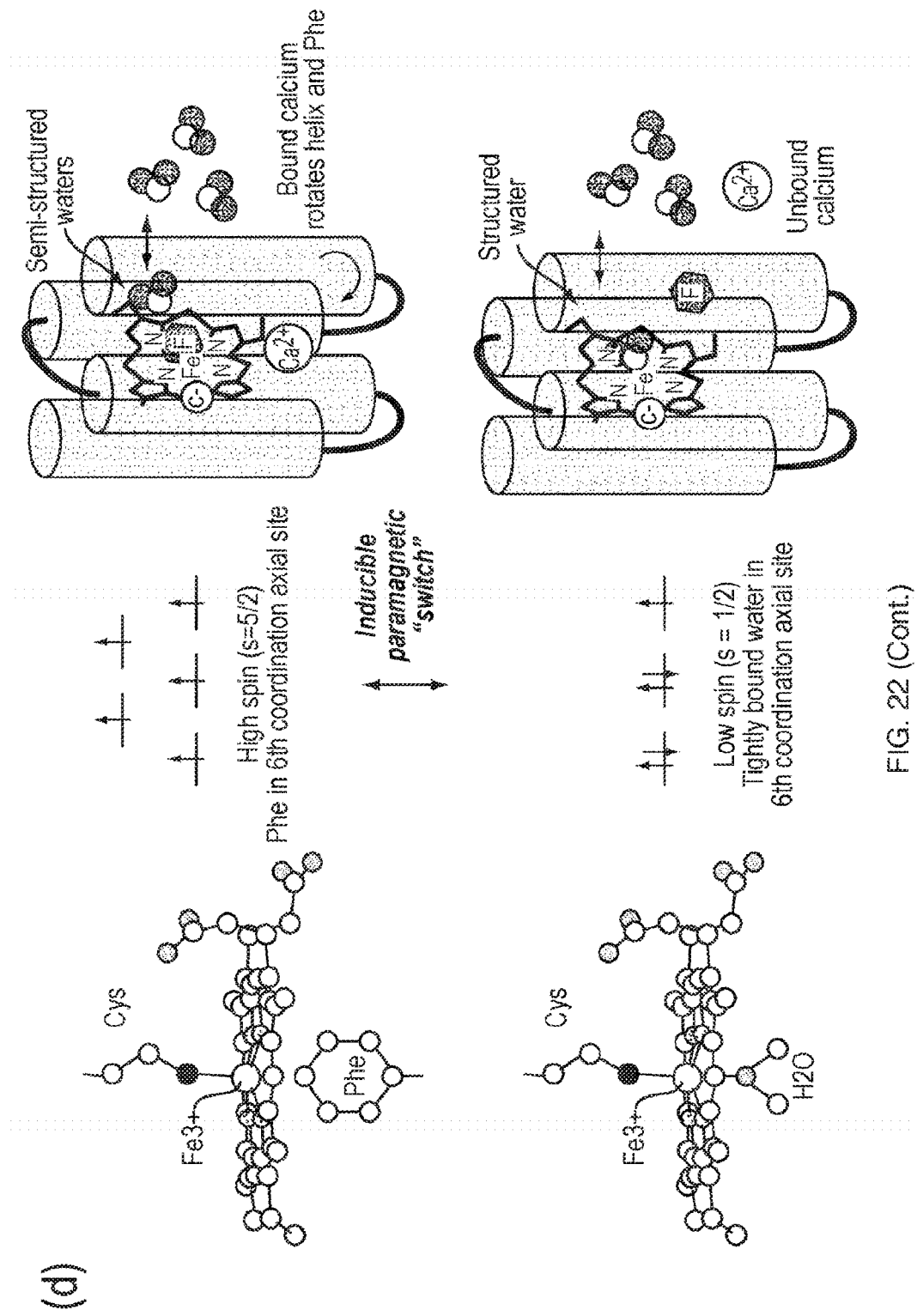

Because T2 is shorter than T1 relaxation, the T2 contrast exhibited is useful for reporting fast physiological processes. Under the configuration proposed, iron is high-spin ($s=5/2$) when the sixth (axial) heme site is empty and low-spin ($s=\frac{1}{2}$) when occupied by water. 3M can be designed to switch between spin-states to "switch on" MR contrast in a ligand-dependent manner. To create a change in magnetic susceptibility upon calcium-induced paramagnetic switching, one can emulate the hemoglobin-bound O2-induced paramagnetism that gives rise to BOLD signals. Specifically, 3M will be engineered to coordinate water in the heme axial site of a transducer heptad, and then this water will be released upon calcium binding in the sensor module to drive the switch (FIG. 22, panel D); spin-spin relaxation will occur and T2 contrast will be enhanced (and T1 by default). The switchable variant can be spectroscopically identified because the Soret-band of an iron porphyrin will shift and the Q-band will appear in the diamagnetic form (FIG. 22, panel B). From here, calcium-induced paramagnetism can be engineered through calcium concentration-dependent spectroscopy and water relaxation studies by T2-weighted imaging. Similar engineering principles can then be applied to further expand the molecular fMRI repertoire to other signaling molecules.

Example 6. Functional Mammalian Expression of De Novo Fluorescent Proteins

De novo proteins of human-made and computational designs are powerful tools for exploring principles and limits of protein folding, protein-protein interaction, and biochemical function without the distributed structure-function constraints imposed by natural scaffolds as starting points for protein engineering. However, despite their biomedical promise, completely non-natural proteins have not been functionally expressed in mammalian systems. Here, a platform is reported for creating optogenetic tools from first principles of protein design using "maquettes," or self-assembling single-chain four-helix bundles that serve as rigid frames for co-factor binding. Specifically, a compact (15 kDalton) and monomeric biliverdin-binding de novo fluorescent protein (dFP) is engineered that possess similar biophysical properties to existing far-red and near-infrared fluorescent proteins derived from natural proteins, despite lacking sequence or structural homology to known biological fluorochromes. The successful crossover of first principles-designed protein scaffolds into mammalian systems opens new doors for de novo protein technology, including as genetically encoded tools of completely artificial origin for elucidating molecular function and cellular structure in targeted cells.

For the purposes of this example, the artificial proteins may be named according to the following key:

| Scaffold Construct | SEQ ID NO. |
|---|---|
| $Z_{net} = -15$ | 103 |
| $Z_{net} = -12$ | 124 |
| $Z_{net} = -8$ | 122 |
| $Z_{net} = -3$ | 25 |
| $Z_{net} = 4$ | 127 |
| $Z_{net} = 8$ | 130 |
| $Z_{net} = 11$ | 108 |
| (1) | 112 |
| (2) | 23 |
| (3) | 113 |
| (4) (i.e., dFP1.0) | 25 |
| No Cys | 120 |
| No d ring stab | 23 |
| Leu Core | 120 |
| dFP [z = −15] | 117 |

Figure 23:
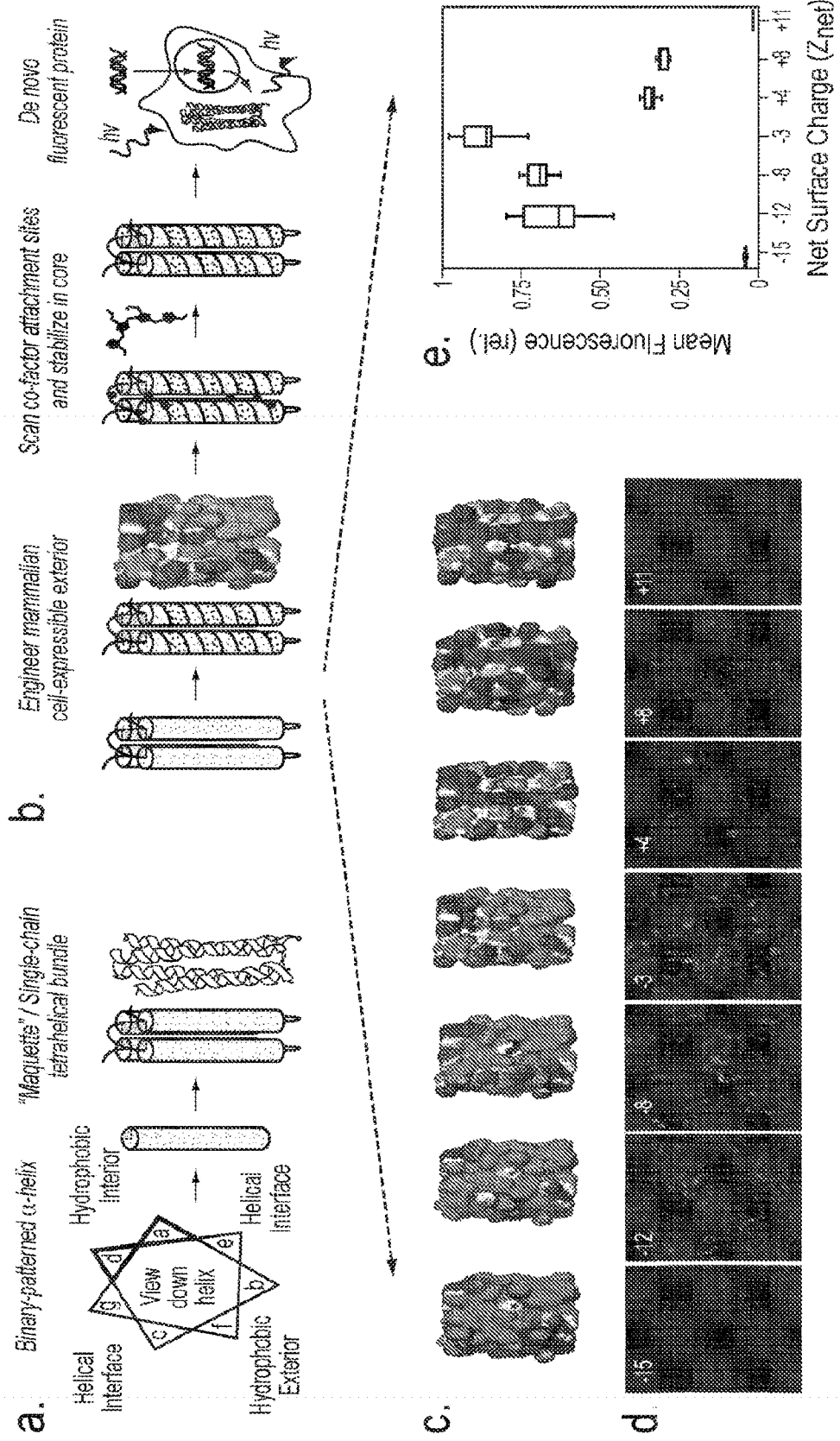
FIG. 23 illustrates the engineering of de novo protein maquettes to functionally express in mammalian cells. (Panel a) Maquettes are self-assembling single-chain tetrahelical bundles created by binary patterning of hydrophobic and hydrophilic residues of high propensity for $\alpha$-helix formation as described by the helical wheel. (Panel b) Strategy for creating a far-red de novo fluorescent protein by covalent attachment and stabilization of biliverdin in a fluorescent conformer within the core of mammalian cell-expressible maquettes (see Panels b-d). (Panel c) Fluorescence micrographs of HEK293 cells transducing maquettes of various net surface charges (Znet from −15 to +11), imaged by C-terminal GFP fusion tags (FOV=832 m). (Panel d) Pymol-generated exterior electrostatic maps (APBS, Adaptive Poisson-Boltzmann Solver) of the tested tetrahelical bundles (red=negative side chains, blue=positive side chains). Surface potentials are pronounced for visualization clarity. (Panel e) Relative GFP fluorescence by image analysis (box=median+/−quartile; whisker=range; N=4 coverslips, 3 FOV each).

Maquettes may be created by the simple binary patterning of hydrophobic and hydrophilic residues with high α-helical propensity, such that the single-chain polypeptide spontaneously forms a de novo tetrahelical bundle protein scaffold as predicted by first principles protein design (FIG. 23, panel A). Because biological co-factors can partition into and stabilize within maquette cores, they are useful for rational engineering of artificial holoproteins in which the structure-function of an individual residue is largely isolated owing to the modularity of the self-assembling frame. As with other de novo protein scaffolds, maquette studies to date have been limited to solid-phase synthesized peptides and bacterially overexpressed proteins. Thus, to fully harness the potential of de novo protein technology as a new platform for building artificial optogenetic tools (FIG. 23, panel B), the determinants for functional mammalian expression of single-chain maquettes were first established.

Figure 26:
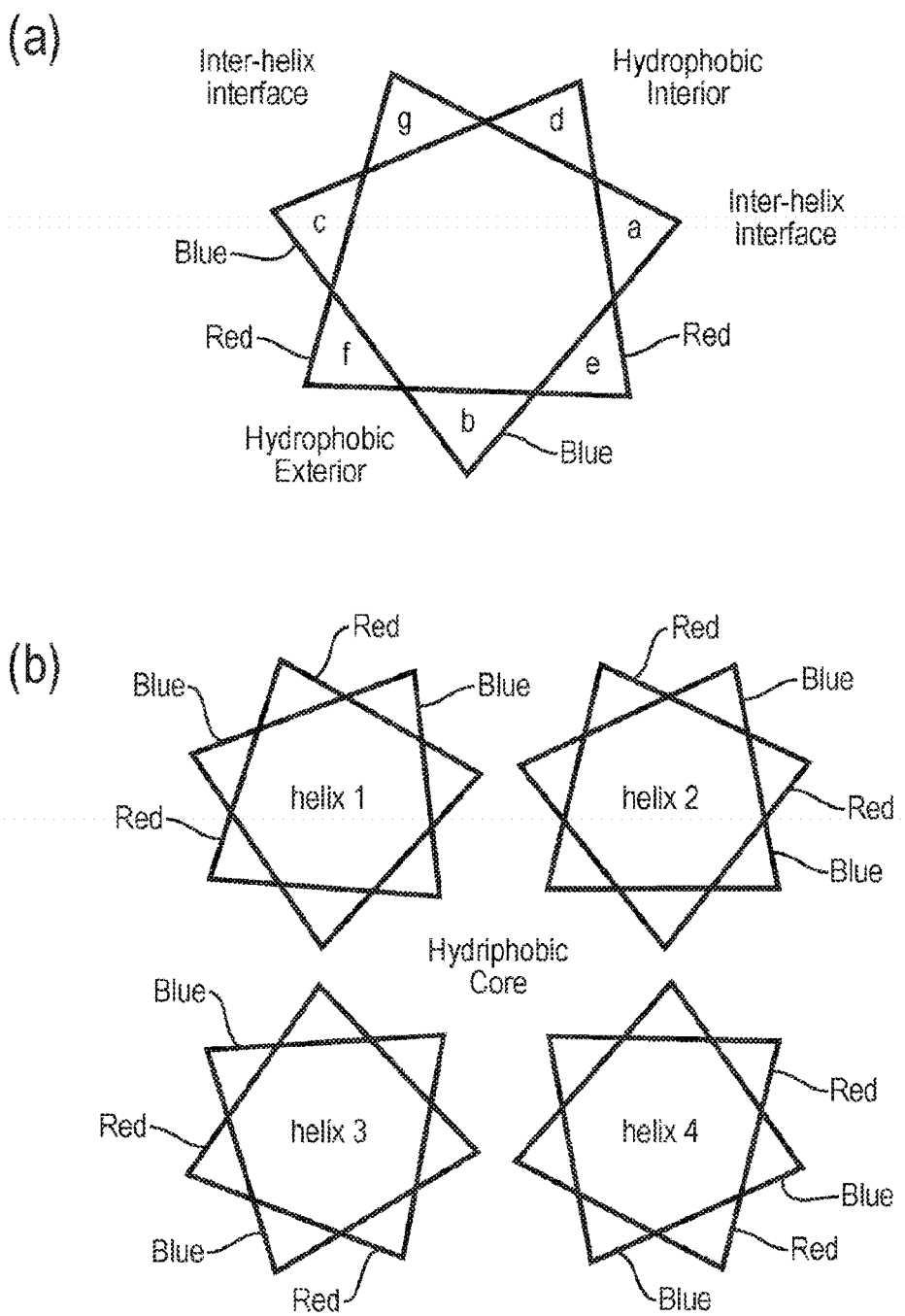
FIG. 26 illustrates a net surface charge scanning library. (Panel a) Helical wheel summarizing the relative positions of hydrophobic and hydrophilic residue placement. (Panel b) Schematic of four helical wheels to denote helix locations in the bundle. (Panel c) Protein sequences for the net surface charge scanning library (Red=negative side chains, Blue=positive side chains).
Figure 26:
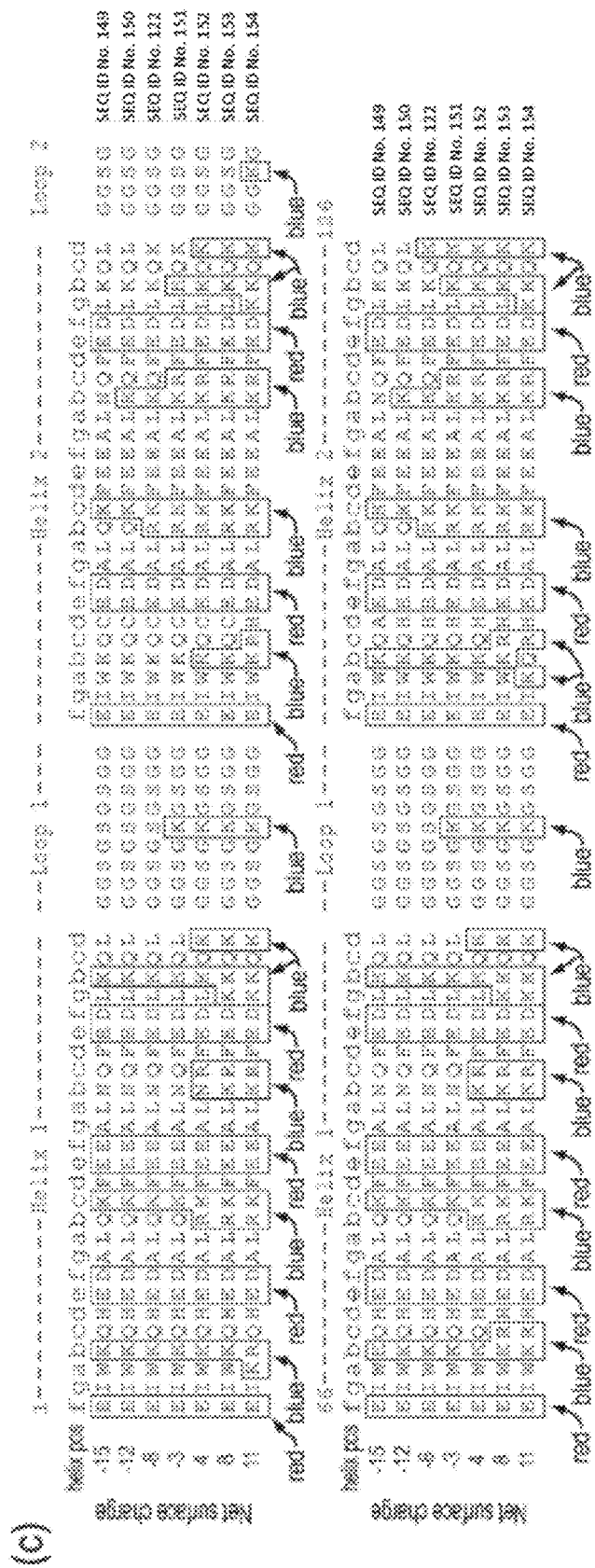
Figure 42:
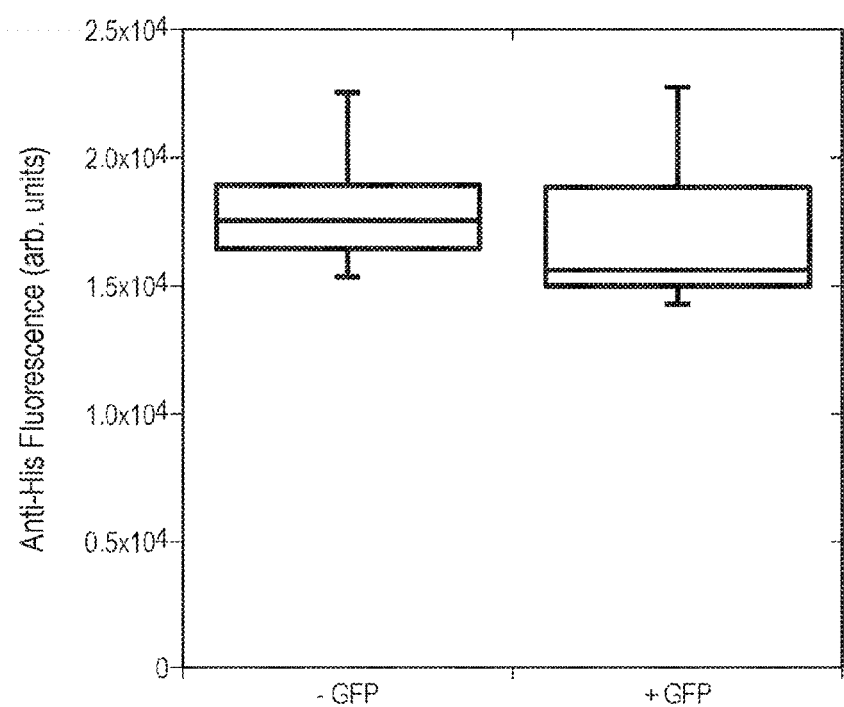
FIG. 42 illustrates an immunocytochemical analysis of the GFP fusion effect on mammalian maquette expression. HEK293 cells expressing 6×-His-tagged variants ([Znet=-3] with or without the GFP fusion) were paraformaldehyde-fixed 48 hours post-transfection, and then stained with DyLight650-conjugated 6×-His antibody (box=median+/-quartile, whisker=range). No difference in expression level is observed.

The role of net surface charge ($Z_{net}$) was determined on cellular expression levels in transfected HEK cells by scanning a range of variants from $Z_{net}=-15$ to $Z_{net}=+12$ (sequences for all in FIG. 26) that were quantified by fluorescence imaging of a C-terminal GFP tag (FIG. 23, panel C). The family of scaffolds was derived from published maquettes ($Z_{net}=-15$ and +11) or intermixtures of them, except with the B-loop between the second and third helices shortened to theoretically tighten the hydrophobic core in anticipation of the goal of creating a fluorescent protein. Like natural proteins, modest negative surface charge was optimal ($Z_{net}=-3$), but a wide range of negative and modest positive surface charges was well tolerated by mammalian cells overall ($Z_{net}$-12 to +8). From here on, all results are for the optimally charged variant ($Z_{net}=-3$), unless stated otherwise. It should be noted that all experiments were done in parallel to eliminate cell passage-specific variation, that the presence of the fusion tag does not alter the maquette expression levels by immunohistochemical analysis, and that protein levels estimated by microscopy correlated well with levels measured by spectroscopy of HEK cell lysate (FIG. 42). Despite the fact that maquettes have no natural orthologs, the first principles-designed scaffold may be applied to constructing diverse genetically encoded tools in numerous cell types and organisms from bacteria to humans, provided that the holoproteins will properly form in the cellular milieu with available protein machinery, which will be demonstrated here.

Figure 24:
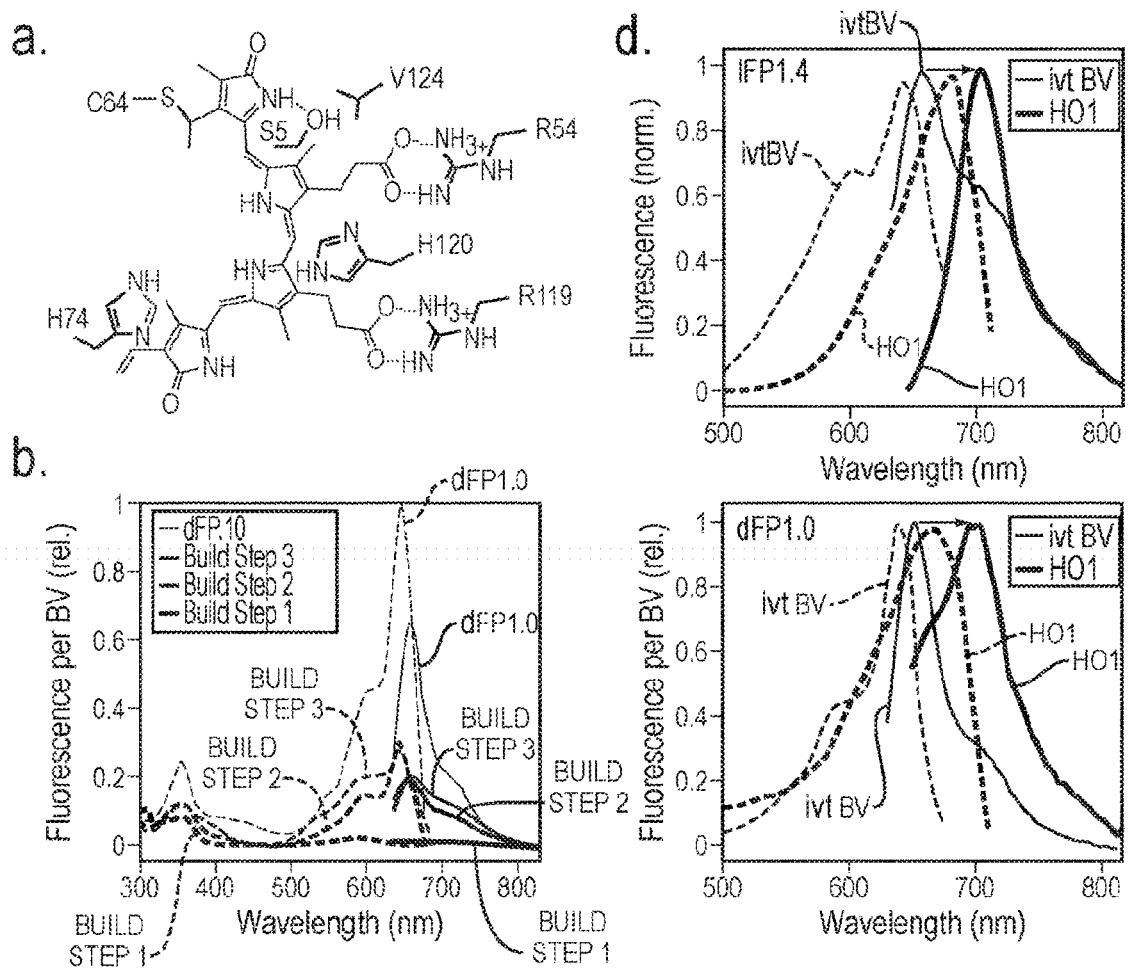
FIG. 24 illustrates the iterative engineering of a human-designed de novo fluorescent protein. (Panel a) Homology-based contact schematic for biliverdin (BV) stabilization within the core (black=side-chains, green=BV). (Panel b) Excitation (dashed line, $\lambda_{em}$>715 nm) and emission spectra (solid line, $\lambda_{ex}$=600 nm) of the iterative construction of dFP1.0. (Panel c) Photophysical summary of the dFP build series and IFP1.4 reference. Holoprotein was formed by either in vitro bilin attachment or in cellulo in HO-1 bacterial co-transformants plus levulinic acid. Brightness is a calculated parameter of quantum yield×BV attachment efficiency ($\varepsilon$=extinction coefficient, QY=relative quantum yield vs. Cy5). (Panel d) Excitation and emission spectra of the nature-derived IFP1.4 and first principles-derived dFP1.0 redshift from far-red to the near infrared by in cellulo holoprotein formation (red arrow for emission shift).

In parallel, maquette protein technology was demonstrated as having the ability to be leveraged to build de novo optogenetic reagents, specifically compact far-red/near-IR fluorescent proteins (iFP) that bind and stabilize mammalian-endogenous biliverdin IXa cofactor (BV), which is a bilin or linear tetrapyrrole (FIG. 24). Numerous fluorescent proteins (FPs) have been derived from natural non-fluorescent proteins such as bilin-binding bacterophytochromes (Bph), phytochromes (Phy), allophycocyanin light-harvesting complexes (AP), and fatty acid-binding muscle proteins (FABP), as well as flavin-binding LOV proteins (light-oxygen-voltage). These engineered variants follow the general principle of rigidifying the protein to stabilize the normally floppy co-factor in a fluorescent conformation, to limit solvent and oxygen access, and to prevent the intrinsic structural re-arrangements associated with their natural signaling roles. Insights from reported crystal structures of fluorescent proteins derived from Bph and Phy proteins led to a strategy for stabilizing the bilin in a fluorescent conformation by hydrogen bonding to the propionates and A-ring of the linear tetrapyrrole, plus the addition of hydrophobic core bulk around the co-factor D-ring (FIG. 24, panel A). Concerns over structural re-arrangements were limited because maquettes can be intentionally designed as less dynamic than natural signaling proteins.

Figure 27:
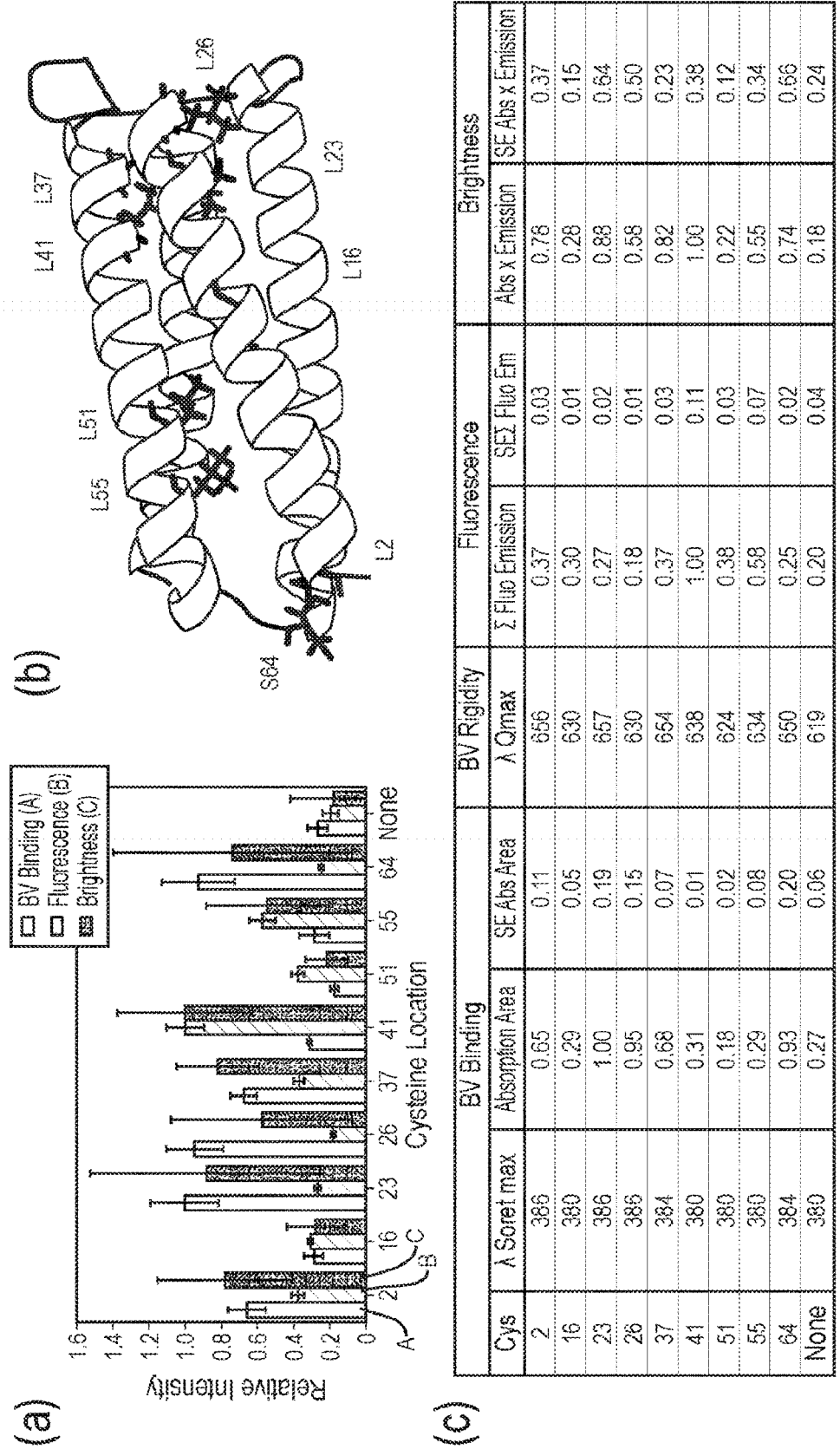
FIG. 27 illustrates a cysteine scanning for biliverdin (BV) attachment efficiency in vitro. (Panel a) Relative levels of BV attachment, fluorescence, and brightness of cysteine scanning library (mean±s.e.). BV attachment was quantified from the absorbance spectrum Soret band after FPLC purification. Fluorescence was measured at fixed holoprotein concentrations, estimated by bound BV levels (kx=600 nm), and brightness was a calculated parameter of absorbance multiplied by fluorescence. (Panel b) Pymol model of scaffold, with candidate cysteine mutation sites denoted. (Panel c) Summary of values including absorbance spectrum Soret- and Q-band peak wavelengths.
Figure 28:
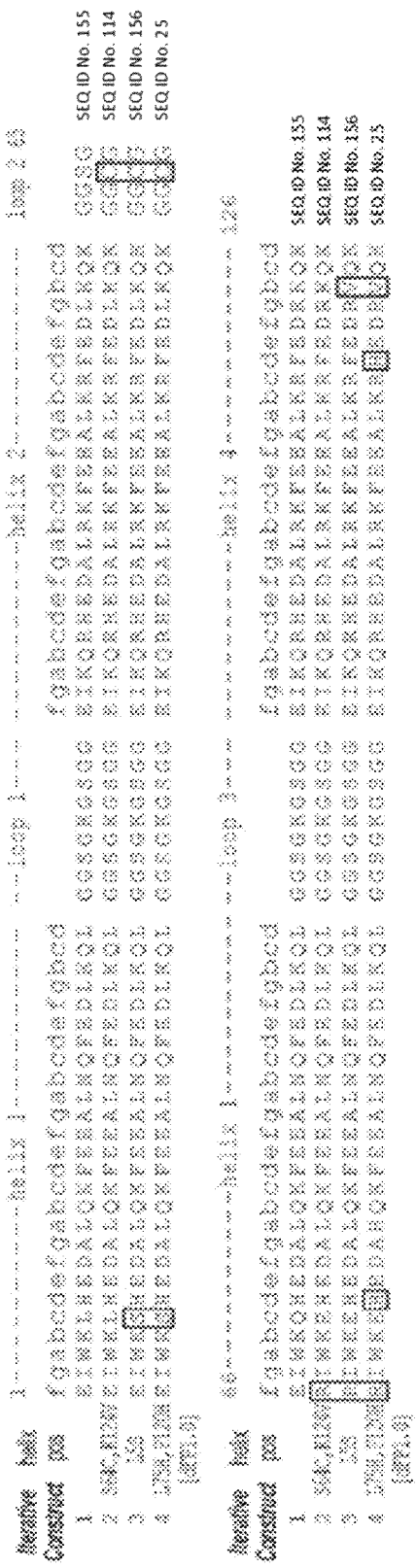
FIG. 28 illustrates protein sequences for iterative build of dFP1.0. Mutated residues from the initial scaffold that likely contribute to biliverdin stabilization are highlighted in yellow. The final iterative construct is untagged dFP1.0. The E66R mutation was introduced with S64C based on a consensus "CXR" motif found in bilin attachment sites of natural proteins, but does not contribute to stabilization.
Figure 29:
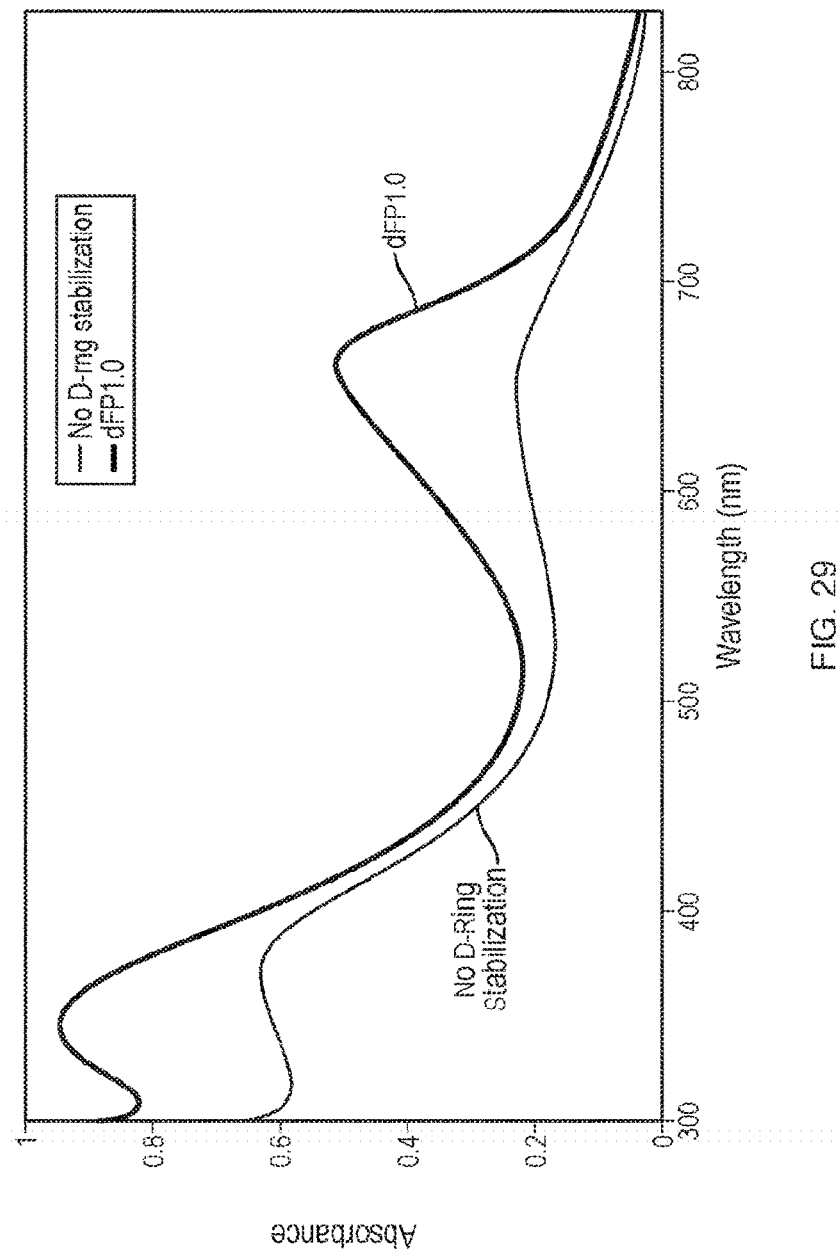
FIG. 29 illustrates spectral evidence for bilin rigidification. Absorbance spectra of fluorescent bili-maquettes before and after D-ring stabilization. Addition of core histidines in dFP1.0 resulted in an increase and sharpening of the Soret and Q-bands ($\lambda$=350-400 nm and 600-700 nm, respectively), which are hallmarks linear tetrapyrrole rigidification.

Cysteine sites were scanned throughout the core and loops for BV covalent attachment efficiency to bacterially overexpressed proteins, which were FPLC-purified after in vitro cofactor addition (FIG. 24, panel A, and FIG. 27). The scaffold was the same as the $Z_{net}=-3$ protein in FIG. 23, except all core residues were leucines to limit their potential contributions to bilin stabilization. It was found that bilin attachment trended with cysteine solvent exposure, with cysteines (S64C) in the solvent exposed B-loop or near the termini (L23C) providing good balances of appreciable cofactor attachment and baseline fluorescence without stabilization beyond partitioning into the hydrophobic core. In selecting initial starting points, a premium was placed on BV attachment efficiency over initial fluorescence based on reported challenges in cofactor uptake in Bph-FPs. Moreover, the E66R mutation was introduced with S64C based on a consensus "CXR" motif found in bilin attachment sites of natural proteins, but was found to not contribute to stabilization (FIG. 28). Subsequent fluorescent bili-maquette engineering progressed more quickly with the S64C variant, and thus, from hereon, all results are for maquettes constructed from the loop-bound starting point. Pymol modeling suggested that the BV proprionates were stabilized by existing arginines of the scaffold, thus defining initial constraints to cofactor conformation around which the binding pocket (FIG. 24, panel B) was designed. Further rational stabilization around this arginine-stabilized BV site was performed by first rigidifying the helical terminus by strategically positioning a valine, then further stabilizing the A-ring placement with a serine to hydrogen bond to the A-ring amine, and finally stabilizing the C- and D-rings with histidine residues positioned to pi-stack to the BV rings and provide hydrophobic core bulk that restricts protein movement and core water access. Each stepwise modification had the intended hierarchical effect of enhancing quantum yield (FIG. 24, panel C) and/or was accompanied by a sharpening of the Q-band peak of the bilin absorbance spectra (FIG. 29), both of which events are indicative of cofactor rigidification.

Figure 30:
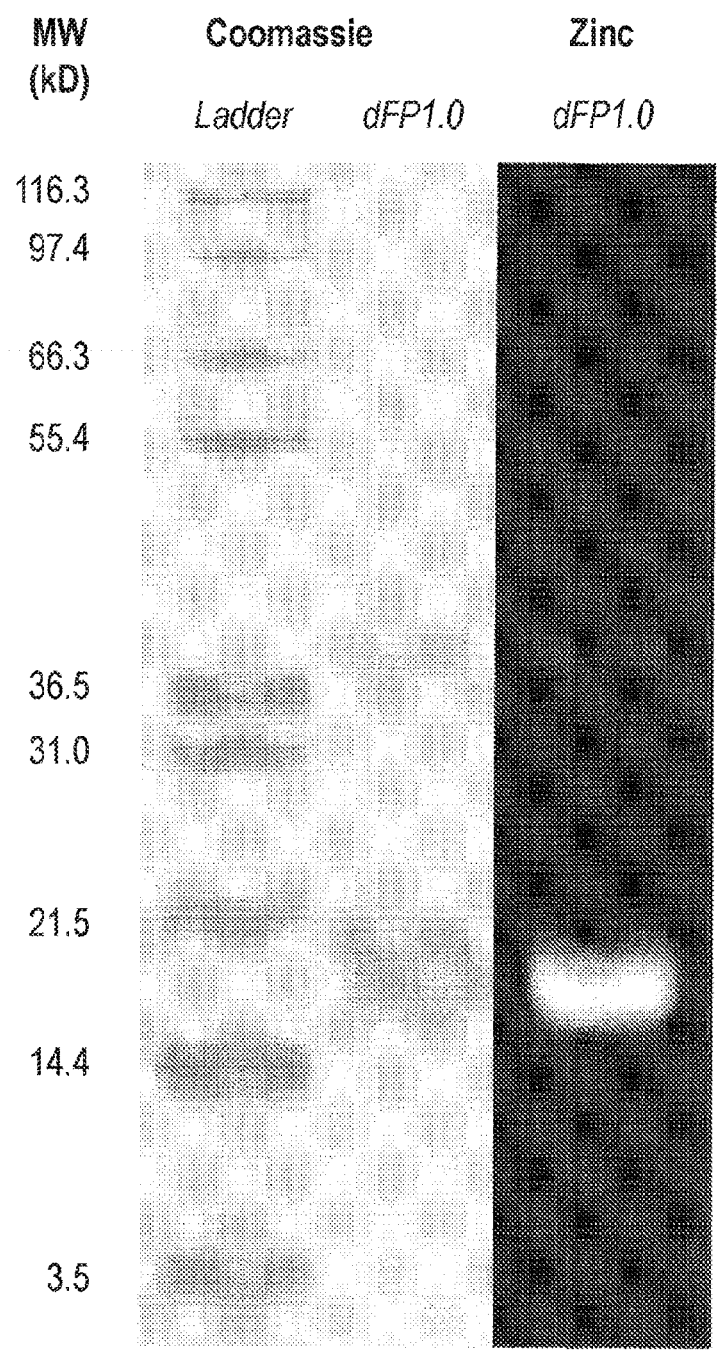
FIG. 30 illustrates covalent attachment of biliverdin to a maquette. Zinc-binding gel assays confirming covalent cofactor attachment in dFP1.0 holoprotein formed in vitro. His-tagged biliverdin-bound protein appears as a monomer at MW=17.4 kD.

The resultant de novo fluorescent protein, hereafter called "dFP1.0," showed far-red fluorescence properties ($\lambda_{ex}$=648 nm, $\lambda_{em}$=662 nm), and a relative quantum yield of 1.6% (vs. Cy5 reference standard). The quantum yield was consistent regardless of when BV was attached in vitro to purified apoprotein or when holoprotein was formed in cellulo by co-expressing heme oxygenase (HO-1) to up-regulate BV biosynthesis. Zinc gel electrophoresis confirms covalent attachment of the cofactor to dFP1.0 (FIG. 30). Thus, it is possible to construct a completely de novo fluorescent protein with biophysical properties within the general range of far-red and near-infrared fluorescent proteins that have been derived from natural photosensory proteins such as bacteriophytochromes and rhodopsins.

Figure 31:
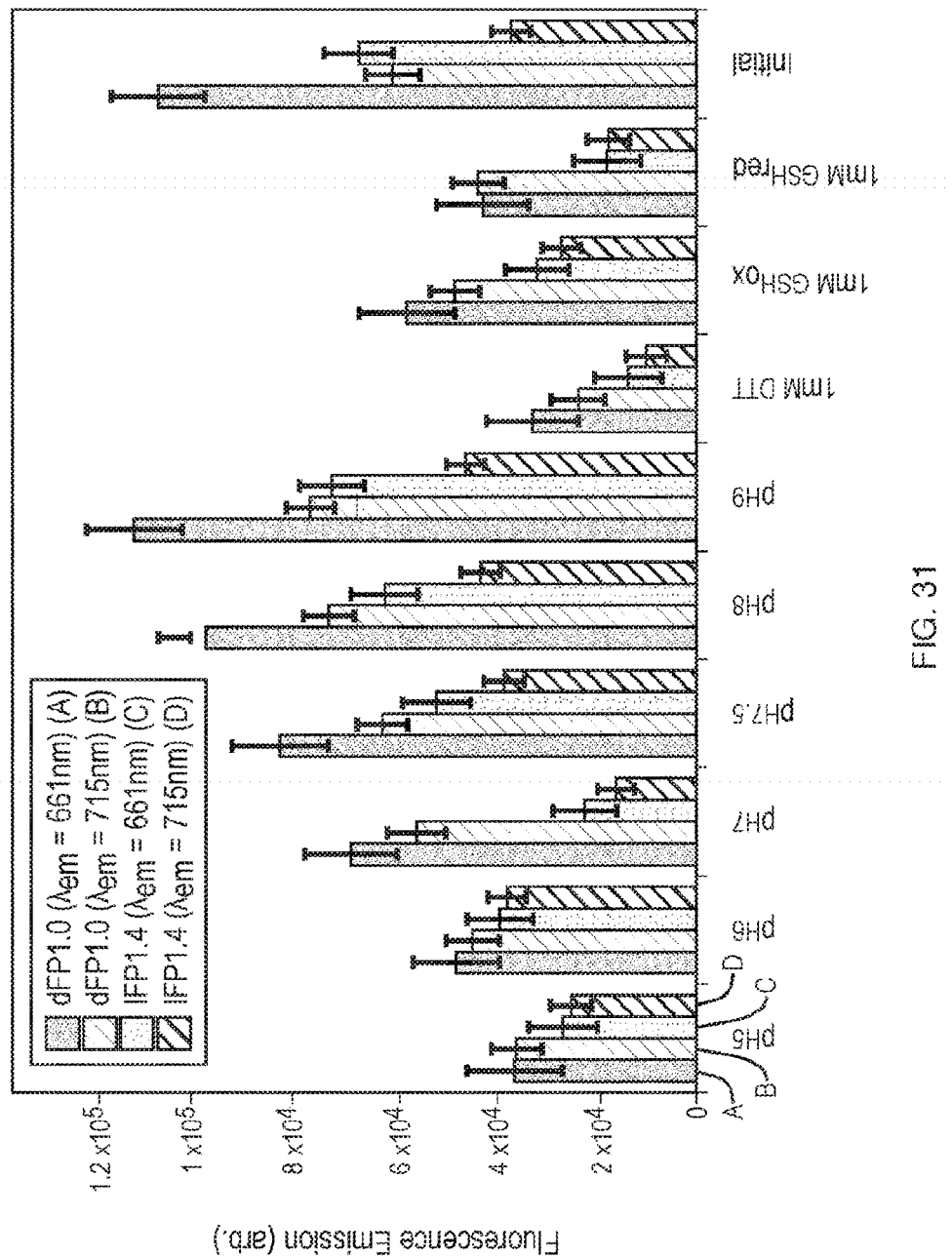
FIG. 31 illustrates spectral properties of in vitro refolded bili-proteins. Relative fluorescence (mean±s.e.) of dFP1.0 and iFP1.4 at $\lambda_{em}$=661 nm and 715 nm ($\lambda_{ex}$=600 nm and 640 nm, respectively) are not dramatically impacted when in vitro refolded with covalently attached cofactor, over a wide range of pH and in the presence of oxidizing/reducing agents at pH7 (DTT=dithiothreiotol, GSH=oxidized and reduced glutathione).

For both dFP1.0 and the Bph-derived iFP1.4 from *Deinococcus radiodurans* as reference control, there were consistent spectral differences between proteins produced by in vitro ligation to purified apoprotein vs. holoproteins formed in HO-1 strains. Specifically, in vitro ligation resulted in blue-shifted proteins ($\Delta\lambda_{ex}$~25 nm and $\Delta\lambda_{em}$~45 nm) (FIG. 24, panel D), presumably because the bilin adopts a more linearized or extended chain conformation. In vitro refolding of thermally denatured or urea-denatured protein with BV covalently attached did not significantly recover a population with the red-shifted spectrum regardless of pH or the presence of oxidant/reductant during refolding, thus suggesting that the difference is not attributable to limitations in cofactor availability or redox environment when folding in cells, and instead result from endogenous cellular factors such as lyases (FIG. 31). This finding is consistent with previously inferred lyase-dependence in ligation efficiency when engineered fluorescent bili-proteins are expressed in *E. coli*. Importantly here and as described below, the blue-shifted spectra are more representative of the properties of both de novo and nature-derived fluorescent bili-proteins when expressed in mammalian cells.

Figure 25:
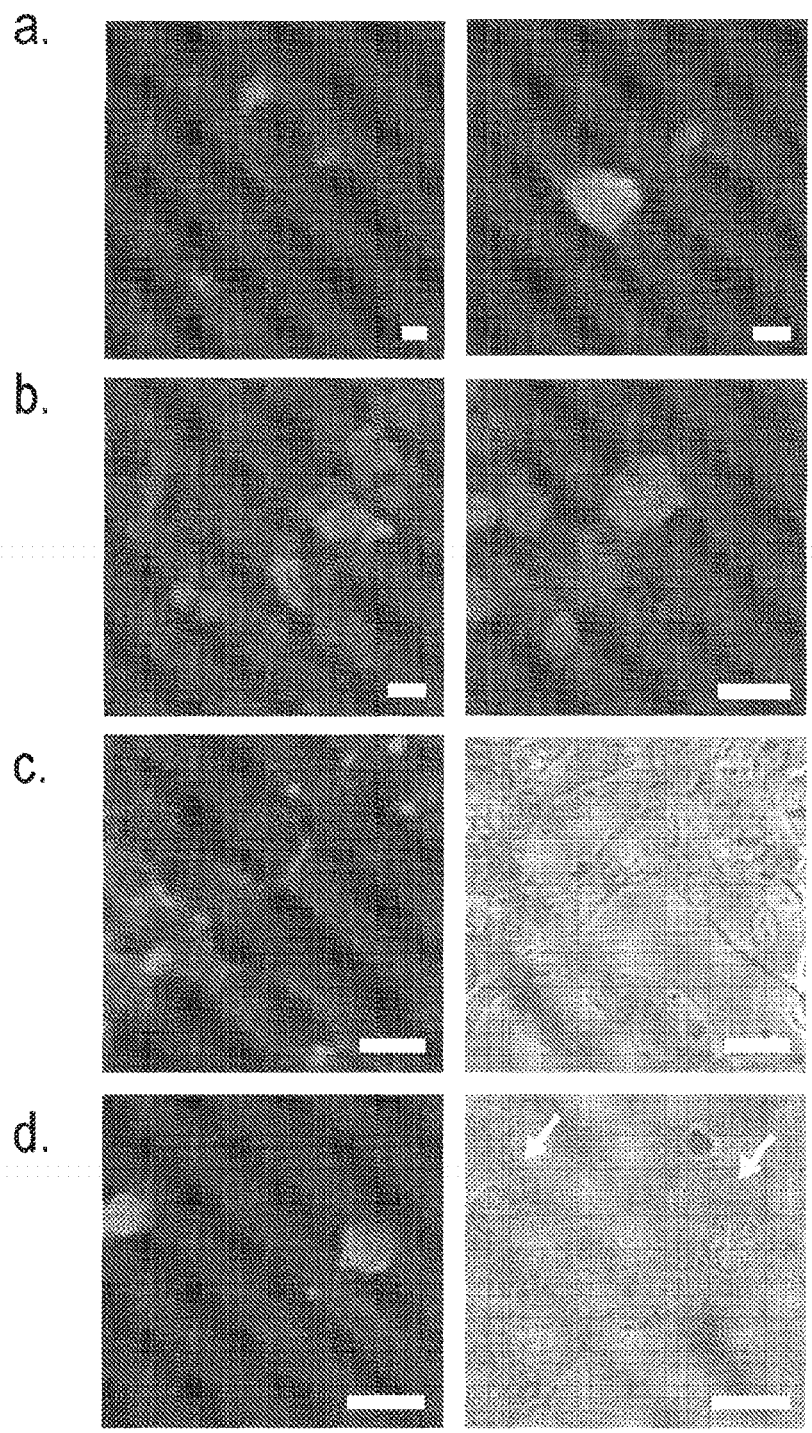
FIG. 25 illustrates the functional expression and cell-specific spectral properties of de novo fluorescent proteins in mammalian cells. Unless noted specifically, holoprotein was formed without the addition of any exogenous cofactor or biosynthetic enzymes and data is from transfected HEK cells. Fluorescence micrographs include (Panel a) lentiviral-transduced rat hippocampal neurons and (Panel b) HEK293 cells expressing dFP1.0; (Panel c) HEK293 expressing the integral membrane protein, human melanopsin with a N-terminal dFP1.0, and (Panel d) dFP1.0 with a C-terminal SV-40 nuclear localization tag (left: fluorescence, right: brightfield; arrow=nucleus). (a-d: $\lambda_{ex}$=631/28 nm, $\lambda_{em}$>665 nm, Scale=15 μm) (e) Total cellular brightness (bottom) and normalized by expression level (bottom) of dFP1.0 and IFP1.4 control (mean+/−stdev, trans=transfected, stable=clonal stably expressing cell line). (Panel f) Summary of mammalian-specific spectral peaks from HEK cell lysate from panels g-h. (Panel g) Mammalian-specific spectra of dFP1.0 from HEK cell lysate (dashed line=excitation ($\lambda_{em}$>715 nm), solid line=emission spectra ($\lambda_{ex}$=600 nm)) and live-cell spectral imaging (dots: emission stack $\lambda_{ex}$=635 nm). (Panel h) Mammalian specific spectra of IFP1.4 as described for in panel g.
Figure 25:
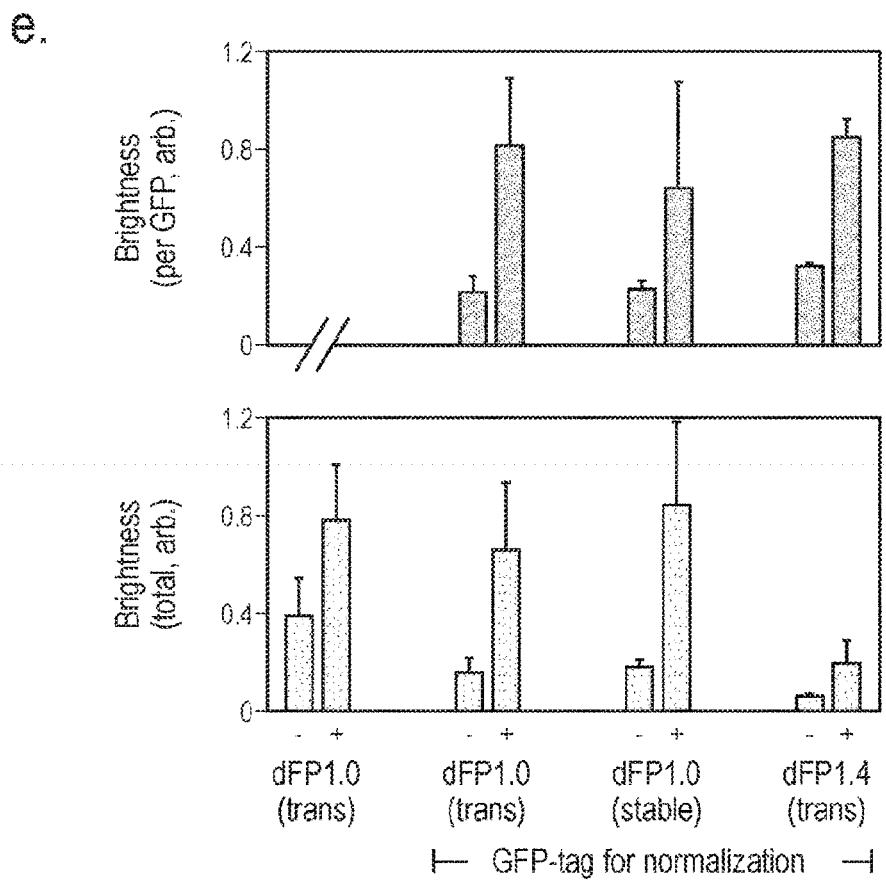
Figure 32:
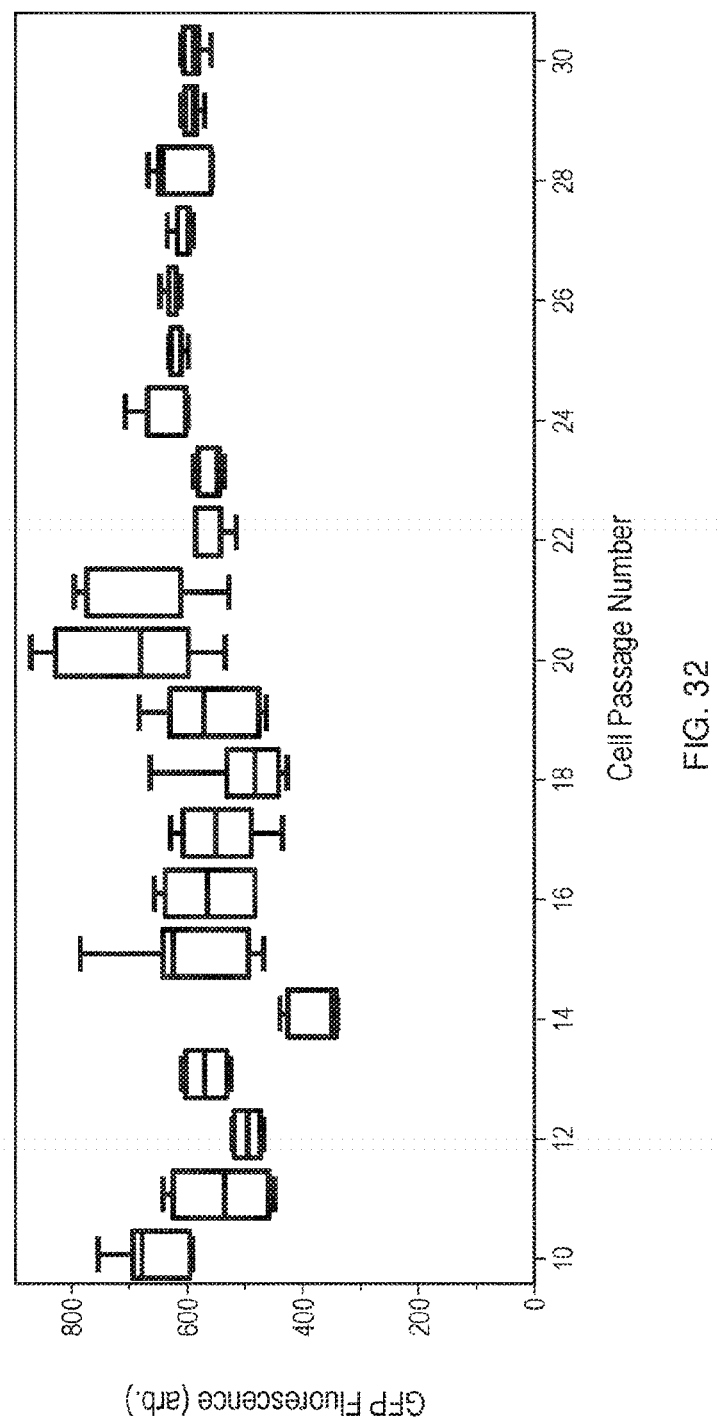
FIG. 32 illustrates dFP 1.0 transduction stability in mammalian cell lines. Stable HEK293 cell lines were produced by lentivirus-mediated infection and clonal selection. Expression of the de novo protein quantified by fluorescence is robust and uniform over 30 cell passages or the typical useful lifetime of immortalized mammalian cell lines (box=median±quartile, whisker=range).

To demonstrate viable de novo holoprotein formation in mammalian cells, dFP1.0 was transduced in numerous cell lines and primary rat hippocampal neurons by chemical transfection and/or lentiviral-mediated delivery (under the CMV promoter for cell lines and CaMKII promoter for excitatory neurons) (FIG. 25). All images shown were acquired without the undesirable supplementation of exogenous BV or overexpression of HO-1. Untagged dFP1.0 had similar characteristics to the GFP-tagged variant used for expression level-normalized assays. Cytosolic dFP1.0 clearly forms holoprotein in transducing mammalian neurons and HEK cells (FIG. 25, panels A and B). It was also viable as a fusion tag for integral membrane proteins that traffic through the endoplasmic reticulum/Golgi pathways (shown here fused to human melanopsin, hOPN4; FIG. 25, panel C), as well as a nuclear localization tracker (shown here fused to a peptidyl nuclear localization sequence, NLS; FIG. 25, panel D). Thus, the compact de novo protein, which is a 15-kilodalton monomer or half the size of GFP as validated by gel electrophoresis of HEK cell lysate (FIG. 42), remains functional and can mature in varied sub-cellular environments and neuronal processes. Moreover, cytosolic expression was highly stable with limited fluctuation in dFP1.0 levels in stably expressing clonal HEK cell lines over 30 trypsinized cell passages or the typical phenotypically useful lifetime of immortalized cell lines (FIG. 32).

Fluorescence increased with co-factor supplementation and/or stable expression that facilitates long maturation times, indicating that biliverdin availability does limit the brightness of dFP1.0 like Bph-derived fluorescent proteins (FIG. 26, panel E). dFP1.0 was brighter overall than IFP1.4 in transfected HEK cells, presumably due to greater expression levels of the compact maquette (FIG. 33) given that the expression-level normalized fluorescence of iFP1.4 is greater than dFP1.0 (consistent with the respective properties of the bacterially produced proteins in FIG. 24, panel D). dFP1.0 was photostable under bright illumination of 63 mW/cm$^2$ on-peak, with a first-order exponential decay of $\tau_{dFP1.0}$=263±18 seconds or roughly half of the stability of the iFP1.4 reference, $\tau_{iFP1.4}$=574±25 seconds.

Figure 34:
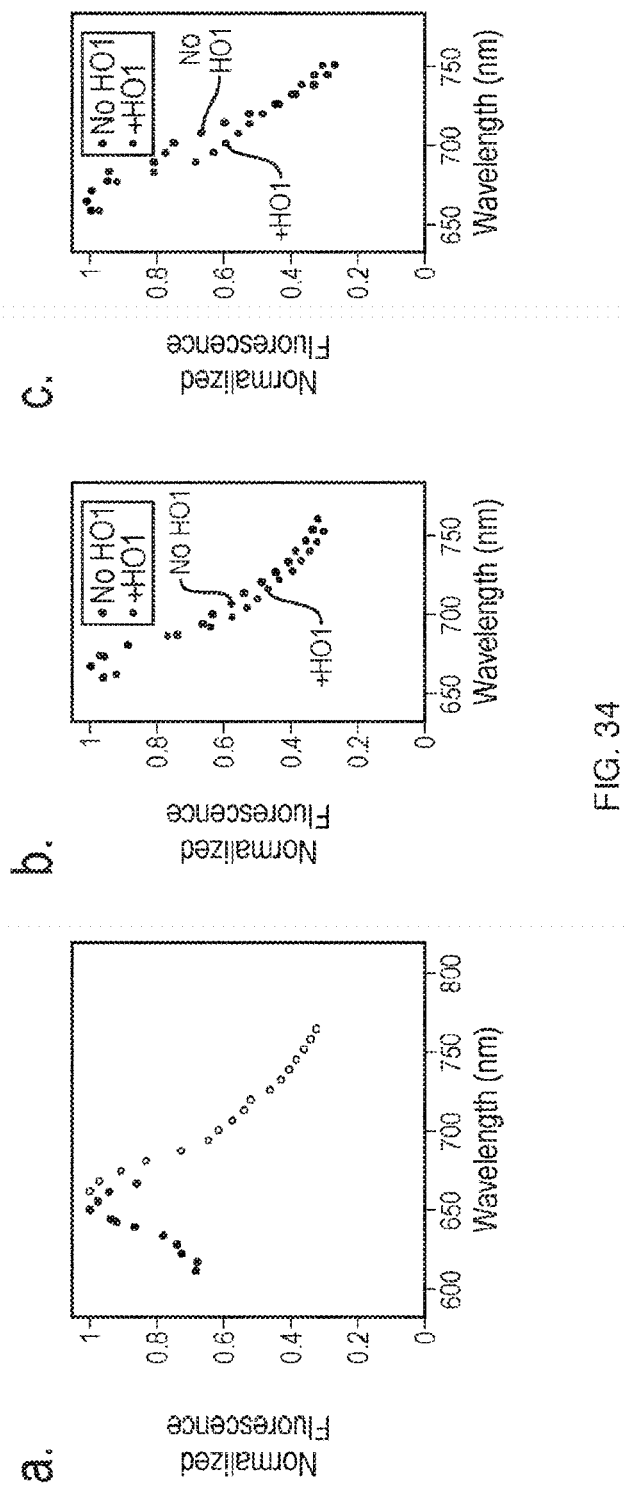
FIG. 34 illustrates that mammalian-specific spectra of dFP1.0 and IFP1.4 do not shift over long protein maturation periods. (Panel a) Spectra of dFP1.0 in rat hippocampal neurons obtained by live-cell spectral imaging (excitation stack $\lambda_{em}$=680-800 nm; emission stack $\lambda_{ex}$=635 nm). The Stokes shift observed by spectral imaging is consistent with that of cell lysate obtained by spectroscopy. (Panel b) Emission spectra for dFP1.0 and IFP1.4 do not shift depending on heme oxygenase co-expression (HO1). Only single-cell spectral imaging is shown because chronic expression of HO1 was overall toxic to cells in our hands, thus hindering cell lysate measurements from pooled cells.
Figure 35:
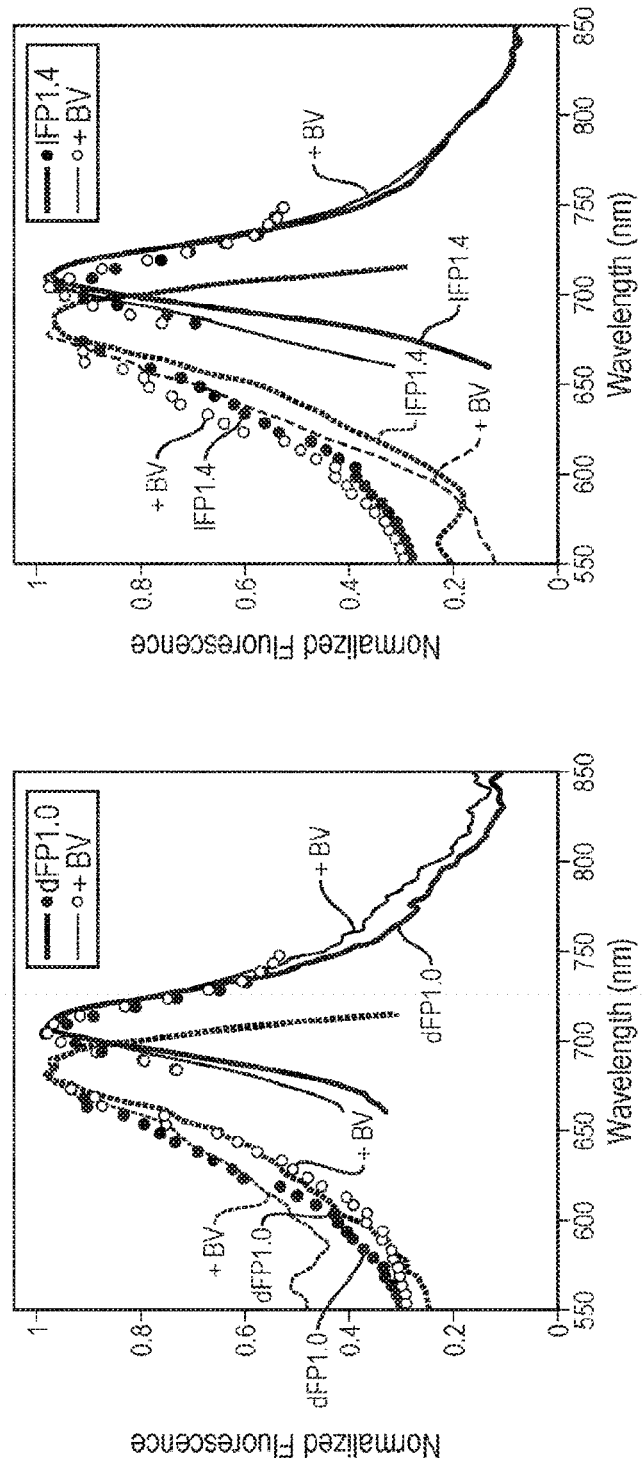
FIG. 35 illustrates spectral properties of fluorescent bili-proteins in yeast. Live-cell spectrum acquired by spectroscopy (lines) and spectral imaging (dots) of dFP1.0 and iFP1.4 expressed in engineered S. cerevisiae. Both the natural and de novo bili-proteins exhibit red-shifted spectra from mammalian live-cell spectra (Lysate: excitation $\lambda_{em}$>735 nm, and emission $\lambda_{ex}$=640 nm; Live cell spectral imaging: excitation stack $\lambda_{em}$=680-800 nm, and emission stack $\lambda_{ex}$=635 nm with 15 nm bandpass on emission).

Because of the aforementioned possible cellular environment-specific differences in spectra, the spectral properties were measured for fluorescent bili-proteins in mammalian cells, which to the best of our knowledge, have not previously been reported. Excitation and emission spectra of HEK cell lysate were measured on a plate reader, and cross-validated by live-cell (unfixed) emission spectral imaging on a confocal microscope equipped with dispersive optics for wavelength selection. Data acquired by both methods were in agreement that both de novo and Bph-derived bili-proteins have spectra that match those formed by in vitro co-factor attachment to bacterially expressed apoproteins, and not the near-infrared spectra of those of produced in HO-1 strains (FIG. 24, panels C and D, and FIG. 25, panels F to H). Neither BV supplementation nor HO-1 co-expression (FIG. 34) shifted the emission spectra in mammalian cells, a finding that in conjunction with the in vitro refolding results further suggest that cell-specific spectral shifts are attributable to endogenous factors that influence bilin conformer rather than cofactor availability or cytosolic milieu during folding. Proteins expressed in *S. cerevisiae* yeast also exhibited cell-specific spectra, in this case of the near-infrared conformer as measured by both spectroscopy and spectral imaging of intact cells (FIG. 35). These numerous data agree with existing hypotheses that bilin attachment can be autocatalytic and an important function of lyases is to promote specific bilin conformations. Thus, optogenetic applications of any fluorescent bili-proteins should be informed by cell-specific spectroscopy to optimize optical filter placement for each expression system.

Figure 33:
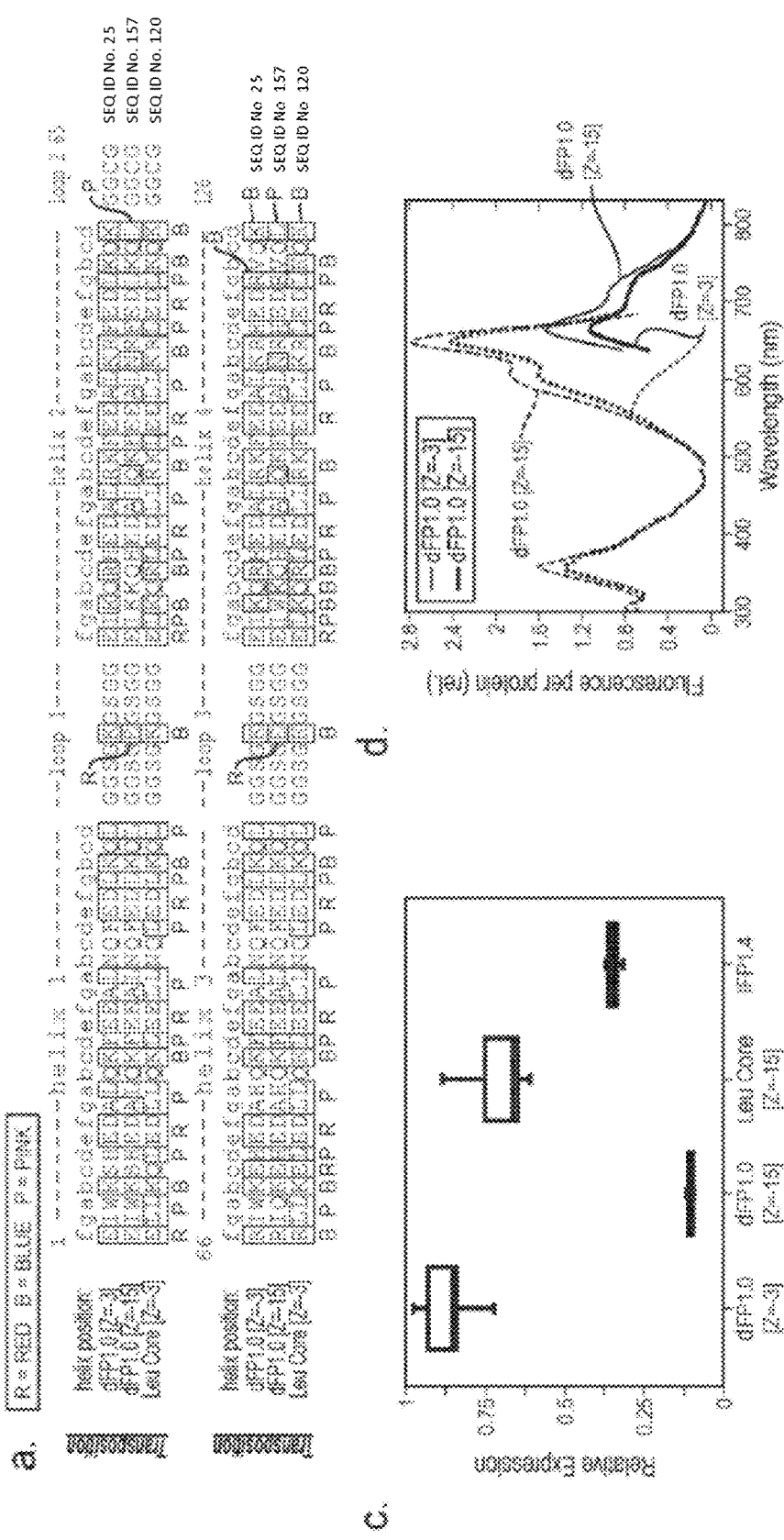
FIG. 33 illustrates isolated structure-function between the dFP hydrophobic core (photophysical determinants) and scaffold exterior (expression determinants). (Panel a) Sequences used for dFP transposition analysis (red=exposed negative side-chain, blue=exposed positive-side chain, pink=core leucine). Supercharged dFP[$Z_{net}$=-15] is a transposition of the hydrophobic bilin-binding core of dFP1.0 into the $Z_{net}$=-15 scaffold. "Leu-Core" has leucine substituted for all hydrophobic core residues of dFP1.0. (Panel b) Schematized dFP[$Z_{net}$=-15] design. (Panel c) Relative protein expression levels in transfected HEK cells assessed by fluorescence imaging of C-terminal GFP tags, including iFP1.4 control (box=mean±s.d., whisker=range). Leu-Core has an identical exterior and similar expression level to dFP1.0, whereas dFP[$Z_{net}$=-15] lacks viable mammalian expression. (Panel d) Excitation ($\lambda_{em}$>715 nm) and emission ($\lambda_{ex}$=600 nm) spectrum of dFP1.0 and dFP[$Z_{net}$=-15]. (e) Summary of spectral properties. dFP absorbance and fluorescence properties governed by the hydrophobic core are preserved during core transposition despite loss of mammalian viability from the change in exterior (QY=relative quantum yield, ɛ=extinction coefficient).
Figure 33:
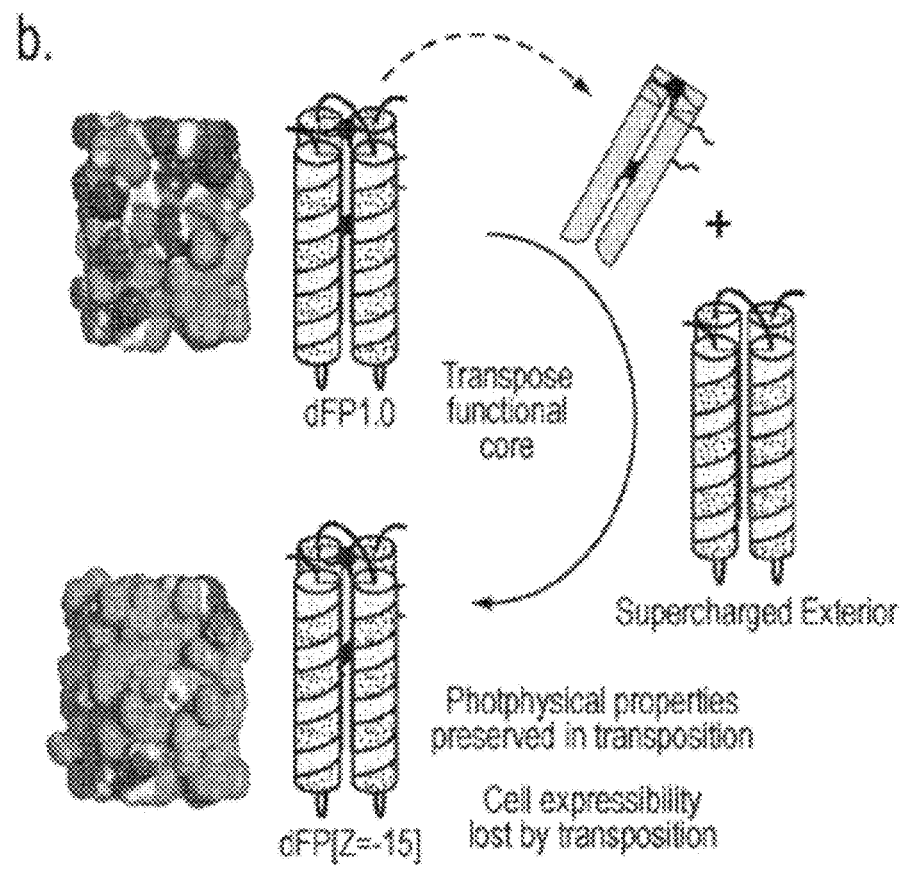

When the dFP1.0 core is transposed into a supercharged frame of $Z_{net}$=−15 that is beyond the limits of viable mammalian expression (FIG. 23, panel C), cellular fluorescence is indeed lost as expected, but the spectra and quantum yield of purified dFP1.0[−15] are largely unchanged from its mammalian cell-expressible counterpart (FIG. 33). Thus, biophysical function is tolerant of dramatic changes to the scaffold exterior. Likewise, expression patterns are similar between mammalian maquettes of dramatically different cores when comparing dFP1.0 to a disordered hydrophobic core composed entirely of leucines (FIG. 33). Together, these findings suggest that the determinants of cellular expression are governed almost entirely by the solvent-exposed exterior residues of the maquette frame regardless of the composition and consequent function designed into the hydrophobic core. Thus, the isolated structure-function of maquette proteins also includes the scaffold exterior and holds true even in the mammalian cellular environment when expressed as genetically encoded tools.

To summarize, a platform for building completely de novo tools has been established by the successful crossover of first principles-designed proteins into mammalian systems, which has been demonstrated by the rational creation and transduction of fluorescent protein that bear no sequence or structural homology to ones engineered from natural proteins. Despite their intentional simplicity and minimalism, tetrahelical bundles like the ones constructed here are capable of complex functions including recently reported enzyme-catalyzed electron transport, ion transport, and even evolutionary gain-of-function. While our de novo mammalian-expressible optogenetic tools were created by rational human-made design, they can be further enhanced by computational protein design approaches (similar to those used create more complex de novo helical structures) and directed evolution strategies (similar to those used to create ultra-bright AP-derived fluorescent proteins). Thus, dFP1.0 represents a tipping point for completely artificial protein scaffolds to expand beyond in vitro and bacterial systems. This work may spawn a diverse new class of protein tools for engineering mammalian systems, which in keeping with the tenets of synthetic biology and computational protein design, are constructed from the bottom-up from first principles rather than engineered from the top-down using natural protein starting points.

Methods

Unless stated otherwise all reagents were from Sigma-Aldrich, all water was Milli-Q purified ddH$_2$O (18.2MΩ·cm), all enzymes were from New England Biolabs, and all DNA constructs were Sanger sequenced.

Protein Production by Bacterial Overexpression

DNA Constructs: All proteins for in vitro studies were expressed in BL21(DE3)RIL or BL21(DE3) *E. coli* strains (Agilent) transformed with pET15b plasmid containing the genes encoding for 6× histidine-tagged protein of interest (with a TEV protease site in between) and for ampicillin resistance, under the T7 promoter. Bili-protein-related constructs and HO-1 were synthesized (IDT or Genscript) except for IFP1.4-encoding genes, which were sub-cloned from Addgene plasmid #54783 (from the Shu Lab, UCSF). Mutants were generated using Quickchange kits (Agilent) and NEB Turbo competent cells.

Protein Expression and Purification: *E. coli* cells were grown to an optical density (OD) of 0.8 at 37° C. (shaken at 240 rpm) in Terrific Broth (TB) media buffered to pH 8.5 (PBS) and containing 10 μM ampicillin. Cultured cells were then induced with 1 mM isopropyl β-D-1-thiogalactopyranoside (IPTG, LabScientific) and incubated at 20° C. for 18 hrs (shaken at 260 rpm). Cell pellets were lysed by sonication (Qsonica Q700 with micro-tip, 4×30-second pulses @ 60% amplitude) in 1 mM octylthioglucoside (OTG, ThermoFisher) in pH 7.4 PBS on ice. Lysate was purified using Ni-NTA columns (GE HisTrap) by fast protein liquid chromatography (FPLC, GE Akta or Akta Prime) over a one-step 500 mM imidazole elution in pH 7.4 PBS. Protein was dialyzed in 3,000 kDa MWCO tubing (Spectrum Labs) immediately back into pH 7.4 PBS. Cleavage of the His-tag was performed by digestion for 48 hours at 4° C. in 50 mM Tris buffer (pH 8 with 1 mM DTT, 150 mM NaCl, and 0.5 mM EDTA) using TEV produced in-house (1:100 molar equivalents). The protein sample was dialyzed twice into pH 7.4 PBS buffer before FPLC purification using a His-trap column by collecting the flow-through.

Holo-protein Formation: For in vitro holo-protein formation, purified apo-proteins were incubated overnight in 1 mM dithiothreitol (DTT, ThermoFisher), which was subsequently removed by PD-10 Sephadex column filtration (GE Healthcare). Samples were immediately prepared at 10 μM protein concentration and incubated with 50 μM biliverdin (BV) in pH 7.4 PBS at 37° C. for 4 hours in the dark. Excess BV was removed by PD-10 filtration. When necessary, samples were centrifugally concentrated at 5,000×g (Vivaspin2 with 3,000 kDa MWCO). For in cellulo holo-protein formation, double transformant *E. coli* strains were developed similarly to those reported by others in BL21(DE3) strains (Agilent). Bili-protein expressing strains were transformed as described in (1b), plus a pACBB plasmid containing the genes encoding for heme oxygenase (HO-1) and chloramphenicol resistance under the T7 promoter. The double transformants were plated on ampicillin and chloramphenicol plates, and verified by both sequencing and the presence of two bands on a 0.5% agar gel loaded with SYBRSafe when each plasmid was cut by a single restriction enzyme (XbaI). Cultures were grown in TB media with 10 μM ampicillin and 25 μM chloramphenicol before induction with 1 mM IPTG enriched with 1 mM levulinic acid (LA). Proteins were purified as described above without TEV cleavage.

Protein Gel Electrophoresis: Protein gels were run on NuPAGE Novex 4-12% Bis-Tris gel (Invitrogen) in MES SDS buffer (ThermoFisher) at 140 mV for 45 minutes on ice. Samples were made by heating to 70° C. for 10 minutes in NuPAGE LDS Sample Buffer (Invitrogen) prepared without reducing agent. BV-binding bands were resolved by running samples in MES buffer containing 1 mM zinc acetate, and then incubating in 1 mM zinc acetate in ddH$_2$O for 1 hour. Zinc bands were imaged using on a ChemiDoc imaging system (BioRad, epi-green illumination and $\lambda_{em}$=605/50 nm). Protein bands were resolved by incubating for 1 hour with InstantBlue (Expedeon), followed by <12 hours of de-staining in ddH$_2$O.

In vitro Refolding: BV-bound proteins, formed in vitro and excess BV removed as described above, were denatured by boiling and then cooled to 23° C. over 30 minutes to refold in pH 5 to pH 9 PBS buffer, a strong reducing environment (1 mM DTT, Thermofisher, pH 7), a mild reducing environment (1 mM reduced glutathione, pH 7), or mild oxidizing environment (1 mM oxidized glutathione, pH 7). Fluorescence emission spectra were taken and compared at $\lambda_{em}$=661 nm and 715 nm ($\lambda_{ex}$=600 nm and 640 nm, respectively) on a Tecan M200 plate reader at constant gain (see Protein Spectra Acquisition, below) to estimate the relative distribution of conformational species.

Mammalian Transduction

DNA Constructs: Maquette constructs for mammalian transfection were cloned into the third generation lentiviral backbone FCK(1.3)GW as previously done under the ubiquitous CMV promoter or the excitatory neuron-specific CamKII promoter, with the maquette-encoding gene cloned between the BamHI and AgeI sites. If used, the C-terminal EGFP fusion-encoding gene was cloned between the AgeI and EcoRI sites. Nuclear localized dFP1.0 was created by cloning the (NLS) SV40 nuclear localization sequence-encoding gene between the AgeI and EcoRI sites. The human melanopsin (hOPN4) maquette fusion was created by replacing the EGFP between AgeI and EcoRI with the gene from the previously reported FCK-hOPN4-EGFP. His-tagged variants were cloned using PCR-amplified inserts from the pET15b vectors described herein. Genes encoding for IFP1.4, iRFP and HO-1 were PCR isolated from plasmids obtained from Addgene (#54783, #31855, #59427).

HEK Cell Culture: Cells were maintained in a standard water-jacketed mammalian cell culture incubator at 37° C. with 5% $CO_2$ (Thermo/Forma 3110). HEK293t cells were grown from P5 frozen aliquots in Dulbecco's Modified Eagle Medium (DMEM) with Glutamax (Invitrogen) with 10% heat-inactivated fetal bovine serum and 1% penicillin/streptomycin (Invitrogen). Cells were passaged using 0.25% trypsin (Invitrogen) to 10% confluence for EGFP imaging and lysate experiments, and to 5% confluence for BV imaging experiments. In experiments involving HO-1 co-expression, media was doped with 25 μM levulinic acid and 4 μM $FeCl_3$ as described by others. Biliverdin doping was done as described by others by incubating cells in media containing 25 μM BV for 3 hours, and washed with PBS three times prior to imaging or lysing.

Primary Neuron Culture: Rat hippocampal neurons (Spague-Dawley) were obtained, plated on matrigel-coated #1 glass coverslips. Neurons were dissociated on day E18 and maintained in Neurobasal media containing B-27 supplement (Invitrogen), and one quarter of the media was replaced every week.

Transfection: HEK293t cells were transiently transfected 24 hours post-passaging using Transit293 (Mirus) according to manufacturer protocols. Media was changed 12-24 hours after transfection. HEK cells were imaged/lysed four days post-transfection for mature dFP1.0 analysis. When quantifying EGFP alone for expression analysis, HEK cells were imaged/lysed two days post-transfection. Hippocampal neurons were transfected using Lipofectamine3000 (ThermoFisher), on day P4.

Virus Production, Cell Line Generation, and Neuron Infection: Lentivirus was produced in HEK cells as previously described. Stable HEK cell line generation and clonal selection were also performed as previously described. Neurons were infected by directly applying low-titer virus-containing media (i.e. virus production HEK supernatant) for 24 hours on day P4, after which the media was replaced with virus-free, conditioned media previously removed from the same cells (Neurobasal plus B-27).

HEK Cell Lysate Preparation: HEK293t cells were transfected at 10% confluence as described in above, and then grown for four days to 95% confluence. Cells were washed with PBS twice and then scraped with L-shaped cell spreader (Fisher) into 300 μL per 35 mm dish lysis buffer (Cell Signaling Technology) with mammalian protease inhibitor cocktail (Sigma). Cells were homogenized by repeated pipetting with a 20-200 μL tip in 0.5 mL centrifuge tubes, bath sonicated for 2 minutes (Branson), and then membranes were spun down at 3000×g for 5 minutes at 4° C. (Eppendorf 5430R). Cell lysate was immediately used for spectral analysis as described below.

Optical Spectroscopy and Imaging

Protein Spectra Acquisition: All spectra were taken in PBS buffer in 96 well black-walled plates plates (Corning) on a monochrometer-based plate reader (Tecan Infinite M200 Pro). Absorbance spectra were taken from 300 nm to 830 nm. Excitation ($\lambda_{em}$>715 nm) and emission spectra ($\lambda_{ex}$=600 nm) were taken every 2 nm, except for holoproteins formed in E. coli HO-1 co-transformants (Excitation scan $\lambda_{em}$>735 nm, Emission scan $\lambda_{ex}$=640 nm). Spectra were averaged over 3-6 separate protein preparations. EGFP fluorescence emission was measured over $\lambda_{em}$=500-650 nm ($\lambda_{ex}$=465 nm).

Quantification of Absorbance/Fluorescence Parameters: Relative quantum yield (QY) was determined using a four-concentration point slope system, where integrated emission spectra were plotted against absorbance at the excitation wavelength. The slopes were compared to that of Cy5, which has an absolute QY of 27%. Extinction coefficients for the bilin Q-bands were determined given a Soret-band maximum extinction coefficient of 39,900 $M^{-1}$ $cm^{-1}$ determined by others; BV-binding efficiency in vitro was determined at a measured protein concentration given the said Soret-peak extinction coefficient. Binding efficiency of holo-proteins formed in E. coli HO-1 co-transformants was similarly determined by the ratio of 280 nm tryptophan absorbance to Soret-peak absorbance. Relative brightness was defined as the product of binding efficiency×QY.

Fluorescence Micrograph Acquisition: Cellular images were collected on a Leica DMI6000B inverted microscope, equipped with a sCMOS camera (pco.edge) and LED illuminator (Lumencor Spectra-X) under Metamorph automation. Objectives used were the Leica HCX PL Fluotar 20×/0.40NA dry and HCX PL Fluotar 100×/1.30NA oil immersion lens. Images were acquired with the following filters: Bili-protein (Chroma): $\lambda_{ex}$=631/28 nm (by Lumencor), $\lambda_{dex}$=655 nm, $\lambda_{em}$>665 nm and GFP (Chroma): $\lambda_{ex}$=460-480 nm (470/24 nm LED with 20 nm filter by Lumencor), $\lambda_{dex}$=495 nm, $\lambda_{em}$=525/50 nm.

Cellular Expression Quantification: Expression levels in HEK cells of non-fluorescent maquettes were quantified by the fluorescence levels of their EGFP C-terminal fusions, and for consistency, EGFP quantification was also employed for fluorescent bili-proteins. Expression was assessed by imaging 48 hours post-transient transfection using three 20× objective fields of view (FOV) per sample×four coverslips, totaling 12 FOVs. The intensity per cell was extracted using Fiji, all values per FOV were averaged, and statistics derived from the 12 FOVs per construct. Cellular expression in stable cell lines was quantified similarly, except for using a 100× objective and measuring 5 FOV per sample. To confirm the fusion had no impact on expression levels, levels of tagged and untagged maquettes with net surface charge $Z_{net}$=−3 were assessed by Western blotting of his-tagged variants using (anti-His strain and vendor). Details of western after finished:

Brightness and Stability in Cells: Overall cellular brightness was quantified from images acquired with a 2-second exposure time (63 $mW/cm^2$ for BV and for 4 $mW/cm^2$ EGFP, measured on a ThorLabs C-series power meter). Brightness was measured on a per cell basis in Fiji for fluorescence from both the bili-protein and EGFP, the latter for normalization to distinguish between brightness contributions from photophysical properties (BV incorporation, holoprotein maturation, and quantum yield) vs. protein expression levels. Photobleaching was assessed through time-course imaging (every 30 seconds for 40 minutes) of bili-protein fluorescence with intense excitation (63 $mW/cm^2$ @ $\lambda_{ex}$=631/28 nm). Intensities per cell were plotted over time, and then the average plot was fit to a single exponential in Kaleidagraph (Synergy).

Live-Cell Spectral Imaging: Spectral imaging of live cells was performed on a Leica TCS SP8 STED laser-scanning confocal microscope, equipped with a pulsed white-light laser that is tunable from 470 nm to 670 nm and dispersive optics for emission wavelength selection. Excitation spectral image stacks were taken in 5 nm steps ($\lambda_{em}$>680), and emission spectral image stacks were taken every 5 nm (6 nm or 15 nm emission bandpass, $\lambda_{ex}$=635 nm), except for the yeast images ($\lambda_{ex}$=670 nm). Images stacks were processed in Fiji. Cell bodies were outlined manually and assigned a region-of-interest (ROI), and then the average pixel intensity for each ROI was extracted for across the spectral stack, using a non-cellular ROI for background for subtraction.

Yeast Transformation and Integration

DNA Constructs: dFP1.0 was fused to GFP via a 21 amino acid glycine/serine-rich flexible linker and inserted into the pCT backbone (Addgene plasmid #41843, from the Wittrup Lab) under the control of the galactose-inducible GAL promoter via Gibson Assembly. Prior to Gibson Assembly, the backbone was linearized by EcoRI and XhoI to remove all of the surface display components of the original vector. The dFP1.0-EGFP fusion was then placed directly under the GAL promoter. DNA constructs were transformed into *Saccharomyces cerevisiae* BJ5465 using the Frozen-EZ Yeast Transformation II Kit (Zymo Research).

Yeast Cell Culture: *Saccharomyces cerevisiae* yeast cultures were inoculated from a glycerol stock into 3 mL of synthetic dextrose (SD; 2% dextrose final concentration, Clontech) dropout media lacking uracil, (SD/SG-URA, 2% dextrose, Clontech). Cultures were grown for 36 hours (30° C., 250 RPM) to saturation, and then the saturated cultures were back-diluted 1:100 and grown to mid log phase ($OD_{600}$=0.8-1.0). Cells were centrifuged and washed twice with synthetic galactose dropout media before being re-suspended and grown for 96 hours in SD/SG-TRP induction media. The induction media was refreshed daily to re-buffer cells. When doping media, 25 µM BV was added at this stage and refreshed daily.

Yeast Preparation for Spectral Assays: Cells were washed twice with 5× equivalent volumes of PBS (without calcium or magnesium) and then re-suspended in 1× equivalent volume of PBS. For spectral imaging and microscopy, 10 µL of cells were added onto 1 mm thick glass slides and covered with a coverslip. For spectroscopy assays, 200 µL of cells aliquoted per well of a black 96-well plate.

Figure 36:
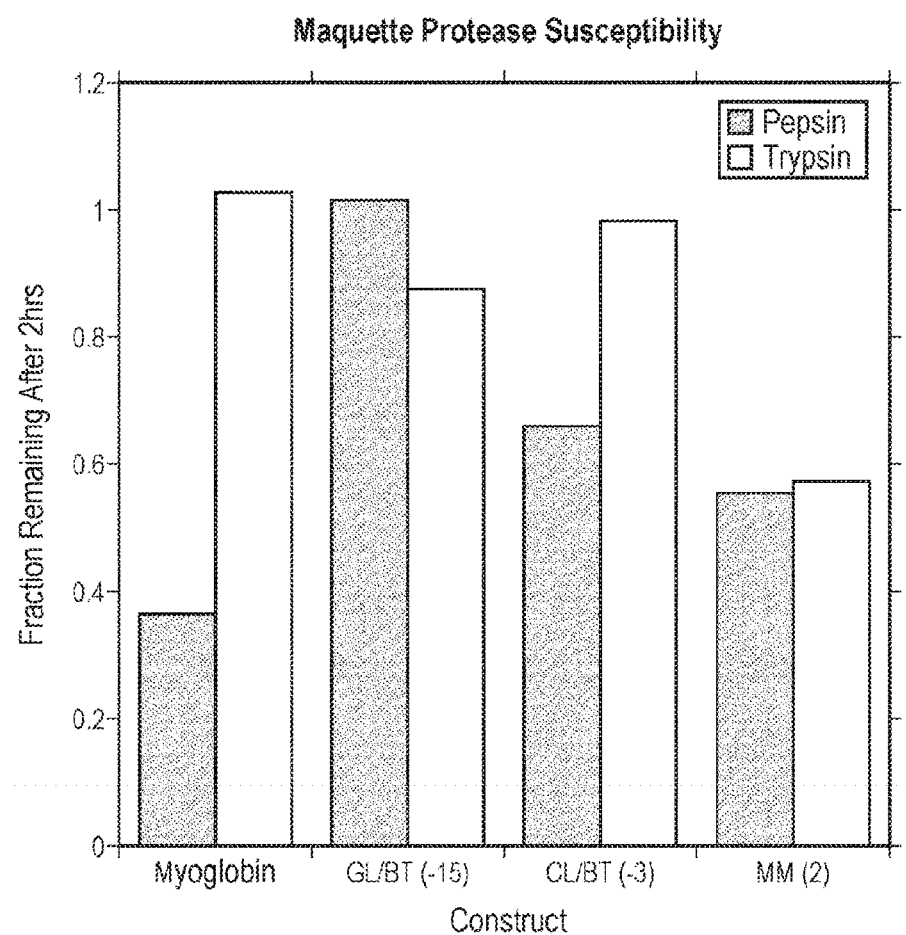
FIG. 36 illustrates a maquette protease susceptibility study comparing the GL/BT maquette scaffolds, and MM scaffold with myoglobin.

Example 7. Maquette Protease Susceptibility Study for MM, GL, and BT Scaffolds In order to examiner maquette protease susceptibility for the MM, GL, and BT scaffolds, a study was prepared to examine such scaffolds at −3 and −15 surface charge as compared to myoglobin. The MM scaffold may be described as a more rigid scaffold without polar residues. The GL and BT scaffolds may be described as more molten, with polar residues. The results of such study are shown in FIG. 36. As shown therein, myoglobin, GL/BT scaffolds, and MM scaffold were treated with pepsin and trypsin at various surface charges, shown in parentheses.

Example 8. Depolarization Study for Three Maquette Designs

Figure 37:
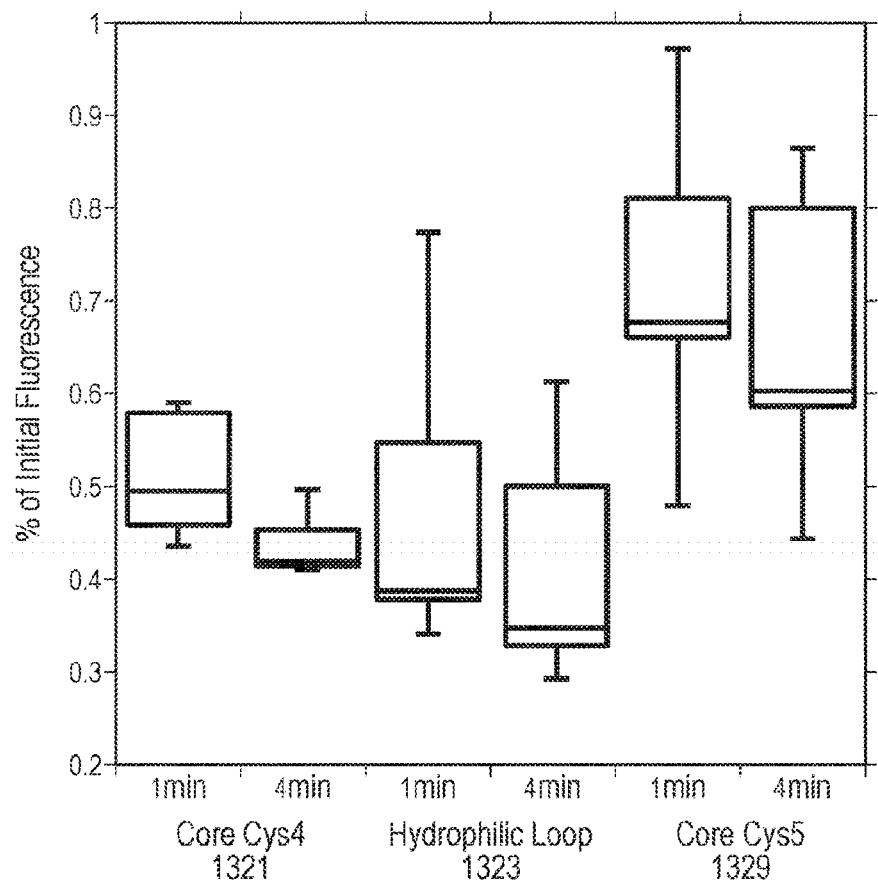
FIG. 37 illustrates the results of a depolarization study for three maquette probes where fluorescence was measured before and after depolarization.

In order to examine the fluorescent properties of various probes of the invention, three maquette probes were examined for cellular intensity with a 665 long pass filter and at a 630 nm excitation. Spectra for the three exemplary probes were examined before and after depolarization in HEK293 cells. The results of this study are shown in FIG. 37, where the three maquette probes include probe 1321 (i.e., SEQ ID NO. 63, AM-528-C4), probe 1323 (i.e., SEQ ID NO. 66, AM-1196), and probe 1329 (i.e., SEQ ID NO. 69, AM-528).

Example 9. Artificial Proteins as Optical Reporters of Cell Physiology

Any mechanism by which a reporter pocket is stabilized or destabilized may change the reporter function. Fluorescence, for example, requires a rigidly bound cofactor in a specific conformation. So, binding to another region of the protein that propagates into even a small scale conformational change, rigidification or increase of dynamics can lead to a change in fluorescence quantum yield. For T2 contrast agents, water access to the paramagnetic core dictates the enhancement capabilities, so any binding event that tightens or loosens the core packing would have an effect on the T2 contrast.

Figure 38:
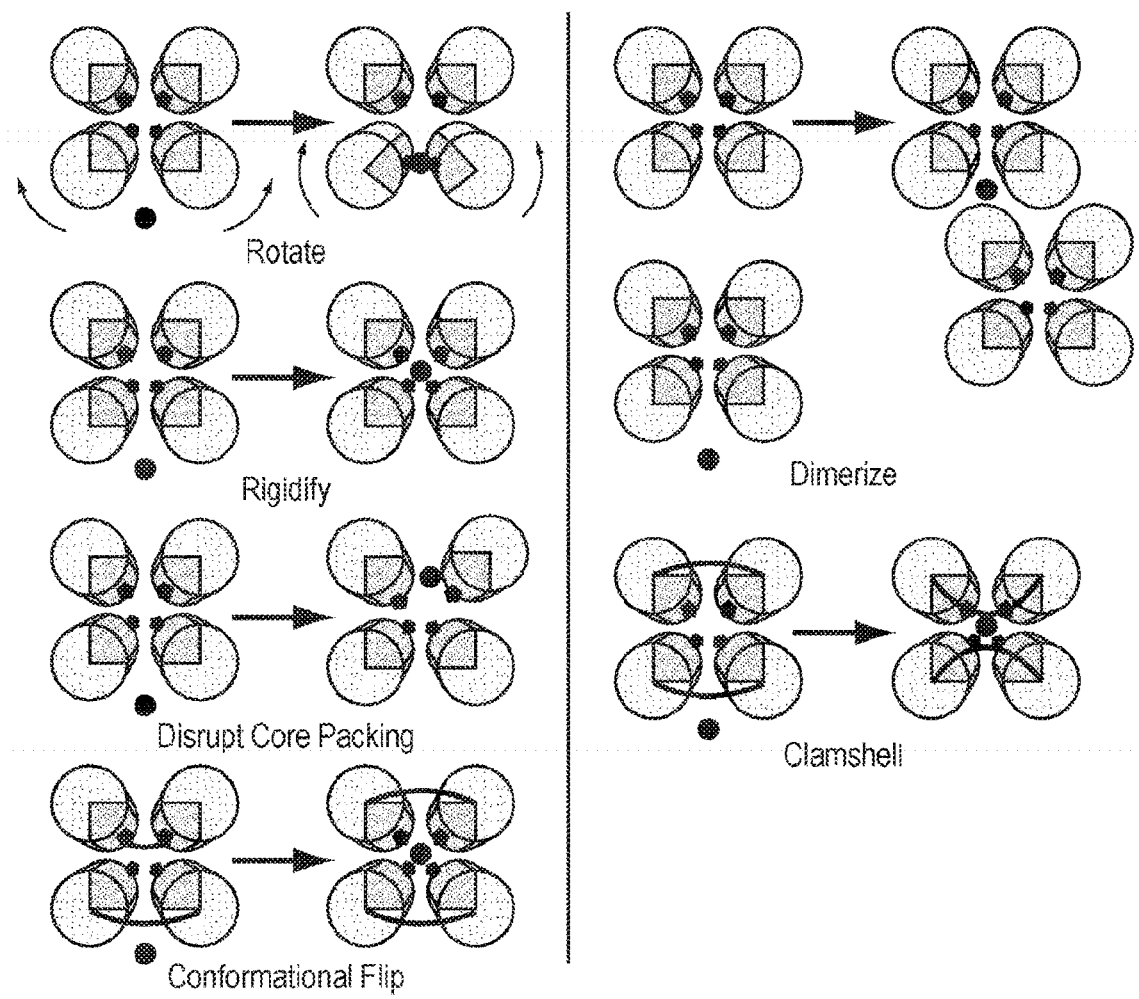
FIG. 38 illustrates potential means of sensing by modifying reporter function.

Examples of mechanisms by which these effects can be seen upon binding of the target molecule include clamshell binding from the N and C termini or loops, induced dimerization, helical rotation, conformational flipping, disruption of core packing and rigidification of interhelical motion (FIG. 38).

Example 10. Artificial Proteins as Physiological Reporters in Functional MRI As described herein, sensors were developed to enhance T2 contrast specifically. This is important relative to T1 because T2-weighted scans may be much shorter than T1-weighted scans, allowing for functional (real-time) imaging akin to BOLD. Current monomeric protein work has focused on T1 contrast enhancement.

T2 caused by changes in magnetic fields at any frequency and is the phenomena of dephasing along the xy axis, or loss of coherence. Some may thing about developing T2 contrast by making larger-scale perturbations in the local magnetic fields, such as an RBC or SPIO, such that waters that come by are exposed to a different magnetic field and lose their initial phasing. This may be "spin-spin" because the magnetic field caused by one nuclear spin is able to dephase nearby other spins. T2 shortening may be greatest if the two spins' tumbling energies are similar.

Although not always though of in a biological context, dephasing/T2 shortening can also occur from chemical exchange. The proteins described herein may meet these needs in the field. In some embodiments, as water protons exchange with protein protons or structured water protons, or if structured waters or hydration layer waters exchange with solvent waters, these protons will be exposed to varied magnetic fields due to the paramagnetic heme center, and hence dephased. They will actually be so dephased likely that they may completely drop out of the signal with no partial rephasing by the next 180 deg. Pulse. So, the T2 shortening that is seen is some combination of exchange rates to the protein core rather than a partial dephasing near a small magnetic variation, which would be seen from an SPIO/RBC. This would look the same in terms of decay, as it may not be possible to distinguish loss of signal from partial dephasing of many spins or total dephasing of a few spins, but it may mean that water exchange rates and proton exchange rates could be modeled to the expected T2 shorting from a "visit-based" model of T2 relaxation.

Figure 39:
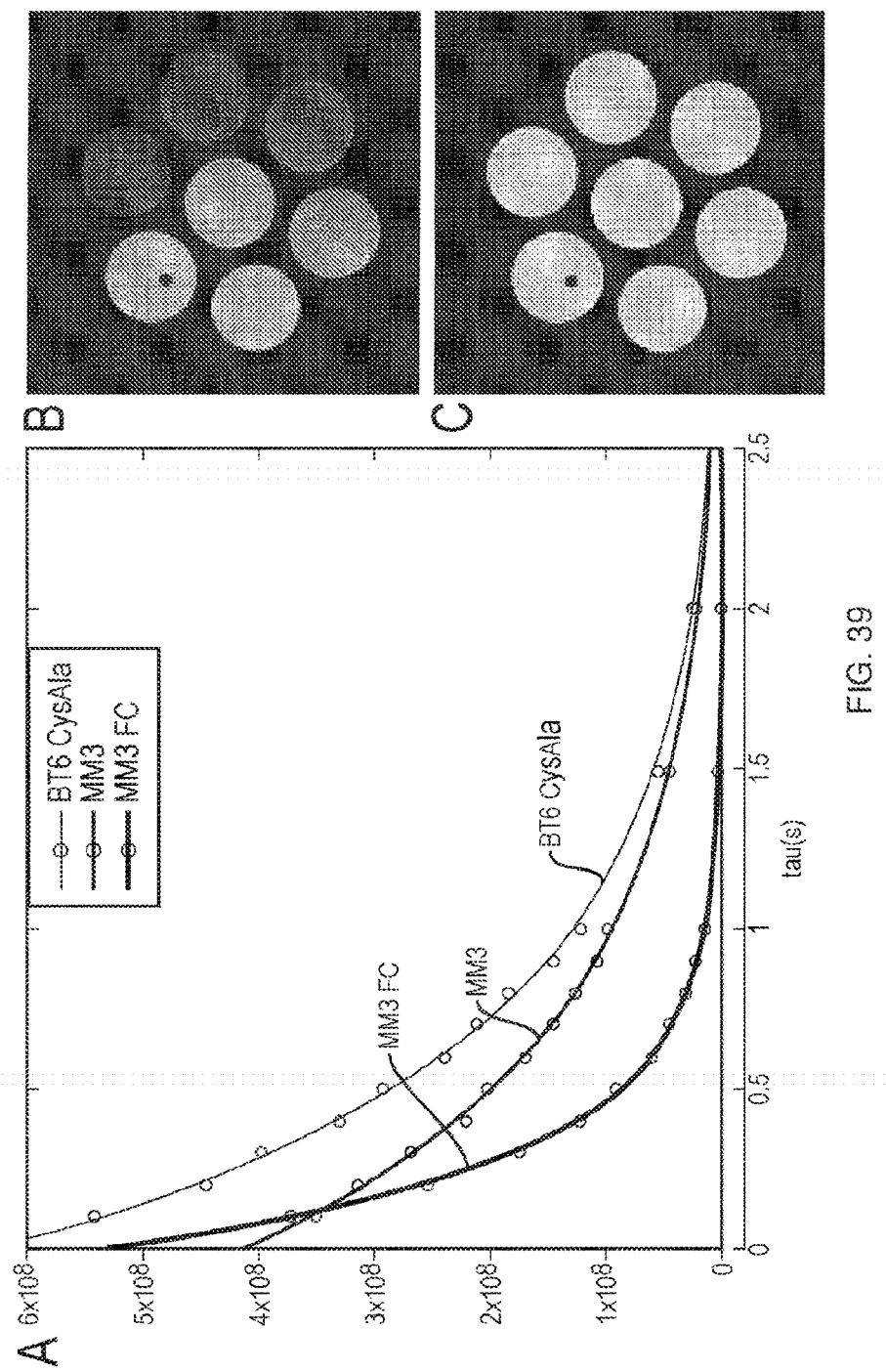
FIG. 39 illustrates T2 and MRI image slices of maquettes on a Bruker Avance III 400, 9.4 T. (Panel A) T2 decay graphs of BT6 CysAla, MM3, and MM3 FC maquettes with T2s of 629 ms, 678 ms, and 275 ms, respectively. These correspond to relaxivities of 111, 7.5, and 3.4 for T2. (Panel B) T2-weighted image using CPMG pulse sequence with TE=100 ms (250 ms effective) a TR=10 s, slice width of 0.5 mm on bundle of 0.5 mm tubes from 1 o'clock clockwise of 640 μM, 320 μM, 160 μM, 80 μM, 40 μM, and 1 μM bound heme concentration in PBS center tube.

The invention includes a few proteins that display a 10-fold T2 contrast enhancement compared to PBS (FIG. 39). These proteins have relaxivities for T2 in the 3.5-10 range but T1 relaxivities will below 1, so are T2-specific contrast enhancers. Strong T2 contrast may be seen by using T2-weighted pulse sequences for concentration of bound heme 40 µM and above (FIG. 39, panel B), but no T1 contrast even at 640 µM. It is understood that mutations may be made to introduce water-binding residues adjacent to the heme core such that the passing of water by the heme site may be slowed, enhancing dephasing of these waters.

Example 11. Possible Co-Factors that May be Bound by the Maquettes of the Invention Maquettes have the potential to bind with fairly good specificity metals and small amphipathic molecules. Metals can be coordinated by internal or loop residues that correspond to the soft/hardness (Irving-Williams Series) of the desired metal to be bound with the preferred geometry of the metal. Currently under investigation is calcium binding due to calcium's ubiquitous importance to neuroscience and cellular physiology. For example, exemplary proteins that bind calcium ($Ca^{2+}$) include SEQ ID NOS. 35-41, 141, and 142.

Maquettes may bind tetrapyrroles with large amphipathic nature (half hydrophobic, half soluble) because they will partition into the hydrophobic core. Without being limited to any one theory of the invention, the foregoing theory can be applied to other small molecules provided they are hydrophobic enough to self-partition to the core. Once in the core, binding can be stabilized by specific residues. Partitioning can also be made specific to a molecule by creating binding pockets and strategically placing residues to shield hydrophilic residues while being buried. Targets that exist that in vivo in large enough quantities to be sensed include metals, steroids, and amphipathic neurotransmitters, such as serotonic, dopamine, and histamine.

Example 12. Expression of MZH3 Variant Fused to eGFP

Figure 40:
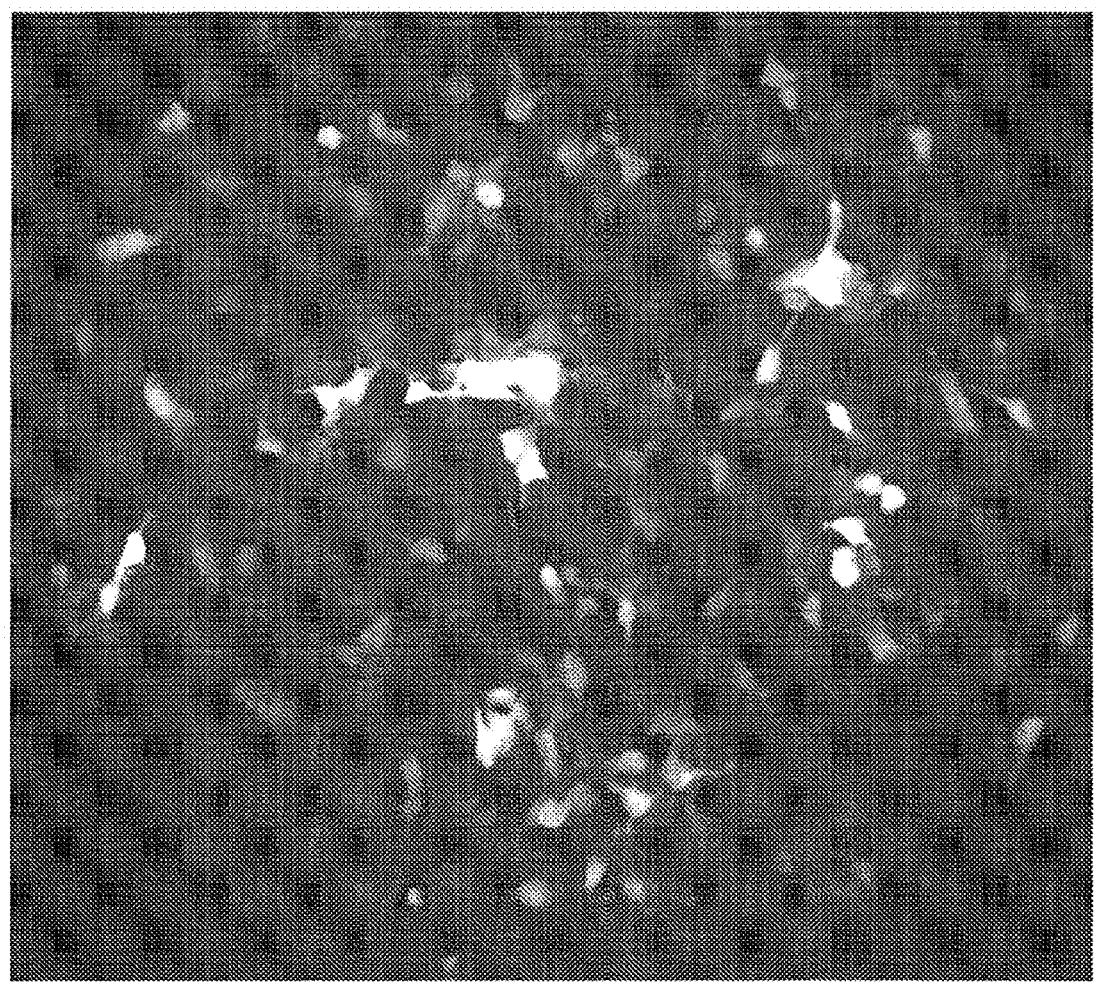
FIG. 40 illustrates GFP expression levels at 2 days post-transfection for an MZH3 variant (SEQ ID NO. 147), fused to eGFP, and transfected into HEK293T cells.

In an embodiment, an MZH3 variant (SEQ ID NO. 147), was fused to eGFP and transfected into HEK293T cells. FIG. 40 illustrates GFP expression levels at 2 days post transfection.

Figure 41:
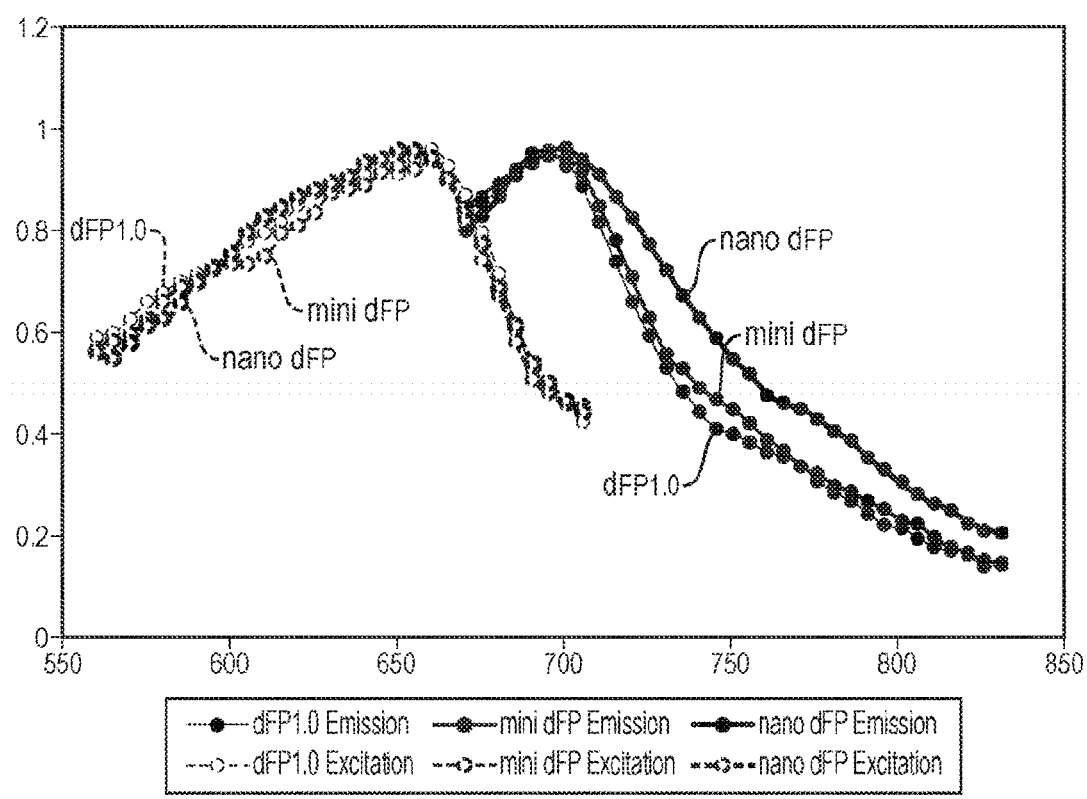
FIG. 41 illustrates the spectral characteristics for dFP, mini dFP, and nano dFP in E. coli BL21 cell lysate after 20 hours of co-expression with heme oxygenase.

Example 13. Spectral Characteristics of Selected Artificial Proteins of the Invention In an embodiment, dFP, minidFP, and nano dFP, as described herein, were prepared in *E. Coli* BL21 cell lysate and the and their spectral characteristics were measured after 20 hours of co-expression with heme oxygenase. As shown in FIG. 41, dFP, mini dFP, and nano dFP demonstrated comparable spectral characteristics.

Example 14. Exemplary Artificial Proteins and Polynucleotides

Exemplary artificial proteins, and encoding polynucleotides, are set forth in Table 4.

TABLE 4

List of Sequences

| Seq ID No | Name | Sequence | |
|---|---|---|---|
| 1 | | EIWKXXEDAL QKFEXXLNQF EDXXQL | 26 |
| 2 | | EIKQRXEDXL RKFEEALKRF EDLKQK | 26 |
| 3 | | RXWKXXEDAX QKFEEALNQF EDLKQL | 26 |
| 4 | | EIKQRXEDAL RKFEEALKRX EDXXQK | 26 |
| 5 | | EXXKXXEDXX QKXEEXXNQX EDXXQL | 26 |
| 6 | | EXKQRXEDXX RKXEEXXKRX EDXKQK | 26 |
| 7 | | RXXKXXEDXX QKXEEXXNQX EDXKQL | 26 |
| 8 | | EXKQRXEDXX RKXEEXXKRX EDXXQK | 26 |
| 9 | | EXXKXXEDXX QKXEEXXNQX EDXXQL | 26 |
| 10 | | EXKQRXEDXX RKXEEXXKRX EDXKQK | 26 |
| 11 | | RXXKXXEDXX QKXEEXXNQX EDXKQL | 26 |
| 12 | | EXKQRXEDXX RKXEEXXKRX EDXXQK | 26 |
| 13 | | EXXKXXEDXX QKXEEXXNQX EDXXQL | 26 |
| 14 | | EXKQRXEDXX RKXEEXXKRX EDXKQK | 26 |
| 15 | | RXXKXXEDXX QKXEEXXNQX EDXKQL | 26 |
| 16 | | EXKQRXEDXX RKXEEXXKRX EDXXQK | 26 |
| A | | -XX+XX--XXO+X--XXOOX--XXOL | |
| B | | -X+O+X--XX++X--XX++X--X+O+ | |
| C | | +XX+XX--XXO+X--XXOOX--X+OL | |
| D | | -XX+O+--XX++X--XX++X--XXO+ | |

TABLE 4-continued

List of Sequences

| Seq ID No | Name | Sequence | |
|---|---|---|---|
| 17 | Loop | GGSGKGSGG | 9 |
| 18 | Loop | GGCG | 4 |
| 19 | Loop | GACG | 4 |
| 20 | Loop | GGSG | 4 |
| 21 | GLSloop | EIWKQHEDAL QKFEEALNQF EDLKQLGGSG KGSGGEIKQR HEDALRKFEE ALKRFEDLKQ | 60 |
|  |  | KGGCGRIWKQ HEDALQKFEE ALNQFEDLKQ LGGSGKGSGG EIKQRHEDAL RKFEEALKRE | 120 |
|  |  | EDLKQK | 126 |
| 22 | PEB Mut B | EIWKSHEDAL QKFEEALNQF EDLKQLGGSG KGSGGEIKQR HEDALRKFEE ALKRFEDLKQ | 60 |
|  |  | KGACGRIWKQ HEDALQKFEE ALNQFEDLKQ LGGSGKGSGG EIKQRHEDAL RKFEEALKRE | 120 |
|  |  | EDRVQK | 126 |
| 23 | PEB Mut C | EIWKLHEDAL QKFEEALNQF EDLKQLGGSG KGSGGEIKQR HEDALRKFEE ALKRFEDLKQ | 60 |
|  |  | KGGCGRIWKE HEDALQKFEE ALNQFEDLKQ LGGSGKGSGG EIKQRHEDAL RKFEEALKRE | 120 |
|  |  | EDRVQK | 126 |
| 24 | PEB Mut D | EIWKQHEDAL QKFEEALNQF EDLKQLGGSG KGSGGEIKQR HEDALRKFEE ALKRFEDLKQ | 60 |
|  |  | KGGCGRIWKQ HEDALQKFEE ALNQFEDLKQ LGGSGKGSGG EIKQRHEDAL RKFEEALKRE | 120 |
|  |  | EDRVQK | 126 |
| 25 | dFP1.0 | EIWKSHEDAL QKFEEALNQF EDLKQLGGSG KGSGGEIKQR HEDALRKFEE ALKRFEDLKQ | 60 |
|  |  | KGGCGRIWKE HEDAHQKFEE ALNQFEDLKQ LGGSGKGSGG EIKQRHEDAL RKFEEALKRH | 120 |
|  |  | EDRVQK | 126 |
| 26 | C-His Stab CGRD | EIWKSHEDAL QKFEEALNQF EDLKQLGGSG KGSGGEIKQR HEDALRKFEE ALKRFEDLKQ | 60 |
|  |  | KGGCGRDWKE HEDAHQKFEE ALNQFEDLKQ LGGSGKGSGG EIKQRHEDAL RKFEEALKRH | 120 |
|  |  | EDRVQK | 126 |
| 27 | C41 Stab Map | EIWKLFEDAL QKFEHELNQF EDRVQLGGSG KGSGGEIKQR CADALRKFEE ALKRFEDLKQ | 60 |
|  |  | KGGSGEIWKL FEDALQKHEE ALNQFEDLKQ LGGSGKGSGG EIKQSHEDAL RKHEEALKRF | 120 |
|  |  | EDLKQK | 126 |
| 28 | C41 Stab Map CARD | EIWKLFEDAL QKFEHELNQF EDRVQLGGSG KGSGGEIKQR CARDLRKFEE ALKRFEDLKQ | 60 |
|  |  | KGGSGEIWKL FEDALQKHEE ALNQFEDLKQ LGGSGKGSGG EIKQSHEDAL RKHEEALKRF | 120 |
|  |  | EDLKQK | 126 |
| 29 | C41 Py Stab | EIWKLFEDAL QKFEEDLNQF EDRVQLGGSG KGSGGEIKQL CARDLRKFEE ALKRFEDLKQ | 60 |
|  |  | KGGSGEIWKL FEDALQKHEE ALNQFEDHKQ LGGSGKGSGG EIKQRSEDAL RKHEEALKRF | 120 |
|  |  | EDLKQK | 126 |
| 30 | 528-GL | EIWKQHEDAL QKFEEALNQF EDLKQLGGSG KGSGGEIWKQ CEDALRKFEE ALKRFEDLKQ | 60 |
|  |  | KGGSGEIWKQ HEDALQKFEE ALNQFEDLKQ LGGSGKGSGG EIWKQHEDAL RKFEEALKRF | 120 |
|  |  | EDLKQK | 126 |
| 31 | MM3 FC | ELLKKHEEAL KKFEELLKKF EEELKKGGSG SGSGGELLKK FEEALKKFEE LLKKFEEELK | 60 |
|  |  | KGGSGWGSGG ELLKKHEEAL KKFEELLKKF EEELKKGGSG SGSGGELLKK CEEALKKFEE | 120 |
|  |  | LLKKFEELLK K | 131 |
| 32 | MM3 FC H6F H76F | ELLKKFEEAL KKFEELLKKF EEELKKGGSG SGSGGELLKK FEEALKKFEE LLKKFEEELK | 60 |
|  |  | KGGSGWGSGG ELLKKFEEAL KKFEELLKKF EEELKKGGSG SGSGGELLKK CEEALKKFEE | 120 |
|  |  | LLKKFEELLK K | 131 |
| 33 | MM3 FC H6F H76F F90D | ELLKKFEEAL KKFEELLKKF EEELKKGGSG SGSGGELLKK FEEALKKFEE LLKKFEEELK | 60 |
|  |  | KGGSGWGSGG ELLKKFEEAL KKFEELLKKD EELLKKGGSG SGSGGELLKK CEEALKKFEE | 120 |
|  |  | LLKKFEELLK K | 131 |
| 34 | AM1 | EIWKQHEDAL QKFFALLLLL ALLLLLALLL HLLAFEGGSG GGSGGKFLLL LALLALLLLA | 60 |
|  |  | LLLHLLAFWE ALNQFEDLAK QGGSGGGSGG EIWKQHEDAL QKFFALLLLL ALLLLLALLL | 120 |
|  |  | HLLAFKGGSG GGSGGEFLLL LALLALLLLA LLLHLLAFWE ALNQFEDLAK Q | 171 |
| 35 | MZH3 | GSPELRQEHQ QLAQEFQQLL QEIQQLGREL LKGELQGIKQ LREASEKARN PEKKSVLQKI | 60 |
|  |  | LEDEEKHIEL LETLQQTGQE AQQLLELQQ TGQELWQLGG SGGPELRQKH QQLAQKIQQL | 120 |
|  |  | LQKHQQLGAK ILEDEEKHIE LLETILGGSG GDELRELLKG ELQGIKQYRE LQQLGQKAQQ | 180 |
|  |  | LVQKLQQTGQ KLWQLG | 196 |

TABLE 4-continued

List of Sequences

| Seq ID No | Name | Sequence | |
|---|---|---|---|
| 36 | MZH3 H138D | GSPELRQEHQ QLAQEFQQLL QEIQQLGREL LKGELQGIKQ LREASEKARN PEKKSVLQKI | 60 |
| | | LEDEEKHIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 37 | MZH3 H138N | GSPELRQEHQ QLAQEFQQLL QEIQQLGREL LKGELQGIKQ LREASEKARN PEKKSVLQKI | 60 |
| | | LEDEEKHIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 38 | MZH3 H67D, H138D | GSPELRQEHQ QLAQEFQQLL QEIQQLGREL LKGELQGIKQ LREASEKARN PEKKSVLQKI | 60 |
| | | LEDEEKDIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 39 | MZH3 H67D, H138N | GSPELRQEHQ QLAQEFQQLL QEIQQLGREL LKGELQGIKQ LREASEKARN PEKKSVLQKI | 60 |
| | | LEDEEKDIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 40 | MZH3 H67N, H138D | GSPELRQEHQ QLAQEFQQLL QEIQQLGREL LKGELQGIKQ LREASEKARN PEKKSVLQKI | 60 |
| | | LEDEEKNIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 41 | MZH3 H67N, H138N | GSPELRQEHQ QLAQEFQQLL QEIQQLGREL LKGELQGIKQ LREASEKARN PEKKSVLQKI | 60 |
| | | LEDEEKNIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 42 | PEB Mut E | EIWKQHEDAL QKFEEALNQF EDLKQLGGSS KGSGGEIKQR HEDALRKFEE ALKRFEDLKQ | 60 |
| | | KGGCGRDWKQ HEDALQHFEE ALNQFEDLKQ LGGSGKGSGG EIKQRHEDAL RKFEEALKRF | 120 |
| | | EDLKQK | 126 |
| 43 | PEB Mut F | EIWKQHEDAL QKFEEALNQF EDLKQLGGCG EIKQRAEDAL RKFEEALKRF EDLKQKGGCG | 60 |
| | | EIWKQHEDAL QKFEEALNQF EDLKQLGGSG EIKQRHEDAL RKFEEALKRF EDLKQK | 116 |
| 44 | PEB Mut G | EIWKQHEDAL QKFEEALNQF EDLKQLGGSG KGSGGEIKQR HEDALRKFEE ALKRFEDLKQ | 60 |
| | | KGGCGREWKQ HEDALQKFEE ALNQFEDLKQ LGGSGKGSGG EIKQRHEDAL RKFEEALKRF | 120 |
| | | EDLKQK | 126 |
| 45 | dFP 1.1 | EIWKQHEDAL QKFEEALNQF EDLKQLGGSG SGSGGEIWKQ CEDALQKFEE ALNQFEDLKQ | 60 |
| | | LGGSGSGSGG EIWKQHEDAL QKFEEALNQF EDLKQLGGSS SGSGGEIWKQ HEDALQHFEE | 120 |
| | | ALNQFEDLKQ L | 131 |
| 46 | dFP 1.0 (EC) | ttctcatgtt tgacagctta tcatcgataa gctttaatgg ggtagtttat acagttaaa | 60 |
| | | ttgctaacgc agtcaggcac cgtgtatgaa atctaacaat gcgctcatcg tcatcctcgg | 120 |
| | | caccgtcacc ctggatgctg taggcatagg cttggttatc ccggtactgc cgggcctctt | 180 |
| | | gcgggatatc cggatatagt tcctcctttc agcaaaaaac ccctcaagac ccgtttagag | 240 |
| | | gccccaaggg gttatgctag ttattgctca gcggtggcag cagccaactc agcttccttt | 300 |
| | | cgggctttgt tagcagccgg atcctcgaga ccggttcact tttgcacacg atcttcgtgg | 360 |
| | | cgcttcagcg cttcctcaaa tttgcgcagc gcatcctcat ggcgctgttt aatctcgcca | 420 |
| | | ccgctgccct tgccgctgcc acccagttgct ttcagatctt caaattgatt cagcgcttcc | 480 |
| | | tcaaacttttt ggtgcgcgtc ttcgtgctcc ttccaaatac gaccgcagcc acctttctgc | 540 |
| | | ttcagatcct caaaacgttt cagcgcttcc tcgaacttac gcagcgcgtc ttcgtgacgt | 600 |
| | | tgcttgatct cgccaccgct gcctttaccg ctgccaccca gttgcttcag atcctcaaac | 660 |
| | | tggttcagcg cttcctcgaa tttctgcagc gctcttcca gatctcgccg | 720 |
| | | gatccctgaa aatacaggtt ttcaccatcg cctccgtggt gatgatggtg atgcccacct | 780 |
| | | ttaccatat gaatatcgcc ttcatggta tatctccttc ttaaagttaa acaaaattat | 840 |
| | | ttctagaggg gaattgttat ccgctcacaa ttcccctata gtgagtcgta ttaatttcgc | 900 |
| | | gggatcgaga tctcgatcct ctacgccgga cgcatcgatg ccggcatcac ggtgcggaca | 960 |
| | | ggtgcggttg ctgcgcccta tcgccgac atcaccgatg ggaagatcg gctcgccac | 1020 |
| | | ttcgggctca tgagcgcttg tttcggcgtg gtatggtgg caggcccgt ggccggggga | 1080 |
| | | ctgttgggcg ccatctcctt gcatgcacca ttccttgcgg cggcggtgct caacggcctc | 1140 |
| | | aacctactac tgggctgctt cctaatgcag gagtcgcata agggagaggcc tcgagatccc | 1200 |
| | | ggacaccatc gaatggcgca aaacctttcg cggtatggca tgatagcgcc cggaagagag | 1260 |
| | | tcaattcagg gtggtgaatg tgaaaccagt aacgttatac gatgtcgcag agtatgccgg | 1320 |
| | | tgtctcttat cagaccgttt cccgcgtggt gaaccaggcc agccacgttt ctgcgaaaac | 1380 |
| | | gcgggaaaaa gtggaagcgg cagggggaaa gctgaattac attcccaacg cgtgcaca | 1440 |
| | | acaactggcg ggcaaacagt cgttgctgat tggcgttgcc acctccagtc tggccctgca | 1500 |
| | | cgcgccgtcg caaattgtcg cggcgattaa atctcgcgcc gatcaactgg gtgccagcgt | 1560 |
| | | ggtggtgtcg atggtagaac gaagcggcgt cgaagcctgt aaagcggcgg tgcacaatct | 1620 |
| | | tctcgcgcaa cgcgtcagtg ggctgatcat taactatccg ctggatgacc aggatgccat | 1680 |
| | | tgctgtggaa gctgcctgca ctaatgttcc ggcgttattt cttgatgtct ctgaccagac | 1740 |

TABLE 4-continued

List of Sequences

| Seq ID No | Name | Sequence | |
|---|---|---|---|
| | | acccatcaac agtattattt tctcccatga agacggtacg cgactgggcg tggagcatct | 1800 |
| | | ggtcgcattg ggtcaccagc aaatcgcgct gttagcgggc ccattaagtt ctgtctcggc | 1860 |
| | | gcgtctgcgt ctggctggct ggcataaata tctcactcgc aatcaaattc agccgatagc | 1920 |
| | | ggaacgggaa ggcgactgga gtgccatgtc cggttttcaa caaaccatgc aaatgctgaa | 1980 |
| | | tgagggcatc gttcccactg cgatgctggt tgccaacgat cagatggcgc tgggcgcaat | 2040 |
| | | gcgcgccatt accgagtccg ggctgcgcgt tggtgcggat atctcggtag tgggatacga | 2100 |
| | | cgataccgaa gacagctcat gttatatccc gccgttaacc accatcaaac aggattttcg | 2160 |
| | | cctgctgggg caaaccagcg tggaccgctt gctgcaactc tctcagggcc aggcggtgaa | 2220 |
| | | gggcaatcag ctgttgcccg tctcactggt gaaaagaaaa accaccctgg cgcccaatac | 2280 |
| | | gcaaaccgcc tctcccgcg cgttggccga ttcattaatg cagctggcac gacaggtttc | 2340 |
| | | ccgactggaa agcgggcagt gagcgcaacg caattaatgt aagttagctc actcattagg | 2400 |
| | | caccgggatc tcgaccgatg cccttgagag ccttcaaccc agtcagctcc ttccggtggg | 2460 |
| | | cgcggggcat gactatcgtc gccgcactta tgactgtctt ctttatcatg caactcgtag | 2520 |
| | | gacaggtgcc ggcagcgctc tgggtcattt tcggcgagga ccgctttcgc tggagcgcga | 2580 |
| | | cgatgatcgg cctgtcgctt gcggtattcg gaatcttgca cgccctcgct caagccttcg | 2640 |
| | | tcactggtcc cgccaccaaa cgtttcggcg agaagcaggc cattatcgcc ggcatggcgg | 2700 |
| | | ccgacgcgct gggctacgtc ttgctggcgt tcgcgacgcg aggctggatg gccttcccca | 2760 |
| | | ttatgattct tctcgcttcc ggcggcatcg ggatgcccgc gttgcaggcc atgctgtcca | 2820 |
| | | ggcaggtaga tgacgaccat cagggacagc ttcaaggatc gctcgcggct cttaccagcc | 2880 |
| | | taacttcgat cactggaccg ctgatcgtca cggcgattta tgccgcctcg gcgagcacat | 2940 |
| | | ggaacgggtt ggcatggatt gtaggcgccg ccctatacct tgtctgcctc cccgcgttgc | 3000 |
| | | gtcgcggtgc atggagccgg gccacctcga cctgaatgga agccggcggc acctcgctaa | 3060 |
| | | cggattcacc actccaagaa ttggagccaa tcaattcttg cggagactg tgaatgcgca | 3120 |
| | | aaccaaccct tggcagaaca tatccatcgc gtccgccatc tccagcagcc gcacgcggcg | 3180 |
| | | catctcgggc agcgttgggt cctggccacg ggtgcgcatg atcgtgctcc tgtcgttgag | 3240 |
| | | gacccggcta ggctggcggg gttgccttac tggttagcag aatgaatcac cgatacgcga | 3300 |
| | | gcgaacgtga agcgactgct gctgcaaaac gtctgcgacc tgagcaacaa catgaatggt | 3360 |
| | | cttcggtttc cgtgtttcgt aaagtctgga aacgcggaag tcagcgccct gcaccattat | 3420 |
| | | gttccggatc tgcatcgcag gatgctgctg gctaccctgt ggaacaccta catctgtatt | 3480 |
| | | aacgaagcgc tggcattgac cctgagtgat ttttctctgg tcccgccgca tccataccgc | 3540 |
| | | cagttgttta ccctcacaac gttccagtaa ccgggcatgt tcatcatcag taacccgtat | 3600 |
| | | cgtgagcatc ctctctcgtt tcatcgtat cattacccc atgaacagaa atccccctta | 3660 |
| | | cacggaggca tcagtgacca aacaggaaaa aaccgcccctt aacatggccc gctttatcag | 3720 |
| | | aagccagaca ttaacgcttc tggagaaact caacgagctg gacgcggatg aacaggcaga | 3780 |
| | | catctgtgaa tcgcttcacg accacgctga tgagcttac cgcagctgcc tcgcgcgttt | 3840 |
| | | cggtgatgac ggtgaaaacc tctgacacat gcagctccg gagacggtca cagcttgtct | 3900 |
| | | gtaagcggat gccgggagca gacaagcccg tcagggcgcg tcagcgggtg ttggcgggtg | 3960 |
| | | tcggggcgca gccatgaccc agtcacgtag cgatagcgga gtgtatactg gcttaactat | 4020 |
| | | gcggcatcag agcagattgt actgagagtg caccatatat gcggtgtgaa ataccgcaca | 4080 |
| | | gatgcgtaag gagaaaatac cgcatcaggc gctcttccgc ttcctcgctc actgactcgc | 4140 |
| | | tgcgctcggt cgttcggctg cggcgagcgg tatcagctca ctcaaaggcg gtaatacggt | 4200 |
| | | tatccacaga atcagggga ggat aacgcaggaa agaacatgtg agcaaaaggc cagcaaaagg | 4260 |
| | | ccaggaaccg taaaaaggcc gcgttgctgg cgtttttcca taggctccgc ccccctgacg | 4320 |
| | | agcatcacaa aaatcgacgc tcaagtcaga ggtggcgaaa cccgacagga ctataaagat | 4380 |
| | | accaggcgtt tccccctgga agctccctcg tgcgctctcc tgttccgacc ctgccgctta | 4440 |
| | | ccggatacct gtccgccttt ctcccttcgg gaagcgtggc gctttctcat agctcacgct | 4500 |
| | | gtaggtatct cagttcggtg taggtcgttc gctccaagct gggctgtgtg cacgaacccc | 4560 |
| | | ccgttcagcc cgaccgctgc gccttatccg gtaactatcg tcttgagtcc aacccggtaa | 4620 |
| | | gacacgactt atcgccactg gcagcagcca ctggtaacag gattagcaga gcgaggtatg | 4680 |
| | | taggcggtgc tacagagttc ttgaagtggt ggcctaacta cggctacact agaaggacag | 4740 |
| | | tatttggtat ctgcgctctg ctgaagccag ttaccttcgg aaaaagagtt ggtagctctt | 4800 |
| | | gatccggcaa acaaaccacc gctggtagcg tggtttttt tgtttgcaag cagcagatta | 4860 |
| | | cgcgcagaaa aaaaggatct caagaagatc cttttgatctt ttctacgggg tctgacgctc | 4920 |
| | | agtggaacga aaactcacgt taagggattt tggtcatgag attatcaaaa aggatcttca | 4980 |
| | | cctagatcct tttaaattaa aaatgaagtt ttaaatcaat ctaaagtata tatgagtaaa | 5040 |
| | | cttggtctga cagttaccaa tgcttaatca gtgaggcacc tatctcagcg atctgtctat | 5100 |
| | | ttcgttcatc catagttgcc tgactccccg tcgtgtagat aactacgata cgggagggct | 5160 |
| | | taccatctgg ccccagtgct gcaatgatac cgcgagaccc acgctcaccg gctccagatt | 5220 |
| | | tatcagcaat aaaccagcca gccggaaggg ccgagcgcag aagtggtcct gcaactttat | 5280 |
| | | ccgcctccat ccagtctatt aattgttgcc gggaagctag agtaagtagt tcgccagtta | 5340 |
| | | atagtttgcg caacgttgtt gccattgctg caggcatcgt ggtgtcacgc tcgtcgtttg | 5400 |
| | | gtatggcttc attcagctcc ggttcccaac gatcaaggcg agttacatga tcccccatgt | 5460 |
| | | tgtgcaaaaa agcggttagc tccttcggtc ctccgatcgt tgtcagaagt aagttggccg | 5520 |
| | | cagtgttatc actcatggtt atggcagcac tgcataattc tcttactgtc atgccatccg | 5580 |
| | | taagatgctt ttctgtgact ggtgagtact caaccaagtc attctgagaa tagtgtatgc | 5640 |
| | | ggcgaccgag ttgctcttgc ccggcgtcaa cacgggataa taccgcgcca catagcagaa | 5700 |
| | | ctttaaaagt gctcatcatt ggaaaacgtt cttcggggcg aaaactctca aggatcttac | 5760 |
| | | cgctgttgag atccagttcg atgtaaccca ctcgtgcacc caactgatct tcagcatctt | 5820 |
| | | ttactttcac cagcgtttct gggtgagcaa aaacaggaag gcaaaatgcc gcaaaaaagg | 5880 |
| | | gaataagggc gacacggaaa tgttgaatac tcatactctt cctttttcaa tattattgaa | 5940 |
| | | gcatttatca gggttattgt ctcatgagcg gatacatatt tgaatgtatt tagaaaaata | 6000 |
| | | aacaaatagg ggttccgcgc acatttcccc gaaaagtgcc acctgacgtc taagaaacca | 6060 |
| | | ttattatcat gacattaacc tataaaaata ggcgtatcac gaggcccttt cgtcttcaag | 6120 |
| | | aa | 6122 |

TABLE 4-continued

List of Sequences

| Seq ID No | Name | Sequence | |
|---|---|---|---|
| 47 | dFP 1.0 (FCM Mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | accccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg cccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagaccctt tagtcagtgt ggaaaatctc tagcagtggc | 1020 |
| | | gcccgaacag ggacttgaaa gcgaaaggga aaccagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc aggggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctgagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attggagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aagggggat | 2460 |
| | | tgggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa atcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagataggg tgagaaagca gacagagtca ttccgtcagc attctgggtc tgtttggtac | 3120 |
| | | ttcttctcac gctaaggtgg cggtgtgata tgcacaatgc ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acgggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagagcg atgatcactt gtggactaag | 3540 |
| | | tttgttcaca tccccttctc caaccccctc atacatcac cctgggagaa caagggaa | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tgttctccca | 3840 |
| | | tttgcactca ggagcacgtg caggcgagtg gccctagtt ctgggggcag cggggatcc | 3900 |
| | | gccaccatgg gcgagatctg aagagccac gaagacgcgc tgcagaaatt cgaggaagcg | 3960 |
| | | ctgaaccagt ttgaggatct gaagcaactg ggtggcagcg gtaaaggcag cggtggcgag | 4020 |
| | | atcaagcaac gtcacgaaga cgcgctgcgt aagtttgaag acgttttgag | 4080 |
| | | gatctgaagc agaaaggtgg ctgcggtcgt atttggaagg agcacgaaga cgcgcaccaa | 4140 |
| | | aagtttgagg aagcgctgaa tcaatttgaa gatctgaaac aactgggtgg cagcggcaag | 4200 |
| | | ggcagcggtg gcgagattaa acagcgccat gaggatgcgc tgcgcaaatt tgaggaagcg | 4260 |
| | | ctgaagcgcc acgaagatcg tgtgcaaaag gcggcaccgg tagtagcagt gagcaaggc | 4320 |
| | | gaggagctgt tcaccggggt ggtgcccatc ctggtcgagc tggacggcga cgtaaacggc | 4380 |

TABLE 4-continued

List of Sequences

| Seq ID No | Name | Sequence | |
|---|---|---|---|
| | | cacaagttca gcgtgtccgg cgagggcgag ggcgatgcca cctacggcaa gctgaccctg | 4440 |
| | | aagttcattt gcaccaccgg caagctgccc gtgccctggc ccaccctcgt gaccaccctg | 4500 |
| | | acctacggcg tgcagtgctt cagccgctac cccgaccaca tgaagcagca cgacttcttc | 4560 |
| | | aagtccgcca tgcccgaagg ctacgtccag gagcgcacca tcttcttcaa ggacgacggc | 4620 |
| | | aactacaaga cccgcgccga ggtgaagttc gagggcgaca ccctggtgaa ccgcatcgag | 4680 |
| | | ctgaagggca tcgacttcaa ggaggacggc aacatcctgg ggcacaagct ggagtacaac | 4740 |
| | | tacaacagcc acaacgtcta tatcatggcc gacaagcaga agaacggcat caaggtgaac | 4800 |
| | | ttcaagatcc gccacaacat cgaggacggc agcgtgcagc tcgccgacca ctaccagcag | 4860 |
| | | aacacccca tcggcgacgg ccccgtgctg ctgcccgaca ccactacct gagcacccag | 4920 |
| | | tccgccctga gcaaagaccc caacgagaag cgcgatcaca tggtcctgct ggagttcgtg | 4980 |
| | | accgccgccg ggatcactct cggcatggac gagctgtaca agtaagaatt cgatatcaag | 5040 |
| | | cttatcgata atcaacctct ggattacaaa atttgtgaaa gattgactgg tattcttaac | 5100 |
| | | tatgttgctc cttttacgct atgtggatac gctgctttaa tgcctttgta tcatgctatt | 5160 |
| | | gcttcccgta tggctttcat tttctcctcc ttgtataaat cctggttgct gtctctttat | 5220 |
| | | gaggagttgt ggcccgttgt caggcaacgt ggcgtggtgt gcactgtgtt tgctgacgca | 5280 |
| | | accccactg gttgggcat tgccaccacc tgtcagctcc tttccgggac tttcgctttc | 5340 |
| | | ccccctccta ttgccacggc ggaactcatc gccgcctgcc ttgcccgctg ctggacaggg | 5400 |
| | | gctcggctgt tgggcactga caattccgtg gtgttgtcgg ggaaatcatc gtcctttcct | 5460 |
| | | tggctgctcg cctgtgttgc cacctggatt ctgcgcggga cgtccttctg ctacgtccct | 5520 |
| | | tcggccctca atccagcgga ccttccttcc cgcggcctgc tgccggctct gcggcctctt | 5580 |
| | | ccgcgtcttc gccttcgccc tcagacgagt cggatctccc tttgggccgc ctccccgcat | 5640 |
| | | cgataccgtc gacctcgaga cctagaaaaa catggagcaa tcacaagtag caatacagca | 5700 |
| | | gctaccaatg ctgattgtgc ctggctagaa gcacaagagg aggaggaggt gggttttcca | 5760 |
| | | gtcacacctc aggtaccttt aagaccaatg acttacaagg cagctgtaga tcttagccac | 5820 |
| | | tttttaaaag aaaaggggg actggaaggg ctaattcact cccaacgaag acaagatatc | 5880 |
| | | cttgatctgt ggatctacca cacacaaggc tacttccctg attggcagaa ctacacacca | 5940 |
| | | gggccaggga tcagatatcc actgacctt ggatggtgct acaagctagt accagttgag | 6000 |
| | | caagagaagg tagaagaagc caatgaagga gagaacaccc gcttgttaca ccctgtgagc | 6060 |
| | | ctgcatggga tggatgaccc ggagagagaa gtattagagt ggaggttga cagccgccta | 6120 |
| | | gcatttcatc acatggcccg agagctgcat ccggactgta ctgggtctct ctggttagac | 6180 |
| | | cagatctgag cctgggagct ctctggctaa ctagggaacc cactgcttaa gcctcaataa | 6240 |
| | | agcttgcctt gagtgcttca agtagtgtgt gcccgtctgt tgtgtgactc tggtaactag | 6300 |
| | | agatccctca gaccctttta gtcagtgtgg aaaatctcta gcagggcccg tttaaacccg | 6360 |
| | | ctgatcagcc tcgactgtgc cttctagttg ccagccatct gttgtttgcc cctccccgt | 6420 |
| | | gccttccttg acctggaag gtgccactcc cactgtcctt tcctaataaa atgaggaaat | 6480 |
| | | tgcatcgcat tgtctgagta ggtgtcattc tattctgggg ggtggggtgg ggcaggacag | 6540 |
| | | caaggggag gattgggaag acaatagcag gcatgctggg gatgcggtgg gctctatggc | 6600 |
| | | ttctgaggcg gaaagaacca gctggggctc tagggggtat ccccacgcgc cctgtagcgg | 6660 |
| | | cgcattaagc gcggcgggtg tggtggttac gcgcagcgtg accgctacac ttgccagcgc | 6720 |
| | | cctagcgccc gctccttcg ctttcttccc ttcctttctc gccacgttcg ccggctttcc | 6780 |
| | | ccgtcaagct ctaaatcgg ggctcccttt agggttccga tttagtgctt tacggcacct | 6840 |
| | | cgaccccaaa aaacttgatt agggtgatgg ttcacgtagt gggccatcgc cctgatagac | 6900 |
| | | ggttttttcgc cctttgacgt tggagtccac gttctttaat agtggactct tgttccaaac | 6960 |
| | | tggaacaaca ctcaaccccta tctcggtcta ttcttttgat ttataaggga ttttgccgat | 7020 |
| | | ttcggcctat tggttaaaaa atgagctgat ttaacaaaaa tttaacgcga attaattctg | 7080 |
| | | tggaatgtgt gtcagttagg gtgtggaaag tccccaggct ccccagcagg cagaagtatg | 7140 |
| | | caaagcatgc atctcaatta gtcagcaacc aggtgtgaa agtcccagg ctccccagca | 7200 |
| | | ggcagaagta tgcaaagcat gcatctcaat tagtcagcaa ccatagtccc gcccctaact | 7260 |
| | | ccgcccatcc cgcccctaac tccgcccagt tccgcccatt ctccgcccca tggctgacta | 7320 |
| | | atttttttta tttatgcaga ggccgaggcc gcctctgcct ctgagctatt ccagaagtag | 7380 |
| | | tgaggaggct ttttggagg cctaggcttt tgcaaaaagc tcccgggagc ttgtatatcc | 7440 |
| | | attttcggat ctgatcagca cgtgttgaca attaatcatc ggcatagtat atcggcatag | 7500 |
| | | tataatacga caaggtgagg aactaaacca tggccaagtt gaccagtgcc gttccggtgc | 7560 |
| | | tcaccgcgcg cgacgtcgcc ggagcggtcg agttctggac cgaccggctc gggttctccc | 7620 |
| | | gggacttcgt ggaggacgac ttcgccggtg tggtccggga cgacgtgacc ctgttcatca | 7680 |
| | | gcgcggtcca ggaccaggtg gtgccggaca caccctggc ctgggtgtgg gtgcgcggcc | 7740 |
| | | tggacgagct gtacgccgag tggtcggagg tcgtgtccga gaacttccgg gacgcctccg | 7800 |
| | | ggccggccat gaccgagatc ggcgagcagc gtggggggcg ggagttcgcc ctgcgcgacc | 7860 |
| | | cggccggcaa ctgcgtgcac ttcgtggccg aggagcagga ctgacacgtg ctacgagatt | 7920 |
| | | tcgattccac cgccgccttc tatgaaaggt tgggcttcgg aatcgtttc cggacgccg | 7980 |
| | | gctggatgat cctccagcgc gggatctca tgctggagtt cttcgccacc cccaacttgt | 8040 |
| | | ttattgcagc ttataatggt tacaaataaa gcaatagcat cacaaatttc acaaataaag | 8100 |
| | | catttttttc actgcattct agttgtggtt tgtccaaact catcaatgta tcttatcatg | 8160 |
| | | tctgtatacc gtcgacctct agctagagct tggcgtaatc atggtcatag ctgtttcctg | 8220 |
| | | tgtgaaattg ttatccgctc acaattccac acaacatacg agccggaagc ataaagtgta | 8280 |
| | | aagcctgggg tgcctaatga gtgagctaac tcacattaat tgcgttgcgc tcactgcccg | 8340 |
| | | ctttccagtc gggaaacctg tcgtgccagc tgcattaatg aatcggccaa cgcgcgggga | 8400 |
| | | gaggcggttt gcgtattggg cgctcttccg cttcctcgct cactgactcg ctgcgctcgg | 8460 |
| | | tcgttcggct gcggcgagcg gtatcagctc actcaaaggc ggtaatacgg ttatccacag | 8520 |
| | | aatcagggga taacgcagga aagaacatgt gagcaaaagg ccagcaaaag gccaggaacc | 8580 |
| | | gtaaaaaggc cgcgttgctg gcgtttttcc ataggctccg ccccctgac gagcatcaca | 8640 |
| | | aaaatcgacg ctcaagtcag aggtggcgaa acccgacagg actataaaga taccaggcgt | 8700 |
| | | ttccccctgg aagctccctc gtgcgctctc ctgttccgac cctgccgctt accggatacc | 8760 |
| | | tgtccgcctt tctccctttcg ggaagcgtgg cgctttctca tagctcacgc tgtaggtatc | 8820 |

TABLE 4-continued

List of Sequences

| Seq ID No | Name | Sequence | |
|---|---|---|---|
| | | tcagttcggt gtaggtcgtt cgctccaagc tgggctgtgt gcacgaaccc ccgttcagc | 8880 |
| | | ccgaccgctg cgccttatcc ggtaactatc gtcttgagtc caacccggta agacacgact | 8940 |
| | | tatcgccact ggcagcagcc actggtaaca ggattagcag agcgaggtat gtaggcggtg | 9000 |
| | | ctacagagtt cttgaagtgg tggcctaact acggctacac tagaagaaca gtatttggta | 9060 |
| | | tctgcgctct gctgaagcca gttaccttcg gaaaaagagt tggtagctct tgatccggca | 9120 |
| | | aacaaaccac cgctggtagc ggtggttttt ttgtttgcaa gcagcagatt acgcgcagaa | 9180 |
| | | aaaaaggatc tcaagaagat cctttgatct tttctacggg gtctgacgct cagtggaacg | 9240 |
| | | aaaactcacg ttaagggatt ttggtcatga gattatcaaa aaggatcttc acctagatcc | 9300 |
| | | ttttaaatta aaaatgaagt tttaaatcaa tctaaagtat atatgagtaa acttggtctg | 9360 |
| | | acagttacca atgcttaatc agtgaggcac ctatctcagc gatctgtcta tttcgttcat | 9420 |
| | | ccatagttgc ctgactcccc gtcgtgtaga taactacgat acgggagggc ttaccatctg | 9480 |
| | | gccccagtgc tgcaatgata ccgcgagacc cacgctcacc ggctccagat ttatcagcaa | 9540 |
| | | taaaccagcc agccggaagg gccgagcgca gaagtggtcc tgcaacttta tccgcctcca | 9600 |
| | | tccagtctat taattgttgc cgggaagcta gagtaagtag ttcgccagtt aatagtttgc | 9660 |
| | | gcaacgttgt tgccattgct acaggcatcg tggtgtcacg ctcgtcgttt ggtatggctt | 9720 |
| | | cattcagctc cggttcccaa cgatcaaggc gagttacatg atcccccatg ttgtgcaaaa | 9780 |
| | | aagcggttag ctccttcggt cctccgatcg ttgtcagaag taagttggcc gcagtgttat | 9840 |
| | | cactcatggt tatggcagca ctgcataatt ctcttactgt catgccatcc gtaagatgct | 9900 |
| | | tttctgtgac tggtgagtac tcaaccaagt cattctgaga atagtgtatg cggcgaccga | 9960 |
| | | gttgctcttg cccggcgtca atacgggata taccgcgcc acatagcaga actttaaaag | 10020 |
| | | tgctcatcat tggaaaacgt tcttcgggc gaaaactctc aaggatctta ccgctgttga | 10080 |
| | | gatccagttc gatgtaaccc actcgtgcac ccaactgatc ttcagcatct tttactttca | 10140 |
| | | ccagcgtttc tgggtgagca aaaacaggaa ggcaaaatgc cgcaaaaaag gaataagggg | 10200 |
| | | cgacacggaa atgttgaata ctcatactct tcctttttca atattattga agcatttatc | 10260 |
| | | agggttattg tctcatgagc ggatacatat ttgaatgtat ttagaaaaat aaacaaatag | 10320 |
| | | gggttccgcg cacatttccc cgaaaagtgc cacctgac | 10358 |
| 48 | dFP 1.0 | EIWKSHEDAL QHFEEALNQF EDLKQLGGSG KGSGGEIKQR HEDALRKFEE ALKRFEDLKQ | 60 |
| | | KGGCGRIWKE HEDAHQKFEE ALNQFEDLKQ LGGSGKGSGG EIKQRHEDAL RKFEEALKRH | 120 |
| | | EDRVQK | 126 |
| 49 | Mini dfP (EC) | ttcttgaaga cgaaagggcc tcgtgatacg cctattttta taggttaatg tcatgataat | 60 |
| | | aatggtttct tagacgtcag gtggcacttt tcggggaaat gtgcgcggaa ccctatttg | 120 |
| | | tttatttttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tcccttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga gaacgttttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc ctttttgata atctcatgac caaaatccct taacgtgagt tttcgttcca | 1200 |
| | | ctgagcgtca gaccccgtag aaaagatcaa aggatcttct tgagatcctt ttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacaccccgcc aacaccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctc cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcggccatg ttaagggcgg ttttttcctg tttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |

TABLE 4-continued

List of Sequences

| Seq ID No | Name | Sequence | |
|---|---|---|---|
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgtgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga cgggcaac agctgattgc | 3900 |
| | | ccttcaccgc ctggccctga gagagttgca gcaagcggtc cacgctggtt tgcccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacgcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc acttttttcc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtcccccgg ccacggggcc tgccaccata cccacgccga acaagcgct catgagcccg | 5100 |
| | | aagtggcgag cccgatcttc cccatcggtg atgtcggcga tataggcgcc agcaaccgca | 5160 |
| | | cctgtggccg cggtgatgcc ggccacgatg cgtccggtat agaggatcga gatctcgatc | 5220 |
| | | ccgcgaaatt aatacgactc actataggggg aattgtgagc ggataacaat tcccctctag | 5280 |
| | | aaataatttt gtttaacttt aagaaggaga tataccatgg cagcagcca tcatcatcat | 5340 |
| | | catcacgcg gcgacggcga gaacttgtat tttcaagcta gcggatccat gggggaaatc | 5400 |
| | | tggaagtcac atgaagatgc tttgcagaag tttgaggaag ccttgaacca agggggtcc | 5460 |
| | | ggcggcgatg cgttacgcaa gttcgaggag gccttgaaac gttttgaaga tttgaaacag | 5520 |
| | | aagggtggct gtggacgtat ctggaaagag catgaagatg cgcatcaaaa gtttgaggag | 5580 |
| | | gctcttaatc aaggaggttc tggtggcgat gcccttcgta aatttgagga agcattgaag | 5640 |
| | | cgtcacgagg atcgcgtgca aaagtgataa gaattcctcg aggctgctaa caaagcccga | 5700 |
| | | aaggaagctg agttggctgc tgccaccgct gagcaataac tagcataacc ccttggggcc | 5760 |
| | | tctaaacggg tcttgagggg ttttttgctg aaaggaggaa ctatatccgg atatcccgca | 5820 |
| | | agaggcccgg cagtaccggc ataaccaagc ctatgcctac agcatccagg gtgacggtgc | 5880 |
| | | cgaggatgac gatgagcgca ttgttagatt tcatacacgg tgcctgactg cgttagcaat | 5940 |
| | | ttaactgtga taaactaccg cattaaagct tatcgatgat aagctgtcaa acatgaaga | 5999 |
| 50 | Mini dfp (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc attgaagaatc | 180 |
| | | tgcttagggt taggcgtttt gcgctgcttc gcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |

TABLE 4-continued

List of Sequences

| Seq ID No | Name | Sequence | |
|---|---|---|---|
| | | tctggtaact agagatccct cagacccttt tagtcagtgt ggaaaatctc tagcagtggc | 1020 |
| | | gcccgaacag ggacttgaaa gcgaaaggga aaccagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccac acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaaag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagataggg tgagaaagca gacagagtca ttccgtcagc attctgggtc tgtttggtac | 3120 |
| | | ttcttctcac gctaaggtgg cggtgtgata tgcacaatgc ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acggggcaaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatccatcc cgtctgttaa | 3480 |
| | | aagggcccta tagttggagg tggggaggt aggaagagcg atgatcactt gtggactaag | 3540 |
| | | tttgttcaca tccccttctc caacccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacgug caggcgagtg gccccctagtt ctgggggcag cggggatcc | 3900 |
| | | atgggggaaa tctggaagtc acatgaagat gctttgcaga agtttgagga agccttgaac | 3960 |
| | | caagggggt ccggcggcga tgcgttacgc aagttcgagg aggccttgaa acgttttgaa | 4020 |
| | | gatttgaaac agaagggtgg ctgtggacgt atctggaaag agcatgaaga tgcgcatcaa | 4080 |
| | | aagtttgagg aggctcttaa tcaaggaggt tctggtggcg atgcccttcg taaatttgag | 4140 |
| | | gaagcattga agcgtcacga ggatcgcgtg caaaaggcgg caccggtagt agcagtgagc | 4200 |
| | | aagggcgagg agctgttcac cggggtggtg cccatcctgg tcgagctgga cggcgacgta | 4260 |
| | | aacggccaca agttcagcgt gtccggcgag ggcgagggcg atgccaccta cggcaagctg | 4320 |
| | | accctgaagt tcatttgcac caccggcaag ctgcccgtgc cctggcccac cctcgtgacc | 4380 |
| | | accctgacct acggcgtgca gtgcttcagc cgctaccccg accacatgaa gcagcacgac | 4440 |
| | | ttcttcaagt ccgccatgcc cgaaggctac gtccaggagc gcaccatctt cttcaaggac | 4500 |
| | | gacggcaact acaagacccg cgccgaggtg aagttcgagg gcgacaccct ggtgaaccgc | 4560 |
| | | atcgagctga agggcatcga cttcaaggag gacggcaaca tcctggggca caagctggag | 4620 |
| | | tacaactaca acagccacaa cgtctatatc atggccgaca agcagaagaa cggcatcaag | 4680 |
| | | gtgaacttca agatccgcca caacatcgag gacggcagcg tgcagctcgc cgaccactac | 4740 |
| | | cagcagaaca cccccatcgg cgacggcccc gtgctgctgc ccgacaacca ctacctgagc | 4800 |
| | | acccagtccg ccctgagcaa agaccccaac gagaagcgcg atcacatggt cctgctggag | 4860 |
| | | ttcgtgaccg ccgccgggat cactctcggc atggacgagc tgtacaagta agaattcgat | 4920 |
| | | atcaagctta tcgataatca acctctggat tacaaaattt gtgaaagatt gactggtatt | 4980 |
| | | cttaactatg ttgctccttt tacgctatgt ggatacgctg ctttaatgcc tttgtatcat | 5040 |
| | | gctattgctt ccgtatggc tttcattttc tcctccttgt ataaatcctg gttgctgtct | 5100 |
| | | ctttatgagg agttgtgcca gttgtcagg caacctggcg gtggtgcac tgtgtttgct | 5160 |
| | | gacgcaaccc ccactggttg ggcattgcca ccacctgtc agctcctttc cgggactttc | 5220 |
| | | gctttccccc tccctattgc cacggcggaa ctcatcgccg cctgccttgc ccgctgctgg | 5280 |
| | | acaggggctc ggctgttggg cactgacaat tccgtggtgt tgtcgggaaa tcatcgtcc | 5340 |
| | | tttccttggc tgctcgcctg tgttgccacc tggattctgc gcgggacgtc cttctgctac | 5400 |

TABLE 4-continued

List of Sequences

| Seq ID No | Name | Sequence | |
|---|---|---|---|
| | | gtcccttcgg ccctcaatcc agcggacctt ccttcccgcg gcctgctgcc ggctctgcgg | 5460 |
| | | cctcttccgc gtcttcgcct tcgccctcag acgagtcgga tctcccttg ggccgcctcc | 5520 |
| | | ccgcatcgat accgtcgacc tcgagaccta gaaaaacatg gagcaatcac aagtagcaat | 5580 |
| | | acagcagcta ccaatgctga ttgtgcctgg ctagaagcac aagaggagga ggaggtgggt | 5640 |
| | | tttccagtca cacctcaggt acctttaaga ccaatgactt acaaggcagc tgtagatctt | 5700 |
| | | agccactttt taaaagaaaa gggggggactg gaagggctaa ttcactccca acgaagacaa | 5760 |
| | | gatatccttg atctgtggat ctaccacaca caaggctact tccctgattg gcagaactac | 5820 |
| | | acaccagggc cagggatcag atatccactg acctttggat ggtgctacaa gctagtacca | 5880 |
| | | gttgagcaag agaaggtaga agaagccaat gaaggagaga cacccgctt gttacaccct | 5940 |
| | | gtgagcctgc atgggatgga tgacccggag agagaagtat tagagtggag gtttgacagc | 6000 |
| | | cgcctagcat ttcatcacat ggcccgagag ctgcatccgg actgtactgg gtctctctgg | 6060 |
| | | ttagaccaga tctgagcctg ggagctctct ggctaactag ggaacccact gcttaagcct | 6120 |
| | | caataaagct tgccttgagt gcttcaagta gtgtgtgccc gtctgttgtg tgactctggt | 6180 |
| | | aactagagat ccctcagacc cttttagtca gtgtggaaaa tctctagcag ggcccgttta | 6240 |
| | | aacccgctga tcagcctcga ctgtgccttc tagttgccag ccatctgttg tttgccctc | 6300 |
| | | ccccgtgcct tccttgaccc tggaaggtgc cactcccact gtcctttcct aataaaatga | 6360 |
| | | ggaaattgca tcgcattgtc tgagtaggtg tcattctatt ctggggggtg gggtggggca | 6420 |
| | | ggacagcaag ggggaggatt gggaagacaa tagcaggcat gctggggatg cggtgggctc | 6480 |
| | | tatggcttct gaggcggaaa gaaccagctg gggctctagg gggtatcccc acgcgccctg | 6540 |
| | | tagcggcgca ttaagcgcgg cgggtgtggt ggttacgcgc agcgtgaccg ctacacttgc | 6600 |
| | | cagcgcccta gcgcccgctc ctttcgcttt cttccccttcc tttctcgcca cgttcgccgg | 6660 |
| | | cttctcccgt caagctctaa atcgggggct ccctttaggg ttccgattta gtgctttacg | 6720 |
| | | gcacctcgac cccaaaaaac ttgattaggg tgatggttca cgtagtgggc catcgccctg | 6780 |
| | | atagacggtt tttcgccctt tgacgttgga gtccacgttc tttaatagtg gactcttgtt | 6840 |
| | | ccaaactgga acaacactca accctatctc ggtctattct tttgatttat aagggatttt | 6900 |
| | | gccgatttcg gcctattggt taaaaaatga gctgatttaa caaaaattta acgcgaatta | 6960 |
| | | attctgtgga atgtgtgtca gttagggtgt ggaaagtccc caggctcccc agcaggcaga | 7020 |
| | | agtatgcaaa gcatgcatct caattagtca gcaaccaggt gtggaaagtc cccaggctcc | 7080 |
| | | ccagcaggca gaagtatgca aagcatgcat ctcaattagt cagcaaccat agtcccgccc | 7140 |
| | | ctaactccgc ccatcccgcc cctaactccg cccagttccg cccattctcc gccccatggc | 7200 |
| | | tgactaattt tttttattta tgcagaggcc gaggccgcct ctgcctctga gctattccag | 7260 |
| | | aagtagtgag gaggcttttt tggaggccta gcttttgcaa aaagctccc gggagcttgt | 7320 |
| | | atatccatttt tcggatctga tcagcacgtg ttgacaatta atcatcggca tagtatatcg | 7380 |
| | | gcatagtata atacgacaag gtgaggaact aaaccatggc caagttgacc agtgccgttc | 7440 |
| | | cggtgctcac cgcgcgcgac gtcgccggag cggtcgagtt ctggaccgac cggctcgggt | 7500 |
| | | tctcccggga cttcgtggag gacgacttcg ccggtgtggt ccgggacgac gtgaccctgt | 7560 |
| | | tcatcagcgc ggtccaggac caggtggtgc cggacaacac cctggcctgc gtgtgggtgc | 7620 |
| | | gcggcctgga cgagctgtac gccgagtggt cggaggtcgt gtccacgaac ttccgggacg | 7680 |
| | | cctccgggcc ggccatgacc gagatcggcg agcagccgtg ggggcgggag ttcgcccctgc | 7740 |
| | | gcgaccgcc cggcaactgc gtgcacttcg tggccgagga gcaggactga cacgtgctac | 7800 |
| | | gagatttcga ttccaccgcc gccttctatg aaaggttggg cttcggaatc gttttccggg | 7860 |
| | | acgccggctg gatgatcctc cagcgcgggg atctcatgct ggagttcttc gcccacccca | 7920 |
| | | acttgtttat tgcagcttat aatggttaca aataaagcaa tagcatcaca aatttcacaa | 7980 |
| | | ataaagcatt tttttcactg cattctagtt gtggtttgtc caaactcatc aatgtatctt | 8040 |
| | | atcatgtctg tataccgtcg acctctagct agagcttggc gtaatcatgg tcatagctgt | 8100 |
| | | ttcctgtgtg aaattgttat ccgctcacaa ttccacacaa catacgagcc ggaagcataa | 8160 |
| | | agtgtaaagc ctggggtgcc taatgagtga gctaactcac attaattgcg ttgcgctcac | 8220 |
| | | tgcccgcttt ccagtcggga aacctgtcgt gccagctgca ttaatgaatc ggccaacgcg | 8280 |
| | | cggggagagg cggtttgcgt attgggcgct cttccgcttc ctcgctcact gactcgctgc | 8340 |
| | | gctcggtcgt tcggctgcgg cgagcggtat cagctcactc aaaggcggta atacggttat | 8400 |
| | | ccacagaatc aggggataac gcaggaaaga acatgtgagc aaaaggccag caaaaggcca | 8460 |
| | | ggaaccgtaa aaaggccgcg ttgctggcgt ttttccatag gctccgcccc cctgacgagc | 8520 |
| | | atcacaaaaa tcgacgctca agtcagaggt ggcgaaaccc gacaggacta taaagatacc | 8580 |
| | | aggcgtttcc ccctggaagc tccctcgtgc gctctcctgt tccgaccctg ccgcttaccg | 8640 |
| | | gatacctgtc cgcctttctc ccttcgggaa gcgtggcgct ttctcatagc tcacgctgta | 8700 |
| | | ggtatctcag ttcggtgtag gtcgttcgct ccaagctggg ctgtgtgcac gaaccccccg | 8760 |
| | | ttcagcccga ccgctgcgcc ttatccggta actatcgtct tgagtccaac ccggtaagac | 8820 |
| | | acgacttatc gccactggca gcagccactg gtaacaggat tagcagagcg aggtatgtag | 8880 |
| | | gcggtgctac agagttcttg aagtggtggc ctaactacgg ctacactaga agaacagtat | 8940 |
| | | ttggtatctg cgctctgctg aagccagtta ccttcggaaa aagagttggt agctcttgat | 9000 |
| | | ccggcaaaca aaccaccgct ggtagcggtg gtttttttgt ttgcaagcag cagattacgc | 9060 |
| | | gcagaaaaaa aggatctcaa gaagatcctt tgatctttc tacgggtct gacgctcagt | 9120 |
| | | ggaacgaaaa ctcacgttaa gggattttgg tcatgagatt atcaaaaagg atcttcacct | 9180 |
| | | agatcctttt aaattaaaaa tgaagtttta atcaatcta agtatatat gagtaaactt | 9240 |
| | | ggtctgacag ttaccaatgc ttaatcagtg aggcacctat ctcagcgatc tgtctatttc | 9300 |
| | | gttcatccat agttgcctga ctccccgtcg tgtagataac tacgatacgg gagggcttac | 9360 |
| | | catctggccc cagtgctgca atgataccgc gagacccacg ctcaccggct ccagatttat | 9420 |
| | | cagcaataaa ccagccagcc ggaagggccg agcgcagaag tggtcctgca actttatccg | 9480 |
| | | cctccatcca gtctattaat tgttgccggg aagctagagt aagtagttcg ccagttaata | 9540 |
| | | gtttgcgcaa cgttgttgcc attgctacag gcatcgtggt gtcacgctcg tcgtttggta | 9600 |
| | | tggcttcatt cagctccggt tcccaacgat caaggcgagt tacatgatcc cccatgttgt | 9660 |
| | | gcaaaaaagc ggttagctcc ttcggtcctc cgatcgttgt cagaagtaag ttggccgcag | 9720 |
| | | tgttatcact catggttatg gcagcactgc ataattctct tactgtcatg ccatccgtaa | 9780 |
| | | gatgcttttc tgtgactggt gagtactcaa ccaagtcatt ctgagaatag tgtatgcggc | 9840 |

TABLE 4-continued

List of Sequences

| Seq ID No | Name | Sequence | | | | | |
|---|---|---|---|---|---|---|---|
| | | gaccgagttg ctcttgcccg gcgtcaatac gggataatac cgcgccacat agcagaactt | | | | | 9900 |
| | | taaaagtgct catcattgga aaacgttctt cggggcgaaa actctcaagg atcttaccgc | | | | | 9960 |
| | | tgttgagatc cagttcgatg taacccactc gtgcacccaa ctgatcttca gcatctttta | | | | | 10020 |
| | | cttttaccag cgtttctggg tgagcaaaaa caggaaggca aaatgccgca aaaaagggaa | | | | | 10080 |
| | | taagggcgac acggaaatgt tgaatactca tactcttcct ttttcaatat tattgaagca | | | | | 10140 |
| | | tttatcaggg ttattgtctc atgagcggat acatatttga atgtatttag aaaaataaac | | | | | 10200 |
| | | aaataggggt tccgcgcaca tttccccgaa aagtgccacc tgac | | | | | 10244 |
| 51 | Mini dfp | EIWKSHEDAL QKFEEALNQG GSGGDALRKF EEALKRFEDL KQKGGCGRIW KEHEDAHQKF EEALNQGGSG GDALRKFEEA LKRHEDRVQK | | | | | 60 90 |
| 52 | Nano dfp (EC) | ttcttgaaga cgaaagggcc tcgtgatacg cctattttta taggttaatg tcatgataat | | | | | 60 |
| | | aatggtttct tagacgtcag gtggcacttt tcggggaaat gtgcgcggaa cccctatttg | | | | | 120 |
| | | tttatttttc taaatacatt caaatatgta tccgctcatg agacaataac cctgataaat | | | | | 180 |
| | | gcttcaataa tattgaaaaa ggaagagtat gagtattcaa cattccgtg tcgcccttat | | | | | 240 |
| | | tccctttttt gcggcatttt gccttcctgt ttttgctcac ccagaaacgc tggtgaaagt | | | | | 300 |
| | | aaaagatgct gaagatcagt tgggtgcacg agtgggttac atcgaactgg atctcaacag | | | | | 360 |
| | | cggtaagatc cttgagagtt ttcgccccga gaacgttttt ccaatgatga gcacttttaa | | | | | 420 |
| | | agttctgcta tgtggcgcgg tattatcccg tgttgacgcc gggcaagagc aactcggtcg | | | | | 480 |
| | | ccgcatacac tattctcaga atgacttggt tgagtactca ccagtcacag aaaagcatct | | | | | 540 |
| | | tacgatggc atgacagtaa gagaattatg cagtgctgcc ataaccatga gtgataacac | | | | | 600 |
| | | tgcggccaac ttacttctga caacgatcgg aggaccgaag gagctaaccg cttttttgca | | | | | 660 |
| | | caacatgggg gatcatgtaa ctcgccttga tcgttgggaa ccggagctga atgaagccat | | | | | 720 |
| | | accaaacgac gagcgtgaca ccacgatgcc tgcagcaatg gcaacaacgt tgcgcaaact | | | | | 780 |
| | | attaactggc gaactactta ctctagcttc ccggcaacaa ttaatagact ggatggaggc | | | | | 840 |
| | | ggataaagtt gcaggaccac ttctgcgctc ggcccttccg gctggctggt ttattgctga | | | | | 900 |
| | | taaatctgga gccggtgagc gtgggtctcg cggtatcatt gcagcactgg ggccagatgg | | | | | 960 |
| | | taagccctcc cgtatcgtag ttatctacac gacgggggagt caggcaacta tggatgaacg | | | | | 1020 |
| | | aaatagacag atcgctgaga taggtgcctc actgattaag cattggtaac tgtcagacca | | | | | 1080 |
| | | agtttactca tatatacttt agattgattt aaaacttcat ttttaattta aaaggatcta | | | | | 1140 |
| | | ggtgaagatc ctttttgata atctcatgac caaaatccct taacgtgagt tttcgttcca | | | | | 1200 |
| | | ctgagcgtca gaccccgtag aaaagatcaa aggatcttct tgagatcctt tttttctgcg | | | | | 1260 |
| | | cgtaatctgc tgcttgcaaa caaaaaaacc accgctacca gcggtggttt gtttgccgga | | | | | 1320 |
| | | tcaagagcta ccaactcttt ttccgaaggt aactggcttc agcagagcgc agataccaaa | | | | | 1380 |
| | | tactgtcctt ctagtgtagc cgtagttagg ccaccacttc aagaactctg tagcaccgcc | | | | | 1440 |
| | | tacatacctc gctctgctaa tcctgttacc agtggctgct gccagtggcg ataagtcgtg | | | | | 1500 |
| | | tcttaccggg ttggactcaa gacgatagtt accggataag gcgcagcggt cgggctgaac | | | | | 1560 |
| | | gggggggttcg tgcacacagc ccagcttgga gcgaacgacc tacaccgaac tgagatacct | | | | | 1620 |
| | | acagcgtgag ctatgagaaa gcgccacgct tcccgaaggg agaaaggcgg acaggtatcc | | | | | 1680 |
| | | ggtaagcggc agggtcggaa caggagagcg cacgagggag cttccagggg gaaacgcctg | | | | | 1740 |
| | | gtatctttat agtcctgtcg ggtttcgcca cctctgactt gagcgtcgat ttttgtgatg | | | | | 1800 |
| | | ctcgtcaggg gggcggagcc tatggaaaaa cgccagcaac gcggcctttt tacggttcct | | | | | 1860 |
| | | ggccttttgc tggccttttg ctcacatgtt ctttcctgcg ttatccctg attctgtgga | | | | | 1920 |
| | | taaccgtatt accgcctttg agtgagctga taccgctcgc cgcagccgaa cgaccgagcg | | | | | 1980 |
| | | cagcgagtca gtgagcgagg aagcggaaga gcgcctgatg cggtattttc tccttacgca | | | | | 2040 |
| | | tctgtgcggt atttcacacc gcatatatgg tgcactctca gtacaatctg ctctgatgcc | | | | | 2100 |
| | | gcatagttaa gccagtatac actccgctat cgctacgtga ctgggtcatg gctgcgcccc | | | | | 2160 |
| | | gacaccgc aacaccccgct gacgcgccct gacgggcttg tctgctcccg gcatccgctt | | | | | 2220 |
| | | acagacaagc tgtgaccgtc tccgggagct gcatgtgtca gaggttttca ccgtcatcac | | | | | 2280 |
| | | cgaaacgcgc gaggcagctg cggtaaagct catcagcgtg gtcgtgaagc gattcacaga | | | | | 2340 |
| | | tgtctgcctg ttcatccgcg tccagctcgt tgagtttctc cagaagcgtt aatgtctggc | | | | | 2400 |
| | | ttctgataaa gcgggccatg ttaagggcgg ttttttcctg tttggtcact gatgcctccg | | | | | 2460 |
| | | tgtaaggggg atttctgttc atgggggtaa tgataccgat gaaacgagag aggatgctca | | | | | 2520 |
| | | cgatacgggt tactgatgat gaacatgccc ggttactgga acgttgtgag ggtaaacaac | | | | | 2580 |
| | | tggcggtatg gatgcggcgg gaccagagaa aaatcactca gggtcaatgc cagcgcttcg | | | | | 2640 |
| | | ttaatacaga tgtaggtgtt ccacagggta gccagcagca tcctgcgatg cagatccgga | | | | | 2700 |
| | | acataatggt gcagggcgct gacttccgcg tttccagact tacgaaaca cggaaaccga | | | | | 2760 |
| | | agaccattca tgttgttgct caggtcgcag acgttttgca gcagcagtcg cttcacgttc | | | | | 2820 |
| | | gctcgcgtat cggtgattca ttctgctaac cagtaaggca accccgccag cctagccggg | | | | | 2880 |
| | | tcctcaacga caggagcacg atcatgcgca cccgtggcca gacccaacg ctgcccgaga | | | | | 2940 |
| | | tgcgccgcgt gcggctgctg gagatggcgg agcgatgga tatgttctgc caagggttgg | | | | | 3000 |
| | | tttgcgcatt cacagttctc cgcaagaatt gattggctcc aattcttgga gtggtgaatc | | | | | 3060 |
| | | cgttagcgag gtgccgccgg cttccattca ggtcgaggtg gcccggctcc atgcaccgcg | | | | | 3120 |
| | | acgcaacgcg gggaggcaga caaggtatag gcggcgcct acaatccatg ccaacccgtt | | | | | 3180 |
| | | ccatgtgctc gccgaggcgg cataaatcgc cgtgacgatc agcggtccag tgatcgaagt | | | | | 3240 |
| | | taggctggta agagccgcga gcgatccttg aagctgtccc tgatggtcgt catctacctg | | | | | 3300 |
| | | cctggacagc atggcctgca acgcgggcat cccgatgccg ccggaagcga agaatcat | | | | | 3360 |
| | | aatggggaag gccatccagc ctcgcgtcgc gaacgccagc aagacgtagc ccagcgcgtc | | | | | 3420 |
| | | ggccgccatg ccggcgataa tggcctgctt ctcgccgaaa cgtttggtgg cgggaccagt | | | | | 3480 |
| | | gacgaaggct tgagcgaggg cgtgcaagat tccgaatacc gcaagcgaca ggccgatcat | | | | | 3540 |
| | | cgtcgcgctc cagcgaaagc ggtcctcgcc gaaaatgacc cagagcgctg ccggcacctg | | | | | 3600 |
| | | tcctacgagt tgcatgataa agaagacagt cataagtgcg gcgacgatag tcatgccccg | | | | | 3660 |
| | | cgcccaccgg aaggagctga ctgggttgaa ggctctcaag ggcatcggtc gagatcccgg | | | | | 3720 |
| | | tgcctaatga gtgagctaac ttcattaat tgcgttgcgc tcactgcccg ctttccagtc | | | | | 3780 |

TABLE 4-continued

List of Sequences

| Seq ID No | Name | Sequence | |
|---|---|---|---|
| | | gggaaacctg tcgtgccagc tgcattaatg aatcggccaa cgcgcgggga gaggcggttt | 3840 |
| | | gcgtattggg cgccagggtg gtttttcttt tcaccagtga dacgggcaac agctgattgc | 3900 |
| | | ccttcaccgc ctggccctga gagagttgca gcaagcggtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggcg gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacggcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc acttttttccc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtcccccgg ccacggggcc tgccaccata cccacgccga acaagcgct catgagcccg | 5100 |
| | | aagtggcgag cccgatcttc cccatcggtg atgtcggcga taggcgcc agcaaccgca | 5160 |
| | | cctgtggcgc cggtgatgcc ggccacgatg cgtccggcgt agaggatcga gatctcgatc | 5220 |
| | | ccgcgaaatt aatacgactc actatagggg aattgtgagc ggataacaat tcccctctag | 5280 |
| | | aaataatttt gtttaacttt aagaaggaga tataccatgg cagcagcca tcatcatcat | 5340 |
| | | catcacgcg gcgacggcga gaacttgtat tttcaagcta gcggatccat gggggaaatc | 5400 |
| | | tggaagtcac atgaagatgc tttgcagaag tttgaggaag ggggtccgg cggccgcttc | 5460 |
| | | gaggaggcct tgaaacgttt tgaagatttg aaacagaagg gtgctgtgg acgtatctgg | 5520 |
| | | aaagagcatg aagatgcgca tcaaaagttt gaggagggag gttctggtgg ccgttttgag | 5580 |
| | | gaagcattga agcgtcacga ggatcgcgtg caaaagtgat aagaattcct cgaggctgct | 5640 |
| | | aacaaagccc gaaaggaagc tgagttggct gctgccaccg ctgagcaata actagcataa | 5700 |
| | | cccccttggg cctctaaacg ggtcttgagg gttttttttgc tgaaaggagg aactatatcc | 5760 |
| | | ggatatcccg caagaggccc ggcagtaccg gcataaccaa gcctatgcct acagcatcca | 5820 |
| | | gggtgacggt gccgaggatg acgatgagcg cattgttaga tttcatacac ggtgcctgac | 5880 |
| | | tgcgttagca atttaactgt gataaactac cgcattaaag cttatcgatg ataagctgtc | 5940 |
| | | aaacatgaga a | 5951 |
| 53 | Nano dfp (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtact | 120 |
| | | gcgcgagcaa aatttaagct acaacaaggc aaggcttgac cgacaattgc atgaagaatc | 180 |
| | | tgcttagggt taggcgtttt cgcgctgcttc gcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatgcccc gcctggctga ccgcccaacg | 360 |
| | | accccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg cccccattg acgtcaatga cggtaaatgg cccgcctggc | 540 |
| | | attatgccca gtacatgacc ttatgggact ttcctactt gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggtcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc aggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga gaaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccaa caattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |

TABLE 4-continued

List of Sequences

| Seq ID No | Name | Sequence | |
|---|---|---|---|
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aagggggat | 2460 |
| | | tgggggtac agtgcagggg aaagaatagt agacataata gcaacagaca tacaaactaa | 2520 |
| | | agaattacaa aaacaaatta caaaaattca aaattttcgg gttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg catgatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagataggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acggggcaat acctgtctct tcagaggagg | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagacg atgatcactt gtggactaag | 3540 |
| | | tttgttcaca tccccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gcccctagtt ctgggggcag cggggatcc | 3900 |
| | | atgggggaaa tctggaagtc acatgaagat gctttgcaga agttgagga agggggtcc | 3960 |
| | | ggcggccgct tcgaggaggc cttgaaacgt tttgaagatt tgaaacagaa gggtggctgt | 4020 |
| | | ggacgtatct ggaaagagca tgaagatgcg catcaaaagt ttgaggaggg aggttctggt | 4080 |
| | | ggccgttttg aggaagcatt gaagcgtcac gaggatcgcg tgcaaaaggc ggcaccggta | 4140 |
| | | gtagcagtga gcaagggcga ggagctgttc accggggtgg tgcccatcct ggtcgagctg | 4200 |
| | | gacggcgacg taaacggcca caagttcagc gtgtccggcg agggcgaggg cgatgccacc | 4260 |
| | | tacggcaagc tgaccctgaa gttcatttgc accaccggca agctgcccgt gccctggccc | 4320 |
| | | accctcgtga ccaccctgac ctacgcgtg cagtgcttca gccgctaccc cgaccacatg | 4380 |
| | | aagcagcacg acttcttcaa gtccgccatg cccgaaggct acgtccagga gcgcaccatc | 4440 |
| | | ttcttcaagg acgacggcaa ctacaagacc cgcgccgagg tgaagttcga gggcgacacc | 4500 |
| | | ctggtgaacc gcatcgagct gaagggcatc gacttcaagg aggacggcaa catcctggg | 4560 |
| | | cacaagctgg agtacaacta caacgccac aacgtctata tcatggccga caagcagaag | 4620 |
| | | aacggcatca aggtgaactt caagatccgc cacaacatcg aggacggcag cgtgcagctc | 4680 |
| | | gccgaccact accagcagaa caccccatc ggcgacggcc ccgtgctgct gcccgacaac | 4740 |
| | | cactacctga gcacccagtc cgccctgagc aaagacccca acgagaagcg cgatcacatg | 4800 |
| | | gtcctgctgg agttcgtgac cgccgcgggg atcactctcg gcatggacga gctgtacaag | 4860 |
| | | taagaattcg atatcaagct tatcgataat caaccctctg attacaaaat ttgtgaaaga | 4920 |
| | | ttgactgta ttccttaacta tgttgctcct tttacgctat gtggatacgc tgctttaatg | 4980 |
| | | cctttgtatc atgctattgc ttcccgtatg gctttcattt tctcctcctt gtataaatcc | 5040 |
| | | tggttgctgt ctctttatga ggagttgtgg cccgttgtca ggcaacgtgg cgtggtgtgc | 5100 |
| | | actgtgtttg ctgacgcaac cccactggt tggggcattg ccaccacctg tcagctcctt | 5160 |
| | | tccgggactt tcgctttccc cctcccatt gccacggcgg aactcatcgc cgcctgcctt | 5220 |
| | | gcccgctgct ggacaggggc tcggctgttg ggcactgaca attccgtggt gttgtcgggg | 5280 |
| | | aaatcatcgt cctttccttg gctgctcgcc tgtgttgcca cctggattct gcgcgggacg | 5340 |
| | | tccttctgct acgtcccttc ggccctcaat ccagcggacc ttccttcccg cggcctgctg | 5400 |
| | | ccggctctgc ggcctcttcc gcgtcttcgc cttcgccctc agacgagtcg gatctccctt | 5460 |
| | | tgggccgcct ccccgcatcg ataccgtcga cctcgagacc tagaaaaaca tggagcaatc | 5520 |
| | | acaagtagca atacagccag taccaatgct gatttgtgct ggctagaagc acaagaggag | 5580 |
| | | gaggaggtgg gttttccagt cacacctcag gtacctttaa gaccaatgac ttacaaggca | 5640 |
| | | gctgtagatc ttagccactt tttaaaagaa aaggggggac tggaaggct aattcactcc | 5700 |
| | | caacgaagac aagatatcct tgatctgtgg atctaccaca cacaaggcta cttccctgat | 5760 |
| | | tggcagaact acacaccagg gccagggatc agatatccac tgacctttgg atggtgctac | 5820 |
| | | aagctagtac cagttgagca agagaaggta gaagaagcca atgaaggaga aacaccgcgc | 5880 |
| | | ttgttacacc ctgtgagcct gcatgggatg gatgacccgg agagagaagt attagagtgg | 5940 |
| | | aggtttgaca gccgcctagc atttcatcac atggcccgag agctgcatcc ggactgtact | 6000 |
| | | gggtctctct ggttagacca gatctgagcc tgggagctct ctggctaact agggaaccca | 6060 |
| | | ctgcttaagc ctcaataaag cttgccttga gtgcttcaag tagtgtgtgc ccgtctgttg | 6120 |
| | | tgtgactctg gtaactagag atccctcaga cccttttagt cagtgtggaa aatctctagc | 6180 |
| | | agggcccgtt taaaccgct gatcagcctc gactgtgcct ctagttgcc agccatcgt | 6240 |
| | | tgtttgccc tccccgtgc cttcctgac cctggaaggt gccactccca ctgtccttc | 6300 |
| | | ctaataaaat gaggaaattg catcgcattg tctgagtagg tgtcattcta ttctgggggg | 6360 |
| | | tggggtgggg caggacagca agggggagga ttgggaagac aatagcaggc atgctgggga | 6420 |
| | | tgcggtgggc tctatggctt ctgaggcgga aagaaccagc tggggctcta ggggtatcc | 6480 |
| | | ccacgcgccc tgtagcggcg cattaagcgc ggcgggtgtg tggttacgc gcagcgtgac | 6540 |
| | | cgctacactt gccagcgccc tagcgcccgc tcctttcgct ttcttccctt cctttctcgc | 6600 |

TABLE 4-continued

List of Sequences

| Seq ID No | Name | Sequence | |
|---|---|---|---|
| | | cacgttcgcc ggctttcccc gtcaagctct aaatcggggg ctccctttag ggttccgatt | 6660 |
| | | tagtgcttta cggcacctcg accccaaaaa acttgattag ggtgatggtt cacgtagtgg | 6720 |
| | | gccatcgccc tgatagacgg ttttcgccc tttgacgttg gagtccacgt tctttaatag | 6780 |
| | | tggactcttg ttccaaactg gaacaacact caaccctatc tcggtctatt cttttgattt | 6840 |
| | | ataagggatt ttgccgattt cggcctattg gttaaaaaat gagctgattt aacaaaaatt | 6900 |
| | | taacgcgaat taattctgtg gaatgtgtgt cagttagggt gtggaaagtc cccaggctcc | 6960 |
| | | ccagcaggca gaagtatgca aagcatgcat ctcaattagt cagcaaccag gtgtggaaag | 7020 |
| | | tccccaggct ccccagcagg cagaagtatg caaagcatgc atctcaatta gtcagcaacc | 7080 |
| | | atagtcccgc ccctaactcc gcccatcccg ccctaactc cgcccagttc cgcccattct | 7140 |
| | | ccgccccatg gctgactaat ttttttatt tatgcagagg ccgaggccgc ctctgcctct | 7200 |
| | | gagctattcc agaagtagtg aggaggcttt tttggaggcc taggcttttg caaaaagctc | 7260 |
| | | ccgggagctt gtatatccat tttcggatct gatcagcacg tgttgacaat taatcatcgg | 7320 |
| | | catagtatat cggcatagta taatacgaca aggtgaggaa ctaaaccatg gccaagttga | 7380 |
| | | ccagtgccgt tccggtgctc accgcgcgcg acgtcgccgg agcggtcgag ttctggaccg | 7440 |
| | | accggctcgg gttctcccgg gacttcgtgg aggacgagtt cgccggtgtg gtccgggacg | 7500 |
| | | acgtgaccct gttcatcagc gcggtccagg accaggtggt gccggacaac accctggcct | 7560 |
| | | gggtgtgggt gcgcggcctg gacgagctgt acgccgagtg gtcggaggtc gtgtccacga | 7620 |
| | | acttccggga cgcctccggg ccgccatga ccgagatcgg cgagcagccg tggggcggg | 7680 |
| | | agttcgccct gcgcgacccg gccggcaact gcgtgcactt cgtggccgag gagcaggact | 7740 |
| | | gacacgtgct acgagatttc gattccaccg ccgccttcta tgaaaggttg ggcttcgaa | 7800 |
| | | tcgttttccg ggacgccggc tggatgatcc tccagcgcgg ggatctcatg ctggagttct | 7860 |
| | | tcgcccaccc caacttgttt attgcagctt ataatggtta caaataaagc aatagcatca | 7920 |
| | | caaatttcac aaataaagca ttttttttcac tgcattctag ttgtggtttg tccaaactca | 7980 |
| | | tcaatgtatc ttatcatgtc tgtataccgt cgacctctag ctagagcttg gcgtaatcat | 8040 |
| | | ggtcatagct gtttcctgtg tgaaattgtt atccgctcac aattccacac aacatacgag | 8100 |
| | | ccggaagcat aaagtgtaaa gcctggggtg cctaatgagt gagctaactc acattaattg | 8160 |
| | | cgttgcgctc actgcccgct ttccagtcgg gaaacctgtc gtgccagctg cattaatgaa | 8220 |
| | | tcggccaacg cgcggggaga ggcggtttgc gtattgggcg ctcttccgct tcctcgctca | 8280 |
| | | ctgactcgct gcgctcggtc gttcggctgc ggcgagcggt atcagctcac tcaaaggcgg | 8340 |
| | | taatacggtt atccacagaa tcaggggata acgcaggaaa gaacatgtga gcaaaaggcc | 8400 |
| | | agcaaaaggc caggaaccgt aaaaaggccg cgttgctggc gttttttccat aggctccgcc | 8460 |
| | | ccctgacga gcatcacaaa aatcgacgct caagtcagag gtggcgaaac ccgacaggac | 8520 |
| | | tataaagata ccaggcgttt ccccctggaa gctccctcgt gcgctctcct gttccgaccc | 8580 |
| | | tgccgcttac cggatacctg tccgcctttc tcccttcggg aagcgtggcg ctttctcata | 8640 |
| | | gctcacgctg taggtatctc agttcggtgt aggtcgttcg ctccaagctg ggctgtgtgc | 8700 |
| | | acgaaccccc cgttcagccc gaccgctgcg ccttatccgg taactatcgt cttgagtcca | 8760 |
| | | acccggtaag acacgactta tcgccactgg cagcagccac tggtaacagg attagcagag | 8820 |
| | | cgaggtatgt aggcggtgct acagagttct tgaagtggtg gcctaactac ggctacacta | 8880 |
| | | gaagaacagt atttggtatc tgcgctctgc tgaagccagt taccttcgga aaaagagttg | 8940 |
| | | gtagctcttg atccggcaaa caaaccaccg ctggtagcgg tggttttttt gtttgcaagc | 9000 |
| | | agcagattac gcgcagaaaa aaaggatctc aagaagatcc tttgatcttt tctacggggt | 9060 |
| | | ctgacgctca gtggaacgaa aactcacgtt aagggatttt ggtcatgaga ttatcaaaaa | 9120 |
| | | ggatcttcac ctagatcctt ttaaattaaa aatgaagttt taaatcaatc taaagtatat | 9180 |
| | | atgagtaaac ttggtctgac agttaccaat gcttaatcag tgaggcacct atctcagcga | 9240 |
| | | tctgtctatt tcgttcatcc atagttgcct gactccccgt cgtgtagata actacgatac | 9300 |
| | | gggagggctt accatctggc cccagtgctg caatgatacc gcgagaccca cgctcaccgg | 9360 |
| | | ctccagattt atcagcaata aaccagccag ccggaagggc cgagcgcaga agtggtcctg | 9420 |
| | | caactttatc cgcctccatc cagtctatta attgttgccg ggaagctaga gtaagtagtt | 9480 |
| | | cgccagttaa tagtttgcgc aacgttgttg ccattgctac aggcatcgtg gtgtcacgct | 9540 |
| | | cgtcgtttgg tatggcttca ttcagctccg gttcccaacg atcaaggcga gttacatgat | 9600 |
| | | cccccatgtt gtgcaaaaaa gcggttagct ccttcggtcc tccgatcgtt gtcagaagta | 9660 |
| | | agttggccgc agtgttatca ctcatggtta tggcagcact gcataattct cttactgtca | 9720 |
| | | tgccatccgt aagatgcttt tctgtgactg gtgagtactc aaccaagtca ttctgagaat | 9780 |
| | | agtgtatgcg gcgaccgagt tgctcttgcc cggcgtcaat acgggataat accgcgccac | 9840 |
| | | atagcagaac tttaaaagtg ctcatcattg gaaaacgttc ttcggggcga aaactctcaa | 9900 |
| | | ggatcttacc gctgttgaga tccagttcga tgtaacccac tcgtgcaccc aactgatctt | 9960 |
| | | cagcatcttt tactttcacc agcgtttctg ggtgagcaaa aacaggaagg caaaatgccg | 10020 |
| | | caaaaaaggg aataagggcg acacggaaat gttgaatact catactcttc ctttttcaat | 10080 |
| | | attattgaag catttatcag ggttattgtc tcatgagcgg atacatattt gaatgtattt | 10140 |
| | | agaaaaataa acaaataggg gttccgcgca catttccccg aaaagtgcca cctgac | 10196 |
| 54 | Nano dfp | EIWKSHEDAL QKFEEGGSGG RFEEALKRFE DLQKGGCGR IWKEHEDAHQ KFEEGGSGGR | 60 |
| | | FEEALKRHED RVQK | 74 |
| 55 | 528-GL (EC) | ttccttgaaga cgaaagggcc tcgtgatacg cctattttta taggttaatg tcatgataat | 60 |
| | | aatggtttct tagacgtcag gtggcacttt tcggggaaat gtgcgcggaa cccctatttg | 120 |
| | | tttatttttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tcccttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |

TABLE 4-continued

List of Sequences

| Seq ID No | Name | Sequence | |
|---|---|---|---|
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc cttttttgata atctcatgac caaaatccct taacgtgagt tttcgttcca | 1200 |
| | | ctgagcgtca gaccccgtag aaaagatcaa aggatcttct tgagatcctt ttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggccttt tacggttcct | 1860 |
| | | ggccttttgc tggccttttg ctcacatgtt ctttcctgcg ttatccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacaccgct gacgcgccct gacgggcttg tctgctcccg gcatccgctt | 2220 |
| | | acagacaagc tgtgaccgtc tccgggagct gcatgtgtca ggggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg tttggtcact gatgcctccg | 2460 |
| | | tgtaaggggg attctgttc atggggtaa tgataccgat gaaacgagag aggatgctca | 2520 |
| | | cgatacgggt tactgatgat gaacatgccc ggttactgga acgttgtgag ggtaaacaac | 2580 |
| | | tggcgtatg gatgcggcgg gaccagagaa aaatcactca gggtcaatgc cagcgcttcg | 2640 |
| | | ttaatacaga tgtaggtgtt ccagggta gccagcagca tcctgcgatg cagatccgga | 2700 |
| | | acataatggt gcaggggcgt gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg ggatggcgg agcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgc cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag gcatcggtc gagatcccgg | 3720 |
| | | tgcctaatga gtgagctaac ttacattaat tgcgttgcgc tcactgcccg cttccagtc | 3780 |
| | | gggaaacctg tcgtgccagc tgcattaatg aatcggccaa cgcgcgggga gaggcggttt | 3840 |
| | | gcgtattggg cgccagggtg ttttctttt caccagtga cgggcaac agctgattgc | 3900 |
| | | ccttcaccgc ctggccctga gagagttgca gcaagcggtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga tatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctgtc agagacatca agaaataacg ccggaacatt agtgcaggca gcttccacag | 4440 |
| | | caatggcatc ctggtcatcc agcggatagt taatgatcac cccactgacg cgttgcgcga | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacgcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc actttttccc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |

TABLE 4-continued

List of Sequences

| Seq ID No | Name | Sequence | |
|---|---|---|---|
| | | agtcccccgg ccacggggcc tgccaccata cccacgccga aacaagcgct catgagcccg | 5100 |
| | | aagtggcgag cccgatcttc cccatcggtg atgtcggcga tataggcgcc agcaaccgca | 5160 |
| | | cctgtggcgc cggtgatgcc ggccacgatg cgtccggcgt agaggatcga gatctcgatc | 5220 |
| | | ccgcgaaatt aatacgactc actatagggg aattgtgagc ggataacaat tcccctctag | 5280 |
| | | aaataatttt gtttaacttt aagaaggaga tataccatgg gcgaaggcga tattcatatg | 5340 |
| | | ggtaaaggtg ggcatcacca tcatcaccac ggaggcgatg gtgaaaacct gtattttcag | 5400 |
| | | ggatccggca tgggcgagat ttggaagcaa cacgaggacg ctctgcagaa gtttgaggaa | 5460 |
| | | gcactgaacc aatttgagga cctgaagcaa ctgggtggca gcggcaaggg cagcggcggt | 5520 |
| | | gagatctgga aacagtgcga agacgcgctg cgtaagttcg aagaggcgct gaagcgtttc | 5580 |
| | | gaggatctga agcagaaagg cggtagcggc gagatctgga agcagcacga agacgctctg | 5640 |
| | | cagaaattcg aagaggcgct gaaccagttt gaggatctga agcagctggg cggtagcggt | 5700 |
| | | aaaggcagcg gcggtgaaat ctggaagcag cacgaagatg ccctgcgtaa gtttgaagaa | 5760 |
| | | gccctgaagc gttttgagga cctgaagcag aagaccggtt gactcgagga tccggctgct | 5820 |
| | | aacaaagccc gaaaggaagc tgagttggct gctgccaccg ctgagcaata actagcataa | 5880 |
| | | cccctt gggg cctctaaacg ggtcttgagg ggttttttgc tgaaaggagg aactatatcc | 5940 |
| | | ggatatcccg caagaggccc ggcagtaccg gcataaccaa gcctatgcct acagcatcca | 6000 |
| | | gggtgacggt gccgaggatg acgatgagcg cattgttaga tttcatacac ggtgcctgac | 6060 |
| | | tgcgttagca atttaactgt gataaactac cgcattaaag cttatcgatg ataagctgtc | 6120 |
| | | aaacatgaga a | 6131 |
| 56 | 528-GL (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aagcttgaac cgacaattgc atgaagaatc | 180 |
| | | tgcttagggt taggcgtttt gcgctgcttc gcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg cccccattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagaccctt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc aggggggaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcata | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagaa aaaaaagagc agtgggaata | 1680 |
| | | ggagcttttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcaggata ttcaccatta | 2280 |
| | | tcgtttcaga cccacctccc aaccccgagg gacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaagaaa aaggggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccga ccacgttcac ctcattatag ttgcctctct cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |

TABLE 4-continued

List of Sequences

| Seq ID No | Name | Sequence | |
|---|---|---|---|
| | | agaaaccatt acagagacta caaggggaa gggaaggaga gatgaattag cttcccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagagcg atgatcactt gtggactaag | 3540 |
| | | tttgttcaca tcccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gccccctagtt ctggggcag cgggggatcc | 3900 |
| | | ggcatgggcg agatttggaa gcaacacgag gacgctctgc agaagtttga ggaagcactg | 3960 |
| | | aaccaatttg aggacctgaa gcaactgggt ggcagcggca agggcagcgg cggtgagatc | 4020 |
| | | tggaaacagt gcgaagacgc gctgcgtaag ttcgaagagg cgctgaagcg tttcgaggat | 4080 |
| | | ctgaagcaga aaggcggtag cggcgagatc cggcggcagc acgaagcgc tctgcagaaa | 4140 |
| | | ttcgaagagg cgctgaacca gtttgaggat ctgaagcagc tgggcggtag cggtaaaggc | 4200 |
| | | agcggcggtg aaatctggaa gcagcacgaa gatgccctgc gtaagtttga agaagccctg | 4260 |
| | | aagcgttttg aggacctgaa gcagaagacc ggtagtagca gtgagcaagg gcgaggagct | 4320 |
| | | gttcaccggg gtggtgccca tcctggtcga gctggacggc gacgtaaacg gccacaagtt | 4380 |
| | | cagcgtgtcc ggcgagggcg agggcgatgc cacctacggc aagctgaccc tgaagttcat | 4440 |
| | | ttgcaccacc ggcaagctgc ccgtgccctg gcccaccctc gtgaccaccc tgacctacgg | 4500 |
| | | cgtgcagtgc ttcagccgct accccgacca catgaagcag cacgacttct tcaagtccgc | 4560 |
| | | catgcccgaa ggctacgtcc aggagcgcac catcttcttc aaggacgacg gcaactacaa | 4620 |
| | | gacccgcgcc gaggtgaagt tcgagggcga cacctggt aaccgcatcg agctgaaggg | 4680 |
| | | catcgacttc aaggaggacg gcaacatcct ggggcacaag ctggagtaca actacaacag | 4740 |
| | | ccacaacgtc tatatcatgg ccgacaagca gaagaacggc atcaaggtga acttcaagat | 4800 |
| | | ccgccacaac atcgaggacg gcagcgtgca gctcgccgac cactaccagc agaacacccc | 4860 |
| | | catcggcgac ggccccgtgc tgctgcccga caaccactac ctgagcaccc agtccgccct | 4920 |
| | | gagcaaagac cccaacgaga gcgcgatca catggtcctg ctggagttcg tgaccgccgc | 4980 |
| | | cgggatcact ctcggcatgg acgagctgta caagtaagaa ttcgatatca agcttatcga | 5040 |
| | | taatcaacct ctggattaca aaatttgtga agattgact ggtattctta actatgttgc | 5100 |
| | | tccttttacg ctatgtggat acgctgcttt aatgcctttg tatcatgcta ttgcttcccg | 5160 |
| | | tatggctttc attttctcct ccttgtataa atcctggttg ctgtctcttt atgaggagtt | 5220 |
| | | gtggcccgtt gtcaggcaac gtggcgtggt gtgcactgtg tttgctgacg caacccccac | 5280 |
| | | tggttgggc attgccacca cctgtcagct cctttccggg actttcgctt tccccctccc | 5340 |
| | | tattgccacg gcggaactca tcgccgcctg ccttgcccgc tgctggacag gggctcggct | 5400 |
| | | gttgggcact gacaattccg tggtgttgtc ggggaaatca tcgtcctttc cttggctgct | 5460 |
| | | cgcctgtgtt gccacctgga ttctgcgcgg gacgtccttc tgctacgtcc cttcggccct | 5520 |
| | | caatccagcg gaccttcctt cccgcggcct gctgccggct ctgcggcctc ttccgcgtct | 5580 |
| | | tcgccttcgc cctcagacga gtcggatctc cctttgggcc gcctccccgc atcgataccg | 5640 |
| | | tcgacctcga gacctagaaa aacatggagc aatcacaagt agcaatacag cagctaccaa | 5700 |
| | | tgctgattgt gcctggctag aagcacaaga ggaggaggag gtgggtttc cagtcacacc | 5760 |
| | | tcaggtacct ttaagaccaa tgacttacaa ggcagctgta gatcttagcc actttttaaa | 5820 |
| | | agaaaagggg ggactggaag ggctaattca ctcccaacga agacaagata tccttgatct | 5880 |
| | | gtggatctac cacacacaag gctacttccc tgattggcag aactacacac cagggccagg | 5940 |
| | | gatcagatat ccactgacct ttggatggtg ctacaagcta gtaccagttg agcaagagaa | 6000 |
| | | ggtagaagaa gccaatgaag gagagaacac ccgcttgtta caccctgtga gcctgcatgg | 6060 |
| | | gatggatgac ccggagagag aagtattaga gtggaggttt gacagccgcc tagcatttca | 6120 |
| | | tcacatggcc cgagagctgc atccggactg tactgggtct ctctggttag accagatctg | 6180 |
| | | agcctgggag ctctctggct aactagggaa cccactgctt aagcctcaat aaagcttgcc | 6240 |
| | | ttgagtgctt caagtagtgt gtgcccgtct gttgtgtgac tctggtaact agagatccct | 6300 |
| | | cagacccttt tagtcagtgt ggaaaatctc tagcagggcc cgtttaaacc cgctgatcag | 6360 |
| | | cctcgactgt gccttctagt tgccagccat ctgttgtttg ccctccccc gtgccttcct | 6420 |
| | | tgaccctgga aggtgccact cccactgtcc tttcctaata aaatgaggaa attgcatcgc | 6480 |
| | | attgtctgag taggtgtcat tctattctgg ggggtggggt gggcaggac agcaagggg | 6540 |
| | | aggattggga agacaatagc aggcatgctg gggatgcggt gggctctatg gcttctgagg | 6600 |
| | | cggaaagaac cagctggggc tctaggggggt atcccccagc gccctgtagc ggcgcattaa | 6660 |
| | | gcgcggcggg tgtggtggtt acgcgcagcg tgaccgctac acttgccagc gccctagcgc | 6720 |
| | | ccgctccttt cgctttcttc ccttcctttc tcgccacgtt cgccggcttt cccgtcaag | 6780 |
| | | ctctaaatcg ggggctccct ttagggttcc gatttagtgc tttacggcac ctcgaccca | 6840 |
| | | aaaaacttga ttagggtgat ggttcacgta gtgggccatc gccctgatag acggttttc | 6900 |
| | | gccctttgac gttggagtcc acgttcttta atagtggact cttgttccaa actggaacaa | 6960 |
| | | cactcaaccc tatctcggtc tattcttttg atttataagg gattttgccg atttcggcct | 7020 |
| | | attggttaaa aaatgagctg atttaacaaa aatttaacgc gaattaattc tgtggaatgt | 7080 |
| | | gtgtcagtta gggtgtggaa agtccccagg ctccccagca ggcagaagta tgcaaagcat | 7140 |
| | | gcatctcaat tagtcagcaa ccaggtgtgg aaagtcccca ggctcccag caggcagaag | 7200 |
| | | tatgcaaagc atgcatctca attagtcagc aaccatagtc ccgcccctaa ctccgcccat | 7260 |
| | | cccgcccta actccgccca gttccgccca ttctccgccc catggctgac taattttttt | 7320 |
| | | tatttatgca gaggccgagg ccgcctctgc ctctgagcta ttccagaagt agtgaggagg | 7380 |
| | | cttttttgga ggcctaggct tttgcaaaaa gctcccggga gcttgtatat ccattttcgg | 7440 |
| | | atctgatcag cacgtgttga caattaatca tcggcatagt atatcggcat agtataatac | 7500 |
| | | gacaaggtga ggaactaaac catggccaag ttgaccagtg ccgttccggt gctcaccgcg | 7560 |
| | | cgcgacgtcg ccggagcggt cgagttctgg accgaccggc tcgggttctc ccgggacttc | 7620 |
| | | gtggaggacg acttcgccgg tgtggtccgg gacgacgtga ccctgttcat cagcgcggtc | 7680 |

TABLE 4-continued

List of Sequences

| Seq ID No | Name | Sequence | |
|---|---|---|---|
| | | caggaccagg tggtgccgga caacaccctg gcctgggtgt gggtgcgcgg cctggacgag | 7740 |
| | | ctgtacgccg agtggtcgga ggtcgtgtcc acgaacttcc gggacgcctc cgggccggcc | 7800 |
| | | atgaccgaga tcgcgagca gccgtggggg cgggagttcg ccctgcgcga cccggccggc | 7860 |
| | | aactgcgtgc acttcgtggc cgaggagcag gactgacacg tgctacgaga tttcgattcc | 7920 |
| | | accgccgcct tctatgaaag gttgggcttc ggaatcgttt tccgggacgc cggctggatg | 7980 |
| | | atcctccagc gcggggatct catgctggag ttcttcgccc accccaactt gtttattgca | 8040 |
| | | gcttataatg gttacaaata aagcaatagc atcacaaatt tcacaaataa agcattttt | 8100 |
| | | tcactgcatt ctagttgtgg tttgtccaaa ctcatcaatg tatcttatca tgtctgtata | 8160 |
| | | ccgtcgacct ctagctagag cttggcgtaa tcatggtcat agctgtttcc tgtgtgaaat | 8220 |
| | | tgttatccgc tcacaattcc acacaacata cgagccgaa gcataaagtg taaagcctgg | 8280 |
| | | ggtgcctaat gagtgagcta actcacatta attgcgttgc gctcactgcc cgctttccag | 8340 |
| | | tcgggaaacc tgtcgtgcca gctgcattaa tgaatcggcc aacgcgcggg gagaggcggt | 8400 |
| | | ttgcgtattg ggcgctcttc cgcttcctcg ctcactgact cgctgcgctc ggtcgttcgg | 8460 |
| | | ctgcggcgag cggtatcagc tcactcaaag gcggtaatac ggttatccac agaatcaggg | 8520 |
| | | gataacgcag gaaagaacat gtgagcaaaa ggccagcaaa aggccaggaa ccgtaaaaag | 8580 |
| | | gccgcgttgc tggcgttttt ccataggctc cgcccccctg acgagcatca caaaaatcga | 8640 |
| | | cgctcaagtc agaggtggcg aaacccgaca ggactataaa gataccaggc gtttccccct | 8700 |
| | | ggaagctccc tcgtgcgctc tcctgttccg accctgccgc ttaccggata cctgtccgcc | 8760 |
| | | tttctccctt cgggaagcgt ggcgctttct catgctcac gctgtaggta tctcagttcg | 8820 |
| | | gtgtaggtcg ttcgctccaa gctgggctgt gtgcacgaac cccccgttca gcccgaccgc | 8880 |
| | | tgcgccttat ccggtaacta tcgtcttgag tccaaccgg taagacacga cttatcgcca | 8940 |
| | | ctggcagcag ccactggtaa caggattagc agagcgaggt atgtaggcgg tgctacagag | 9000 |
| | | ttcttgaagt ggtggcctaa ctacggctac actagaagaa cagtatttgg tatctgcgct | 9060 |
| | | ctgctgaagc cagttacctt cggaaaaaga gttggtagct cttgatccgg caaacaaacc | 9120 |
| | | accgctggta gcggtggttt ttttgtttgc aagcagcaga ttacgcgcag aaaaaaagga | 9180 |
| | | tctcaagaag atcctttgat cttttctacg gggtctgacg ctcagtggaa cgaaaactca | 9240 |
| | | cgttaaggga ttttggtcat gagattatca aaaaggatct tcacctagat cctttaaat | 9300 |
| | | taaaaatgaa gttttaaatc aatctaaagt atatatgagt aaacttggtc tgacagttac | 9360 |
| | | caatgcttaa tcagtgaggc acctatctca gcgatctgtc tatttcgttc atccatagtt | 9420 |
| | | gcctgactcc ccgtcgtgta gataactacg atacgggagg gcttaccatc tggccccagt | 9480 |
| | | gctgcaatga taccgcgaga cccacgctca ccggctccag atttatcagc aataaaccag | 9540 |
| | | ccagccggaa gggccgagca cagaagtggt cctgcaactt tatccgcctc catccagtct | 9600 |
| | | attaattgtt gccgggaagc tagagtaagt agttcgccag ttaatagttt gcgcaacgtt | 9660 |
| | | gttgccattg ctacaggcat cgtggtgtca cgctcgtcgt ttggtatggc ttcattcagc | 9720 |
| | | tccggttccc aacgatcaag gcgagttaca tgatccccca tgttgtgcaa aaaagcggtt | 9780 |
| | | agctccttcg gtcctccgat cgttgtcaga aagtaagttgg ccgcagtgtt atcactcatg | 9840 |
| | | gttatggcag cactgcataa ttctcttact gtcatgccat ccgtaagatg cttttctgtg | 9900 |
| | | actggtgagt actcaaccaa gtcattctga gaatagtgta tgcggcgacc gagttgctct | 9960 |
| | | tgcccggcgt caatacggga taataccgcg ccacatagca gaactttaaa agtgctcatc | 10020 |
| | | attggaaaac gttcttcggg gcgaaaactc tcaaggatct taccgctgtt gagatccagt | 10080 |
| | | tcgatgtaac ccactcgtgc acccaactga tcttcagcat cttttacttt caccagcgtt | 10140 |
| | | tctgggtgag caaaaacagg aaggcaaaat gccgcaaaaa agggaataag ggcgacacgg | 10200 |
| | | aaatgttgaa tactcatact cttcctttt caatattatt gaagcattta tcagggttat | 10260 |
| | | tgtctcatga gcggatacat atttgaatgt atttagaaaa ataaacaaat agggggttccg | 10320 |
| | | cgcacatttc cccgaaaagt gccacctgac | 10350 |
| 57 | 528-GL | EIWKQHEDAL QKFEEALNQF EDLKQLGGSG KGSGGEIWKQ CEDALRKFEE ALKRFEDLKQ | 60 |
| | | KGGSGEIWKQ HEDALQKFEE ALNQFEDLKQ LGGSGKGSGG EIWKQHEDAL RKFEEALKRF | 120 |
| | | EDLKQK | 126 |
| 58 | MM3 FC (EC) | cccgtagaaa agatcaaagg atcttcttga gatccttttt ttctgcgcgt aatctgctgc | 60 |
| | | ttgcaaacaa aaaaaccacc gctaccagcg gtggtttgtt tgccggatca agagctacca | 120 |
| | | actcttttc cgaaggtaac tggcttcagc agagcgcaga taccaaatac tgttcttcta | 180 |
| | | gtgtagccgt agttagccca ccacttcaag aactctgtag caccgcctac atacctcgct | 240 |
| | | ctgctaatcc tgttaccagt ggctgctgcc agtggcgata agtcgtgtct taccgggttg | 300 |
| | | gactcaagac gatagttacc ggataaggcg cagcggtcgg gctgaacggg gggttcgtgc | 360 |
| | | acacagccca gcttggagcg aacgacctac accgaactga gatacctaca gcgtgagcta | 420 |
| | | tgagaaagcg ccacgcttcc cgaagggaga aaggcggaca ggtatccggt aagcggcagg | 480 |
| | | gtcggaacag gagagcgcac gagggagctt ccaggggaa acgcctggta tctttatagt | 540 |
| | | cctgtcgggt ttcgccacct ctgacttgag cgtcgatttt tgtgatgctc gtcaggggg | 600 |
| | | cggagcctat ggaaaaacgc cagcaacgcg gcctttttac ggttcctggc ctttgctggc | 660 |
| | | ccttttgctc acatgttctt tcctgcgtta tcccctgatt ctgtggataa ccgtattacc | 720 |
| | | gcctttgagt gagctgatac cgctcgccgc agccgaacga ccgagcgcag cgagtcagtg | 780 |
| | | agcgaggaag cggaaggcga gagtagggaa ctgccaggca tcaaactaag cagaaggccc | 840 |
| | | ctgacggatg gcctttttgc gtttctacaa actctttctg tgttgtaaaa cgacggccag | 900 |
| | | tcttaagctc gggcccctg gcggttctg ataacgagta atcgttaatc cgcaaataac | 960 |
| | | gtaaaaaccc gcttcggcgg gtttttttat gggggagtt taggggaaaga gcatttgtca | 1020 |
| | | gaatatttaa gggcgcctgt cactttgctt gatatatgag aattatttaa cctataaat | 1080 |
| | | gagaaaaaag caacgcactt taaataagat agttgattgt ttcgattgat gaacacctat | 1140 |
| | | aattaaacta ttcatctatt atttatgatt ttttgtatat acaatatttc tagtttgtta | 1200 |
| | | aagagaatta agaaaataaa tctcgaaaat aataaaggga aaatcagttt ttgatatcaa | 1260 |
| | | aattatacat gtcaacgata atacaaaata taatacaaac tataagatgt tatcagtatt | 1320 |
| | | tattatcatt tagaataaat tttgtgtcgc ccttccgcga aattaatacg actcactata | 1380 |
| | | ggggaattgt gagcggataa caattcccct ctagaaataa ttttgtttaa cttttaggag | 1440 |

TABLE 4-continued

List of Sequences

| Seq ID No | Name | Sequence | |
|---|---|---|---|
| | | gtaaaacata tgcatcatca tcatcaccac ggcggcggtg gcgaaaatct ttattttcaa | 1500 |
| | | ggtgaactac taaaaaaaca tgaagaagct ctcaagaagt ttgaagaact cctgaagaaa | 1560 |
| | | ttcgaggaag agctaaagaa aggtggctct gggtcgggaa gcggggtga attactgaaa | 1620 |
| | | aagcacgaag aggcacttaa gaagttcgag gagttactaa agaagtttga ggaggaactc | 1680 |
| | | aaaaagggtg gctccggttg ggggtctggt ggcgagctgc ttaaaaagca tgaggaggcg | 1740 |
| | | ttgaagaaat ttgaagaact actgaagaag ttcgaagagt tgctaaagaa gggagggtca | 1800 |
| | | ggcagcggtt caggaggaga gcttttaaag aaacacgaag aagcccttaa aaaattcgag | 1860 |
| | | gaattgctca aaaaatttga ggaacttttg aaaaaatgac tcgagccccc tagcataacc | 1920 |
| | | ccttggggcc tctaaacggg tcttgagggg ttttttgccc ctgagacgcg tcaatcgagt | 1980 |
| | | tcgtacctaa gggcgacacc cctaattag cccgggcgaa aggcccagtc tttcgactga | 2040 |
| | | gcctttcgtt ttatttgatg cctggcagtt ccctactctc gcatgggag tccccacact | 2100 |
| | | accatcggcg ctacggcgtt tcacttctga gttcggcatg gggtcaggtg ggaccaccgc | 2160 |
| | | gctactgccg ccaggcaaac aaggggtgtt atgagccata ttcaggtata aatgggctcg | 2220 |
| | | cgataatgtt cagaattggt taattggttg taacactgac ccctatttgt ttatttttct | 2280 |
| | | aaatacattc aaatatgtat ccgctcatga gacaataacc ctgataaatg cttcaataat | 2340 |
| | | attgaaaaag gaagaatatg agtattcaac atttccgtgt cgcccttatt ccctttttgt | 2400 |
| | | cggcatttttg ccttcctgtt tttgctcacc cagaaacgct ggtgaaagta aaagatgctg | 2460 |
| | | aagatcagtt gggtgcacga gtgggttaca tcgaactgga tctcaacagc ggtaagatcc | 2520 |
| | | ttgagagttt tcgccccgaa gaacgttttc caatgatgag cactttaaa gttctgctat | 2580 |
| | | gtggcgcggt attatcccgt attgacgccg ggcaagagca actcggtcgc cgcatacact | 2640 |
| | | attctcagaa tgacttggtt gagtactcac cagtcacaga aaagcatctt acggatggca | 2700 |
| | | tgacagtaag agaattatgc agtgctgcca taaccatgag tgataacact gcggccaact | 2760 |
| | | tacttctgac aacgatcgga ggaccgaagg agctaaccgc ttttttgcac aacatggggg | 2820 |
| | | atcatgtaac tcgccttgat cgttgggaac cggagctgaa tgaagccata ccaaacgacg | 2880 |
| | | agcgtgacac cacgatgcct gtagcgatgg caacaacgtt gcgcaaacta ttaactggcg | 2940 |
| | | aactacttac tctagcttcc cggcaacaat taatagactg atggaggcg gataaagttg | 3000 |
| | | caggaccact tctgcgctcg gcccttccgg ctggctggtt tattgctgat aaatccggag | 3060 |
| | | ccggtgagcg tggttctcgc ggtatcatcg cagcgctggg gccagatggt aagccctccc | 3120 |
| | | gtatcgtagt tatctcacacg acggggagtc aggcaactat ggatgaacga atagacaga | 3180 |
| | | tcgctgagat aggtgcctca ctgattaagc attggtaagc ggcgcgccat cgaatggcgc | 3240 |
| | | aaaaccttttc gcggtatggc atgatagcgc ccggaagaga gtcaattcag ggtggtgaat | 3300 |
| | | atgaaaccag taacgttata cgatgtcgca gagtacgtg gtgtctctta tcagaccgtt | 3360 |
| | | tcccgcgtgg tgaaccaggc cagccacgtt tctgcgaaaa cgcgggaaaa agtggaagcg | 3420 |
| | | gcgatggcgg agctgaatta cattcccaac cgcgtggcac aacaactggc gggcaaacag | 3480 |
| | | tcgttgctga ttggcgttgc cacctccagt ctggccctgc acgcgccgtc gcaaattgtc | 3540 |
| | | gcggcgatta aatctcgcgc cgatcaactg ggtgccagcg tggtggtgtc gatggtagaa | 3600 |
| | | cgaagcggcg tcgaagcctg taaagcggcg gtgcacaatc ttctcgcgca acgcgtcagt | 3660 |
| | | gggctgatca ttaactatcc gctggatgac caggatgcca ttgctgtgga agctgcctgc | 3720 |
| | | actaatgttc cggcgttatt tcttgatgtc tctgaccaga cacccatcaa cagtattatt | 3780 |
| | | ttctcccatg aggacggtac gcgactgggc gtggagcatc tggtcgcatt gggtcaccag | 3840 |
| | | caaatcgcgc tgttagcggg cccattaagt tctgtctcgg cgcgtctgcg tctggctggc | 3900 |
| | | tggcataaat atctcactcg caatcaaatt cagccgatag cggaacggga aggcgactgg | 3960 |
| | | agtgccatgt ccggttttca acaaaccatg caaatgctga atgagggcat cgttcccact | 4020 |
| | | gcgatgctgg ttgccaacga tcagatggcg ctgggcgcaa tgcgcgccat taccgagtcc | 4080 |
| | | gggctgcgcg ttggtgcgga tatctcggta gtgggatacg acgataccga agatagctca | 4140 |
| | | tgttatatcc gccgttaac caccatcaaa caggattttc gcctgctggg gcaaaccagc | 4200 |
| | | gtggaccgct tgctgcaact ctctcagggc caggcggtga agggcaatca gctgttgcca | 4260 |
| | | gtctcactgg tgaaaagaaa aaccaccctg gcgcccaata cgcaaaccgc ctctccccgc | 4320 |
| | | gcgttggccg attcattaat gcagctggca cgacaggttt cccgactgga aagcgggcag | 4380 |
| | | tgactcatga ccaaaatccc ttaacgtgag ttacgcgcgc gtcgttccac tgagcgtcag | 4440 |
| | | ac | 4442 |
| 59 | MM43 FC (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aattaagct acaacaaggc aaggcttgac cgacaattgc atgaagaatc | 180 |
| | | tgcttagggt taggcgtttt gcgctgcttc gcgatgtacg gccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | accccccgcc attgacgtca ataatgacgt atgttccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |

TABLE 4-continued

List of Sequences

| Seq ID No | Name | Sequence | |
|---|---|---|---|
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaagagc agtgggaata | 1680 |
| | | ggagcttttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tgggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagccc aggagaccaa atcttcatgg tccctctggg | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatccatcc cgtctgttaa | 3480 |
| | | aagggcccta tagttggagg tggggaggt aggaagagcg atgatcactt gtggactaag | 3540 |
| | | tttgttcaca tccccttctc caacccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gccctagtt ctggggcag cggggatcc | 3900 |
| | | atgggtgaac tactaaaaaa acatgaagaa gctctcaaga agtttgaaga actcctgaag | 3960 |
| | | aaattcgagg aagagctaaa gaaaggtggc tctgggtcgg gaagcggggg tgaattactg | 4020 |
| | | aaaaagcacg aagaggcact taagaagttc gaggagttac taaagaagtt tgaggaggaa | 4080 |
| | | ctcaaaaagg gtggctccgg ttgggggtct ggtggcgagc tgcttaaaaa gcatgaggag | 4140 |
| | | gcgttgaaga aatttgaaga actactgaag aagttgctaaa agaggaggag | 4200 |
| | | tcaggcagcg gttcaggagg agagctttta agaaacacg aagaagccct taaaaaattc | 4260 |
| | | gaggaattgc tcaaaaaatt tgaggaactt ttgaaaaaag cggcaccggt agtagcagtg | 4320 |
| | | agcaagggcg aggagctgtt caccggggtg gtgcccatcc tggtcgagct ggacggcgac | 4380 |
| | | gtaaacggcc acaagttcag cgtgtccggc gagggcgagg gcgatgccac ctacggcaag | 4440 |
| | | ctgaccctga agttcatttg caccaccggc aagctgcccg tgccctggcc caccctcgtg | 4500 |
| | | accaccctga cctacggcgt gcagtgcttc agccgctacc ccgaccacat gaagcagcac | 4560 |
| | | gacttcttca gtccgccat gcccgaaggc tacgtccagg agcgcaccat cttcttcaag | 4620 |
| | | gacgacggca actacaagac ccgcgccgag gtgaagttcg agggcgacac cctggtgaac | 4680 |
| | | cgcatcgagc tgaagggcat cgacttcaag gaggacggca acatcctggg gcacaagctg | 4740 |
| | | gagtacaact acaacagcca caacgtctat atcatggccg acaagcagaa gaacggcatc | 4800 |
| | | aaggtgaact tcaagatccg ccacaacatc gaggacggca gcgtgcagct cgccgaccac | 4860 |
| | | taccagcaga acacccccat cggcgacggc cccgtgctgc tgcccgacaa ccactacctg | 4920 |
| | | agcacccagt ccgccctgag caaagacccc aacgagaagc gcgatcacat ggtcctgctg | 4980 |
| | | gagttcgtga ccgccgccgg gatcactctc ggcatggacg agctgtacaa gtaagaattc | 5040 |
| | | gatatcaagc ttatcgataa tcaacctctg gattacaaaa tttgtgaaag attgactggt | 5100 |
| | | attcttaact atgttgctcc tttacgcta tgtggatacg ctgctttaat gcctttgtat | 5160 |
| | | catgctattg cttcccgtat ggctttcatt ttctcctcct tgtataaatc ctggttgctg | 5220 |
| | | tctctttatg aggagttgtg gcccgttgtc aggcaacgtg gcgtggtgtg cactgtgttt | 5280 |
| | | gctgacgcaa ccccactgg ttggggcatt gccaccacct gtcagctcct ttccgggact | 5340 |
| | | ttcgctttcc ccctccctat tgccacggcg gaactcatcg ccgcctgcct tgcccgctgc | 5400 |
| | | tggacagggg ctcggctgtt gggcactgac aattccgtgg tgttgtcggg gaaatcatcg | 5460 |
| | | tcctttcctt ggctgctcgc ctgtgttgcc acctggattc tgcgcgggac gtcctctgc | 5520 |
| | | tacgtccctt cggccctcaa tccagcggac cttccttccc gcggcctgct gccggctctg | 5580 |
| | | cggcctcttc cgcgtcttcg ccttcgccct cagacgagtc ggatctccct ttgggccgcc | 5640 |
| | | tccccgcatc gataccgtcc acctcgagac ctagaaaaac atgagcaat cacaagtagc | 5700 |
| | | aatacagcag ctaccaatgc tgattgtgcc tggctagaag cacaagagga ggaggaggtg | 5760 |

TABLE 4-continued

List of Sequences

| Seq ID No | Name | Sequence | |
|---|---|---|---|
| | | ggtttccag tcacacctca ggtaccttta agaccaatga cttacaaggc agctgtagat | 5820 |
| | | cttagccact ttttaaaaga aaaggggga ctggaagggc taattcactc ccaacgaaga | 5880 |
| | | caagatatcc ttgatctgtg gatctaccac acacaaggct acttccctga ttggcagaac | 5940 |
| | | tacacaccag ggccagggat cagatatcca ctgacctttg gatggtgcta caagctagta | 6000 |
| | | ccagttgagc aagaagaggt agaagaagcc aatgaaggag agaacacccg cttgttacac | 6060 |
| | | cctgtgagcc tgcatgggat ggatgacccg gagagagaag tattagagtg gaggtttgac | 6120 |
| | | agccgcctag catttcatca catggcccga gagctgcatc cggactgtac tgggtctctc | 6180 |
| | | tggttagacc agatctgagc ctgggagctc tctggctaac tagggaaccc actgcttaag | 6240 |
| | | cctcaataaa gcttgccttg agtgcttcaa gtagtgtgtg cccgtctgtt gtgtgactct | 6300 |
| | | ggtaactaga gatccctcag accctttag tcagtgtgga aaatctctag cagggcccgt | 6360 |
| | | ttaaacccgc tgatcagcct cgactgtgcc ttctagttgc cagccatctg ttgtttgccc | 6420 |
| | | ctccccgtg ccttccttga ccctgaaggg tgccactccc actgtccttt cctaataaaa | 6480 |
| | | tgaggaaatt gcatcgcatt gtctgagtag gtgtcattct attctggggg gtggggtggg | 6540 |
| | | gcaggacagc aaggggagg attgggaaga caatagcagg catgctgggg atgcggtggg | 6600 |
| | | ctctatggct tctgaggcgg aaagaaccag ctggggctct aggggtatc cccacgcgcc | 6660 |
| | | ctgtagcggc gcattaagcg cggcgggtgt ggtggttacg cgcagcgtga ccgctacact | 6720 |
| | | tgccagcgcc ctagcgcccg ctcctttcgc tttcttccct cctttctcg ccacgttcgc | 6780 |
| | | cggctttccc cgtcaagctc taaatcgggg gctccctta gggttccgat ttagtgcttt | 6840 |
| | | acggcacctc gacccccaaa aacttgatta gggtgatggt tcacgtagtg ggccatcgcc | 6900 |
| | | ctgatagacg gttttcgcc ctttgacgtt ggagtccacg ttctttaata gtggactctt | 6960 |
| | | gttccaaact ggaacaacac tcaaccctat ctcggtctat tcttttgatt tataagggat | 7020 |
| | | tttgccgatt tcggcctatt ggttaaaaaa tgagctgatt taacaaaaat ttaacgcgaa | 7080 |
| | | ttaattctgt ggaatgtgtg tcagttaggg tgtggaaagt ccccaggctc cccagcaggc | 7140 |
| | | agaagtatgc aaagcatgca tctcaattag tcagcaacca ggtgtggaaa gtccccaggc | 7200 |
| | | tccccagcag gcagaagtat gcaaagcatg catctcaatt agtcagcaac catagtcccg | 7260 |
| | | cccctaactc cgcccatccc gcccctaact ccgcccagtt ccgcccattc tccgccccat | 7320 |
| | | ggctgactaa tttttttat ttatgcagag gccgaggccg cctctgcctc tgagctattc | 7380 |
| | | cagaagtagt gaggaggctt ttttggaggc ctaggcttt gcaaaaagct cccgggagct | 7440 |
| | | tgtatatcca ttttcggatc tgatcagcac gtgttgacaa ttaatcatcg gcatagtata | 7500 |
| | | tcggcatagt ataatacgac aaggtgagga actaaaccat ggccaagttg accagtgccg | 7560 |
| | | ttccggtgct caccgcgcgc gacgtcgccg gagcggtcga gttctggacc gaccggctcg | 7620 |
| | | ggttctcccg ggacttcgtg gaggacgact tcgccggtgt ggtccgggac gacgtgaccc | 7680 |
| | | tgttcatcag cgcggtccag gaccaggtgg tgccgacaa caccctggcc tgggtgtggg | 7740 |
| | | tgcgcggcct ggacgagctg tacgccgagt ggtcggaggt cgtgtccacg aacttccggg | 7800 |
| | | acgcctccgg gccgccatg accgagatcg gcgagcagcc gtgggggcgg gagttcgccc | 7860 |
| | | tgcgcgaccc ggccggcaac tgcgtgcact cgtggccga ggagcaggac tgacacgtgc | 7920 |
| | | tacgagattt cgattccacc gccgccttct atgaaaggtt gggcttcgga atcgttttcc | 7980 |
| | | gggacgccgg ctggatgatc ctccagcgcg gggatctcat gctggagttc ttcgcccacc | 8040 |
| | | ccaacttgtt tattgcagct tataatggtt acaaataaag caatagcatc acaaatttca | 8100 |
| | | caaataaagc atttttttca ctgcattcta gttgtggttt gtccaaactc atcaatgtat | 8160 |
| | | cttatcatgt ctgtataccg tcgacctcta gctagagctt ggcgtaatca tggtcatagc | 8220 |
| | | tgtttcctgt gtgaaattgt tatccgctca caattccaca acatacga gccggaagca | 8280 |
| | | taaagtgtaa agcctggggt gcctaatgag tgagctaact cacattaatt gcgttgcgct | 8340 |
| | | cactgcccgc tttccagtcg ggaaacctgt cgtgccaact gcattaatga atcggccaac | 8400 |
| | | gcgcggggag aggcggtttg cgtattgggc gctcttccgc ttcctcgctc actgactcgc | 8460 |
| | | tgcgctcggt cgttcggctg cggcgagcgg tatcagctca ctcaaaggcg gtaatacggt | 8520 |
| | | tatccacaga atcagggat aacgcaggaa agaacatgtg agcaaaaggc cagcaaaagg | 8580 |
| | | ccaggaaccg taaaaaggcc gcgttgctgg cgtttttcca taggctccgc cccctgacg | 8640 |
| | | agcatcacaa aaatcgacgc tcaagtcaga ggtggcgaaa cccgacagga ctataaagat | 8700 |
| | | accaggcgtt tccccctgga agctccctcg tgcgctctcc tgttccgacc ctgccgctta | 8760 |
| | | ccggatacct gtccgccttt ctcccttcgg aagcgtggc gctttctcat agctcacgct | 8820 |
| | | gtaggtatct cagttcggtg taggtcgttc gctccaagct gggctgtgtg cacgaacccc | 8880 |
| | | ccgttcagcc cgaccgctgc gccttatccg gtaactatcg tcttgagtcc aacccggtaa | 8940 |
| | | gacacgactt atcgccactg gcagcagcca ctggtaacag gattagcaga gcgaggtatg | 9000 |
| | | taggcggtgc tacagagttc ttgaagtggt ggcctaacta cggctacact agaagaacag | 9060 |
| | | tatttggtat ctgcgctctg ctgaagccag ttaccttcgg aaaaagagtt ggtagctctt | 9120 |
| | | gatccggcaa acaaaccacc gctggtagcg gtggttttt tgtttgcaag cagcagatta | 9180 |
| | | cgcgcagaaa aaaaggatct caagaagatc ctttgatctt ttctacgggg tctgacgctc | 9240 |
| | | agtggaacga aaactcacgt taagggattt tggtcatgag attatcaaaa aggatcttca | 9300 |
| | | cctagatcct tttaaattaa aaatgaagtt ttaaatcaat ctaaagtata tatgagtaaa | 9360 |
| | | cttggtctga cagttaccaa tgcttaatca gtgaggcacc tatctcagcg atctgtctat | 9420 |
| | | ttcgttcatc catagttgcc tgactccccg tcgtgtagat aactacgata cgggagggct | 9480 |
| | | taccatctgg ccccagtgct gcaatgatac gcgagaccc acgctcaccg gctccagatt | 9540 |
| | | tatcagcaat aaaccagcca gccggaaggg ccgagcgcag aagtggtcct gcaactttat | 9600 |
| | | ccgcctccat ccagtctatt aattgttgcc gggaagctag agtaagtagt tcgccagtta | 9660 |
| | | atagtttgcg caacgttgtt gccattgcta caggcatcgt ggtgtcacgc tcgtcgtttg | 9720 |
| | | gtatggcttc attcagctcc ggttcccaac gatcaaggcg agttacatga tcccccatgt | 9780 |
| | | tgtgcaaaaa agcggttagc tccttcggtc ctccgatcgt tgtcagaagt aagttggccg | 9840 |
| | | cagtgttatc actcatggtt atggcagcac tgcataattc tcttactgtc atgccatccg | 9900 |
| | | taagatgctt ttctgtgact ggtgagtact caaccaagtc attctgagaa tagtgtatgc | 9960 |
| | | ggcgaccgag ttgctcttgc ccggcgtcaa tacgggataa taccgcgcca catagcagaa | 10020 |
| | | cttttaaagt gctcatcatt ggaaaacgtt cttcgggcg aaaactctca aggatcttac | 10080 |
| | | cgctgttgag atccagttcg atgtaaccca ctcgtgcacc caactgatct tcagcatctt | 10140 |
| | | ttactttcac cagcgtttct gggtgagcaa aaacaggaag gcaaaatgcc gcaaaaaagg | 10200 |

TABLE 4-continued

List of Sequences

| Seq ID No | Name | Sequence | | | | | |
|---|---|---|---|---|---|---|---|
| | | gaataagggc | gacacggaaa | tgttgaatac | tcatactctt | cctttttcaa | tattattgaa | 10260 |
| | | gcatttatca | gggttattgt | ctcatgagcg | gatacatatt | tgaatgtatt | tagaaaaata | 10320 |
| | | aacaaatagg | ggttccgcgc | acatttcccc | gaaaagtgcc | acctgac | | 10367 |
| 60 | MM3 FC | ELLKKHEEAL | KKFEELLKKF | EEELKKGGSG | SGSGGELLKK | FEEALKKFEE | LLKKFEEELK | 60 |
| | | KGGSGWGSGG | ELLKKHEEAL | KKFEELLKKF | EELLKKGGSG | SGSGGELLKK | CEEALKKFEE | 120 |
| | | LLKKFEELLK | K | | | | | 131 |
| 61 | AM-528-C4 (EC) | tggcgaatgg | gacgcgccct | gtagcggcgc | attaagcgcg | gcgggtgtgg | tggttacgcg | 60 |
| | | cagcgtgacc | gctacacttg | ccagcgccct | agcgcccgct | cctttcgctt | tcttcccttc | 120 |
| | | ctttctcgcc | acgttcgccg | gctttcccg | tcaagctcta | aatcgggtgc | tcccttagg | 180 |
| | | gttccgattt | agtgctttac | ggcacctcga | ccccaaaaaa | cttgattagg | gtgatggttc | 240 |
| | | acgtagtggg | ccatcgccct | gatagacggt | ttttcgccct | ttgacgttgg | agtccacgtt | 300 |
| | | ctttaatagt | ggactcttgt | tccaaactgg | aacaacactc | aaccctatct | cggtctattc | 360 |
| | | ttttgattta | taagggattt | tgccgatttc | ggcctattgg | ttaaaaaatg | agctgattta | 420 |
| | | acaaaaattt | aacgcgaatt | ttaacaaaat | attaacgttt | acaatttcag | gtggcacttt | 480 |
| | | tcggggaaat | gtgcgcggaa | ccctatttg | tttattttc | taaatacatt | caaatatgta | 540 |
| | | tccgctcatg | agacaataac | cctgataaat | gcttcaataa | tattgaaaaa | ggaagagtat | 600 |
| | | gagtattcaa | catttccgtg | tcgcccttat | tccctttttt | gcggcatttt | gccttcctgt | 660 |
| | | ttttgctcac | ccagaaacgc | tggtgaaagt | aaaagatgct | gaagatcagt | tgggtgcacg | 720 |
| | | agtgggttac | atcgaactgg | atctcaacag | cggtaagatc | cttgagagtt | ttcgccccga | 780 |
| | | agaacgtttt | ccaatgatga | gcacttttaa | agttctgcta | tgtggcgcgg | tattatcccg | 840 |
| | | tattgacgcc | gggcaagagc | aactcggtcg | ccgcatacac | tattctcaga | atgacttggt | 900 |
| | | tgagtactca | ccagtcacag | aaaagcatct | tacgatggc | atgacagtaa | gagaattatg | 960 |
| | | cagtgctgcc | ataaccatga | gtgataacac | tgcggccaac | ttacttctga | caacgatcgg | 1020 |
| | | aggaccgaag | gagctaaccg | ctttttgca | caacatgggg | gatcatgtaa | ctcgccttga | 1080 |
| | | tcgttgggaa | ccggagctga | atgaagccat | accaaacgac | gagcgtgaca | ccacgatgcc | 1140 |
| | | tgcagcaatg | gcaacaacgt | tgcgcaaact | attaactggc | gaactactta | ctctagcttc | 1200 |
| | | ccggcaacaa | ttaatagact | ggatggaggc | ggataaagtt | gcaggaccac | ttctgcgctc | 1260 |
| | | ggcccttccg | gctggctggt | ttattgctga | taaatctgga | gccggtgagc | gtgggtctcg | 1320 |
| | | cggtatcatt | gcagcactgg | ggccagatgg | taagccctcc | cgtatcgtag | ttatctacac | 1380 |
| | | gacggggagt | caggcaacta | tggatgaacg | aaatagacag | atcgctgaga | taggtgcctc | 1440 |
| | | actgattaag | cattggtaac | tgtcagacca | agtttactca | tatatacttt | agattgattt | 1500 |
| | | aaaacttcat | ttttaattta | aaaggatcta | ggtgaagatc | ctttttgata | atctcatgac | 1560 |
| | | caaaatccct | taacgtgagt | tttcgttcca | ctgagcgtca | gaccccgtag | aaaagatcaa | 1620 |
| | | aggatcttct | tgagatcctt | tttttctgcg | cgtaatctgc | tgcttgcaaa | caaaaaaacc | 1680 |
| | | accgctacca | gcggtggttt | gtttgccgga | tcaagagcta | ccaactcttt | ttccgaaggt | 1740 |
| | | aactggcttc | agcagagcgc | agataccaaa | tactgtcctt | ctagtgtagc | cgtagttagg | 1800 |
| | | ccaccacttc | aagaactctg | tagcaccgcc | tacatacctc | gctctgctaa | tcctgttacc | 1860 |
| | | agtggctgcc | ggcgataagt | cgtgtcttac | cgggttggac | tcaagacgat | agttaccgga | 1920 |
| | | taaggcgcag | cggtcgggct | gaacggggg | ttcgtgcaca | cagcccagct | tggagcgaac | 1980 |
| | | gacctacacc | gaactgagat | acctacagcg | tgagctatga | gaaagcgcca | cgcttcccga | 2040 |
| | | agggagaaag | gcggacaggt | atccgtaag | cggcagggtc | ggaacaggag | agcgcacgag | 2100 |
| | | ggagcttcca | gggggaaacg | cctggtatct | ttatagtcct | gtcgggtttc | gccacctctg | 2160 |
| | | acttgagcgt | cgatttttgt | gatgctcgtc | aggggggcgg | agcctatgga | aaaacgccag | 2220 |
| | | caacgcggcc | tttttacggt | tcctggcctt | ttgctggcct | tttgctcaca | tgttctttcc | 2280 |
| | | tgcgttatcc | cctgattctg | tggataaccg | tattaccgcc | tttgagtgag | ctgataccgc | 2340 |
| | | tcgccgcagc | cgaacgaccg | agcgcagcga | gtcagtgagc | gaggaagcgg | aagagcgcct | 2400 |
| | | gatgcggtat | tttctcctta | cgcatctgtg | cggtatttca | caccgcatat | atggtgcact | 2460 |
| | | ctcagtacaa | tctgctctga | tgccgcatag | ttaagccagt | atacactccg | ctatcgctac | 2520 |
| | | gtgactgggt | catggctgcg | ccccgacacc | cgccaacacc | cgctgacgcg | ccctgacggg | 2580 |
| | | cttgtctgct | cccggcatcc | gcttacagac | aagctgtgac | cgtctccggg | agctgcatgt | 2640 |
| | | gtcagaggtt | ttcaccgtca | tcaccgaaac | gcgcgaggca | gctgcggtaa | agctcatcag | 2700 |
| | | cgtggtcgtg | aagcgattca | cagatgtctg | cctgttcatc | cgcgtccagc | tcgttgagtt | 2760 |
| | | tctccagaag | cgttaatgtc | tggcttctga | taaagcgggc | catgttaagg | gcggtttttt | 2820 |
| | | cctgtttggt | cactgatgcc | tccgtgtaag | ggggatttct | gttcatgggg | gtaatgatac | 2880 |
| | | cgatgaaacg | agagaggatg | ctcacgatat | gggttactga | tgatgaacat | gcccggttac | 2940 |
| | | tggaacgttg | tgagggtaaa | caactggcgg | tatgatgcg | gcgggaccag | agaaaaatca | 3000 |
| | | ctcagggtca | atgccagcgc | ttcgttaata | cagatgtagg | tgttccacag | ggtagccagc | 3060 |
| | | agcatcctgc | gatgcagatc | cggaacataa | tggtgcaggg | cgctgacttc | cgcgtttcca | 3120 |
| | | gactttacga | aacacggaaa | ccgaagacca | ttcatgttgt | tgctcaggtc | gcagacgttt | 3180 |
| | | tgcagcagca | gtcgcttcac | gttcgctcgc | gtatcggtga | ttcattctgc | taaccagtaa | 3240 |
| | | ggcaaccccg | ccagcctagc | cgggtcctca | acgacaggag | cacgatcatg | cgcacccgtg | 3300 |
| | | gggccgccat | gccggcgata | atggcctgct | tctcgccgaa | acgtttggtg | gcgggaccag | 3360 |
| | | tgacgaaggc | ttgagcgagg | gcgtgcaaga | ttccgaatac | cgcaagcgac | aggccgatca | 3420 |
| | | tcgtcgcgct | ccagcgaaag | cggtcctcgc | cgaaaatgac | ccagagcgct | gccggcacct | 3480 |
| | | gtcctacgag | ttgcatgata | aagaagacag | tcataagtgc | ggcgacgata | gtcatgcccc | 3540 |
| | | gcgcccaccg | gaaggagctg | actgggttga | aggctctcaa | gggcatcggt | cgagatcccg | 3600 |
| | | gtgcctaatg | agtgagctaa | cttacattaa | ttgcgttgcg | ctcactgccc | gctttccagt | 3660 |
| | | cgggaaacct | gtcgtgccag | ctgcattaat | gaatcggcca | acgcgcgggg | agaggcggtt | 3720 |
| | | tgcgtattgg | gcgccagggt | ggtttttctt | ttcaccagtg | agacgggcaa | cagctgattg | 3780 |
| | | cccttcaccg | cctggccctg | agagagttgc | agcaagcggt | ccacgctggt | ttgccccagc | 3840 |
| | | aggcgaaaat | cctgtttgat | ggtggttaac | ggcgggatat | aacatgagct | gtcttcggta | 3900 |
| | | tcgtcgtatc | ccactaccga | gatatccgca | ccaacgcgca | gcccggactc | ggtaatggcg | 3960 |

TABLE 4-continued

List of Sequences

| Seq ID No | Name | Sequence | |
|---|---|---|---|
| | | cgcattgcgc ccagcgccat ctgatcgttg gcaaccagca tcgcagtggg aacgatgccc | 4020 |
| | | tcattcagca tttgcatggt ttgttgaaaa ccggacatgg cactccagtc gccttcccgt | 4080 |
| | | tccgctatcg gctgaatttg attgcgagtg agatatttat gccagccagc cagacgcaga | 4140 |
| | | cgcgccgaga cagaacttaa tgggcccgct aacagcgcga tttgctggtg acccaatgcg | 4200 |
| | | accagatgct ccacgcccag tcgcgtaccg tcttcatggg agaaaataat actgttgatg | 4260 |
| | | ggtgtctggt cagagacatc aagaaataac gccggaacat tagtgcaggc agcttccaca | 4320 |
| | | gcaatggcat cctggtcatc cagcggatag ttaatgatca gcccactgac gcgttgcgcg | 4380 |
| | | agaagattgt gcaccgccgc tttacaggct tcgacgccgc ttcgttctac catcgacacc | 4440 |
| | | accacgctgg cacccagttg atcggcgcga gatttaatcg ccgcgacaat ttgcgacggg | 4500 |
| | | gcgtgcaggg ccagactgga ggtggcaacg ccaatcagca acgactgttt gcccgccagt | 4560 |
| | | tgttgtgcca cgcggttggg aatgtaattc cgccgcttc cacttttttcc | 4620 |
| | | cgcgttttcg cagaaacgtg gctggcctgg ttcaccacgc gggaaacggt ctgataagag | 4680 |
| | | acaccggcat actctgcgac atcgtataac gttactggtt tcacattcac caccctgaat | 4740 |
| | | tgactctctt ccgggcgcta tcatgccata ccgcgaaagg ttttgcgcca ttcgatggtg | 4800 |
| | | tccgggatct cgacgctctc ccttatgcga ctcctgctt aggaagcagc ccagtagtag | 4860 |
| | | gttgaggccg ttgagcaccg ccgccgcaag gaatggtgca tgcaaggaga tggcgcccaa | 4920 |
| | | cagtcccccg gccacggggc ctgccaccat acccacgccg aaacaagcgc tcatgagccc | 4980 |
| | | gaagtggcga gcccgatctt ccccatcggt gatgtcggcg atataggcgc cagcaaccgc | 5040 |
| | | acctgtgggc ccggtgatgc cggccacgat gcgtccggcg tagaggatcg agatctcgat | 5100 |
| | | cccgcgaaat taatacgact cactataggg gaattgtgag cggataacaa ttcccctcta | 5160 |
| | | gaaataattt tgtttaactt taagaaggag atatacatat gcataccca gaacacatca | 5220 |
| | | ccgccgtggt acagcgcttt gtggctgcgc tcaatgccgg cgatctggac ggcatcgtcg | 5280 |
| | | cgctgtttgc cgatgacgcc acggtggaag accccgctgg gttccgagcc aggtccggta | 5340 |
| | | cggctgcgat tcgtgagttt tacgccaact cgctcaaact gcctttggcg gtggagctga | 5400 |
| | | cgcaggaggt acgcgcggtc gccaacgaag cggccttcgc tttcaccgtc agcttcgagt | 5460 |
| | | atcagggccg caagaccgta gttgcgccca tcgatcactt tcgcttcaat ggcgccggca | 5520 |
| | | aggtggtgag catccgcgcc ttgtttggcg agaagaatat tcacgcatgc cagatgctga | 5580 |
| | | atggtaccca tcatcatcat catcatggcg gcgaacgcga gaacttgtat tttcaagcta | 5640 |
| | | gcggatccat gggagaaatc tggaaacaat tcgaggacgc actgcaaaag ttcttcgccc | 5700 |
| | | tgcacctgct gctggcactg ctgctgctgc tggctctgct gctgttcctg ctggcttttg | 5760 |
| | | agggcggtag cggcggtggc agcggtggca agttcctgtg cctgctggcg ctgctggccc | 5820 |
| | | tgttactgct ggccctgtta ctgttcctgc tggccttttg ggaggctctg aaccagttcg | 5880 |
| | | aagacctggc taagcagggt ggcagcggtg gcggtagcgg cggtgagatc tggaagcagt | 5940 |
| | | ttgaagatgc gctgcagaaa ttctttgctc tgcacctgct gctggcgctg ctgttactgc | 6000 |
| | | tggcgctgtt actgttcctg ctggcgttta agggcggtag cggcggtggc agcggtggcg | 6060 |
| | | aatttctgct gcacctggct ctgctggcgc tgctgctgct ggccctgctg ctgttcctgc | 6120 |
| | | tggctttctg ggaggcactg aaccaatttg aagacctggc taaacaaacc ggttaagaat | 6180 |
| | | tcctcgagca ccaccaccac caccactgag atccggctgc taacaaagcc cgaaaggaag | 6240 |
| | | ctgagttggc tgctgccacc gctgagcaat aactagcata accccttggg gcctctaaac | 6300 |
| | | gggtcttgag gggttttttg ctgaaaggag gaactatatc cggat | 6345 |
| 62 | AM-528-C4 (FCK mam) | ggatccgcca ccatggagat ctggaagagc cacgaagacg ctctgcagaa attctttgct | 60 |
| | | ctgctgctgc tgctggccct gctgctgctg ctggctctgc tgctgcacct gctggccttc | 120 |
| | | gagggcggta gcggcggtgg cagcggtggc aagtttctgc tgctgctggc gctgctggcc | 180 |
| | | ctgttactgc tggctctgtt attacacctg ctggccttct ggggaggcgct gaagcgtttc | 240 |
| | | gaagacctga agcagaaagg tggctgcggc cgtatctgga aggagcacga agatgcgcac | 300 |
| | | cagaaattct tgcgttatt attactgctg gctctgttgt tactgctggc gctgttactg | 360 |
| | | cacctgctgg cgttcaaggg tggcagcggt ggcggtagcg gcggtgaatt tctgttgctg | 420 |
| | | ctggctctgc tggcgctgct tctgctgcc ctgttgttac acctgctggc gttctgggag | 480 |
| | | gccctgaagc gtcacgaaga tcgtgtgcag aaagcaccgg t | 521 |
| 63 | AM-528-C4 | EIWKQFEDAL QKFFALHLLL ALLLLLALLL FLLAFEGGSG GGSGGKFLCL LALLALLLLA | 60 |
| | | LLLFLLAFWE ALNQFEDLAK QGGSGGGSGG EIWKQFEDAL QKFFALHLLL ALLLLLALLL | 120 |
| | | FLLAFKGGSG GGSGGEFLLH LALLALLLLA LLLFLLAFWE ALNQFEDLAK Q | 171 |
| 64 | AM-1196 (EC) | tggcgaatgg gacgcgccct gtagcggcgc attaagcgcg gcgggtgtgg tggttacgcg | 60 |
| | | cagcgtgacc gctacacttg ccagcgccct agcgcccgct cctttgcttt tcttccctca | 120 |
| | | ctttctcgcc acgttcgccg gctttccccg tcaagctcta atcggggggc tccctttagg | 180 |
| | | gttccgattt agtgctttac ggcacctcga cccaaaaaaa cttgattagg gtgatggttc | 240 |
| | | acgtagtggg ccatcgccct gatagacggt ttttcgccct ttgacgttgg agtccacgtt | 300 |
| | | ctttaatagt ggactcttgt tccaaactgg aacaacactc aaccctatct cggtctattc | 360 |
| | | ttttgattta agggatttt gccgatttc ggcctattgg ttaaaaaatg agctgattta | 420 |
| | | acaaaaattt aacgcgaatt ttaacaaaat attaacgttt acaatttcag gtggcacttt | 480 |
| | | tcggggaaat gtgcgcggaa cccctatttg tttatttttc taaatacatt caaatatgta | 540 |
| | | tccgctcatg agacaataac cctgataaat gcttcaataa tattgaaaaa ggaagagtat | 600 |
| | | gagtattcaa catttccgtg tcgcccttat tccctttttt gcggcatttt gccttcctgt | 660 |
| | | ttttgctcac ccagaaacgc tggtgaaagt aaaagatgct gaagatcagt tgggtgcacg | 720 |
| | | agtgggttac atcgaactgg atctcaacag cggtaagatc cttgagagtt ttcgccccga | 780 |
| | | agaacgtttt ccaatgatga gcacttttaa agttctgcta tgtggcgcgg tattatccgta | 840 |
| | | tattgacgcc gggcaagagc aactcggtcg ccgcatacac tattctcaga atgacttggt | 900 |
| | | tgagtactca ccagtcacag aaaagcatct tacggatggc atgacagtaa gagaattatg | 960 |
| | | cagtgctgcc ataaccatga gtgataacac tgcggccaac ttacttctga caacgatcgg | 1020 |
| | | aggaccgaag gagctaaccg cttttttgca caacatgggg gatcatgtaa ctcgccttga | 1080 |
| | | tcgttgggaa ccggagctga atgaagccat accaaacgac gagcgtgaca ccacgatgcc | 1140 |

TABLE 4-continued

List of Sequences

| Seq ID No | Name | Sequence | |
|---|---|---|---|
| | | tgcagcaatg gcaacaacgt tgcgcaaact attaactggc gaactactta ctctagcttc | 1200 |
| | | ccggcaacaa ttaatagact ggatggaggc ggataaagtt gcaggaccac ttctgcgctc | 1260 |
| | | ggcccttccg gctggctggt ttattgctga taaatctgga gccggtgagc gtgggtctcg | 1320 |
| | | cggtatcatt gcagcactgg ggccagatgg taagccctcc cgtatcgtag ttatctacac | 1380 |
| | | gacggggagt caggcaacta tggatgaacg aaatagacag atcgctgaga taggtgcctc | 1440 |
| | | actgattaag cattggtaac tgtcagacca agtttactca tatatacttt agattgattt | 1500 |
| | | aaaacttcat ttttaattta aaaggatcta ggtgaagatc cttttttgata atctcatgac | 1560 |
| | | caaaatccct taacgtgagt tttcgttcca ctgagcgtca gaccccgtag aaaagatcaa | 1620 |
| | | aggatcttct tgagatcctt ttttctgcg cgtaatctgc tgcttgcaaa caaaaaaacc | 1680 |
| | | accgctacca gcggtggttt gtttgccgga tcaagagcta ccaactcttt ttccgaaggt | 1740 |
| | | aactggcttc agcagagcgc agataccaaa tactgtcctt ctagtgtagc cgtagttagg | 1800 |
| | | ccaccacttc aagaactctg tagcaccgcc tacatacctc gctctgctaa tcctgttacc | 1860 |
| | | agctgccagt ggcgataagt cgtgtcttac cgggttggac tcaagacgat agttaccgga | 1920 |
| | | taaggcgcag cggtcgggct gaacgggggg ttcgtgcaca cagcccagct tggagcgaac | 1980 |
| | | gacctacacc gaactgagat acctacagcg tgagctatga gaaagcgcca cgcttcccga | 2040 |
| | | agggagaaag gcggacaggt atccggtaag cggcagggtc ggaacaggag agcgcacgag | 2100 |
| | | ggagcttcca gggggaaacg cctggtatct ttatagtcct gtcgggtttc gccacctctg | 2160 |
| | | acttgagcgt cgatttttgt gatgctcgtc aggggggcgg agcctatgga aaaacgccag | 2220 |
| | | caacgcggcc ttttacggt tcctggcctt ttgctggcct tttgctcaca tgttctttcc | 2280 |
| | | tgcgttatcc cctgattctg tggataaccg tattaccgcc tttgagtgag ctgataccgc | 2340 |
| | | tcgccgcagc cgaacgaccg agcgcagcga gtcagtgagc gaggaagcgg aagagcgcct | 2400 |
| | | gatgcggtat tttctcctta cgcatctgtg cggtatttca caccgcatat atggtgcact | 2460 |
| | | ctcagtacaa tctgctctga tgccgcatag ttaagccagt atacactccg ctatcgctac | 2520 |
| | | gtgactgggt catggctgcg ccccgacacc cgccaacacc cgctgacgcg ccctgacggg | 2580 |
| | | cttgtctgct cccggcatcc gcttacagac aagctgtgac cgtctccggg agctgcatgt | 2640 |
| | | gtcagaggtt ttcaccgtca tcaccgaaac gcgcgaggca gctgcggtaa agctcatcag | 2700 |
| | | cgtggtcgtg aagcgattca cagatgtctg cctgttcatc cgcgtccagc tcgttgagtt | 2760 |
| | | tctccagaag cgttaatgtc tggcttctga taaagcgggc catgttaagg gcggttttt | 2820 |
| | | cctgtttggt cactgatgcc tccgtgtaag ggggatttct gttcatgggg gtaatgatac | 2880 |
| | | cgatgaaacg agagaggatg ctcacgatac gggttactga tgatgaacat gcccggttac | 2940 |
| | | tggaacgttg tgagggtaaa caactggcgg tatggatgcg gcgggaccag agaaaaatca | 3000 |
| | | ctcagggtca atgccagcgc ttcgttaata cagatgtagg tgttccacag ggtagccagc | 3060 |
| | | agcatcctgc gatgcagatc cggaacataa tggtgcaggg cgctgacttc cgcgtttcca | 3120 |
| | | gactttacga aacacggaaa ccgaagacca ttcatgttgt tgctcaggtc gcagacgttt | 3180 |
| | | tgcagcagca gtcgcttcac gttcgctcgc gtatcggtga ttcattctgc taaccagtaa | 3240 |
| | | ggcaaccccg ccagcctagc cgggtcctca acgacaggag cacgatcatg cgcacccgtg | 3300 |
| | | gggccgccat gccggcgata atggcctgct tctcgccgaa acgtttggtg gcgggaccag | 3360 |
| | | tgacgaaggc ttgagcgagg gcgtgcaaga ttccgaatac cgcaagcgac aggccgatca | 3420 |
| | | tcgtcgcgct ccagcgaaag cggtcctcgc cgaaaatgac ccagagcgct gccggcacct | 3480 |
| | | gtcctacgag ttgcatgata aagaagacag tcataagtgc ggcgacgata gtcatgcccc | 3540 |
| | | gcgcccaccg gaaggagctg actgggttga aggctctcaa gggcatcggt cgagatcccg | 3600 |
| | | gtgcctaatg agtgagctaa cttacattaa ttgcgttgcg ctcactgccc gctttccagt | 3660 |
| | | cgggaaacct gtcgtgccag ctgcattaat gaatcggcca acgcgcgggg agaggcggtt | 3720 |
| | | tgcgtattgg gcgccaggt ggttttctt ttcaccagtg agacgggcaa cagctgattg | 3780 |
| | | cccttcaccg cctggccctg agagagttgc agcaagcggt ccacgctggt ttgccccagc | 3840 |
| | | aggcgaaaat cctgtttgat ggtggttaac ggcgggatat aacatgagct gtcttcggta | 3900 |
| | | tcgtcgtatc ccactaccga gatatccgca ccaacgcgca gcccggactc ggtaatggcg | 3960 |
| | | cgcattgcgc ccagcgccat ctgatcgttg gcaaccagca tcgcagtggg aacgatgccc | 4020 |
| | | tcattcagca tttgcatggt ttgttgaaaa ccggacatgg cactccagtc gccttcccgt | 4080 |
| | | tccgctatcg gctgaatttg attgcgagtg agatatttat gccagccagc cagacgcaga | 4140 |
| | | cgcgccgaga cagaacttaa tgggcccgct aacagcgcga tttgctggtg acccaatgcg | 4200 |
| | | accagatgct ccacgcccag tcgcgtaccg tcttcatggg agaaaataat actgttgatg | 4260 |
| | | ggtgtctggt cagagacatc aagaaataac gccggaacat tagtgcaggc agcttccaca | 4320 |
| | | gcaatggcat cctggtcatc cagcggatag ttaatgatca gcccactgac gcgttgcgcg | 4380 |
| | | agaagattgt gcaccgccgc tttacaggct tcgacgccgc ttcgttctac catcgacacc | 4440 |
| | | accacgctgg cacccagttg atcggcgcga gatttaatcg ccgcgacaat ttgcgacggc | 4500 |
| | | gcgtgcaggg ccagactgga ggtggcaacg ccaatcagca acgactgttt gcccgccagt | 4560 |
| | | tgttgtgcca cgcggttggg aatgtaattc agctccgcca tcgccgcttc cacttttcc | 4620 |
| | | cgcgttttcg cagaaacgtg gctggcctgg ttcaccacgc gggaaacggt ctgataagag | 4680 |
| | | acaccggcat actctgcgac atcgtataac gttactggtt tcacattcac caccctgaat | 4740 |
| | | tgactctctt ccgggcgcta tcatgccata ccgcgaaagg ttttgcgcca ttcgatggtg | 4800 |
| | | tccgggatct cgacgctctc ccttatgcga ctcctgcatt aggaagcagc ccagtagtag | 4860 |
| | | gttgaggccg ttgagcaccg ccgccgcaag gaatggtgca tgcaaggaga tggcgcccaa | 4920 |
| | | cagtcccccg gccacggggc ctgccaccat acccacgccg aaacaagcgc tcatgagccc | 4980 |
| | | gaagtggcga gcccgatctt ccccatcggt gatgtcggcg atataggcgc cagcaaccgc | 5040 |
| | | acctgtggcg ccggtgatgc cggccacgat gcgtccggcg tagaggatcg agatctcgat | 5100 |
| | | cccgcgaaat taatacgact cactataggg gaattgtgag cggataacaa ttcccctcta | 5160 |
| | | gaaataattt tgtttaactt taagaaggag atatacatat gcataccccca gaacacatca | 5220 |
| | | ccgccgtggt acagcgtttt gtgctcgcgc tcaatgccgg cgatctggac gcatcgtcg | 5280 |
| | | cgctgtttgc cgatgacgcc acgttggaag acccgtggg ttccgagccc aggtccggta | 5340 |
| | | cggctgcgat tcgtgagttt tacgccaact cgctcaaact gcctttggcg gtgagctga | 5400 |
| | | cgcaggaggt acgcgcggtc gccaacgaag cggccttcgc tttcaccgtc agcttcgagt | 5460 |
| | | atcagggccg caagaccgta gttgcgccca tcgatcactt tcgcttcaat ggcgccggca | 5520 |
| | | aggtggtgag catccgcgcc ttgtttggcg agaagaatat tcacgcatgc cagatgctga | 5580 |

TABLE 4-continued

List of Sequences

| Seq ID No | Name | Sequence | |
|---|---|---|---|
| | | atggtaccca tcatcatcat catcatggcg gcgacggcga gaacttgtat tttcaagcta | 5640 |
| | | gcggatccat gggagagatc tggaagagcc acgaagacgc tctgcagaaa ttctttgctc | 5700 |
| | | tgctgctgct gctggccctg ctgctgctgc tggctctgct gctgcacctg ctggccttcg | 5760 |
| | | agggcggtag cggcggtggc agcggtggca agtttctgct gctgctggcg ctgctggccc | 5820 |
| | | tgttactgct ggctctgtta ttacacctgc tggccttctg ggaggcgctg aagcgtttcg | 5880 |
| | | aagacctgaa gcagaaaggt ggctgcggcc gtatctggaa ggagcacgaa gatgcgcacc | 5940 |
| | | agaaattctt tgcgttatta ttactgctgg ctctgttgtt actgctggcg ctgttactgc | 6000 |
| | | acctgctggc gttcaagggt ggcagcggtg gcggtagcgg cggtgaattt ctgttgctgc | 6060 |
| | | tggctctgct ggcgctgctt ctgctggccc tgttgttaca cctgctggcg ttctgggagg | 6120 |
| | | ccctgaagcg tcacgaagat cgtgtgcaga aaaccggtta agaattcctc gagcaccacc | 6180 |
| | | accaccacca ctgagatccg gctgctaaca aagcccgaaa ggaagctgag ttggctgctg | 6240 |
| | | ccaccgctga gcaataacta gcataacccc ttggggcctc taaacgggtc ttgaggggtt | 6300 |
| | | ttttgctgaa aggaggaact atatccggat | 6330 |
| 65 | AM-1196 (FCK mam) | ggatccgcca ccatggagat ctggaagagc cacgaagacg ctctgcagaa attctttgct | 60 |
| | | ctgctgctgc tgctggccct gctgctgctg ctggctctgc tgctgcacct gctggccttc | 120 |
| | | gagggcggta gcggcggtgg cagcggtggc aagtttctgc tgctgctggc gctgctggcc | 180 |
| | | ctgttactgc tggctctgtt attacacctg ctggccttct ggaggcgct gaagcgtttc | 240 |
| | | gaagacctga agcagaaagg tggctgcggc cgtatctgga aggagcacga agatgcgcac | 300 |
| | | cagaaattct tgcgttatt attactgctg ctctgttgt tactgctggc gctgttactg | 360 |
| | | cacctgctgg cgttcaaggg tggcagcggt ggcggtagcg gcggtgaatt tctgttgctg | 420 |
| | | ctggctctgc tggcgctgct tctgctggcc ctgttgttac acctgctggc gttctgggag | 480 |
| | | gccctgaagc gtcacgaaga tcgtgtgcag aaagcaccgg t | 521 |
| 66 | AM-1196 | EIWKSHEDAL QKFFALLLLL ALLLLLALLL HLLAFEGGSG GGSGGKFLLL LALLALLLLA | 60 |
| | | LLLHLLAFWE ALKRFEDLKQ KGGCGRIWKE HEDAHQKFFA LLLLLALLLL LALLLHLLAF | 120 |
| | | KGGSGGGSGG EFLLLLALLA LLLLALLLHL LAFWEALKRH EDRVQK | 166 |
| 67 | AM-528 (EC) | tggcgaatgg gacgcgccct gtagcggcgc attaagcgcg gcgggtgtgg tggttacgcg | 60 |
| | | cagcgtgacc gctacacttg ccagcgccct agcgcccgct ccttttcgct tcttcccttc | 120 |
| | | cttttctcgc cacgttcgcc ggctttcccg tcaagctcta atcgggggc tccctttagg | 180 |
| | | gttccgattt agtgctttac ggcacctcga ccccaaaaaa cttgattagg gtgatgttcc | 240 |
| | | acgtagtggg ccatcgccct gatagacggt ttttcgccct tgacgttgg agtccacgtt | 300 |
| | | ctttaatagt ggactcttgt tccaaactgg aacaacactc aaccctatct cggtctattc | 360 |
| | | ttttgattta agggatttt tgccgatttc ggccattgg ttaaaaaatg agctgattta | 420 |
| | | acaaaaattt aacgcgaatt ttaacaaaat attaagttt acaatttcag gtggcacttt | 480 |
| | | tcggggaaat gtgcgcggaa cccctatttg tttatttttc taaatacatt caaatatgta | 540 |
| | | tccgctcatg agacaataac cctgataaat gcttcaataa tattgaaaaa ggaagagtat | 600 |
| | | gagtattcaa catttccgtg tcgcccttat tcctttttt gcggcatttt gccttcctgt | 660 |
| | | ttttgctcac ccagaaacgc tggtgaaagt aaaagatgct gaagatcagt tgggtgcacg | 720 |
| | | agtgggttac atcgaactgg atctcaacag cggtaagatc cttgagagtt ttcgccccga | 780 |
| | | agaacgtttt ccaatgatga gcacttttaa agttctgcta tgtggcgcgg tattatcccg | 840 |
| | | tattgacgcc gggcaagagc aactcggtcg ccgcatacac tattctcaga atgacttggt | 900 |
| | | tgagtactca ccagtcacag aaaagcatct tacgatgatg caacagtaa gagaattatg | 960 |
| | | cagtgctgcc ataaccatga gtgataacac tgcggccaac ttacttctga caacgatcgg | 1020 |
| | | aggaccgaag gagctaaccg ctttttttgca caacatgggg gatcatgtaa ctcgccttga | 1080 |
| | | tcgttgggaa ccggagctga atgaagccat accaaacgac gagcgtgaca ccacgatgcc | 1140 |
| | | tgcagcaatg gcaacaacgt tgcgcaaact attaactggc gaactactta ctctagcttc | 1200 |
| | | ccggcaacaa ttaatagact ggatggaggc ggataaagtt gcaggaccac ttctgcgctc | 1260 |
| | | ggcccttccg gctggctggt ttattgctga taaatctgga gccggtgagc gtgggtctcg | 1320 |
| | | cggtatcatt gcagcactgg ggccagatgg taagccctcc cgtatcgtag ttatctacac | 1380 |
| | | gacggggagt caggcaacta tggatgaacg aaatagacag atcgctgaga taggtgcctc | 1440 |
| | | actgattaag cattggtaac tgtcagacca agtttactca tatatacttt agattgattt | 1500 |
| | | aaaacttcat ttttaattta aaaggatcta ggtgaagatc ctttttgata atctcatgac | 1560 |
| | | caaaatccct taacgtgagt tttcgttcca ctgagcgtca gaccccgtag aaaagatcaa | 1620 |
| | | aggatcttct tgagatcctt ttttttctgcg cgtaatctgc tgcttgcaaa caaaaaaacc | 1680 |
| | | accgctacca gcggtggttt gtttgccgga tcaagagcta ccaactcttt ttccgaaggt | 1740 |
| | | aactggcttc agcagagcgc agataccaaa tactgtcctt ctagtgtagc cgtagttagg | 1800 |
| | | ccaccacttc aagaactctg tagcaccgcc tacataccct gctctgctaa tcctgttacc | 1860 |
| | | agtggctgcc agtggcgata agtcgtgtct tacccgggttgac tcaagacgat agttaccgga | 1920 |
| | | taaggcgcag cggtcgggct gaacgggggg ttcgtgcaca cagcccagct tggacgcaag | 1980 |
| | | gacctacacc gaactgagat acctacagcg tgagctatga gaaagcgcca cgcttcccga | 2040 |
| | | agggagaaag gcggacaggt atccggtaag cggcagggtc ggaacaggag agcgcacgag | 2100 |
| | | ggagcttcca gggggaaacg cctggtatct ttatagtcct gtcgggtttc gccacctctg | 2160 |
| | | acttgagcgt cgatttttgt gatgctcgtc aggggggcgg agcctatgga aaaacgccag | 2220 |
| | | caacgcggcc tttttacggt tcctggcctt ttgctggcct tttgctcaca tgttctttcc | 2280 |
| | | tgcgttatcc cctgattctg tggataaccg tattaccgcc tttgagtgag ctgataccgc | 2340 |
| | | tcgccgcagc cgaacgaccg agcgcagcga gtcagtgagc gaggaagcgg aagagcgcct | 2400 |
| | | gatgcggtat tttcctccta cgcatctgtg cggtatttca caccgcatat atggtgcact | 2460 |
| | | ctcagtacaa tctgctctga tgccgcatag ttaagccagt atacactccg ctatcgctac | 2520 |
| | | gtgactgggt catggctgcg ccccgacacc cgccaacacc cgctgacgcg ccctgacggg | 2580 |
| | | cttgtctgct cccggcatcc gcttacagac aagctgtgac cgtctccggg agctgcatgt | 2640 |
| | | gtcagaggtt ttcaccgtca tcaccgaaac gcgcgaggca gctgcggtaa agctcatcag | 2700 |
| | | cgtggtcgtg aagcgattca cagatgtctg cctgttcatc cgcgtccagc tcgttgagtt | 2760 |

TABLE 4-continued

List of Sequences

| Seq ID No | Name | Sequence | | | | | |
|---|---|---|---|---|---|---|---|
| | | tctccagaag | cgttaatgtc | tggcttctga | taaagcgggc | catgttaagg gcggttttt | 2820 |
| | | cctgtttggt | cactgatgcc | tccgtgtaag | ggggattct | gttcatgggg gtaatgatac | 2880 |
| | | cgatgaaacg | agagaggatg | ctcacgatac | gggttactga | tgatgaacat gcccggttac | 2940 |
| | | tggaacgttg | tgagggtaaa | caactggcgg | tatgatgcg | gcgggaccag agaaaaatca | 3000 |
| | | ctcagggtca | atgccagcgc | ttcgttaata | cagatgtagg | tgttccacag ggtagccagc | 3060 |
| | | agcatcctgc | gatgcagatc | cggaacataa | tggtgcaggg | cgctgacttc cgcgtttcca | 3120 |
| | | gactttacga | aacacggaaa | ccgaagacca | ttcatgttgt | tgctcaggtc gcagacgttt | 3180 |
| | | tgcagcagca | gtcgcttcac | gttcgctcgc | gtatcggtga | ttcattctgc taaccagtaa | 3240 |
| | | ggcaaccccg | ccagcctagc | cgggtcctca | acgacaggag | cacgatcatg cgcacccgtg | 3300 |
| | | gggccgccat | gccggcgata | atggcctgct | ctcgccgaa | acgtttggtg gcgggaccag | 3360 |
| | | tgacgaaggc | ttgagcgagg | gcgtgcaaga | ttccgaatac | cgcaagcgac aggccgatca | 3420 |
| | | tcgtcgcgct | ccagcgaaag | cggtcctcgc | cgaaaatgac | ccagagcgct gccggcacct | 3480 |
| | | gtcctacgag | ttgcatgata | aagaagacag | tcataagtgc | ggcgacgata gtcatgcccc | 3540 |
| | | gcgcccaccg | gaaggagctg | actgggttga | aggctctcaa | gggcatcggt cgagatcccg | 3600 |
| | | gtgcctaatg | agtgagctaa | cttacattaa | ttgcgttgcg | ctcactgccc gctttccagt | 3660 |
| | | cgggaaacct | gtcgtgccag | ctgcattaat | gaatcggcca | acgcgcgggg agaggcggtt | 3720 |
| | | tgcgtattgg | gcgccagggt | ggttttctt | ttcaccagtg | agacgggcaa cagctgattg | 3780 |
| | | cccttcaccg | cctggccctg | agagagttgc | agcaagcggt | ccacgctggt ttgccccagc | 3840 |
| | | aggcgaaaat | cctgtttgat | ggtggttaac | ggcgggatat | aacatgagct gtcttcggta | 3900 |
| | | tcgtcgtatc | ccactaccga | gatatccgca | ccaacgcgca | gcccgactc ggtaatggca | 3960 |
| | | cgcattgcgc | ccagcgccat | ctgatcgttg | gcaaccagca | tcgcagtggg aacgatgccc | 4020 |
| | | tcattcagca | tttgcatggt | ttgttgaaaa | ccggacatgg | cactccagtc gccttcccgt | 4080 |
| | | tccgctatcg | gctgaatttg | attgcgagtg | agatatttat | gccagccagc cagacgcaga | 4140 |
| | | cgcgccgaga | cagaacttaa | tgggcccgct | aacagcgcga | tttgctggtg acccaatgcg | 4200 |
| | | accagatgct | ccacgcccca | tcgcgtaccg | tcttcatggg | agaaaataat actgttgatg | 4260 |
| | | ggtgtctggt | cagagacatc | aagaaataac | gccggaacat | tagtgcaggc agcttccaca | 4320 |
| | | gcaatggcat | cctggtcatc | cagcggatag | ttaatgatca | gcccactgac gcgttgcgcg | 4380 |
| | | agaagattgt | gcaccgccgc | tttacaggct | tcgacgccgc | ttcgttctac catcgacacc | 4440 |
| | | accacgctgg | caccccagttg | atcggcgcga | gatttaatcg | ccgcgacaat ttgcgacggc | 4500 |
| | | gcgtgcaggg | ccagactgga | ggtggcaacg | ccaatcagca | acgactgttt gcccgccagt | 4560 |
| | | tgttgtgcca | cgcggttggg | aatgtaattc | agctccgcca | tcgccgcttc cacttttcc | 4620 |
| | | cgcgttttcg | cagaaacgtg | gctggcctgg | ttcaccacgc | gggaaacggt ctgataagag | 4680 |
| | | acaccggcat | actctgcgac | atcgtataac | gttactggtt | tcacattcac caccctgaat | 4740 |
| | | tgactctctt | ccgggcgcta | tcatgccata | ccgcgaaagg | ttttgcgcca ttcgatggtg | 4800 |
| | | tccgggatct | cgacgctctc | ccttatgcga | ctcctgcatt | aggaagcagc ccagtagtag | 4860 |
| | | gttgaggccg | ttgagcaccg | ccgccgcaag | gaatggtgca | tgcaaggaga tggcgcccaa | 4920 |
| | | cagtccccg | gccacggggc | ctgccaccat | acccacgccg | aaacaagcgc tcatgagccc | 4980 |
| | | gaagtggcga | gcccgatctt | ccccatcggt | gatgtcggcg | atataggcgc cagcaaccgc | 5040 |
| | | acctgtgcg | ccggtgatgc | cggccacgat | gcgtccgcg | tagaggatcg agatctcgat | 5100 |
| | | cccgcgaaat | taatacgact | cactataggg | gaattgtgag | cggataacaa ttcccctcta | 5160 |
| | | gaaataattt | tgtttaactt | taagaaggag | atatacatat | gcatacccca gaacacatca | 5220 |
| | | ccgccgtggt | acagcgcttt | gtggctgcgc | tcaatgccgg | cgatctggac ggcatcgtcg | 5280 |
| | | cgctgtttgc | cgatgacgcc | acggtggaag | accccgtggg | ttccgagccc aggtccggta | 5340 |
| | | cggctgcgat | tcgtgagttt | tacgccaact | cgctcaaact | gccttttggcg gtggagctga | 5400 |
| | | cgcaggaggt | acgcgcggtc | gccaacgaag | cggccttcgc | tttcaccgtc agcttcgagt | 5460 |
| | | atcagggccg | caagaccgta | gttgcgccca | tcgatcactt | tcgcttcaat ggcgccggca | 5520 |
| | | aggtggtgag | catccgcgcc | ttgtttggcg | agaagaatat | tcacgcatgc cagatgctga | 5580 |
| | | atggtaccca | tcatcatcat | catcatgcg | gcgacggcga | gaacttgtat tttcaagcta | 5640 |
| | | gcggatccat | gggagaaatc | tggaaacaat | tcgaggacgc | actgcaaaag ttcttcgccc | 5700 |
| | | tgcacctgct | gctggcactg | ctgctgctgc | tggctctgct | gctgttcctg ctggctttg | 5760 |
| | | agggcggtag | cggcggtggc | agcggtggca | agttcctgct | gtgcctggcg ctgctggccc | 5820 |
| | | tgttactgct | ggccctgtta | ctgttcctgc | tggcttttg | ggaggctctg aaccagttcg | 5880 |
| | | aagacctggc | taagcagggt | ggcagcggt | gcggtagcg | gcggtgagatc tggaagcagt | 5940 |
| | | ttgaagatgc | gctgcagaaa | ttctttgctc | tgcacctgct | gctggcgct gctgttactg | 6000 |
| | | tggcgctgtt | actgttcctg | ctggcgttta | agggcggtag | cggcggtggc agcggtggcg | 6060 |
| | | aatttctgct | gcacctggct | ctgctggcgc | tgctgctgct | ggccctgctg ctgttcctgc | 6120 |
| | | tggcttttcg | ggaggcactg | aaccaatttg | aagacctggc | taaacaaacc ggttaagaat | 6180 |
| | | tcctcgagca | ccaccaccac | caccactgag | atccggctgc | taacaaagcc cgaaaggaag | 6240 |
| | | ctgagttggc | tgctgccacc | gctgagcaat | aactagcata | acccctgggg cctctaaac | 6300 |
| | | gggtcttgag | gggttttttg | ctgaaaggag | gaactatatc | cggat | 6345 |
| 68 | AM-528 (FCK mam) | ggatccgcca | ccatggaaat | ctggaaacaa | ttcgaggacg | cactgcaaaa gttcttcgcc | 60 |
| | | ctgcacctgc | tgctggcact | gctgctgctg | ctgctctcgc | tgctgttcct gctggctttt | 120 |
| | | gagggcgta | gcggcggtgg | cagcggtggc | aagttcctgc | tgtgcctggc gctgctggcc | 180 |
| | | ctgttactgc | tggccctgtt | actgttcctg | ctggcttttg | ggaggctctg gaaccagtc | 240 |
| | | gaagacctgg | ctaagcaggg | tggcagcggt | ggcggtagcg | gcggtgagat ctggaagcag | 300 |
| | | tttgaagatg | cgctgcagaa | attctttgct | ctgcacctgc | tgctggcgct gctgttactg | 360 |
| | | ctggcgctgt | tactgttcct | gctggcgttt | aagggcggta | gcggcggtgg cagcggtggc | 420 |
| | | gaatttctgc | tgcacctggc | tctgctggcg | ctgctggcgc | tggccctgct gctgttcctg | 480 |
| | | ctggcttcct | gggaggcact | gaaccaattt | gaagacctgg | ctaaacaagc accggttggat | 540 |
| | | ccgccaccat | ggaaatctgg | aaacaattcg | aggacgcact | gcaaaagttc ttcgccctg | 600 |
| | | acctgctgct | ggcactgctg | ctgctgctgg | ctctgctgct | gttcctgctg cttttgagg | 660 |
| | | gcggtagcgg | cggtggcagc | ggtggcaagt | tcctgctgtg | cctggcgctg ctggccctgt | 720 |
| | | tactgctggc | cctgttactg | ttcctgctgg | ccttttggga | ggctctgaac cagttcgaag | 780 |

TABLE 4-continued

List of Sequences

| Seq ID No | Name | Sequence | |
|---|---|---|---|
| | | acctggctaa gcagggtggc agcggtggcg gtagcggcgg tgagatctgg aagcagtttg | 840 |
| | | aagatgcgct gcagaaattc tttgctctgc acctgctgct ggcgctgctg ttactgctgg | 900 |
| | | cgctgttact gttcctgctg gcgtttaagg gcggtagcgg cggtggcagc ggtggcgaat | 960 |
| | | ttctgctgca cctggctctg ctggcgctgc tgctgctggc cctgctgctg ttcctgctgg | 1020 |
| | | ctttctggga ggcactgaac caatttgaag acctggctaa caagcaccg gtggatccgc | 1080 |
| | | caccatggaa atctggaaac aattcgagga cgcactgcaa aagttcttcg ccctgcacct | 1140 |
| | | gctgctggca ctgctgctgc tgctggctct gctgctgttc ctgctggctt ttgagggcgg | 1200 |
| | | tagcggcggt ggcagcggtg gcaagttcct gctgtgcctg gcgctgctgg ccctgttact | 1260 |
| | | gctggccctg ttactgttcc tgctggcctt tgggaggct ctgaaccagt tcgaagacct | 1320 |
| | | ggctaagcag gtggcagcg gtggcggtag cggcggtgag atctggaagc agtttgaaga | 1380 |
| | | tgcgctgcag aaattctttg ctctgcacct gctgctgctg ctgctggcgct | 1440 |
| | | gttactgttc ctgctggcgt taagggcgg tagcggcggt ggcagcggtg gcgaatttct | 1500 |
| | | gctgcacctg gctctgctgg cgctgctgct gctggccctg ctgctgttcc tgctggcttt | 1560 |
| | | ctgggaggca ctgaaccaat ttgaagacct ggctaaacaa gcaccggt | 1608 |
| 69 | AM-528 | EIWKQFEDAL QKFFALHLLL ALLLLLALLL FLLAFEGGSG GGSGGKFLLC LALLALLLLA | 60 |
| | | LLLFLLAFWE ALNQFEDLAK QGGSGGGSGG EIWKQFEDAL QKFFALHLLL ALLLLLALLL | 120 |
| | | FLLAFKGGSG GGGGEFLLHL ALALLLLAL LLFLLAFWEA LNQFEDLAKQ | 170 |
| 70 | GLSloop (EC) | ggtaagttcc ctctagatat tttgtttaac ttttaggagg taaaacatat gggtaaaggc | 60 |
| | | ggtcaccatc atcaccacca cggcggcgac ggcgagaatt tgtattttca gggtgaaatt | 120 |
| | | tggaagcaac atgaggatgc actgcagaag tttgaagaag cgctgaacca attcgaggat | 180 |
| | | ctgaagcagc tgggtggttc cggtaaaagc tctgtggtg aaatcaaaca acgtcatgga | 240 |
| | | gacgccctgc gcaaattcga agaggcgttg aaacgtttg aggacctgaa gcaaaaaggt | 300 |
| | | ggcagcgtg agatctggaa acagcacgag gatgctctgc agaaatttga agaggcactg | 360 |
| | | aaccagttcg aggacctgaa caactgggc ggtagcggca agggcagcgg tggtgagatt | 420 |
| | | aagcagcgtc acgaggacgc gctgcgtaag ttcgaagaag ccctgaaacg cttcgaagat | 480 |
| | | cgtgtacaaa agtaactcga gccccctagc ataacccctt ggggcctcta aacgggtctt | 540 |
| | | gaggggtttt ttgcccctga gacgcgtcaa tcgagttcgt acctaagggc gacacccccat | 600 |
| | | aattagcccg ggcgaaaggc ccagtctttc gactgagcct ttcgttttat ttgatgcctg | 660 |
| | | gcagttccct actctcgcat ggggagtccc cacactacca tcggcgctac ggcgtttcac | 720 |
| | | ttctgagttc ggcatggggt caggtgggac caccgcta ctgccgccag gcaaacaagg | 780 |
| | | gtgttatgag ccatattcag gtataaatgg gctcgcgata atgttcagaa ttggttaatt | 840 |
| | | ggttgtaaca ctgacccta tttgttattt ttctaataca ttcaaat | 887 |
| 71 | GLSloop (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg gccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | accccgccc attgacgtca ataatgacgt atgttcccat agtaacgcca ataggacgtt | 420 |
| | | tccattgacg tcaatgggtg gagtatttac ggtaaactgc ccacttggca gtacatcaag | 480 |
| | | tgtatcatat gccaagtacg cccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggc actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga gaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga taccctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagaaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |

TABLE 4-continued

List of Sequences

| Seq ID No | Name | Sequence | |
|---|---|---|---|
| | | gaaggtggag agagagacag agacagatcc attcgattag tgaacggatc ggcactgcgt | 2400 |
| | | gcgccaattc tgcagacaaa tggcagtatt catccacaat ttttaaaagaa aaggggggat | 2460 |
| | | tgggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctgag | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaa cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttgagg tggggaggt aggaagagcg atgatcactt gtggactaag | 3540 |
| | | tttgttcaca tccccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggagc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gcccctagtt ctggggcag cggggatcc | 3900 |
| | | gccaccatgg gtgaaatttg aagcaacat gaggatgcac tgcagaagtt tgaagaagcg | 3960 |
| | | ctgaaccaat tcgaggatct gaagcagctg ggtggttcg gtaaaggctc tggtggtgaa | 4020 |
| | | atcaaacaac gtcatgagga cgccctgcgc aaattcgaag aggcgttgaa acgttttgag | 4080 |
| | | gacctgaagc aaaaaggtgg cagcggtgag atctggaaac agcacgagga tgctctgcag | 4140 |
| | | aaatttgaag aggcactgaa ccagttcgag gacctgaaac aactgggcgg tagcggcaag | 4200 |
| | | ggcagcggtg gtgagattaa gcagcgtcac gaagacgcgc tgcgtaagtt cgaagaagcc | 4260 |
| | | ctgaaacgct tcgaagatcg tgtacaaaag gcggcaccgg tagtagcagt gagcaagggc | 4320 |
| | | gaggagctgt tcaccggggt ggtgcccatc ctggtcgagc tggacggcga cgtaaacggc | 4380 |
| | | cacaagttca gcgtgtccgc cgagggcgag ggcgatgcca cctacggcaa gctgaccctg | 4440 |
| | | aagttcattt gcaccaccgg caagctgccc gtgccctgc ccacctcgt gaccaccctg | 4500 |
| | | acctacgcg tgcagtgctt cagccgctac cccgaccaca tgaagcagca cgacttcttc | 4560 |
| | | aagtccgcca tgcccgaagg ctacgtccag gagcgcacca tcttcttcaa ggacgacggc | 4620 |
| | | aactacaaga cccgcgccga ggtgaagttc gagggcgaca ccctggtgaa ccgcatcgag | 4680 |
| | | ctgaagggcg tcgacttcaa ggaggacggc aacatcctgg ggcacaagct ggagtacaac | 4740 |
| | | tacaacagcc acaacgtcta tatcatggcc gacaagcaga agaacggcat caaggtgaac | 4800 |
| | | ttcaagatcc gccacaacat cgaggacggc agcgtgcagc tcgccgacca ctaccagcag | 4860 |
| | | aacacccca tcggcgacgg ccccgtgctg ctgcccgaca ccactacct gagcacccag | 4920 |
| | | tccgccctga gcaaagaccc caacgagaag cgcgatcaca tggtcctgct ggagttcgtg | 4980 |
| | | accgccgcg ggatcactct cggcatggac gagctgtaca agtaagaatt cgatatcaag | 5040 |
| | | cttatcgata atcaacctct ggattacaaa atttgtgaaa gattgactgg tattcttaac | 5100 |
| | | tatgttgctc cttttacgct atgtggatac gctgctttaa tgcctttgta tcatgctatt | 5160 |
| | | gcttcccgta tggctttcat tttctcctcc ttgtataaat cctgagtct gtctctttat | 5220 |
| | | gaggagttgt ggcccgttgt caggcaacgt ggcgtggtgt gcactgtgtt tgctgacgca | 5280 |
| | | acccccactg gttgggcat tgccaccacc tgtcagctcc tttccgggac tttcgctttc | 5340 |
| | | cccctccta ttgccacggc ggaactcatc gccgcctgcc ttgcccgctg ctggacaggg | 5400 |
| | | gctcggctgt tgggcactga caattccgtg gtgttgtcgg ggaaatcatc gtcctttcct | 5460 |
| | | tggctgctcg cctgtgttgc cacctggatt ctgcgcggga cgtccttctg ctacgtccct | 5520 |
| | | tcggccctca atccagcgga ccttcttcc cgcggcctgc tgccggctct gcggcctctt | 5580 |
| | | ccgcgtcttc gccttcgccc tcagacgagt cggatctccc tttgggccgc ctccccgcat | 5640 |
| | | cgataccgtc gacctcgaga cctagaaaaa catggagcaa tcacaagtag caatacagca | 5700 |
| | | gctaccaatg ctgattgtgc ctggctagaa gcacaagagg aggaggaggt gggttttcca | 5760 |
| | | gtcacacctc aggtaccttt aagaccaatg acttacaagg cagctgtaga tcttagccac | 5820 |
| | | ttttttaaaag aaaagggggg actgaagggg ctaattcact cccaacgaag acaagatatc | 5880 |
| | | cttgatctgt ggatctacca cacacaaggc tacttccctg attggcagaa ctacacacca | 5940 |
| | | gggccaggga tcagatatcc actgaccttt ggatggtgct acaagctagt accagttgag | 6000 |
| | | caagagaagg tagaagaagc caatgaagga gaacaccc gcttgttaca ccctgtgagc | 6060 |
| | | ctgcatggga tggatgaccc ggagagagaa gtattagagt ggaggtttga cagccgccta | 6120 |
| | | gcatttcatc acatggcccg agagctgcat ccggactgta ctgggtctct ctggttagac | 6180 |
| | | cagatctgag cctgggagct ctctggctaa ctagggaacc cactgcttaa gcctcaataa | 6240 |
| | | agcttgcctt gagtgcttca agtagtgtgt gcccgtctgt tgtgtgactc tggtaactag | 6300 |
| | | agatccctca gaccctttta gtcagtgtgg aaaatctcta gcagggcccg tttaaacccg | 6360 |
| | | ctgatcagcc tcgactgtgc cttctagttg ccagccatct gttgtttgcc cctcccccgt | 6420 |
| | | gccttccttg accctggaag gtgccactcc cactgtcctt tcctaataaa atgaggaaat | 6480 |
| | | tgcatcgcat tgtctgagta ggtgtcattc tattctgggg gtgggtgg gcaggacag | 6540 |
| | | caaggggag gattgggaag acaatagcag gcatgctggg gatgcggtgg gctctatggc | 6600 |
| | | ttctgaggcg gaaagaacca gctggggctc tagggggtat ccccacgcgc cctgtagcgg | 6660 |
| | | cgcattaagc gcggcgggtg tggtggttac gcgcagcgtg accgctacac ttgccagcgc | 6720 |
| | | cctagcgccc gctcctttcg ctttcttccc ttcctttctc gccacgttcg ccggctttcc | 6780 |

TABLE 4-continued

List of Sequences

| Seq ID No | Name | Sequence | |
|---|---|---|---|
| | | ccgtcaagct ctaaatcggg ggctcccttt agggttccga tttagtgctt tacggcacct | 6840 |
| | | cgaccccaaa aaacttgatt agggtgatgg ttcacgtagt gggccatcgc cctgatagac | 6900 |
| | | ggttttttcgc cctttgacgt tggagtccac gttctttaat agtggactct tgttccaaac | 6960 |
| | | tggaacaaca ctcaaccccta tctcggtcta ttcttttgat ttataaggga ttttgccgat | 7020 |
| | | ttcggcctat tggttaaaaa atgagctgat ttaacaaaaa tttaacgcga attaattctg | 7080 |
| | | tggaatgtgt gtcagttagg gtgtggaaag tccccaggct ccccagcagg cagaagtatg | 7140 |
| | | caaagcatgc atctcaatta gtcagcaacc aggtgtggaa agtccccagg ctccccagca | 7200 |
| | | ggcagaagta tgcaaagcat gcatctcaat tagtcagcaa ccatagtccc gcccctaact | 7260 |
| | | ccgcccatcc cgcccctaac tccgcccagt tccgcccatt ctccgcccca tggctgacta | 7320 |
| | | attttttttta tttatgcaga ggccgaggcc gcctctgcct ctgagctatt ccagaagtag | 7380 |
| | | tgaggaggct tttttggagg cctaggcttt tgcaaaaagc tcccgggagc tttgtatatcc | 7440 |
| | | attttcggat ctgatcagca cgtgttgaca attaatcatc ggcatagtat atcggcatag | 7500 |
| | | tataatacga caaggtgagg aactaaacca tggccaagtt gaccagtgcc gttccggtgc | 7560 |
| | | tcaccgcgcg cgacgtcgcc ggagcggtcg agttctggac cgaccggctc gggttctccc | 7620 |
| | | gggacttcgt ggaggacgac ttcgccgggt gtgcccggga cgactgacgc ctgttcatca | 7680 |
| | | gcgcggtcca ggaccaggtg gtgccggaca caccctggc ctgggtgtgg gtgcgcggcc | 7740 |
| | | tggacgagct gtacgccgag tggtcggagg tcgtgtccac gaacttccgg gacgcctccg | 7800 |
| | | ggccggccat gaccgagatc ggcgagcagc cgtggggggcg ggagttcgcc ctgcgcgacc | 7860 |
| | | cggccggaa ctgcgtgcac ttcgtggccg aggagcagga ctgacacgtg ctacgagatt | 7920 |
| | | tcgattccac cgccgccttc tatgaaaggt tgggcttcgg aatcgttttc cgggacgccg | 7980 |
| | | gctggatgat cctccagcgc ggggatctca tgctggagtt cttcgcccac cccaacttgt | 8040 |
| | | ttattgcagc ttataatggt tacaaataaa gcaatagcat cacaaatttc acaaataaag | 8100 |
| | | cattttttttc actgcattct agttgtggtt tgtccaaact catcaatgta tcttatcatg | 8160 |
| | | tctgtatacc gtcgacctct agctagagct tggcgtaatc atggtcatag ctgtttcctg | 8220 |
| | | tgtgaaattg ttatccgctc acaattccac acaacatacg agccggaagc ataaagtgta | 8280 |
| | | aagcctgggg tgcctaatga gtgagctaac tcacattaat tgcgttgcgc tcactgcccg | 8340 |
| | | ctttccagtc gggaaacctg tcgtgccagc tgcattaatg aatcggccaa cgcgcgggga | 8400 |
| | | gaggcggttt gcgtattggg cgctcttccg cttcctcgct cactgactcg ctgcgctcgg | 8460 |
| | | tcgttcggct gcggcgagcg gtatcagctc actcaaaggc ggtaatacgg ttatccacag | 8520 |
| | | aatcagggga taacgcagga agaacatgt gagcaaaagg ccagcaaaag gccaggaacc | 8580 |
| | | gtaaaaaggc cgcgttgctg gcgtttttcc ataggctccg ccccccctgac gagcatcaca | 8640 |
| | | aaaatcgacg ctcaagtcag aggtggcgaa acccgacagg actataaaga taccaggcgt | 8700 |
| | | ttccccctgg aagctccctc gtgcgctctc ctgttccgac cctgccgctt accggatacc | 8760 |
| | | tgtccgcctt tctcccttcg ggaagcgtgg cgctttctca tagctcacgc tgtaggtatc | 8820 |
| | | tcagttcggt gtaggtcgtt cgctccaagc tgggctgtgt gcacgaaccc cccgttcagc | 8880 |
| | | ccgaccgctg cgccttatcc ggtaactatc gtcttgagtc caacccggta agacacgact | 8940 |
| | | tatcgccact ggcagcagcc actggtaaca ggattagcag agcgaggtat gtaggcggtg | 9000 |
| | | ctacagagtt cttgaagtgg tggcctaact acggctacac tagaagaaca gtatttggta | 9060 |
| | | tctgcgctct gctgaagcca gttaccttcg gaaaaagagt tggtagctct tgatccggca | 9120 |
| | | aacaaaccac cgctggtagc ggtggttttt ttgtttgcaa gcagcagatt acgcgcagaa | 9180 |
| | | aaaaaggatc tcaagaagat cctttgatct tttctacggg gtctgacgct cagtggaacg | 9240 |
| | | aaaactcacg ttaagggatt ttggtcatga gattatcaaa aaggatcttc acctagatcc | 9300 |
| | | ttttaaatta aaaatgaagt tttaaatcaa tctaaagtat atatgagtaa acttggtctg | 9360 |
| | | acagttacca atgcttaatc agtgaggcac ctatctcagc gatctgtcta tttcgttcat | 9420 |
| | | ccatagttgc ctgactcccc gtcgtgtaga taactacgat acgggagggc ttaccatctg | 9480 |
| | | gccccagtgc tgcaatgata ccgcgagacc cacgctcacc ggctccagat ttatcagcaa | 9540 |
| | | taaaccagcc agccggaagg gccgagcgca gaagtggtcc tgcaactta tccgcctcca | 9600 |
| | | tccagtctat taattgttgc cgggaagcta gagtaagtag ttcgccagtt aatagtttgc | 9660 |
| | | gcaacgttgt tgccattgct acaggcatcg tggtgtcacg ctcgtcgttt ggtatggctt | 9720 |
| | | cattcagctc cggttcccaa cgatcaaggc gagttacatg atccccccatg ttgtgcaaaa | 9780 |
| | | aagcggttag ctccttcggt cctccgatcg ttgtcagaag taagttggcc gcagtgttat | 9840 |
| | | cactcatggt tatggcagca ctgcataatt ctcttactgt catgccatcc gtaagatgct | 9900 |
| | | ttttctgtgac tggtgagtac tcaaccaagt cattctgaga atagtgtatg cggcgaccga | 9960 |
| | | gttgctcttg cccggcgtca atacgggata taccgcgcc acatagcaga actttaaaag | 10020 |
| | | tgctcatcat tggaaaacgt tcttcgggc gaaaactctc aaggatctta ccgctgttga | 10080 |
| | | gatccagttc gatgtaaccc actcgtgcac ccaactgatc ttcagcatct tttactttca | 10140 |
| | | ccagcgtttc tgggtgagca aaaacaggaa ggcaaaatgc cgcaaaaaag ggaataaggg | 10200 |
| | | cgacacgaa atgttgaata ctcatactct tcctttttca atattattga agcatttatc | 10260 |
| | | agggttattg tctcatgagc ggatacatat ttgaatgtat ttagaaaaat aaacaaatag | 10320 |
| | | gggttccgcg cacatttccc cgaaaagtgc cacctgac | 10358 |
| 72 | GLSloop | EIWKQHEDAL QKFEEALNQF EDLKQLGGSG KGSGGEIKQR HEDALRKFEE ALKRFEDLKQ | 60 |
| | | EGGCGRIWKQ HEDALQKFEE ALNQFEDLKQ LGGSGKGSGG EIKQRHEDAL RKFEEALKRF | 120 |
| | | EDLKQK | 126 |
| 73 | PEB Mut B | EIWKSHEDAL QKFEEALNQF EDLKQLGGSG KGSGGEIKQR HEDALRKFEE ALKRFEDLKQ | 60 |
| | | KGACGRIWKQ HEDALQKFEE ALNQFEDLKQ LGGSGKGSGG EIKQRHEDAL RKFEEALKRF | 120 |
| | | EDRVQK | 126 |
| 74 | PEB Mut C | EIWKLHEDAL QKFEEALNQF EDLKQLGGSG KGSGGEIKQR HEDALRKFEE ALKRFEDLKQ | 60 |
| | | KGGCGRIWKE HEDALQKFEE ALNQFEDLKQ LGGSGEGSGG EIKQRHEDAL RKFEEALKRF | 120 |
| | | EDRVQK | 126 |

TABLE 4-continued

List of Sequences

| Seq ID No | Name | Sequence | |
|---|---|---|---|
| 75 | PEB Mut D | EIWKQHEDAL QKFEEALNQF EDLKQLGGSG KGSGGEIKQR HEDALRKFEE ALKRFEDLKQ | 60 |
| | | KGGCGRIWKQ HEDALQKFEE ALNQFEDLKQ LGGSGKGSGG EIKQRHEDAL RKFEEALKRF | 120 |
| | | EDRVQK | 126 |
| 76 | PEB Mut E | EIWKQHEDAL QKFEEALNQF EDLKQLGGSG KGSGGEIKQR HEDALRKFEE ALKRFEDLKQ | 60 |
| | | KGGCGRDWKQ HEDALQKFEE ALNQFEDLKQ LGGSGKGSGG EIKQRHEDAL RKFEEALKRF | 120 |
| | | EDLKQK | 126 |
| 77 | PEB Mut F | EIWKQHEDAL QKFEEALNQF EDLKQLGGCG EIKQRAEDAL RKFEEALKRF EDLKQKGGCG | 60 |
| | | EIWKQHEDAL QKFEEALNQF EDLKQLGGSG EIKQRHEDAL RKFEEALKRF EDLKQK | 116 |
| 78 | PEB Mut G | EIWKQHEDAL QKFEEALNQF EDLKQLGGSG KGSGGEIKQR HEDALRKFEE ALKRFEDLKQ | 60 |
| | | KGGCGREWKQ HEDALQKFEE ALNQFEDLKQ LGGSGKGSGG EIKQRHEDAL RKFEEALKRF | 120 |
| | | EDLKQK | 126 |
| 79 | 35 | EIWKQHEDAL QKFEEALNQF EDLKQLGGSG SGSGGECLRD HEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 80 | 36 | EIWKQHEDAL QKFEEALNQF EDLKQLGGSG SGSGGEICLR DEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 81 | 37 | EIWKQHEDAL QKFEEALNQF EDLKQLGGSG SGSGGEIWKQ HEDALQKFEE ALNQFEDCLR | 60 |
| | | DGGSGSGSGG EIWKQHEDAL QKFEEALNQF EDLKQLGGSG SGSGGEIWKQ HEDALQKFEE | 120 |
| | | ALNQFEDLKQ L | 131 |
| 82 | 38 | EIWKQHEDAL QKFEEALNQF EDLKQLGGSG SGSGGEIWKQ HEDALQKFEE ALNQFEDLCL | 60 |
| | | RDGSGSGSGG EIWKQHEDAL QKFEEALNQF EDLKQLGGSG SGSGGEIWKQ HEDALQKFEE | 120 |
| | | ALNQFEDLKQ L | 131 |
| 83 | 39 | EIWKQHEDAL QKFEEALNQF EDLKQLGGSG SGSGGEIWKQ HEDALQKFEE ALNQFEDLKC | 60 |
| | | LRDSGSGSGG EIWKQHEDAL QKFEEALNQF EDLKQLGGSG SGSGGEIWKQ HEDALQKFEE | 120 |
| | | ALNQFEDLKQ L | 131 |
| 84 | 61 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDLKQLGGSG SGSGGEIWKQ HEDALQKFEE | 120 |
| | | ALNQFEDLKQ L | 131 |
| 85 | 214 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDALQLGGSG SGSGEIWKQG EDALQKFEEA | 120 |
| | | LNQFEDLKQ | 129 |
| 86 | 215 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDALQLGGSG SGSGEIWKQG EDALQKFEEH | 120 |
| | | LNQFEDLKQL | 130 |
| 87 | 216 | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKHEEALNQF EDALQKHEEA LNQFEDLKQL GGSGSGSGEI | 120 |
| | | WKQGEDALQK FEEALNQFED LKQL | 144 |
| 88 | 528 | EIWKQHEDAL QKFEEALNQF EDLKQLGGSG SGSGGEIWKQ CEDALQKFEE ALNQFEDLKQ | 60 |
| | | LGGSGSGSGG EIWKQHEDAL QKFEEALNQF EDLKQLGGSG SGSGGEIWKQ HEDALQKFEE | 120 |
| | | ALNQFEDLKQ L | 131 |
| 89 | C-His Stab CGRD (EC) | ttctcatgtt tgacagctta tcatcgataa gctttaatgc ggtagtttat cacagttaaa | 60 |
| | | ttgctaacgc agtcaggcac cgtgtatgaa atctaacaat gcgctcatcg tcatcctcgg | 120 |
| | | caccgtcacc ctgatgctg taggcatagg cttggttatg ccgtactgc gggcctctt | 180 |
| | | gcgggatatc cggatatagt tcctcctttc agcaaaaaac ccctcaagac ccgtttagag | 240 |
| | | gccccaaggg gttatgctag ttattgctca gcggtggcag cagccaactc agcttccttt | 300 |
| | | cgggctttgt tagcagccgg atcctcgaga ccggttcact tttgcacacg atcttcgtgg | 360 |
| | | cgcttcagcg cttcctcaaa tttgcgcagc gcatcctcat ggcgctgttt aatctcgcca | 420 |
| | | ccgctgccct tgccgctgcc acccagttgt tcagatcttc aaattgatt cagcgcttcc | 480 |
| | | tcaaactttt ggtgcgcgtc ttcgtgctcc ttccaatcac gaccgcagcc acctttctgc | 540 |
| | | tcagatcct caaaacgttt cagcgcttcc tcgaacttac gcagcgcgtc ttcgtgacgt | 600 |
| | | tgcttgatct cgccaccgct gcctttaccg ctgccaccca gttgcttcag atcctcaaac | 660 |
| | | tggttcagcg cttcctcgaa tttctgcagc gcgtcttcgt ggctcttcca gatctcgccg | 720 |
| | | gatccctgaa atacaggtt tcaccatcg cctcgtggt gatgatggtg atgcccacct | 780 |
| | | ttaccccatat gaatatcgcc ttcatggta tatctccttc ttaaagttaa acaaaattat | 840 |
| | | ttctagaggg gaattgttat ccgctcacaa ttccccctata gtgagtcgta ttaatttcgc | 900 |
| | | gggatcgaga tctcgatcct ctacgccgga cgcatcgtgt ccggcatcac cggcgccaca | 960 |
| | | ggtgcggttg ctggcgccta tcgccgac atcaccgatg ggaagatcg ggctcgccac | 1020 |
| | | ttcgggctca tgagcgcttg tttcggcgtg gtatggtgg caggcccgt ggccggggga | 1080 |
| | | ctgttgggcg ccatctcctt gcatgcacca ttccttgcgg cggcggtgct caacggcctc | 1140 |

TABLE 4-continued

List of Sequences

| Seq ID No | Name | Sequence | |
|---|---|---|---|
| | | aacctactac tgggctgctt cctaatgcag gagtcgcata agggagagcg tcgagatccc | 1200 |
| | | ggacaccatc gaatggcgca aaacctttcg cggtatggca tgatagcgcc cggaagagag | 1260 |
| | | tcaattcagg gtggtgaatg tgaaaccagt aacgttatac gatgtcgcag agtatgccgg | 1320 |
| | | tgtctcttat cagaccgttt cccgcgtggt gaaccaggcc agccacgttt ctgcgaaaac | 1380 |
| | | gcgggaaaaa gtggaagcgg cgatggcgga gctgaattac attcccaacc gcgtggcaca | 1440 |
| | | acaactggcg ggcaaacagt cgttgctgat tggcgttgcc acctccagtc tggccctgca | 1500 |
| | | cgcgccgtcg caaattgtcg cggcgattaa atctcgcgcc gatcaactgg gtgccagcgt | 1560 |
| | | ggtggtgtcg atggtagaac gaagcggcgt cgaagcctgt aaagcggcgg tgcacaatct | 1620 |
| | | tctcgcgcaa cgcgtcagtg ggctgatcat taactatccg ctggatgacc aggatgccat | 1680 |
| | | tgctgtgaa gctgcctgca ctaatgttcc ggcgttattt cttgatgtct ctgaccagac | 1740 |
| | | acccatcaac agtattattt tctcccatga agacggtacg cgactgggtg aggagcatct | 1800 |
| | | ggtcgcattg ggtcaccagc aaatcgcgct gttagcgggc ccattaagtt ctgtctcggc | 1860 |
| | | gcgtctgcgt ctggctggct ggcataaata tctcactcgc aatcaaattc agccgatagc | 1920 |
| | | ggaacgggaa ggcgactgga gtgccatgtc cggttttcaa caaaccatgc aaatgctgaa | 1980 |
| | | tgagggcatc gttcccactg cgatgctggt tgccaacgat cagatggcgc tgggcgcaat | 2040 |
| | | gcgcgccatt accgagtccg ggctgcgcgt tggtgcggat atctcggtag tgggatacga | 2100 |
| | | cgataccgaa gacagctcat gttatatccc gccgttaacc accatcaaac aggattttcg | 2160 |
| | | cctgctgggg caaaccagcg tggaccgctt gctgcaactc tctcagggcc aggcggtgaa | 2220 |
| | | gggcaatcag ctgttgcccg tctcactggt gaaaagaaaa accaccctgg cgcccaatac | 2280 |
| | | gcaaaccgcc tctccccgcg cgttggccga ttcattaatg cagctggcac gacaggtttc | 2340 |
| | | ccgactggaa agcgggcagt gagcgcaacg caattaatgt aagttagctc actcattagg | 2400 |
| | | caccgggatc tcgaccgatg cccttgagag ccttcaaccc agtcagctcc ttccggtggg | 2460 |
| | | cgcggggcat gactatcgtc gccgcactta tgactgtctt ctttatcatg caactcgtag | 2520 |
| | | gacaggtgcc ggcagcgctc tgggtcattt tcggcgagga ccgctttcgc tggagcgcga | 2580 |
| | | cgatgatcgg cctgtcgctt gcggtattcg gaatcttgca cgccctcgct caagccttcg | 2640 |
| | | tcactggtcc cgccaccaaa cgtttcggcg agaagcaggc cattatcgcc ggcatggcgg | 2700 |
| | | ccgacgcgct gggctacgtc ttgctggcgt tcgcgacgcg aggctggatg gccttcccca | 2760 |
| | | ttatgattct tctcgcttcc ggcggcatcg ggatgcccag gttgcaggcc atgctgtcca | 2820 |
| | | ggcaggtaga tgacgaccat cagggacagc ttcaaggatc gctcgcggct cttaccagcc | 2880 |
| | | taacttcgat cactggaccg ctgatcgtca cggcgattta tgccgcctcg gcgagcacat | 2940 |
| | | ggaacgggtt ggcatggatt gtaggcgccg ccctataact tgtctgcctc cccgcgttgc | 3000 |
| | | gtcgcggtgc atggagccgg gccacctcga cctgaatgga agccggcggc acctcgctaa | 3060 |
| | | cggattcacc actccaagaa ttggagccaa tcaattcttg cggagaactg tgaatgcgca | 3120 |
| | | aaccaaccct tggcagaaca tatccatcgc gtccgccatc tccagcagcc gcacgcggcg | 3180 |
| | | catctcgggc agcgttgggt cctggccacg ggtgcgcatg atcgtgctcc tgtcgttgag | 3240 |
| | | gacccggcta ggctggcggg gttgccttac tggttagcag aatgaatcac cgatacgcga | 3300 |
| | | gcgaacgtga agcgactgct gctgcaaaac gtctgcgacc tgagcaacaa catgaatggt | 3360 |
| | | cttcggtttc cgtgtttcgt aaagtctgga aacgcggaag tcagcgccct gcaccattat | 3420 |
| | | gttccggatc tgcatcgcag gatgctgctg gctacccgtg gaacaccta catctgtatt | 3480 |
| | | aacgaagcgc tggcattgac cctgagtgat ttttctcggg tcccgccgca tccataccgc | 3540 |
| | | cagttgttta ccctcacaac gttccagtaa ccgggcatgt tcatcatcag taacccgtat | 3600 |
| | | cgtgagcatc ctctctcgtt tcatcggtat cattacccc atgaacagaa atcccccttta | 3660 |
| | | cacggaggca tcagtgacca aacaggaaaa aaccgccctt aacatggccc gctttatcag | 3720 |
| | | aagccagaca ttaacgcttc tggagaaact caacggcagtg gacgcggatg aacagcaga | 3780 |
| | | catctgtgaa tcgcttcacg accacgctga tgagctttac cgcagctgcc tcgcgcgttt | 3840 |
| | | cggtgatgac ggtgaaaacc tctgacacat gcagctcccg gagacggtca cagcttgtct | 3900 |
| | | gtaagcggat gccgggagca gacaagcccg tcagggcgcg tcagcgggtg ttggcgggtg | 3960 |
| | | tcggggcgca gccatgaccc agtcacgtag cgatagcgga gtgtatactg gcttaactat | 4020 |
| | | gcggcatcag agcagattgt actgagagtg caccatatat gcggtgtgaa ataccgcaca | 4080 |
| | | gatgcgtaag gagaaaatac cgcatcaggc gctcttccgc ttcctcgctc actgactcgc | 4140 |
| | | tgcgctcggt cgttcggctg cggcgagcgg tatcagctca ctcaaaggcg gtaatacggt | 4200 |
| | | tatccacaga atcagggga t aacgcaggaa agaacatgtg agcaaaaggc cagcaaaagg | 4260 |
| | | ccaggaaccg taaaaaggcc gcgttgctgg cgtttttcca taggctccgc cccctgacga | 4320 |
| | | agcatcacaa aaatcgacgc tcaagtcaga ggtggcgaaa cccgacagga ctataaagat | 4380 |
| | | accaggcgtt tccccctgga agctccctcg tgcgctctcc tgttccgacc ctgccgctta | 4440 |
| | | ccggatacct gtccgccttt ctcccttcgg gaagcgtggc gctttctcat agctcacgct | 4500 |
| | | gtaggtatct cagttcggtg taggtcgttc gctccaagct gggctgtgtg cacgaacccc | 4560 |
| | | ccgttcagcc cgaccgctgc gccttatccg gtaactatcg tcttgagtcc aacccggtaa | 4620 |
| | | gacacgactt atcgccactg gcagcagcca ctggtaacag gattagcaga gcgaggtatg | 4680 |
| | | taggcggtgc tacagagttc ttgaagtggt ggcctaacta cggctacact agaaggacag | 4740 |
| | | tatttggtat ctgcgctctg ctgaagccag ttaccttcgg aaaaagagtt ggtagctctt | 4800 |
| | | gatccggcaa acaaaccacc gctggtagcg gtggtttttt tgtttgcaag cagcagatta | 4860 |
| | | cgcgcagaaa aaaaggatct caagaagatc ctttgatctt ttctacgggg tctgacgctc | 4920 |
| | | agtggaacga aaactcacgt taagggattt tggtcatgag attatcaaaa aggatcttca | 4980 |
| | | cctagatcct tttaaattaa aaatgaagtt ttaaatcaat ctaaagtata tatgagtaaa | 5040 |
| | | cttggtctga cagttaccaa tgcttaatca gtgaggcacc tatctcagcg atctgtctat | 5100 |
| | | ttcgttcatc catagttgcc tgactcccg tcgtgtagat aactacgata cgggagggct | 5160 |
| | | taccatctgg ccccagtgct gcaatgatac cgcgagaccc acgctcaccg gctccagatt | 5220 |
| | | tatcagcaat aaaccagcca gccggaaggg ccgagcgcag aagtggtcct gcaactttat | 5280 |
| | | ccgcctccat ccagtctatt aattgttgcc gggaagctag agtaagtagt tcgccagtta | 5340 |
| | | atagtttgcg caacgttgtt gccattgctg caggcatcgt ggtgtcacgc tcgtcgtttg | 5400 |
| | | gtatggcttc attcagctcc ggttcccaac gatcaaggcg agttacatga tcccccatgt | 5460 |
| | | tgtgcaaaaa agcggttagc tccttcggtc ctccgatcgt tgtcagaagt aagttggccg | 5520 |
| | | cagtgttatc actcatggtt atggcagcac tgcataattc tcttactgtc atgccatccg | 5580 |

TABLE 4-continued

List of Sequences

| Seq ID No | Name | Sequence | |
|---|---|---|---|
| | | taagatgctt ttctgtgact ggtgagtact caaccaagtc attctgagaa tagtgtatgc | 5640 |
| | | ggcgaccgag ttgctcttgc ccggcgtcaa cacgggataa taccgcgcca catagcagaa | 5700 |
| | | ctttaaaagt gctcatcatt ggaaaacgtt cttcggggcg aaaactctca aggatcttac | 5760 |
| | | cgctgttgag atccagttcg atgtaaccca ctcgtgcacc caactgatct tcagcatctt | 5820 |
| | | ttactttcac cagcgttct gggtgagcaa aaacaggaag gcaaaatgcc gcaaaaaagg | 5880 |
| | | gaataagggc gacacggaaa tgttgaatac tcatactctt ccttttcaa tattattgaa | 5940 |
| | | gcatttatca gggttattgt ctcatgagcg gatacatatt tgaatgtatt tagaaaaata | 6000 |
| | | aacaaatagg ggttccgcgc acatttcccc gaaaagtgcc acctgacgtc taagaaacca | 6060 |
| | | ttattatcat gacattaacc tataaaaata ggcgtatcac gaggcccttt cgtcttcaag | 6120 |
| | | aa | 6122 |
| 90 | C-His Stab CGRD (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg ggccagatat acgcggttac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttccat agtaacgcca atagggactt | 420 |
| | | tccattgacg tcaatgggtg gagtatttac ggtaaactgc ccacttggca gtacatcaag | 480 |
| | | tgtatcatat gccaagtacg cccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc aggggggaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagcttttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttgaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg gacccgaca ggcccgaagg aatagaagaa | 2340 |
| | | gaaggtggag agagacag agacagatcc attcgattag tgaacggatc ggcactgcgt | 2400 |
| | | gcgccaattc tgcagacaaa tggcagtatt catccacaat tttaaaagaa aagggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactaatc taaattccat | 2760 |
| | | gccttggggg catgcaagta cgatatacag aaggagtgaa ctcattaggg cagatgacca | 2820 |
| | | atgagtttag gaaagaaag tccagggcag gtacatcta caccaccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctgag | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaa cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acgggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatccatcc cgtctgtaa | 3480 |
| | | aagggccta tagttggagg tggggaggt aggaagagc atgatcactt gtggactaag | 3540 |
| | | tttgttcaca tccccttctc caacccctc agtacatcac cctgggagaa caggtccac | 3600 |
| | | ttgcttctgg gcccacacag tcctgcagta ttgtgtatat aaggccaggg caacggagga | 3660 |
| | | gcaggtttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |

TABLE 4-continued

List of Sequences

| Seq ID No | Name | Sequence | |
|---|---|---|---|
| | | gtgagcagcc acagtgccct gctcagaagc cccaagctcg tcaatcaagc tggttctcca | 3840 |
| | | tttgcactca ggagcacggg caggcgagtg gcccctagtt ctggggcag cggggatcc | 3900 |
| | | ggcgagatct ggaagagcca cgaagacgcg ctgcagaaat tcgaggaagc gctgaaccag | 3960 |
| | | tttgaggatc tgaagcaact gggtggcagc ggtaaaggca gcggtggcga gatcaagcaa | 4020 |
| | | cgtcacgaag acgcgctgcg taagttcgag gaagcgctga acgttttga ggatctgaag | 4080 |
| | | cagaaaggtg gctgcggtcg tgattggaag gagcacgaag acgcgcacca aaagtttgag | 4140 |
| | | gaagcgctga atcaatttga agatctgaaa caactgggtg gcagcggcaa gggcagcggt | 4200 |
| | | ggcgagatta acagcgcca tgaggatgcg ctgcgcaaat ttgaggaagc gctgaagcgc | 4260 |
| | | cacgaagatc gtgtgcaaaa gtgaaccggt agtagcagtg agcaagggcg aggagctgtt | 4320 |
| | | caccggggtg gtgcccatcc tggtcgagct ggacggcgac gtaaacggcc acaagttcag | 4380 |
| | | cgtgtccggc gagggcgagg gcgatgccac ctacggcaag ctgaccctga agttcatttg | 4440 |
| | | caccaccggc aagctgcccg tgccctggcc cacctcgtg accaccctga cctacggcgt | 4500 |
| | | gcagtgcttc agccgctacc ccgaccacat gaagcagcac gacttcttca gtccgccat | 4560 |
| | | gcccgaaggc tacgtccagg agcgcaccat cttcttcaag gacgacggca actacaagac | 4620 |
| | | ccgcgccgag gtgaagttcg agggcgacac cctggtgaac cgcatcgagc tgaagggcat | 4680 |
| | | cgacttcaag gaggacggca acatcctggg gcacaagctg gagtacaact acaacagcca | 4740 |
| | | caacgtctat atcatggccg caagcagaa gaacggcatc aaggtgaact tcaagatccg | 4800 |
| | | ccacaacatc gaggacggca gcgtgcagct cgccgaccac taccagcaga cacccccat | 4860 |
| | | cggcgacggc cccgtgctgc tgcccgacaa ccactacctg agcacccagt ccgccctgag | 4920 |
| | | caaagacccc aacgagaagc gcgatcacat ggtcctgctg gagttcgtga ccgccgccgg | 4980 |
| | | gatcactctc ggcatggacg agctgtacaa gtaagaattc gatatcaagc ttatcgataa | 5040 |
| | | tcaacctctg gattacaaaa tttgtgaaag attgactggt attcttaact atgttgctcc | 5100 |
| | | ttttacgcta tgtggatacg ctgctttaat gcctttgtat catgctattg cttcccgtat | 5160 |
| | | ggctttcatt ttctcctcct tgtataaatc ctggttgctg tctctttatg aggagttgtg | 5220 |
| | | gcccgttgtc aggcaacgtg gcgtggtgtg cactgtgttt gctgacgcaa cccccactgg | 5280 |
| | | ttggggcatt gccaccacct gtcagctcct ttccgggact ttcgctttcc cctcccctat | 5340 |
| | | tgccacgcg gaactcatcg ccgcctgcct tgcccgctgc tggacagggg ctcggctgtt | 5400 |
| | | gggcactgac aattccgtgg tgttgtcggg gaaatcatcg tcctttcctt ggctgctcgc | 5460 |
| | | ctgtgttgcc acctggattc tgcgcgggac gtccttctgc tacgtccctt cggccctcaa | 5520 |
| | | tccagcggac cttccttccc gcggcctgct gccggctctg cggcctcttc cgcgtcttcg | 5580 |
| | | ccttcgccct cagacgagtc ggatctccct ttgggccgcc tccccgcatc gataccgtcg | 5640 |
| | | acctcgagac ctagaaaaac atggagcaat cacaagtagc aatacagcag ctaccaatgc | 5700 |
| | | tgattgtgcc tggctagaag cacaagagga ggaggagtg ggttttccag tcacacctca | 5760 |
| | | ggtaccttta agaccaatga cttacaaggc agctgtagat cttagccact ttttaaaaga | 5820 |
| | | aaaggggga ctggaagggc taattcactc ccaacgaaga caagatatcc ttgatctgtg | 5880 |
| | | gatctaccac acacaaggct acttccctga ttggcagaac tacaccaccag ggccagggat | 5940 |
| | | cagatatcca ctgacctttg gatggtgcta caagctagta ccagttgagc aagagaaggt | 6000 |
| | | agaagaagcc aatgaaggag agaacacccg cttgttacac cctgtgagcc tgcatgggat | 6060 |
| | | ggatgacccg gagagagaag tattagagtg gaggtttgac agccgcctag catttcatca | 6120 |
| | | catggcccga gagctgcatc cggactgtac tgggtctctc tggttagacc agatctgagc | 6180 |
| | | ctgggagctc tctggctaac tagggaaccc actgcttaag cctcaataaa gcttgccttg | 6240 |
| | | agtgcttcaa gtagtgtgtg cccgtctgtt gtgtgactct ggtaactaga gatccctcag | 6300 |
| | | accctttag tcagtgtgga aaatctctag cagggcccgt ttaaacccgc tgatcagcct | 6360 |
| | | cgactgtgcc ttctagttgc cagccatctg ttgtttgccc ctccccgtg ccttccttga | 6420 |
| | | ccctggaagg tgccactccc actgtccttt cctaataaaa tgaggaaatt gcatcgcatt | 6480 |
| | | gtctgagtag gtgtcattct attctggggg gtgggtggg gcaggacagc aagggggagg | 6540 |
| | | attggggaaga caatagcagg catgctgggg atgcggtggg ctctatggct tctgaggcgg | 6600 |
| | | aaagaaccag ctggggctct aggggggtatc cccacgcgcc ctgtagcggc gcattaagcg | 6660 |
| | | cggcgggtgt ggtggttacg cgcagcgtga ccgctacact gccagcgccc ctagcgcccg | 6720 |
| | | ctcctttcgc tttcttccct ccttctcg ccacgttcgc cggctttccc cgtcaagctc | 6780 |
| | | taaatcgggg gctccctta gggttccgat ttagtgcttt acggcacctc gaccccaaaa | 6840 |
| | | aacttgatta gggtgatggt tcacgtagtg ggccatcgcc ctgatagacg ttttttcgcc | 6900 |
| | | ctttgacgtt ggagtccacg ttctttaata gtggactctt gttccaaact ggaacaacac | 6960 |
| | | tcaacccctat ctcggtctat tcttttgatt tataagggat tttgccgatt tcggcctatt | 7020 |
| | | ggttaaaaaa tgagctgatt taacaaaaat ttaacgcgaa ttaattctgt ggaatgtgtg | 7080 |
| | | tcagttaggg tgtggaaagt ccccaggctc cccagcaggc agaagtatgc aaagcatgca | 7140 |
| | | tctcaattag tcagcaacca ggtgtggaaa gtccccaggc tccccagcag gcagaagtat | 7200 |
| | | gcaaagcatg catctcaatt agtcagcaac catagtcccg cccctaactc cgcccatccc | 7260 |
| | | gcccctaact ccgcccagtt ccgcccattc tccgccccat ggctgactaa ttttttttat | 7320 |
| | | ttatgcagag gccgaggccg cctctgcctc tgagctattc cagaagtagt gaggaggctt | 7380 |
| | | ttttggaggc ctaggctttt gcaaaaagct cccgggagct gtatatcca ttttcgatcc | 7440 |
| | | tgatcagcac gtgttgacaa ttaatcatcg gcatagtata tcggcatagt ataatacgac | 7500 |
| | | aaggtgagga actaaaccat ggccaagttg accagtgccg ttccggtgct caccgcgcgc | 7560 |
| | | gacgtcgccg gagcggtcga gttctggacc gaccggctcg gcttctccg gacttcgtg | 7620 |
| | | gaggcagact tcgccggtgt ggtccgggac gacgtgaccc tgttcatcag cgcggtccag | 7680 |
| | | gaccaggtgg tgccggacaa cacccctggcc tgggtgtggg tgcgcggcct ggacgagctg | 7740 |
| | | tacgccgagt ggtcggaggt cgtgtccacg aacttccggg acgcctccgg ccggccatg | 7800 |
| | | accagatcg gcgagcagcc gtggggcgg gagttcgccc tgcgcgaccc ggccggcaac | 7860 |
| | | tgcgtgcact tcgtggccga gagcaggac tgacacgtgc tacgagattt cgattccacc | 7920 |
| | | gccgccttct atgaaaggtt gggcttcgga atcgttttcc gggacgccgg ctggatgatc | 7980 |
| | | ctccagcgcg gggatctcat gctggagttc ttcgcccacc ccaacttgtt tattgcagct | 8040 |
| | | tataatggtt acaaataaag caatagcatc acaaatttca caaataaagc atttttttca | 8100 |
| | | ctgcattcta gttgtggttt gtccaaactc atcaatgtat cttatcatgt ctgtataccg | 8160 |
| | | tcgacctcta gctagagctt ggcgtaatca tggtcatagc tgtttcctgt gtgaaattgt | 8220 |

TABLE 4-continued

List of Sequences

| Seq ID No | Name | Sequence | |
|---|---|---|---|
| | | tatccgctca caattccaca caacatacga gccggaagca taaagtgtaa agcctggggt | 8280 |
| | | gcctaatgag tgagctaact cacattaatt gcgttgcgct cactgcccgc tttccagtcg | 8340 |
| | | ggaaacctgt cgtgccagct gcattaatga atcggccaac gcgcggggag aggcggtttg | 8400 |
| | | cgtattgggc gctcttccgc ttcctcgctc actgactcgc tgcgctcggt cgttcggctg | 8460 |
| | | cggcgagcgg tatcagctca ctcaaaggcg gtaatacggt tatccacaga atcaggggat | 8520 |
| | | aacgcaggaa agaacatgtg agcaaaaggc cagcaaaagg ccaggaaccg taaaaaggcc | 8580 |
| | | gcgttgctgg cgttttttcca taggctccgc cccccgacg agcatcacaa aaatcgacgc | 8640 |
| | | tcaagtcaga ggtggcgaaa cccgacagga ctataaagat accaggcgtt tccccctgga | 8700 |
| | | agctccctcg tgcgctctcc tgttccgacc ctgccgctta ccggatacct gtccgccttt | 8760 |
| | | ctcccttcgg gaagcgtggc gctttctcat agctcacgct gtaggtatct cagttcggtg | 8820 |
| | | taggtcgttc gctccaagct gggctgtgtg cacgaacccc ccgttcagcc cgaccgctgc | 8880 |
| | | gccttatccg gtaactatcg tcttgagtcc aacccggtaa gacacgactt atcgccactg | 8940 |
| | | gcagcagcca ctggtaacag gattagcaga gcgaggtatg taggcggtgc tacagagttc | 9000 |
| | | ttgaagtggt ggcctaacta cggctacact agaagaacag tatttggtat ctgcgctctg | 9060 |
| | | ctgaagccag ttaccttcgg aaaaagagtt ggtagctctt gatccggcaa acaaaccacc | 9120 |
| | | gctggtagcg gtggtttttt tgtttgcaag cagcagatta cgcgcagaaa aaaaggatct | 9180 |
| | | caagaagatc ctttgatctt ttctacgggg tctgacgctc agtggaacga aaactcacgt | 9240 |
| | | taagggattt tggtcatgag attatcaaaa aggatcttca cctagatcct tttaaattaa | 9300 |
| | | aaatgaagtt ttaaatcaat ctaaagtata tatgagtaaa cttggtctga cagttaccaa | 9360 |
| | | tgcttaatca gtgaggcacc tatctcagcg atctgtctat ttcgttcatc catagttgcc | 9420 |
| | | tgactccccg tcgtgtagat aactacgata cgggagggct taccatctgg ccccagtgct | 9480 |
| | | gcaatgatac cgcgagaccc acgctcaccg gctccagatt tatcagcaat aaaccagcca | 9540 |
| | | gccggaaggg ccgagcgcag aagtggtcct gcaactttat ccgcctccat ccagtctatt | 9600 |
| | | aattgttgcc gggaagctag agtaagtagt tcgccagtta atagtttgcg caacgttgtt | 9660 |
| | | gccattgcta caggcatcgt ggtgtcacgc tcgtcgtttg gtatggcttc attcagctcc | 9720 |
| | | ggttcccaac gatcaaggcg agttacatga tcccccatgt tgtgcaaaaa agcggttagc | 9780 |
| | | tccttcggtc ctccgatcgt tgtcagaagt aagttggccg cagtgttatc actcatggtt | 9840 |
| | | atggcagcac tgcataattc tcttactgtc atgccatccg taagatgctt ttctgtgact | 9900 |
| | | ggtgagtact caaccaagtc attctgagaa tagtgtatgc ggcgaccgag ttgctcttgc | 9960 |
| | | ccggcgtcaa tacgggataa taccgcgcca catagcagaa ctttaaaagt gctcatcatt | 10020 |
| | | ggaaaacgtt cttcggggcg aaaactctca aggatcttac cgctgttgag atccagttcg | 10080 |
| | | atgtaaccca ctcgtgcacc caactgatct tcagcatctt ttactttcac cagcgtttct | 10140 |
| | | gggtgagcaa aaacaggaag gcaaaatgcc gcaaaaaagg gaataagggc gacacggaaa | 10200 |
| | | tgttgaatac tcatactctt ccttttcaa tattattgaa gcatttatca gggttattgt | 10260 |
| | | ctcatgagcg gatacatatt tgaatgtatt tagaaaaata acaaataggg gttccgcgc | 10320 |
| | | acatttcccc gaaaagtgcc acctgac | 10347 |
| 91 | C-His Stab CGRD | EIWKSHEDAL QKFEEALNQF EDLKQLGGSG KGSGGEIKQR HEDALRKFEE ALKRFEDLKQ | 60 |
| | | KGGCGRDWKE HEDAHQKFEE ALNQFEDLKQ LGGSGKGSGG EIKQRHEDAL RKFEEALKRH | 120 |
| | | EDRVQK | 126 |
| 92 | C41 Stab Map (EC) | ttctcatgtt tgacagctta tcatcgataa gctttaatgc ggtagtttat cacagttaaa | 60 |
| | | ttgctaacgc agtcaggcac cgtgtatgaa atctaacaat gcgctcatcg tcatcctcgg | 120 |
| | | caccgtcacc ctggatgctg taggcatagg cttggttatg ccggtactgc cgggcctctt | 180 |
| | | gcgggatatc cggatatagt tcctcctttt cagcaaaaaac ccctcaagac ccgtttagag | 240 |
| | | gccccaaggg gttatgctag ttattgctca gcggtggcag cagccaactc agcttccttt | 300 |
| | | cgggctttgt tagcagccgg atcctcgaga ccggttcatt tttgcttcag atcctcaaag | 360 |
| | | cgcttcagcg cttcctcatg tttacgcagc gcgtcttcgt ggctctgctt aatctcgcca | 420 |
| | | ccgctgcctt taccgctgcc acccagctgt ttcagatctt cgaactggtt cagcgcttcc | 480 |
| | | tcgtgctttt gcagcgcgtc ttcaaacagt ttccaaatct cgccgctgcc acctttctgc | 540 |
| | | ttcagatcct cgaaacgttt cagcgcttcc tcaaacttac gcagcgcgtc cgcgcaacgt | 600 |
| | | tgtttgattt cgccaccgct gcccttgccg ctgccaccca gttgcacacg atcctcgaac | 660 |
| | | tggttcagtt cgtgctcaaa cttctgcagc gcgtcttcga acagtttcca gatctcgccg | 720 |
| | | gatccctgaa aatacaggtt ttcaccatcg cctccgtggt gatgatggtg atgcccacct | 780 |
| | | ttacccatat gaatatcgcc ttccatggta tatctccttc ttaaagttaa acaaaattat | 840 |
| | | ttctagaggg gaattgttat ccgctcacaa ttcccctata gtgagtcgta ttaatttcgc | 900 |
| | | gggatcgaga tctcgatcct ctacgccgga cgcatcgtgg ccggcatcac gatgccaca | 960 |
| | | ggtgcggttg ctggcgccta tcgccgac atcaccgatg gggaagatcg gctcgccac | 1020 |
| | | ttcgggctca tgagcgcttg tttcggcgtg gtatggtgg caggcccgt ggcggggga | 1080 |
| | | ctgttgggcg ccatctcctt gcatgcacca ttccttgcgg cggcggtgct caacgccctc | 1140 |
| | | aacctactac tgggctgctt cctaatgcag gagtcgcata agggagagcg tcgagatcc | 1200 |
| | | ggacaccatc gaatggcgca aaacctttcg cggtatggca tgatagcgcc cggaagagag | 1260 |
| | | tcaattcagg gtggtgaatg tgaaaccagt aacgttatac gatgtcgcag agtatgccgg | 1320 |
| | | tgtctcttat cagaccgttt cccgcgtggt gaaccaggcc agccacgttt ctgcgaaaac | 1380 |
| | | gcgggaaaaa gtggaagcgg cgatggcgga gctgaattac attcccaacc gcgtggcaca | 1440 |
| | | acaactggcg ggcaaacagt cgttgctgat tggcgttgcc acctccagtc tggccctgca | 1500 |
| | | cgcgccgtcg caaattgtcg cggcgattaa atctcgcgcc gatcaactgg gtgccagcgt | 1560 |
| | | ggtggtgtcg atggtagaac gaagcggcgt cgaagcctgt aaagcggcgg tgcacaatct | 1620 |
| | | tctcgcgcaa cgcgtcagtg ggctgatcat taactatccg ctggatgacc aggatgccat | 1680 |
| | | tgctgtggaa gctgcctgca ctaatgttcc ggcgttattt cttgatgtct ctgaccagac | 1740 |
| | | acccatcaac agtattattt tctcccatga agacggtacg cgactgggcg tggagcatct | 1800 |
| | | ggtcgcattg ggtcaccagc aaatcgcgct gttagcgggc ccattaagtt ctgtctcggc | 1860 |
| | | gcgtctgcgt ctggctggct ggcataaata tctcactcgc aatcaaattc agccgatagc | 1920 |
| | | ggaacgggaa ggcgactgga tgccatgtc cggttttcaa caaaccatgc aaatgctgaa | 1980 |

TABLE 4-continued

List of Sequences

| Seq ID No | Name | Sequence | |
|---|---|---|---|
| | | tgagggcatc gttcccactg cgatgctggt tgccaacgat cagatggcgc tgggcgcaat | 2040 |
| | | gcgcgccatt accgagtccg ggctgcgcgt tggtgcggat atctcggtag tgggatacga | 2100 |
| | | cgataccgaa gacagctcat gttatatccc gccgttaacc accatcaaac aggattttcg | 2160 |
| | | cctgctgggg caaaccagcg tggaccgctt gctgcaactc tctcagggcc aggcggtgaa | 2220 |
| | | gggcaatcag ctgttgcccg tctcactggt gaaaagaaaa accaccctgg cgcccaatac | 2280 |
| | | gcaaaccgcc tctcccccgcg cgttggccga ttcattaatg cagctggcac gacaggtttc | 2340 |
| | | ccgactggaa agcgggcagt gagcgcaacg caattaatgt aagttagctc actcattagg | 2400 |
| | | caccgggatc tcgaccgatg cccttgagag ccttcaaccc agtcagctcc ttccggtggg | 2460 |
| | | cgcggggcat gactatcgtc gccgcactta tgactgtctt ctttatcatg caactcgtag | 2520 |
| | | gacaggtgcc ggcagcgctc tgggtcattt tcggcgagga ccgctttcgc tggagcgcga | 2580 |
| | | cgatgatcgg cctgtcgctt gcggtattcg gaatcttgca cgccctcgct caagccttcg | 2640 |
| | | tcactggtcc cgccaccaaa cgtttcggcg agaagcaggc cattatcgcc ggcatggcgg | 2700 |
| | | ccgacgcgct gggctacgtc ttgctggcgt tcgcgacgcg aggctggatg gccttcccca | 2760 |
| | | ttatgattct tctcgcttcc ggcggcatcg gatgcccgc gttgcaggcc atgctgtcca | 2820 |
| | | ggcaggtaga tgacgaccat cagggacagc ttcaaggatc gctcgcggct cttaccagcc | 2880 |
| | | taacttcgat cactggaccg ctgatcgtca cggcgattta tgccgcctcg gcgagcacat | 2940 |
| | | ggaacgggtt ggcatggatt gtaggcgccg ccctatacct tgtctgcctc cccgcgttgc | 3000 |
| | | gtcgcggtgc atggagccgg gccacctcga cctgaatgga agccggcggc acctcgctaa | 3060 |
| | | cggattcacc actccaagaa ttggagccaa tcaattcttg cggagaactg tgaatgcgca | 3120 |
| | | aaccaaccct tggcagaaca tatccatcgc gtccgccatc tccagcagcc gcacgcggcg | 3180 |
| | | catctcgggc agcgttgggt cctggccacg ggtgcgcatg atcgtgctcc tgtcgttgag | 3240 |
| | | gacccggcta ggctggcggg gttgccttac tggttagcag aatgaatcac cgatacgcga | 3300 |
| | | gcgaacgtga agcgactgct gctgcaaaac gtctgcgacc tgagcaacaa catgaatggt | 3360 |
| | | cttcggtttc cgtgtttcgt aaagtctgga aacgcggaag tcagcgccct gcaccattat | 3420 |
| | | gttccggatc tgcatcgcag gatgctgctg gctaccctgt ggaacaccta catctgtatt | 3480 |
| | | aacgaagcgc tggcattgac cctgagtgat ttttctctgg tcccgccgca tccataccgc | 3540 |
| | | cagttgttta ccctcacaac gttccagtaa ccgggcatgt tcatcatcag taacccgtat | 3600 |
| | | cgtgagcatc ctctctcgtt tcatcggtat cattaccccc atgaacagaa atcccccta | 3660 |
| | | cacggaggca tcagtgacca aacaggaaaa aaccgccctt aacatggccc gctttatcag | 3720 |
| | | aagccagaca ttaacgcttc tggagaaact caacgagctg gacgcggatg aacaggcaga | 3780 |
| | | catctgtgaa tcgcttcacg accacgctga tgagcttac cgcagctgcc tcgcgcgttt | 3840 |
| | | cggtgatgac ggtgaaaacc tctgacacat cccctgcccg gagacggtca cagcttgtct | 3900 |
| | | gtaagcggat gccgggagca gacaagcccg tcagggcgcg tcagcgggtg ttggcgggtg | 3960 |
| | | tcggggcgca gccatgaccc agtcacgtag cgatagcgga gtgtatactg gcttaactat | 4020 |
| | | gcggcatcag agcagattgt actgagagtg caccatatat gcggtgtgaa ataccgcaca | 4080 |
| | | gatgcgtaag gagaaaatac cgcatcaggc gctcttccgc ttcctcgctc actgactcgc | 4140 |
| | | tgcgctcggt cgttcggctg cggcgagcgg tatcagctca ctcaaaggcg gtaatacggt | 4200 |
| | | tatccacaga atcaggggat aacgcaggaa agaacatgtg agcaaaaggc cagcaaaagg | 4260 |
| | | ccaggaaccg taaaaaggcc gcgttgctgg cgtttttcca taggctccgc cccctgacg | 4320 |
| | | agcatcacaa aaatcgacgc tcaagtcaga ggtggcgaaa cccgacagga ctataaagat | 4380 |
| | | accaggcgtt tccccctgga agctccctcg tgcgctctcc tgttccgacc ctgccgctta | 4440 |
| | | ccggatacct gtccgccttt ctcccttcgg gaagcgtggc gctttctcat agctcacgct | 4500 |
| | | gtaggtatct cagttcggtg taggtcgttc gctccaagct gggctgtgtg cacgaacccc | 4560 |
| | | ccgttcagcc cgaccgctgc gccttatccg gtaactatcg tcttgagtcc aacccggtaa | 4620 |
| | | gacacgactt atcgccactg gcagcagcca ctggtaacag gattagcaga gcgaggtatg | 4680 |
| | | taggcggtgc tacagagttc ttgaagtggt ggcctaacta cggctacact agaaggacag | 4740 |
| | | tatttggtat ctgcgctctg ctgaagccag ttaccttcgg aaaaagagtt ggtagctctt | 4800 |
| | | gatccggcaa acaaaccacc gctggtagcg gtggttttt tgtttgcaag cagcagatta | 4860 |
| | | cgcgcagaaa aaaaggatct caagaagatc ctttgatctt ttctacgggg tctgacgctc | 4920 |
| | | agtggaacga aaactcacgt taagggattt tggtcatgag attatcaaaa aggatcttca | 4980 |
| | | cctagatcct tttaaattaa aaatgaagtt ttaaatcaat ctaaagtata tatgagtaaa | 5040 |
| | | cttggtctga cagttaccaa tgcttaatca gtgaggcacc tatctcagcg atctgtctat | 5100 |
| | | ttcgttcatc catagttgcc tgactccccg tcgtgtagat aactacgata cgggagggct | 5160 |
| | | taccatctgg ccccagtgct gcaatgatac cgcgagaccc acgctcaccg gctccagatt | 5220 |
| | | tatcagcaat aaaccagcca gccggaaggg ccgagcgcag aagtggtcct gcaactttat | 5280 |
| | | ccgcctccat ccagtctatt aattgttgcc gggaagctag agtaagtagt tcgccagtta | 5340 |
| | | atagtttgcg caacgttgtt gccattgctg caggcatcgt ggtgtcacgc tcgtcgtttg | 5400 |
| | | gtatggcttc attcagctcc ggttcccaac gatcaaggcg agttacatga tcccccatgt | 5460 |
| | | tgtgcaaaaa agcggttagc tccttcggtc ctccgatcgt tgtcagaagt aagttggccg | 5520 |
| | | cagtgttatc actcatggtt atggcagcac tgcataattc tcttactgtc atgccatccg | 5580 |
| | | taagatgctt ttctgtgact ggtgagtact caaccaagtc attctgagaa tagtgtatgc | 5640 |
| | | ggcgaccgag ttgctcttgc ccggcgtcaa cacgggataa taccgcgcca catagcagaa | 5700 |
| | | ctttaaaagt gctcatcatt ggaaaacgtt cttcggggcg aaaactctca aggatcttac | 5760 |
| | | cgctgttgag atccagttcg atgtaaccca ctcgtgcacc caactgatct tcagcatctt | 5820 |
| | | ttactttcac cagcgtttct gggtgagcaa aaacaggaag gcaaaatgcc gcaaaaaagg | 5880 |
| | | gaataagggc gacacggaaa tgttgaatac tcatactctt cctttttcaa tattattgaa | 5940 |
| | | gcatttatca gggttattgt ctcatgagcg gatacatatt tgaatgtatt tagaaaaata | 6000 |
| | | aacaaatagg ggttccgcgc acatttcccc gaaaagtgcc acctgacgtc taagaaacca | 6060 |
| | | ttattatcat gacattaacc tataaaaata ggcgtatcac gaggcccttt cgtcttcaag | 6120 |
| | | aa | 6122 |
| 93 | C41 Stab Map | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |

TABLE 4-continued

List of Sequences

| Seq ID No | Name | Sequence | | | | | |
|---|---|---|---|---|---|---|---|
| | (FCK mam) | tgcttagggt | taggcgtttt | gcgctgcttc | gcgatgtacg | ggccagatat | acgcgttgac | 240 |
| | | attgattatt | gactagttat | taatagtaat | caattacggg | gtcattagtt | catagcccat | 300 |
| | | atatggagtt | ccgcgttaca | taacttacgg | taaatggccc | gcctggctga | ccgcccaacg | 360 |
| | | accccgcc | attgacgtca | ataatgacgt | atgttccat | agtaacgcca | atagggactt | 420 |
| | | tccattgacg | tcaatgggtg | gagtatttac | ggtaaactgc | ccacttggca | gtacatcaag | 480 |
| | | tgtatcatat | gccaagtacg | ccccctattg | acgtcaatga | cggtaaatgg | cccgcctggc | 540 |
| | | attatgccca | gtacatgacc | ttatgggact | ttcctacttg | gcagtacatc | tacgtattag | 600 |
| | | tcatcgctat | taccatggtg | atgcggtttt | ggcagtacat | caatgggcgt | ggatagcggt | 660 |
| | | ttgactcacg | ggatttccaa | gtctccacc | ccattgacgt | caatgggagt | ttgttttggc | 720 |
| | | accaaaatca | acgggacttt | ccaaaatgtc | gtaacaactc | cgccccattg | acgcaaatgg | 780 |
| | | gcggtaggcg | tgtacggtgg | gaggtctata | taagcagcgc | gttttgcctg | tactgggtct | 840 |
| | | ctctggttag | accagatctg | agcctgggag | ctctctggct | aactagggaa | cccactgctt | 900 |
| | | aagcctcaat | aaagcttgcc | ttgagtgctt | caagtagtgt | gtgcccgtct | gttgtgtgac | 960 |
| | | tctggtaact | agagatccct | cagaccctt | tagtcagtgt | ggaaaatctc | tagcagtggc | 1020 |
| | | gcccgaacag | ggacttgaaa | gcgaaaggga | aaccagagga | gctctctcga | cgcaggactc | 1080 |
| | | ggcttgctga | agcgcgcacg | gcaagaggcg | aggggcggcg | actggtgagt | acgccaaaaa | 1140 |
| | | ttttgactag | cggaggctag | aaggagagag | atgggtgcga | gagcgtcagt | attaagcggg | 1200 |
| | | ggagaattag | atcgcgatgg | gaaaaaattc | ggttaaggcc | aggggaaag | aaaaaatata | 1260 |
| | | aattaaaaca | tatagtatgg | gcaagcaggg | agctagaacg | attcgcagtt | aatcctgacc | 1320 |
| | | tgttagaaac | atcagaaggc | tgtagacaaa | tactgggaca | gctacaacca | tcccttcaga | 1380 |
| | | caggatcaga | agaacttaga | tcattatata | atacagtagc | aaccctctat | tgtgtgcatc | 1440 |
| | | aaaggataga | gataaaagac | accaaggaag | ctttagacaa | gatagaggaa | gagcaaaaca | 1500 |
| | | aaagtaagac | caccgcacag | caagcggccg | ctgatcttca | gacctggagg | aggagatatg | 1560 |
| | | agggacaatt | ggagaagtga | attatataaa | tataaagtag | taaaaattga | accattagga | 1620 |
| | | gtagcaccca | ccaaggcaaa | gagaagagtg | gtgcagagag | aaaaaagagc | agtgggaata | 1680 |
| | | ggagctttgt | tccttgggtt | cttgggagca | gcaggaagca | ctatgggcgc | agcgtcaatg | 1740 |
| | | acgctgacgg | tacaggccag | acaattattg | tctggtatag | tgcagcagca | gaacaatttg | 1800 |
| | | ctgagggcta | ttgaggcgca | acagcatctg | ttgcaactca | cagtctgggg | catcaagcag | 1860 |
| | | ctccaggcaa | gaatcctggc | tgtggaaaga | tacctaaagg | atcaacagct | cctggggatt | 1920 |
| | | tggggttgct | ctggaaaact | catttgcacc | actgctgtgc | cttggaatgc | tagttggagt | 1980 |
| | | aataaatctc | tggaacagat | ttggaatcac | acgacctgga | tggagtggga | cagagaaatt | 2040 |
| | | aacaattaca | caagcttaat | acactcctta | attgaagaat | cgcaaaacca | gcaagaaaag | 2100 |
| | | aatgaacaag | aattattgga | attagataaa | tgggcaagtt | tgtggaattg | gtttaacata | 2160 |
| | | acaaattggc | tgtggtatat | aaaattattc | ataatgatag | taggaggctt | ggtaggttta | 2220 |
| | | agaatagttt | ttgctgtact | ttctatagtg | aatagagtta | ggcagggata | ttcaccatta | 2280 |
| | | tcgtttcaga | cccacctccc | aaccccgagg | ggacccgaca | ggcccgaagg | aatagaagaa | 2340 |
| | | gaaggtggag | agagagacag | agacagatcc | attcgattag | tgaacggatc | ggcactgcgt | 2400 |
| | | gcgccaattc | tgcagacaaa | tggcagtatt | catccacaat | tttaaaagaa | aaggggggat | 2460 |
| | | tggggggtac | agtgcagggg | aaagaatagt | agacataata | gcaacagaca | tacaaactaa | 2520 |
| | | agaattacaa | aaacaaatta | caaaaattca | aaattttcgg | gtttattaca | gggacagcag | 2580 |
| | | agatccagtt | tggttaatta | acattatggc | cttaggtcac | ttcatctcca | tggggttctt | 2640 |
| | | cttctgattt | tctagaaaat | gagatggggg | tgcagagagc | ttcctcagtg | acctgcccag | 2700 |
| | | ggtcacatca | gaaatgtcag | agctagaact | tgaactcaga | ttactaatct | taaattccat | 2760 |
| | | gccttgggg | catgcaagta | cgatatacag | aaggagtgaa | ctcattaggg | cagatgacca | 2820 |
| | | atgagtttag | gaaagaagag | tccagggcag | ggtacatcta | caccacccgc | ccagccctgg | 2880 |
| | | gtgagtccag | ccacgttcac | ctcattatag | ttgcctctct | ccagtcctac | cttgacggga | 2940 |
| | | agcacaagca | gaaactggga | caggagcccc | aggagaccaa | atcttcatgg | tccctctggg | 3000 |
| | | aggatgggtg | gggagagctg | tggcagaggc | ctcaggaggg | gccctgctgc | tcagtggtga | 3060 |
| | | cagatagggg | tgagaaagca | gacagagtca | ttccgtcagc | attctgggtc | tgtttggtac | 3120 |
| | | ttcttctcac | gctaaggtgg | cggtgtgata | tgcacaatgg | ctaaaaagca | gggagagctg | 3180 |
| | | gaaagaaaca | aggacagaga | cagaggccaa | gtcaaccaga | ccaattccca | gaggaagcaa | 3240 |
| | | agaaaccatt | acagagacta | caaggggaa | gggaaggaga | gatgaattag | cttcccctgt | 3300 |
| | | aaaccttaga | acccagctgt | tgccagggca | acggggcaaat | acctgtctct | tcagaggaga | 3360 |
| | | tgaagttgcc | agggtaacta | catcctgtct | ttctcaagga | ccatcccaga | atgtggcacc | 3420 |
| | | cactagccgt | taccatagca | actgcctctt | tgccccactt | aatcccatcc | cgtctgttaa | 3480 |
| | | aagggcccta | tagttggagg | tgggggaggt | aggaagagcg | atgatcactt | gtggactaag | 3540 |
| | | tttgttcaca | tcccctttctc | caacccctc | actacatcac | cctgggaaa | caaggtccac | 3600 |
| | | ttgcttctgg | gcccacacag | tcctgcagta | ttgtgtatat | aaggccaggg | caacggagga | 3660 |
| | | gcaggttttg | aagtgaaagg | caggcaggtg | ttggggaggc | agttaccggg | gcaacgggaa | 3720 |
| | | cagggcgttt | cggaggtggt | tgccatgggg | acctggatgc | tgacgaaggc | tcgcgaggct | 3780 |
| | | gtgagcagcc | aacgtgccct | gctcagaagc | cccaagctcg | tcaatcaagc | tggttctcca | 3840 |
| | | tttgcactca | ggagcacggg | caggcgagtg | gcccctagtt | ctggggcag | cggggatcc | 3900 |
| | | ggcgagatct | ggaaactgtt | cgaagacgcg | ctgcagaagt | ttgagcacga | actgaaccag | 3960 |
| | | ttcgaggatc | gtgtgcaact | gggtggcagc | ggcaagggca | gcggtgcga | aatcaaacaa | 4020 |
| | | cgttgcgcgg | acgcgctgcg | taagtttgag | gaagcgttcg | aacgtttcga | ggatctgacca | 4080 |
| | | cagaaaggtg | gcagcggcga | gatttggaaa | ctgtttgaag | acgcgctgca | aaagcacgag | 4140 |
| | | gaagcgctga | accagttcga | agatctgaaa | cagctgggtg | gcagcggtaa | aggcagcggt | 4200 |
| | | ggcgagatta | agcagagcca | cgaagacgcg | ctgcgtaaac | atgaggaagc | gctgaagcgc | 4260 |
| | | tttgaggatc | tgaagcaaaa | atgaaccggt | agtagcagtg | agcaagggcg | aggagctgtt | 4320 |
| | | caccggggtg | gtgcccatcc | tggtcgagct | ggacggcgac | gtaaacggcc | acaagttcag | 4380 |
| | | cgtgtccggc | gagggcgagg | gcgatgccac | ctacggcaag | ctgaccctga | agttcatttg | 4440 |
| | | caccaccggc | aagctgcccg | tgccctggcc | caccctcgtg | accaccctga | cctacggcgt | 4500 |
| | | gcagtgcttc | agccgctacc | ccgaccacat | gaagcagcac | gacttcttca | agtccgccat | 4560 |
| | | gcccgaaggc | tacgtccagg | agcgcaccat | cttcttcaag | gacgacggca | actacaagac | 4620 |

TABLE 4-continued

List of Sequences

| Seq ID No | Name | Sequence | |
|---|---|---|---|
| | | ccgcgccgag gtgaagttcg agggcgacac cctggtgaac cgcatcgagc tgaagggcat | 4680 |
| | | cgacttcaag gaggacggca acatcctggg gcacaagctg gagtacaact acaacagcca | 4740 |
| | | caacgtctat atcatggccg acaagcagaa gaacggcatc aaggtgaact tcaagatccg | 4800 |
| | | ccacaacatc gaggacggca gcgtgcagct cgccgaccac taccagcaga acacccccat | 4860 |
| | | cggcgacggc cccgtgctgc tgcccgacaa ccactacctg agcacccagt ccgccctgag | 4920 |
| | | caaagacccc aacgagaagc gcgatcacat ggtcctgctg gagttcgtga ccgccgccgg | 4980 |
| | | gatcactctc ggcatggacg agctgtacaa gtaagaattc gatatcaagc ttatcgataa | 5040 |
| | | tcaacctctg gattacaaaa tttgtgaaag attgactggt attcttaact atgttgctcc | 5100 |
| | | ttttacgcta tgtggatacg ctgctttaat gcctttgtat catgctattg cttcccgtat | 5160 |
| | | ggctttcatt ttctcctcct tgtataaatc ctggttgctg tctctttatg aggagttgtg | 5220 |
| | | gcccgttgtc aggcaacgtg gcgtggtgtg cactgtgttt gctgacgcaa cccccactcg | 5280 |
| | | ttggggcatt gccaccacct gtcagctcct ttccgggact ttcgctttcc cctccctat | 5340 |
| | | tgccacgcgc gaactcatcg ccgcctgcct tgcccgctgc tggacagggg ctcggctgtt | 5400 |
| | | gggcactgac aattccgtgg tgttgtcggg gaaatcatcg tcctttcctt ggctgctcgc | 5460 |
| | | ctgtgttgcc acctggattc tgcgcgggac gtccttctgc tacgtccctt cggccctcaa | 5520 |
| | | tccagcggac cttccttccc gcggcctgct gccggctctg cggcctcttc cgcgtcttcg | 5580 |
| | | ccttcgccct cagacgagtc ggatctcccct tgggccgcc tcccgcatc gataccgtcg | 5640 |
| | | acctcgagac ctagaaaaac atggagcaat cacaagtagc aatacagcag ctaccaatgc | 5700 |
| | | tgattgtgcc tggctagaag cacaagagga ggaggaggtg ggttttccag tcacacctca | 5760 |
| | | ggtacccttta agaccaatga cttacaaggc agctgtagat cttagccact ttttaaaaga | 5820 |
| | | aaaggggga ctggaagggc taattcactc ccaacgaaga caagatatcc ttgatctgtg | 5880 |
| | | gatctaccac acacaaggct acttccctga ttggcagaac tacacaccag ggccagggat | 5940 |
| | | cagatatcca ctgacctttg gatggtgcta caagctagta ccagttgagc aagagaaggt | 6000 |
| | | agaagaagcc aatgaaggag agaacacccg cttgttacac cctgtgagcc tgcatgggat | 6060 |
| | | ggatgacccg gagagagaag tattagagtg gaggtttgac agccgcctag catttcatca | 6120 |
| | | catggcccga gagctgcatc cggactgtac tgggtctctc tggttagacc agatctgagc | 6180 |
| | | ctgggagctc tctggctaac tagggaaccc actgcttaag cctcaataaa gcttgccttg | 6240 |
| | | agtgcttcaa gtagtgtgtg cccgtctgtt gtgtgactct ggtaactaga gatccctcag | 6300 |
| | | acccttttag tcagtgtgga aaatctctag cagggcccgt ttaaacccgc tgatcagcct | 6360 |
| | | cgactgtgcc ttctagttgc cagccatctg ttgtttgccc ctcccccgtg ccttccttga | 6420 |
| | | ccctggaagg tgccactccc actgtcctt cctaataaaa tgaggaaatt gcatcgcatt | 6480 |
| | | gtctgagtag tgtgcattct attctggggg gtgggtggg gcaggacagc aagggggagg | 6540 |
| | | attgggaaga caatagcagg catgctgggg atgcggtggg ctctatggct tctgaggcgg | 6600 |
| | | aaagaaccag ctggggctct aggggggtatc cccacgcgcc ctgtagcggc gcattaagcg | 6660 |
| | | cggcgggtgt ggtggttacg cgcagcgtga ccgctacact gccagcgcc ctagcgcccg | 6720 |
| | | ctcctttcgc tttcttccct tcctttctcg ccacgttcgc cggctttccc cgtcaagctc | 6780 |
| | | taaatcgggg gctcccttta gggttccgat ttagtgcttt acggcacctc gaccccaaaa | 6840 |
| | | aacttgatta gggtgatggt tcacgtagtg gccatcgcc ctgatagacg ttttttcgcc | 6900 |
| | | ctttgacgtt ggagtccacg ttctttaata gtggactctt gttccaaact ggaacaacac | 6960 |
| | | tcaaccctat ctcggtctat tcttttgatt tataaggatt tttgccgatt tcggcctatt | 7020 |
| | | ggttaaaaaa tgagctgatt taacaaaaat ttaacgcgaa ttaattctgt ggaatgtgtg | 7080 |
| | | tcagttaggg tgtggaaagt ccccaggctc cccagcaggc agaagtatgc aaagcatgca | 7140 |
| | | tctcaattag tcagcaacca ggtgtggaaa gtccccaggc tccccagcag gcagaagtat | 7200 |
| | | gcaaagcatg catctcaatt agtcagcaac catagtcccg ccctaactc cgcccatccc | 7260 |
| | | gcccctaact ccgcccagtt ccgcccattc tccgccccat ggctgactaa ttttttttat | 7320 |
| | | ttatgcagag gccgaggccg cctctgcctc tgagctattc cagaagtagt gaggaggctt | 7380 |
| | | ttttggaggc ctaggctttt gcaaaaagct cccgggagct gtatatcca ttttcggatc | 7440 |
| | | tgatcagcac gtgttgacaa ttaatcatcg gcatagtata tcggcatagt ataatacgac | 7500 |
| | | aaggtgagga actaaaccat ggccaagttg accagtgccg ttccggtgct caccgcgcgc | 7560 |
| | | gacgtcgccg gagcggtcga gttctggacc gaccggctcg ggttctcccg gacttcgtg | 7620 |
| | | gaggacgact cgccggtgt ggtccgggac gacgtgaccc tgttcatcag cgcggtccag | 7680 |
| | | gaccaggtgg tgccggacaa caccctggcc tgggtgtggg tgcgcggcct ggacgagctg | 7740 |
| | | tacgccgagt ggtcggaggt cgtgtccacg aacttccggg acgcctccgg gccggccatg | 7800 |
| | | accgagatcg gcgagcagcc gtggggggcgg gagttcgccc tgcgcgaccc ggccggcaac | 7860 |
| | | tgcgtgcact tcgtggccga ggagcaggac tgacacgtgc tacgagattt cgattccacc | 7920 |
| | | gccgccttct atgaaaggtt gggcttcgga atcgttttcc gggacgccgg ctggatgatc | 7980 |
| | | ctccagcgcg gggatctcat gctggagttc tcgcccacc ccaacttgtt tattgcagct | 8040 |
| | | tataatggtt acaaataaag caatagcatc acaaatttca caaataaagc atttttttca | 8100 |
| | | ctgcattcta gttgtggttt gtccaaactc atcaatgtat cttatcatgt ctgtataccg | 8160 |
| | | tcgacctcta gctagagctt ggcgtaatca tggtcatagc tgtttcctgt gtgaaattgt | 8220 |
| | | tatccgctca caattccaca acatacga gccggaagca taaagtgtaa agcctgggt | 8280 |
| | | gcctaatgag tgagctaact cacattaatt gcgttgcgct cactgcccgc tttccagtcg | 8340 |
| | | ggaaacctgt cgtgccagct gcattaatga atcggccaac gcgcggggag aggcggtttg | 8400 |
| | | cgtattgggc gctcttccgc ttcctcgctc actgactcgc tgcgctcggt cgttcggctg | 8460 |
| | | cggcgagcgg tatcagctca ctcaaaggcg gtaatacggt tatccacaga atcagggggat | 8520 |
| | | aacgcaggaa agaacatgtg agcaaaaggc cagcaaaagg ccaggaaccg taaaaaggcc | 8580 |
| | | gcgttgctgg cgtttttcca taggctccgc cccctgacg agcatcacaa aaatcgacgc | 8640 |
| | | tcaagtcaga ggtggcgaaa cccgacagga ctataaagat accaggcgtt tccccctgga | 8700 |
| | | agctccctcg tgcgctctcc tgttccgacc ctgccgctta ccggatacct gtccgccttt | 8760 |
| | | ctcccttcgg gaagcgtggc gctttctcat agctcacgct gtaggtatct cagttcggtg | 8820 |
| | | taggtcgttc gctccaagct gggctgtgtg cacgaacccc cgttcagc cgaccgctgc | 8880 |
| | | gccttatccg gtaactatcg tcttgagtcc aacccggtaa gacacgactt atcgccactg | 8940 |
| | | gcagcagcca ctggtaacag gattagcaga gcgaggtatg taggcggtgc tacagagttc | 9000 |
| | | ttgaagtggt ggcctaacta cggctacact agaagaacag tatttggtat ctgcgctctg | 9060 |

TABLE 4-continued

List of Sequences

| Seq ID No | Name | Sequence | |
|---|---|---|---|
| | | ctgaagccag ttaccttcgg aaaaagagtt ggtagctctt gatccggcaa acaaaccacc | 9120 |
| | | gctggtagcg gtggttttt tgtttgcaag cagcagatta cgcgcagaaa aaaaggatct | 9180 |
| | | caagaagatc ctttgatctt ttctacgggg tctgacgctc agtggaacga aaactcacgt | 9240 |
| | | taagggattt tggtcatgag attatcaaaa aggatcttca cctagatcct tttaaattaa | 9300 |
| | | aaatgaagtt ttaaatcaat ctaaagtata tatgagtaaa cttggtctga cagttaccaa | 9360 |
| | | tgcttaatca gtgaggcacc tatctcagcg atctgtctat ttcgttcatc catagttgcc | 9420 |
| | | tgactccccg tcgtgtagat aactacgata cgggagggct taccatctgg ccccagtgct | 9480 |
| | | gcaatgatac cgcgagaccc acgctcaccg gctccagatt tatcagcaat aaaccagcca | 9540 |
| | | gccggaaggg ccgagcgcag aagtggtcct gcaactttat ccgcctccat ccagtctatt | 9600 |
| | | aattgttgcc gggaagctag agtaagtagt tcgccagtta atagtttgcg caacgttgtt | 9660 |
| | | gccattgcta caggcatcgt ggtgtcacgc tcgtcgtttg gtatggcttc attcagctcc | 9720 |
| | | ggttcccaac gatcaaggcg agttacatga tcccccatgt tgtgcaaaaa agcggttagc | 9780 |
| | | tccttcggtc ctccgatcgt tgtcagaagt aagttggccg cagtgttatc actcatggtt | 9840 |
| | | atggcagcac tgcataattc tcttactgtc atgccatccg taagatgctt ttctgtgact | 9900 |
| | | ggtgagtact caaccaagtc attctgagaa tagtgtatgc ggcgaccgag ttgctcttgc | 9960 |
| | | ccggcgtcaa tacgggataa taccgcgcca catagcagaa ctttaaaagt gctcatcatt | 10020 |
| | | ggaaaacgtt cttcggggcg aaaactctca aggatcttac cgctgttgag atccagttcg | 10080 |
| | | atgtaaccca ctcgtgcacc caactgatct tcagcatctt ttactttcac cagcgtttct | 10140 |
| | | gggtgagcaa aaacaggaag gcaaaatgcc gcaaaaaagg gaataagggc gacacggaaa | 10200 |
| | | tgttgaatac tcatactctt cctttttcaa tattattgaa gcatttatca gggttattgt | 10260 |
| | | ctcatgagcg gatacatatt tgaatgtatt tagaaaaata aacaaatagg ggttccgcgc | 10320 |
| | | acatttcccc gaaaagtgcc acctgac | 10347 |
| 94 | C41 Stab Map | EIWKLFEDAL QKFEHELNQF EDRVQLGGSG KGSGGEIKQR CADALRKFEE ALKRFEDLKQ | 60 |
| | | KGGSGEIWKL FEDALQKHEE ALNQFEDLKQ LGGSGKGSGG EIKQSHEDAL RKHEEALKRF | 120 |
| | | EDLKQK | 126 |
| 95 | C41 Stab Map CARD (EC) | ttctcatgtt tgacagctta tcatcgataa gctttaatgc ggtagtttat cacagttaaa | 60 |
| | | ttgctaacgc agtcaggcac cgtgtatgaa atctaacaat gcgctcatcg tcatcctcgg | 120 |
| | | caccgtcacc ctggatgctg taggcatagg cttggttatg ccggtactgc cgggcctctt | 180 |
| | | gcgggatatc cggatatagt tcctcctttc agcaaaaaac ccctcaagac ccgtttagag | 240 |
| | | gccccaaggg gttatgctag ttattgctca gcggtggcag cagcaactc agcttccttt | 300 |
| | | cggctttgt tagcagccgg atcctcgaga ccggttcatt tttgcttcag atcctcaaag | 360 |
| | | cgcttcagcg cttcctcatg tttacgcagc gcgtcttcgt ggctctgctt aatctcgcca | 420 |
| | | ccgctgcctt taccgctgcc acccagctgt tcagatcttc gaactggttc agcgcttcc | 480 |
| | | tcgtgctttt gcagcgcgtc ttcaaacagt ttccaaatct cgccgctgcc acctttctgc | 540 |
| | | ttcagatcct cgaaacgttt cagcgcttcc tcaaacttac gcagatcacg cgcgcaacgt | 600 |
| | | tgtttgattt cgccaccgct gcccttgccg ctgccaccca gttgcacacg atcctcgaac | 660 |
| | | tggttcagtt cgtgctcaaa cttctgcagc gcgtcttcga acagtttcca gatctcgccg | 720 |
| | | gatccctgaa aatacaggtt ttcaccatcg cctccgttgt gatgatggtg atgctccacct | 780 |
| | | ttacccatat gaatatcgcc ttccatggta tatctccttc ttaaagttaa acaaaattat | 840 |
| | | ttctagaggg gaattgttat ccgctcacaa ttcccctata gtgagtcgta ttaatttcgc | 900 |
| | | gggatcgaga tctcgatcct ctacgccgga cgcatcgtgg ccggcatcac cggcgccaca | 960 |
| | | ggtgcggttg ctggcgccta tatcgccgac atcaccgatg gggaagatcg ggctcgccac | 1020 |
| | | ttcgggctca tgagcgcttg tttcggcgtg ggtatggtgg caggccccgt ggccggggga | 1080 |
| | | ctgttggcg ccatctcctt gcatgcacca ttccttgcgg cggcggtgct caacggcctc | 1140 |
| | | aacctactac tgggctgctt cctaatgcag gagtcgcata agggagagcg tcgagatccc | 1200 |
| | | ggacaccatc gaatggcgca aaacctttcg cggtatggca tgatagcgcc cggaagagag | 1260 |
| | | tcaattcagg gtggtgaatg tgaaaccagt aacgttatac gatgtcgcag agtatgccgg | 1320 |
| | | tgtctcttat cagaccgttt cccgcgtggt gaaccaggcc agccacgttt ctgcgaaaac | 1380 |
| | | gcgggaaaaa gtggaagcgg cgatgcgga gctgaattac attcccaacc gcgtggcaca | 1440 |
| | | acaactggcg ggcaaacagt cgttgctgat tggcgttgcc acctccagtc tggccctgca | 1500 |
| | | cgcgccgtcg caaattgtcg cggcgattaa atctcgcgcc gatcaactgg gtgccagcgt | 1560 |
| | | ggtggtgtcg atggtagaac gaagcggcgt cgaagcctgt aaagcggcgg tgcacaatct | 1620 |
| | | tctcgcgcaa cgcgtcagtg ggctgatcat taactatccg ctggatgacc aggatgccat | 1680 |
| | | tgctgtggaa gctgcctgca ctaatgttcc ggcgttattt cttgatgtct ctgaccagac | 1740 |
| | | acccatcaac agtattattt tctcccatga agacggtacg cgactgggcg tggagcatct | 1800 |
| | | ggtcgcattg ggtcaccagc aaatcgcgct gttagcgggc ccattaagtt ctgtctcggc | 1860 |
| | | gcgtctgcgt ctggctggct ggcataaata tctcactcgc aatcaaattc agccgatagc | 1920 |
| | | ggaacgggaa ggcgactgga gtgccatgtc cggttttcaa caaaccatgc aaatgctgaa | 1980 |
| | | tgagggcatc gttcccactg cgatggtt tgccaacgat cagatggcgc taagcgcgcaa | 2040 |
| | | gcgcgccatt accgagtccg gctgcgcgt tggtgcggat atctcggtag tgggatacga | 2100 |
| | | cgataccgaa gacagctcat gttatatccc gccgttaacc accatcaaac aggattttcg | 2160 |
| | | cctgctgggg caaaccagcg tggaccgctt gctgcaactc tctcagggcc aggcggtgaa | 2220 |
| | | gggcaatcag ctgttgcccg tctcactggt gaaaagaaaa accaccctgg cgcccaatac | 2280 |
| | | gcaaaccgcc tctccccgc gcgttggccg attcattaatg cagctggcac gacaggtttc | 2340 |
| | | ccgactggaa agcgggcagt gagcgcaacg caattaatgt aagttagctc actcattagg | 2400 |
| | | caccgggatc tcgaccgatg cccttgagag ccttcaaccc agtcagctcc ttccggtggg | 2460 |
| | | cgcggggcat gactatcgtc gccgcactta tgactgtctt ctttatcatg caactcgtag | 2520 |
| | | gacaggtgcc ggcagcgctc tgggtcattt tcggcgagga ccgctttcgc tggagcgcga | 2580 |
| | | cgatgatcgg cctgtcgctt gcggtattcg gaatcttgca cgccctcgct caagccttcg | 2640 |
| | | tcactggtcc cgccaccaaa cgtttcggcg agaagcaggc cattatcgcc ggcatggcgg | 2700 |
| | | ccgacgcgct gggctacgtc ttgctggcgt tcgcgacgcg aggctggatg gccttcccca | 2760 |
| | | ttatgattct tctcgcttcc ggcggcatcg gatgcccgc gttgcaggcc atgctgtcca | 2820 |

TABLE 4-continued

List of Sequences

| Seq ID No | Name | Sequence | |
|---|---|---|---|
| | | ggcaggtaga tgacgaccat cagggacagc ttcaaggatc gctcgcggct cttaccagcc | 2880 |
| | | taacttcgat cactggaccg ctgatcgtca cggcgattta tgccgcctcg gcgagcacat | 2940 |
| | | ggaacgggtt ggcatggatt gtaggcgccg ccctatacct tgtctgcctc cccgcgttgc | 3000 |
| | | gtcgcggtgc atggagccgg gccacctcga cctgaatgga agccggcggc acctcgctaa | 3060 |
| | | cggattcacc actccaagaa ttggagccaa tcaattcttg cggagaactg tgaatgcgca | 3120 |
| | | aaccaaccct tggcagaaca tatccatcgc gtccgccatc tccagcagcc gcacgcggcg | 3180 |
| | | catctcgggc agcgttgggt cctggccacg ggtgcgcatg atcgtgctcc tgtcgttgag | 3240 |
| | | gacccggcta ggctggcggg gttgccttac tggttagcag aatgaatcac cgatacgcga | 3300 |
| | | gcgaacgtga agcgactgct gctgcaaaac gtctgcgacc tgagcaacaa catgaatggt | 3360 |
| | | cttcggtttc cgtgtttcgt aaagtctgga aacgcggaag tcagcgccct gcaccattat | 3420 |
| | | gttccggatc tgcatcgcag gatgctgctg gctaccctgt ggaacaccta catctgtatt | 3480 |
| | | aacgaagcgc tggcattgac cctgagtgat ttttctctgg tcccgccgca tccataccgc | 3540 |
| | | cagttgttta ccctcacaac gttccagtaa ccgggcatgt tcatcatcag taacccgtat | 3600 |
| | | cgtgagcatc ctctctcgtt tcatcggtat cattacccc atgaacagaa atcccccta | 3660 |
| | | cacggaggca tcagtgacca aacaggaaaa aaccgcctct aacatggccc gctttatcag | 3720 |
| | | aagccagaca ttaacgcttc tggagaaact caacgagctg gacgcggatg aacaggcaga | 3780 |
| | | catctgtgaa tcgcttcacg accacgctga tgagctttac cgcagctgcc tcgcgcgttt | 3840 |
| | | cggtgatgac ggtgaaaacc tctgacacat gcagctcccg gagacggtca cagcttgtct | 3900 |
| | | gtaagcggat gccgggagca gacaagcccg tcagggcgcg tcagcgggtg ttggcgggtg | 3960 |
| | | tcggggcgca gccatgaccc agtcacgtag cgatagcgca gtgtatactg gcttaactat | 4020 |
| | | gcggcatcag agcagattgt actgagagtg caccatatat gcggtgtgaa ataccgcaca | 4080 |
| | | gatgcgtaag gagaaaatac cgcatcaggc gctcttccgc ttcctcgctc actgactcgc | 4140 |
| | | tgcgctcggt cgttcggctg cggcgagcgg tatcagctca ctcaaaggcg gtaatacggt | 4200 |
| | | tatccacaga atcagggggat aacgcaggaa agaacatgtg agcaaaaggc cagcaaaagg | 4260 |
| | | ccaggaaccg taaaaaggcc gcgttgctgg cgtttttcca taggctccgc cccctgacg | 4320 |
| | | agcatcacaa aaatcgacgc tcaagtcaga ggtggcgaaa cccgacagga ctataaagat | 4380 |
| | | accaggcgtt tccccctgga agctccctcg tgcgctctcc tgttccgacc ctgccgctta | 4440 |
| | | ccggatacct gtccgccttt ctcccttcgg gaagcgtggc gctttctcat agctcacgct | 4500 |
| | | gtaggtatct cagttcggtg taggtcgttc gctccaagct gggctgtgtg cacgaacccc | 4560 |
| | | ccgttcagcc cgaccgctgc gccttatccg gtaactatcg tcttgagtcc aacccggtaa | 4620 |
| | | gacacgactt atcgccactg gcagcagcca ctggtaacag gattagcaga gcgaggtatg | 4680 |
| | | taggcggtgc tacagagttc ttgaagtggt ggcctaacta cggctacact agaaggacag | 4740 |
| | | tatttggtat ctgcgctctg ctgaagccag ttaccttcgg aaaaagagtt ggtagctctt | 4800 |
| | | gatccggcaa acaaaccacc gctggtagcg gtggtttttt tgtttgcaag cagcagatta | 4860 |
| | | cgcgcagaaa aaaaggatct caagaagatc ctttgatctt ttctacgggg tctgacgctc | 4920 |
| | | agtggaacga aaactcacgt taagggattt tggtcatgag attatcaaaa aggatcttca | 4980 |
| | | cctagatcct tttaaattaa aaatgaagtt ttaaatcaat ctaaagtata tatgagtaaa | 5040 |
| | | cttggtctga cagttaccaa tgcttaatca gtgaggcacc tatctcagcg atctgtctat | 5100 |
| | | ttcgttcatc catagttgcc tgactccccg tcgtgtagat aactacgata cgggagggct | 5160 |
| | | taccatctgg ccccagtgct gcaatgatac cgcgagaccc acgctcaccg gctccagatt | 5220 |
| | | tatcagcaat aaaccagcca gccggaaggg ccgagcgcag aagtggtcct gcaactttat | 5280 |
| | | ccgcctccat ccagtctatt aattgttgcc gggaagctag agtaagtagt tcgccagtta | 5340 |
| | | atagtttgcg caacgttgtt gccattgctg caggcatcgt ggtgtcacgc tcgtcgtttg | 5400 |
| | | gtatggcttc attcagctcc ggttcccaac gatcaaggcg agttacatga tcccccatg | 5460 |
| | | tgtgcaaaaa agcggttagc tccttcggtc ctccgatcgt tgtcagaagt aagttggccg | 5520 |
| | | cagtgttatc actcatggtt atggcagcac tgcataattc tcttactgtc atgccatccg | 5580 |
| | | taagatgctt ttctgtgact ggtgagtact caaccaagtc attctgagaa tagtgtatgc | 5640 |
| | | ggcgaccgag ttgctcttgc ccggcgtcaa cacggataa taccgcgcca catgcagaa | 5700 |
| | | cttttaaaagt gctcatcatt ggaaaacgtt cttcggggcg aaaactctca aggatcttac | 5760 |
| | | cgctgttgag atccagttcg atgtaaccca ctcgtgcacc caactgatct tcagcatctt | 5820 |
| | | ttactttcac cagcgtttct gggtgagcaa aaacaggaag gcaaaatgcc gcaaaaaagg | 5880 |
| | | gaataagggc gacacgaaa tgttgaatac tcatactctt cctttttcaa tattattgaa | 5940 |
| | | gcatttatca gggttattgt ctcatgagcg gatacatatt tgaatgtatt tagaaaaata | 6000 |
| | | aacaaatagg ggttccgcgc acatttcccc gaaaagtgcc acctgacgtc taagaaacca | 6060 |
| | | ttattatcat gacattaacc tataaaaata ggcgtatcac gaggcccttt cgtcttcaag | 6120 |
| | | aa | 6122 |
| 96 | C41 Stab Map CARD (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg ggcagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcgtaggcg tgtacggtgg gaggtctata taagcagcgc gttttgcctg tactgggtct | 840 |
| | | ctctggttag accagatctg agcctgggag ctctctggct aactagggaa ccactgcttt | 900 |
| | | aagcctcaat aaagcttgcc ttgagtgctt caagtagtgt gtgcccgtct gttgtgtgac | 960 |
| | | tctggtaact agagatccct cagaccctt tagtcagtgt ggaaaatctc tagcagtggc | 1020 |

TABLE 4-continued

List of Sequences

| Seq ID No | Name | Sequence | |  |  |  |  |
|---|---|---|---|---|---|---|---|
| | | gcccgaacag | ggacttgaaa | gcgaaaggga | aaccagagga | gctctctcga | cgcaggactc | 1080 |
| | | ggcttgctga | agcgcgcacg | gcaagaggcg | aggggcggcg | actggtgagt | acgccaaaaa | 1140 |
| | | ttttgactag | cggaggctag | aaggagagag | atgggtgcga | gagcgtcagt | attaagcggg | 1200 |
| | | ggagaattag | atcgcgatgg | gaaaaaattc | ggttaaggcc | aggggggaaag | aaaaaatata | 1260 |
| | | aattaaaaca | tatagtatgg | gcaagcaggg | agctagaacg | attcgcagtt | aatcctggcc | 1320 |
| | | tgttagaaac | atcagaaggc | tgtagacaaa | tactgggaca | gctacaacca | tcccttcaga | 1380 |
| | | caggatcaga | agaacttaga | tcattatata | atacagtagc | aaccctctat | tgtgtgcatc | 1440 |
| | | aaaggataga | gataaaagac | accaaggaag | ctttagacaa | gatagaggaa | gagcaaaaca | 1500 |
| | | aaagtaagac | caccgcacag | caagcggccg | ctgatcttca | gacctggagg | aggagatatg | 1560 |
| | | agggacaatt | ggagaagtga | attatataaa | tataaagtag | taaaaattga | accattagga | 1620 |
| | | gtagcaccca | ccaaggcaaa | gagaagagtg | gtgcagagaa | aaaaaagagc | agtgggaata | 1680 |
| | | ggagctttgt | tccttgggtt | cttgggagca | gcaggaagca | ctatgggcgc | agcgtcaatg | 1740 |
| | | acgctgacgg | tacaggccag | acaattattg | tctggtatag | tgcagcagca | gaacaatttg | 1800 |
| | | ctgagggcta | ttgaggcgca | acagcatctg | ttgcaactca | cagtctgggg | catcaagcag | 1860 |
| | | ctccaggcaa | gaatcctggc | tgtggaaaga | tacctaaagg | atcaacagct | cctggggatt | 1920 |
| | | tggggttgct | ctggaaaact | catttgcacc | actgctgtgc | cttggaatgc | tagttggagt | 1980 |
| | | aataaatctc | tggaacagat | ttggaatcac | acgacctgga | tggagtggga | cagagaaatt | 2040 |
| | | aacaattaca | caagcttaat | acactcctta | attgaagaat | cgcaaaacca | gcaagaaaag | 2100 |
| | | aatgaacaag | aattattgga | attagataaa | tgggcaagtt | tgtggaattg | gtttaacata | 2160 |
| | | acaaattggc | tgtggtatat | aaaattattc | ataatgatag | taggaggctt | ggtaggttta | 2220 |
| | | agaatagttt | ttgctgtact | ttctatagtg | aatagagtta | ggcagggata | ttcaccatta | 2280 |
| | | tcgtttcaga | cccacctccc | aaccccgagg | ggacccgaca | ggcccgaagg | aatagaagaa | 2340 |
| | | gaaggtggag | agagagacag | agacagatcc | attcgattag | tgaacggatc | ggcactgcgt | 2400 |
| | | gcgccaattc | tgcagacaaa | tggcagtatt | catccacaat | tttaaaagaa | aaggggggat | 2460 |
| | | tggggggtac | agtgcagggg | aaagaatagt | agacataata | gcaacagaca | tacaaactaa | 2520 |
| | | agaattacaa | aaacaaatta | caaaaattca | aaattttcgg | gtttattaca | gggacagcag | 2580 |
| | | agatccagtt | tggttaatta | acattatggc | cttaggtcac | ttcctctcca | tggggttctt | 2640 |
| | | cttctgattt | tctagaaaat | gagatggggg | tgcagagagc | ttcctcagtg | acctgcccag | 2700 |
| | | ggtcacatca | gaaatgtcag | agctagaact | tgaactcaga | ttactaatct | taaattccat | 2760 |
| | | gccttggggg | catgcaagta | cgatatacag | aaggagtgaa | ctcattaggg | cagatgacca | 2820 |
| | | atgagtttag | gaaagaagag | tccagggcag | ggtacatcta | caccacccgc | ccagccctgg | 2880 |
| | | gtgagtccag | cccacgttcac | ctcattatag | ttgcctctct | ccagtcctac | cttgacggga | 2940 |
| | | agcacaagca | gaaactggga | caggagcccc | aggagaccaa | atcttcatgg | tccctctggg | 3000 |
| | | aggatgggtg | gggagagctg | tggcagaggc | ctcaggaggg | gccctgctgc | tcagtggtga | 3060 |
| | | cagataggggg | tgagaaagca | gacagagtca | ttccgtcagc | attctgggtc | tgtttggtac | 3120 |
| | | ttcttctcac | gctaaggtgg | cggtgtgata | tgcacaatgg | ctaaaaagca | aggggggaga | 3180 |
| | | gaaagaaaca | aggacagaga | cagaggccaa | gtcaaccaga | ccaattccca | gaggaagcaa | 3240 |
| | | agaaaccatt | acagagacta | caaggggggaa | gggaaggaga | atgaattag | cttcccctgt | 3300 |
| | | aaaccttaga | acccagctgt | tgccagggca | acggggcaat | acctgtctct | tcagaggaga | 3360 |
| | | tgaagttgcc | agggtaacta | catcctgtct | ttctcaagga | ccatcccaga | atgtggcacc | 3420 |
| | | cactagccgt | taccatagca | actgcctctt | tgccccactt | aatcccatcc | cgtctgttaa | 3480 |
| | | aagggcccta | tagttggagg | tgggggaggt | aggaagagcg | atgatcactt | gtggactaag | 3540 |
| | | tttgttcaca | tccccttctc | caacccctc | agtacatcac | cctgggagaa | caaggtccac | 3600 |
| | | ttgcttctgg | gcccacacag | tcctgcagta | ttgtgtatat | aaggccaggg | caacggaggga | 3660 |
| | | gcaggttttg | aagtgaaagg | caggcaggtg | ttggggaggc | agttaccggg | gcaacggaaa | 3720 |
| | | cagggcgttt | cggaggtggt | tgccatgggg | acctggatgc | tgacgaaggc | tcgcgaggct | 3780 |
| | | gtgagcagcc | acagtgccct | gctcagaagc | cccaagctcg | tcaatcaagc | tggttctcca | 3840 |
| | | tttgcactca | ggagcacggg | caggcgagtg | gcccctagtt | ctgggggcag | cggggggatcc | 3900 |
| | | ggcgagatct | ggaaactgtt | cgaagacgcg | ctgcagaagt | ttgagcacga | actgaaccag | 3960 |
| | | ttcgaggatc | gtgtgcaact | gggtggcagc | ggcaagggca | gcggtggcga | aatcaaacaa | 4020 |
| | | cgttgcgcgc | gtgatctgcg | taagtttgag | gaagcgctga | aacgtttcga | ggatctgaag | 4080 |
| | | cagaaaggtg | gcagcggcga | gatttggaaa | ctgtttgaag | acgcgctgca | aaagcacgag | 4140 |
| | | gaagcgctga | accagttcga | agatctgaaa | cagctgggtg | gcagcggtaa | aggcagcggt | 4200 |
| | | ggcgagatta | gcagagcca | cgaagacgcg | ctgcgtaaac | atgaggaagc | gctgaagcgc | 4260 |
| | | tttgaggatc | tgaagcaaaa | atgaaccggt | agtagcagtg | agcaagggcg | aggagctgtt | 4320 |
| | | caccggggtg | gtgcccatcc | tggtcgagct | ggacggcgac | gtaaacggcc | acaagttcag | 4380 |
| | | cgtgtccggc | gagggcgagg | gcgatgccac | ctacggcaag | ctgaccctga | agttcatttg | 4440 |
| | | caccaccggc | aagctgcccg | tgccctggcc | caccctcgtg | accaccctga | cctacggcgt | 4500 |
| | | gcagtgcttc | agccgctacc | ccgaccacat | gaagcagcac | gacttcttca | agtccgccat | 4560 |
| | | gcccgaaggc | tacgtccagg | agcgcaccat | cttcttcaag | gacgacggca | actacaagac | 4620 |
| | | ccgcgccgag | gtgaagttcg | agggcgacac | cctggtgaac | cgcatcgagc | tgaagggcat | 4680 |
| | | cgacttcaag | gaggacggca | acatcctggg | gcacaagctg | gagtacaact | acaacagcca | 4740 |
| | | caacgtctat | atcatgcccg | acaagcagaa | gaacggcatc | aaggtgaact | tcaagatccg | 4800 |
| | | ccacaacatc | gaggacggca | gcgtgcagct | cgccgaccac | taccagcaga | acacccccat | 4860 |
| | | cggcgacggc | cccgtgctgc | tgcccgacaa | ccactacctg | agcacccagt | ccgccctgtc | 4920 |
| | | caaagacccc | aacgagaagc | gcgatcacat | ggtcctgctg | gagttcgtga | ccgccgccgg | 4980 |
| | | gatcactctc | ggcatgacg | agctgtacaa | gtaagaattc | gatatcaagc | ttatcgataa | 5040 |
| | | tcaacctctg | gattacaaaa | tttgtgaaag | attgactggt | attcttaact | atgttgctcc | 5100 |
| | | ttttacgcta | tgtggatacg | ctgctttaat | gcctttgtat | catgctattg | cttcccgtat | 5160 |
| | | ggctttcatt | ttctcctcct | tgtataaatc | ctggttgctg | tctctttatg | aggagttgtg | 5220 |
| | | gcccgttgtc | aggcaacgtg | gcgtggtgtg | cactgtgttt | gctgacgcaa | cccccactgg | 5280 |
| | | ttggggcatt | gccaccacct | gtcagctcct | ttccgggact | ttcgctttcc | cctccctat | 5340 |
| | | tgccacgcg | gaactcatcg | ccgcctgcct | tgcccgctgc | tggacagggg | ctcggctgtt | 5400 |
| | | gggcactgac | aattccgtgg | tgttgtcggg | gaaatcatcg | tcctttcctt | ggctgctcgc | 5460 |

TABLE 4-continued

List of Sequences

| Seq ID No | Name | Sequence | |
|---|---|---|---|
| | | ctgtgttgcc acctggattc tgcgcgggac gtccttctgc tacgtccctt cggccctcaa | 5520 |
| | | tccagcggac cttccttccc gcggcctgct gccggctctg cggcctcttc cgcgtcttcg | 5580 |
| | | ccttcgccct cagacgagtc ggatctccct ttgggccgcc tccccgcatc gataccgtcg | 5640 |
| | | acctcgagac ctagaaaaac atggagcaat cacaagtagc aatacagcag ctaccaatgc | 5700 |
| | | tgattgtgcc tggctagaag cacaagagga ggaggaggtg ggttttccag tcacacctca | 5760 |
| | | ggtaccttta agaccaatga cttacaaggc agctgtagat cttagccact ttttaaaaga | 5820 |
| | | aaagggggga ctggaagggc taattcactc ccaacgaaga caagatatcc ttgatctgtg | 5880 |
| | | gatctaccac acacaaggct acttccctga ttggcagaac tacacaccag ggccaggat | 5940 |
| | | cagatatcca ctgacctttg gatggtgcta caagctagta ccagttgagc aagagaaggt | 6000 |
| | | agaagaagcc aatgaaggag agaacacccg cttgttacac cctgtgagcc tgcatgggat | 6060 |
| | | ggatgaccgg gagagagaa tattagagtg gaggtttgac agccgcctag catttcatca | 6120 |
| | | catggcccga gagctgcatc cggactgtac tgggtctctc tggttagacc agatctgagc | 6180 |
| | | ctgggagctc tctggctaac tagggaaccc actgcttaag cctcaataaa gcttgccttg | 6240 |
| | | agtgcttcaa gtagtgtgtg cccgtctgtt gtgtgactct ggtaactaga gatccctcag | 6300 |
| | | acccttttag tcagtgtgga aaatctctag cagggcccgt ttaaacccgc tgatcagcct | 6360 |
| | | cgactgtgcc ttctagttgc cagccatctg ttgtttgccc ctcccccgtg ccttccttga | 6420 |
| | | ccctggaagg tgccactccc actgtccttt cctaataaaa tgaggaaatt gcatcgcatt | 6480 |
| | | gtctgagtag tgtgcattct attctggggg gtggggtggg caggacagc aagggggagg | 6540 |
| | | attgggaaga caatagcagg catgctgggg atgcggtggg ctctatggct tctgaggcgg | 6600 |
| | | aaagaaccag ctggggctct aggggggtatc cccacgcgcg ctgtagcggc gcattaagcg | 6660 |
| | | cggcgggtgt ggtggttacg cgcagcgtga ccgctacact tgccagcgcc ctagcgcccg | 6720 |
| | | ctcctttcgc tttcttccct tcctttctcg ccacgttcgc cggctttccc cgtcaagctc | 6780 |
| | | taaatcgggg gctcccttta gggttccgat ttagtgcttt acggcacctc gaccccaaaa | 6840 |
| | | aacttgatta gggtgatggt tcacgtagtg ggccatcgcc ctgatagacg gtttttcgcc | 6900 |
| | | ctttgacgtt ggagtccacg ttctttaata gtggactctt gttccaaact ggaacaacac | 6960 |
| | | tcaaccctat ctcggtctat tcttttgatt tataagggat tttgccgatt tcggcctatt | 7020 |
| | | ggttaaaaaa tgagctgatt taacaaaaat ttaacgcgaa ttaattctgt ggaatgtgtg | 7080 |
| | | tcagttaggg tgtggaaagt ccccaggctc ccagcaggc agaagtatgc aaagcatgca | 7140 |
| | | tctcaattag tcagcaacca ggtgtggaaa gtccccaggc tccccagcag gcagaagtat | 7200 |
| | | gcaaagcatg catctcaatt agtcagcaac catagtcccg ccctaactc cgcccatccc | 7260 |
| | | gcccctaact ccgcccagtt ccgcccattc tccgcccat ggctgactaa ttttttttat | 7320 |
| | | ttatgcagag gccgaggccg cctctgcctc tgagctattc cagaagtagt gaggaggctt | 7380 |
| | | ttttggaggc ctaggctttt gcaaaaagct cccgggagct gtatatcca ttttcggatc | 7440 |
| | | tgatcagcac gtgttgacaa ttaatcatcg gcatagtata tcggcatagt ataatacgac | 7500 |
| | | aaggtgagga actaaaccat ggccaagttg accagtgccg ttccggtgct caccgcgcgc | 7560 |
| | | gacgtcgccg gagcggtcga gttctggacc gaccggctcg ggttctcccg ggacttcgtg | 7620 |
| | | gaggacgact tcgccggtgt ggtccgggac gacgtgaccc tgttcatcag cgccggtccag | 7680 |
| | | gaccaggtgg tgccggacaa caccctggcc tgggtgtggg tgcgcggcct ggacgagctg | 7740 |
| | | tacgccgagt ggtcggaggt cgtgtccacg aacttccggg acgcctccgg gccggccatg | 7800 |
| | | accgagatcg gcgagcagcc gtgggggcgg gagttcgccc tgcgcgaccc ggccggcaac | 7860 |
| | | tgcgtgcact tcgtggccga ggagcaggac tgacacgtgc tacgagattt cgattccacc | 7920 |
| | | gccgccttct atgaaaggtt gggcttcgga atcgttttcc gggacgccgg ctggatgatc | 7980 |
| | | ctccagcgcg gggatctcat gctggagttc ttcgcccacc ccaacttgtt tattgcagct | 8040 |
| | | tataatggtt acaaataaag caatagcatc acaaatttca caaataaagc attttttca | 8100 |
| | | ctgcattcta gttgtggttt gtccaaactc atcaatgtat cttatcatgt ctgtataccg | 8160 |
| | | tcgacctcta gctagagctt ggcgtaatca tggtcatagc tgtttcctgt gtgaaattgt | 8220 |
| | | tatccgctca caattccaca acatacga gccggaagca taaagtgtaa agcctggggt | 8280 |
| | | gcctaatgag tgagctaact cacattaatt gcgttgcgct cactgcccgc tttccagtcg | 8340 |
| | | ggaaacctgt cgtgccagct gcattaatga atcggccaac gcgcggggag aggcggtttg | 8400 |
| | | cgtattgggc gctcttccgc ttcctcgctc actgactcgc tgcgctcggt cgttcggctg | 8460 |
| | | cggcgagcgg tatcagctca ctcaaaggcg gtaatacggt tatccacaga atcaggggat | 8520 |
| | | aacgcaggaa agaacatgtg agcaaaaggc cagcaaaagg ccaggaaccg taaaaaggcc | 8580 |
| | | gcgttgctgg cgtttttcca taggctccgc ccccctgacg agcatcacaa aaatcgacgc | 8640 |
| | | tcaagtcaga ggtggcgaaa cccgacagga ctataaagat accaggcgtt tcccctgga | 8700 |
| | | agctccctcg tgcgctctcc tgttccgacc ctgccgctta ccggatacct gtccgccttt | 8760 |
| | | ctcccttcgg gaagcgtggc gctttctcat agctcacgct gtaggtatct cagttcggtg | 8820 |
| | | taggtcgttc gctccaagct gggctgtgtg cacgaacccc ccgttcagcc cgaccgctgc | 8880 |
| | | gccttatccg gtaactatcg tcttgagtcc aacccggtaa gacacgactt atcgccactg | 8940 |
| | | gcagcagcca ctggtaacag gattagcaga gcgaggtatg taggcggtgc tacagagttc | 9000 |
| | | ttgaagtggt ggcctaacta cggctacact agaagaacag tatttggtat ctgcgctctg | 9060 |
| | | ctgaagccag ttaccttcgg aaaaagagtt ggtagctctt gatccggcaa acaaaccacc | 9120 |
| | | gctggtagcg gtggtttttt tgtttgcaag cagcagatta cgcgcagaaa aaaaggatct | 9180 |
| | | caagaagatc ctttgatctt ttctacgggg tctgacgctc agtggaacga aaactcacgt | 9240 |
| | | taagggattt tggtcatgag attatcaaaa aggatcttca cctagatcct tttaaattaa | 9300 |
| | | aaatgaagtt ttaaatcaat ctaaagtata tatgagtaaa cttggtctga cagttaccaa | 9360 |
| | | tgcttaatca gtgaggcacc tatctcagcg atctgtctat ttcgttcatc catagttgcc | 9420 |
| | | tgactccccg tcgtgtagat aactacgata cgggagggct taccatctgg ccccagtgct | 9480 |
| | | gcaatgatac cgcgagaccc acgctcaccg gctccagatt tatcagcaat aaaccagcca | 9540 |
| | | gccggaaggg ccgagcgcag aagtggtcct gcaactttat ccgcctccat ccagtctatt | 9600 |
| | | aattgttgcc gggaagctag agtaagtagt tcgccagtta atagtttgcg caacgttgtt | 9660 |
| | | gccattgcta caggcatcgt ggtgtcacgc tcgtcgtttg gtatggcttc attcagctcc | 9720 |
| | | ggttcccaac gatcaaggcg agttacatga tcccccatgt tgtgcaaaaa agcggttagc | 9780 |
| | | tccttcggtc ctccgatcgt tgtcagaagt aagttggccg cagtgttatc actcatggtt | 9840 |
| | | atggcagcac tgcataattc tcttactgtc atgccatccg taagatgctt ttctgtgact | 9900 |

TABLE 4-continued

List of Sequences

| Seq ID No | Name | Sequence | |
|---|---|---|---|
| | | ggtgagtact caaccaagtc attctgagaa tagtgtatgc ggcgaccgag ttgctcttgc | 9960 |
| | | ccggcgtcaa tacgggataa taccgcgcca catagcagaa ctttaaaagt gctcatcatt | 10020 |
| | | ggaaaacgtt cttcggggcg aaaactctca aggatcttac cgctgttgag atccagttcg | 10080 |
| | | atgtaaccca ctcgtgcacc caactgatct tcagcatctt ttactttcac cagcgtttct | 10140 |
| | | gggtgagcaa aaacaggaag gcaaaatgcc gcaaaaaagg gaataagggc gacacggaaa | 10200 |
| | | tgttgaatac tcatactctt cctttttcaa tattattgaa gcatttatca gggttattgt | 10260 |
| | | ctcatgagcg gatacatatt tgaatgtatt tagaaaaata aacaaataggg gttccgcgc | 10320 |
| | | acatttcccc gaaaagtgcc acctgac | 10347 |
| 97 | C41 Stab Map CARD | EIWKLFEDAL QKFEHELNQF EDRVQLGGSG KGSGGEIKQR CARDLRKFEE ALKRFEDLKQ | 60 |
| | | KGGSGEIWKL FEDALQKHEE ALNQFEDLKQ LGGSGKGSGG EIKQSHEDAL RKHEEALKRF | 120 |
| | | EDLKQK | 126 |
| 98 | C41 Py Stab (EC) | ttctcatgtt tgacagctta tcatcgataa gctttaatgc ggtagtttat cacagttaaa | 60 |
| | | ttgctaacgc agtcaggcac cgtgtatgaa atctaacaat gcgctcatcg tcatcctcgg | 120 |
| | | caccgtcacc ctggatgctg taggcatagg cttggttatg ccggtactgc cgggcctctt | 180 |
| | | gcgggatatc cggatatagt tcctcctttc agcaaaaaac ccctcaagac ccgtttagag | 240 |
| | | gccccaaggg gttatgctag ttattgctca gcggtggcag cagccaactc agcttccttt | 300 |
| | | cgggctttgt tagcagccgg atcctcgaga ccggttcatt tttgcttcag atcctcaaag | 360 |
| | | cgcttcagcg cttcctcatg tttacgcagc gcgtcttcgc tacgctgctt aatctcgcca | 420 |
| | | ccgctgcctt taccgctgcc acccagctgt tgtgatcttc gaactggttc agcgcttcc | 480 |
| | | tcgtgctttt gcagcgcgtc ttcaaacagt ttccaaatct cgccgctgcc acctttctgc | 540 |
| | | ttcagatcct cgaaacgttt cagcgcttcc tcaaacttac gcaggtcacg cgctgcacagt | 600 |
| | | tgtttgattt cgccaccgct gcccttgccg ctgccaccca gttgcacacg atcctcgaac | 660 |
| | | tggttcaggt cttcctcaaa cttctgcagc gcgtcttcga acagtttcca gatctcgccg | 720 |
| | | gatccctgaa aatacaggtt ttcaccatcg cctccgtggt gatgatggtg atgcccacct | 780 |
| | | ttacccatat gaatatcgcc ttccatggta tatctccttc ttaaagttaa acaaaattat | 840 |
| | | ttctagaggg gaattgttat ccgctcacaa ttccccctata gtgagtcgta ttaatttcgc | 900 |
| | | gggatcgaga tctcgatcct ctacgccgga cgcatcgtgg ccggcatcac cggcgccaca | 960 |
| | | ggtgcggttg ctggcgccta tatcgccgac atcaccgatg ggaagatcg ggctcgccac | 1020 |
| | | ttcgggctca tgagcgcttg tttcggcgtg ggtatggtgg caggccccgt ggccgggggga | 1080 |
| | | ctgttgggcg ccatctcctt gcatgcacca ttccttgcgg cggcggtgct caacggcctc | 1140 |
| | | aacctactac tgggctgctt cctaatgcag gagtcgcata agggagagcg tcgagatccc | 1200 |
| | | ggacaccatc gaatggcgca aaacctttcg cggtatggca tgatagcgcc cggaagagag | 1260 |
| | | tcaattcagg gtggtgaatg tgaaaccagt aacgttatac gatgtcgcag agtatgccggg | 1320 |
| | | tgtctcttat cagaccgttt cccgcgtggt gaaccaggcc agccacgttt ctgcgaaaac | 1380 |
| | | gcgggaaaaa gtggaagcgg cgatgcggga gctgaattac attcccaacc gcgtggcaca | 1440 |
| | | acaactggcg ggcaaacagt cgttgctgat tggcgttgcc acctccagtc tggccctgca | 1500 |
| | | cgcgccgtcg caaattgtcg cggcgattaa atctcgcgcg atcaactgg tggagcaatt | 1560 |
| | | ggtggtgtcg atggtagaac gaagcggcgt cgaagcctgt aaagcggcgg tgcacaatct | 1620 |
| | | tctcgcgcaa cgcgtcagtg ggctgatcat taactatccg ctggatgacc aggatgccat | 1680 |
| | | tgctgtgaa gctgcctgca ctaatgttcc ggcgttattt cttgatgtct ctgaccagac | 1740 |
| | | acccatcaac agtattattt tctcccatga agacggtacg cgactgggcg tggagcatct | 1800 |
| | | ggtcgcattg ggtcaccagc aaatcgcgct gttagcgggc ccattaagtt ctgtctcggc | 1860 |
| | | gcgtctgcgt ctggctggct ggcataaata tctcactcgc aatcaaattc agccgatagc | 1920 |
| | | ggaacgggaa ggcgactgga gtgccatgtc cggttttcaa caaaccatgc aaatgctgaa | 1980 |
| | | tgagggcatc gttcccactg gcgtcgcatc cagatgcgc tgccaacgat cagatgcgc tggcgcaat | 2040 |
| | | gcgcgccatt accgagtccg ggctgcgcgt tggtgcggat atctcggtag tgggatacga | 2100 |
| | | cgataccgaa gacagctcat gttatatccc gccgttaacc accatcaaac aggattttcg | 2160 |
| | | cctgctgggg caaaccagcg tggaccgctt gctgcaactc tctcagggcc aggcggtgaa | 2220 |
| | | gggcaatcag ctgttgcccg tctcactggt gaaaagaaaa accaccctgg cgcccaatac | 2280 |
| | | gcaaaccgcc tctccccgcg cgttggccga ttcattaatg cagctggcac gacaggtttc | 2340 |
| | | ccgactggaa agcgggcagt gagcgcaacg caattaatgt aagttagctc actcattagg | 2400 |
| | | caccgggatc tcgaccgatg cccttgagag ccttcaaccc agtcagctcc ttccggtggg | 2460 |
| | | cgcggggcat gactatcgtc gccgcactta tgactgtctt ctttatcatg caactcgtag | 2520 |
| | | gacaggtgcc ggcagcgctc tgggtcattt tcggcgcgag ccgctttcgc tggagcgcga | 2580 |
| | | cgatgatcgg cctgtcgctt gcggtattcg gaatcttgca cgccctcgct caagccttcg | 2640 |
| | | tcactggtcc cgccaccaaa cgtttcggcg agaagcaggc cattatcgcc ggcatggcgg | 2700 |
| | | ccgacgcgct gggctacgtc ttgctggcgt tcgcgacgcg aggctggatg gccttcccca | 2760 |
| | | ttatgattct tctcgcttcc ggcggcatcg ggatgcccgc gttgcaggcc atgctgtcca | 2820 |
| | | ggcaggtaga tgacgaccat cagggacagc ttcaaggatc gctcgcggct cttaccagcc | 2880 |
| | | taacttcgat cactggaccg ctgatcgtca cggcgattta tgccgcctcg gcgagcacat | 2940 |
| | | ggaacgggtt ggcatggatt gtaggcgccg ccctataacct tgtctgcctc ccgcgttgc | 3000 |
| | | gtcgcggtgc atggagccgg gccacctcga cctgaatgga agccggcggc acctcgctaa | 3060 |
| | | cggattcacc actccaagaa ttggagccaa tcaattcttg cggagaactg tgaatgcgca | 3120 |
| | | aaccaaccct tggcagaaca tatccatcgc gtccgccatc tccagcagcc gcacgcggcg | 3180 |
| | | catctcgggc agcgttgggt cctggccacg ggtgcgcatg atcgtgctcc tgtcgttgag | 3240 |
| | | gacccggcta ggctggcggg gttgccttac tggttagcag aatgaatcac cgatacgcga | 3300 |
| | | gcgaacgtga agcgactgct gctgcaaaac gtctgcgacc tgagcaacaa catgaatggt | 3360 |
| | | cttcggtttc cgtgtttcgt aaagtctgga aacgcggaag tcagcgccct gcaccattat | 3420 |
| | | gttccggatc tgcatcgcag gatgctgctg gctaccctgt ggaacaccta catctgtatt | 3480 |
| | | aacgaagcgc tggcattgac cctgagtgat ttttctctgg tcccgccgca tccataccgc | 3540 |
| | | cagttgttta cccctcacaac gttccagtaa ccgggcatgt tcatcatcag taacccgtat | 3600 |

TABLE 4-continued

List of Sequences

| Seq ID No | Name | Sequence | |
|---|---|---|---|
| | | cgtgagcatc ctctctcgtt tcatcggtat cattacccc atgaacagaa atcccccta | 3660 |
| | | cacggaggca tcagtgacca aacaggaaaa aaccgccctt aacatggccc gctttatcag | 3720 |
| | | aagccagaca ttaacgcttc tggagaaact caacgagctg gacgcggatg aacaggcaga | 3780 |
| | | catctgtgaa tcgcttcacg accacgctga tgagctttac cgcagctgcc tcgcgcgttt | 3840 |
| | | cggtgatgac ggtgaaaacc tctgacacat gcagctcccg gagacggtca cagcttgtct | 3900 |
| | | gtaagcggat gccgggagca gacaagcccg tcaggcgcg tcagcgggtg ttggcgggtg | 3960 |
| | | tcggggcgca gccatgaccc agtcacgtag cgatagcgga gtgtatactg gcttaactat | 4020 |
| | | gcggcatcag agcagattgt actgagagtg caccatatat gcggtgtgaa ataccgcaca | 4080 |
| | | gatgcgtaag gagaaaatac cgcatcaggc gctcttccgc ttcctcgctc actgactcgc | 4140 |
| | | tgcgctcggt cgttcggctg cggcgagcgg tatcagctca ctcaaaggcg gtaatacggt | 4200 |
| | | tatccacaga atcaggggat aacgcaggaa agaacatgtg agcaaaaggc cagcaaaagg | 4260 |
| | | ccaggaaccg taaaaaggcc gcgttgctgg cgtttttcca taggctccgc cccctgacg | 4320 |
| | | agcatcacaa aaatcgacgc tcaagtcaga ggtggcgaaa cccgacagga ctataaagat | 4380 |
| | | accaggcgtt tccccctgga agctccctcg tgcgctctcc tgttccgacc ctgccgctta | 4440 |
| | | ccggatacct gtccgccttt ctcccttcgg gaagcgtggc gctttctcat agctcacgct | 4500 |
| | | gtaggtatct cagttcggtg taggtcgttc gctccaagct gggctgtgtg cacgaacccc | 4560 |
| | | ccgttcagcc cgaccgctgc gccttatccg gtaactatcg tcttgagtcc aacccggtaa | 4620 |
| | | gacacgactt atcgccactg gcagcagcca ctggtaacag gattagcaga gcgaggtatg | 4680 |
| | | taggcggtgc tacagagttc ttgaagtggt ggcctaacta cggctacact agaaggacag | 4740 |
| | | tatttggtat ctgcgctctg ctgaagccag ttaccttcgg aaaaagagtt ggtagctctt | 4800 |
| | | gatccggcaa acaaaccacc gctggtagcg gtggtttttt tgtttgcaag cagcagatta | 4860 |
| | | cgcgcagaaa aaaggatct caagaagatc ctttgatctt ttctacgggg tctgacgctc | 4920 |
| | | agtggaacga aaactcacgt taagggattt tggtcatgag attatcaaaa aggatcttca | 4980 |
| | | cctagatcct tttaaattaa aaatgaagtt ttaaatcaat ctaaagtata tatgagtaaa | 5040 |
| | | cttggtctga cagttaccaa tgcttaatca gtgaggcacc tatctcagcg atctgtctat | 5100 |
| | | ttcgttcatc catagttgcc tgactccccg tcgtgtagat aactacgata cgggagggct | 5160 |
| | | taccatctgg ccccagtgct gcaatgatac cgcgagaccc acgctcaccg gctccagatt | 5220 |
| | | tatcagcaat aaaccagcca gccggaaggg ccgagcgcag aagtggtcct gcaactttat | 5280 |
| | | ccgcctccat ccagtctatt aattgttgcc gggaagctag agtaagtagt tcgccagtta | 5340 |
| | | atagtttgcg caacgttgtt gccattgctg caggcatcgt ggtgtcacgc tcgtcgtttg | 5400 |
| | | gtatggcttc attcagctcc ggttcccaac gatcaaggcg agttacatga tcccccatgt | 5460 |
| | | tgtgcaaaaa agcggttagc tccttcggtc ctccgatcgt tgtcagaagt aagttggccg | 5520 |
| | | cagtgttatc actcatggtt atggcagcac tgcataattc tcttactgtc atgccatccg | 5580 |
| | | taagatgctt ttctgtgact ggtgagtact caaccaagtc attctgagaa tagtgtatgc | 5640 |
| | | ggcgaccgag ttgctcttgc ccggcgtcaa cacgggataa taccgcgcca catagcagaa | 5700 |
| | | ctttaaaagt gctcatcatt ggaaaacgtt cttcggggcg aaaactctca aggatcttac | 5760 |
| | | cgctgttgag atccagttcg atgtaaccca ctcgtgcacc caactgatct tcagcatctt | 5820 |
| | | ttactttcac cagcgtttct gggtgagcaa aaacaggaag gcaaaatgcc gcaaaaaagg | 5880 |
| | | gaataagggc gacacgaaa tgttaatac tcatactctt ccttttttcaa tattattgaa | 5940 |
| | | gcatttatca gggttattgt ctcatgagcg gatacatatt tgaatgtatt tagaaaaata | 6000 |
| | | aacaaatagg ggttccgcgc acatttcccc gaaaagtgcc acctgacgtc taagaaacca | 6060 |
| | | ttattatcat gacattaacc tataaaaata ggcgtatcac gaggcccttt cgtcttcaag | 6120 |
| | | aa | 6122 |
| 99 | C41 Py Stab (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg ggccagatat acgcgttgac | 240 |
| | | attgattatt gactagttat taatagtaat caattacgg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg cccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggc actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |

TABLE 4-continued

List of Sequences

| Seq ID No | Name | Sequence | |
|---|---|---|---|
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catcccacat tttaaaagaa aaggggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggaa gggaaggaga gatgaattag cttccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagagcg atgatcactt gtggactaag | 3540 |
| | | tttgttcaca tcccccttctc caacccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gccctagtt ctggggcag cggggatcc | 3900 |
| | | ggcgagatct ggaaactgtt cgaagacgcg ctgacagtt ttgaggaaga cctgaaccag | 3960 |
| | | ttcgaggatc gtgtgcaact gggtggcagc ggcaagggca gcggtggcga aatcaaacaa | 4020 |
| | | ctgtgcgcgc gtgacctgcg taagtttgag gaagcgctga acgtttcga ggatctgaag | 4080 |
| | | cagaaaggtg gcagcggcga gatttggaaa ctgtttgaag acgcgctgca aaagcacgag | 4140 |
| | | gaagcgctga accagttcga agatcacaaa cagctgggtg gcagcggtaa aggcagcggt | 4200 |
| | | ggcgagatta gcagcgtag cgaagacgcg ctgcgtaaac atgaggaagc gctgaagcgc | 4260 |
| | | tttgaggatc tgaagcaaaa atgaaccggt agtagcagtg agcaagggcg aggagctgtt | 4320 |
| | | caccggggtg gtgcccatcc tggtcgagct ggacggcgac gtaaacggcc acaagttcag | 4380 |
| | | cgtgtccggc gagggcgagg gcgatgccac ctacggcaag ctgaccctga agttcatttg | 4440 |
| | | caccaccggc aagctgcccg tgcctggcc caccctcgtg accacctga cctacggcgt | 4500 |
| | | gcagtgcttc agccgctacc ccgaccacat gaagcagcac gacttcttca gtccgccat | 4560 |
| | | gcccgaaggc tacgtccagg agcgcaccat cttcttcaag gacgacggca actacaagac | 4620 |
| | | ccgcgccgag gtgaagttcg agggcgacac cctggtgaac cgcatcgagc tgaagggcat | 4680 |
| | | cgacttcaag gaggacggca acatcctggg gcacaagctg gagtacaact acaacagcca | 4740 |
| | | caacgtctat atcatggccg acaagcagaa gaacggcatc aaggtgaact tcaagatccg | 4800 |
| | | ccacaacatc gaggacggca gcgtgcagct cgccgaccac taccagcaga cacccccat | 4860 |
| | | cggcgacggc cccgtgctgc tgcccgacaa ccactacctg agcacccagt ccgccctgag | 4920 |
| | | caaagacccc aacgagaagc gcgatcacat ggtcctgctg gagttcgtga ccgccgcggg | 4980 |
| | | gatcactctc ggcatgacg agctgtacaa gtaagaattc gatatcaagc ttatcgataa | 5040 |
| | | tcaacctctg gattacaaaa tttgtgaaag attgactggt attcttaact atgttgctcc | 5100 |
| | | ttttacgcta tgtggatacg ctgctttaat gcctttgtat catgctattg cttcccgtat | 5160 |
| | | ggctttcatt ttctcctcct tgtataaatc atggttgctg tctttttatg aggagttgtg | 5220 |
| | | gcccgttgtc aggcaacgtg gcgtggtgtg cactgtgttt gctgacgcaa cccccactgg | 5280 |
| | | ttggggcatt gccaccacct gtcagctcct ttccgggact ttcgctttcc cctccctat | 5340 |
| | | tgccacgcg gaactcatcg ccgcctgcct tgcccgctgc tggacagggg ctcggctgtt | 5400 |
| | | gggcactgac aattccgtgg tgttgtcggg gaaatcatcg tcctttcctt ggctgctcgc | 5460 |
| | | ctgtgttgcc acctggattc tgcgcgggac gtccttctgc tacgtccctt cggccctcaa | 5520 |
| | | tccagcggac cttccttccc gcggcctgct gccggctctg cggcctcttc cgcgtcttcg | 5580 |
| | | ccttcgccct cagacgagtc ggatctccct ttgggccgcc tccccgcatc gataccgtcg | 5640 |
| | | acctcgagac ctagaaaaac atggagcaat cacaagtagc aataacagca | 5700 |
| | | tgattgtgcc tggctagaag cacaagagga ggaggaggtg gttttccag tcacacctca | 5760 |
| | | ggtacctta agaccaatga cttacaaggc agctgtagat cttagccact ttttaaaga | 5820 |
| | | aaaggggga ctggaagggc taattcactc ccaacgaaga caagatatcc ttgatctgtg | 5880 |
| | | gatctaccac acacaaggct acttccctga ttggcagaac tacacaccag ggccagggat | 5940 |
| | | cagatatcca ctgacctttg gatggtgcta caagctagta ccagttgagc agagaaggt | 6000 |
| | | agaagaagcc aatgaaggag agaacacccg cttgttacac cctgtgagcc tgcatggat | 6060 |
| | | ggatgacccg gagagagaag tattagagtg gaggtttgac agccgcctag catttcatca | 6120 |
| | | catggcccga gagctgcatc cggactgtac tgggtctctc tggttagacc agatctgagc | 6180 |
| | | ctgggagctc tctggctaac tagggaaccc actgcttaag cctcaataaa gcttgccttg | 6240 |

TABLE 4-continued

List of Sequences

| Seq ID No | Name | Sequence | |
|---|---|---|---|
| | | agtgcttcaa gtagtgtgtg cccgtctgtt gtgtgactct ggtaactaga gatccctcag | 6300 |
| | | acccttttag tcagtgtgga aaatctctag cagggcccgt ttaaacccgc tgatcagcct | 6360 |
| | | cgactgtgcc ttctagttgc cagccatctg ttgtttgccc ctcccccgtg ccttccttga | 6420 |
| | | ccctggaagg tgccactccc actgtccttt cctaataaaa tgaggaaatt gcatcgcatt | 6480 |
| | | gtctgagtag gtgtcattct attctggggg gtggggtggg caggacagc aaggggagg | 6540 |
| | | attgggaaga caatagcagg catgctgggg atgcggtggg ctctatggct tctgaggcgg | 6600 |
| | | aaagaaccag ctgggggctct aggggggtatc cccacgcgcc ctgtagcggc gcattaagcg | 6660 |
| | | cggcgggtgt ggtggttacg cgcagcgtga ccgctacact tgccagcgcc ctagcgcccg | 6720 |
| | | ctcctttcgc ttttcttccct tcctttctcg ccacgttcgc cggctttccc cgtcaagctc | 6780 |
| | | taaatcgggg gctccctta gggttccgat ttagtgcttt acggcacctc gaccccaaaa | 6840 |
| | | aacttgatta gggtgatggt tcacgtagtg ggccatcgcc ctgatagacg gtttttcgcc | 6900 |
| | | ctttgacgtt ggagtccacg ttctttaata gtggactctt gttccaaact ggaacaacac | 6960 |
| | | tcaaccctat ctcggtctat tcttttgatt tataagggat tttgccgatt tcggcctatt | 7020 |
| | | ggttaaaaaa tgagctgatt taacaaaaat ttaacgcgaa ttaattctgt ggaatgtgtg | 7080 |
| | | tcagttaggg tgtggaaagt ccccaggctc cccagcagcc agaagtatgc aaagcatgca | 7140 |
| | | tctcaattag tcagcaacca ggtgtggaaa gtccccaggc tccccagcag gcagaagtat | 7200 |
| | | gcaaagcatg catctcaatt agtcagcaac catagtcccg cccctaactc cgcccatccc | 7260 |
| | | gccccctaact ccgcccagtt ccgcccattc tccgccccat ggctgactaa ttttttttat | 7320 |
| | | ttatgcagag gccgaggccg cctctgcctc tgagctattc cagaagtagt gaggaggctt | 7380 |
| | | ttttggaggc ctaggctttt gcaaaaagct cccgggagct tgtatatcca ttttcggatc | 7440 |
| | | tgatcagcac gtgttgacaa ttaatcatcg gcatagtata tcggcatagt ataatacgac | 7500 |
| | | aaggtgagga actaaaccat ggccaagttg accagtgccg ttccggtgct caccgcgcgc | 7560 |
| | | gacgtcgcg gagcggtcga gttctggacc gaccggctcg ggttctcccg ggacttcgtg | 7620 |
| | | gaggacgact tcgccggtgt ggtccgggac gacgtgaccc tgttcatcag cgcggtccag | 7680 |
| | | gaccaggtgg tgccggacaa caccctggcc tgggtgtggg tgcgcggcct ggacgagctg | 7740 |
| | | tacgccgagt ggtcggaggt cgtgtccacg aacttccggg acgcctccgg gccggccatg | 7800 |
| | | accgagatcg gcgagcagcc gtggggcgg gagttcgccc tgcgcgaccc ggccggcaac | 7860 |
| | | tgcgtgcact tcgtggccga ggagcaggac tgacacgtgc tacgagattt cgattccacc | 7920 |
| | | gccgccttct atgaaaggtt gggcttcgga atcgttttcc gggacgccgg ctggatgatc | 7980 |
| | | ctccagcgcg ggatctccat gctggagttc ttcgcccacc ccaacttgtt tattgcagct | 8040 |
| | | tataatggtt acaaataaag caatagcatc acaaatttca caaataaagc atttttttca | 8100 |
| | | ctgcattcta gttgtggttt gtccaaactc atcaatgtat cttatcatgt ctgtataccg | 8160 |
| | | tcgacctcta gctagagctt ggcgtaatca tggtcatagc tgtttcctgt gtgaaattgt | 8220 |
| | | tatccgctca caattccaca acatacga gccggaagca taaagtgtaa agcctggggt | 8280 |
| | | gcctaatgag tgagctaact cacattaatt gcgttgcgct cactgcccgc tttccagtcg | 8340 |
| | | ggaaacctgt cgtgccagct gcattaatga atcggccaac gcgcggggag aggcggtttg | 8400 |
| | | cgtattgggc gctcttccgc ttcctcgctc actgactcgc tgcgctcggt cgttcggctg | 8460 |
| | | cggcgagcgg tatcagctca ctcaaaggcg gtaatacggt tatccacaga atcaggggat | 8520 |
| | | aacgcaggaa agaacatgtg agcaaaaggc cagcaaaagg ccaggaaccg taaaaaggcc | 8580 |
| | | gcgttgctgg cgtttttcca taggctccgc cccctgacg agcatcacaa aaatcgacgc | 8640 |
| | | tcaagtcaga ggtggcgaaa cccgacagga ctataaagat accaggcgtt tccccctgga | 8700 |
| | | agctccctcg tgcgctctcc tgttccgacc ctgccgctta ccggatacct gtccgccttt | 8760 |
| | | ctcccttcgg gaagcgtggc gctttctcat agctcacgct gtaggtatct cagttcggtg | 8820 |
| | | taggtcgttc gctccaagct gggctgtgtg cacgaacccc ccgttcagcc cgaccgctgc | 8880 |
| | | gccttatccg gtaactatcg tcttgagtcc aacccggtaa gacacgactt atcgccactg | 8940 |
| | | gcagcagcca ctggtaacag gattagcaga gcgaggtatg taggcggtgc tacagagttc | 9000 |
| | | ttgaagtggt ggcctaacta cggctacact agaagaacag tatttggtat ctgcgctctg | 9060 |
| | | ctgaagccag ttaccttcgg aaaaagagtt ggtagctctt gatccggcaa acaaaccacc | 9120 |
| | | gctggtagcg gtggtttttt tgtttgcaag cagcagatta cgcgcagaaa aaaaggatct | 9180 |
| | | caagaagatc ctttgatctt ttctacgggg tctgacgctc agtggaacga aaactcacgt | 9240 |
| | | taagggattt tggtcatgag attatcaaaa aggatcttca cctagatcct ttttaaattaa | 9300 |
| | | aaatgaagtt ttaaatcaat ctaaagtata tatgagtaaa cttggtctga cagttaccaa | 9360 |
| | | tgcttaatca gtgaggcacc tatctcagcg atctgtctat ttcgttcatc catagttgcc | 9420 |
| | | tgactccccg tcgtgtagat aactacgata cgggagggct taccatctgg ccccagtgct | 9480 |
| | | gcaatgatac cgcgagaccc acgctcaccg gctccagatt tatcagcaat aaaccagcca | 9540 |
| | | gccggaaggg ccgagcgcag aagtggtcct gcaactttat ccgcctccat ccagtctatt | 9600 |
| | | aattgttgcc gggaagctag agtaagtagt tcgccagtta atagtttgcg caacgttgtt | 9660 |
| | | gccattgcta caggcatcgt ggtgtcacgc tcgtcgtttg gtatggcttc attcagctcc | 9720 |
| | | ggttcccaac gatcaaggcg agttacatga tcccccatgt tgtgcaaaaa agcggttagc | 9780 |
| | | tccttcggtc ctccgatcgt tgtcagaagt aagttggccg cagtgttatc actcatggtt | 9840 |
| | | atggcagcac tgcataattc tcttactgtc atgccatccg taagatgctt ttctgtgact | 9900 |
| | | ggtgagtact caaccaagtc attctgagaa tagtgtatgc ggcgaccgag ttgctcttgc | 9960 |
| | | ccggcgtcaa tacgggataa taccgcgcca catagcagaa ctttaaaagt gctcatcatt | 10020 |
| | | ggaaaacgtt cttcggggcg aaaactctca aggatcttac cgctgttgag atccagttcg | 10080 |
| | | atgtaaccca ctcgtgcacc caactgatct tcagcatctt ttactttcac cagcgtttct | 10140 |
| | | gggtgagcaa aaacaggaag gcaaaatgcc gcaaaaaagg gaataagggc gacacggaaa | 10200 |
| | | tgttgaatac tcatactctt cctttttcaa tattattgaa gcatttatca gggttattgt | 10260 |
| | | ctcatgagcg gatacatatt tgaatgtatt tagaaaaata aacaaatagg ggttccgcgc | 10320 |
| | | acatttcccc gaaaagtgcc acctgac | 10347 |
| 100 | C41 Py Stab | EIWKLFEDAL QKFEEDLNQF EDRVQLGGSG KGSGGEIKQL CARDLRKFEE ALKRFEDLKQ | 60 |
| | | KGGSGEIWKL FEDALQKHEE ALNQFEDHKQ LGGSGKGSGG EIKQRSEDAL RKHEEALKRF | 120 |
| | | EDLKQK | 126 |

TABLE 4-continued

List of Sequences

| Seq ID No | Name | Sequence | | | | | |
|---|---|---|---|---|---|---|---|
| 101 | BT6 CysAla (EC) | cccgtagaaa | agatcaaagg | atcttcttga | gatccttttt | ttctgcgcgt | aatctgctgc | 60 |
| | | ttgcaaacaa | aaaaaccacc | gctaccagcg | gtggtttgtt | tgccggatca | agagctacca | 120 |
| | | actcttttc | cgaaggtaac | tggcttcagc | agagcgcaga | taccaaatac | tgttcttcta | 180 |
| | | gtgtagccgt | agttagccca | ccacttcaag | aactctgtag | caccgcctac | atacctcgct | 240 |
| | | ctgctaatcc | tgttaccagt | ggctgctgcc | agtgcgata | agtcgtgtct | taccgggttg | 300 |
| | | gactcaagac | gatagttacc | ggataaggcg | cagcggtcgg | gctgaacggg | gggttcgtgc | 360 |
| | | acacagccca | gcttggagcg | aacgacctac | accgaactga | gatacctaca | gcgtgagcta | 420 |
| | | tgagaaagcg | ccacgcttcc | cgaagggaga | aaggcgaaca | ggtatccggt | aagcggcagg | 480 |
| | | gtcggaacag | gagagcgcac | gagggagctt | ccaggggaa | acgcctggta | tctttatagt | 540 |
| | | cctgtcgggt | ttcgccacct | ctgacttgag | cgtcgatttt | tgtgatgctc | gtcaggggg | 600 |
| | | cggagcctat | ggaaaaacgc | cagcaacgcg | gccttttac | ggttcctggc | cttttgctgg | 660 |
| | | cctttgctc | acatgttctt | tcctgcgtta | tcccctgatt | ctgtggataa | ccgtattacc | 720 |
| | | gcctttgagt | gagctgatac | cgctcgccgc | agccgaacga | ccgagcgcag | cgagtcagtg | 780 |
| | | agcgaggaag | cggaaggcga | gagtagggaa | ctgccaggca | tcaaactaag | cagaaggccc | 840 |
| | | ctgacggatg | gcctttttgc | gtttctacaa | actctttctg | tgttgtaaaa | cgacggccag | 900 |
| | | tcttaagctc | gggccccctg | ggcggttctg | ataacgagta | atcgttaatc | cgcaaataac | 960 |
| | | gtaaaaaccc | gcttcggcgg | gtttttttat | gggggagtt | tagggaaaga | gcatttgtca | 1020 |
| | | gaatatttaa | gggcgcctgt | cactttgctt | gatatatgag | aattatttaa | ccttataaat | 1080 |
| | | gagaaaaaag | caacgcactt | taaataagat | acgttgcttt | ttcgattgat | gaacacctat | 1140 |
| | | aattaaacta | ttcatctatt | atttatgatt | ttttgtatat | acaatatttc | tagtttgtta | 1200 |
| | | aagagaatta | agaaaataaa | tctcgaaaat | aataaaggga | aaatcagttt | ttgatatcaa | 1260 |
| | | aattatacat | gtcaacgata | atacaaaata | taatacaaac | tataagatgt | tatcagtatt | 1320 |
| | | tattatcatt | tagaataaat | tttgtgtcgc | ccttccgcga | aattaatacg | actcactata | 1380 |
| | | ggggaattgt | gagcggataa | caattcccct | ctagaaataa | ttttgtttaa | cttttgaagg | 1440 |
| | | agatatacat | atgggcaaag | gcgccacca | ccaccaccac | cacggcggcg | acggcgagaa | 1500 |
| | | tctgtacttt | cagggcgaga | tctggaaaca | acacgaggac | gctctgcaga | agtttgaaga | 1560 |
| | | agccctgaat | cagtttgaag | atctgaaaca | actgggcggc | agcggctccg | gttcgggtgg | 1620 |
| | | tgagatctgg | aagcagcacg | aggatgcgct | gcagaagttc | gaagaggcgc | tgaaccagtt | 1680 |
| | | cgaggacctg | aagcagctgg | gtggcagcgg | ttccggcagc | ggcggtgaga | tttggaaaca | 1740 |
| | | gcacgaagat | gccctgcaga | aattcgaaga | ggcgctgaac | cagtttgagg | acttgaagca | 1800 |
| | | actgggtggt | agcggctctg | gtagcggtgg | tgagattgg | aagcaacatg | aagatgcact | 1860 |
| | | gcaaaagttc | gaagaggcgc | tgaaccaatt | tgaagatctg | aagcaattgt | aactcgagcc | 1920 |
| | | ccctagcata | acccttggg | gcctctaaac | gggtcttgag | gggttttttg | ccctgagac | 1980 |
| | | gcgtcaatcg | agttcgtacc | taagggcgac | accccctaat | tagcccgggc | gaaaggccca | 2040 |
| | | gtctttcgac | tgagcctttc | gtttatttg | atgcctggca | gttccctact | ctcgcatggg | 2100 |
| | | gagtccccac | actaccatcg | gcgctacggc | gtttcacttc | tgagttcggc | atggggtcag | 2160 |
| | | gtgggaccac | cgcgctactg | ccgccaggca | aacaagggg | gttatgagcc | atattcaggt | 2220 |
| | | ataaatgggc | tcgcgataat | gttcagaatt | ggttaattgg | ttgtaacact | gaccctatt | 2280 |
| | | tgtttatttt | tctaaataca | ttcaaatatg | tatccgctca | tgagacaata | accctgataa | 2340 |
| | | atgcttcaat | aatattgaaa | aaggaagaat | atgagtattc | aacatttccg | tgtcgccctt | 2400 |
| | | attccctttt | ttgcggcatt | ttgccttcct | gtttttgctc | acccagaaac | gctggtgaaa | 2460 |
| | | gtaaaagatg | ctgaagatca | gttgggtgca | cgagtgggtt | acatcgaact | ggatctcaac | 2520 |
| | | agcggtaaga | tccttgagag | ttttcgcccc | gaagaacgtt | ttccaatgat | gagcactttt | 2580 |
| | | aaagttctgc | tatgtggcgc | ggtattatcc | cgtattgacg | ccgggcaaga | gcaactcggt | 2640 |
| | | cgccgcatac | actattctca | gaatgacttg | gttgagtact | caccagtcac | agaaaagcat | 2700 |
| | | cttacggatg | gcatgacagt | aagagaatta | tgcagtgctg | ccataaccat | gagtgataac | 2760 |
| | | actgcggcca | acttacttct | gacaacgatc | ggaggaccga | aggagctaac | cgcttttttg | 2820 |
| | | cacaacatgg | gggatcatgt | aactcgcctt | gatcgttggg | aaccggagct | gaatgaagcc | 2880 |
| | | ataccaaacg | acgagcgtga | caccacgatg | cctgtagcga | tggcaacaac | gttgcgcaaa | 2940 |
| | | ctattaactg | gcgaactact | tactctagct | tcccggcaac | aattaataga | ctggatggag | 3000 |
| | | gcggataaag | ttgcaggacc | acttctgcgc | tcggcccttc | cggctggctg | gtttattgct | 3060 |
| | | gataaatccg | gagccgtga | gcgtggttct | cgcggtatca | tcgcagcgct | ggggccagat | 3120 |
| | | ggtaagccct | cccgtatcgt | agttatctac | acgacgggga | gtcaggcaac | tatggatgaa | 3180 |
| | | cgaaatagac | agatcgctga | gataggtgcc | tcactgatta | agcattggta | agcggcgcgc | 3240 |
| | | catcgaatgg | cgcaaaacct | ttcgcggtat | ggcatgatag | cgcccggaag | agagtcaatt | 3300 |
| | | cagggtggtg | aatatgaaac | cagtaacgtt | atacgatgtc | gcagagtatg | ccggtgtctc | 3360 |
| | | ttatcagacc | gtttcccgcg | tggtgaacca | ggccagccac | gtttctgcga | aaacgcggga | 3420 |
| | | aaaagtggaa | gcggcgatgc | ggagctgaa | ttacattccc | aaccgcgtgg | cacaacaact | 3480 |
| | | ggcgggcaaa | cagtcgttgc | tgattggcgt | tgccacctcc | agtctggccc | tgcacgcgcc | 3540 |
| | | gtcgcaaatt | gtcgcggcga | ttaaatctcg | cgccgatcaa | ctgggtgcca | gcgtggtggt | 3600 |
| | | gtcgatggta | gaacgaagcg | gcgtcgaagc | ctgtaaagcg | gcggtgcaca | atcttctcgc | 3660 |
| | | gcaacgcgtc | agtgggctga | tcattaacta | tccgctggat | gaccaggatg | ccattgctgt | 3720 |
| | | ggaagctgcc | tgcactaatg | ttccggcgtt | atttcttgat | gtctctgacc | agacacccat | 3780 |
| | | caacagtatt | attttctccc | atgaggacgg | tacgcgactg | ggcgtggagc | atctggtcgc | 3840 |
| | | attgggtcac | cagcaaatcg | cgctgttagc | gggcccatta | agttctgtct | cggcgcgtct | 3900 |
| | | gcgtctggct | ggctggcata | aatatctcac | tcgcaatcaa | attcagccga | tagcggaacg | 3960 |
| | | ggaaggcgac | tggagtgcca | tgtccggttt | tcaacaaacc | atgcaaatgc | tgaatgaggg | 4020 |
| | | catcgttccc | actgcgatgc | tggttgccaa | cgatcagatg | gcgctgggcg | caatgcgcgc | 4080 |
| | | cattaccgag | tccgggctgc | gcgttggtgc | ggatatctcg | gtagtgggat | acgacgatac | 4140 |
| | | cgaagatagc | tcatgttata | tcccgccgtt | aaccaccatc | aaacaggatt | ttcgcctgct | 4200 |

TABLE 4-continued

List of Sequences

| Seq ID No | Name | Sequence | | | | | |
|---|---|---|---|---|---|---|---|
| | | ggggcaaacc | agcgtggacc | gcttgctgca | actctctcag | ggccaggcgg | tgaagggcaa | 4260 |
| | | tcagctgttg | ccagtctcac | tggtgaaaag | aaaaaccacc | ctggcgccca | atacgcaaac | 4320 |
| | | cgcctctccc | cgcgcgttgg | ccgattcatt | aatgcagctg | gcacgacagg | tttcccgact | 4380 |
| | | ggaaagcggg | cagtgactca | tgaccaaaat | cccttaacgt | gagttacgcg | cgcgtcgttc | 4440 |
| | | cactgagcgt | cagac | | | | | 4455 |
| 102 | BT6 CysAla (FCK mam) | gtcgacggat | cgggagatct | cccgatcccc | tatggtgcac | tctcagtaca | atctgctctg | 60 |
| | | atgccgcata | gttaagccag | tatctgctcc | ctgcttgtgt | gttggaggtc | gctgagtagt | 120 |
| | | gcgcgagcaa | aatttaagct | acaacaaggc | aaggcttgac | cgacaattgc | atgaagaatc | 180 |
| | | tgcttagggt | taggcgtttt | gcgctgcttc | gcgatgtacg | ggccagatat | acgcgttgac | 240 |
| | | attgattatt | gactagttat | taatagtaat | caattacggg | gtcattagtt | catagcccat | 300 |
| | | atatggagtt | ccgcgttaca | taacttacgg | taaatggccc | gcctggctga | ccgcccaacg | 360 |
| | | accccgcc | attgacgtca | ataatgacgt | atgttcccat | agtaacgcca | atagggactt | 420 |
| | | tccattgacg | tcaatgggtg | gagtatttac | ggtaaactgc | ccacttggca | gtacatcaag | 480 |
| | | tgtatcatat | gccaagtacg | cccccattg | acgtcaatga | cggtaaatgg | cccgcctggc | 540 |
| | | attatgccca | gtacatgacc | ttatgggact | ttcctacttg | gcagtacatc | tacgtattag | 600 |
| | | tcatcgctat | taccatggtg | atgcggtttt | ggcagtacat | caatgggcgt | ggatagcggt | 660 |
| | | ttgactcacg | gggatttcca | agtctccacc | ccattgacgt | caatgggagt | ttgttttggc | 720 |
| | | accaaaatca | acgggacttt | ccaaaatgtc | gtaacaactc | cgccccattg | acgcaaatgg | 780 |
| | | gcggtaggcg | tgtacggtgg | gaggtctata | taagcagcgc | gttttgcctg | tactgggtct | 840 |
| | | ctctggttag | accagatctg | agcctgggag | ctctctggct | aactagggaa | cccactgctt | 900 |
| | | aagcctcaat | aaagcttgcc | ttgagtgctt | caagtagtgt | gtgcccgtct | gttgtgtgac | 960 |
| | | tctggtaact | agagatccct | cagacccttt | tagtcagtgt | ggaaaatctc | tagcagtggc | 1020 |
| | | gcccgaacag | ggacttgaaa | gcgaaaggga | accagagga | gctctctcga | cgcaggactc | 1080 |
| | | ggcttgctga | agcgcgcacg | gcaagaggcg | aggggcggcg | actggtgagt | acgccaaaaa | 1140 |
| | | ttttgactag | cggaggctag | aaggagagag | atgggtgcga | gagcgtcagt | attaagcggg | 1200 |
| | | ggagaattag | atcgcgatgg | gaaaaaattc | ggttaaggcc | aggggggaag | aaaaaatata | 1260 |
| | | aattaaaaca | tatagtatg | gcaagcaggg | gctagaacg | attcgcagtt | aatcctggcc | 1320 |
| | | tgttagaaac | atcagaaggc | tgtagacaaa | tactgggaca | gctacaacca | tcccttcaga | 1380 |
| | | caggatcaga | agaacttaga | tcattatata | atacagtagc | aaccctctat | tgtgtgcatc | 1440 |
| | | aaaggataga | gataaaagac | accaaggaag | ctttagacaa | gatagaggaa | gagcaaaaca | 1500 |
| | | aaagtaagac | caccgcacag | caagcggccg | ctgatcttca | gacctggagg | aggagatatg | 1560 |
| | | agggacaatt | ggagaagtga | attatataaa | tataaagtag | taaaaattga | accattagga | 1620 |
| | | gtagcaccca | ccaaggcaaa | gagaagagtg | gtgcagagag | aaaaaagagc | agtgggaata | 1680 |
| | | ggagctttgt | tccttgggtt | cttgggagca | gcaggaagca | ctatgggcgc | agcgtcaatg | 1740 |
| | | acgctgacgg | tacaggccag | acaattattg | tctggtatag | tgcagcagca | gaacaatttg | 1800 |
| | | ctgagggcta | ttgaggcgca | acagcatctg | ttgcaactca | cagtctgggg | catcaagcag | 1860 |
| | | ctccaggcaa | gaatcctggc | tgtggaaaga | tacctaaagg | atcaacagct | cctggggatt | 1920 |
| | | tggggttgct | ctggaaaact | catttgcacc | actgctgtgc | cttggaatgc | tagttggagt | 1980 |
| | | aataaatctc | tggaacagat | ttggaatcac | acgacctgga | tggagtggga | cagagaaatt | 2040 |
| | | aacaattaca | caagcttaat | acactcctta | attgaagaat | cgcaaaacca | gcaagaaaag | 2100 |
| | | aatgaacaag | aattattgga | attagataaa | tgggcaagtt | tgtggaattg | gtttaacata | 2160 |
| | | acaaattggc | tgtggtatat | aaaattattc | ataatgatag | taggaggctt | ggtaggttta | 2220 |
| | | agaatagttt | ttgctgtact | ttctatagtg | aatagagtta | ggcagggata | ttcaccatta | 2280 |
| | | tcgtttcaga | cccacctccc | aacccgagg | gacccgaca | ggcccgaagg | aatagaagaa | 2340 |
| | | gaaggtggag | agagagacag | agacagatcc | attcgattag | tgaacggatc | ggcactgcgt | 2400 |
| | | gcgccaattc | tgcagacaaa | tggcagtatt | catccacaat | tttaaaagaa | aaggggggat | 2460 |
| | | tggggggtac | agtgcagggg | aaagaatagt | agacataata | gcaacagaca | tacaaactaa | 2520 |
| | | agaattacaa | aaacaaatta | caaaaattca | aaattttcgg | gtttattaca | gggacagcag | 2580 |
| | | agatccagtt | tggttaatta | acattatggc | cttaggtcac | ttcatctcca | tggggttctt | 2640 |
| | | cttctgattt | tctagaaaat | gagatgggg | tgcagagagc | ttcctcagtg | acctgcccag | 2700 |
| | | ggtcacatca | gaaatgtcag | agctagaact | tgaactcaga | ttactaatct | taaattccat | 2760 |
| | | gccttggggg | catgcaagta | cgatatacag | aaggagtgaa | ctcattaggg | cagatgacca | 2820 |
| | | atgagtttag | gaaagaagag | tccagggcag | ggtacatcta | caccacccgc | ccagccctgg | 2880 |
| | | gtgagtccag | ccacgttcac | ctcattatag | ttgcctctct | ccagtcctac | cttgacggga | 2940 |
| | | agcacaagca | gaaactggga | caggagcccc | aggagaccaa | atcttcatgg | tccctctggg | 3000 |
| | | aggatgggtg | ggagagagctg | tggcagaggc | ctcaggagga | gcctgctgc | tcagtggtga | 3060 |
| | | cagatagggg | tgagaaagca | gacagagtca | ttccgtcagc | attctgggtc | tgtttggtac | 3120 |
| | | ttcttctcac | gctaaggtgg | cggtgtgata | tgcacaatgg | ctaaaagca | gggagagctg | 3180 |
| | | gaaagaaaca | aggacagaga | cagaggccaa | gtcaaccaga | ccaattccca | gaggaagcaa | 3240 |
| | | agaaaccatt | acagagacta | caagggggaa | gggaaggaga | gatgaattag | cttccccgat | 3300 |
| | | aaaccttaga | acccagctgt | tgccagggca | acggggcaat | acctgtctct | tcagaggaga | 3360 |
| | | tgaagttgcc | agggtaacta | catcctgtct | ttctcaagga | ccatcccaga | atgtggcacc | 3420 |
| | | cactagccgt | taccatagca | actgcctctt | tgccccactt | aatcccatcc | cgtctgttaa | 3480 |
| | | aagggcccta | tagttggagg | tgggggaggt | aggaagagcg | atgatcactt | gtggactaag | 3540 |
| | | tttgttcaca | tccccttctc | caaccccctc | agtacatcac | cctgggagaa | caaggtccac | 3600 |
| | | ttgcttctgg | gcccacacag | tcctgcagta | ttgtgtatat | aaggccaggg | caacggagga | 3660 |
| | | gcaggttttg | aagtgaaagg | caggcaggtg | ttggggaggc | agttaccggg | gcaacgggaa | 3720 |
| | | cagggcgttt | cggaggtggt | tgccatgggg | acctggctgc | tgacgaaggc | tcgcagagct | 3780 |
| | | gtgagcagcc | acagtgccct | gctcagaagc | cccaagctcg | tcaatgaagc | tggttctcca | 3840 |
| | | tttgcactca | ggagcacggg | caggcgagtg | gcccctagtt | ctggggcag | cggggatcc | 3900 |
| | | atgggcgaga | tctgaaaca | acacgaggac | gctctgcaga | agtttgaaga | agccctgaat | 3960 |
| | | cagtttgaag | atctgaaaca | actgggcggc | agcggctccg | gttcgggtgg | tgagatctgg | 4020 |
| | | aagcagcacg | aggatgcgct | gcagaagttc | gaagaggcgc | tgaaccagtt | cgaggacctg | 4080 |

TABLE 4-continued

List of Sequences

| Seq ID No | Name | Sequence | | | | |
|---|---|---|---|---|---|---|
| | | aagcagctgg | gtggcagcgg | ttccggcagc | ggcggtgaga | tttggaaaca gcacgaagat | 4140 |
| | | gccctgcaga | aattcgaaga | ggcgctgaac | cagtttgagg | acttgaagca actgggtggt | 4200 |
| | | agcggctctg | gtagcggtgg | tgagatttgg | aagcaacatg | aagatgcact gcaaaagttc | 4260 |
| | | gaagaggcgc | tgaaccaatt | tgaagatctg | aagcaattgg | cggcaccggt agtagcagtg | 4320 |
| | | agcaagggcg | aggagctgtt | caccggggtg | gtgcccatcc | tggtcgagct ggacggcgac | 4380 |
| | | gtaaacggcc | acaagttcag | cgtgtccggc | gagggcgagg | gcgatgccac ctacggcaag | 4440 |
| | | ctgaccctga | agttcatttg | caccaccggc | aagctgcccg | tgccctggcc cacccctcgtg | 4500 |
| | | accaccctga | cctacggcgt | gcagtgcttc | agccgctacc | ccgaccacat gaagcagcac | 4560 |
| | | gacttcttca | agtccgccat | gcccgaaggc | tacgtccagg | agcgcaccat cttcttcaag | 4620 |
| | | gacgacggca | actacaagac | ccgcgccgag | gtgaagttcg | agggcgacac cctggtgaac | 4680 |
| | | cgcatcgagc | tgaagggcat | cgacttcaag | gaggacggca | acatcctggg gcacaagctg | 4740 |
| | | gagtacaact | acaacagcca | caacgtctat | atcatggccg | acaagcagaa gaacggcatc | 4800 |
| | | aaggtgaact | tcaagatccg | ccacaacatc | gaggacggca | gcgtgcagct cgccgaccac | 4860 |
| | | taccagcaga | acacccccat | cggcgacggc | cccgtgctgc | tgcccgacaa ccactacctg | 4920 |
| | | agcacccagt | ccgccctgag | caaagacccc | aacgagaagc | gcgatcacat ggtcctgctg | 4980 |
| | | gagttcgtga | ccgccgccgg | gatcactctc | ggcatggacg | agctgtacaa gtaagaattc | 5040 |
| | | gatatcaagc | ttatcgataa | tcaacctctg | gattacaaaa | tttgtgaaag attgactggt | 5100 |
| | | attcttaact | atgttgctcc | ttttacgcta | tgtggatacg | ctgctttaat gcctttgtat | 5160 |
| | | catgctattg | cttcccgtat | ggctttcatt | ttctcctcct | tgtataaatc ctggttgcta | 5220 |
| | | tctctttatg | aggagttgtg | gcccgttgtc | aggcaacgtg | gcgtggtgtg cactgtgttt | 5280 |
| | | gctgacgcaa | ccccccactgg | ttggggcatt | gccaccacct | gtcagctcct ttccgggact | 5340 |
| | | ttcgctttcc | ccctccctat | tgccacggcg | gaactcatcg | ccgcctgcct tgcccgctgc | 5400 |
| | | tggacagggg | ctcggctgtt | gggcactgac | aattccgtgg | tgttgtcggg gaaatcatcg | 5460 |
| | | tccttttcctt | ggctgctcgc | ctgtgttgcc | acctggattc | tgcgcgggac gtccttctgc | 5520 |
| | | tacgtccctt | cggccctcaa | tccagcggac | cttcttccc | gcggcctgct gccggctctg | 5580 |
| | | cggcctcttc | cgcgtcttcg | ccttcgccct | cagacgagtc | ggatctccct ttgggccgcc | 5640 |
| | | tccccgcatc | gataccgtcg | acctcgagac | ctagaaaaac | atggagcaat cacaagtagc | 5700 |
| | | aatacagcag | ctaccaatgc | tgattgtgcc | tggctagaag | cacaagagga ggaggaggtg | 5760 |
| | | ggttttccag | tcacacctca | ggtaccttta | agaccaatga | cttacaaggc agctgtagat | 5820 |
| | | cttagccact | ttttaaaaga | aaaggggga | ctggaagggc | taattcactc ccaacgaaga | 5880 |
| | | caagatatcc | ttgatctgtg | gatctaccac | acacaaggct | acttccctga ttggcagaac | 5940 |
| | | tacacacagg | ggccagggat | cagatatcca | ctgacctttg | gatggtgcta caagctagta | 6000 |
| | | ccagttgagc | aagagaaggt | agaagaagcc | aatgaaggag | agaacacccg cttgttacac | 6060 |
| | | cctgtgagcc | tgcatgggat | ggatgacccg | gagagagaag | tattagagtg gaggtttgac | 6120 |
| | | agccgcctag | catttcatca | catggcccga | gagctgcatc | cggactgtac tgggtctctc | 6180 |
| | | tggttagacc | agatctgagc | ctgggagctc | tctggctaac | tagggaacc actgcttaag | 6240 |
| | | cctcaataaa | gcttgccttg | agtgcttcaa | gtagtgtgtg | cccgtctgtt gtgtgactct | 6300 |
| | | ggtaactaga | gatccctcag | accctttag | tcagtgtgga | aaatctctag cagggcccgt | 6360 |
| | | ttaaacccgc | tgatcagcct | cgactgtgcc | ttctagttgc | cagccatctg ttgtttgccc | 6420 |
| | | ctcccccgtg | ccttccttga | ccctggaagg | tgccactccc | actgtccttt cctaataaaa | 6480 |
| | | tgaggaaatt | gcatcgcatt | gtctgagtag | gtgtcattct | attctggggg gtggggtggg | 6540 |
| | | gcaggacagc | aagggggagg | attgggaaga | caatagcagg | catgctgggg atgcggtggg | 6600 |
| | | ctctatggct | tctgaggcgg | aaagaaccag | ctggggctct | agggggtatc cccacgcgcc | 6660 |
| | | ctgtagcggc | gcattaagcg | cggcgggtgt | ggtggttacg | cgcagcgtga ccgctacact | 6720 |
| | | tgccagcgcc | ctagcgcccg | ctcctttcgc | tttcttccct | tcctttctcg ccacgttcgc | 6780 |
| | | cggctttccc | cgtcaagctc | taaatcgggg | gctccctta | gggttcgat ttagtgcttt | 6840 |
| | | acggcacctc | gacccccaaa | aacttgatta | gggtgatggt | tcacgtagtg ggccatcgcc | 6900 |
| | | ctgatacacg | gttttttcgcc | ctttgacgtt | ggagtccacg | ttctttaata gtggactctt | 6960 |
| | | gttccaaact | ggaacaacac | tcaacccctat | ctcggtctat | tcttttgatt tataagggat | 7020 |
| | | tttgccgatt | tcggcctatt | ggttaaaaaa | tgagctgatt | taacaaaaat ttaacgcgaa | 7080 |
| | | ttaattctgt | ggaatgtgtg | tcagttaggg | tgtggaaagt | ccccaggctc cccagcaggc | 7140 |
| | | agaagtatgc | aaagcatgca | tctcaattag | tcagcaacca | ggtgtggaaa gtcccaggc | 7200 |
| | | tccccagcag | gcagaagtat | gcaaagcatg | catctcaatt | agtcagcaac catagtcccg | 7260 |
| | | cccctaactc | cgcccatccc | gcccctaact | ccgcccagtt | ccgcccattc tccgccccat | 7320 |
| | | ggctgactaa | ttttttttat | ttatgcagag | gccgaggccg | cctctgcctc tgagctattc | 7380 |
| | | cagaagtagt | gaggaggctt | ttttggaggc | ctaggctttt | gcaaaaagct cccgggagct | 7440 |
| | | tgtatatcca | ttttcggatc | tgatcagcac | gtgttgacaa | ttaatcatcg gcatagtata | 7500 |
| | | tcggcatagt | ataatacgac | aaggtgagga | actaaaccat | ggccaagttg accagtgccg | 7560 |
| | | ttccggtgct | caccgcgcgc | gacgtcgccg | gagcggtcga | ttctggacc gaccggctcg | 7620 |
| | | ggttctcccg | ggacttcgtg | gaggacgact | tcgccggtgt | ggtccgggac gacgtgaccc | 7680 |
| | | tgttcatcag | cgcggtccag | gaccaggtgg | tgccggacaa | cacctgtc tgggtgtggg | 7740 |
| | | tgcgcggcct | ggacagctg | tacgccgagt | ggtcggaggt | cgtgtccacg aacttccggg | 7800 |
| | | acgcctccgg | ccggccatg | accgagatcg | gcgagcagcc | gtgggggcgg gagttcgcc | 7860 |
| | | tgcgcgaccc | ggccggcaac | tgcgtgcact | cgtggccga | ggagcaggac tgacacgtgc | 7920 |
| | | tacgagattt | cgattccacc | gccgccttct | atgaaaggtt | gggcttcgga atcgttttcc | 7980 |
| | | gggacgccgg | ctggatgatc | ctccagcgcg | ggatctcat | gctggagttc ttcgcccacc | 8040 |
| | | ccaacttgtt | tattgcagct | tataatggtt | acaaataaag | caatagcatc acaaatttca | 8100 |
| | | caaataaagc | atttttttca | ctgcattcta | gttgtggttt | gtccaaactc atcaatgtat | 8160 |
| | | cttatcatgt | ctgtataccg | tcgacctcta | gctagagctt | ggcgtaatca tggtcatagc | 8220 |
| | | tgtttcctgt | gtgaaattgt | tatccgctca | caattccaca | acatacga gccgaagca | 8280 |
| | | taaagtgtaa | agcctggggt | gcctaatgag | tgagctaact | cacattaatt gcgttgcgct | 8340 |
| | | cactgcccgc | tttccagtcg | ggaaacctgt | cgtgccagct | gcattaatga atcggccaac | 8400 |
| | | gcgcgggggag | aggcggtttg | cgtattgggc | gctcttccgc | ttcctcgctc actgactcgc | 8460 |
| | | tgcgctcggt | cgttcggctg | cggcgagcgg | tatcagctca | ctcaaaggcg gtaatacggt | 8520 |

TABLE 4-continued

List of Sequences

| Seq ID No | Name | Sequence | |
|---|---|---|---|
| | | tatccacaga atcaggggat aacgcaggaa agaacatgtg agcaaaaggc cagcaaaagg | 8580 |
| | | ccaggaaccg taaaaaggcc gcgttgctgg cgttttttcca taggctccgc ccccctgacg | 8640 |
| | | agcatcacaa aaatcgacgc tcaagtcaga ggtggcgaaa cccgacagga ctataaagat | 8700 |
| | | accaggcgtt tccccctgga agctccctcg tgcgctctcc tgttccgacc ctgccgctta | 8760 |
| | | ccggatacct gtccgccttt ctcccttcgg aagcgtggc gctttctcat agctcacgct | 8820 |
| | | gtaggtatct cagttcggtg taggtcgttc gctccaagct gggctgtgtg cacgaacccc | 8880 |
| | | ccgttcagcc cgaccgctgc gccttatccg gtaactatcg tcttgagtcc aacccggtaa | 8940 |
| | | gacacgactt atcgccactg gcagcagcca ctggtaacag gattagcaga gcgaggtatg | 9000 |
| | | taggcggtgc tacagagttc ttgaagtggt ggcctaacta cggctacact agaagaacag | 9060 |
| | | tatttggtat ctgcgctctg ctgaagccag ttaccttcgg aaaaagagtt ggtagctctt | 9120 |
| | | gatccggcaa acaaaccacc gctggtagcg gtggtttttt tgtttgcaag cagcagatta | 9180 |
| | | cgcgcagaaa aaaaggatct caagaagatc ctttgatctt ttctacgggg tctgacgctc | 9240 |
| | | agtggaacga aaactcacgt taagggattt tggtcatgag attatcaaaa aggatcttca | 9300 |
| | | cctagatcct tttaaattaa aaatgaagtt ttaaatcaat ctaaagtata tatgagtaaa | 9360 |
| | | cttggtctga cagttaccaa tgcttaatca gtgaggcacc tatctcagcg atctgtctat | 9420 |
| | | ttcgttcatc catagttgcc tgactccccg tcgtgtagat aactacgata cgggagggct | 9480 |
| | | taccatctgg ccccagtgct gcaatgatac cgcgagaccc acgctcaccg gctccagatt | 9540 |
| | | tatcagcaat aaaccagcca gccggaaggg ccgagcgcag aagtggtcct gcaactttat | 9600 |
| | | ccgcctccat ccagtctatt aattgttgcc gggaagctag agtaagtagt tcgccagtta | 9660 |
| | | atagtttgcg caacgttgtt gccattgcta caggcatcgt ggtgtcacgc tcgtcgtttg | 9720 |
| | | gtatggcttc attcagctcc ggttcccaac gatcaaggcg agttacatga tcccccatgt | 9780 |
| | | tgtgcaaaaa agcggttagc tccttcggtc ctccgatcgt tgtcagaagt aagttggccg | 9840 |
| | | cagtgttatc actcatggtt atggcagcac tgcataattc tcttactgtc atgccatccg | 9900 |
| | | taagatgctt ttctgtgact ggtgagtact caaccaagtc attctgagaa tagtgtatgc | 9960 |
| | | ggcgaccgag ttgctcttgc ccggcgtcaa tacgggataa taccgcgcca catagcagaa | 10020 |
| | | cttttaaaagt gctcatcatt ggaaaacgtt cttcggggcg aaaactctca aggatcttac | 10080 |
| | | cgctgttgag atccagttcg atgtaaccca ctcgtgcacc caactgatct tcagcatctt | 10140 |
| | | ttactttcac cagcgttttc gggtgagcaa aaacaggaag gcaaaatgcc gcaaaaaagg | 10200 |
| | | gaataagggc gacacggaaa tgttaatac tcatactctt ccttttttcaa tattattgaa | 10260 |
| | | gcatttatca gggttattgt ctcatgagcg gatacatatt tgaatgtatt tagaaaaata | 10320 |
| | | aacaaatagg ggttccgcgc acatttcccc gaaaagtgcc acctgac | 10367 |
| 103 | BT6 CysAla | EIWKQFEDAL QKFEEALNQF EDLKQLGGSG SGSGGEIWKQ CEDALQKFEE ALNQFEDLKQ | 60 |
| | | LGGSGSGSGG EIWKQFEDAL QKFEEALNQF EDLKQLGGSG SGSGGEIWKQ AEDALQKFEE | 120 |
| | | ALNQFEDLKQ L | 131 |
| 104 | MM3 FC H6F H76F | ELLKKFEEAL KKFEELLKKF EEELKKGGSG SGSGGELLKK FEEALKKFEE LLKKFEEELK | 60 |
| | | KGGSGWGSGG ELLKKFEEAL KKFEELLKKF EELLKKGGSG SGSGGELLKK CEEALKKFEE | 120 |
| | | LLKKFEELLK K | 131 |
| 105 | MM3 FC H6F H76F F90D | ELLKKFEEAL KKFEELLKKF KEELKKGGSG SGSGGELLKK FEEALKKFEE LLKKFEEELK | 60 |
| | | KGGSGWGSGG ELLKKFEEAL KKFEELLKKD EELLKKGGSG SGSGGELLKK CEEALKKFEE | 120 |
| | | LLKKFEELLK K | 131 |
| 106 | Positive (EC) | agcagacaag cccgtcaggg cgcgtcagcg ggtgttggcg ggtgtcgggg ctggcttaac | 60 |
| | | tatgcggcat cagagcagat tgtactgaga gtgcaccata tgcggtgtga ataccgcgca | 120 |
| | | agatgcgtaa ggagaaaata ccgcatcagg cgccattcgc cattcaggct gcgcaactgt | 180 |
| | | tgggaagggc gatcggtgcg ggcctcttcg ctattacgcc agctggcgaa aggggggatgt | 240 |
| | | gctgcaaggc gattaagttg ggtaacgcca gggttttccc agtcacgacg ttgtaaaacg | 300 |
| | | acggccagtg ccaagcttaa ttaatctttc tgcgaattga gatgacgcca ctggctgggc | 360 |
| | | gtcatcccgg tttcccgggt aaacaccacc gaaaatagt tactatcttc aaagccacat | 420 |
| | | tcggtcgaaa tatcactgat taacaggcgg ctatgctgga gaagatattg cgcatgacac | 480 |
| | | actctgacct gtcgcagata ttgattgatg gtcattccag tctgctggcg aaattgctga | 540 |
| | | cgcaaaacgc gctcactgca cgatgcctca tcacaaaatt tatccagcgc aaagggactt | 600 |
| | | ttcaggctag ccgccagccg ggtaatcagc ttatccagca acgtttcgct ggatgttggc | 660 |
| | | ggcaacgaat cactggtgta acgatgcgga ttcagcaaca tcaccaactg cccgaacagc | 720 |
| | | aactcagcca tttcgttagc aaacggcaca tgctgactac tttcatgctc aagctgacca | 780 |
| | | ataacctgcc gcgcctcgc catccccatg ctacctaagc gccagtgtgg ttgccctgcg | 840 |
| | | ctggcgttaa atcccggaat cgcccctgc cagtcaagat tcagcttcag acgctccggg | 900 |
| | | caataaataa tattctgcaa aaccagatcg ttaacgaag cgtaggagtg tttatcatca | 960 |
| | | gcatgaatgt aaaagagatc gccacgggta atgcgataag ggcgatcgtt gagtacatgc | 1020 |
| | | aggccattac cgcgccagac aatcaccagc tcacaaaaat catgtgtatg ttcagcaaag | 1080 |
| | | acatcttgcg gataacggtc agccacagcg actgctgct ggtcgctggc aaaaaaatca | 1140 |
| | | tctttgagaa gttttaactg atgcgccacc gtggctacct cggccagaga acgaagttga | 1200 |
| | | ttattcgcaa tatggcgtac aaatacgttg agaagattcg cgttattgca gaaagccatc | 1260 |
| | | ccgtccctgg cgaatatcac gcggtgacca gttaaactct cggcgaaaaa gcgtcgaaaa | 1320 |
| | | gtggttactg tcgctgaatc cacagcgata ggcgatgtca gtaacgctgg cctcgctgtg | 1380 |
| | | gcgtagcaga tgtcgggctt tcatcagtcg caggcggttc aggtatcgct gaaggtgacc | 1440 |
| | | tcccgtttgc tgcttaagct gccgatgtag cgtaccgcagt gaaagagaaa attgatccgc | 1500 |
| | | cacggcatcc caattcacct catcggcaaa atggtcctcc agccaggcca gaagcaagtt | 1560 |
| | | gagacgtgat gcgctgtttt ccaggttctc ctgcaaactg cttttacgca gcaagagcag | 1620 |
| | | taattgcata aacaagatct cgcgactggc ggtcgagggt aaatcatttt cccccttcctg | 1680 |
| | | ctgttccatc tgtgcaacca gctgtcgcac ctgctgcaat acgctgtggt taacgcgcca | 1740 |

TABLE 4-continued

List of Sequences

| Seq ID No | Name | Sequence | |
|---|---|---|---|
| | | gtgagacgga tactgcccat ccagctcttg tggcagcaac tgattcagcc cggcgagaaa | 1800 |
| | | ctgaaatcga tccggcgagc gatacagcac attggtcaga cacagattat cggtatgttc | 1860 |
| | | atacagatgc cgatcatgat cgcgtacgaa acagaccgtg ccaccggtga tggtataggg | 1920 |
| | | ctgcccatta aacacatgaa tacccgtgcc atgttcgaca atcacaattt catgaaaatc | 1980 |
| | | atgatgatgt tcaggaaaat ccgcctgcgg gagccggggt tctatcgcca cggacgcgtt | 2040 |
| | | accagacgga aaaaaatcca cactatgtaa tacggtcata ctggcctcct gatgtcgtca | 2100 |
| | | acacggcgaa atagtaatca cgaggtcagg ttcttacctt aaattttcga cggaaaacca | 2160 |
| | | cgtaaaaaac gtcgattttt caagatacag cgtgaatttt caggaaatgc ggtgagcatc | 2220 |
| | | acatcaccac aattcagcaa attgtgaaca tcatcacgtt catctttccc tggttgccaa | 2280 |
| | | tggcccattt tcctgtcagt aacgagaagg tcgcgaattc aggcgctttt tagactggtc | 2340 |
| | | gtaatgaaat tcttttagga gataaaacat atgggcggcg acggtcatca tcatcaccac | 2400 |
| | | cacggcggca aaggcgagaa cttgtatttc caaggtgaga ttaagcgtca gcatgaggac | 2460 |
| | | gcgctgcgca agttcgaaga agcgctgaag cgcttcgagg acaagaaaca aaagggtggt | 2520 |
| | | agcggtaaag gttccggcgc tgagatttgg aagcgtcacg aagatgcctt gcgtaagttt | 2580 |
| | | gaagaggcgc tgaaacgttt cgaggataag aagcagaaag gtggttctgg taaaggtagc | 2640 |
| | | ggtggtgaaa tctggaaacg ccacgaggac gctctgcgca aatttgaaga agcactgaag | 2700 |
| | | cgttttgagg acaaaaagca aagggcggc agcggtaagg cagcggtgg cgagatcaaa | 2760 |
| | | caacgtcacg aggatgcgct gcgtaaattc gaagaggcac tgaaacgctt tgaagataag | 2820 |
| | | aaacagaaat aactcgagcc cctcatccga aagggcgtat tggtaccgag ctcgaattcg | 2880 |
| | | taatcatgtc atagctgttt cctgtgtgaa attgttatcc gctcacaatt ccacacaaca | 2940 |
| | | tacgagccgg aagcataaag tgtaaagcct ggggtgccta atgagtgagc taactcacat | 3000 |
| | | taattgcgtt gcgctcactg cccgctttcc agtcgggaaa cctgtcgtgc cagctgcatt | 3060 |
| | | aatgaatcgg ccaacgcgcg gggagaggcg gtttgcgtat tgggcgctct tccgcttcct | 3120 |
| | | cgctcactga ctcgctgcgc tcggtcgttc ggctgcggcg agcggtatca gctcactcaa | 3180 |
| | | aggcggtaat acggttatcc acagaatcag gggataacgc aggaaagaac atgtgagcaa | 3240 |
| | | aaggccagca aaaggccagg aaccgtaaaa aggccgcgtt gctggcgttt ttccataggc | 3300 |
| | | tccgcccccc tgacgagcat cacaaaaatc gacgctcaag tcagaggtgg cgaaacccga | 3360 |
| | | caggactata aagataccag gcgtttcccc ctggaagctc cctcgtgcgc tctcctgttc | 3420 |
| | | cgaccctgcc gcttaccgga tacctgtccg cctttctccc ttcgggaagc gtggcgcttt | 3480 |
| | | ctcatagctc acgctgtagg tatctcagtt cggtgtaggt cgttcgctcc aagctgggct | 3540 |
| | | gtgtgcacga accccccgtt cagcccgacc gctgcgcctt atccggtaac tatcgtcttg | 3600 |
| | | agtccaaccc ggtaagacac gacttatcgc cactggcagc agccactggt aacaggatta | 3660 |
| | | gcagagcgag gtatgtaggc ggtgctacag agttcttgaa gtggtggcct aactacggct | 3720 |
| | | acactagaag gacagtattt ggtatctgcg ctctgctgaa gccagttacc ttcggaaaaa | 3780 |
| | | gagttggtag ctcttgatcc ggcaaacaaa ccaccgctgg tagcggtggt ttttttgttt | 3840 |
| | | gcaagcagca gattacgcgc agaaaaaaag gatctcaaga agatcctttg atcttttcta | 3900 |
| | | cggggtctga cgctcagtga acgaaaaact cacgttaagg gattttggtc atgagattat | 3960 |
| | | caaaaaggat cttcacctag atccttttaa attaaaaatg aagttttaaa tcaatctaaa | 4020 |
| | | gtatatatga gtaaacttgg tctgacagtt accaatgctt aatcagtgag gcacctatct | 4080 |
| | | cagcgatctg tctatttcgt tcatccatag ttgcctgact ccccgtcgtg tagataacta | 4140 |
| | | cgatacggga gggcttacca tctggcccca gtgctgcaat gataccgcgg cacccacgct | 4200 |
| | | caccggctcc agatttatca gcaataaacc agccagccgg aagggccgag cgcagaagtg | 4260 |
| | | gtcctgcaac tttatccgcc tccatccagt ctattaattg ttgccgggaa gctagagtaa | 4320 |
| | | gtagttcgcc agttaatagt ttgcgcaacg ttgttgccat tgctacaggc atcgtggtgt | 4380 |
| | | cacgctcgtc gtttggtatg gcttcattca gctccggttc ccaacgatca aggcgagtta | 4440 |
| | | catgatcccc catgttgtgc aaaaaagcgg ttagctcctt cggtcctccg atcgttgtca | 4500 |
| | | gaagtaagtt ggccgcagtg ttatcactca tggttatggc agcactgcat aattctctta | 4560 |
| | | ctgtcatgcc atccgtaaga tgcttttctg tgactggtga gtactcaacc aagtcattct | 4620 |
| | | gagaatagtg tatgcggcga ccgagttgct cttgcccggc gtcaatacgg gataataccg | 4680 |
| | | cgccacatag cagaacttta aaagtgctca tcattggaaa acgttcttcg gggcgaaaac | 4740 |
| | | tctcaaggat cttaccgctg ttgagatcca gttcgatgta acccactcgt gcacccaact | 4800 |
| | | gatcttcagc atcttttact ttcaccagcg tttctgggtg agcaaaaaca ggaaggcaaa | 4860 |
| | | atgccgcaaa aaagggaata agggcgacac ggaaatgttg aatactcata ctcttccttt | 4920 |
| | | ttcaatatta ttgaagcatt tatcagggtt attgtctcat gagcggatac atatttgaat | 4980 |
| | | gtatttagaa aaataaacaa atagggttc cgcgcacatt tccccgaaaa gtgccacctg | 5040 |
| | | acgtctaaga aaccattatt atcatgacat taacctataa aaataggcgt atcacgaggc | 5100 |
| | | cctttcgtct cgcgcgtttc ggtgatgacg tgaaaacct ctgacacatg cagctcccgg | 5160 |
| | | agacggtcac agcttgtctg taagcggatg ccggg | 5195 |
| 107 | Positive (FCK mam) | gtcgacggat cgggagatct cccgatcccc tatggtgcac tctcagtaca atctgctctg | 60 |
| | | atgccgcata gttaagccag tatctgctcc tgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt cgcgctgctt cgcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatgcccg gcctgcctga ccgcccaacg | 360 |
| | | accccgcc attgacgtca ataatgacgt atgttccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |

TABLE 4-continued

List of Sequences

| Seq ID No | Name | Sequence | |
|---|---|---|---|
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga aaccagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tggggggtac agtgcagggg aaagaatagt agacataata gcaaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aagtagtgaa ctcattaggg cagatgacca | 2820 |
| | | atgagtttag gaaagaagag tccagggcag ggtacatcta caccaccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatggtg agagagcgtg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caagggggaa gggaaggaga gatgaattag cttccccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagagcg atgatcactt gtggactaag | 3540 |
| | | tttgttcaca tcccctctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgaccaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gcccctagtt ctggggcag cggggatcc | 3900 |
| | | atgggtgaga ttaagcgtca gcatgaggac gcgctgcgca agttcgaaga agcgctgaag | 3960 |
| | | cgcttcgagg acaagaaaca aaagggtggt agcggtaaag gttccggcgg tgagatttgg | 4020 |
| | | aagcgtcacg aagatgcctt gcgtaagttt gaagaggcgc tgaaacgttt cgaggataag | 4080 |
| | | aagcagaaag gtggttctgg taaaggtagc ggtggtgaaa tctggaaacg ccacgaggac | 4140 |
| | | gctctgcgca aatttgaaga agcactgaag cgttttgagg acaaaaagca gaagggcggc | 4200 |
| | | agcggtaagg gcagcggtgg cgagatcaaa aacgtcacg aggatgcgct cgctaaattc | 4260 |
| | | gaagaggcac tgaaacgctt tgaagataag aaacagaaaa cggcaccggt agtagcagtg | 4320 |
| | | agcaagggcg aggagctgtt caccggggtg gtgcccatcc tggtcgagct ggacggcgac | 4380 |
| | | gtaaacggcc acaagttcag cgtgtccggc gagggcgagg gcgatgccac ctacggcaag | 4440 |
| | | ctgaccctga agttcatttg caccaccggc aagctgcccg tgccctggcc caccctcgtg | 4500 |
| | | accacccctga cctacggcgt gcagtgcttc gccgctacc ccgaccacat gaagcagcac | 4560 |
| | | gacttcttca gtccgccat gcccgaaggc tacgtccagg agcgcaccat cttcttcaag | 4620 |
| | | gacgacggca actacaagac ccgcgccgag gtgaagttcg agggcgacac cctggtgaac | 4680 |
| | | cgcatcgagc tgaagggcat cgacttcaag gaggacggca acatcctggg gcacaagctg | 4740 |
| | | gagtacaact acaacagcca caacgtctat atcatggccg acaagcagaa gaacggcatc | 4800 |
| | | aaggtgaact tcaagatccg ccacaacatc gaggacggca gcgtgcagct cgccgaccac | 4860 |
| | | taccagcaga acaccccat cggcgacggc cccgtgctgc tgcccgacaa ccactacctg | 4920 |
| | | agcacccagt ccgccctgag caaagacccc aacgagaagc gcgatcacat ggtcctgctg | 4980 |
| | | gagttcgtga ccgccgcggg gatcactctc ggcatggacg agctgtacaa gtaagaattc | 5040 |
| | | gatatcaagc ttatcgataa tcaacctctg gattacaaaa tttgtgaaag attgactggt | 5100 |
| | | attcttaact atgttgctcc ttttacgcta tgtggatacg ctgctttaat gcctttgtat | 5160 |
| | | catgctattg cttcccgtat ggctttcatt ttctcctcct tgtataaatc ctggttgctg | 5220 |
| | | tctctttatg aggagttgtg gcccgttgtc aggcaacgtg gcgtggtgtg cactgtgttt | 5280 |
| | | gctgacgcaa cccccactgg ttggggcatt gccaccacct gtcagctcct ttccgggact | 5340 |

TABLE 4-continued

List of Sequences

| Seq ID No | Name | Sequence | |
|---|---|---|---|
| | | ttcgctttcc ccctccctat tgccacggcg gaactcatcg ccgcctgcct tgcccgctgc | 5400 |
| | | tggacagggg ctcggctgtt gggcactgac aattccgtgg tgttgtcggg gaaatcatcg | 5460 |
| | | tcctttcctt ggctgctcgc ctgtgttgcc acctggattc tgcgcgggac gtccttctgc | 5520 |
| | | tacgtcccct cggccctcaa tccagcggac cttccttccc gcggcctgct gccggctctg | 5580 |
| | | cggcctcttc cgcgtcttcg ccttcgccct cagacgagtc ggatctccct ttgggccgcc | 5640 |
| | | tccccgcatc gataccgtcg acctcgagac ctagaaaaac atggagcaat cacaagtagc | 5700 |
| | | aatacagcag ctaccaatgc tgattgtgcc tggctagaag cacaagagga ggaggaggtg | 5760 |
| | | ggttttccag tcacacctca ggtaccttta agaccaatga cttacaaggc agctgtagat | 5820 |
| | | cttagccact tttttaaaaga aaaggggggga ctggaagggc taattcactc ccaacgaaga | 5880 |
| | | caagatatcc ttgatctgtg gatctaccac acacaaggct acttccctga ttggcagaac | 5940 |
| | | tacacaccag ggccagggat cagatatcca ctgacctttg gatggtgcta caagctagta | 6000 |
| | | ccagttgagc aagagaaggt agaagaagcc aatgaaggag agaacacccg cttgttacac | 6060 |
| | | cctgtgagcc tgcatgggat ggatgacccg gagagagaag tattagagtg gaggtttgac | 6120 |
| | | agccgcctag catttcatca catggcccga gagctgcatc cggactgtac tgggtctctc | 6180 |
| | | tggttagacc agatctgagc ctgggagctc tctggctaac tagggaaccc actgcttaag | 6240 |
| | | cctcaataaa gcttgccttg agtgcttcaa gtagtgtgtg cccgtctgtt gtgtgactct | 6300 |
| | | ggtaactaga gatccctcag accctttttag tcagtgtgga aaatctctag cagggcccgt | 6360 |
| | | ttaaacccgc tgatcagcct cgactgtgcc ttctagttgc cagccatctg ttgtttgccc | 6420 |
| | | ctcccccgtg ccttccttga ccctggaagg tgccactccc actgtccttt cctaataaaa | 6480 |
| | | tgaggaaatt gcatcgcatt gtctgagtag gtgtcattct attctgggggg gtgggtgggg | 6540 |
| | | gcaggacagc aaggggggagg attgggaaga caatagcagg catgctgggg atgcggtggg | 6600 |
| | | ctctatggct tctgaggcgg aaagaaccag ctgggggctct aggggggtatc cccacgcgcc | 6660 |
| | | ctgtagccgc gcattaagcg cggcgggtgt ggtggttacg cgcagcgtga ccgctacact | 6720 |
| | | tgccagcgcc ctagcgcccg ctccttttcgc tttcttccct tccttctctcg ccacgttcgc | 6780 |
| | | cggctttccc cgtcaagctc taaatcgggg ctccctttta gggttccgat ttagtgcttt | 6840 |
| | | acggcacctc gaccccaaaa aacttgatta gggtgatggt tcacgtagtg ggccatcgcc | 6900 |
| | | ctgatagacg ttttttcgcc ctttgacgtt ggagtccacg ttctttttaata gtggactctt | 6960 |
| | | gttccaaact ggaacaacac tcaacctat ctcggtctat tcttttgatt tataagggat | 7020 |
| | | tttgccgatt tcggcctatt ggttaaaaaa tgagctgatt taacaaaaat ttaacgcgaa | 7080 |
| | | ttaattctgt ggaatgtgtg tcagttaggg tgtggaaagt ccccaggctc cccagcaggc | 7140 |
| | | agaagtatgc aaagcatgca tctcaattag tcagcaacca ggtgtggaaa gtcccccaggc | 7200 |
| | | tccccagcag gcagaagtac agcaaagcatg catctcaatt agtcagcaac catgtcccg | 7260 |
| | | cccctaactc cgcccatccc gcccctaact ccgcccagtt ccgcccattc tccgccccat | 7320 |
| | | ggctgactaa ttttttttat ttatgcagag gccgaggccg cctctgcctc tgagctattc | 7380 |
| | | cagaagtagt gaggaggctt ttttggaggc ctaggctttt gcaaaaagct cccgggagct | 7440 |
| | | tgtatatcca ttttcggatc tgatcagcac gtgttgacaa ttaatcatcg gcatagtata | 7500 |
| | | tcggcatagt ataatacgac aaggtgagga actaaaccat ggccaagttg accagtgccg | 7560 |
| | | ttccggtgct caccgcgcgc gacgtcgccg gagcggtcga gttctggacc gaccggctcg | 7620 |
| | | ggttctcccg ggacttcgtg gaggacgact tcgccggtgt ggtccgggac gacgtgaccc | 7680 |
| | | tgttcatcag cgcggtccag gaccaggtgg tgccggacaa cacctggcc tgggtgtggg | 7740 |
| | | tgcgcggcct ggacgagctc tacgccgagt ggtcggaggt cgtgtccacg aacttccggg | 7800 |
| | | acgcctccgg ccggccatg accgagatcg gcgagcagcc gtgggggcgg gagttcgccc | 7860 |
| | | tgcgcgaccc ggccggcaac tgcgtgcact tcgtggccga ggagcaggac tgacacgtgc | 7920 |
| | | tacgagattt cgattccacc gccgccttct atgaaaggtt gggcttcgga atcgttttcc | 7980 |
| | | gggacgccgg ctggatgatc ctccagcgcg gggatctcat gctggagttc ttcgcccacc | 8040 |
| | | ccaacttgtt tattgcagct tataatggtt acaaataaag caatagcatc acaaatttca | 8100 |
| | | caaataaagc attttttcca ctgcattcta gttgtggttt gtccaaactc atcaatgtat | 8160 |
| | | cttatcatgt ctgtataccg tcgacctcta gctagagctc ggcgtaatca tggtcatagc | 8220 |
| | | tgtttcctgt gtgaaattgt tatccgctca caattccaca caatacga gccgaagca | 8280 |
| | | taaagtgtaa agcctggggt gcctaatgag tgagctaact cacattaatt gcgttgcgct | 8340 |
| | | cactgcccgc tttccagtcg ggaaacctgt cgtgccagct gcattaatga atcggccaac | 8400 |
| | | gcgcggggag aggcggtttg cgtattgggc gctcttccgc ttcctcgctc actgactcgc | 8460 |
| | | tgcgctcggt cgttcggctg cggcgagcgg tatcagctca ctcaaaggcg gtaatacggt | 8520 |
| | | tatccacaga atcagggat aacgcaggaa agaacatgtg agcaaaaggc cagcaaaagg | 8580 |
| | | ccaggaaccg taaaaaggcc gcgttgctgg cgtttttcca taggctccgc cccctgacg | 8640 |
| | | agcatcacaa aaatcgacgc tcaagtcaga ggtggcgaaa cccgacagga ctataaagat | 8700 |
| | | accaggcgtt tccccctgga agctccctcg tgcgctctcc tgttccgacc ctgccgctta | 8760 |
| | | ccggatacct gtccgccttt ctcccttcgg aagcgtggc gctttctcat agctcacgct | 8820 |
| | | gtaggtatct cagttcggtg taggtcgttc gctccaagct gggctgtgtg cacgaacccc | 8880 |
| | | ccgttcagcc cgaccgctgc gccttatccg gtaactatcg tcttgagtcc aacccggtaa | 8940 |
| | | gacacgactt atcgccactg gcagcagcca ctggtaacag gattagcaga gcgaggtatg | 9000 |
| | | taggcggtgc tacagagttc ttgaagtggt ggcctaacta cggctacact agaagaacag | 9060 |
| | | tatttggtat ctgcgctctg ctgaagccag ttaccttcgg aaaaagagtt ggtagctctt | 9120 |
| | | gatccggcaa acaaaccacc gctggtagcg tggtttttt tgtttgcaag cagcagatta | 9180 |
| | | cgcgcagaaa aaaaggatct caagaagatc ctttgatctt ttctacgggg tctgacgctc | 9240 |
| | | agtggaacga aaactcacgt taagggattt tggtcatgag attatcaaaa aggatcttca | 9300 |
| | | cctagatcct tttaaattaa aaatgaagtt ttaaatcaat ctaaagtata tatgagtaaa | 9360 |
| | | cttggtctga cagttaccaa tgcttaatca gtgaggcacc tatctcagcg atctgtctat | 9420 |
| | | ttcgttcatc catagttgcc tgactccccg tcgtgtagat aactacgata cgggagggct | 9480 |
| | | taccatctgg ccccagtgct gcaatgatac cgcgagaccc acgctcaccg gctccagatt | 9540 |
| | | tatcagcaat aaaccagcca gccggaaggg ccgagcgcag aagtggtcct gcaactttat | 9600 |
| | | ccgcctccat ccagtctatt aattgttgcc gggaagctag agtaagtagt tcgccagtta | 9660 |
| | | atagtttgcg caacgttgtt gccattgcta caggcatcgt ggtgtcacgc tcgtcgtttg | 9720 |
| | | gtatggcttc attcagctcc ggttcccaac gatcaaggcg agttacatga tcccccatgt | 9780 |

TABLE 4-continued

List of Sequences

| Seq ID No | Name | Sequence | |
|---|---|---|---|
| | | tgtgcaaaaa agcggttagc tccttcggtc ctccgatcgt tgtcagaagt aagttggccg | 9840 |
| | | cagtgttatc actcatggtt atggcagcac tgcataattc tcttactgtc atgccatccg | 9900 |
| | | taagatgctt ttctgtgact ggtgagtact caaccaagtc attctgagaa tagtgtatgc | 9960 |
| | | ggcgaccgag ttgctcttgc ccggcgtcaa tacgggataa taccgcgcca catagcagaa | 10020 |
| | | cttaaaagt gctcatcatt ggaaaacgtt cttcggggcg aaaactctca aggatcttac | 10080 |
| | | cgctgttgag atccagttcg atgtaaccca ctcgtgcacc caactgatct tcagcatctt | 10140 |
| | | ttactttcac cagcgtttct gggtgagcaa aaacaggaag gcaaaatgcc gcaaaaaagg | 10200 |
| | | gaataagggc gacacggaaa tgttaatac tcatactctt ccttttcaa tattattgaa | 10260 |
| | | gcatttatca gggttattgt ctcatgagcg gatacatatt tgaatgtatt tagaaaaata | 10320 |
| | | aacaaatagg ggttccgcgc acatttcccc gaaaagtgcc acctgac | 10367 |
| 108 | Positive | EIKRQHEDAL RKFEEALKRF EDKKQKGGSG KGSGGEIWKR HEDALRKFEE ALKRFEDKKQ | 60 |
| | | KGGSGKGSGG EIWKRHEDAL RKFEEALKRF EDKKQKGGSG KGSGGEIKQR HEDALRKFEE | 120 |
| | | ALKRFEDKKQ K | 131 |
| 109 | AM1 (EC) | atccggatat agttcctcct ttcagcaaaa aacccctcaa gacccgttta gaggcccaa | 60 |
| | | ggggttatgc tagtattgc tcagcggtgg cagcagccaa ctcagcttcc tttcgggctt | 120 |
| | | tgttagcagc cggatctcag tggtggtggt ggtggtgctc gagttactgt ttcgccaggt | 180 |
| | | cctcaaattg gttcagtgct tcccagaacg ccagcaggtg cagcaacaga gccagcaaca | 240 |
| | | gcaaggccaa cagcgccaac aacaacagaa actcaccacc ggaaccacca ccgctaccac | 300 |
| | | ctttgaaggc caacaaatgc aacagcagag ccaacagcag caacaatgcc aacaacagca | 360 |
| | | acaacgcgaa gaatttctgc agcgcatcct catgctgttt ccaaatctca ccgccgctac | 420 |
| | | cgccaccgct gccaccctgc ttcgaactg attcagcgct tcccaaaaag | 480 |
| | | ccagcagatg caacaacagc gccagcagca gcagggccaa caacgccaac agcagcaaga | 540 |
| | | acttaccgcc gctgccgcca ccagaaccac cttcaaatgc cagcaagtgc agcagcagtg | 600 |
| | | ccagcagcag caacaggggcc aacagcaaca gcaatgcaaa gaacttttgc agtgcgtcct | 660 |
| | | catgttgctt ccagatttcg ccttgaaaat acaagttctc gccgtcgccg ccatgatgat | 720 |
| | | gatgatgatg ggtaccattc agcatctggc ctgcgtgaat attcttctcg ccaaacaagg | 780 |
| | | cgcggatgct caccaccttg ccggcgccat gaagcgaaa gtgatcgatg ggcgcaacta | 840 |
| | | cggtcttgcg gccctgatac tcgaagctga cggtgaaagc gaaggccgct tcgttggcga | 900 |
| | | ccgcgcgtac ctcctgcgtc agctccaccg ccaaaggcag tttgagcgag ttggcgtaaa | 960 |
| | | actcacgaat cgcagccgta ccggacctgg gctcggaacg cacggggtct tccaccgtgg | 1020 |
| | | cgtcatcggc aaacagcgcg acgatgccgt ccagatcgcc ggcattgagc gcagccacaa | 1080 |
| | | agcgctgtac cacggcggtg atgtgttctg gggtatgcat atgtatatct ccttcttaaa | 1140 |
| | | gttaaacaaa attatttcta gagggggaatt gttatccgct cacaattccc ctatagtgag | 1200 |
| | | tcgtattaat ttcgcggat cgagatctcg atcctctacg ccggacgcat cgtggccggc | 1260 |
| | | atcaccggcg ccacaggtgc ggttgctggc gcctatatcg ccgacatcac cgatgggaa | 1320 |
| | | gatcgggctc gccacttcgg gctcatgagc gcttgtttcg gcgtgggtat ggtggcaggc | 1380 |
| | | cccgtggccg ggggactgtt gggcgccatc tccttgcatg caccattcct tgcggcggcg | 1440 |
| | | gtgctcaacg gcctcaacct actactggag tgcttcctaa tgcaggagtc gcataaggga | 1500 |
| | | gagcgtcgag atccccgaca ccatcgaatg gcgcaaaacc tttcgcggta tggcatgata | 1560 |
| | | gcgcccggaa gagagtcaat tcagggtggt gaatgtgaaa ccagtaacgt tatacgatgt | 1620 |
| | | cgcagagtat gccggtgtct cttatcagac cgtttcccgc gtggtgaacc aggccagcca | 1680 |
| | | cgtttctgcg aaaacgcggg aaaaagtgga agcggcgatg gcggagctga attacattcc | 1740 |
| | | caaccgcgtg gcacaacaac tggcgggcaa acagtcgttg ctgattggcg ttgccacctc | 1800 |
| | | cagtctgccc ctgcacgcgc cgtcgcaaat tgtcgcggcg attaaatctc gcgccgatca | 1860 |
| | | actgggtgcc agcgtggtgg tgtcgatggt agaacgaagc ggcgtcgaag cctgtaaagc | 1920 |
| | | ggcggtgcac aatcttctcg cgcaacgcgt cagtgggctg atcattaact atccgctgga | 1980 |
| | | tgaccaggat gccattgctg tggaagctgc ctgcactaat gttccggcgt tatttcttga | 2040 |
| | | tgtctctgac cagacaccca tcaacagtat tattttctcc catgaagacg gtacgcgact | 2100 |
| | | gggcgtggag catctggtcg cattgggtca ccagcaaatc gcgctgttag cgggcccatt | 2160 |
| | | aagttctgtc tcggcgcgtc tgcgtctggc tggctggcat aaatatctca ctcgcaatca | 2220 |
| | | aattcagccg atagcggaac gggaaggcga ctggagtgcc atgtccggtt ttcaacaaac | 2280 |
| | | catgcaaatg ctgaatgagg gcatcgttcc cactgcgatg ctggttgcca acgatcagat | 2340 |
| | | ggcgctgggc gcaatgcgcg ccattaccga gtccgggctg cgcgttggtg cggatatctc | 2400 |
| | | ggtagtggga tacgacgata ccgaagacag ctcatgttat atccgccgt taaccaccat | 2460 |
| | | caaacaggat tttcgcctgc tggggcaaac cagcgtggac cgcttgctgc aactctctca | 2520 |
| | | gggccaggcg gtgaagggca atcagctgtt gcccgtctca ctggtgaaaa gaaaaaccac | 2580 |
| | | cctggcgccc aatacgcaaa ccgcctctcc ccgcgcgttg gccgattcat taatgcagct | 2640 |
| | | ggcacgacag gtttcccgac tggaaagcgg gcagtgagcg caacgcaatt aatgtaagtt | 2700 |
| | | agctcactca ttaggcaccg ggatctcgac cgatgcccttt gagacgcttc aacccagtca | 2760 |
| | | gctccttccg gtgggcgcgg ggcatgacta tcgtcgccgc acttatgact gtcttcttta | 2820 |
| | | tcatgcaact cgtaggacag gtgccggcag cgctctgggt cattttcggc gaggaccgct | 2880 |
| | | ttcgctggag cgcgacgatg atcggcctgt cgcttgcggt attcggaatc ttgcacgccc | 2940 |
| | | tcgctcaagc cttcgtcact ggtcccgcca caaacgtttt cggcgagaag caggccatta | 3000 |
| | | tcgccggcat ggcggcccca cgggtgcgca tgatcgtgct cctgtcgttg aggacccggc | 3060 |
| | | taggctggcg gggttgcctt actggttagc agaatgaatc accgatacgc gagcgaacgt | 3120 |
| | | gaagcgactg ctgctgcaaa acgtctgcga cctgagcaac aacatgaatg gtcttcggtt | 3180 |
| | | tccgtgtttc gtaaagtctg gaaacgcgga agtcagcgcc ctgcaccatt atgttccgga | 3240 |
| | | tctgcatcgc aggatgctgc tggctaccct gtggaacacc tacatctgta ttaacgaagc | 3300 |
| | | gctggcattg accctgagtg atttttctct ggtcccgccg catccatacc gccagttgtt | 3360 |
| | | taccctcaca acgttccagt aaccgggcat gttcatcatc agtaacccgt atcgtgagca | 3420 |
| | | tcctctctcg tttcatcggt atcattaccc ccatgaacag aaatccccct tacacggagg | 3480 |
| | | catcagtgac caaacaggaa aaaaccgccc ttaacatggc ccgctttatc agaagccaga | 3540 |

TABLE 4-continued

List of Sequences

| Seq ID No | Name | Sequence | |
|---|---|---|---|
| | | cattaacgct tctggagaaa ctcaacgagc tggacgcgga tgaacaggca gacatctgtg | 3600 |
| | | aatcgcttca cgaccacgct gatgagcttt accgcagctg cctcgcgcgt ttcggtgatg | 3660 |
| | | acggtgaaaa cctctgacac atgcagctcc cggagacggt cacagcttgt ctgtaagcag | 3720 |
| | | atgccgggag cagacaagcc cgtcagggcg cgtcagcggg tgttggcggg tgtcggggcg | 3780 |
| | | cagccatgac ccagtcacgt agcgatagcg gagtgtatac tggcttaact atgcggcatc | 3840 |
| | | agagcagatt gtactgagag tgcaccatat atgcggtgtg aaataccgca cagatgcgta | 3900 |
| | | aggagaaaat accgcatcag gcgctcttcc gcttcctcgc tcactgactc gctgcgctcg | 3960 |
| | | gtcgttcggc tgccggcgag ggtatcagct cactcaaagg cggtaatacg gttatccaca | 4020 |
| | | gaatcagggg ataacgcagg aaagaacatg tgagcaaaag gccagcaaaa ggccaggaac | 4080 |
| | | cgtaaaaagg ccgcgttgct ggcgtttttc cataggctcc gcccccctga cgagcatcac | 4140 |
| | | aaaaatcgac gctcaagtca gaggtggcga aacccgacag gactataaag ataccaggcg | 4200 |
| | | tttccccctg gaagctccct cgtgcgctct cctgttccga ccctgccgct taccggatac | 4260 |
| | | ctgtccgcct ttctcccttc gggaagcgtg gcgctttctc atagctcacg ctgtaggtat | 4320 |
| | | ctcagttcgg tgtaggtcgt tcgctccaag ctgggctgtg tgcacgaacc cccgttcag | 4380 |
| | | cccgaccgct gcgccttatc cggtaactat cgtcttgagt ccaacccggt aagacacgac | 4440 |
| | | ttatcgccac tggcagctgg taacaggatt agcagagcga ggtatgtagg cggtgctaca | 4500 |
| | | gagttcttga agtggtggcc taactacggc tacactagaa ggacagtatt tggtatctgc | 4560 |
| | | gctctgctga agccagttac cttcggaaaa agagttggta gctcttgatc cggcaaacaa | 4620 |
| | | accaccgctg gtagcggtgg ttttttttgtt tgcaagcagc agattacgcg cagaaaaaaa | 4680 |
| | | ggatctcaag aagatccttt gatcttttct acggggtctg acgctcagtg gaacgaaaac | 4740 |
| | | tcacgttaag ggattttggt catgagatta tcaaaaagga tcttcaccta gatccttta | 4800 |
| | | aattaaaaat gaagttttaa atcaatctaa agtatatatg agtaaacttg gtctgacagt | 4860 |
| | | taccaatgct taatcagtga ggcacctatc tcagcgatct gtctatttcg ttcatccata | 4920 |
| | | gttgcctgac tccccgtcgt gtagataact acgatacggg agggcttacc atctggcccc | 4980 |
| | | agtgctgcaa tgataccgcg agaccacgc tcaccggctc cagatttatc agcaataaac | 5040 |
| | | cagccagccg gaagggccga gcgcagaagt ggtcctgcaa ctttatccgc ctccatccag | 5100 |
| | | tctattaatt gttgccggga agctagagta agtagttcgc cagttaatag tttgcgcaac | 5160 |
| | | gttgttgcca ttgctgcagg catcgtggtg tcacgctcgt cgtttggtat ggcttcattc | 5220 |
| | | agctccggtt cccaacgatc aaggcgagtt acatgatccc ccatgttgtg caaaaaagcg | 5280 |
| | | gttagctcct tcggtcctcc gatcgttgtc agaagtaagt tggccgcagt gttatcactc | 5340 |
| | | atggttatgg cagcactgca taattctctt actgtcatgc catccgtaag atgcttttct | 5400 |
| | | gtgactggtg agtactcaac caagtcattc tgagaatagt gtatgcggcg accgagttgc | 5460 |
| | | tcttgcccgg cgtcaatacg ggataatacc gcgccacata gcagaacttt aaaagtgctc | 5520 |
| | | atcattggaa aacgttcttc ggggcgaaaa ctctcaagga tcttaccgct gttgagatcc | 5580 |
| | | agttcgatgt aacccactcg tgcacccaac tgatcttcag catcttttac tttcaccagc | 5640 |
| | | gtttctgggt gagcaaaaac aggaaggcaa aatgccgcaa aaaagggaat aagggcgaca | 5700 |
| | | cggaaatgtt gaatactcat actcttcctt tttcaatatt attgaagcat ttatcagggt | 5760 |
| | | tattgtctca tgagcggata catatttgaa tgtatttaga aaaataaaca aataggggtt | 5820 |
| | | ccgcgcacat ttccccgaaa agtgccacct gaaattgtaa acgttaatat tttgttaaaa | 5880 |
| | | ttcgcgttaa atttttgtta aatcagctca ttttttaacc aataggccga aatcggcaaa | 5940 |
| | | atcccttata atcaaaaga atagaccgag ataggggttga gtgttgttcc agtttggaac | 6000 |
| | | aagagtccac tattaaagaa cgtggactcc aacgtcaaag ggcgaaaaac cgtctatcag | 6060 |
| | | ggcgatggcc cactacgtga accatcaccc taatcaagtt ttttggggtc gaggtgccgt | 6120 |
| | | aaagcactaa atcggaaccc taaagggagc ccccgattta gagcttgacg ggaaagccg | 6180 |
| | | gcgaacgtgg cgagaaagga agggaagaaa gcgaaaggag cgggcgctag gcgcgctggca | 6240 |
| | | agtgtagcgg tcacgctgcg cgtaaccacc acacccgccg cgcttaatgc gccgctacag | 6300 |
| | | ggcgcgtccc attcgcca | 6318 |
| 110 | AM1 (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg gccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | accccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acaaatggc | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga gaacttagat cattatata atacagtagc aaccctctat tgtgtgcatc | 1440 |
| | | aaaggataga gataaaagac accaaggaag ctttagacaa gatagaggaa gagcaaaaca | 1500 |
| | | aaagtaagac caccgcacag caagcggccg ctgatcttca gacctggagg aggagatatg | 1560 |

TABLE 4-continued

List of Sequences

| Seq ID No | Name | Sequence | |
|---|---|---|---|
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aacccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aagggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctgaact tgaactcaga ttactaatct taaattccat | 2760 |
| | | gccttgggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggggaa gggaaggaga gatgaattag cttccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tgggggaggt aggaagagcg atgatcactt gtggactaag | 3540 |
| | | tttgttcaca tccccttctc caacccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttgggggagc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gccccctagtt ctggggcag cggggatcc | 3900 |
| | | gccaccatgg gcgaaatctg gaagcaacat gaggacgcac tgcaaaagtt ctttgcattg | 3960 |
| | | ctgttgctgt tggcccctgtt gctgctgctg gcactgctgc tgcacttgct ggcatttgaa | 4020 |
| | | ggtggttctg gtggcggcag cggcggtaag ttcttgctgc tgttggcgtt gctggccctg | 4080 |
| | | ctgctgctgg cgctgttgtt gcatctgctg gcttttggg aagcgctgaa tcagttcgaa | 4140 |
| | | gatctggcga agcaggggtgg cagcggtggc ggtagcgcg gtgagatttg gaaacagcat | 4200 |
| | | gaggatgcgc tgcagaaatt cttcgcgttg ttgctgttgt tggcattgtt gctgctgttg | 4260 |
| | | gctctgctgt tgcatttgtt ggcctttcaaa ggtggtagcg gtggtggttc cggtggtgag | 4320 |
| | | tttctgttgt tgttggcgct gctggccttg ctgttgctgg ctctgttgct gcacctgctg | 4380 |
| | | gcgttctggg aagcactgaa ccaatttgag gacctggcga aacaggcggc accggtagta | 4440 |
| | | gcagtgagca agggcgagga gctgttcacc ggggtggtgc ccatcctggt cgagctggac | 4500 |
| | | ggcgacgtaa acggccacaa gttcagcgtg tccggcgagg gcgagggcga tgccacctac | 4560 |
| | | ggcaagctga ccctgaagtt catttgcacc accggcaagc tgcccgtgcc ctggcccacc | 4620 |
| | | ctcgtgacca ccctgaccta cggcgtgcag tgcttcagcc gctaccccga ccacatgaag | 4680 |
| | | cagcacgact tcttcaagtc cgccatgccc gaaggctacg tccaggagcg caccatcttc | 4740 |
| | | ttcaaggacg acggcaacta caagacccgc gccgaggtga agttcgaggg cgacaccctg | 4800 |
| | | gtgaaccgca tcgagctgaa gggcatcgac ttcaaggagg acggcaacat cctggggcac | 4860 |
| | | aagctggagt acaactacaa cagccacaac gtctatatca tggccgacaa gcagaagaac | 4920 |
| | | ggcatcaagg tgaacttcaa gatccgccac aacatcgagg acggcagcgt gcagctcgcc | 4980 |
| | | gaccactacc agcagaacac ccccatcggc gacggccccg tgctgctgcc cgacaaccac | 5040 |
| | | tacctgagca cccagtccgc cctgagcaaa gaccccaacg agaagcgcga tcacatggtc | 5100 |
| | | ctgctggagt tcgtgaccgc cgccgggatc actctcggca tggacgagct gtacaagtaa | 5160 |
| | | gaattcgata tcaagcttat cgataatcaa cctctgatt acaaaatttg tgaaagattg | 5220 |
| | | actggtattc ttaactatgt tgctccttt acgctatgtg gatacgctgc tttaatgcct | 5280 |
| | | ttgtatcatg ctattgcttc ccgtatggct ttcatttct cctccttgta taaatcctgg | 5340 |
| | | ttgctgtctc tttatgagga gttgtggccc gttgtcaggc aacgtggcgt ggtgtgcact | 5400 |
| | | gtgtttgctg acgcaacccc cactggttgg ggcattgcca ccacctgtca gctcctttcc | 5460 |
| | | gggactttcg ctttccccct cccattgcc acggcggaac tcatcgccgc ctgccttgcc | 5520 |
| | | cgctgctgga caggggctcg gctgttgggc actgacaatt ccgtggtgtt gtcggggaaa | 5580 |
| | | tcatcgtcct ttccttggct gtctgcctgt gttgccacct ggattctgcg cgggacgtcc | 5640 |
| | | ttctgctacg tcccttcggc cctcaatcca gcggaccttc cttcccgcgg cctgctgccg | 5700 |
| | | gctctgcggc ctcttccgcg tcttcgcctt cgccctcaga cgagtcggat ctccctttgg | 5760 |
| | | gccgcctccc cgcatcgata ccgtcgacct cgagacctag aaaaacatgg agcaatcaca | 5820 |
| | | agtagcaata cagcagctac caatgctgat tgtgcctggc tagaagcaca agaggaggag | 5880 |
| | | gaggtgggtt ttccagtcac acctcaggta cctttaagac caatgactta caaggcagct | 5940 |
| | | gtagatctta gccactttttt aaaagaaaag gggggactgg aagggctaat tcactcccaa | 6000 |

TABLE 4-continued

List of Sequences

| Seq ID No | Name | Sequence | |
|---|---|---|---|
| | | cgaagacaag atatccttga tctgtggatc taccacacac aaggctactt ccctgattgg | 6060 |
| | | cagaactaca caccagggcc agggatcaga tatccactga cctttggatg gtgctacaag | 6120 |
| | | ctagtaccag ttgagcaaga gaaggtagaa gaagccaatg aaggagagaa caccccgcttg | 6180 |
| | | ttacaccctg tgagcctgca tgggatggat gacccggaga gagaagtatt agagtggagg | 6240 |
| | | tttgacagcc gcctagcatt tcatcacatg gcccgagagc tgcatccgga ctgtactggg | 6300 |
| | | tctctctggt tagaccagat ctgagcctgg gagctctctg gctaactagg gaacccactg | 6360 |
| | | cttaagcctc aataaagctt gccttgagtg cttcaagtag tgtgtgcccg tctgttgtgt | 6420 |
| | | gactctggta actagagatc cctcagaccc ttttagtcag tgtggaaaat ctctagcagg | 6480 |
| | | gcccgtttaa acccgctgat cagcctcgac tgtgccttct agttgccagc catctgttgt | 6540 |
| | | ttgcccctcc cccgtgcctt ccttgaccct ggaaggtgcc actcccactg tcctttccta | 6600 |
| | | ataaaatgag gaaattgcat cgcattgtct gagtaggtgt cattctattc ttgatttata | 6660 |
| | | ggtggggcag gacagcaagg gggaggattg ggaagacaat agcaggcatg ctggggatgc | 6720 |
| | | ggtgggctct atggcttctg aggcggaaag aaccagctgg ggctctaggg ggtatcccca | 6780 |
| | | cgcgcccgt agcggcgcat taagcgcggc gggtgtggtg gttacgcgca gcgtgaccgc | 6840 |
| | | tacacttgcc agcgccctag cgcccgctcc tttcgctttc ttcccttcct ttctcgccac | 6900 |
| | | gttcgccggc tttccccgtc aagctctaaa tcggggggctc ccttttagggt tccgatttag | 6960 |
| | | tgctttacgg cacctcgacc ccaaaaaact tgattagggt gatggttcac gtagtgggcc | 7020 |
| | | atcgccctga tagacgtttt ttcgcccttt gacgttggag tccacgttct ttaatagtgg | 7080 |
| | | actcttgttc caaactggaa caacactcaa ccctatctcg gtctattctt ttgatttata | 7140 |
| | | agggattttg ccgatttcgg cctattggtt aaaaaatgag ctgatttaac aaaaatttaa | 7200 |
| | | cgcgaattaa ttctgtggaa tgtgtgtcag ttagggtgtg gaaagtcccc aggctcccca | 7260 |
| | | gcaggcagaa gtatgcaaag catgcatctc aattagtcag caaccaggtg tggaaagtcc | 7320 |
| | | ccaggctccc cagcaggcag aagtatgcaa agcatgcata tcaattagtc agcaaccata | 7380 |
| | | gtcccgcccc taactccgcc catcccgccc ctaactccgc ccagttccgc ccattctccg | 7440 |
| | | ccccatggct gactaatttt ttttatttat gcagaggccg aggccgcctc tgcctctgag | 7500 |
| | | ctattccaga agtagtgagg aggcttttt ggaggcctag gcttttgcaa aaagctcccg | 7560 |
| | | ggagcttgta tatccatttt cggatctgat cagcacgtgt tgacaattaa tcatcggcat | 7620 |
| | | agtatatcgg catagtataa tacgacaagg tgaggaacta aaccatggcc aagttgacca | 7680 |
| | | gtgccgttcc ggtgctcacc gcgcgcgacg tcgccggagc ggtcgagttc tggaccgacc | 7740 |
| | | ggctcgggtt ctcccgggac ttcgtggagg acgacttcgc cggtgtggtc cgggacgacg | 7800 |
| | | tgaccctgtt catcagcgcg gtccaggacc aggtggtgcc ggacaacacc ctggcctggg | 7860 |
| | | tgtgggtgcg cggcctggac gagctgtacg ccgagtggtc ggaggtcgtg tccacgaact | 7920 |
| | | tccgggacgc ctccgggccg gccatgaccg agatcggcga gcagccgtgg gggcgggagt | 7980 |
| | | tcgccctgcg cgacccggcc ggcaactgcg tgcacttcgt ggccgaggag caggactgac | 8040 |
| | | acgtgctacg agatttcgat tccaccgccg ccttctatga aaggttgggc ttcggaatcg | 8100 |
| | | ttttccggga cgccggctgg atgatcctcc agcgcgggga tctcatgctg gagttcttcg | 8160 |
| | | cccaccccaa cttgttttat gcagcttata atggttacaa ataaagcaat agcatcacaa | 8220 |
| | | atttcacaaa taaagcattt ttttcactgc attctagttg tggtttgtcc aaactcatca | 8280 |
| | | atgtatctta tcatgtctgt ataccgtcga cctctagcta gagcttggcg taatcatggt | 8340 |
| | | catagctgtt tcctgtgtga aattgttatc cgctcacaat tccacacaac atacgagccg | 8400 |
| | | gaagcataaa gtgtaaagcc tggggtgcct aatgagtgag ctaactcaca ttaattgcgt | 8460 |
| | | tgcgctcact gcccgctttc cagtcgggaa acctgtcgtg ccagctgcat taatgaatcg | 8520 |
| | | gccaacgcgc ggggagaggc ggtttgcgta ttgggcgctc ttccgcttcc tcgctcactg | 8580 |
| | | actcgctgcg ctcggtcgtt cggctgcggc gagcggtatc agctcactca aaggcggtaa | 8640 |
| | | tacggttatc cacagaatca ggggataacg caggaaagaa catgtgagca aaaggccagc | 8700 |
| | | aaaaggccag gaaccgtaaa aaggccgcgt tgctggcgtt ttttccatagg ctccgcccc | 8760 |
| | | ctgacgagca tcacaaaaat cgacgctcaa gtcagaggtg gcgaaacccg acaggactat | 8820 |
| | | aaagatacca ggcgtttccc cctggaagct ccctcgtgcg ctctcctgtt ccgaccctgc | 8880 |
| | | cgcttaccgg atacctgtcc gcctttctcc cttcgggaag cgtggcgctt tctcatagct | 8940 |
| | | cacgctgtag gtatctcagt tcggtgtagg tcgttcgctc caagctgggc tgtgtgcacg | 9000 |
| | | aaccccccgt tcagcccgac cgctgcgcct tatccggtaa ctatcgtctt gagtccaacc | 9060 |
| | | cggtaagaca cgacttatcg ccactggcag cagccactgg taacaggatt agcagagcga | 9120 |
| | | ggtatgtagg cggtgctaca gagttcttga agtggtggcc taactacggc tacactagaa | 9180 |
| | | gaacagtatt tggtatctgc gctctgctga agccagttac cttcggaaaa agagttggta | 9240 |
| | | gctcttgatc cggcaaacaa accaccgctg gtagcggtgg ttttttttgtt tgcaagcagc | 9300 |
| | | agattacgcg cagaaaaaaa ggatctcaag aagatccttt gatcttttct acggggtctg | 9360 |
| | | acgctcagtg gaacgaaaac tcacgttaag ggattttggt catgagatta tcaaaaagga | 9420 |
| | | tcttcaccta gatccttta aattaaaaat gaagttttaa atcaatctaa agtatatatg | 9480 |
| | | agtaaacttg gtctgacagt taccaatgct taatcagtga ggcacctatc tcagcgatct | 9540 |
| | | gtctatttcg ttcatccata gttgcctgac tccccgtcgt gtagataact acgatacggg | 9600 |
| | | agggcttacc atctggcccc agtgctgcaa tgataccgcg agacccacgc tcaccggctc | 9660 |
| | | cagatttatc agcaataaac cagccagccg gaagggccga gcgcagaagt ggtcctgcaa | 9720 |
| | | ctttatccgc ctccatccag tctattaatt gttgccggga agctagagta agtagttcgc | 9780 |
| | | cagttaatag tttgcgcaac gttgttgcca ttgctacagg catcgtggtg tcacgctcgt | 9840 |
| | | cgtttggtat ggcttcattc agctccggtt cccaacgatc aaggcgagtt acatgatccc | 9900 |
| | | ccatgttgtg caaaaaagcg gttagctcct tcggtcctcc gatcgttgtc agaagtaagt | 9960 |
| | | tggccgcagt gttatcactc atggttatgg cagcactgca taattctctt actgtcatgc | 10020 |
| | | catccgtaag atgcttttct gtgactggtg agtactcaac caagtcattc tgagaatagt | 10080 |
| | | gtatgcggcg accgagttgc tcttgcccgg cgtcaatacg ggataatacc gcgccacata | 10140 |
| | | gcagaacttt aaaagtgctc atcattggaa aacgttcttc gggcgaaaa ctctcaagga | 10200 |
| | | tcttaccgct gttgagatcc agttcgatgt aacccactcg tgcacccaac tgatcttcag | 10260 |
| | | catcttttac tttcaccagc gtttctgggt gagcaaaaac aggaaggcaa aatgccgcaa | 10320 |
| | | aaaagggaat aagggcgaca cggaaatgtt gaatactcat actcttcctt tttcaatatt | 10380 |
| | | attgaagcat ttatcagggt tattgtctca tgagcggata catatttgaa tgtatttaga | 10440 |

TABLE 4-continued

List of Sequences

| Seq ID No | Name | Sequence | |
|---|---|---|---|
| | | aaaataaaca aatagggtt ccgcgcacat ttccccgaaa agtgccacct gac | 10493 |
| 111 | AM1 | EIWKQHEDAL QKFFALLLLL ALLLLLALLL HLLAFEGGSG GGSGGKFLLL LALLALLLLA | 60 |
| | | LLLHLLAFWE ALNQFEDLAK QGGSGGGSGG EIWKQHEDAL QKFFALLLLL ALLLLLALLL | 120 |
| | | HLLAFKGGSG GGSGGEFLLL LALLALLLLA LLLHLLAFWE ALNQFEDLAK Q | 171 |
| 112 | GLSloop Q5L | EIWKQHEDAL QKFEEALNQF EDLKQLGGSG KGSGGEIKQR HEDALRKFEE ALKRFEDLKQ | 60 |
| | | KGGSGEIWKQ HEDALQKFEE ALNQFEDLKQ LGGSGKGSGG EIKQRHEDAL RKFEEALKRF | 120 |
| | | EDRVQK | 126 |
| 113 | C L5S | EIWKSHEDAL QKFEEALNQF EDLKQLGGSG KGSGGEIKQR HEDALRKFEE ALKRFEDLKQ | 60 |
| | | EGGCGRIWKE HEDALQKFEE ALNQFEDLKQ LGGSGKGSGG EIKQRHEDAL RKFEEALKRF | 120 |
| | | EDRVQK | 126 |
| 114 | C V124K | EIWKLHEDAL QKFEEALNQF EDLKQLGGSG KGSGGEIKQR HEDALRKFEE ALKRFEDLKQ | 60 |
| | | KGGCGRIWKE HEDALQKFEE ALNQFEDLKQ LGGSGKGSGG EIKQRHEDAL RKFEEALKRF | 120 |
| | | EDRKQK | 126 |
| 115 | 1191 min1 5 (EC) | ttcttgaaga cgaaagggcc tcgtgatacg cctattttta taggttaatg tcatgataat | 60 |
| | | aatggtttct tagacgtcag gtggcacttt tcggggaaat gtgcgcggaa ccctatttg | 120 |
| | | tttattttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt tcgccccga agaacgtttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc ctttttgata atctcatgac caaaatccct aacgtgagt tttcgttcca | 1200 |
| | | ctgagcgtca gaccccgtag aaaagatcaa aggatcttct tgagatcctt ttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacataccte gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | gggggggttcg tgcacacaga cccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatgaaaaa cgccagcaac gcggcctttt tacggttcct | 1860 |
| | | ggccttttgc tggccttttg ctcacatgtt ctttcctgcg ttatccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacaccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctc cggtaaagct catcacagga ttcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg ttttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttaactgg acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca gacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattgcgtca aatttggga gtggtgaatc | 3060 |
| | | cgttagcgag gtgccgccga cttccattca ggtcgaggtg gcccggctcc atgcaccgcg | 3120 |
| | | acgcaacgcg gggaggcaga caaggtatag gcggcgccct acaatcatg caacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga agaatcat | 3360 |

TABLE 4-continued

List of Sequences

| Seq ID No | Name | Sequence | |
|---|---|---|---|
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg cttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga gacgggcaac agctgattgc | 3900 |
| | | ccttcaccgc ctggccctga gagagttgca gcaagcggtc cacgctggtt tgcccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgcaccca | 4560 |
| | | ccacgctggc acccagttga tcggcgcgag atttaatcgc cgcgacaatt tgcgacggcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc acttttttccc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggcgt tgagcaccgc ccgcaagg aatggtgcat gcaaggagat ggcgcccaac | 5040 |
| | | agtcccccgg ccacggggcc tgccaccata cccacgccga aacaagcgct catgagcccg | 5100 |
| | | aagtggcgag cccgatcttc cccatcggtg atgtcggcga tataggcgcc agcaaccgca | 5160 |
| | | cctgtggcgc cggtgatgcc ggccacgatg cgtccggcgt agaggatcga gatctcgatc | 5220 |
| | | ccgcgaaatt aatacgactc actataggg aattgtgagc ggataacaat tcccctctag | 5280 |
| | | aaataatttt gtttaacttt aagaaggaga tataccatgg gcagcagcca tcatcatcat | 5340 |
| | | catcacggcg gcgacggcga gaacttgtat tttcaagcta gcggatccat gggagagatc | 5400 |
| | | tggaagagcc acgaagacgc gctgcagaaa ttcgaggaag ccctgaacca gtttgaggat | 5460 |
| | | ctgaagcagc tgggcggtag cggtgaaggt gcggcgggt aaatctgaag acgcacgag | 5520 |
| | | gacgctctgc agaaattcga agaggcgctg aaccgtttcg aagatctgaa acaactgggc | 5580 |
| | | ggttgcgcc gtatctggaa ggagcacgaa gacgccacc agaaattcga ggaagctctg | 5640 |
| | | aaccaattcg aggatctgaa acagctgggc ggtagcggtg aaggtagcgg cggtgaaata | 5700 |
| | | tggaaacaac acgaggatgc tctgcaaaag tttgaggaag ccctgaaccg tcacgaagat | 5760 |
| | | cgtgtgcagc tggcaccggt ttaagaattc ctcgaggctg ctaacaaagc ccgaaaggaa | 5820 |
| | | gctgagttgg ctgctgccac cgctgagcaa taactagcat aacccttgg ggcctctaaa | 5880 |
| | | cgggtcttga ggggttttt gctgaaagga gaactatat ccggatatcc gcaagaggcc | 5940 |
| | | ccggcagtac cggcataacc aagcctatgc ctacagcatc cagggtgacg gtgccgagga | 6000 |
| | | tgacgatgag cgcattgtta gatttcatac acggtgcctg actgcgttag caatttaact | 6060 |
| | | gtgataaact accgcattaa agcttatcga tgataagctg tcaaacatga gaa | 6113 |
| 116 | 1191 min1 5 (FCK mam) | gctgcggcga gcggtatcag ctcactcaaa ggcggtaata cggttatcca cagaatcagg | 60 |
| | | ggataacgca ggaaagaaca tgtgagcaaa aggccagcaa aaggccagga accgtaaaaa | 120 |
| | | ggccgcgttg ctggcgtttt tccataggct ccgcccccct gacgagcatc acaaaaatcg | 180 |
| | | acgctcaagt cagaggtggc gaaacccgac aggactataa agataccagg cgtttccccc | 240 |
| | | tggaagctcc ctcgtgcgct ctcctgttcc gaccctgccg cttaccggat acctgtcgc | 300 |
| | | cttttctcct tcgggaagcg tggcgcttc tcatagctca cgctgtaggt atctcagttc | 360 |
| | | ggtgtaggtc gttcgctcca agctgggctg tgtgcacgaa ccccccgttc agcccgaccg | 420 |
| | | ctgcgcctta tccggtaact atcgtcttga gtccaacccg gtaagacacg acttatcgcc | 480 |
| | | actggcagca gccactggta acaggattag cagagcgagg tatgtaggcg gtgctacaga | 540 |
| | | gttcttgaag tggtggccta actacggcta cactagaaga acagtatttg gtatctgcgc | 600 |
| | | tctgctgaag ccagttacct tcggaaaaag agttggtagc tcttgatccg gcaaacaaac | 660 |
| | | caccgctggt agcggtggtt tttttgtttg caagcagcag attacgcgca gaaaaaaagg | 720 |
| | | atctcaagaa gatcctttga tcttttctac ggggtctgac gctcagtgga acgaaaactc | 780 |
| | | acgttaaggg attttggtca tgagattatc aaaaaggatc ttcacctaga tccttttaaa | 840 |
| | | ttaaaaatga agttttaaat caatctaaag tatatatgag taaacttggt ctgacagtta | 900 |
| | | ccaatgctta atcagtgagg cacctatctc agcgatctgt ctatttcgtt catccatagt | 960 |
| | | tgcctgactc cccgtcgtgt agataactac gatacgggag ggcttaccat ctggccccag | 1020 |
| | | tgctgcaatg ataccgcgag acccacgctc accggctcca gatttatcag caataaacca | 1080 |
| | | gccagccgga agggccgagc gcagaagtgg tcctgcaact ttatccgcct ccatccagtc | 1140 |
| | | tattaattgt tgccgggaag ctagagtaag tagttcgcca gttaatagtt tgcgcaacgt | 1200 |
| | | tgttgccatt gctacaggca tcgtggtgtc acgctcgtcg tttggtatgg cttcattcag | 1260 |
| | | ctccggttcc caacgatcaa ggcgagttac atgatccccc atgttgtgca aaaaagcggt | 1320 |
| | | tagctccttc ggtcctccga tcgttgtcag aagtaagttg gccgcagtgt tatcactcat | 1380 |
| | | ggttatggca gcactgcata attctcttac tgtcatgcca tccgtaagat gcttttctgt | 1440 |
| | | gactggtgag tactcaacca agtcattctg agaatagtgt atgcggcgac cgagttgctc | 1500 |
| | | ttgcccggcg tcaatacggg ataataccgc gccacatagc agaactttaa aagtgctcat | 1560 |
| | | cattggaaaa cgttcttcgg ggcgaaaact ctcaaggatc ttaccgctgt tgagatccag | 1620 |

TABLE 4-continued

List of Sequences

| Seq ID No | Name | Sequence | |
|---|---|---|---|
| | | ttcgatgtaa cccactcgtg cacccaactg atcttcagca tcttttactt tcaccagcgt | 1680 |
| | | ttctgggtga gcaaaaacag gaaggcaaaa tgccgcaaaa aagggaataa gggcgacacg | 1740 |
| | | gaaatgttga atactcatac tcttccttt tcaatattat tgaagcattt atcagggtta | 1800 |
| | | ttgtctcatg agcggataca tatttgaatg tatttagaaa aataaacaaa taggggttcc | 1860 |
| | | gcgcacattt ccccgaaaag tgccacctga c | 1891 |
| 117 | 1191 min1 5 | EIWKSHEDAL QKFEEALNQF EDLKQLGGSG EGSGGEIWKQ HEDALQKFEE ALNRFEDLKQ | 60 |
| | | LGGCGRIWKE HEDAHQKFEE ALNQFEDLKQ LGGSGEGSGG EIWKQHEDAL QKFEEALNRH | 120 |
| | | EDRVQL | 126 |
| 118 | GL Van Core (EC) | ttcttgaaga cgaaagggcc tcgtgatacg cctattttta taggttaatg tcatgataat | 60 |
| | | aatggtttct tagacgtcag gtggcacttt tcggggaaat gtgcgcggaa ccctatttg | 120 |
| | | tttatttttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt tcgccccga gaacgttttt ccaatgatga gcacttttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacgatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc ctttttgata atctcatgac caaaatccct aacgtgagt tttcgttcca | 1200 |
| | | ctgagcgtca gaccccgtag aaaagatcaa aggatcttct tgagatcctt ttttttctgcg | 1260 |
| | | cgtaatctgc tgcttgcaaa caaaaaaacc accgcgccag cggtggtttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaa | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacacccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg tttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca acccccgcca cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctgg aattcttgga tggttgaatcc | 3060 |
| | | cgttagcgag gtgccgccgg cttccattca ggtcgaggtg gcccggctcc atgcaccgcg | 3120 |
| | | acgcaacgcg gggaggcaga caaggtatag gcggcgcct acaatccatg ccaacccgtt | 3180 |
| | | ccatgtgctc gccgaggcgg cataaatcgc cgtgacgatc agcggtccag tgatcgaagt | 3240 |
| | | taggctgta agagccgcga gcgatccttg aagctgtccc tgatggtcgt catctacctg | 3300 |
| | | cctggacagc atggcctgca acgcgggcat cccgatgccg ccggaagcga agaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |

TABLE 4-continued

List of Sequences

| Seq ID No | Name | Sequence | | | | | |
|---|---|---|---|---|---|---|---|
| | | gcgtattggg | cgccagggtg | gtttttcttt | tcaccagtga | gacgggcaac | agctgattgc | 3900 |
| | | ccttcaccgc | ctggccctga | gagagttgca | gcaagcggtc | cacgctggtt | tgccccagca | 3960 |
| | | ggcgaaaatc | ctgtttgatg | gtggttaacg | gcgggatata | acatgagctg | tcttcggtat | 4020 |
| | | cgtcgtatcc | cactaccgag | atatccgcac | caacgcgcag | cccggactcg | gtaatggcgc | 4080 |
| | | gcattgcgcc | cagcgccatc | tgatcgttgg | caaccagcat | cgcagtggga | acgatgccct | 4140 |
| | | cattcagcat | ttgcatggtt | tgttgaaaac | cggacatggc | actccagtcg | ccttcccgtt | 4200 |
| | | ccgctatcgg | ctgaatttga | ttgcgagtga | gatatttatg | ccagccagcc | agacgcagac | 4260 |
| | | gcgccgagac | agaacttaat | gggcccgcta | acagcgcgat | ttgctggtga | cccaatgcga | 4320 |
| | | ccagatgctc | cacgcccagt | cgcgtaccgt | cttcatggga | gaaaataata | ctgttgatgg | 4380 |
| | | gtgtctggtc | agagacatca | agaaataacg | ccggaacatt | agtgcaggca | gcttccacag | 4440 |
| | | caatggcatc | ctggtcatcc | agcggatagt | taatgatcag | cccactgacg | cgttgcgcga | 4500 |
| | | gaagattgtg | caccgccgct | ttacaggctt | cgacgccgct | tcgttctacc | atcgacacca | 4560 |
| | | ccacgctggc | acccagttga | tcggcgcgag | atttaatcgc | cgcgacaatt | tgcgacggcg | 4620 |
| | | cgtgcagggc | cagactggag | gtggcaacgc | caatcagcaa | cgactgtttg | cccgccagtt | 4680 |
| | | gttgtgccac | gcggttggga | atgtaattca | gctccgccat | cgccgcttcc | actttttccc | 4740 |
| | | gcgttttcgc | agaaacgtgg | ctggcctggt | tcaccacgcg | ggaaacggtc | tgataagaga | 4800 |
| | | caccggcata | ctctgcgaca | tcgtataacg | ttactggttt | cacattcacc | accctgaatt | 4860 |
| | | gactctcttc | cgggcgctat | catgccatac | cgcgaaaggt | tttgcgccat | tcgatggtgt | 4920 |
| | | ccgggatctc | gacgctctcc | cttatgcgac | tcctgcatta | ggaagcagcc | cagtagtagg | 4980 |
| | | ttgaggccgt | tgagcaccgc | cgccgcaagg | aatggtgcat | gcaaggagat | ggcgcccaac | 5040 |
| | | agtccccccgg | ccacggggcc | tgccaccata | cccacgccga | aacaagcgct | catgagcccg | 5100 |
| | | aagtggcgag | cccgatcttc | cccatcggtg | atgtcggcga | tataggcgcc | agcaaccgca | 5160 |
| | | cctgtggcgc | cggtgatgcc | ggccacgatg | cgtccggcgt | agaggatcga | gatctcgatc | 5220 |
| | | ccgcgaaatt | aatcgactc | actataggg | aattgtgagc | ggataacaat | tcccctctag | 5280 |
| | | aaataatttt | gtttaacttt | aagaaggaga | tataccatgg | gcagcagcca | tcatcatcat | 5340 |
| | | catcacggcg | gcgacggcga | gaacttgtat | tttcaagcta | gcggatccat | gggagagctg | 5400 |
| | | ctgaagcagc | tggaagacct | gctgcagaaa | ctggaggaac | tgctgaacca | gctggaggat | 5460 |
| | | ctgaagcagc | tgggcggtag | cggcaaaggt | agcggcggtg | agctgaagca | gcgtctggaa | 5520 |
| | | gacctgctgc | gtaagctgga | ggaactgctg | aaacgtctgg | aggatctgaa | acaaaaaggc | 5580 |
| | | ggttgcgcc | gtctgctgaa | ggaactggaa | gacctgctgc | aaaagctgga | ggagctgctg | 5640 |
| | | aaccagctgg | aagatctgaa | acaactgggc | ggtagcggca | agggtagcgg | cggtgagctg | 5700 |
| | | aaacagcgtc | tggaagacct | gctgagaaag | ttcgaagagc | tgctgaaacg | tctggaggat | 5760 |
| | | ctgaagcaaa | aagcaccggt | ttaagaattc | ctcgaggctg | ctaacaaagc | ccgaaaggaa | 5820 |
| | | gctgagttgg | ctgctgccac | cgctgagcaa | taactagcat | aaccccttgg | ggcctctaaa | 5880 |
| | | cgggtcttga | ggggttttt | gctgaaagga | ggaactatat | ccggatatcc | cgcaagaggc | 5940 |
| | | ccggcagtac | cggcataacc | aagcctatgc | ctacagcatc | caggtgacg | gtgccgagga | 6000 |
| | | tgacgatgag | cgcattgtta | gatttcatac | acggtgcctg | actgcgttag | caatttaact | 6060 |
| | | gtgataaact | accgcattaa | agcttatcga | tgataagctg | tcaaacatga | gaa | 6113 |
| 119 | GL Van Core (FCK mam) | gtcgacggat | cgggagatct | cccgatcccc | tatggtgcac | tctcagtaca | atctgctctg | 60 |
| | | atgccgcata | gttaagccag | tatctgctcc | ctgcttgtgt | gttggaggtc | gctgagtagt | 120 |
| | | gcgcgagcaa | aatttaagct | acaacaaggc | aaggcttgac | cgacaattgc | atgaagaatc | 180 |
| | | tgcttagggt | taggcgtttt | gcgctgcttc | gcgatgtacg | ggccagatat | acgcgttgac | 240 |
| | | attgattatt | gactagttat | taatagtaat | caattacggg | gtcattagtt | catagcccat | 300 |
| | | atatggagtt | ccgcgttaca | taacttacgg | taaatggccc | gcctggctga | ccgcccaacg | 360 |
| | | acccccgccc | attgacgtca | ataatgacgt | atgttcccat | agtaacgcca | atagggactt | 420 |
| | | tccattgacg | tcaatgggtg | gagtatttac | ggtaaactgc | ccacttggca | gtacatcaag | 480 |
| | | tgtatcatat | gccaagtacg | ccccctattg | acgtcaatga | cggtaaatgg | cccgcctggc | 540 |
| | | attatgccca | gtacatgacc | ttatgggact | ttcctacttg | gcagtacatc | tacgtattag | 600 |
| | | tcatcgctat | taccatggtg | atgcggtttt | ggcagtacat | caatgggcgt | ggatagcggt | 660 |
| | | ttgactcacg | gggatttcca | agtctccacc | ccattgacgt | caatgggagt | ttgttttggc | 720 |
| | | accaaaatca | acgggacttt | ccaaaatgtc | gtaacaactc | cgccccattg | acgcaaatgg | 780 |
| | | gcggtaggcg | tgtacggtgg | gaggtctata | taagcagcgc | gttttgcctg | tactgggtct | 840 |
| | | ctctggttag | accagatctg | agcctgggag | ctctctggct | aactagggaa | cccactgctt | 900 |
| | | aagcctcaat | aaagcttgcc | ttgagtgctt | caagtagtgt | gtgcccgtct | gttgtgtgac | 960 |
| | | tctggtaact | agagatccct | cagaccctt | tagtcagtgt | ggaaaatctc | tagcagtggc | 1020 |
| | | gcccgaacag | ggacttgaaa | gcgaaaggga | aaccagagga | gctctctcga | cgcaggactc | 1080 |
| | | ggcttgctga | agcgcgcacg | gcaagaggcg | aggggcggcg | actggtgagt | acgccaaaaa | 1140 |
| | | ttttgactag | cggaggctag | aaggagagag | atgggtgcga | gagcgtcagt | attaagcggg | 1200 |
| | | ggagaattag | atcgcgatgg | gaaaaaattc | ggttaaggcc | aggggggaaag | aaaaaatata | 1260 |
| | | aattaaaaca | tatagtatgg | gcaagcaggg | gctagaacg | attcgcagtt | aatcctggcc | 1320 |
| | | tgttagaaac | atcagaaggc | tgtagacaaa | tactgggaca | gctacaacca | tcccttcaga | 1380 |
| | | caggatcaga | gaacttagat | cattatata | atacagtagc | aaccctctat | tgtgtgcatc | 1440 |
| | | aaaggataga | gataaaagac | accaaggaag | ctttagacaa | gatagaggaa | gagcaaaaca | 1500 |
| | | aaagtaagac | caccgcacag | caagcggccg | ctgatcttca | gacctggagg | aggagatatg | 1560 |
| | | agggacaatt | ggagaagtga | attatataaa | tataaagtag | taaaaattga | accattagga | 1620 |
| | | gtagcaccca | ccaaggcaaa | gagaagagtg | gtgcagagag | aaaaaagagc | agtgggaata | 1680 |
| | | ggagctttgt | tccttgggtt | cttgggagca | gcaggaagca | ctatgggcgc | agcgtcaatg | 1740 |
| | | acgctgacgg | tacaggccag | acaattattg | tctgatatag | tgcagcagca | gaacaatttg | 1800 |
| | | ctgagggcta | ttgaggcgca | acagcatctg | ttgcaactca | cagtctgggg | catcaagcag | 1860 |
| | | ctccaggcaa | gaatcctggc | tgtggaaaga | tacctaaagg | atcaacagct | cctggggatt | 1920 |
| | | tggggttgct | ctggaaaact | catttgcacc | actgctgtgc | cttggaatgc | tagttggagt | 1980 |
| | | aataaatctc | tggaacagat | ttggaatcac | acgacctgga | tggagtggga | cagagaaatt | 2040 |
| | | aacaattaca | caagcttaat | acactcctta | attgaagaat | cgcaaaacca | gcaagaaaag | 2100 |

TABLE 4-continued

List of Sequences

| Seq ID No | Name | Sequence | |
|---|---|---|---|
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tgggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatggggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggggaa gggaaggaga gatgaattag cttccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttggagg tggggggaggt aggaagagcg atgatcactt gtggactaag | 3540 |
| | | tttgttcaca tccccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcagtcaagc cggttctccg | 3840 |
| | | tttgcactca ggagcacggg caggcgagtg gcccctagtt ctggggcag cggggatcc | 3900 |
| | | atgggagagc tgctgaagca gctggaagac ctgctgcaga aactggagga actgctgaac | 3960 |
| | | cagctggagg atctgaagca gctgggcggt agcggcagag gtagcggcgg tgagctgaag | 4020 |
| | | cagcgtctgg aagacctgct gcgtaagctg gaggaactgc tgaaacgtct ggaggatctg | 4080 |
| | | aaacaaaaag gcggttgcgg ccgtctgctg aaggaactgg aagacctgct gcaaaagctg | 4140 |
| | | gaggagctgc tgaaccagct ggaagatctg aaacaactgg gcggtagcgg caagggtagc | 4200 |
| | | ggcggtgagc tgaaacagcg tctggaagac ctgctgaaga agttcgaaga gctgctgaaa | 4260 |
| | | cgtctggagg atctgaagca aaaagcaccg gtagtagcag tgagcaaggg cgaggagctg | 4320 |
| | | ttcaccgggg tggtgcccat cctggtcgag ctggacggc acgtaaacgg ccacaagttc | 4380 |
| | | agcgtgtccg gcgagggcga gggcgatgcc acctacggca agctgaccct gaagttcatt | 4440 |
| | | tgcaccaccg gcaagctgcc cgtgccctgg cccaccctcg tgaccaccct gacctacggc | 4500 |
| | | gtgcagtgct tcagccgcta ccccgaccac atgaagcagc acgacttctt caagtccgcc | 4560 |
| | | atgcccgaag gctacgtcca ggagcgcacc atcttcttca aggacgacgg caactacaag | 4620 |
| | | acccgcgccg aggtgaagtt cgagggcgac accctggtga accgcatcga gctgaagggc | 4680 |
| | | atcgacttca aggaggacgg caacatcctg gggcacaagc tggagtacaa ctacaacagc | 4740 |
| | | cacaacgtct atatcatggc cgacaagcag aagaacggca tcaaggtgaa cttcaagatc | 4800 |
| | | cgccacaaca tcgaggacgg cagcgtgcag ctcgccgacc actaccagca gaacacccc | 4860 |
| | | atcggcgacg gccccgtgct gctgcccgac aaccactacc tgagcaccca gtccgccctg | 4920 |
| | | agcaaagacc ccaacgagaa gcgcgatcac atggtcctgc tggagttcgt gaccgccgcc | 4980 |
| | | gggatcactc tcggcatgga cgagctgtac aagtaagaat tcgatatcaa gcttatcgat | 5040 |
| | | aatcaacctc tggattacaa aatttgtgaa agattgactg gtattcttaa ctatgttgct | 5100 |
| | | cctttacgc tatgtggata cgctgcttta atgcctttgt atcatgctat tgcttcccgt | 5160 |
| | | atggctttca ttttctcctc cttgtataaa tcctggttgc tgtctcttta tgaggagttg | 5220 |
| | | tggcccgttg tcaggcaacg tggcgtggtg tgcactgtgt ttgctgacgc aaccccccact | 5280 |
| | | ggttgggca ttgccaccac ctgtcagctc ctttccggga ctttcgcttt ccccctcct | 5340 |
| | | attgccacg cggaactcat cgccgcctgc cttgcccgct gctggacagg ggctcggctg | 5400 |
| | | ttgggcactg acaattccgt ggtgttgtcg gggaaatcat cgtcctttcc ttggctgctc | 5460 |
| | | gcctgtgttg ccacctggat tctgcgcggg acgtccttct gctacgtccc ttcggccctc | 5520 |
| | | aatccagcgg accttcctc ccgcggcctg ctgccggctc tgcggcctct tccgcgtctt | 5580 |
| | | cgccttcgcc ctcagacgag tcggatctcc ctttgggccg cctccccgca tcgataccgt | 5640 |
| | | cgacctcgag acctagaaaa acatggagca atcacaagta gcaatacagc agctaccaat | 5700 |
| | | gctgattgtg cctggctaga agcacaagag gaggaggagg tgggttttcc agtcacacct | 5760 |
| | | caggtaccctt taagaccaat gacttacaag gcagctgtag atcttagcca cttttttaaaa | 5820 |
| | | gaaaaggggg gactgaaggg gctaattcac tcccaacgaa gacaagatat ccttgatctg | 5880 |
| | | tggatctacc acacacaagg ctacttccct gattggcaga actacacacc agggccaggg | 5940 |
| | | atcagatatc cactgacctt tggatggtgc tacaagctag taccagttga gcaagagaag | 6000 |
| | | gtagaagaag ccaatgaagg agaacaccc gcttgttac accctgtgag cctgcatggg | 6060 |
| | | atggatgacc cggagagaga agtattagag tggaggtttg acagccgcct agcatttcat | 6120 |
| | | cacatggccc gagagctgca tccggactgt actgggtctc tctggttaga ccagatctga | 6180 |
| | | gcctgggagc tctctggcta actagggaac ccactgctta agcctcaata aagcttgcct | 6240 |
| | | tgagtgcttc aagtagtgtg tgcccgtctg ttgtgtgact ctggtaacta gagatccctc | 6300 |
| | | agaccctttt agtcagtgtg gaaaatctct agcagggccc gtttaaaccc gctgatcagc | 6360 |
| | | ctcgactgtg ccttctagtt gccagccatc tgttgtttgc cctcccccg tgccttcctt | 6420 |
| | | gaccctggaa ggtgccactc ccactgtcct ttcctaataa aatgaggaaa ttgcatcgca | 6480 |
| | | ttgtctgagt aggtgtcatt ctattctggg gggtggggtg ggcaggaca gcaagggga | 6540 |

TABLE 4-continued

List of Sequences

| Seq ID No | Name | Sequence | |
|---|---|---|---|
| | | ggattgggaa gacaatagca ggcatgctgg ggatgcggtg ggctctatgg cttctgaggc | 6600 |
| | | ggaaagaacc agctgggggct ctaggggggta tccccacgcg ccctgtagcg gcgcattaag | 6660 |
| | | cgcggcgggt gtggtggtta cgcgcagcgt gaccgctaca cttgccagcg ccctagcgcc | 6720 |
| | | cgctcctttc gctttcttcc cttcctttct cgccacgttc gccggctttc cccgtcaagc | 6780 |
| | | tctaaatcgg gggctcccctt tagggttccg atttagtgct ttacggcacc tcgaccccaa | 6840 |
| | | aaaacttgat tagggtgatg gttcacgtag tgggccatcg ccctgataga cggttttttcg | 6900 |
| | | cccttttgacg ttggagtcca cgttctttaa tagtggactc ttgttccaaa ctggaacaac | 6960 |
| | | actcaaccct atctcggtct attcttttga tttataaggg attttgccga tttcggccta | 7020 |
| | | ttggttaaaa aatgagctga tttaacaaaa atttaacgcg aattaattct gtggaatgtg | 7080 |
| | | tgtcagttag ggtgtgaaa gtccccaggc tccccagcag gcagaagtat gcaaagcatg | 7140 |
| | | catctcaatt agtcagcaac caggtgtgga aagtccccag gctccccagc aggcagaagt | 7200 |
| | | atgcaaagca tgcatctcaa ttagtcagca accatagtcc cgcccctaac tccgcccatc | 7260 |
| | | ccgcccctaa ctccgcccag ttccgcccat tctccgcccc atggctgact aattttttttt | 7320 |
| | | atttatgcag aggccgaggc cgcctctgcc tctgagctat tccagaagta gtgaggaggc | 7380 |
| | | ttttttggag gcctaggctt ttgcaaaaag ctcccgggag cttgtatatc catttttcgga | 7440 |
| | | tctgatcagc acgtgttgac aattaatcat cggcatagta tatcggcata gtataatacg | 7500 |
| | | acaaggtgag gaactaaacc atggccaagt tgaccagtgc cgttccggtg ctcaccgcgc | 7560 |
| | | gcgacgtcgc cggagcggtc gagttctgga ccgaccggct cgggttctcc cgggacttcg | 7620 |
| | | tggaggacga cttcgccggt gtggtccggg acgacgtgac cctgttcatc agcgcggtcc | 7680 |
| | | aggaccaggt ggtgccggac aacacccctgg cctgggtgtg ggtgcgcggc ctggacgagc | 7740 |
| | | tgtacgccga gtggtcggag gtcgtgtcca cgaacttccg ggacgcctcc gggccggcca | 7800 |
| | | tgaccgagat cggcgagcag ccgtggggggc gggagttcgc cctgcgcgac ccggccggca | 7860 |
| | | actgcgtgca cttcgtggcc gaggagcagg actgacagagt gctacgagat ttcgattcca | 7920 |
| | | ccgccgcctt ctatgaaagg ttgggcttcg gaatcgtttt ccgggacgcc ggctggatga | 7980 |
| | | tcctccagcg cggggatctc atgctggagt tcttcgccca ccccaacttg tttattgcag | 8040 |
| | | cttataatgg ttacaaataa agcaatagca tcacaaattt cacaaataaa gcattttttt | 8100 |
| | | cactgcattc tagttgtggt ttgtccaaac tcatcaatgt atcttatcat gtctgtatac | 8160 |
| | | cgtcgacctc tagctagagc ttggcgtaat catggtcata gctgtttcct gtgtgaaatt | 8220 |
| | | gttatccgct cacaattcca cacaacatac gagccggaag cataaagtgt aaagcctggg | 8280 |
| | | gtgcctaatg agtgagctaa ctcacattaa ttgcgttgcg ctcactgccc gctttccagt | 8340 |
| | | cgggaaacct gtcgtgccaa ctgcattaat gaatcggcca acgcgcgggg agaggcggtt | 8400 |
| | | tgcgtattgg gcgctcttcc gcttcctcgc tcactgactc gctgcgctcg gtcgttcggc | 8460 |
| | | tgcggcgagc ggtatcagct cactcaaagg cggtaatacg gttatccaca gaatcagggg | 8520 |
| | | ataacgcagg aaagaacatg tgagcaaaag gccagcaaaa ggccaggaac cgtaaaaagg | 8580 |
| | | ccgcgttgct ggcgtttttc cataggctcc gcccccctga cgagcatcac aaaaatcgac | 8640 |
| | | gctcaagtca gaggtggcga aacccgacag gactataaag ataccaggcg tttccccctg | 8700 |
| | | gaagctccct cgtgcgctct cctgttccga ccctgccgct taccggatac ctgtccgcct | 8760 |
| | | ttctcccttc gggaagcgtg gcgctttctc atagctcacg ctgtaggtat ctcagttcgg | 8820 |
| | | tgtaggtcgt tcgctccaag ctgggctgtg tgcacgaacc ccccgttcag cccgaccgct | 8880 |
| | | gcgccttatc cggtaactat cgtcttgagt ccaacccggt aagacacgac ttatcgccac | 8940 |
| | | tggcagcagc cactggtaac aggattagca gagcgaggta tgtaggcggt gctacagagt | 9000 |
| | | tcttgaagtg gtggcctaac tacggctaca ctagaagaac agtatttggt atctgcgctc | 9060 |
| | | tgctgaagcc agttaccttc ggaaaaagag ttggtagctc ttgatccggc aaacaaacca | 9120 |
| | | ccgctggtag cggtggtttt tttgtttgca agcagcagat tacgcgcaga aaaaaaggat | 9180 |
| | | ctcaagaaga tcctttgatc ttttctacgg gtctgacgc tcagtggaac gaaaactcac | 9240 |
| | | gttaagggat tttggtcatg agattatcaa aaaggatctt cacctagatc cttttaaatt | 9300 |
| | | aaaaatgaag ttttaaatca atctaaagta tatatgagta aacttggtct gacagttacc | 9360 |
| | | aatgcttaat cagtgaggca cctatctcag cgatctgtct atttcgttca tccatagttg | 9420 |
| | | cctgactccc cgtcgtgtag ataactacga tacgggaggg cttaccatct ggccccagtg | 9480 |
| | | ctgcaatgat accgcgagac ccacgctcac cggctccaga tttatcagca ataaaccagc | 9540 |
| | | cagccggaag ggccgagcgc agaagtggtc ctgcaacttt atccgcctcc atccagtcta | 9600 |
| | | ttaattgttg ccgggaagct agagtaagta gttcgccagt taatagtttg cgcaacgttg | 9660 |
| | | ttgccattgc tacaggcatc gtggtgtcac gctcgtcgtt tggtatggct tcattcagct | 9720 |
| | | ccggttccca acgatcaagg cgagttacat gatccccccat gttgtgcaaa aaagcggtta | 9780 |
| | | gctccttcgg tcctccgatc gttgtcagaa gtaagttggc cgcagtgtta tcactcatgg | 9840 |
| | | ttatggcagc actgcataat tctcttactg tcatgccatc cgtaagatgc ttttctgtga | 9900 |
| | | ctggtgagta ctcaaccaag tcattctgag aatagtgtat gcggcgaccg agttgctctt | 9960 |
| | | gcccggcgtc aatacgggat aataccgcgc cacatagcag aactttaaaa gtgctcatca | 10020 |
| | | ttggaaaacg ttcttcgggg cgaaaactct caaggatctt accgctgttg agatccagtt | 10080 |
| | | cgatgtaacc cactcgtgca cccaactgat cttcagcatc ttttactttc accagcgttt | 10140 |
| | | ctgggtgagc aaaaacagga aggcaaaatg ccgcaaaaaa gggaataagg gcgacacgga | 10200 |
| | | aatgttgaat actcatactc ttcctttttc aatattattg aagcatttat cagggttatt | 10260 |
| | | gtctcatgag cggatacata tttgaatgta tttagaaaaa taaacaaata ggggttccgc | 10320 |
| | | gcacatttcc ccgaaaagtg ccacctgac | 10349 |
| 120 | GL Van Core | ELLKQLEDLL QKLEELLNQL EDLKQLGGSG KGSGGELKQR LEDLLRKLEE LLKRLEDLKQ | 60 |
| | | KGGCGRLLKE LEDLLQKLEE LLNQLEDLKQ LGGSGKGSGG ELKQRLEDLL RKFEELLKRL | 120 |
| | | EDLKQK | 126 |
| 121 | minus 8ma quette (EC) | ttcttgaaga cgaaagggcc tcgtgatacg cctatttta taggttaatg tcatgataat | 60 |
| | | aatggtttct tagacgtcag gtggcacttt tcggggaaat gtgcgcggaa cccctatttg | 120 |
| | | tttatttttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tcccttttt gcggcatttt gccttcctgt ttttgctcac ccagaaacgc tggtgaaagt | 300 |

TABLE 4-continued

List of Sequences

| Seq ID No | Name | Sequence | |
|---|---|---|---|
| | | aaaagatgct gaagatcagt tgggtgcacg agtgggttac atcgaactgg atctcaacag | 360 |
| | | cggtaagatc cttgagagtt ttcgcccga agaacgtttt ccaatgatga gcactttaa | 420 |
| | | agttctgcta tgtggcgcgt tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg ctttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc cttttttgata atctcatgac caaaatccct taacgtgagt tttcgttcca | 1200 |
| | | ctgagcgtca gaccccgtag aaaagatcaa aggatcttct tgagatcctt ttttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacataccctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgccttg agtgagctga taccgctcgc cgcagccgaa cgaccgagcg | 1980 |
| | | cagcgagtca gtgagcgagg aagcggaaga cgcctgatg cggtatttttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacaccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg tcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttccgtc tttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgc cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccaggggt gttttctttt tcaccagtga cgggcaac agctgattgc | 3900 |
| | | ccttcaccgc ctggccctga gagagttgca gcaagcggtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga tatttatg ccagccagc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaataaca ctgttgatgg | 4380 |
| | | gtgtctggtc agagacatca agaaataacg ccgaacatt agtgcaggca gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgacacca | 4560 |
| | | ccacgctggc acccagttga tcgcgcgag atttaatcgc cgcgacaatt tgcgacgcg | 4620 |
| | | cgtgcagggc cagactggag gtgcaacgc caatcagcaa cgactgtttg cccgccagtt | 4680 |
| | | gttgtgccac gcggttggga atgtaattca gctccgccat cgccgcttcc acttttttccc | 4740 |

TABLE 4-continued

List of Sequences

| Seq ID No | Name | Sequence | |
|---|---|---|---|
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtcccccgg ccacgggggcc tgccaccata cccacgccga aacaagcgct catgagcccg | 5100 |
| | | aagtggcgag cccgatcttc cccatcggtg atgtcggcga tataggcgcc agcaaccgca | 5160 |
| | | cctgtggcgc cggtgatgcc ggcacgatg cgtccggcgt agaggatcga gatctcgatc | 5220 |
| | | ccgcgaaatt aatacgactc actataggg aattgtgagc ggataacaat tcccctctag | 5280 |
| | | aaataatttt gtttaacttt aagaaggaga tataccatgg gcagcagcca tcatcatcat | 5340 |
| | | catcacggcg gcgacggcga gaacttgtat tttcaagcta gcggatccat gggagagatc | 5400 |
| | | tggaagcagc acgaagacgc gctgcagaaa ttcgaggaag ccctgaacca gtttgaggat | 5460 |
| | | ctgaagcagc tgggcggtag cggcagcggt agcggcggtg agatctggaa acagtgcgaa | 5520 |
| | | gacgctctgc gtaagttcga agaggcgctg aagcaattcg aggatctgaa gcagaaaggc | 5580 |
| | | ggtagcggcg aaatttggaa acaacacgaa gacgccctgc aaaagttcga ggaagctctg | 5640 |
| | | aaccagtttg aagatctgaa acaactgggc ggtagcggca gcggtagcgg cggtgagata | 5700 |
| | | tggaaacagc atgaggacgc gctgcgtaag ttcgaggaag ccctgaaaca attcgaagat | 5760 |
| | | ctgaagcaga aaaccggtta agaattcctc gaggatccgg ctgctaacaa agcccgaaag | 5820 |
| | | gaagctgagt tggctgctgc caccgctgag caataactag cataaccct tggggcctct | 5880 |
| | | aaacgggtct tgaggggttt tttgctgaaa ggaggaacta tatccggata tcccgcaaga | 5940 |
| | | ggcccggcag taccggcata accaagccta tgcctacagc atccagggtg acggtgccga | 6000 |
| | | ggatgacgat gagcgcattg ttagatttca tacacggtgc ctgactgcgt tagcaattta | 6060 |
| | | actgtgataa actaccgcat taaagcttat cgatgataag ctgtcaaaca tgagaa | 6116 |
| 122 | minus 8ma quette | EIWKQHEDAL QKFEEALNQF EDLKQLGGSG SGSGGEIWKQ CEDALRKFEE ALKQFEDLKQ | 60 |
| | | KGGSGEIWKQ HEDALQKFEE ALNQFEDLKQ LGGSGSGSGG EIWKQHEDAL RKFEEALKQF | 120 |
| | | EDLKQK | 126 |
| 123 | minus 12ma quette (EC) | ttcttgaaga cgaaagggcc tcgtgatacg cctatttta taggttaatg tcatgataat | 60 |
| | | aatggttct tagacgtcag gtggcacttt cggggaaat gtgcgcggaa cccctatttg | 120 |
| | | tttatttttc taaatacatt caaatatgta tccgctcatg agacaataac cctgataaat | 180 |
| | | gcttcaataa tattgaaaaa ggaagagtat gagtattcaa cattccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcacttttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatggga gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc cttttttgata atctcatgac caaaatccct taacgtgagt tttcgttcca | 1200 |
| | | ctgagcgtca gaccccgtag aaaagatcaa aggatcttct tgagatcctt tttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacacccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg tttggtcact gatgcctccg | 2460 |
| | | tgtaagggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |

TABLE 4-continued

List of Sequences

| Seq ID No | Name | Sequence | |
|---|---|---|---|
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtgggca ggacccaacg ctgcccgaga | 2940 |
| | | tgcgccgcgt gcggctgctg gagatggcgg acgcgatgga tatgttctgc caaggggttga | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccaag aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgcccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga gacgggcaac agctgattgc | 3900 |
| | | ccttcaccgc ctggccctga gagagttgca gcaagcggtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacgcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc actttttccc | 4740 |
| | | gcgttttcgc agaaacgtgg ctgcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtcccccgg ccacggggcc tgccaccata cccacgccga acaagcgct catgagcccg | 5100 |
| | | aagtggcgag cccgatcttc ccatcggtg atgtcggcga tataggcgcc agcaaccgca | 5160 |
| | | cctgtggcgc cggtgatgcc ggccacgatg cgtccggcgt agaggatcga gatctcgatc | 5220 |
| | | ccgcgaaatt aatacgactc actatagggg aattgtgagc ggataacaat tcccctctag | 5280 |
| | | aaataatttt gtttaacttt aagaaggaga tataccatgg gcagcagcca tcatcatcat | 5340 |
| | | catcacggcg gcgacggcga gaacttgtat tttcaagcta gcggatccat gggagagatc | 5400 |
| | | tggaagcagc acgaagacgc gctgcagaaa ttcgaggaag ccctgaacca gtttgaggat | 5460 |
| | | ctgaagcagc tgggcggtag cggcagcggt agcggcggtg agatctggaa acagtgcgaa | 5520 |
| | | gacgctctgc agaagttcga agaggcgctg aagcaattcg aagatctgaa acaactgggc | 5580 |
| | | ggtagcggtg aaatttggaa acaacacgaa gacgccctgc aaaagttcga ggaagctctg | 5640 |
| | | aaccagtttg aagatctgaa acagctgggc ggtagcggca gcggtagcgg cggtagagata | 5700 |
| | | tggaaacagc atgaggatgc tctgcaaaag tttgaggaag ccctgaagca gtttgaggat | 5760 |
| | | ctgaaacagc tgaccggtta agaattcctc gaggatccgg ctgctaacaa agcccgaaag | 5820 |
| | | gaagctgagt tggctgctgc caccgctgag caataactag cataacccct ggggcctct | 5880 |
| | | aaacgggtct tgaggggtt tttgctgaaa ggaggaacta tatccggata tcccgcaaga | 5940 |
| | | ggcccggcag taccggcata accaagccta tgcctacagc atccagggtg acggtgccga | 6000 |
| | | ggatgacgat gagcgcattg ttagatttca tacacggtgc ctgactgcgt tagcaattta | 6060 |
| | | actgtgataa actaccgcat taaagcttat cgatgataag ctgtcaaaca tgagaa | 6116 |
| 124 | minus 12maquette | EIWKQHEDAL QKFEEALNQF EDLKQLGGSG SGSGGEIWKQ CEDALQKFEE ALKQFEDLKQ | 60 |
| | | LGGSGEIWKQ HEDALQKFEE ALNQFEDLKQ LGGSGSGSGG EIWKQHEDAL QKFEEALKQF | 120 |
| | | EDLKQL | 126 |
| 125 | plus 4maquette (EC) | ttcttgaaga cgaaagggcc tcgtgatacg cctatttta taggttaatg tcatgataat | 60 |
| | | aatggtttct tagacgtcag gtggcacttt tcggggaaat gtgcgcggaa cccctatttg | 120 |
| | | tttatttttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tcccttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |

TABLE 4-continued

List of Sequences

| Seq ID No | Name | Sequence | |
|---|---|---|---|
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc cttttttgata atctcatgac caaaatccct taacgtgagt tttcgttcca | 1200 |
| | | ctgagcgtca gaccccgtag aaaagatcaa aggatcttct tgagatcctt tttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacataccte gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacacccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg tttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg cggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga cgggcaac agctgattgc | 3900 |
| | | ccttcaccgc ctggccctga gagttgca gcaagcgtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgcgcga | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacgcg | 4620 |
| | | cgtgcaggc cagactggag gtggcaacgc caatcagcaa cgactgtttg cccgccagtt | 4680 |
| | | gttgtgccac gcggttggga atgtaattca gctccgccat cgccgcttcc actttttccc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta gaagcagcc cagtagtagg | 4980 |
| | | ttgaggccgt tgagcaccgc cgccgcaagg aatggtgcat gcaaggagat ggcgcccaac | 5040 |
| | | agtcccccgg ccacggggcc tgccaccata cccacgccga aacaagcgct catgagcccg | 5100 |
| | | aagtggcgag cccgatcttc cccatcggtg atgtcggcga tataggcgcc agcaaccgca | 5160 |
| | | cctgtggcgc cggtgatgcc ggccacgatg cgtccggcgt agaggatcga gatctcgatc | 5220 |

TABLE 4-continued

List of Sequences

| Seq ID No | Name | Sequence | |
|---|---|---|---|
| | | ccgcgaaatt aatacgactc actataggg aattgtgagc ggataacaat tcccctctag | 5280 |
| | | aaataatttt gtttaacttt aagaaggaga tataccatgg gcagcagcca tcatcatcat | 5340 |
| | | catcacggcg gcgacggcga gaacttgtat tttcaagcta gcggatccat gggagagatc | 5400 |
| | | tggaagcagc acgaagacgc gctgcgtaag ttcgaggaag cgctgaaacg ttttgaggat | 5460 |
| | | ctgaagcaga aaggtggcag cggcaagggt agcggtggcg agatctggaa acaatgcgag | 5520 |
| | | gatgcgctgc gcaaatttga ggaagcgctg aagcgcttcg aagacctgaa acaaaaaggt | 5580 |
| | | ggcagcggcg agatttggaa acaacatgag gatgcgctgc gcaagtttga ggaagcgctg | 5640 |
| | | cgtaaatttg aagacctgaa acagaaaggt ggcagcggca aggtagcgg tggcgagatt | 5700 |
| | | tggaagcagc atgaggatgc gctgcgtaaa ttcgaggaag cgctgaagcg ttttgaagat | 5760 |
| | | ctgaagcaaa aagcaccggt ttaagaattc ctcgaggctg ctaacaaagc ccgaaaggaa | 5820 |
| | | gctgagttgg ctgctgccac cgctgagcaa taactagcat aaccccttgg ggcctctaaa | 5880 |
| | | cgggtcttga gggttttttt gctgaaagga ggaactatat ccggatatcc cgcaagaggc | 5940 |
| | | ccggcagtac cggcataacc aagcctatgc ctacagcatc cagggtgacg gtgccgagga | 6000 |
| | | tgacgatgag cgcattgtta gatttcatac acggtgcctg actgcgttag caatttaact | 6060 |
| | | gtgataaact accgcattaa agcttatcga tgataagctg tcaaacatga gaa | 6113 |
| 126 | plus 4maquette (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgtttt gcgctgcttc gcgatgtacg ggccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttcccat agtaacgcca ataggqactt | 420 |
| | | tccattgacg tcaatgggtg gagtatttac ggtaaactgc ccacttggca gtacatcaag | 480 |
| | | tgtatcatat gccaagtacg cccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagaccctt tagtcagtgt ggaaaatctc tagcagtggc | 1020 |
| | | gcccgaacag ggacttgaaa gcgaaaggga accagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga gaacttaga tcattatata atacagtagc aaccctctat tgtgtgcatc | 1440 |
| | | aaaggataga gataaaagac accaaggaag ctttagcaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagctttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg gacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacggga | 2940 |
| | | agcacaagca gaaactggga caggagcccc aggagaccaa atcttcatgg tccctctggg | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaatgg gggagagctg | 3180 |
| | | gaaagaaaca aggacagcag cagaggccaa gtcaaccaga ccaattccca gaggaagcaa | 3240 |
| | | agaaaccatt acagagacta caaggggaa gggaaggaga gatgaattag cttcccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |

TABLE 4-continued

List of Sequences

| Seq ID No | Name | Sequence | |
|---|---|---|---|
| | | aagggcccta tagttggagg tggggaggt aggaagagcg atgatcactt gtggactaag | 3540 |
| | | tttgttcaca tccccttctc caacccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacggaaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gcccctagtt ctgggggcag cgggggatcc | 3900 |
| | | atgggagaga tctggaagca gcacgaagac gcgctgcgta agttcgagga agcgctgaaa | 3960 |
| | | cgttttgagg atctgaagca gaaaggtggc agcggcaagg gtagcggtgg cgagatctgg | 4020 |
| | | aaacaatgcg aggatgcgct gcgcaaattt gaggaagcgc tgaagcgctt cgaagacctg | 4080 |
| | | aaacaaaaag gtggcagcgg cgagatttgg aaacaacatg aggatgcgct gcgcaagttt | 4140 |
| | | gaggaagcgc tgcgtaaatt tgaagacctg aaacagaaag gtggcagcgg caaaggtagc | 4200 |
| | | ggtggcgaga tttggaagca gcatgaggat gcgctgcgta aattcgagga agcgctgaag | 4260 |
| | | cgttttgaag atctgaagca aaaagcaccg gtagtagcag tgagcaaggg cgaggagctg | 4320 |
| | | ttcaccgggg tggtgcccat cctggtcgag ctggacgggg acgtaaacgg ccacaagttc | 4380 |
| | | agcgtgtccg gcgagggcga gggcgatgcc acctacggca agctgaccct gaagttcatt | 4440 |
| | | tgcaccaccg gcaagctgcc cgtgccctgg cccaccctcg tgaccaccct gacctacggc | 4500 |
| | | gtgcagtgct tcagccgcta ccccgaccac atgaagcagc acgacttctt caagtccgcc | 4560 |
| | | atgcccgaag gctacgtcca ggagcgcacc atcttcttca aggacgacgg caactacaag | 4620 |
| | | acccgcgccg aggtgaagtt cgagggcgac accctggtga accgcatcga gctgaagggc | 4680 |
| | | atcgacttca aggaggacgg caacatcctg gggcacaagc tggagtacaa ctacaacagc | 4740 |
| | | cacaacgtct atatcatggc cgacaagcag aagaacggca tcaaggtgaa cttcaagatc | 4800 |
| | | cgccacaaca tcgaggacgg cagcgtgcag ctcgccgacc actaccagca gaacacccc | 4860 |
| | | atcggcgacg gccccgtgct gctgcccgac aaccactacc tgagcaccca gtccgccctg | 4920 |
| | | agcaaagacc ccaacgagaa gcgcgatcac atggtcctgc tggagttcgt gaccgccgcc | 4980 |
| | | gggatcactc tcggcatgga cgagctgtac aagtaagaat tcgatatcaa gcttatcgat | 5040 |
| | | aatcaacctc tggattacaa aatttgtgaa agattgactg gtattcttaa ctatgttgct | 5100 |
| | | ccttttacgc tatgtggata cgctgcttta atgcctttgt atcatgctat tgcttcccgt | 5160 |
| | | atggctttca ttttctcctc cttgtataaa tcctggttgc tgtctcttta tgaggagttg | 5220 |
| | | tggcccgttg tcaggcaacg tggcgtggtg tgcactgtgt ttgctgacgc aacccccact | 5280 |
| | | ggttgggca ttgccaccac ctgtcagctc ctttccggga ctttcgcttt ccccctccct | 5340 |
| | | attgccacgg cggaactcat cgccgcctgc cttgcccgct gctggacagg ggctcggctg | 5400 |
| | | ttgggcactg acaattccgt ggtgttgtcg gggaaatcat cgtcctttcc ttggctgctc | 5460 |
| | | gcctgtgttg ccacctggat tctgcgcggg acgtccttct gctacgtccc ttcggccctc | 5520 |
| | | aatccagcgg accttccttc ccgcggcctg ctgccggctc tgcggcctct tccgcgtctt | 5580 |
| | | cgccttcgcc ctcagacgag tcggatctcc ctttgggccg cctccccgca tcgataccgt | 5640 |
| | | cgacctcgag acctagaaaa acatggagca atcacaagta gcaatacagc agctaccaat | 5700 |
| | | gctgattgtg cctggctaga agcacaagag gaggaggagg tgggttttcc agtcacacct | 5760 |
| | | caggtacctt taagaccaat gacttacaag gcagctgtag atcttagcca ctttttaaaa | 5820 |
| | | gaaaaggggg gactggaagg gctaattcac tcccaacgaa gacaagatat ccttgatctg | 5880 |
| | | tggatctacc acacacaagg ctacttccct gattggcaga actacacacc agggccaggg | 5940 |
| | | atcagatatc cactgacctt tggatggtgc tacaagctag taccagttga gcaagagaag | 6000 |
| | | gtagaagaag ccaatgaagg agagaacacc cgcttgttac accctgtgag cctgcatggg | 6060 |
| | | atggatgacc cggagagaga agtattagag tggaggtttg acagccgcct agcatttcat | 6120 |
| | | cacatggccc gagagctgca tccggactgt actgggtctc tctggttaga ccagatctga | 6180 |
| | | gcctgggagc tctctggcta actagggaac ccactgctta agcctcaata agcttgcct | 6240 |
| | | tgagtgcttc aagtagtgtg tgcccgtctg ttgtgtgact ctggtaacta gagatccctc | 6300 |
| | | agacccttt agtcagtgtg gaaaatctct agcagggccc gtttaaaccc gctgatcagc | 6360 |
| | | ctcgactgtg ccttctagtt gccagccatc tgttgtttgc ccctccccg tgccttcctt | 6420 |
| | | gaccctggaa ggtgccactc ccactgtcct ttcctaataa aatgaggaaa ttgcatcgca | 6480 |
| | | ttgtctgagt aggtgtcatt ctattctggg gggtggggtg ggcaggaca gcaagggga | 6540 |
| | | ggattgggaa gacaatagca ggcatgctgg gatgcggtg ggctctatgg cttctgaggc | 6600 |
| | | ggaaagaacc agctgggggta ctaggggta tccccacgcg ccctgtgacg gcgcattaag | 6660 |
| | | cgcggcgggt gtggtggtta cgcgcagcgt gaccgctaca cttgccagcg ccctagcgcc | 6720 |
| | | cgctcctttc gctttcttcc cttcctttct cgccacgttc gccggctttc cccgtcaagc | 6780 |
| | | tctaaatcgg gggctccctt tagggttccg atttagtgct ttacggcacc tcgaccccaa | 6840 |
| | | aaaacttgat tagggtgatg gttcacgtag tgggccatcg cccctgataga cggttttttcg | 6900 |
| | | cccttttgacg ttggagtcca cgttctttaa tagtggactc ttgttccaaa ctggaacaac | 6960 |
| | | actcaaccct atctcggtct attcttttga tttataaggg attttgccga tttcggccta | 7020 |
| | | ttggttaaaa aatgagctga tttaacaaaa atttaacgcg aattaattct gtggaatgtg | 7080 |
| | | tgtcagttag ggtgtggaaa gtccccagg tccccagcag cagaagtag gcaaagcatg | 7140 |
| | | catctcaatt agtcagcaac caggtgtgga aagtcccag gctcccagca aggcagaagt | 7200 |
| | | atgcaaagca tgcatctcaa ttagtcagca accatagtcc cgcccctaac tccgcccatc | 7260 |
| | | ccgcccctaa ctccgcccag ttccgcccat tctccgcccc atggctgact aatttttttt | 7320 |
| | | atttatgcag aggccgagc cgcctctgcc tctgagctat tccagaagta ggtgaggagg | 7380 |
| | | cttttttgga gcctaggct tgcaaaaag ctcccggag cttgtatatc catttttcgga | 7440 |
| | | tctgatcagc acgtgttgac aattaatcat cggcatagta tatcggcata gtaaatacg | 7500 |
| | | acaaggtgag gaactaaacc atgccaagt tgaccagtgc cgttccggtg ctcaccgcgc | 7560 |
| | | gcgacgtcgc cggagcggtc gagttctgga ccgaccggct cgggttctcc cggacttcg | 7620 |
| | | tggaggacga cttcgccggt gtggtccggg acgacgtgac cctgttcatc agcgcggtcc | 7680 |
| | | aggaccaggt ggtgccggac aaccctggg cctggtgtg gtgcgcggc ctgacgagc | 7740 |
| | | tgtacgccga gtggtcggag gtcgtgtcca cgaacttccg ggacgcctcc gggccggca | 7800 |
| | | tgaccgagat cggcgagcag ccgtggggc gggagttcgc cctgcgcgac ccggccggca | 7860 |
| | | actgcgtgca cttcgtggcc gaggagcagg actgacacgt gctacgagat ttcgattcca | 7920 |

TABLE 4-continued

List of Sequences

| Seq ID No | Name | Sequence | |
|---|---|---|---|
| | | ccgccgcctt ctatgaaagg ttgggcttcg gaatcgtttt ccgggacgcc ggctggatga | 7980 |
| | | tcctccagcg cggggatctc atgctggagt tcttcgccca ccccaacttg tttattgcag | 8040 |
| | | cttataatgg ttacaaataa agcaatagca tcacaaattt cacaaataaa gcatttttt | 8100 |
| | | cactgcattc tagttgtggt ttgtccaaac tcatcaatgt atcttatcat gtctgtatac | 8160 |
| | | cgtcgacctc tagctagagc ttggcgtaat catggtcata gctgtttcct gtgtgaaatt | 8220 |
| | | gttatccgct cacaattcca cacaacatac gagccggaag cataaagtgt aaagcctggg | 8280 |
| | | gtgcctaatg agtgagctaa ctcacattaa ttgcgttgcg ctcactgccc gctttccagt | 8340 |
| | | cgggaaacct gtcgtgccag ctgcattaat gaatcggcca acgcgcgggg agaggcggtt | 8400 |
| | | tgcgtattgg gcgctcttcc gcttcctcgc tcactgactc gctgcgctcg gtcgttcggc | 8460 |
| | | tgcggcgagc ggtatcagct cactcaaagg cggtaatacg gttatccaca gaatcagggg | 8520 |
| | | ataacgcagg aaagaacatg tgagcaaaag gccagcaaaa ggccaggaac cgtaaaaagg | 8580 |
| | | ccgcgttgct ggcgtttttc cataggctcc gcccccctga cgagcatcac aaaaatcgac | 8640 |
| | | gctcaagtca gaggtggcga aacccgacag gactataaag ataccaggcg tttccccctg | 8700 |
| | | gaagctccct cgtgcgctct cctgttccga ccctgccgct taccggatac ctgtccgcct | 8760 |
| | | ttctcccttc gggaagcgtg gcgctttctc atagctcacg ctgtaggtat ctcagttcgg | 8820 |
| | | tgtaggtcgt tcgctccaag ctgggctgtg tgcacgaacc ccccgttcag cccgaccgct | 8880 |
| | | gcgccttatc cggtaactat cgtcttgagt ccaacccggt aagacacgac ttatcgccac | 8940 |
| | | tggcagcagc cactggtaac aggattagca gagcgaggta tgtaggcggt gctacagagt | 9000 |
| | | tcttgaagtg gtggcctaac tacggctaca ctagaagaac agtatttggt atctgcgctc | 9060 |
| | | tgctgaagcc agttaccttc ggaaaaagag ttggtagctc ttgatccggc aaacaaacca | 9120 |
| | | ccgctggtag cggtggtttt tttgtttgca agcagcagat tacgcgcaga aaaaaaggat | 9180 |
| | | ctcaagaaga tcctttgatc ttttctacgg ggtctgacgc tcagtggaac gaaaactcac | 9240 |
| | | gttaagggat tttggtcatg agattatcaa aaaggatctt cacctagatc ctttaaatt | 9300 |
| | | aaaaatgaag ttttaaatca atctaaagta tatatgagta aacttggtct gacagttacc | 9360 |
| | | aatgcttaat cagtgaggca cctatctcag cgatctgtct atttcgttca tccatagttg | 9420 |
| | | cctgactccc cgtcgtgtag ataactacga tacgggaggg cttaccatct ggccccagtg | 9480 |
| | | ctgcaatgat accgcgagac ccacgctcac cggctccaga tttatcagca ataaaccagc | 9540 |
| | | cagccggaag ggccgagcgc agaagtggtc ctgcaacttt atccgcctcc atccagtcta | 9600 |
| | | ttaattgttg ccgggaagct agagtaagta gttcgccagt taatagtttg cgcaacgttg | 9660 |
| | | ttgccattgc tacaggcatc gtggtgtcac gctcgtcgtt tggtatggct tcattcagct | 9720 |
| | | ccggttccca acgatcaagg cgagttacat gatccccat gttgtgcaaa aaagcggtta | 9780 |
| | | gctccttcgg tcctccgatc gttgtcagaa gtaagttggc cgcagtgtta tcactcatgg | 9840 |
| | | ttatggcagc actgcataat tctcttactg tcatgccatc cgtaagatgc ttttctgtga | 9900 |
| | | ctggtgagta ctcaaccaag tcattctgag aatagtgtat gcggcgaccg agttgctctt | 9960 |
| | | gcccggcgtc aatacggat aataccgcgc cacatagcag aactttaaaa gtgctcatca | 10020 |
| | | ttggaaaacg ttcttcgggg cgaaaactct caaggatctt accgctgttg agatccagtt | 10080 |
| | | cgatgtaacc cactcgtgca cccaactgat cttcagcatc ttttactttc accagcgttt | 10140 |
| | | ctgggtgagc aaaaacagga aggcaaaatg ccgcaaaaa gggaataagg gcgacacgga | 10200 |
| | | aatgttgaat actcatactc ttccttttc aatattattg aagcatttat cagggttatt | 10260 |
| | | gtctcatgag cggatacata tttgaatgta tttagaaaaa taaacaaata ggggttccgc | 10320 |
| | | gcacatttcc ccgaaaagtg ccacctgac | 10349 |
| 127 | plus4ma quette | EIWKQHEDAL RKFEEALKRF EDLKQKGGSG KGSGGEIWKQ CEDALRKFEE ALKRFEDLKQ | 60 |
| | | KGGSGEIWKQ HEDALRKFEE ALRKFEDLKQ KGGSGKGSGG EIWKQHEDAL RKFEEALKRF | 120 |
| | | EDLKQK | 126 |
| 128 | plus8ma quette (EC) | ttcttgaaga cgaaagggcc tcgtgatacg cctattttta taggttaatg tcatgataat | 60 |
| | | aatggtttct tagacgtcag gtggcacttt tcggggaaat gtgcgcggaa ccctatttg | 120 |
| | | tttattttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcacttttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc ctttttgata atctcatgac caaaatccct taacgtgagt tttcgttcca | 1200 |
| | | ctgagcgtca gaccccgtag aaaagatcaa aggatcttct tgagatcctt ttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgc acaggtatcc | 1680 |

TABLE 4-continued

List of Sequences

| Seq ID No | Name | Sequence | |
|---|---|---|---|
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggccttt tacggttcct | 1860 |
| | | ggcctttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgccc | 2160 |
| | | gacacccgcc aacaccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcctg tttggtcact gatgcctccg | 2460 |
| | | tgtaagggg atttctgttc atggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgcccg | 3660 |
| | | cgcccaccgg aaggagctga ctgggttgaa ggctctcaag gcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga cgggcaac agctgattgc | 3900 |
| | | ccttcaccgc ctggccctga gagagttgca gcaagcggtc cacgctggtt tgcccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccgactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgcgcga | 4500 |
| | | gaagattgta caccgccgct ttacaggctt cgacgccgct tcgttctacc atcgacacca | 4560 |
| | | ccacgctggc acccagttga tcggcgcgag atttaatcgc cgcgacaatt tgcgacggcg | 4620 |
| | | cgtgcagggc cagactggag gtggcaacgc caatcagcaa cgactgtttg cccgccagtt | 4680 |
| | | gttgtgccac gcggttggga atgtaattca gctccgccat cgccgcttcc acttttttcc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc acctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtccccgg ccacggggcc tgccaccata cccacgccga aacaagcgct catgagcccg | 5100 |
| | | aagtggcgag cccgatcttc cccatcggtg atgtcggcga tataggcgcc agcaaccgca | 5160 |
| | | cctgtggcgc cggtgatgcc ggccacgatg cgtccggcgt agaggatcga gatctcgatc | 5220 |
| | | ccgcgaaatt aatacgactc actataggg aattgtgagc ggataacaat tcccctctag | 5280 |
| | | aaataattt gtttaacttt aagaaggaga tataccatg gcagcagcca tcatcatcat | 5340 |
| | | catcacggcg gcgacgcga gaacttgtat tttcaagcta gcggatccat gggagagatc | 5400 |
| | | tggaagcagc acgaagacgc gctgcgtaag ttcgaggaag cgctgaaacg ttttgaggat | 5460 |
| | | aagaaacaga agggtggcag cggtaaaggc agcggtgcg agatctggaa gcaatgcgag | 5520 |
| | | gatgcgctgc gcaaatttga ggaagcgctg aagcgtttg aggatctgaa gcagaaaggt | 5580 |
| | | ggcagcggcg agatttggaa acgtcatgag gatgcgctgc gcaagttga ggaagcgctg | 5640 |
| | | cgtaaatttg aagataagaa acaaaagggt ggcagcggca agggcagcgg tggcgagatt | 5700 |
| | | tggaagcgcc atgaggatgc gctgcgtaaa ttcgaggaag cgctgaagcg ctttgaagat | 5760 |
| | | ctgaagcaaa aagcaccggt ttaagaattc ccaaaggctc tcaacaagcc ccgaaaggaa | 5820 |
| | | gctgagttgg ctgctgccac cgctgagcaa taactagcat aaccccttgg ggcctctaaa | 5880 |
| | | cgggtcttga gggtttttt gctgaaagga ggaactatat ccggatatcc cgcaagaggc | 5940 |
| | | ccggcagtac cggcataacc aagcctatgc ctacagcatc caggtgacg gtgccgagga | 6000 |
| | | tgacgatgag cgcattgtta gatttcatac acggtgcctg actgcgttag caatttaact | 6060 |
| | | gtgataaact accgcattaa agcttatcga tgataagctg tcaaacatga gaa | 6113 |

TABLE 4-continued

List of Sequences

| Seq ID No | Name | Sequence | | | | | |
|---|---|---|---|---|---|---|---|
| 129 | plus8ma quette (FCK mam) | gtcgacggat cgggagatct cccgatcccc tatggtgcac tctcagtaca atctgctctg | | | | | 60 |
| | | atgccgcata gttaagccag tatctgctcc ctgcttgtgt gttggaggtc gctgagtagt | | | | | 120 |
| | | gcgcgagcaa aatttaagct acaacaaggc aaggcttgac cgacaattgc atgaagaatc | | | | | 180 |
| | | tgcttagggt taggcgtttt gcgctgcttc gcgatgtacg ggccagatat acgcgttgac | | | | | 240 |
| | | attgattatt gactagttat taatagtaat caattacggg gtcattagtt catagcccat | | | | | 300 |
| | | atatggagtt ccgcgttaca taacttacgg taaatggccc gcctggctga ccgcccaacg | | | | | 360 |
| | | accccgccc attgacgtca ataatgacgt atgttcccat agtaacgcca atagggactt | | | | | 420 |
| | | tccattgacg tcaatgggtg gagtatttac ggtaaactgc ccacttggca gtacatcaag | | | | | 480 |
| | | tgtatcatat gccaagtacg ccccctattg acgtcaatga cggtaaatgg cccgcctggc | | | | | 540 |
| | | attatgccca gtacatgacc ttatgggact ttcctacttg gcagtacatc tacgtattag | | | | | 600 |
| | | tcatcgctat taccatggtg atgcggtttt ggcagtacat caatgggcgt ggatagcggt | | | | | 660 |
| | | ttgactcacg gggatttcca agtctccacc ccattgacgt caatgggagt ttgttttggc | | | | | 720 |
| | | accaaaatca acgggacttt ccaaaatgtc gtaacaactc cgccccattg acgcaaatgg | | | | | 780 |
| | | gcggtaggcg tgtacggtgg gaggtctata taagcagcgc gttttgcctg tactgggtct | | | | | 840 |
| | | ctctggttag accagatctg agcctgggag ctctctggct aactagggaa cccactgctt | | | | | 900 |
| | | aagcctcaat aaagcttgcc ttgagtgctt caagtagtgt gtgcccgtct gttgtgtgac | | | | | 960 |
| | | tctggtaact agagatccct cagacccttt tagtcagtgt ggaaaatctc tagcagtggc | | | | | 1020 |
| | | gcccgaacag ggacttgaaa gcgaaaggga aaccagagga gctctctcga cgcaggactc | | | | | 1080 |
| | | ggcttgctga agcgcgcacg gcaagaggcg aggggcggcg actggtgagt acgccaaaaa | | | | | 1140 |
| | | ttttgactag cggaggctag aaggagagag atgggtgcga gagcgtcagt attaagcggg | | | | | 1200 |
| | | ggagaattag atcgcgatgg gaaaaaattc ggttaaggcc aggggggaag aaaaaatata | | | | | 1260 |
| | | aattaaaaca tatagtatgg gcaagcaggg agctagaacg attcgcagtt aatcctggcc | | | | | 1320 |
| | | tgttagaaac atcagaaggc tgtagacaaa tactgggaca gctacaacca tcccttcaga | | | | | 1380 |
| | | caggatcaga agaacttaga tcattatata atacagtagc aaccctctat tgtgtgcatc | | | | | 1440 |
| | | aaaggataga gataaaagac accaaggaag ctttagacaa gatagaggaa gagcaaaaca | | | | | 1500 |
| | | aaagtaagac caccgcacag caagcggccg ctgatcttca gacctggagg aggagatatg | | | | | 1560 |
| | | agggacaatt ggagaagtga attatataaa tataaagtag accattagga | | | | | 1620 |
| | | gtagcaccca ccaaggcaaa gagaagagtg gtgcagagag aaaaaagagc agtgggaata | | | | | 1680 |
| | | ggagctttgt tccttgggtt cttgggagca gcaggaagca ctatgggcgc agcgtcaatg | | | | | 1740 |
| | | acgctgacgg tacaggccac acaattattg tctggtatag tgcagcagca gaacaatttg | | | | | 1800 |
| | | ctgagggcta ttgaggcgca acagcatctg ttgcaactca cagtctgggg catcaagcag | | | | | 1860 |
| | | ctccaggcaa gaatcctggc tgtggaaaga tacctaaagg atcaacagct cctggggatt | | | | | 1920 |
| | | tggggttgct ctggaaaact catttgcacc actgctgtgc cttggaatgc tagttggagt | | | | | 1980 |
| | | aataaatctc tggaacagat ttggaatcac acgacctgga tggagtggga cagagaaatt | | | | | 2040 |
| | | aacaattaca caagcttaat acactcctta attggaagaa tcgcaaaacca gcaagaaaag | | | | | 2100 |
| | | aatgaacaag aattattgga attagataaa tgggcaagtt tgtggaattg gtttaacata | | | | | 2160 |
| | | acaaattggc tgtggtatat aaaattattc ataatgatag taggaggctt ggtaggttta | | | | | 2220 |
| | | agaatagttt ttgctgtact ttctatagtg aatagagtta ggcagggata ttcaccatta | | | | | 2280 |
| | | tcgtttcaga cccacctccc aaccccgagg ggacccgaca ggcccgaagg aatagaagaa | | | | | 2340 |
| | | gaaggtggag agagagacag agacagatcc attcgattag tgaacggatc ggcactgcgt | | | | | 2400 |
| | | gcgccaattc tgcagacaaa tggcagtatt catccacaat tttaaaagaa aagggggggat | | | | | 2460 |
| | | tggggggtac agtgcagggg aaagaatagt agacataata gcaacagaca tacaaactaa | | | | | 2520 |
| | | agaattacaa aaacaaatta caaaaattca aaattttcgg gtttattaca gggacagcag | | | | | 2580 |
| | | agatccagtt tggttaatta acattatggc cttaggtcac ttcatctcca tggggttctt | | | | | 2640 |
| | | cttctgattt tctagaaaat gagatgggg tgcagagagc ttcctcagtg acctgcccag | | | | | 2700 |
| | | ggtcacatca gaaatgtcag agctagaact tgaactcaga ttactaatct taaattccat | | | | | 2760 |
| | | gccttggggg catgcaagta cgatatacag aaggagtgaa ctcattaggg cagatgacca | | | | | 2820 |
| | | atgagtttag gaaagaagag tccagggcag ggtacatcta caccacccgc ccagccctgg | | | | | 2880 |
| | | gtgagtccag ccacgttcac ctcattatag ttgcctctct ccagtcctac cttgacggga | | | | | 2940 |
| | | agcacaagca gaaactggga caggagcccc aggagaccaa atcttcatgg tccctctggg | | | | | 3000 |
| | | aggatgggtg gggagagctg tggcagaggc ctcaggaggg gccctgctgc tcagtggtga | | | | | 3060 |
| | | cagataggg tgagaaagca gacagagtca ttccgtcagc attctgggtc tgtttggtac | | | | | 3120 |
| | | ttcttctcac gctaaggtgg cggtgtgata tgcacaatgg ctaaaaagca gggagagctg | | | | | 3180 |
| | | gaaagaaaca aggacagaga cagaggccaa gtcaaccaga ccaattccca gaggaagcaa | | | | | 3240 |
| | | agaaaccatt acagagacta caaggggggaa gggaaggaga gatgaattag cttcccctgt | | | | | 3300 |
| | | aaaccttaga acccagctgt tgccagggca acggggcaat acctgtctct tcagaggaga | | | | | 3360 |
| | | tgaagttgcc agggtaacta catcctgtct ttctcaagga ccatcccaga atgtggcacc | | | | | 3420 |
| | | cactagccgt taccatagca actgcctctt tgccccactt aatccatcc cgtctgttaa | | | | | 3480 |
| | | aagggcccta tagttggagg tgggggaggt aggaagagcg atgatcactt gtggactaag | | | | | 3540 |
| | | tttgttcaca tcccccttctc caacccccctc atacatcac cctgggagaa caaggtccac | | | | | 3600 |
| | | ttgcttctgg gcccacacag tcctgcagta ttgtgtatat aaggccaggg caacggagga | | | | | 3660 |
| | | gcaggttttg aagtgaaagg caggcaggtg ttggggaggc agttaccggg gcaacgggaa | | | | | 3720 |
| | | cagggcgttt cggaggtggt tgccatgggg acctggatgc tgacgaaggc tcgcgaggct | | | | | 3780 |
| | | gtgagcagcc acagtgccct gctcagaagc cccaagctcg tcaatcaagc tgttctcca | | | | | 3840 |
| | | tttgcactca ggacacgggg caggcgagtg gcccctagtt ctggggcag cggggatcc | | | | | 3900 |
| | | atgggagaga tctggaagca gcacgaagac gcgctgcgta agtcgagga agcgctgaaa | | | | | 3960 |
| | | cgttttgagg ataagaaaca gaagggtggc agcggtaaag gcagcgtgg cgagatctgg | | | | | 4020 |
| | | aagcaatgcg aggatgcgct gcgcaaattt gaggaagcgc tgaagctttt tgaagatctg | | | | | 4080 |
| | | aagcagaaag gtggcagcgg cgagatttgg aaacgtcatg aggatgcgct gcgcaagttt | | | | | 4140 |
| | | gaggaagcgc tgcgtaaatt tgaagataag aaacaaaagg gtgcagcgg caagggcagc | | | | | 4200 |
| | | ggtggcgaga tttgaagcg ccatgaggat gcgctgcgta aattcgagga agcgctgaag | | | | | 4260 |
| | | cgcttttgaag atctgaagca aaaagcaccg gtagtagcag tgagcaaggg cgaggagctg | | | | | 4320 |
| | | ttcaccgggg tggtgcccat cctggtcgag ctggacgcg acgtaaacgg ccacaagttc | | | | | 4380 |

TABLE 4-continued

List of Sequences

| Seq ID No | Name | Sequence | |
|---|---|---|---|
| | | agcgtgtccg gcgagggcga gggcgatgcc acctacggca agctgaccct gaagttcatt | 4440 |
| | | tgcaccaccg gcaagctgcc cgtgccctgg cccacccteg tgaccaccet gacctacggc | 4500 |
| | | gtgcagtgct tcagccgcta ccccgaccac atgaagcagc acgacttctt caagtccgcc | 4560 |
| | | atgcccgaag gctacgtcca ggagcgcacc atcttcttca aggacgacgg caactacaag | 4620 |
| | | acccgcgccc aggtgaagtt cgagggcgac accctggtga accgcatcga gctgaagggc | 4680 |
| | | atcgacttca aggaggacgg caacatcctg ggcacaagc tggagtacaa ctacaacagc | 4740 |
| | | cacaacgtct atatcatggc cgacaagcag aagaacggca tcaaggtgaa cttcaagatc | 4800 |
| | | cgccacaaca tcgaggacgg cagcgtgcag ctcgccgacc actaccagca gaacaccccc | 4860 |
| | | atcggcgacg gccccgtgct gctgcccgac aaccactacc tgagcaccca gtccgccctg | 4920 |
| | | agcaaagacc ccaacgagaa gcgcgatcac atggtcctgc tggagttcgt gaccgccgcc | 4980 |
| | | gggatcactc tcggcatgga cgagctgtac aagtaagaat tcgatatcaa gcttatcgat | 5040 |
| | | aatcaacctc tggattacaa aatttgtgaa agattgactg gtattcttaa ctatgttgct | 5100 |
| | | ccttttacgc tatgtggata cgctgcttta atgcctttgt atcatgctat tgcttcccgt | 5160 |
| | | atggctttca ttttctcctc cttgtataaa tcctggttgc tgtctcttta tgaggagttg | 5220 |
| | | tggcccgttg tcaggcaacg tggcgtggtg tgcactgtgt ttgctgacgc aaccccact | 5280 |
| | | ggttgggca ttgccaccac ctgtcagctc ctttccggga ctttcgcttt ccccctcct | 5340 |
| | | attgccacgg cggaactcat cgccgcctgc cttgcccgct gctggacagg ggctcggctg | 5400 |
| | | ttgggcactg acaattccgg ggtgttgtcg gggaaatcat cgtcctttcc ttggctgctc | 5460 |
| | | gcctgtgttg ccacctggat tctgcgcggg acgtccttct gctacgtccc ttcggccctc | 5520 |
| | | aatccagcgg accttccttc ccgcggcctg ctgccggctc tgcggcctct tccgcgtctt | 5580 |
| | | cgccttcgcc ctcagacgcg tcggatctcc ctttgggccg cctccccgca tcgataccgt | 5640 |
| | | cgacctcgag acctagaaaa acatggagca atcacaagta gcaatacagc agctaccaat | 5700 |
| | | gctgattgtg cctggctaga agcacaagag gaggaggagg tgggttttcc agtcacacct | 5760 |
| | | caggtacctt taagaccaat gacttacaag gcagctgtga atcttagcca cttttttaaaa | 5820 |
| | | gaaaaggggg gactggaagg gctaattcac tcccaacgaa gacaagatat ccttgatctg | 5880 |
| | | tggatctacc acacacaagg ctacttccct gattggcaga actacacacc agggccaggg | 5940 |
| | | atcagatatc cactgaccett tggatggtgc tacaagctag taccagttga gcaagagaag | 6000 |
| | | gtagaagaag ccaatgaagg agagaacacc cgcttgttac accctgtgag cctgcatggg | 6060 |
| | | atggatgacc cggagagaga agtattagag tggaggtttg acagccgcct agcatttcat | 6120 |
| | | cacatggccc gagagctgca tccggactgt actgggtctc tctggttaga ccagatctga | 6180 |
| | | gcctgggagc tctctggcta actagggaac ccactgctta agcctcaata agcttgcct | 6240 |
| | | tgagtgcttc aagtagtgtg tgcccgtctg ttgtgtgact ctggtaacta gagatccctc | 6300 |
| | | agacccttttt agtcagtgtg gaaaatctct agcagggccc gtttaaaccc gctgatcagc | 6360 |
| | | ctcgactgtg ccttctagtt gccagccatc tgttgtttgc cctcccccg tgccttcctt | 6420 |
| | | gaccctggaa ggtgccactc ccactgtcct ttcctaataa aatgaggaaa ttgcatcgca | 6480 |
| | | ttgtctgagt aggtgtcatt ctattctggg gggtggggtg gggcaggaca gcaaggggga | 6540 |
| | | ggattgggaa gacaatagca ggcatgctgg ggatgcggtg ggctctatgg cttctgaggc | 6600 |
| | | ggaaagaacc agctggggct ctaggggta tccccacgcg ccctgtagcg cgcattaag | 6660 |
| | | cgcggcgggt gtggtggtta cgcgcagcgt gaccgctaca cttgccagcg ccctagcgcc | 6720 |
| | | cgctcctttc gctttcttcc cttcctttct cgccacgttc gccggctttc cccgtcaagc | 6780 |
| | | tctaaatcgg gggctccctt tagggttccg atttagtgct ttacggcacc tcgaccccaa | 6840 |
| | | aaaacttgat tagggtgatg gttcacgtag tgggccatcg ccctgataga cggttttcg | 6900 |
| | | cccttgacg ttggagtcca cgttctttaa tagtggactc ttgttccaaa ctggaacaac | 6960 |
| | | actcaaccct atctcggtct attcttttga tttataaggg attttgccga tttcggccta | 7020 |
| | | ttggttaaaa aatgagctga tttaacaaaa atttaacgcg aattaattct gtggaatgtg | 7080 |
| | | tgtcagttag ggtgtggaaa gtcccaggc tccccagcag gcagaagtat gcaaagcatg | 7140 |
| | | catctcaatt agtcagcaac caggtgtgga aagtcccag gctcccagc aggcagaagt | 7200 |
| | | atgcaaagca tgcatctcaa ttagtcagca accatagtcc cgcccctaac tccgcccatc | 7260 |
| | | ccgcccctaa ctccgcccag ttccgcccat tctccgcccc atggctgact aatttttttt | 7320 |
| | | atttatgcag aggccgaggc cgcctctgcc tctgagctat tccagaagta gtgaggaggc | 7380 |
| | | tttttggag gcctaggctt ttgcaaaaag ctcccgggag cttgtatatc catttcgga | 7440 |
| | | tctgatcagc acgtgttgac aattaatcat cggcatagta tcggcata gtataatacg | 7500 |
| | | acaaggtgag gaactaaacc atggccaagt tgaccagtgc cgttccggtg ctcaccgcga | 7560 |
| | | gcgacgtcgc cggagcggtc gagttctgga ccgaccggct cgggttctcc cgggacttcg | 7620 |
| | | tggaggacga cttcgccggt gtggtccggg acgacgtgac cctgttcatc agcgcggtcc | 7680 |
| | | aggaccaggt ggtgccggac aacaccctgg cctgggtgtg ggtgcgcggc ctggacgagc | 7740 |
| | | tgtacgccga ggtgtccggg gtcgtgtcca cgaacttccg ggacgcctcc gggccggcca | 7800 |
| | | tgaccgagat cggcgagcag ccgtgggggc gggagttcgc cctgcgcgac ccgccggcca | 7860 |
| | | actgcgtgca cttcgtggcc gaggagcagg actgacacgt gctacgagat ttcgattcca | 7920 |
| | | ccgccgcctt ctatgaaagg ttgggcttcg gaatcgtttt ccgggacgcc ggctggatga | 7980 |
| | | tcctccagcg cggggatctc atgctggagt tcttcgccca cccaacttg tttattgcag | 8040 |
| | | cttataatgg ttacaaataa agcaatagca tcacaaattt cacaaataaa gcatttttt | 8100 |
| | | cactgcattc tagttgtggt ttgtccaaac tcatcaatgt atcttatcat gtctgtatac | 8160 |
| | | cgtcgacctc tagctagagc ttggcgtaat catggtcata gctgtttcct gtgtgaaatt | 8220 |
| | | gttatccgct cacaattcca cacaacatac gagccggaag cataaagtgt aaagcctggg | 8280 |
| | | gtgcctaatg agtgagctaa ctcacattaa ttgcgttgcg ctcactgccc gctttccagt | 8340 |
| | | cgggaaacct gtcgtgccag ctgcattaat gaatcggcca acgcgcgggg agaggcggtt | 8400 |
| | | tgcgtattgg gcgctcttcc gcttcctcgc tcactgactc gctgcgctcg gtcgttcggc | 8460 |
| | | tgcggcgagc ggtatcagct cactcaaagg cggtaatacg gttatccaca gaatcagggg | 8520 |
| | | ataacgcagg aaaagaacatg tgagcaaaag gccagcaaaa ggccaggaac cgtaaaaagg | 8580 |
| | | ccgcgttgct ggcgtttttc cataggctcc gcccccctga cgagcatcac aaaaatcgac | 8640 |
| | | gctcaagtca gaggtggcga aacccgacag gactataaag ataccaggcg tttccccctg | 8700 |
| | | gaagctccct cgtgcgctct cctgttccga ccctgccgct taccggatac ctgtccgcct | 8760 |
| | | ttctcccttc gggaagcgtg gcgctttctc atagctcacg ctgtaggtat ctcagttcgg | 8820 |

TABLE 4-continued

List of Sequences

| Seq ID No | Name | Sequence | |
|---|---|---|---|
| | | tgtaggtcgt tcgctccaag ctgggctgtg tgcacgaacc ccccgttcag cccgaccgct | 8880 |
| | | gcgccttatc cggtaactat cgtcttgagt ccaacccggt aagacacgac ttatcgccac | 8940 |
| | | tggcagcagc cactggtaac aggattagca gagcgaggta tgtaggcggt gctacagagt | 9000 |
| | | tcttgaagtg gtggcctaac tacggctaca ctagaagaac agtatttggt atctgcgctc | 9060 |
| | | tgctgaagcc agttaccttc ggaaaaagag ttggtagctc ttgatccggc aaacaaacca | 9120 |
| | | ccgctggtag cggtggtttt tttgtttgca agcagcagat tacgcgcaga aaaaaaggat | 9180 |
| | | ctcaagaaga tcctttgatc ttttctacgg ggtctgacgc tcagtggaac gaaaactcac | 9240 |
| | | gttaagggat tttggtcatg agattatcaa aaaggatctt cacctagatc cttttaaatt | 9300 |
| | | aaaaatgaag ttttaaatca atctaaagta tatatgagta aacttggtct gacagttacc | 9360 |
| | | aatgcttaat cagtgaggca cctatctcag cgatctgtct atttcgttca tccatagttg | 9420 |
| | | cctgactccc cgtcgtgtag ataactacga tacgggaggg cttaccatct ggccccagtg | 9480 |
| | | ctgcaatgat accgcgagac ccacgctcac cggctccaga tttatcagca ataaaccagc | 9540 |
| | | cagccggaag ggccgagcgc agaagtggtc ctgcaacttt atccgcctcc atccagtcta | 9600 |
| | | ttaattgttg ccgggaagct agagtaagta gttcgccagt taatagtttg cgcaacgttg | 9660 |
| | | ttgccattgc tacaggcatc gtggtgtcac gctcgtcgtt tggtatggct tcattcagct | 9720 |
| | | ccggttccca acgatcaagg cgagttacat gatcccccat gttgtgcaaa aaagcggtta | 9780 |
| | | gctccttcgg tcctccgatc gttgtcagaa gtaagttggc cgcagtgtta tcactcatgg | 9840 |
| | | ttatggcagc actgcataat tctcttactg tcatgccatc cgtaagatgc ttttctgtga | 9900 |
| | | ctggtgagta ctcaaccaag tcattctgag aatagtgtat gcggcgaccg agttgctctt | 9960 |
| | | gcccggcgtc aatacgggat aataccgcgc cacatagcag aactttaaaa gtgctcatca | 10020 |
| | | ttggaaaacg ttcttcgggg cgaaaactct caaggatctt accgctgttg agatccagtt | 10080 |
| | | cgatgtaacc cactcgtgca cccaactgat cttcagcatc ttttactttc accagcgttt | 10140 |
| | | ctgggtgagc aaaaacagga aggcaaaatg ccgcaaaaaa gggaataagg gcgacacgga | 10200 |
| | | aatgttgaat actcatactc ttcctttttc aatattattg aagcatttat cagggttatt | 10260 |
| | | gtctcatgag cggatacata tttgaatgta tttagaaaaa taaacaaata ggggttccgc | 10320 |
| | | gcacatttcc ccgaaaagtg ccacctgac | 10349 |
| 130 | plus8ma quette | EIWKQHEDAL RKFEEALKRF EDKKQKGGSG KGSGGEIWKQ CEDALRKFEE ALKRFEDLKQ | 60 |
| | | KGGSGEIWKR HEDALRKFEE ALRKFEDKKQ KGGSGKGSGG EIWKRHEDAL RKFEEALKRF | 120 |
| | | EDLKQK | 126 |
| 131 | MMmin4 (EC) | ttcttgaaga cgaaagggcc tcgtgatacg cctatttta taggttaatg tcatgataat | 60 |
| | | aatggtttct tagacgtcag gtggcacttt tcggggaaat gtgcgcggaa cccctatttg | 120 |
| | | tttattttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg cttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc ctttttgata atctcatgac caaaatccct aacgtgagt tttcgttcca | 1200 |
| | | ctgagcgtca gaccccgtag aaaagatcaa aggatcttct tgagatcctt ttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacatacctc gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcgaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgacg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacacccgcc aacacccgct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctc cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcggccatg ttaagggcgg ttttttcctg tttggtcact gatgcctccg | 2460 |
| | | tgtaagggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |

TABLE 4-continued

List of Sequences

| Seq ID No | Name | Sequence | |
|---|---|---|---|
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca ggacccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag gcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga gaagaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |
| | | gacgaaggct tgagcgaggg cgtgcaagat tccgaatacc gcaagcgaca ggccgatcat | 3540 |
| | | cgtcgcgctc cagcgaaagc ggtcctcgcc gaaaatgacc cagagcgctg ccggcacctg | 3600 |
| | | tcctacgagt tgcatgataa agaagacagt cataagtgcg gcgacgatag tcatgccccg | 3660 |
| | | cgcccaccgg aaggagctga ctgggttgaa ggctctcaag ggcatcggtc gagatcccgg | 3720 |
| | | tgcctaatga gtgagctaac ttacattaat tgcgttgcgc tcactgcccg ctttccagtc | 3780 |
| | | gggaaacctg tcgtgccagc tgcattaatg aatcggccaa cgcgcgggga gaggcggttt | 3840 |
| | | gcgtattggg cgccagggtg gtttttcttt tcaccagtga cgggcaac agctgattgc | 3900 |
| | | ccttcaccgc ctggccctga gagagttgca gcaagcggtc cacgctggtt tgccccagca | 3960 |
| | | ggcgaaaatc ctgtttgatg gtggttaacg gcgggatata acatgagctg tcttcggtat | 4020 |
| | | cgtcgtatcc cactaccgag atatccgcac caacgcgcag cccggactcg gtaatggcgc | 4080 |
| | | gcattgcgcc cagcgccatc tgatcgttgg caaccagcat cgcagtggga acgatgccct | 4140 |
| | | cattcagcat ttgcatggtt tgttgaaaac cggacatggc actccagtcg ccttcccgtt | 4200 |
| | | ccgctatcgg ctgaatttga ttgcgagtga gatatttatg ccagccagcc agacgcagac | 4260 |
| | | gcgccgagac agaacttaat gggcccgcta acagcgcgat ttgctggtga cccaatgcga | 4320 |
| | | ccagatgctc cacgcccagt cgcgtaccgt cttcatggga gaaaataata ctgttgatgg | 4380 |
| | | gtgtctggtc agagacatca agaaataacg ccggaacatt agtgcaggca gcttccacag | 4440 |
| | | caatggcatc ctggtcatcc agcggatagt taatgatcag cccactgacg cgttgccgag | 4500 |
| | | gaagattgtg caccgccgct ttacaggctt cgacgccgct tcgttctacc atcgacacca | 4560 |
| | | ccacgctggc acccagttga tcggcgcgag atttaatcgc cgcgacaatt tgcgacggcg | 4620 |
| | | cgtgcagggc cagactggag gtggcaacgc caatcagcaa cgactgtttg cccgccagtt | 4680 |
| | | gttgtgccac gcggttggga atgtaattca gccccgcttcc acttttttcc | 4740 |
| | | gcgttttcgc agaaacgtgg ctggcctggt tcaccacgcg ggaaacggtc tgataagaga | 4800 |
| | | caccggcata ctctgcgaca tcgtataacg ttactggttt cacattcacc accctgaatt | 4860 |
| | | gactctcttc cgggcgctat catgccatac cgcgaaaggt tttgcgccat tcgatggtgt | 4920 |
| | | ccgggatctc gacgctctcc cttatgcgac tcctgcatta ggaagcagcc cagtagtagg | 4980 |
| | | ttgaggccgt tgagcaccgc cgccgcaagg aatggtgcat gcaaggagat ggcgcccaac | 5040 |
| | | agtcccccgg ccacggggcc tgccaccata cccacgccga acaagcgct catgagcccg | 5100 |
| | | aagtggcgag cccgatcttc cccatcggtg atgtcggcga tataggcgcc agcaaccgca | 5160 |
| | | cctgtggccg cggtgatgcc ggccacgatg cgtccggcgt agaggatcga gatctcgatc | 5220 |
| | | ccgcgaaatt aatacgactc actataggg aattgtgagc ggataacaat tcccctctag | 5280 |
| | | aaataatttt gtttaacttt aagaaggaga tataccatgg gcagcagcca tcatcatcat | 5340 |
| | | catcacgcg gcgacggcga gaacttgtat tttcaagcta gcggatccat gggagagctg | 5400 |
| | | tggaagaaac acgaggaagc gctgaagaaa tttgaggaac tgctgaagaa atttgaggaa | 5460 |
| | | gagctgaaac tgggtggcag cggcgagggt agcggtggcg aactgctgaa gaaatgcgaa | 5520 |
| | | gaggcgctga gaaattcga agagctgctg aagaaattg aagaggaact gaagctgggt | 5580 |
| | | ggcagcggtg aactgctgaa gaaacatgag gaagcgctga gaaatttga ggagttactg | 5640 |
| | | aagaaattcg aggagctgtt aaagctgggt ggcagcggcg aaggcagcgg tggcgaatta | 5700 |
| | | ctgaagaaac acgaggaagc gctgaagaaa ttcgaggaat tactgaagaa atttgaagag | 5760 |
| | | ctgctgaaac tggcaccggt ttaagaattc ctcgaggctg ctaacaaagc ccgaaaggaa | 5820 |
| | | gctgagttgg ctgctgccac cgctgagcaa taactagcat aaccccttgg ggcctctaaa | 5880 |
| | | cgggtcttga ggggttttt gctgaaagga ggaactatat ccggatatcc gcaagaggc | 5940 |
| | | ccggcagtac cggcataacc aagcctatgc ctacagacgt cagggtgacg gtgccgagga | 6000 |
| | | tgacgatgag cgcattgtta gatttcatac acggtgcctg actgcgttag caatttaact | 6060 |
| | | gtgataaact accgcattaa agcttatcga tgataagctg tcaaacatga gaa | 6113 |
| 132 | MMmin4 (FCK mam) | gtcgacggat cgggagatct cccgatcccc tatggtgcac tctcagtaca atctgctctg | 60 |
| | | atgccgcata gttaagccag tatctgctcc ctgcttgtgt gttggaggtc gctgagtagt | 120 |
| | | gcgcgagcaa aatttaagct acaacaaggc aaggcttgac cgacaattgc atgaagaatc | 180 |
| | | tgcttagggt taggcgttt gcgctgcttc gcgatgtacg gccagatat acgcgttgac | 240 |
| | | attgattatt gactagttat taatagtaat caattacggg gtcattagtt catagcccat | 300 |
| | | atatggagtt ccgcgttaca taacttacgg taaatggccc gcctggctga ccgcccaacg | 360 |
| | | acccccgccc attgacgtca ataatgacgt atgttcccat agtaacgcca atagggactt | 420 |
| | | tccattgacg tcaatgggtg gagtatttac ggtaaactgc ccacttggca gtacatcaag | 480 |
| | | tgtatcatat gccaagtacg ccccctattg acgtcaatga cggtaaatgg cccgcctggc | 540 |
| | | attatgccca gtacatgacc ttatgggact ttcctacttg gcagtacatc tacgtattag | 600 |
| | | tcatcgctat taccatggtg atgcggtttt ggcagtacat caatgggcgt ggatagcggt | 660 |
| | | ttgactcacg gggatttcca agtctccacc ccattgacgt caatgggagt ttgttttggc | 720 |
| | | accaaaatca acgggacttt ccaaaatgtc gtaacaactc cgccccattg acgcaaatgg | 780 |
| | | gcggtaggcg tgtacggtgg gaggtctata taagcagcgc gttttgcctg tactgggtct | 840 |

TABLE 4-continued

List of Sequences

| Seq ID No | Name | Sequence | |
|---|---|---|---|
| | | ctctggttag accagatctg agcctgggag ctctctggct aactagggaa cccactgctt | 900 |
| | | aagcctcaat aaagcttgcc ttgagtgctt caagtagtgt gtgcccgtct gttgtgtgac | 960 |
| | | tctggtaact agagatccct cagacccttt tagtcagtgt ggaaaatctc tagcagtggc | 1020 |
| | | gcccgaacag ggacttgaaa gcgaaaggga aaccagagga gctctctcga cgcaggactc | 1080 |
| | | ggcttgctga agcgcgcacg gcaagaggcg aggggcggcg actggtgagt acgccaaaaa | 1140 |
| | | ttttgactag cggaggctag aaggagagag atgggtgcga gagcgtcagt attaagcggg | 1200 |
| | | ggagaattag atcgcgatgg gaaaaaattc ggttaaggcc agggggaaag aaaaaatata | 1260 |
| | | aattaaaaca tatagtatgg gcaagcaggg agctagaacg attcgcagtt aatcctggcc | 1320 |
| | | tgttagaaac atcagaaggc tgtagacaaa tactgggaca gctacaacca tcccttcaga | 1380 |
| | | caggatcaga agaacttaga tcattatata atacagtagc aaccctctat tgtgtgcatc | 1440 |
| | | aaaggataga gataaaagac accaaggaag cttagacaa gatagaggaa gagcaaaaca | 1500 |
| | | aaagtaagac caccgcacag caagcggccg ctgatcttca gacctggagg aggagatatg | 1560 |
| | | agggacaatt ggagaagtga attatataaa tataaagtag taaaaattga accattagga | 1620 |
| | | gtagcaccca ccaaggcaaa gagaagagtg gtgcagagag aaaaaagagc agtgggaata | 1680 |
| | | ggagcttttgt tccttgggtt cttgggagca gcaggaagca ctatgggcgc agcgtcaatg | 1740 |
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttctatagtg aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aaggggggat | 2460 |
| | | tggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaaagg tccagggcag ggtacatcta caccaccgcc cagccctgg | 2880 |
| | | gtgagtccag ccacgttcac ctcattatag ttgcctctct ccagtcctac cttgacggga | 2940 |
| | | agcacaagca gaaactggga caggagccc aggagaccaa atcttcatgg tccctctgag | 3000 |
| | | aggatgggtg gggagagctg tggcagaggc ctcaggaggg gccctgctgc tcagtggtga | 3060 |
| | | cagatagggg tgagaaagca gacagagtca ttccgtcagc attctgggtc tgtttggtac | 3120 |
| | | ttcttctcac gctaaggtgg cggtgtgata tgcacaatgg ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggga gggaaggaga gatgaattag cttccccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccatcc aatcccatcc cgtctgttaa | 3480 |
| | | aagggcccta tagttggagg tgggggaggt aggaagagcg atgatcactt gtggactaag | 3540 |
| | | tttgttcaca tccccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggagc agttaccggg gcaacgggaa | 3720 |
| | | gcaggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gcccctagtt ctggggcag cgggggatcc | 3900 |
| | | atgggagagc tgtgaagaa acacgaggaa gcgctgaaga aattcgagga actgctgaag | 3960 |
| | | aaatttgagg aagagctgaa actgggtggc agcggcggtgg gtagcggttgg cgaactgctg | 4020 |
| | | aagaaatgcg aagaggcgct gaagaaattc gaagagctgc tgaagaaatt tgaagaggaa | 4080 |
| | | ctgaagctgg gtggcagcgg tgaactgctg aagaaacatg aggaagcgct gaagaaattt | 4140 |
| | | gaggagttac tgaagaaatt cgaggagctg ttaaagctgg gtggcagcgg cgaaggcagc | 4200 |
| | | ggtggcgaat tactgaagaa acacgaggaa gcgctgaaga aattcgagga attactgaag | 4260 |
| | | aaatttgaag agctgctgaa actggcaccg gtagtagcag tgagcaaggg cgaggagctg | 4320 |
| | | ttcaccgggg tggtgcccat cctggtcgag ctggacggcg acgtaaacgg ccacaagttc | 4380 |
| | | agcgtgtccg gcgagggcga ggcgatgcc acctacggca agctgaccct gaagttcatt | 4440 |
| | | tgcaccaccg gcaagctgcc cgtgccctgg cccaccctcg tgaccaccct gacctacggc | 4500 |
| | | gtgcagtgct tcagccgcta ccccgaccac atgaagcagc acgacttctt caagtccgcc | 4560 |
| | | atgcccgaag gctacgtcca ggagcgcacc atcttcttca aggacgacgg caactacaag | 4620 |
| | | acccgcgccg aggtgaagtt cgagggcgac accctggtga accgcatcga gctgaagggc | 4680 |
| | | atcgacttca aggaggacgg caacatcctg gggcacaagc tggagtacaa ctacaacagc | 4740 |
| | | cacaacgtct atatcatggc cgacaagcag aagaacggca tcaaggtgaa cttcaagatc | 4800 |
| | | cgccacaaca tcgaggacgg cagcgtgcag ctcgccgacc actaccagca gaacaccccc | 4860 |
| | | atcggcgacg gccccgtgct gctgcccgac aaccactacc tgagcaccca gtccgccctg | 4920 |
| | | agcaaagacc ccaacgagaa gcgcgatcac atggtcctgc tggagttcgt gaccgccgcc | 4980 |
| | | gggatcactc tcggcatgga cgagctgtac aagtaagaat tcgatatcaa gcttatcgat | 5040 |
| | | aatcaacctc tggattacaa aatttgtgaa agattgactg gtattcttaa ctatgttgct | 5100 |
| | | ccttttacgc tatgtggata cgctgcttta atgcctttgt atcatgctat tgcttcccgt | 5160 |
| | | atggctttca ttttctcctc cttgtataaa tcctggttgc tgtctcttta tgaggagttg | 5220 |
| | | tggcccgttg tcaggcaacg tggcgtggtg tgcactgtgt ttgctgacgc aacccccact | 5280 |

TABLE 4-continued

List of Sequences

| Seq ID No | Name | Sequence | |
|---|---|---|---|
| | | ggttggggca ttgccaccac ctgtcagctc ctttccggga cttttcgcttt ccccctccct | 5340 |
| | | attgccacgg cggaactcat cgccgcctgc cttgcccgct gctggacagg ggctcggctg | 5400 |
| | | ttgggcactg acaattccgt ggtgttgtcg gggaaatcat cgtcctttcc ttggctgctc | 5460 |
| | | gcctgtgttg ccacctggat tctgcgcggg acgtccttct gctacgtccc ttcggccctc | 5520 |
| | | aatccagcgg accttccttc ccgcggcctg ctgccggctc tgcggcctct tccgcgtctt | 5580 |
| | | cgccttcgcc ctcagacgag tcggatctcc ctttgggccg cctccccgca tcgataccgt | 5640 |
| | | cgacctcgag acctagaaaa acatggagca atcacaagta gcaatacagc agctaccaat | 5700 |
| | | gctgattgtg cctggctaga agcacaagag gaggaggagg tgggttttcc agtcacacct | 5760 |
| | | caggtacctt taagaccaat gacttacaag gcagctgtag atcttagcca ctttttaaaa | 5820 |
| | | gaaaaggggg gactggaagg gctaattcac tcccaacgaa gacaagatat ccttgatctg | 5880 |
| | | tggatctacc acacacaagg ctacttccct gattggcaga actacacacc agggccaggg | 5940 |
| | | atcagatatc cactgacctt tggatggtgc tacaagctag taccagttga gcaagagaag | 6000 |
| | | gtagaagaag ccaatgaagg agagaacacc cgcttgttac accctgtgag cctgcatggg | 6060 |
| | | atggatgacc cggagagaga agtattagag tggaggtttg acagccgcct agcatttcat | 6120 |
| | | cacatggccc gagagctgca tccggactgt actgggtctc tctggttaga ccagatctga | 6180 |
| | | gcctgggagc tctctggcta actagggaac ccactgctta agcctcaata aagcttgcct | 6240 |
| | | tgagtgcttc aagtagtgtg tgcccgtctg ttgtgtgact ctggtaacta gagatccctc | 6300 |
| | | agacccttt agtcagtgtg gaaaatctct agcagggccc gtttaaaccc gctgatcagc | 6360 |
| | | ctcgactgtg ccttctagtt gccagccatc tgttgtttgc ccctccccg tgccttcctt | 6420 |
| | | gaccctggaa ggtgccactc ccactgtcct ttcctaataa aatgaggaaa ttgcatcgca | 6480 |
| | | ttgtctgagt aggtgtcatt ctattctggg gggtggggtg gggcaggaca gcaagggga | 6540 |
| | | ggattgggaa gacaatagca ggcatgctgg ggatgcggtg ggctctatgg cttctgaggc | 6600 |
| | | ggaaagaacc agctggggct ctaggggta tccccacgcg ccctgtagcg gcgcattaag | 6660 |
| | | cgcggcgggt gtggtggtta cgcgcagcgt gaccgctaca cttgccagcg ccctagcgcc | 6720 |
| | | cgctcctttc gctttcttcc cttcctttct cgccacgttc gccggctttc cccgtcaagc | 6780 |
| | | tctaaatcgg gggctccctt tagggttccg atttagtgct ttacggcacc tcgaccccaa | 6840 |
| | | aaaacttgat tagggtgatg gttcacgtag tgggccatcg ccctgataga cggtttttcg | 6900 |
| | | ccctttgacg ttggagtcca cgttctttaa tagtggactc ttgttccaaa ctggaacaac | 6960 |
| | | actcaaccct atctcggtct attcttttga tttataaggg attttgccga tttcggccta | 7020 |
| | | ttggttaaaa aatgagctga tttaacaaaa atttaacgcg aattaattct gtggaatgtg | 7080 |
| | | tgtcagttag ggtgtggaaa gtccccaggc tccccagcag gcagaagtat gcaaagcatg | 7140 |
| | | catctcaatt agtcagcaac caggtgtgga aagtccccag gctccccagc aggcagaagt | 7200 |
| | | atgcaaagca tgcatctcaa ttagtcagca accatagtcc cgcccctaac tccgcccatc | 7260 |
| | | ccgcccctaa ctccgcccag ttccgcccat tctccgcccc atggctgact aattttttt | 7320 |
| | | atttatgcag aggccgaggc cgcctctgcc tctgagctat tccagaagta gtgaggaggc | 7380 |
| | | ttttttggag gcctaggctt ttgcaaaaag ctcccgggag cttgtatatc cattttcgga | 7440 |
| | | tctgatcagc acgtgttgac aattaatcat cggcatagta tatcggcata gtataatacg | 7500 |
| | | acaaggtgag gaactaaacc atgccaagt tgaccagtgc cgttccggtg ctcaccgcgc | 7560 |
| | | gcgacgtcgc cggagcggtc gagttctgga ccgaccggct cgggttctcc cggacttcg | 7620 |
| | | tggaggacga cttcgccggt gtgctccggg acgcgtgc cctgttcatc agccgcgtcc | 7680 |
| | | aggaccaggt ggtgccggac aacaccctgg cctgggtgtg ggtgcgcggc ctggacgagc | 7740 |
| | | tgtacgccga gtggtcggag gtcgtgtcca cgaacttccg ggacgcctcc gggccggcca | 7800 |
| | | tgaccgagat cggcgagcag ccgtggggc gggagttcgc cctgcgcgac ccggccggca | 7860 |
| | | actgcgtgca cttcgtggcc gaggagcagg actgacacgt gctacgagat ttcgattcca | 7920 |
| | | ccgccgcctt ctatgaaagg ttgggcttcg gaatcgtttt ccgggacgcc ggctggatga | 7980 |
| | | tcctccagcg cggggatctc atgctggagt tcttcgccca ccccaacttg tttattgcag | 8040 |
| | | cttataatgg ttacaaataa agcaatagca tcacaaattt cacaaataaa gcatttttt | 8100 |
| | | cactgcattc tagttgtggt ttgtccaaac tcatcaatgt atcttatcat gtctgtatac | 8160 |
| | | cgtcgacctc tagctacagt ttggcgtaat catggtcata gctgtttcct gtgtgaaatt | 8220 |
| | | gttatccgct cacaattcca cacaacatac gagccggaag cataaagtgt aaagcctggg | 8280 |
| | | gtgcctaatg agtgagctaa ctcacattaa ttgcgttgcg ctcactgccc gctttccagt | 8340 |
| | | cgggaaacct gtcgtgccag ctgcattaat gaatcggcca acgcgcgggg agaggcggtt | 8400 |
| | | tgcgtattgg gcgctcttcc gcttcctcgc tcactgactc gctgcgctcg gtcgttcggc | 8460 |
| | | tgcggcgagc ggtatcagct cactcaaagg cggtaatacg gttatccaca gaatcaggg | 8520 |
| | | ataacgcagg aaagaacatg tgagcaaaag gccagcaaaa ggccaggaac cgtaaaaagg | 8580 |
| | | ccgcgttgct ggcgtttttc cataggctcc gcccccctga cgagcatcac aaaaatcgac | 8640 |
| | | gctcaagtca gaggtggcga aacccgacag gactataaag ataccaggcg tttccccctg | 8700 |
| | | gaagctccct cgtgcgctct cctgttccga ccctgccgct taccggatac ctgtccgcct | 8760 |
| | | ttctcccttc gggaagcgtg gcgctttctc atagctcacg ctgtaggtat ctcagttcgg | 8820 |
| | | tgtaggtcgt tcgctccaag ctgggctgtg tgcacgaacc ccccgttcag cccgaccgct | 8880 |
| | | gcgccttatc cggtaactat cgtcttgagt ccaacccggt aagacacgac ttatcgccac | 8940 |
| | | tggcagcagc cactggtaac aggattagca gagcgaggta tgtaggcggt gctacagagt | 9000 |
| | | tcttgaagtg gtggcctaac tacggctaca ctagaagaac agtatttggt atctgcgctc | 9060 |
| | | tgctgaagcc agttaccttc ggaaaaagag ttggtagctc ttgatccggc aaacaaacca | 9120 |
| | | ccgctggtag cggtggtttt tttgtttgca acagccagca tacgcgcaga aaaaaaggat | 9180 |
| | | ctcaagaaga tcctttgatc ttttctacgg ggtctgacgc tcagtggaac gaaaactcac | 9240 |
| | | gttaagggat tttggtcatg agattatcaa aaaggatctt cacctagatc cttttaaatt | 9300 |
| | | aaaaatgaag ttttaaatca atctaaagta tatatgagta aacttggtct gacagttacc | 9360 |
| | | aatgcttaat cagtgaggca cctatctcag cgatctgtct atttcgttca tccatagttg | 9420 |
| | | cctgactccc cgtcgtgtag ataactacga tacgggaggg cttaccatct ggccccagtg | 9480 |
| | | ctgcaatgat accgcgagac ccacgctcac cggctccaga tttatcagca ataaaccagc | 9540 |
| | | cagccggaag ggccgagcgc agaagtggtc ctgcaacttt atccgcctcc atccagtcta | 9600 |
| | | ttaattgttg ccgggaagct agagtaagta gttcgccagt taatagtttg cgcaacgttg | 9660 |
| | | ttgccattgc tacaggcatc gtggtgtcac gctcgtcgtt tggtatggct tcattcagct | 9720 |

TABLE 4-continued

List of Sequences

| Seq ID No | Name | Sequence | |
|---|---|---|---|
| | | ccggttccca acgatcaagg cgagttacat gatcccccat gttgtgcaaa aaagcggtta | 9780 |
| | | gctccttcgg tcctccgatc gttgtcagaa gtaagttggc cgcagtgtta tcactcatgg | 9840 |
| | | ttatggcagc actgcataat tctcttactg tcatgccatc cgtaagatgc tttttctgtga | 9900 |
| | | ctggtgagta ctcaaccaag tcattctgag aatagtgtat gcggcgaccg agttgctctt | 9960 |
| | | gcccggcgtc aatacgggat aataccgcgc cacatagcag aactttaaaa gtgctcatca | 10020 |
| | | ttggaaaacg ttcttcgggg cgaaaactct caaggatctt accgctgttg agatccagtt | 10080 |
| | | cgatgtaacc cactcgtgca cccaactgat cttcagcatc ttttactttc accagcgttt | 10140 |
| | | ctgggtgagc aaaaacagga aggcaaaatg ccgcaaaaaa gggaataagg gcgacacgga | 10200 |
| | | aatgttgaat actcatactc ttcctttttc aatattattg aagcatttat cagggttatt | 10260 |
| | | gtctcatgag cggatacata tttgaatgta tttagaaaaa taaacaaata ggggttccgc | 10320 |
| | | gcacatttcc ccgaaaagtg ccacctgac | 10349 |
| 133 | MMmin4 | ELWKKHEEAL KKFEELLKKF EEELKLGGSG EGSGGELLKK CEEALKKFEE LLKKFEEELK | 60 |
| | | LGGSGELLKK HEEALKKFEE LLKKFEELLK LGGSGEGSGG ELLKKHEEAL KKFEELLKKF | 120 |
| | | EELLKL | 126 |
| 134 | GL-MM (EC) | ttcttgaaga cgaaagggcc tcgtgatacg cctatttta taggttaatg tcatgataat | 60 |
| | | aatggtttct tagacgtcag gtggcacttt tcggggaaat gtgcgcggaa cccctatttg | 120 |
| | | tttattttc taaatacatt caaatatgta tccgctcatg agacaataac cctgataaat | 180 |
| | | gcttcaataa tattgaaaaa ggaagagtat gagtattcaa catttccgtg tcgcccttat | 240 |
| | | tccctttttt gcggcatttt gccttcctgt ttttgctcac ccagaaacgc tggtgaaagt | 300 |
| | | aaaagatgct gaagatcagt tgggtgcacg agtgggttac atcgaactgg atctcaacag | 360 |
| | | cggtaagatc cttgagagtt ttcgccccga agaacgtttt ccaatgatga gcactttaa | 420 |
| | | agttctgcta tgtggcgcgg tattatcccg tgttgacgcc gggcaagagc aactcggtcg | 480 |
| | | ccgcatacac tattctcaga atgacttggt tgagtactca ccagtcacag aaaagcatct | 540 |
| | | tacggatggc atgacagtaa gagaattatg cagtgctgcc ataaccatga gtgataacac | 600 |
| | | tgcggccaac ttacttctga caacgatcgg aggaccgaag gagctaaccg ctttttttgca | 660 |
| | | caacatgggg gatcatgtaa ctcgccttga tcgttgggaa ccggagctga atgaagccat | 720 |
| | | accaaacgac gagcgtgaca ccacgatgcc tgcagcaatg gcaacaacgt tgcgcaaact | 780 |
| | | attaactggc gaactactta ctctagcttc ccggcaacaa ttaatagact ggatggaggc | 840 |
| | | ggataaagtt gcaggaccac ttctgcgctc ggcccttccg gctggctggt ttattgctga | 900 |
| | | taaatctgga gccggtgagc gtgggtctcg cggtatcatt gcagcactgg ggccagatgg | 960 |
| | | taagccctcc cgtatcgtag ttatctacac gacggggagt caggcaacta tggatgaacg | 1020 |
| | | aaatagacag atcgctgaga taggtgcctc actgattaag cattggtaac tgtcagacca | 1080 |
| | | agtttactca tatatacttt agattgattt aaaacttcat ttttaattta aaaggatcta | 1140 |
| | | ggtgaagatc cttttttgata atctcatgac caaaatccct taacgtgagt tttcgttcca | 1200 |
| | | ctgagcgtca gaccccgtag aaaagatcaa aggatcttct tgagatcctt ttttttctgcg | 1260 |
| | | cgtaatctgc tgcttgcaaa caaaaaaacc accgctacca gcggtggttt gtttgccgga | 1320 |
| | | tcaagagcta ccaactcttt ttccgaaggt aactggcttc agcagagcgc agataccaaa | 1380 |
| | | tactgtcctt ctagtgtagc cgtagttagg ccaccacttc aagaactctg tagcaccgcc | 1440 |
| | | tacataccte gctctgctaa tcctgttacc agtggctgct gccagtggcg ataagtcgtg | 1500 |
| | | tcttaccggg ttggactcaa gacgatagtt accggataag gcgcagcggt cgggctgaac | 1560 |
| | | ggggggttcg tgcacacagc ccagcttgga gcgaacgacc tacaccgaac tgagatacct | 1620 |
| | | acagcgtgag ctatgagaaa gcgccacgct tcccgaaggg agaaaggcgg acaggtatcc | 1680 |
| | | ggtaagcggc agggtcggaa caggagagcg cacgagggag cttccagggg gaaacgcctg | 1740 |
| | | gtatctttat agtcctgtcg ggtttcgcca cctctgactt gagcgtcgat ttttgtgatg | 1800 |
| | | ctcgtcaggg gggcggagcc tatggaaaaa cgccagcaac gcggcctttt tacggttcct | 1860 |
| | | ggccttttgc tggccttttg ctcacatgtt ctttcctgcg ttatcccctg attctgtgga | 1920 |
| | | taaccgtatt accgcctttg agtgagctga taccgctcgc cgcagccgaa cgaccgagcg | 1980 |
| | | cagcgagtca gtgagcgagg aagcggaaga gcgcctgatg cggtattttc tccttacgca | 2040 |
| | | tctgtgcggt atttcacacc gcatatatgg tgcactctca gtacaatctg ctctgatgcc | 2100 |
| | | gcatagttaa gccagtatac actccgctat cgctacgtga ctgggtcatg gctgcgcccc | 2160 |
| | | gacaccgcc aacaccgcct gacgcgccct gacgggcttg tctgctcccg gcatccgctt | 2220 |
| | | acagacaagc tgtgaccgtc tccgggagct gcatgtgtca gaggttttca ccgtcatcac | 2280 |
| | | cgaaacgcgc gaggcagctg cggtaaagct catcagcgtg gtcgtgaagc gattcacaga | 2340 |
| | | tgtctgcctg ttcatccgcg tccagctcgt tgagtttctc cagaagcgtt aatgtctggc | 2400 |
| | | ttctgataaa gcgggccatg ttaagggcgg ttttttcct tttggtcact gatgcctccg | 2460 |
| | | tgtaaggggg atttctgttc atgggggtaa tgataccgat gaaacgagag aggatgctca | 2520 |
| | | cgatacgggt tactgatgat gaacatgccc ggttactgga acgttgtgag ggtaaacaac | 2580 |
| | | tggcggtatg gatgcggcgg gaccagagaa aaatcactca gggtcaatgc cagcgcttcg | 2640 |
| | | ttaatacaga tgtaggtgtt ccacagggta gccagcagca tcctgcgatg cagatccgga | 2700 |
| | | acataatggt gcagggcgct gacttccgcg tttccagact ttacgaaaca cggaaaccga | 2760 |
| | | agaccattca tgttgttgct caggtcgcag acgttttgca gcagcagtcg cttcacgttc | 2820 |
| | | gctcgcgtat cggtgattca ttctgctaac cagtaaggca accccgccag cctagccggg | 2880 |
| | | tcctcaacga caggagcacg atcatgcgca cccgtggcca gaccccaacg ctgcccgaga | 2940 |
| | | tgcgccgcgt gcggctgctg gagatggcgg acgcgatgga tatgttctgc caagggttgg | 3000 |
| | | tttgcgcatt cacagttctc cgcaagaatt gattggctcc aattcttgga gtggtgaatc | 3060 |
| | | cgttagcgag gtgccgccgg cttccattca ggtcgaggtg gcccggctcc atgcaccgcg | 3120 |
| | | acgcaacgcg gggaggcaga caaggtatag ggcggcgcct acaatccatg ccaacccgtt | 3180 |
| | | ccatgtgctc gccgaggcgg cataaatcgc cgtgacgatc agcggtccag tgatcgaagt | 3240 |
| | | taggctggta agagccgcga gcgatccttg aagctgtccc tgatggtcgt catctacctg | 3300 |
| | | cctggacagc atggcctgca acgcgggcat cccgatgccg ccggaagcga agaatcat | 3360 |
| | | aatggggaag gccatccagc ctcgcgtcgc gaacgccagc aagacgtagc ccagcgcgtc | 3420 |
| | | ggccgccatg ccggcgataa tggcctgctt ctcgccgaaa cgtttggtgg cgggaccagt | 3480 |

TABLE 4-continued

List of Sequences

| Seq ID No | Name | Sequence | | | | | |
|---|---|---|---|---|---|---|---|
| | | gacgaaggct | tgagcgaggg | cgtgcaagat | tccgaatacc | gcaagcgaca ggccgatcat | 3540 |
| | | cgtcgcgctc | cagcgaaagc | ggtcctcgcc | gaaaatgacc | cagagcgctg ccggcacctg | 3600 |
| | | tcctacgagt | tgcatgataa | agaagacagt | cataagtgcg | gcgacgatag tcatgccccg | 3660 |
| | | cgcccaccgg | aaggagctga | ctgggttgaa | ggctctcaag | ggcatcggtc gagatcccgg | 3720 |
| | | tgcctaatga | gtgagctaac | ttacattaat | tgcgttgcgc | tcactgcccg ctttccagtc | 3780 |
| | | gggaaacctg | tcgtgccagc | tgcattaatg | aatcggccaa | cgcgcgggga gaggcggttt | 3840 |
| | | gcgtattggg | cgccagggtg | gtttttcttt | tcaccagtga | gacgggcaac agctgattgc | 3900 |
| | | ccttcaccgc | ctggccctga | gagagttgca | gcaagcggtc | cacgctggtt tgccccagca | 3960 |
| | | ggcgaaaatc | ctgtttgatg | gtggttaacg | gcgggatata | acatgagctg tcttcggtat | 4020 |
| | | cgtcgtatcc | cactaccgag | atatccgcac | caacgcgcag | cccggactcg gtaatggcgc | 4080 |
| | | gcattgcgcc | cagcgccatc | tgatcgttgg | caaccagcat | cgcagtggga acgatgccct | 4140 |
| | | cattcagcat | ttgcatggtt | tgttgaaaac | cggacatggc | actccagtcg ccttcccgtt | 4200 |
| | | ccgctatcgg | ctgaatttga | ttgcgagtga | gatatttatg | ccagccagcc agacgcagac | 4260 |
| | | gcgccgagac | agaacttaat | gggcccgcta | acagcgcgat | ttgctggtga cccaatgcga | 4320 |
| | | ccagatgctc | cacgcccagt | cgcgtaccgt | cttcatggga | gaaataata ctgttgatgg | 4380 |
| | | gtgtctggtc | agagacatca | agaaataacg | ccggaacatt | agtgcaggca gcttccacag | 4440 |
| | | caatggcatc | ctggtcatcc | agcggatagt | taatgatcag | cccactgacg cgttgcgcga | 4500 |
| | | gaagattgtg | caccgccgct | ttacaggctt | cgacgccgct | tcgttctacc atcgacacca | 4560 |
| | | ccacgctggc | acccagttga | tcggcgcgag | atttaatcgc | cgcgacaatt tgcgacggcg | 4620 |
| | | cgtgcagggc | cagactggag | gtggcaacgc | caatcagcca | cgactgtttg cccgccagtt | 4680 |
| | | gttgtgccac | gcggttggga | atgtaattca | gctccgccat | cgccgcttcc acttttcc | 4740 |
| | | gcgttttcgc | agaaacgtgt | ctggcctggt | tcaccacgcg | ggaaacggtc tgataagaga | 4800 |
| | | caccggcata | ctctgcgaca | tcgtataacg | ttactggttt | cacattcacc accctgaatt | 4860 |
| | | gactctcttc | cgggcgctat | catgccctac | cgcgaaaggt | tttgcgccat tcgatggtgt | 4920 |
| | | ccgggatctc | gacgctctcc | cttatgcgac | tcctgcatta | ggaagcagcc cagtagtagg | 4980 |
| | | ttgaggccgt | tgagcaccgc | cgccgcaagg | aatggtgcat | gcaaggagat ggcgcccaac | 5040 |
| | | agtcccccgg | ccacggggcc | tgccaccata | cccgcgcga | aacaagcgct catgagcccg | 5100 |
| | | aagtggcgag | cccgatcttc | cccatcggtg | atgtcggcga | taggcgcc agcaaccgca | 5160 |
| | | cctgtggcgc | cggtgatgcc | ggccacgatg | cgtccggcgt | agaggatcga gatctcgatc | 5220 |
| | | ccgcgaaatt | aatacgactc | actataggg | aattgtgagc | ggataacaat tccctctag | 5280 |
| | | aaataatttt | gtttaacttt | aagaaggaga | tataccatgg | gcagcagcca tcatcatcat | 5340 |
| | | catcacggcg | gcgacggcga | gaacttgtat | tttcaagcta | gcggatccat gggagagatc | 5400 |
| | | tggaagcagc | acgaggaagc | gctgaagaaa | ttcgaggaac | tgctgaaaca atttgaggaa | 5460 |
| | | gagctgaaga | aaggtggcag | cggtagcggt | agcggtggcg | agatctggaa gcagtgcgaa | 5520 |
| | | gaggcgctga | agaaattcga | agagctgctg | aagaaatttg | aagaggaact gaagaaaggt | 5580 |
| | | ggcagcgggg | aaatttggaa | acaacatgag | gaagcgctga | agaaatttga ggagctgctg | 5640 |
| | | aagcaatttg | aggaacttct | gaagaaaggt | ggcagcggca | gcgtagcgg tggcgaaatt | 5700 |
| | | tggaaacaac | acgaggaagc | gctgaagaaa | ttcgaggagt | tactgaagaa attcgaggag | 5760 |
| | | ctgctgaaga | agcaccggt | ttaagaattc | ctcgaggctg | ctaacaaagc ccgaaaggaa | 5820 |
| | | gctgagttgg | ctgctgccac | cgctgagcaa | taactagcat | aaccccttgg gcctctaaa | 5880 |
| | | cgggtcttga | ggggttttt | gctgaaagga | ggaactatat | ccggatatcc cgcaagaggc | 5940 |
| | | ccggcagtac | cggcataacc | aagcctatgc | ctacagcatc | caggtgacg gtgccgagga | 6000 |
| | | tgacgatgag | cgcattgtta | gatttcatac | acggtgcctg | actgcgttag caatttaact | 6060 |
| | | gtgataaact | accgcattaa | agcttatcga | tgataagctg | tcaaacatga gaa | 6113 |
| 135 | GL-MM (FCK mam) | gtcgacggat | cgggagatct | cccgatcccc | tatggtgcac | tctcagtaca atctgctctg | 60 |
| | | atgccgcata | gttaagccag | tatctgctcc | ctgcttgtgt | gttggaggtc gctgagtagt | 120 |
| | | gcgcgagcaa | aatttaagct | acaacaaggc | aaggcttgac | cgacaattgc attaagcggg | 180 |
| | | tgcttagggt | taggcgtttt | gcgctgcttc | gcgatgtacg | ggccagatat acgcgttgac | 240 |
| | | attgattatt | gactagttat | taatagtaat | caattacggg | gtcattagtt catagcccat | 300 |
| | | atatggagtt | ccgcgttaca | taacttacgg | taaatggccc | gcctggctga ccgcccaacg | 360 |
| | | acccccgccc | attgacgtca | ataatgacgt | atgttcccat | agtaacgcca atagggactt | 420 |
| | | tccattgacg | tcaatgggtg | gagtatttac | ggtaaactgc | ccacttggca gtacatcaag | 480 |
| | | tgtatcatat | gccaagtacg | cccctattg | acgtcaatga | cggtaaatgg cccgcctggc | 540 |
| | | attatgccca | gtacatgacc | ttatgggact | ttcctacttg | gcagtacatc tacgtattag | 600 |
| | | tcatcgctat | taccatggtg | atgcggtttt | ggcagtacat | caatgggcgt ggatagcggt | 660 |
| | | ttgactcacg | gggatttcca | agtctccacc | ccattggtgc | caatgggagt ttgttttggc | 720 |
| | | accaaaatca | acgggacttt | ccaaaatgtc | gtaacaactc | cgccccattg acgcaaatgg | 780 |
| | | gcggtaggcg | tgtacggtgg | gaggtctata | taagcagcgc | gttttgcctg tactgggtct | 840 |
| | | ctctggttag | accagatctg | agcctgggag | ctctctggct | aactagggaa cccactgctt | 900 |
| | | aagcctcaat | aaagcttgcc | ttgagtgctc | caagtagtgt | gtgcccgtct gttgtgtgac | 960 |
| | | tctggtaact | agagatccct | cagacccttt | tagtcagtgt | ggaaaatctc tagcagtggc | 1020 |
| | | gcccgaacag | ggacttgaaa | gcgaaaggga | aaccagagga | gctctctcga cgcaggactc | 1080 |
| | | ggcttgctga | agcgcgcacg | gcaagaggcg | aggggcggcg | actggtgagt acgccaaaaa | 1140 |
| | | ttttgactag | cggaggctag | aaggagagag | atgggtgcga | gagcgtcagt attaagcggg | 1200 |
| | | ggagaattag | atcgcgatgg | gaaaaaattc | ggttaaggcc | aggggaaag aaaaaatata | 1260 |
| | | aattaaaaca | tatagtatgg | gcaagcaggg | agctagaacg | attcgcagtt aatcctggcc | 1320 |
| | | tgttagaaac | atcagaaggc | tgtagacaaa | tactgggaca | gctacaacca tcccttcaga | 1380 |
| | | caggatcaga | agaacttaga | tcattatata | atacagtagc | aaccctcact gtgtgcata | 1440 |
| | | aaaggataga | gataaaagac | accaaggaag | ctttagacaa | gatagaggaa gagcaaaaca | 1500 |
| | | aaagtaagac | caccgcacag | caagcggccg | ctgatcttca | gacctggagg aggagatatg | 1560 |
| | | agggacaatt | ggagaagtga | attatataaa | tataaagtag | taaaaattga accattagga | 1620 |
| | | gtagcaccca | ccaaggcaaa | gagaagagtg | gtgcagagag | aaaaagagc agtgggaata | 1680 |
| | | ggagctttgt | tccttgggtt | cttgggagca | gcaggaagca | ctatgggcgc agcgtcaatg | 1740 |

TABLE 4-continued

List of Sequences

| Seq ID No | Name | Sequence | |
|---|---|---|---|
| | | acgctgacgg tacaggccag acaattattg tctggtatag tgcagcagca gaacaatttg | 1800 |
| | | ctgagggcta ttgaggcgca acagcatctg ttgcaactca cagtctgggg catcaagcag | 1860 |
| | | ctccaggcaa gaatcctggc tgtggaaaga tacctaaagg atcaacagct cctgggggatt | 1920 |
| | | tggggttgct ctggaaaact catttgcacc actgctgtgc cttggaatgc tagttggagt | 1980 |
| | | aataaatctc tggaacagat ttggaatcac acgacctgga tggagtggga cagagaaatt | 2040 |
| | | aacaattaca caagcttaat acactcctta attgaagaat cgcaaaacca gcaagaaaag | 2100 |
| | | aatgaacaag aattattgga attagataaa tgggcaagtt tgtggaattg gtttaacata | 2160 |
| | | acaaattggc tgtggtatat aaaattattc ataatgatag taggaggctt ggtaggttta | 2220 |
| | | agaatagttt ttgctgtact ttcatatagt aatagagtta ggcagggata ttcaccatta | 2280 |
| | | tcgtttcaga cccacctccc aaccccgagg ggacccgaca ggcccgaagg aatagaagaa | 2340 |
| | | gaaggtggag agagagacag agacagatcc attcgattag tgaacggatc ggcactgcgt | 2400 |
| | | gcgccaattc tgcagacaaa tggcagtatt catccacaat tttaaaagaa aagggggggat | 2460 |
| | | tgggggggtac agtgcagggg aaagaatagt agacataata gcaacagaca tacaaactaa | 2520 |
| | | agaattacaa aaacaaatta caaaaattca aaattttcgg gtttattaca gggacagcag | 2580 |
| | | agatccagtt tggttaatta acattatggc cttaggtcac ttcatctcca tgggggttctt | 2640 |
| | | cttctgattt tctagaaaat gagatggggg tgcagagagc ttcctcagtg acctgcccag | 2700 |
| | | ggtcacatca gaaatgtcag agctagaact tgaactcaga ttactaatct taaattccat | 2760 |
| | | gccttggggg catgcaagta cgatatacag aaggagtgaa ctcattaggg cagatgacca | 2820 |
| | | atgagtttag gaaagaagag tccagggcag ggtacatcta caccacccgc ccagccctgg | 2880 |
| | | gtgagtccag ccacgttcac ctcattatag ttgcctctct ccagtcctac cttgacgggta | 2940 |
| | | agcacaagca gaaactggga caggagcccc aggagaccaa atcttcatgg tccctctggg | 3000 |
| | | aggatggggtg gggagagctg tggcagaggc ctcaggaggg gccctgctgc tcagtggtga | 3060 |
| | | cagataggg tgagaaagca gacagagtca ttccgtcaga attctgggtc tgtttggtac | 3120 |
| | | ttcttctcac gctaaggtgg cggtgtgata tgcacaatgc ctaaaaagca gggagagctg | 3180 |
| | | gaaagaaaca aggacagaga cagaggccaa gtcaaccaga ccaattccca gaggaagcaa | 3240 |
| | | agaaaccatt acagagacta caaggggggaa gggaaggaga gatgaattag cttcccctgt | 3300 |
| | | aaaccttaga acccagctgt tgccagggca acggggcaat acctgtctct tcagaggaga | 3360 |
| | | tgaagttgcc agggtaacta catcctgtct ttctcaagga ccatcccaga atgtggcacc | 3420 |
| | | cactagccgt taccatagca actgcctctt tgccccactt aatcccatcc cgtctgttaa | 3480 |
| | | aagggcccta tagttgagg tgggggaggt aggaagagcg atgatcactt gtggactaag | 3540 |
| | | tttgttcaca tcccttctc caaccccctc agtacatcac cctgggagaa caaggtccac | 3600 |
| | | ttgcttctgg gcccacacag tcctgcagta ttgtgtatat aaggccaggg caacggagga | 3660 |
| | | gcaggttttg aagtgaaagg caggcaggtg ttggggaggc agttaccggg gcaacgggaa | 3720 |
| | | cagggcgttt cggaggtggt tgccatgggg acctggatgc tgacgaaggc tcgcgaggct | 3780 |
| | | gtgagcagcc acagtgccct gctcagaagc cccaagctcg tcaatcaagc tggttctcca | 3840 |
| | | tttgcactca ggagcacggg caggcgagtg gccccctagtt ctggggggcag cgggggatcc | 3900 |
| | | atgggagaga tctggaagca gcacgaggaa gcgctgaaga aattcgagga actgctgaaa | 3960 |
| | | caatttgagg aagagctgaa gaaggtggc agcggtagcg gtagcggtgg cgagatctgg | 4020 |
| | | aagcagtgcg aagaggcgct gaagaaattc gaagagctgc tgaagaaatt tgaagaggaa | 4080 |
| | | ctgaagaaag gtgcagcgg ggaaatttgg aaacaacatg aggaagcgct gaagaaattt | 4140 |
| | | gaggagctgc tgaagcaatt tgaggaactt ctgaagaaag gtggcagcgga cagcggtagc | 4200 |
| | | ggtggcgaaa tttggaaaca acacgaggaa gcgctgaaga aattcgagga gttactgaag | 4260 |
| | | aaattcgagg agctgctgaa gaaagcaccg gtagtagcag tgagcaaggg cgaggagctg | 4320 |
| | | ttcaccgggg tggtgcccat cctggtcgag ctggacggcg acgtaaacgg ccacaagttc | 4380 |
| | | agcgtgtccg gcgagggcga gggcgatgcc acctacggca agctgaccct gaagttcatt | 4440 |
| | | tgcaccaccg gcaagctgcc cgtgccctgg cccaccctcg tgaccaccct gacctacggc | 4500 |
| | | gtgcagtgct tcagccgcta ccccgaccac atgaagcagc acgacttctt caagtccgcc | 4560 |
| | | atgcccgaag gctacgtcca ggagcgcacc atcttcttca aggacgacgg caactacaag | 4620 |
| | | acccgcgccg aggtgaagtt cgagggcgac accctggtga accgcatcga gctgaagggc | 4680 |
| | | atcgacttca aggaggacgg caacatcctg ggcacaagc tggagtacaa ctacaacagc | 4740 |
| | | cacaacgtct atatcatggc cgacaagcag aagaacggca tcaaggtgaa cttcaagatc | 4800 |
| | | cgccacaaca tcgaggacgg cagcgtgcag ctcgccgacc actaccagca gaacacccc | 4860 |
| | | atcggcgacg gccccgtgct gctgcccgac aaccactacc tgagcaccca gtccgccctg | 4920 |
| | | agcaaagacc ccaacgagaa gcgcgatcac atggtcctgc tggagttcgt gaccgccgcc | 4980 |
| | | gggatcactc tcggcatgga cgagctgtac aagtaagaat tcgatatcaa gcttatcgat | 5040 |
| | | aatcaacctc tggattacaa aatttgtgaa agattgactg gtattcttaa ctatgttgct | 5100 |
| | | ccttttacgc tatgtggata cgctgcttta atgcctttgt atcatgctat tgcttcccgt | 5160 |
| | | atggctttca ttttctcctc cttgtataaa tcctggttgc tgtctcttta tgaggagttg | 5220 |
| | | tggcccgttg tcaggcaacg tggcgtggtg tgcactgtgt tgctgacgc aacccccact | 5280 |
| | | ggttggggca ttgccaccac ctgtcagctc ctttccggga cttcgctttc cccctccct | 5340 |
| | | attgccacgg cggaactcat cgccgcctgc cttgcccgct gctggacagg ggctcggctg | 5400 |
| | | ttgggcactg acaattccgt ggtgttgtcg gggaaatcat cgtcctttcc ttggctgctc | 5460 |
| | | gcctgtgttg ccacctggat tctgcgcggg acgtccttct gctacgtccc ttcggccctc | 5520 |
| | | aatccagcgg accttccttc ccgcggcctg ctgccggctc tgcggcctct tccgcgtctt | 5580 |
| | | cgccttcgcc ctcagacgag tcggatctcc ctttgggccg cctccccgca tcgataccgt | 5640 |
| | | cgacctcgag acctagaaaa acatggagca atcacaagta gcaatacagc agctaccaat | 5700 |
| | | gctgattgtg cctggctaga agcacaagag gaggaggagg tgggttttcc agtcacacct | 5760 |
| | | caggtacctt taagaccaat gacttacaag gcagctgtag atcttagcca cttttaaaa | 5820 |
| | | gaaaaggggg gactggaagg gctaattcac tcccaacgaa gacaagatat ccttgatctg | 5880 |
| | | tggatctacc acacacaagg ctacttccct gattagcaga actacacacc agggccaggg | 5940 |
| | | atcagatatc cactgacctt tggatggtgc tacaagctag taccagttga gcaagagaag | 6000 |
| | | gtagaagaag ccaatgaagg agagaacacc cgcttgttac accctgtgag cctgcatggg | 6060 |
| | | atggatgacc cggagagaga agtattagag tggaggtttg acagccgcct agcatttcat | 6120 |
| | | cacatggccc gagagctgca tccggactgt actgggtctc tctggttaga ccagatctga | 6180 |

TABLE 4-continued

List of Sequences

| Seq ID No | Name | Sequence | |
|---|---|---|---|
| | | gcctgggagc tctctggcta actagggaac ccactgctta agcctcaata aagcttgcct | 6240 |
| | | tgagtgcttc aagtagtgtg tgcccgtctg ttgtgtgact ctggtaacta gagatccctc | 6300 |
| | | agacccttt agtcagtgtg gaaaatctct agcagggccc gtttaaaccc gctgatcagc | 6360 |
| | | ctcgactgtg ccttctagtt gccagccatc tgttgtttgc ccctccccg tgccttcctt | 6420 |
| | | gaccctggaa ggtgccactc ccactgtcct ttcctaataa aatgaggaaa ttgcatcgca | 6480 |
| | | ttgtctgagt aggtgtcatt ctattctggg gggtggggtg gggcaggaca gcaaggggga | 6540 |
| | | ggattgggaa gacaatagca ggcatgctgg ggatgcggtg ggctctatgg cttctgaggc | 6600 |
| | | ggaaagaacc agctggggct ctaggggta tccccacgcg ccctgtagcg gcgcattaag | 6660 |
| | | cgcggcgggt gtggtggtta cgcgcagcgt gaccgctaca cttgccagcg ccctagcgcc | 6720 |
| | | cgctcctttc gctttcttcc cttcctttct cgccacgttc gccggctttc cccgtcaagc | 6780 |
| | | tctaaatcgg gggctccctt tagggttccg atttagtgct ttacggcacc tcgaccccaa | 6840 |
| | | aaaacttgat tagggtgatg gttcacgtag tgggccatcg ccctgataga cggttttcg | 6900 |
| | | cctttgacg ttggagtcca cgttcttaa tagtggactc ttgttccaaa ctggaacaac | 6960 |
| | | actcaaccct atctcggtct attctttga tttataaggg attttgccga tttcggccta | 7020 |
| | | ttggttaaaa aatgagctga tttaacaaaa atttaacgcg aattaattct gtggaatgtg | 7080 |
| | | tgtcagttag ggtgtgaaa gtcccaggc tccccagcag gcagaagtat gcaaagcatg | 7140 |
| | | catctcaatt agtcagcaac caggtgtgga aagtcccag gctcccagc aggcagaagt | 7200 |
| | | atgcaaagca tgcatctcaa ttagtcagca accatagtcc cgcccctaac tccgcccatc | 7260 |
| | | ccgcccctaa ctccgcccca ttccgcccat ctccgcccc atggctgact aatttttttt | 7320 |
| | | atttatgcag aggccgaggc cgcctctgcc tctgagctat tccagaagta gtgaggaggc | 7380 |
| | | ttttttggag gcctaggctt ttgcaaaaag ctcccggag cttgtatatc cattttcgga | 7440 |
| | | tctgatcagc acgtgttgac aattaatcat cggcatagta tatcggcata gtataatacg | 7500 |
| | | acaaggtgag gaactaaaacc atggccaagt tgaccagtgc cgttccggtg ctcaccgccg | 7560 |
| | | gcgacgtcgc cggagcggtc gagttctgga ccgaccggct cgggttctcc cgggacttcg | 7620 |
| | | tggaggacga cttcgccggt gtggtccggg acgacgtgac cctgttcatc agcgcggtcc | 7680 |
| | | aggaccaggt ggtgccggac aacaccctgg cctgggtgtg gtgcgcggc ctggacgagc | 7740 |
| | | tgtacgccga gtggtcggag gtcgtgtcca cgaacttccg ggacgcctcc gggccggca | 7800 |
| | | tgaccgagat cggcgagcag ccgtggggc ggagttcgc cctgcgcgac cggccgcgga | 7860 |
| | | actgcgtgca cttcgtggcc gaggagcagg actgacacgt gctacgagat ttcgattcca | 7920 |
| | | ccgccgcctt ctatgaaagg ttgggcttcg gaatcgtttt ccgggacgcc ggctggatga | 7980 |
| | | tcctccagcg cggggatctc atgctggagt tcttcgccca ccccaacttg tttattgcag | 8040 |
| | | cttataatgg ttacaaataa agcaatagca tcacaaattt cacaaataaa gcattttttt | 8100 |
| | | cactgcattc tagttgtggt ttgtccaaac tcatcaatgt atcttatcat gtctgtatac | 8160 |
| | | cgtcgacctc tagctagagc ttggcgtaat catggtcata gctgtttcct gtgtgaaatt | 8220 |
| | | gttatccgct cacaattcca cacaacatac gagccggaag cataaagtgt aaagcctggg | 8280 |
| | | gtgcctaatg agtgagctaa ctcacattaa ttgcgttgcg ctcactgccc gctttccagt | 8340 |
| | | cgggaaacct gtcgtgccag ctgcattaat gaatcggcca acgcgcgggg agaggcggtt | 8400 |
| | | tgcgtattgg gcgctcttcc gcttcctcgc tcactgactc gctgcgctcg gtcgttcggc | 8460 |
| | | tgcggcgagc ggtatcagct cactcaaagg cggtaatacg gttatccaca gaatcagggg | 8520 |
| | | ataacgcagg aaagaacatg tgagcaaaag gccagcaaaa ggccaggaac cgtaaaaagg | 8580 |
| | | ccgcgttgct ggcgtttttc cataggctcc gcccccctga cgagcatcac aaaaatcgac | 8640 |
| | | gctcaagtca gaggtggcga aacccgacag gactataaag ataccaggcg tttccccctg | 8700 |
| | | gaagctccct cgtgcgctct cctgttccga ccctgccgct taccggatac ctgtccgcct | 8760 |
| | | ttctcccttc gggaagcgtg gcgctttctc atagctcacg ctgtaggtat ctcagttcgg | 8820 |
| | | tgtaggtcgt tcgctccaag ctgggctgtg tgcacgaacc ccccgttcag cccgaccgct | 8880 |
| | | gcgccttatc cggtaactat cgtcttgagt ccaacccggt aagacacgac ttatcgccac | 8940 |
| | | tggcagcagc cactggtaac aggattagca gagcgaggta tgtaggcggt gctacagagt | 9000 |
| | | tcttgaagtg gtggcctaac tacggctaca ctagaagaac agtatttggt atctgcgctc | 9060 |
| | | tgctgaagcc agttaccttc ggaaaaagag ttggtagctc ttgatccggc aaacaaacca | 9120 |
| | | ccgctggtag cggtggtttt tttgtttgca agcagcagat tacgcgcaga aaaaaaggat | 9180 |
| | | ctcaagaaga tcctttgatc ttttctacgg ggtctgacgc tcagtggaac gaaaactcac | 9240 |
| | | gttaagggat tttggtcatg agattatcaa aaaggatctt cacctagatc cttttaaatt | 9300 |
| | | aaaaatgaag ttttaaatca atctaaagta tatatgagta aacttggtct gacagttacc | 9360 |
| | | aatgcttaat cagtgaggca cctatctcag cgatctgtct atttcgttca tccatagttg | 9420 |
| | | cctgactccc cgtcgtgtag ataactacga tacgggaggg cttaccatct ggccccagtg | 9480 |
| | | ctgcaatgat accgcgagac ccacgctcac cggctccaga tttatcagca ataaaccagc | 9540 |
| | | cagccggaag ggccgagcgc agaagtggtc ctgcaactt atccgcctcc atccagtcta | 9600 |
| | | ttaattgttg ccgggaagct agagtaagta gttcgccagt taatagtttg cgcaacgttg | 9660 |
| | | ttgccattgc tacaggcatc gtggtgtcac gctcgtcgtt tggtatggct tcattcagct | 9720 |
| | | ccggttccca acgatcaagg cgagttacat gatccccat gttgtgcaaa aaagcggtta | 9780 |
| | | gctccttcgg tcctccgatc gttgtcagaa gtaagttggc cgcagtgtta tcactcatgg | 9840 |
| | | ttatggcagc actgcataat tctcttactg tcatgccatc cgtaagatgc ttttctgtga | 9900 |
| | | ctggtgagta ctcaaccaag tcattctgag aatagtgtat gcggcgaccg agttgctctt | 9960 |
| | | gcccggcgtc aatacggat aataccgcgc cacatagcag aactttaaaa gtgctcatca | 10020 |
| | | ttggaaaacg ttcttcgggg cgaaaactct caaggatctt accgctgttg agatccagtt | 10080 |
| | | cgatgtaacc cactcgtgca cccaactgat cttcagcatc ttttactttc accagcgttt | 10140 |
| | | ctgggtgagc aaaaacagga aggcaaaatg ccgcaaaaaa gggaataagg gcgacacgga | 10200 |
| | | aatgttgaat actcatactc ttcctttttc aatattattg aagcatttat cagggttatt | 10260 |
| | | gtctcatgag cggatacata tttgaatgta tttagaaaaa taaacaaata ggggttccgc | 10320 |
| | | gcacatttcc ccgaaaagtg ccacctgac | 10349 |
| 136 | GL-MM | EIWKQHEEAL KKFEELLKQF EEELKKGGSG SGSGGEIWKQ CEEALKKFEE LLKKFEEELK | 60 |
| | | KGGSGEIWKQ HEEALKKFEE LLKQFEELLK KGGSGSGSGG EIWKQHEEAL KKFEELLKKF | 120 |
| | | EELLKK | 126 |

TABLE 4-continued

List of Sequences

| Seq ID No | Name | Sequence | | | | | |
|---|---|---|---|---|---|---|---|
| 137 | MZH3 (EC) | ctcatgacca | aaatcccttc | acgtgagtta | cgcgcgcgtc | gttccactga | gcgtcagacc | 60 |
| | | ccgtagaaaa | gatcaaagga | tcttcttgag | atccttttt | tctgcgcgta | atctgctgct | 120 |
| | | tgcaaacaaa | aaaaccaccg | ctaccagcgg | tggtttgttt | gccggatcaa | gagctaccaa | 180 |
| | | ctcttttcc | gaaggtaact | ggcttcagca | gagcgcagat | accaaatact | gttcttctag | 240 |
| | | tgtagccgta | gttagcccac | cacttcaaga | actctgtagc | accgcctaca | tacctcgctc | 300 |
| | | tgctaatcct | gttaccagtg | gctgctgcca | gtggcgataa | gtcgtgtctt | accgggttgg | 360 |
| | | actcaagacg | atagttaccg | gataaggcgc | agcggtcggg | ctgaacgggg | ggtcgtgca | 420 |
| | | cacagcccag | cttggagcga | acgacctaca | ccgaactgag | atacctacag | cgtgagctat | 480 |
| | | gagaaagcgc | cacgcttccc | gaagggagaa | aggcggacag | gtatccggta | agcggcaggg | 540 |
| | | tcggaacagg | agagcgcacg | agggagcttc | caggggggaa | cgcctggtat | ctttatagtc | 600 |
| | | ctgtcggggtt | tcgccacctc | tgacttgagc | gtcgattttt | gtgatgctcg | tcagggggc | 660 |
| | | ggagcctatg | gaaaaacgcc | agcaacgcgg | ccttttacg | gttcctggcc | ttttgctggc | 720 |
| | | cttttgctca | catgttcttt | cctgcgttat | ccctgattc | tgtggataac | cgtattaccg | 780 |
| | | cctttgagtg | agctgatacc | gctcgccgca | gccgaacgac | cgagcgcagc | gagtcagtga | 840 |
| | | gcgaggaagc | ggaaggcgag | agtagggaac | tgccaggcat | caaactaagc | agaaggcccc | 900 |
| | | tgacggatgg | cctttttgcg | tttctacaaa | ctctttctgt | gttgtaaaac | gacggccagt | 960 |
| | | cttaagctcg | ggccccctgg | gcggttctga | taacgagtaa | tcgttaatcc | gcaaataacg | 1020 |
| | | taaaaaaccg | cttcggcggg | tttttttatg | ggggaagttt | agggaaagag | catttgtcag | 1080 |
| | | aatatttaag | ggcgcctgtc | actttgcttg | atatatgaga | attatttaac | cttataaatg | 1140 |
| | | agaaaaagc | aacgcacttt | aaataagata | cgttgcttt | tcgattgatg | aacacctata | 1200 |
| | | attaaactat | tcatctatta | tttatgattt | tttgtatata | caatatttct | agtttgttaa | 1260 |
| | | agagaattaa | gaaaataaat | ctcgaaaata | ataaaggaaa | aatcagtttt | tgatatcaaa | 1320 |
| | | attatacatg | tcaacgataa | tacaaaatat | aatacaaact | ataagatgtt | atcagtattt | 1380 |
| | | attatcattt | agaataaatt | ttgtgtcgcc | cttccgcgaa | attaatacga | ctcactatag | 1440 |
| | | gggaattgtg | agcggataac | aattcccctc | tagaaataat | tttgtttaac | ttttaggagg | 1500 |
| | | taaaacatat | gggtaagggc | ggtcatcatc | atcaccatca | tggcggcgac | ggcgagaatt | 1560 |
| | | tgtattttca | ggcagcccg | gagttgcgcc | aagagcacca | gcagctggca | caagagttcc | 1620 |
| | | aacaactgtt | gcaggagatt | caacaactgg | gccgtgagct | gttgaaaggt | gagctgcagg | 1680 |
| | | gcattaaaca | gctgcgtgag | gcgagcgaga | aagcgcgtaa | cccggagaag | aaatctgtgt | 1740 |
| | | tgcagaagat | cctgaagat | gaagagaaac | acattgagct | gctggaaacc | ctgcaacaga | 1800 |
| | | cgggtcaaga | ggcgcaacag | ctgctgcaaga | agttgcagca | gaccggtcaa | gaactgtgc | 1860 |
| | | aactgggcgg | ttccggtggc | ccggagctgc | gccagaaaca | ccaacagctg | gcccagaaga | 1920 |
| | | ttcagcaact | gctgcagaag | caccaacagt | gggtgcaaa | aatcttggaa | gatgaagaaa | 1980 |
| | | aacacatcga | actgctggag | actatcctgg | gtggcagcgg | cggtgacgaa | ctgcgtgaac | 2040 |
| | | tgctgaaggg | tgaactgcag | ggtatcaagc | aataccgcga | actgcagcaa | ctgggtcaaa | 2100 |
| | | aagctcagca | attggttcaa | aagctgcagc | aaaccggtca | gaagctgtgg | cagctgggtt | 2160 |
| | | aactcgagcc | cctagcata | accccttggg | gcctctaaac | gggtcttgag | gggttttttg | 2220 |
| | | ccccctgagac | gcgtcaatcg | agttcgtacc | taagggcgac | accccctaat | tagcccgggc | 2280 |
| | | gaaaggccca | gtctttcgac | tgagcctttc | gttttatttg | atgcctggca | gttcctact | 2340 |
| | | ctcgcatggg | gagtccccac | actaccatcg | gcgctacggc | gtttcactc | tgagttcggc | 2400 |
| | | atggggtcag | gtgggaccac | cgcgctactg | ccgccaggca | acaagggtt | gttatgagcc | 2460 |
| | | atattcaggt | ataaatgggc | tcgcgataat | gttcagaatt | ggttaattgg | ttgtaacact | 2520 |
| | | gacccctatt | tgtttatttt | tctaaataca | ttcaaatata | tatccgctca | tgagacaata | 2580 |
| | | accctgataa | atgcttcaat | aatattgaaa | aaggaagaat | atgagtattc | aacatttccg | 2640 |
| | | tgtcgccctt | attcccttt | ttgcggcatt | ttgccttcct | gttttgctc | acccagaaac | 2700 |
| | | gctggtgaaa | gtaaaagatg | ctgaagatca | gttgggtgca | cgagtgggtt | acatcgaact | 2760 |
| | | ggatctcaac | agcggtaaga | tccttgagag | ttttcgcccc | gaagaacgtt | ttccaatgat | 2820 |
| | | gagcacttt | aaagttctgc | tatgtggcgc | ggtattatcc | cgtattgacg | ccgggcaaga | 2880 |
| | | gcaactcggt | cgccgcatac | actattctca | gaatgacttg | gttgagtact | caccagtcac | 2940 |
| | | agaaaagcat | cttacggatg | gcatgacagt | aagagaatta | tgcagtgctg | ccataaccat | 3000 |
| | | gagtgataac | actgcggcca | acttacttct | gacaacgatc | ggaggaccga | aggagctaac | 3060 |
| | | cgctttttg | cacaacatgg | gggatcatgt | aactcgcctt | gatcgttggg | aaccggagct | 3120 |
| | | gaatgaagcc | ataccaaacg | acgagcgtga | caccacgatg | cctgtagcga | tggcaacaac | 3180 |
| | | gttgcgcaaa | ctattaactg | gcgaactact | tactctagct | tcccggcaac | aattaataga | 3240 |
| | | ctggatggag | gcggataaag | ttgcaggacc | acttctgcgc | tcggcccttc | cggctggctg | 3300 |
| | | gtttattgct | gataaatccg | gagccggtga | gcgtgttctc | gcggtatcat | tcgcagcgct | 3360 |
| | | ggggccagat | ggtaagccct | cccgtatcgt | agttatctac | acgacgggga | gtcaggcaac | 3420 |
| | | tatggatgaa | cgaaatagac | agatcgctga | gataggtgcc | tcactgatta | agcattggta | 3480 |
| | | agcggcgcgc | catcgaatgg | cgcaaaacct | ttcgcggtat | ggcatgatag | cgcccggaag | 3540 |
| | | agagtcaatt | cagggtggtg | aatatgaaac | cagtaacgtt | atacgatgtc | gcagagtatg | 3600 |
| | | ccggtgtctc | ttatcagacc | gtttcccgcg | tggtgaacca | ggccagccac | gtttctgcga | 3660 |
| | | aaacgcggga | aaaagtggaa | gcggcgatgg | cggagctgaa | ttacattccc | aaccgcgtgg | 3720 |
| | | cacaacaact | ggcgggcaaa | cagtcgttgc | tgattggcgt | tgccacctcc | agtctggccc | 3780 |
| | | tgcacgcgcc | gtcgcaaatt | gtcgcggcga | ttaaatctcg | cgccgatcaa | gttcctact | 3840 |
| | | gcgtggtggt | gtcgatggta | gaacgaagcg | gcgtcgaagc | ctgtaaagcg | gcggtgcaca | 3900 |
| | | atcttctcgc | gcaacgcgtc | agtgggctga | tcattaacta | tccgctggat | gaccaggatg | 3960 |
| | | ccattgctgt | ggaagctgcc | tgcactaatg | ttccggcgtt | atttcttgat | gtctctgacc | 4020 |
| | | agacacccat | caacagtatt | atttctccc | atgaggacgg | tacgcgactg | ggcgtggaga | 4080 |
| | | atctcggtcg | attgggtcac | cagcaaatcg | cgctgttagc | gggcccatta | agttctgtct | 4140 |
| | | cggcgcgtct | gcgtctggct | ggctggcata | aatatctcac | tcgcaatcaa | attcagccga | 4200 |
| | | tagcggaacg | ggaaggcgac | tggagtgcca | tgtccggttt | tcaacaaacc | atgcaaatgc | 4260 |
| | | tgaatgaggg | catcgttccc | actgcgatgc | tggttgccaa | cgatcagatg | gcgctgggcg | 4320 |
| | | caatgcgcgc | cattaccgag | tccgggctgc | gcgttggtgc | ggatatctcg | gtagtgggat | 4380 |

TABLE 4-continued

List of Sequences

| Seq ID No | Name | Sequence | |
|---|---|---|---|
| | | acgacgatac cgaagatagc tcatgttata tcccgccgtt aaccaccatc aaacaggatt | 4440 |
| | | ttcgcctgct ggggcaaacc agcgtggacc gcttgctgca actctctcag ggccaggcgg | 4500 |
| | | tgaagggcaa tcagctgttg ccagtctcac tggtgaaaag aaaaaccacc ctggcgccca | 4560 |
| | | atacgcaaac cgcctctccc cgcgcgttgg ccgattcatt aatgcagctg gcacgacagg | 4620 |
| | | tttcccgact ggaaagcggg cagtga | 4646 |
| 138 | MZH3 | GSPELRQEHQ QLAQEFQQLL QEIQQLGREL LKGELQGIKQ LREASEKARN PEKKSVLQKI | 60 |
| | | LEDEEKHIEL LETLQQTGQE AQQLLQELQQ TGQELWQLGG SGGPELRQKH QQLAQKIQQL | 120 |
| | | LQKHQQLGAK ILEDEEKHIE LLETILGGSG GDELRELLKG ELQGIKQYRE LQQLGQKAQQ | 180 |
| | | LVQKLQQTGQ KLWQLG | 196 |
| 139 | MZH3 H138D | GSPELRQEHQ QLAQEFQQLL QEIQQLGREL LKGELQGIKQ LREASEKARN PEKKSVLQKI | 60 |
| | | LEDEEKHIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 140 | MZH3 H138N | GSPELRQEHQ QLAQEFQQLL QEIQQLGREL LKGELQGIKQ LREASEKARN PEKKSVLQKI | 60 |
| | | LEDEEKHIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 141 | MZH3 H67D | GSPELRQEHQ QLAQEFQQLL QEIQQLGREL LKGELQGIKQ LREASEKARN PEKKSVLQKI | 60 |
| | | LEDEEKDIEL LETLQQTGQE AQQLLQELQQ TGQELWQLGG SGGPELRQKH QQLAQKIQQL | 120 |
| | | LQKHQQLGAK ILEDEEKHIE LLETILGGSG GDELRELLKG ELQGIKQYRE LQQLGQKAQQ | 180 |
| | | LVQKLQQTGQ KLWQLG | 196 |
| 142 | MZH3 H67N | GSPELRQEHQ QLAQEFQQLL QEIQQLGREL LKGELQGIKQ LREASEKARN PEKKSVLQKI | 60 |
| | | LEDEEKNIEL LETLQQTGQE AQQLLQELQQ TGQELWQLGG SGGPELRQKH QQLAQKIQQL | 120 |
| | | LQKHQQLGAK ILEDEEKHIE LLETILGGSG GDELRELLKG ELQGIKQYRE LQQLGQKAQQ | 180 |
| | | LVQKLQQTGQ KLWQLG | 196 |
| 143 | MZH3 H67D, H138D | GSPELRQEHQ QLAQEFQQLL QEIQQLGREL LKGELQGIKQ LREASEKARN PEKKSVLQKI | 60 |
| | | LEDEEKDIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 144 | MZH3 H67D, H138N | GSPELRQEHQ QLAQEFQQLL QEIQQLGREL LKGELQGIKQ LREASEKARN PEKKSVLQKI | 60 |
| | | LEDEEKDIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 145 | MZH3 H67N, H138D | GSPELRQEHQ QLAQEFQQLL QEIQQLGREL LKGELQGIKQ LREASEKARN PEKKSVLQKI | 60 |
| | | LEDEEKNIEL LETLQQTGQE AQQLLQELQQ TGQELWQLGG SGGPELRQKH QQLAQKIQQL | 120 |
| | | LQKHQQLGAK ILEDEEKDIE LLETILGGSG GDELRELLKG ELQGIKQYRE LQQLGQKAQQ | 180 |
| | | LVQKLQQTGQ KLWQLG | 196 |
| 146 | MZH3 H67N, H138N | GSPELRQEHQ QLAQEFQQLL QEIQQLGREL LKGELQGIKQ LREASEKARN PEKKSVLQKI | 60 |
| | | LEDEEKNIEL LETLQQTGQE AQQLLQELQQ TGQELWQLGG SGGPELRQKH QQLAQKIQQL | 120 |
| | | LQKHQQLGAK ILEDEEKNIE LLETILGGSG GDELRELLKG ELQGIKQYRE LQQLGQKAQQ | 180 |
| | | LVQKLQQTGQ KLWQLG | 196 |
| 147 | MZH3 P3G H9A Q10D L12I A13R F16L T91R G92E L95G G100N P105T L106R R107L Q108E H110I A114G Q115R Q118R V182M Q183E L185C Q186G | GSGELRQEAD QIRQELQQLL QEIQQLGREL LKGELQGIKQ LREASEKARN PEKKSVLQKI | 60 |
| | | LEDEEKHIEL LETLQQTGQE AQQLLQELQQ REQEGWQLGN SGGTERLEKI QQLGRKIRQL | 120 |
| | | LQKHQQLGAK ILEDEEKHIE LLETILGGSG GDELRELLKG ELQGIKQYRE LQQLGQKAQQ | 180 |
| | | LMEKCGQRAM KRNQLG | 196 |

TABLE 4-continued

List of Sequences

| Seq ID No | Name | Sequence |
|---|---|---|
| | T188R | |
| | G189A | |
| | Q190M | |
| | L192R | |
| | W193N | |

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All embodiments of the invention described herein can, in alternate embodiments, be more specifically defined by any of the transitional terms "comprising," "consisting essentially of," and "consisting of."

---

What is claimed is:

1. A composition comprising a peptide comprising one or more amino acid sequences of a formula selected from the group consisting of:

-XX+XX--XX0+X--XX00X--XX0L (Generic Sequence A);
-X+0+X--XX++X--XX++X--X+0+(Generic Sequence B);
+XX+XX--XX0+X--XX00X--X+0L (Generic Sequence C); and
-XX+0+--XX++X--XX++X--XX0+(Generic Sequence D);

wherein (+) represents a positively charged amino acid, (−) represents a negatively charged amino acid, (0) represents an amino acid having an amide side-chain, and (X) represents any amino acid; and wherein the peptide comprises (SEQ ID No: 5)-LOOP-(SEQ ID No: 6)-LOOP-(SEQ ID No: 7)-LOOP-(SEQ ID No: 8), and wherein each occurrence of LOOP is independently selected from the group consisting of GGSGKGSGG (SEQ ID No: 17), GGCG (SEQ ID No: 18), GACG (SEQ ID No: 19), and GGSG (SEQ ID No; 20).

2. The composition according to claim 1, further comprising one or more cofactors, wherein the peptide binds the one or more cofactors to form a complex.

3. The composition according to claim 2, wherein the one or more cofactors include an electrochromic cofactor, a heme, a metal ion, a cluster of metal ions, or a fluorophore.

4. The composition according to claim 1, wherein the peptide is artificial and capable of being expressed in eukaryotic cells.

5. The composition according to claim 4, wherein the artificial peptide has a cytosolic portion, a transmembrane portion, and an extracellular portion.

6. The composition according to claim 4, wherein the artificial peptide functions as a voltage sensor, an MRI contrast agent, a metal binding reporter, and/or a cellular probe.

7. A method of detecting electrical activity in a cell comprising: providing the cell with a composition comprising a peptide, wherein the peptide comprises: one or more amino acid sequences having a formula selected from the group consisting of:

-XX+XX--XX0+X--XX00X--XX0L (Generic Sequence A);
-X+0+X--XX++X--XX++X--X+0+(Generic Sequence B);
+XX+XX--XX0+X--XX00X--X+0L (Generic Sequence C); and
-XX+0+--XX++X--XX++X--XX0+(Generic Sequence D), wherein (+) represents a positively charged amino acid, (−) represents a negatively charged amino acid, (0) represents an amino acid having an amide side-chain, and (X) represents any amino acid, and wherein the peptide comprises (SEQ ID No: 5)-LOOP-(SEQ ID No: 6)-LOOP-(SEQ ID No: 7)-LOOP-(SEQ ID No: 8), and wherein each occurrence of LOOP is independently selected from the group consisting of GGSGKGSGG (SEQ ID No: 17), GGCG (SEQ ID No: 18), GACG (SEQ ID No: 19), and GGSG (SEQ ID No: 20), and an electrochromic cofactor that is naturally occurring within the cell;

contacting the peptide with the electrochromic cofactor to bind the electrochromic cofactor with the peptide;

detecting light emitted by the electrochromic cofactor; and correlating the detected light of the electrochromic cofactor to an electrical activity of the cell.

* * * * *

SEQUENCE LISTING

```
<160> NUMBER OF SEQ ID NOS: 157

<210> SEQ ID NO 1
<211> LENGTH: 26
<212> TYPE: PRT
<213> ORGANISM: Artificial Sequence
<220> FEATURE:
<223> OTHER INFORMATION: Synthetic Sequence Exemplary Helix Protein 1
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 1

Glu Ile Trp Lys Xaa Xaa Glu Asp Ala Leu Gln Lys Phe Glu Xaa Xaa
1               5                   10                  15

Leu Asn Gln Phe Glu Asp Xaa Xaa Gln Leu
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Sequence Exemplary Helix Protein 2
<220> FEATURE:
<221> NAME/KEY: misc_feature
<222> LOCATION: (5)..(6)
<223> OTHER INFORMATION: Xaa can be any naturally occurring amino acid
<220> FEATURE:
```

```
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 2

Glu Ile Trp Lys Xaa Xaa Glu Asp Ala Leu Gln Lys Phe Glu Xaa Xaa
1               5                   10                  15

Leu Asn Gln Phe Glu Asp Xaa Xaa Gln Leu
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic sequence Exemplary Helix Protein 3
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 3

Arg Xaa Trp Lys Xaa Xaa Glu Asp Ala Xaa Gln Lys Phe Glu Glu Ala
1               5                   10                  15

Leu Asn Gln Phe Glu Asp Leu Lys Gln Leu
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic Sequence Exemplary Helix Protein 4
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 4

Glu Ile Lys Gln Arg Xaa Glu Asp Ala Leu Arg Lys Phe Glu Glu Ala
1               5                   10                  15

Leu Lys Arg Xaa Glu Asp Xaa Xaa Gln Lys
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Sequence Exemplary Helix Protein 5
```

```
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 5

Glu Xaa Xaa Lys Xaa Xaa Glu Asp Xaa Xaa Gln Lys Xaa Glu Glu Xaa
1               5                   10                  15

Xaa Asn Gln Xaa Glu Asp Xaa Xaa Gln Leu
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Sequence Exemplary Helix Protein 6
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 6

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Lys Gln Lys
```

20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic Sequence Exemplary Helix Protein 7
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 7

Arg Xaa Xaa Lys Xaa Xaa Glu Asp Xaa Xaa Gln Lys Xaa Glu Glu Xaa
1               5                   10                  15

Xaa Asn Gln Xaa Glu Asp Xaa Lys Gln Leu
            20                  25

<210> SEQ ID NO 8
<211> LENGTH: 26
<212> TYPE: PRT
<213> ORGANISM: Artificial Sequence
<220> FEATURE:
<223> OTHER INFORMATION: Synthetic Sequence Exemplary Helix Protein 8
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature

```
<222> LOCATION: (23)..(24)
<223> OTHER INFORMATION: Xaa can be any naturally occurring amino acid

<400> SEQUENCE: 8

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Xaa Gln Lys
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic Sequence Exemplary Helix Protein 9
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 9

Glu Xaa Xaa Lys Xaa Xaa Glu Asp Xaa Xaa Gln Lys Xaa Glu Glu Xaa
1               5                   10                  15

Xaa Asn Gln Xaa Glu Asp Xaa Xaa Gln Leu
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic Sequence Exemplary Helix Protein 10
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
```

```
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 10

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Lys Gln Lys
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic Sequence Exemplary Helix Protein 11
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 11

Arg Xaa Xaa Lys Xaa Xaa Glu Asp Xaa Xaa Gln Lys Xaa Glu Glu Xaa
1               5                   10                  15

Xaa Asn Gln Xaa Glu Asp Xaa Lys Gln Leu
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Sequence Exemplary Helix Protein 12
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
```

```
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 12

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Xaa Gln Lys
            20                  25

<210> SEQ ID NO 13
<211> LENGTH: 26
<212> TYPE: PRT
<213> ORGANISM: Artificial Sequence
<220> FEATURE:
<223> OTHER INFORMATION: Synthetic Sequence Exemplary Helix Protein 13
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 13

Glu Xaa Xaa Lys Xaa Xaa Glu Asp Xaa Xaa Gln Lys Xaa Glu Glu Xaa
1               5                   10                  15

Xaa Asn Gln Xaa Glu Asp Xaa Xaa Gln Leu
            20                  25

<210> SEQ ID NO 14
<211> LENGTH: 26
<212> TYPE: PRT
<213> ORGANISM: Artificial Sequence
<220> FEATURE:
```

<223> OTHER INFORMATION: Synthetic Sequence Exemplary Helix Protein 14
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 14

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Lys Gln Lys
            20                  25

<210> SEQ ID NO 15
<211> LENGTH: 26
<212> TYPE: PRT
<213> ORGANISM: Artificial Sequence
<220> FEATURE:
<223> OTHER INFORMATION: Synthetic Sequence Exemplary Helix Protein 15
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 15

Arg Xaa Xaa Lys Xaa Xaa Glu Asp Xaa Xaa Gln Lys Xaa Glu Glu Xaa
1               5                   10                  15

```
Xaa Asn Gln Xaa Glu Asp Xaa Lys Gln Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Synthetic Sequence Exemplary Helix Protein 16
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 16

Glu Xaa Lys Gln Arg Xaa Glu Asp Xaa Xaa Arg Lys Xaa Glu Glu Xaa
1               5                   10                  15

Xaa Lys Arg Xaa Glu Asp Xaa Xaa Gln Lys
            20                  25

<210> SEQ ID NO 17
<211> LENGTH: 9
<212> TYPE: PRT
<213> ORGANISM: Artificial Sequence
<220> FEATURE:
<223> OTHER INFORMATION: Synthetic Sequence Loop sequence in maquette

<400> SEQUENCE: 17

Gly Gly Ser Gly Lys Gly Ser Gly Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic Sequence Loop sequence in maquette

<400> SEQUENCE: 18

Gly Gly Cys Gly
1

<210> SEQ ID NO 19
<211> LENGTH: 4
<212> TYPE: PRT
<213> ORGANISM: Artificial Sequence
<220> FEATURE:
```

```
<223> OTHER INFORMATION: Synthetic Sequence Loop sequence in maquette

<400> SEQUENCE: 19

Gly Ala Cys Gly
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Sequence Loop sequence in maquette

<400> SEQUENCE: 20

Gly Gly Ser Gly
1

<210> SEQ ID NO 21
<211> LENGTH: 126
<212> TYPE: PRT
<213> ORGANISM: Artificial Sequence
<220> FEATURE:
<223> OTHER INFORMATION: Synthetic Sequence GLSLoop

<400> SEQUENCE: 21

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Leu Lys Gln Lys
        115                 120                 125

<210> SEQ ID NO 22
<211> LENGTH: 126
<212> TYPE: PRT
<213> ORGANISM: Artificial Sequence
<220> FEATURE:
<223> OTHER INFORMATION: Synthetic Sequence PEB Mut B

<400> SEQUENCE: 22

Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Ala Cys
    50                  55                  60

Gly Arg Ile Trp Lys Gln His Glu Asp Ala Leu Gln Lys Phe Glu Glu
65                  70                  75                  80
```

Ala Leu Asn Gln Phe Glu Asp Leu Lys Gln Leu Gly Gly Ser Gly Lys
            85                  90                  95

Gly Ser Gly Gly Glu Ile Lys Gln Arg His Glu Asp Ala Leu Arg Lys
        100                 105                 110

Phe Glu Glu Ala Leu Lys Arg Phe Glu Asp Arg Val Gln Lys
        115                 120                 125

<210> SEQ ID NO 23
<211> LENGTH: 126
<212> TYPE: PRT
<213> ORGANISM: Artificial Sequence
<220> FEATURE:
<223> OTHER INFORMATION: Synthetic Sequence PEB Mut C

<400> SEQUENCE: 23

Glu Ile Trp Lys Leu His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
50                  55                  60

Gly Arg Ile Trp Lys Glu His Glu Asp Ala Leu Gln Lys Phe Glu Glu
65                  70                  75                  80

Ala Leu Asn Gln Phe Glu Asp Leu Lys Gln Leu Gly Gly Ser Gly Lys
            85                  90                  95

Gly Ser Gly Gly Glu Ile Lys Gln Arg His Glu Asp Ala Leu Arg Lys
        100                 105                 110

Phe Glu Glu Ala Leu Lys Arg Phe Glu Asp Arg Val Gln Lys
        115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Synthetic Sequence PEB Mut D

<400> SEQUENCE: 24

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
        50                  55                  60

Gly Arg Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
            85                  90                  95

Gly Ser Gly Gly Glu Ile Lys Gln Arg His Glu Asp Ala Leu Arg Lys
        100                 105                 110

Phe Glu Glu Ala Leu Lys Arg Phe Glu Asp Arg Val Gln Lys
        115                 120                 125

<210> SEQ ID NO 25

-continued

```
<211> LENGTH: 126
<212> TYPE: PRT
<213> ORGANISM: Artificial Sequence
<220> FEATURE:
<223> OTHER INFORMATION: Synthetic Sequence dFP1.0

<400> SEQUENCE: 25

Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Glu His Glu Asp Ala His Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg His Glu Asp Arg Val Gln Lys
        115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Synthetic Sequence C-His Stab CGRD

<400> SEQUENCE: 26

Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Asp Trp Lys Glu His Glu Asp Ala His Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg His Glu Asp Arg Val Gln Lys
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Synthetic Sequence C41 Stab Map

<400> SEQUENCE: 27

Glu Ile Trp Lys Leu Phe Glu Asp Ala Leu Gln Lys Phe Glu His Glu
1               5                   10                  15
```

```
Leu Asn Gln Phe Glu Asp Arg Val Gln Leu Gly Gly Ser Gly Lys Gly
            20                  25                  30

Ser Gly Gly Glu Ile Lys Gln Arg Cys Ala Asp Ala Leu Arg Lys Phe
        35                  40                  45

Glu Glu Ala Leu Lys Arg Phe Glu Asp Leu Lys Gln Lys Gly Gly Ser
 50                  55                  60

Gly Glu Ile Trp Lys Leu Phe Glu Asp Ala Leu Gln Lys His Glu Glu
 65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Ser His Glu Asp Ala Leu Arg Lys
            100                 105                 110

His Glu Glu Ala Leu Lys Arg Phe Glu Asp Leu Lys Gln Lys
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic Sequence C41 Stab Map CARD

<400> SEQUENCE: 28

Glu Ile Trp Lys Leu Phe Glu Asp Ala Leu Gln Lys Phe Glu His Glu
 1               5                  10                  15

Leu Asn Gln Phe Glu Asp Arg Val Gln Leu Gly Gly Ser Gly Lys Gly
            20                  25                  30

Ser Gly Gly Glu Ile Lys Gln Arg Cys Ala Arg Asp Leu Arg Lys Phe
        35                  40                  45

Glu Glu Ala Leu Lys Arg Phe Glu Asp Leu Lys Gln Lys Gly Gly Ser
 50                  55                  60

Gly Glu Ile Trp Lys Leu Phe Glu Asp Ala Leu Gln Lys His Glu Glu
 65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Ser His Glu Asp Ala Leu Arg Lys
            100                 105                 110

His Glu Glu Ala Leu Lys Arg Phe Glu Asp Leu Lys Gln Lys
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic Sequence C41 Py Stab

<400> SEQUENCE: 29

Glu Ile Trp Lys Leu Phe Glu Asp Ala Leu Gln Lys Phe Glu Glu Asp
 1               5                  10                  15

Leu Asn Gln Phe Glu Asp Arg Val Gln Leu Gly Gly Ser Gly Lys Gly
            20                  25                  30

Ser Gly Gly Glu Ile Lys Gln Leu Cys Ala Arg Asp Leu Arg Lys Phe
        35                  40                  45

Glu Glu Ala Leu Lys Arg Phe Glu Asp Leu Lys Gln Lys Gly Gly Ser
 50                  55                  60

Gly Glu Ile Trp Lys Leu Phe Glu Asp Ala Leu Gln Lys His Glu Glu
 65                  70                  75                  80
```

Ala Leu Asn Gln Phe Glu Asp His Lys Gln Leu Gly Gly Ser Gly Lys
                85                  90                  95

Gly Ser Gly Gly Glu Ile Lys Gln Arg Ser Glu Asp Ala Leu Arg Lys
            100                 105                 110

His Glu Glu Ala Leu Lys Arg Phe Glu Asp Leu Lys Gln Lys
        115                 120                 125

<210> SEQ ID NO 30
<211> LENGTH: 126
<212> TYPE: PRT
<213> ORGANISM: Artificial Sequence
<220> FEATURE:
<223> OTHER INFORMATION: Synthetic Sequence 528-GL

<400> SEQUENCE: 30

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Trp Lys Gln Cys Glu Asp Ala Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Trp Lys Gln His Glu Asp Ala Leu Arg Lys
            100                 105                 110

Phe Glu Glu Ala Leu Lys Arg Phe Glu Asp Leu Lys Gln Lys
        115                 120                 125

<210> SEQ ID NO 31
<211> LENGTH: 131
<212> TYPE: PRT
<213> ORGANISM: Artificial Sequence
<220> FEATURE:
<223> OTHER INFORMATION: Synthetic Sequence MM3 FC

<400> SEQUENCE: 31

Glu Leu Leu Lys Lys His Glu Ala Leu Lys Lys Phe Glu Glu Leu
1               5                   10                  15

Leu Lys Lys Phe Glu Glu Leu Lys Lys Gly Gly Ser Gly Ser Gly
            20                  25                  30

Ser Gly Gly Glu Leu Leu Lys Lys Phe Glu Glu Ala Leu Lys Lys Phe
        35                  40                  45

Glu Glu Leu Leu Lys Lys Phe Glu Glu Leu Lys Lys Gly Gly Ser
    50                  55                  60

Gly Trp Gly Ser Gly Gly Glu Leu Leu Lys Lys His Glu Glu Ala Leu
65                  70                  75                  80

Lys Lys Phe Glu Glu Leu Leu Lys Lys Phe Glu Glu Leu Leu Lys Lys
                85                  90                  95

Gly Gly Ser Gly Ser Gly Ser Gly Gly Glu Leu Leu Lys Lys Cys Glu
            100                 105                 110

Glu Ala Leu Lys Lys Phe Glu Glu Leu Leu Lys Lys Phe Glu Glu Leu
        115                 120                 125

Leu Lys Lys

130

<210> SEQ ID NO 32
<211> LENGTH: 131
<212> TYPE: PRT
<213> ORGANISM: Artificial Sequence
<220> FEATURE:
<223> OTHER INFORMATION: Synthetic Sequence MM3 FC H6F H76F

<400> SEQUENCE: 32

```
Glu Leu Leu Lys Lys Phe Glu Glu Ala Leu Lys Lys Phe Glu Glu Leu
1               5                   10                  15

Leu Lys Lys Phe Glu Glu Glu Leu Lys Lys Gly Gly Ser Gly Ser Gly
                20                  25                  30

Ser Gly Gly Glu Leu Leu Lys Lys Phe Glu Glu Ala Leu Lys Lys Phe
            35                  40                  45

Glu Glu Leu Leu Lys Lys Phe Glu Glu Leu Lys Lys Gly Gly Ser
        50                  55                  60

Gly Trp Gly Ser Gly Gly Glu Leu Leu Lys Lys Phe Glu Glu Ala Leu
65                  70                  75                  80

Lys Lys Phe Glu Glu Leu Leu Lys Lys Phe Glu Glu Leu Leu Lys Lys
                85                  90                  95

Gly Gly Ser Gly Ser Gly Ser Gly Gly Glu Leu Leu Lys Lys Cys Glu
            100                 105                 110

Glu Ala Leu Lys Lys Phe Glu Glu Leu Leu Lys Lys Phe Glu Glu Leu
        115                 120                 125

Leu Lys Lys
    130
```

<210> SEQ ID NO 33
<211> LENGTH: 131
<212> TYPE: PRT
<213> ORGANISM: Artificial Sequence
<220> FEATURE:
<223> OTHER INFORMATION: Synthetic Sequence MM3 FC H6F H76F F90D

<400> SEQUENCE: 33

```
Glu Leu Leu Lys Lys Phe Glu Glu Ala Leu Lys Lys Phe Glu Glu Leu
1               5                   10                  15

Leu Lys Lys Phe Glu Glu Glu Leu Lys Lys Gly Gly Ser Gly Ser Gly
                20                  25                  30

Ser Gly Gly Glu Leu Leu Lys Lys Phe Glu Glu Ala Leu Lys Lys Phe
            35                  40                  45

Glu Glu Leu Leu Lys Lys Phe Glu Glu Leu Lys Lys Gly Gly Ser
        50                  55                  60

Gly Trp Gly Ser Gly Gly Glu Leu Leu Lys Lys Phe Glu Glu Ala Leu
65                  70                  75                  80

Lys Lys Phe Glu Glu Leu Leu Lys Lys Asp Glu Glu Leu Leu Lys Lys
                85                  90                  95

Gly Gly Ser Gly Ser Gly Ser Gly Gly Glu Leu Leu Lys Lys Cys Glu
            100                 105                 110

Glu Ala Leu Lys Lys Phe Glu Glu Leu Leu Lys Lys Phe Glu Glu Leu
        115                 120                 125

Leu Lys Lys
    130
```

<210> SEQ ID NO 34
<211> LENGTH: 171

```
<212> TYPE: PRT
<213> ORGANISM: Artificial Sequence
<220> FEATURE:
<223> OTHER INFORMATION: Synthetic Sequence AM1

<400> SEQUENCE: 34

Glu Ile Trp Lys Gln His Glu Asp Ala Leu Gln Lys Phe Phe Ala Leu
1               5                   10                  15

Leu Leu Leu Leu Ala Leu Leu Leu Leu Ala Leu Leu Leu His Leu
            20                  25                  30

Leu Ala Phe Glu Gly Gly Ser Gly Gly Gly Ser Gly Gly Lys Phe Leu
            35                  40                  45

Leu Leu Leu Ala Leu Leu Ala Leu Leu Leu Leu Ala Leu Leu Leu His
        50                  55                  60

Leu Leu Ala Phe Trp Glu Ala Leu Asn Gln Phe Glu Asp Leu Ala Lys
65                  70                  75                  80

Gln Gly Gly Ser Gly Gly Gly Ser Gly Gly Glu Ile Trp Lys Gln His
                85                  90                  95

Glu Asp Ala Leu Gln Lys Phe Phe Ala Leu Leu Leu Leu Leu Ala Leu
            100                 105                 110

Leu Leu Leu Leu Ala Leu Leu Leu His Leu Leu Ala Phe Lys Gly Gly
            115                 120                 125

Ser Gly Gly Gly Ser Gly Gly Glu Phe Leu Leu Leu Leu Ala Leu Leu
            130                 135                 140

Ala Leu Leu Leu Leu Ala Leu Leu Leu His Leu Leu Ala Phe Trp Glu
145                 150                 155                 160

Ala Leu Asn Gln Phe Glu Asp Leu Ala Lys Gln
                165                 170

<210> SEQ ID NO 35
<211> LENGTH: 196
<212> TYPE: PRT
<213> ORGANISM: Artificial Sequence
<220> FEATURE:
<223> OTHER INFORMATION: Synthetic Sequence MZH3

<400> SEQUENCE: 35

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
            35                  40                  45

Arg Asn Pro Glu Lys Lys Ser Val Leu Gln Lys Ile Leu Glu Asp Glu
        50                  55                  60

Glu Lys His Ile Glu Leu Glu Thr Leu Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
            115                 120                 125

Ala Lys Ile Leu Glu Asp Glu Lys His Ile Glu Leu Leu Glu Thr
        130                 135                 140

Ile Leu Gly Gly Ser Gly Gly Asp Glu Leu Arg Glu Leu Leu Lys Gly
145                 150                 155                 160
```

```
Glu Leu Gln Gly Ile Lys Gln Tyr Arg Glu Leu Gln Gln Leu Gly Gln
            165                 170                 175

Lys Ala Gln Gln Leu Val Gln Lys Leu Gln Gln Thr Gly Gln Lys Leu
        180                 185                 190

Trp Gln Leu Gly
        195

<210> SEQ ID NO 36
<211> LENGTH: 196
<212> TYPE: PRT
<213> ORGANISM: Artificial Sequence
<220> FEATURE:
<223> OTHER INFORMATION: Synthetic Sequence MZH3 H138D

<400> SEQUENCE: 36

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys His Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Gln Lys His Gln Gln Leu Gly
            115                 120                 125

Ala Lys Ile Leu Glu Asp Glu Lys Asp Ile Glu Leu Leu Glu Thr
        130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
            165                 170                 175

Lys Ala Gln Gln Leu Val Gln Lys Leu Gln Gln Thr Gly Gln Lys Leu
        180                 185                 190

Trp Gln Leu Gly
        195

<210> SEQ ID NO 37
<211> LENGTH: 196
<212> TYPE: PRT
<213> ORGANISM: Artificial Sequence
<220> FEATURE:
<223> OTHER INFORMATION: Synthetic Sequence MZH3 H138N

<400> SEQUENCE: 37

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
```

```
                    50                  55                  60

Glu Lys His Ile Glu Leu Leu Glu Thr Leu Gln Gln Thr Gly Gln Glu
 65                  70                  75                  80

Ala Gln Gln Leu Leu Gln Glu Leu Gln Gln Thr Gly Gln Glu Leu Trp
                     85                  90                  95

Gln Leu Gly Gly Ser Gly Gly Pro Glu Leu Arg Gln Lys His Gln Gln
                100                 105                 110

Leu Ala Gln Lys Ile Gln Gln Leu Leu Gln Lys His Gln Gln Leu Gly
                115                 120                 125

Ala Lys Ile Leu Glu Asp Glu Glu Lys Asn Ile Glu Leu Leu Glu Thr
                130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
                180                 185                 190

Trp Gln Leu Gly
        195

<210> SEQ ID NO 38
<211> LENGTH: 196
<212> TYPE: PRT
<213> ORGANISM: Artificial Sequence
<220> FEATURE:
<223> OTHER INFORMATION: Synthetic Sequence MZH3 H67D, H138D

<400> SEQUENCE: 38

Gly Ser Pro Glu Leu Arg Gln Glu His Gln Gln Leu Ala Gln Glu Phe
 1                   5                  10                  15

Gln Gln Leu Leu Gln Glu Ile Gln Gln Leu Gly Arg Glu Leu Leu Lys
                    20                  25                  30

Gly Glu Leu Gln Gly Ile Lys Gln Leu Arg Glu Ala Ser Glu Lys Ala
                    35                  40                  45

Arg Asn Pro Glu Lys Lys Ser Val Leu Gln Lys Ile Leu Glu Asp Glu
 50                  55                  60

Glu Lys Asp Ile Glu Leu Leu Glu Thr Leu Gln Gln Thr Gly Gln Glu
 65                  70                  75                  80

Ala Gln Gln Leu Leu Gln Glu Leu Gln Gln Thr Gly Gln Glu Leu Trp
                     85                  90                  95

Gln Leu Gly Gly Ser Gly Gly Pro Glu Leu Arg Gln Lys His Gln Gln
                100                 105                 110

Leu Ala Gln Lys Ile Gln Gln Leu Leu Gln Lys His Gln Gln Leu Gly
                115                 120                 125

Ala Lys Ile Leu Glu Asp Glu Glu Lys Asp Ile Glu Leu Leu Glu Thr
                130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
                180                 185                 190

Trp Gln Leu Gly
        195
```

<210> SEQ ID NO 39
<211> LENGTH: 196
<212> TYPE: PRT
<213> ORGANISM: Artificial Sequence
<220> FEATURE:
<223> OTHER INFORMATION: Synthetic Sequence MZH3 H67D, H138N

<400> SEQUENCE: 39

```
Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys Asp Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
        115                 120                 125

Ala Lys Ile Leu Glu Asp Glu Glu Lys Asn Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Thr Gly Gln Lys Leu
            180                 185                 190

Trp Gln Leu Gly
        195
```

<210> SEQ ID NO 40
<211> LENGTH: 196
<212> TYPE: PRT
<213> ORGANISM: Artificial Sequence
<220> FEATURE:
<223> OTHER INFORMATION: Synthetic Sequence MZH3 H67N, H138D

<400> SEQUENCE: 40

```
Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys Asn Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110
```

Leu Ala Gln Lys Ile Gln Gln Leu Leu Gln Lys His Gln Gln Leu Gly
            115                 120                 125

Ala Lys Ile Leu Glu Asp Glu Lys Asp Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 41
<211> LENGTH: 196
<212> TYPE: PRT
<213> ORGANISM: Artificial Sequence
<220> FEATURE:
<223> OTHER INFORMATION: Synthetic Sequence MZH3 H67N, H138N

<400> SEQUENCE: 41

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys Asn Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
            115                 120                 125

Ala Lys Ile Leu Glu Asp Glu Lys Asn Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 42
<211> LENGTH: 126
<212> TYPE: PRT
<213> ORGANISM: Artificial Sequence
<220> FEATURE:
<223> OTHER INFORMATION: Synthetic Sequence PEB Mut E

<400> SEQUENCE: 42

Glu Ile Trp Lys Gln His Glu Asp Ala Leu Gln Lys Phe Glu Glu Ala
1               5                   10                  15

```
Leu Asn Gln Phe Glu Asp Leu Lys Gln Leu Gly Gly Ser Gly Lys Gly
         20                  25                  30

Ser Gly Gly Glu Ile Lys Gln Arg His Glu Asp Ala Leu Arg Lys Phe
         35                  40                  45

Glu Glu Ala Leu Lys Arg Phe Glu Asp Leu Lys Gln Lys Gly Gly Cys
 50                  55                  60

Gly Arg Asp Trp Lys Gln His Glu Asp Ala Leu Gln Lys Phe Glu Glu
 65                  70                  75                  80

Ala Leu Asn Gln Phe Glu Asp Leu Lys Gln Leu Gly Gly Ser Gly Lys
             85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Leu Lys Gln Lys
            115                 120                 125

<210> SEQ ID NO 43
<211> LENGTH: 116
<212> TYPE: PRT
<213> ORGANISM: Artificial Sequence
<220> FEATURE:
<223> OTHER INFORMATION: Synthetic Sequence PEB Mut F

<400> SEQUENCE: 43

Glu Ile Trp Lys Gln His Glu Asp Ala Leu Gln Lys Phe Glu Glu Ala
 1               5                  10                  15

Leu Asn Gln Phe Glu Asp Leu Lys Gln Leu Gly Gly Cys Gly Glu Ile
             20                  25                  30

Lys Gln Arg Ala Glu Asp Ala Leu Arg Lys Phe Glu Glu Ala Leu Lys
         35                  40                  45

Arg Phe Glu Asp Leu Lys Gln Lys Gly Gly Cys Gly Glu Ile Trp Lys
     50                  55                  60

Gln His Glu Asp Ala Leu Gln Lys Phe Glu Glu Ala Leu Asn Gln Phe
 65                  70                  75                  80

Glu Asp Leu Lys Gln Leu Gly Gly Ser Gly Glu Ile Lys Gln Arg His
             85                  90                  95

Glu Asp Ala Leu Arg Lys Phe Glu Glu Ala Leu Lys Arg Phe Glu Asp
            100                 105                 110

Leu Lys Gln Lys
        115

<210> SEQ ID NO 44
<211> LENGTH: 126
<212> TYPE: PRT
<213> ORGANISM: Artificial Sequence
<220> FEATURE:
<223> OTHER INFORMATION: Synthetic Sequence PEB Mut G

<400> SEQUENCE: 44

Glu Ile Trp Lys Gln His Glu Asp Ala Leu Gln Lys Phe Glu Glu Ala
 1               5                  10                  15

Leu Asn Gln Phe Glu Asp Leu Lys Gln Leu Gly Gly Ser Gly Lys Gly
             20                  25                  30

Ser Gly Gly Glu Ile Lys Gln Arg His Glu Asp Ala Leu Arg Lys Phe
         35                  40                  45

Glu Glu Ala Leu Lys Arg Phe Glu Asp Leu Lys Gln Lys Gly Gly Cys
 50                  55                  60

Gly Arg Glu Trp Lys Gln His Glu Asp Ala Leu Gln Lys Phe Glu Glu
```

```
                65                  70                  75                  80
Ala Leu Asn Gln Phe Glu Asp Leu Lys Gln Leu Gly Gly Ser Gly Lys
                    85                  90                  95

Gly Ser Gly Gly Glu Ile Lys Gln Arg His Glu Asp Ala Leu Arg Lys
                100                 105                 110

Phe Glu Glu Ala Leu Lys Arg Phe Glu Asp Leu Lys Gln Lys
                115                 120                 125

<210> SEQ ID NO 45
<211> LENGTH: 131
<212> TYPE: PRT
<213> ORGANISM: Artificial Sequence
<220> FEATURE:
<223> OTHER INFORMATION: Synthetic Sequence dFP 1.1

<400> SEQUENCE: 45

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
                20                  25                  30

Ser Gly Gly Glu Ile Trp Lys Gln Cys Glu Asp Ala Leu Gln Lys Phe
            35                  40                  45

Glu Glu Ala Leu Asn Gln Phe Glu Asp Leu Lys Gln Leu Gly Gly Ser
        50                  55                  60

Gly Ser Gly Ser Gly Gly Glu Ile Trp Lys Gln His Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
                100                 105                 110

Asp Ala Leu Gln Lys Phe Glu Glu Ala Leu Asn Gln Phe Glu Asp Leu
                115                 120                 125

Lys Gln Leu
    130

<210> SEQ ID NO 46
<211> LENGTH: 6122
<212> TYPE: DNA
<213> ORGANISM: Artificial Sequence
<220> FEATURE:
<223> OTHER INFORMATION: Synthetic Sequence dFP 1.0 (E. Coli)

<400> SEQUENCE: 46
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atcctcgaga ccggttcact tttgcacacg atcttcgtgg     360
cgcttcagcg cttcctcaaa tttgcgcagc gcatcctcat ggcgctgttt aatctcgcca     420
ccgctgccct tgccgctgcc acccagttgt ttcagatctt caaattgatt cagcgcttcc     480
tcaaactttt ggtgcgcgtc ttcgtgctcc ttccaaatac gaccgcagcc acctttctgc     540
ttcagatcct caaaacgttt cagcgcttcc tcgaacttac gcagcgcgtc ttcgtgacgt     600
tgcttgatct cgccaccgct gcctttaccg ctgccaccca gttgcttcag atcctcaaac     660
```

```
tggttcagcg cttcctcgaa tttctgcagc gcgtcttcgt ggctcttcca gatctcgccg    720
gatccctgaa aatacaggtt ttcaccatcg cctccgtggt gatgatggtg atgcccacct   780
ttacccatat gaatatcgcc ttccatggta tatctccttc ttaaagttaa acaaaattat   840
ttctagaggg gaattgttat ccgctcacaa ttcccctata gtgagtcgta ttaatttcgc   900
gggatcgaga tctcgatcct ctacgccgga cgcatcgtgg ccggcatcac cggcgccaca   960
ggtgcggttg ctggcgccta tatcgccgac atcaccgatg ggaagatcg ggctcgccac   1020
ttcgggctca tgagcgcttg tttcggcgtg gtatggtgg caggcccgt ggccggggga   1080
ctgttgggcg ccatctcctt gcatgcacca ttccttgcgg cggcggtgct caacggcctc   1140
aacctactac tgggctgctt cctaatgcag gagtcgcata agggagagcg tcgagatccc   1200
ggacaccatc gaatggcgca aaacctttcg cggtatggca tgatagcgcc cggaagagag   1260
tcaattcagg gtggtgaatg tgaaaccagt aacgttatac gatgtcgcag agtatgccgg   1320
tgtctcttat cagaccgttt cccgcgtggt gaaccaggcc agccacgttt ctgcgaaaac   1380
gcgggaaaaa gtggaagcgg cgatggcgga gctgaattac attcccaacc gcgtggcaca   1440
acaactggcg ggcaaacagt cgttgctgat tggcgttgcc acctccagtc tggccctgca   1500
cgcgccgtcg caaattgtcg cggcgattaa atctcgcgcc gatcaactgg gtgccagcgt   1560
ggtggtgtcg atggtagaac gaagcggcgt cgaagcctgt aaagcggcgg tgcacaatct   1620
tctcgcgcaa cgcgtcagtg gctgatcat taactatccg ctggatgacc aggatgccat   1680
tgctgtggaa gctgcctgca ctaatgttcc ggcgttattt cttgatgtct ctgaccagac   1740
acccatcaac agtattattt tctcccatga agacggtacg cgactgggcg tggagcatct   1800
ggtcgcattg ggtcaccagc aaatcgcgct gttagcgggc ccattaagtt ctgtctcggc   1860
gcgtctgcgt ctggctggct ggcataaata tctcactcgc aatcaaattc agccgatagc   1920
ggaacgggaa ggcgactgga gtgccatgtc cggttttcaa caaaccatgc aaatgctgaa   1980
tgagggcatc gttcccactg cgatgctggt tgccaacgat cagatggcgc tgggcgcaat   2040
gcgcgccatt accgagtccg gctgcgcgt tggtgcggat atctcggtag tgggatacga   2100
cgataccgaa gacagctcat gttatatccc gccgttaacc accatcaaac aggattttcg   2160
cctgctgggg caaaccagcg tggaccgctt gctgcaactc tctcagggcc aggcggtgaa   2220
gggcaatcag ctgttgcccg tctcactggt gaaaagaaaa accaccctgg cgcccaatac   2280
gcaaaccgcc tctccccgcg cgttggccga ttcattaatg cagctggcac gacaggtttc   2340
ccgactggaa agcgggcagt gagcgcaacg caattaatgt aagttagctc actcattagg   2400
caccgggatc tcgaccgatg cccttgagag ccttcaaccc agtcagctcc ttccggtggg   2460
cgcggggcat gactatcgtc gccgcactta tgactgtctt ctttatcatg caactcgtag   2520
gacaggtgcc ggcagcgctc tgggtcattt tcggcgagga ccgctttcgc tggagcgcga   2580
cgatgatcgg cctgtcgctt gcggtattcg gaatcttgca cgccctcgct caagccttcg   2640
tcactggtcc cgccaccaaa cgtttcggcg agaagcaggc cattatcgcc ggcatggcgg   2700
ccgacgcgct gggctacgtc ttgctggcgt tcgcgacgcg aggctggatg gccttcccca   2760
ttatgattct tctcgcttcc ggcggcatcg ggatgcccgc gttgcaggcc atgctgtcca   2820
ggcaggtaga tgacgaccat cagggacagc ttcaaggatc gctcgcggct cttaccagcc   2880
taacttcgat cactggaccg ctgatcgtca cggcgattta tgccgcctcg gcgagcacat   2940
ggaacgggtt ggcatggatt gtaggcgccg ccctatacct tgtctgcctc cccgcgttgc   3000
```

```
gtcgcggtgc atggagccgg gccacctcga cctgaatgga agccggcggc acctcgctaa    3060
cggattcacc actccaagaa ttggagccaa tcaattcttg cggagaactg tgaatgcgca    3120
aaccaaccct tggcagaaca tatccatcgc gtccgccatc tccagcagcc gcacgcggcg    3180
catctcggga agcgttgggt cctggccacg ggtgcgcatg atcgtgctcc tgtcgttgag    3240
gacccggcta ggctggcggg gttgccttac tggttagcag aatgaatcac cgatacgcga    3300
gcgaacgtga agcgactgct gctgcaaaac gtctgcgacc tgagcaacaa catgaatggt    3360
cttcggtttc cgtgtttcgt aaagtctgga aacgcggaag tcagcgccct gcaccattat    3420
gttccggatc tgcatcgcag gatgctgctg ctaccctgt ggaacaccta catctgtatt    3480
aacgaagcgc tggcattgac cctgagtgat ttttctctgg tcccgccgca tccataccgc    3540
cagttgttta ccctcacaac gttccagtaa ccgggcatgt tcatcatcag taacccgtat    3600
cgtgagcatc ctctctcgtt tcatcggtat cattacccc atgaacagaa atccccctta    3660
cacggaggca tcagtgacca aacaggaaaa aaccgccctt aacatggccc gctttatcag    3720
aagccagaca ttaacgcttc tggagaaact caacgagctg gacgcggatg aacaggcaga    3780
catctgtgaa tcgcttcacg accacgctga tgagctttac cgcagctgcc tcgcgcgttt    3840
cggtgatgac ggtgaaaacc tctgacacat gcagctcccg gagacggtca cagcttgtct    3900
gtaagcggat gccgggagca gacaagcccg tcagggcgcg tcagcgggtg ttggcgggtg    3960
tcggggcgca gccatgaccc agtcacgtag cgatagcgga gtgtatactg gcttaactat    4020
gcggcatcag agcagattgt actgagagtg caccatatat gcggtgtgaa ataccgcaca    4080
gatgcgtaag gagaaaatac cgcatcaggc gctcttccgc ttcctcgctc actgactcgc    4140
tgcgctcggt cgttcggctg cggcgagcgg tatcagctca ctcaaaggcg gtaatacggt    4200
tatccacaga atcaggggat aacgcaggaa agaacatgtg agcaaaaggc cagcaaaagg    4260
ccaggaaccg taaaaaggcc gcgttgctgg cgtttttcca taggctccgc cccctgacg    4320 agcatcacaa aaatcgacgc tcaagtcaga ggtggcgaaa cccgacagga ctataaagat    4380
accaggcgtt ccccctggaa gctccctcg tgcgctctcc tgttccgacc ctgccgctta    4440
ccggatacct gtccgccttt ctcccttcgg aagcgtggc gctttctcat agctcacgct    4500
gtaggtatct cagttcggtg taggtcgttc gctccaagct gggctgtgtg cacgaacccc    4560
ccgttcagcc cgaccgctgc gccttatccg gtaactatcg tcttgagtcc aacccggtaa    4620
gacacgactt atcgccactg gcagcagcca ctggtaacag gattagcaga gcgaggtatg    4680
taggcggtgc tacagagttc ttgaagtggt ggcctaacta cggctacact agaaggacag    4740
tatttggtat ctgcgctctg ctgaagccag ttaccttcgg aaaaagagtt ggtagctctt    4800
gatccggcaa acaaaccacc gctggtagcg gtggtttttt tgtttgcaag cagcagatta    4860
cgcgcagaaa aaaaggatct caagaagatc ctttgatctt ttctacgggg tctgacgctc    4920
agtggaacga aaactcacgt taagggattt tggtcatgag attatcaaaa aggatcttca    4980
cctagatcct tttaaattaa aaatgaagtt ttaaatcaat ctaaagtata tatgagtaaa    5040
cttggtctga cagttaccaa tgcttaatca gtgaggcacc tatctcagcg atctgtctat    5100
ttcgttcatc catagttgcc tgactccccg tcgtgtagat aactacgata cgggagggct    5160
taccatctgg ccccagtgct gcaatgatac cgcgagaccc acgctcaccg gctccagatt    5220
tatcagcaat aaaccagcca gccggaaggg ccgagcgcag aagtggtcct gcaactttat    5280
ccgcctccat ccagtctatt aattgttgcc gggaagctag agtaagtagt tcgccagtta    5340
atagtttgcg caacgttgtt gccattgctg caggcatcgt ggtgtcacgc tcgtcgtttg    5400
```

-continued

| | |
|---|---|
| gtatggcttc attcagctcc ggttcccaac gatcaaggcg agttacatga tcccccatgt | 5460 |
| tgtgcaaaaa agcggttagc tccttcggtc ctccgatcgt tgtcagaagt aagttggccg | 5520 |
| cagtgttatc actcatggtt atggcagcac tgcataattc tcttactgtc atgccatccg | 5580 |
| taagatgctt ttctgtgact ggtgagtact caaccaagtc attctgagaa tagtgtatgc | 5640 |
| ggcgaccgag ttgctcttgc ccggcgtcaa cacgggataa taccgcgcca catagcagaa | 5700 |
| ctttaaaagt gctcatcatt ggaaaacgtt cttcggggcg aaaactctca aggatcttac | 5760 |
| cgctgttgag atccagttcg atgtaaccca ctcgtgcacc caactgatct tcagcatctt | 5820 |
| ttactttcac cagcgtttct gggtgagcaa aaacaggaag gcaaaatgcc gcaaaaaagg | 5880 |
| gaataagggc gacacggaaa tgttgaatac tcatactctt ccttttttcaa tattattgaa | 5940 |
| gcatttatca gggttattgt ctcatgagcg gatacatatt tgaatgtatt tagaaaaata | 6000 |
| aacaaatagg ggttccgcgc acatttcccc gaaaagtgcc acctgacgtc taagaaacca | 6060 |
| ttattatcat gacattaacc tataaaaata ggcgtatcac gaggccctttt cgtcttcaag | 6120 |
| aa | 6122 |

<210> SEQ ID NO 47
<211> LENGTH: 10358
<212> TYPE: DNA
<213> ORGANISM: Artificial Sequence
<220> FEATURE:
<223> OTHER INFORMATION: Synthetic Sequence dFP 1.0 (FCM Mam)

<400> SEQUENCE: 47

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |

```
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggat     2460
tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggt tgaaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tgggggaggt aggaagagcg atgatcactt gtggactaag    3540
tttgttcaca tcccccttctc caaccccctc agtacatcac cctgggagaa caaggtccac    3600
ttgcttctgg gcccacacag tcctgcagta ttgtgtatat aaggccaggg caacggagga    3660
```

```
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggggatcc    3900 gccaccatgg gcgagatctg gaagagccac gaagacgcgc tgcagaaatt cgaggaagcg    3960
ctgaaccagt tgaggatct gaagcaactg ggtggcagcg gtaaaggcag cggtggcgag    4020
atcaagcaac gtcacgaaga cgcgctgcgt aagttcgagg aagcgctgaa cgttttgag    4080 gatctgaagc agaaaggtgg ctgccggtcgt atttggaagg agcacgaaga cgcgcaccaa    4140
aagtttgagg aagcgctgaa tcaatttgaa gatctgaaac aactgggtgg cagcggcaag    4200
ggcagcggtg gcgagattaa acagcgccat gaggatgcgc tgcgcaaatt tgaggaagcg    4260
ctgaagcgcc acgaagatcg tgtgcaaaag gcggcaccgg tagtagcagt gagcaagggc    4320
gaggagctgt tcaccggggt ggtgcccatc ctggtcgagc tggacggcga cgtaaacggc    4380
cacaagttca gcgtgtccgg cgagggcgag ggcgatgcca cctacggcaa gctgaccctg    4440
aagttcattt gcaccaccgg caagctgccc gtgccctggc ccacccctcgt gaccaccctg    4500 acctacggcg tgcagtgctt cagccgctac cccgaccaca tgaagcagca cgacttcttc    4560
aagtccgcca tgcccgaagg ctacgtccag gagcgcacca tcttcttcaa ggacgacggc    4620
aactacaaga cccgcgccga ggtgaagttc gagggcgaca ccctggtgaa ccgcatcgag    4680
ctgaagggca tcgacttcaa ggaggacggc aacatcctgg ggcacaagct ggagtacaac    4740
tacaacagcc acaacgtcta tatcatggcc gacaagcaga agaacggcat caaggtgaac    4800
ttcaagatcc gccacaacat cgaggacggc agcgtgcagc tcgccgacca ctaccagcag    4860 aacacccccca tcggcgacgg ccccgtgctg ctgcccgaca ccactacct gagcacccag    4920 tccgccctga gcaaagaccc caacgagaag cgcgatcaca tggtcctgct ggagttcgtg    4980
accgccgccg ggatcactct cggcatggac gagctgtaca agtaagaatt cgatatcaag    5040
cttatcgata tcaacctct ggattacaaa atttgtgaaa gattgactgg tattcttaac    5100
tatgttgctc cttttacgct atgtggatac gctgctttaa tgcctttgta tcatgctatt    5160
gcttcccgta tggctttcat tttctcctcc ttgtataaat cctggttgct gtctctttat    5220
gaggagttgt ggcccgttgt caggcaacgt ggcgtggtgt gcactgtgtt tgctgacgca    5280
acccccactg gttggggcat tgccaccacc tgtcagctcc tttccgggac tttcgctttc    5340
cccctcccta ttgccacggc ggaactcatc gccgcctgcc ttgcccgctg ctggacaggg    5400
gctcggctgt tgggcactga caattccgtg tgttgtcgg ggaaatcatc gtcctttcct    5460
tggctgctcg cctgtgttgc cacctggatt ctgcgcggga cgtccttctg ctacgtccct    5520
tcggccctca atccagcgga ccttccttcc cgcggcctgc tgccggctct gcggcctctt    5580
ccgcgtcttc gccttcgccc tcagacgagt cggatctccc tttgggccgc ctccccgcat    5640
cgataccgtc gacctcgaga cctagaaaaa catggagcaa tcacaagtag caatacagca    5700
gctaccaatg ctgattgtgc ctggctagaa gcacaagagg aggaggaggt gggttttcca    5760
gtcacacctc aggtaccttt aagaccaatg acttacaagg cagctgtaga tcttagccac    5820 ttttttaaaag aaaaggggggg actggaaggg ctaattcact cccaacgaag acaagatatc    5880
cttgatctgt ggatctacca cacacaaggc tacttccctg attggcagaa ctacacacca    5940
gggccaggga tcagatatcc actgaccttt ggatggtgct acaagctagt accagttgag    6000
```

```
caagagaagg tagaagaagc caatgaagga gagaacaccc gcttgttaca ccctgtgagc    6060
ctgcatggga tggatgaccc ggagagaaa gtattagagt ggaggtttga cagccgccta    6120
gcatttcatc acatggcccg agagctgcat ccggactgta ctgggtctct ctggttagac    6180
cagatctgag cctgggagct ctctggctaa ctagggaacc cactgcttaa gcctcaataa    6240
agcttgcctt gagtgcttca agtagtgtgt gcccgtctgt tgtgtgactc tggtaactag    6300
agatccctca gacccttta gtcagtgtgg aaaatctcta gcagggcccg tttaaacccg    6360
ctgatcagcc tcgactgtgc cttctagttg ccagccatct gttgtttgcc cctccccgt    6420
gccttccttg accctggaag gtgccactcc cactgtcctt tcctaataaa atgaggaaat    6480
tgcatcgcat tgtctgagta ggtgtcattc tattctgggg ggtggggtgg ggcaggacag    6540
caaggggag gattgggaag acaatagcag gcatgctggg gatgcggtgg gctctatggc    6600
ttctgaggcg gaaagaacca gctggggctc taggggtat ccccacgcgc cctgtagcgg    6660
cgcattaagc gcggcgggtg tggtggttac gcgcagcgtg accgctacac ttgccagcgc    6720
cctagcgccc gctcctttcg ctttcttccc ttcctttctc gccacgttcg ccggctttcc    6780
ccgtcaagct ctaaatcggg ggctcccttt agggttccga tttagtgctt tacggcacct    6840
cgaccccaaa aaacttgatt agggtgatgg ttcacgtagt gggccatcgc cctgatagac    6900
ggttttcgc cctttgacgt tggagtccac gttctttaat agtggactct tgttccaaac    6960
tggaacaaca ctcaacccta tctcggtcta ttcttttgat ttataaggga ttttgccgat    7020
ttcggcctat tggttaaaaa atgagctgat ttaacaaaaa tttaacgcga attaattctg    7080
tggaatgtgt gtcagttagg gtgtggaaag tccccaggct ccccagcagg cagaagtatg    7140
caaagcatgc atctcaatta gtcagcaacc aggtgtggaa agtccccagg ctccccagca    7200
ggcagaagta tgcaaagcat gcatctcaat tagtcagcaa ccatagtccc gcccctaact    7260
ccgcccatcc cgcccctaac tccgcccagt tccgcccatt ctccgcccca tggctgacta    7320
atttttttta tttatgcaga ggccgaggcc gcctctgcct ctgagctatt ccagaagtag    7380
tgaggaggct tttttggagg cctaggcttt tgcaaaaagc tcccgggagc ttgtatatcc    7440
attttcggat ctgatcagca cgtgttgaca attaatcatc ggcatagtat atcggcatag    7500
tataatacga caaggtgagg aactaaacca tggccaagtt gaccagtgcc gttccggtgc    7560
tcaccgcgcg cgacgtcgcc ggagcggtcg agttctggac cgaccggctc gggttctccc    7620
gggacttcgt ggaggacgac ttcgccggtg tggtccggga cgacgtgacc ctgttcatca    7680
gcgcggtcca ggaccaggtg gtgccggaca acacccctgg ctgggtgtgg gtgcgcggcc    7740
tggacgagct gtacgccgag tggtcggagg tcgtgtccac gaacttccgg gacgcctccg    7800
ggccggccat gaccgagatc ggcgagcagc cgtgggggcg ggagttcgcc ctgcgcgacc    7860
cggccggcaa ctgcgtgcac ttcgtggccg aggagcagga ctgacacgtg ctacgagatt    7920
tcgattccac cgccgccttc tatgaaaggt tgggcttcgg aatcgttttc cgggacgccg    7980
gctggatgat cctccagcgc ggggatctca tgctggagtt cttcgcccac ccaacttgt    8040
ttattgcagc ttataatggt tacaaataaa gcaatagcat cacaaatttc acaaataaag    8100
cattttttc actgcattct agttgtggtt tgtccaaact catcaatgta tcttatcatg    8160
tctgtatacc gtcgacctct agctagagct tggcgtaatc atggtcatag ctgtttcctg    8220
tgtgaaattg ttatccgctc acaattccac acaacatacg agccggaagc ataaagtgta    8280
aagcctgggg tgcctaatga gtgagctaac tcacattaat tgcgttgcgc tcactgcccg    8340
ctttccagtc gggaaacctg tcgtgccagc tgcattaatg aatcggccaa cgcgcgggga    8400
```

```
gaggcggttt gcgtattggg cgctcttccg cttcctcgct cactgactcg ctgcgctcgg   8460
tcgttcggct gcggcgagcg gtatcagctc actcaaaggc ggtaatacgg ttatccacag   8520
aatcagggga taacgcagga agaacatgt gagcaaaagg ccagcaaaag gccaggaacc    8580
gtaaaaaggc cgcgttgctg gcgttttcc ataggctccg cccccctgac gagcatcaca    8640
aaaatcgacg ctcaagtcag aggtggcgaa acccgacagg actataaaga taccaggcgt   8700
ttccccctgg aagctccctc gtgcgctctc ctgttccgac cctgccgctt accggatacc   8760
tgtccgcctt tctcccttcg ggaagcgtgg cgctttctca tagctcacgc tgtaggtatc   8820
tcagttcggt gtaggtcgtt cgctccaagc tgggctgtgt gcacgaaccc cccgttcagc   8880
ccgaccgctg cgccttatcc ggtaactatc gtcttgagtc caacccggta agacacgact   8940
tatcgccact ggcagcagcc actggtaaca ggattagcag agcgaggtat gtaggcggtg   9000
ctacagagtt cttgaagtgg tggcctaact acggctacac tagaagaaca gtatttggta   9060
tctgcgctct gctgaagcca gttaccttcg gaaaaagagt tggtagctct tgatccggca   9120
aacaaaccac cgctggtagc ggtggttttt ttgtttgcaa gcagcagatt acgcgcagaa   9180
aaaaaggatc tcaagaagat cctttgatct tttctacggg gtctgacgct cagtggaacg   9240
aaaactcacg ttaagggatt ttggtcatga gattatcaaa aaggatcttc acctagatcc   9300
ttttaaatta aaaatgaagt tttaaatcaa tctaaagtat atatgagtaa acttggtctg   9360
acagttacca atgcttaatc agtgaggcac ctatctcagc gatctgtcta tttcgttcat   9420
ccatagttgc ctgactcccc gtcgtgtaga taactacgat acgggagggc ttaccatctg   9480
gccccagtgc tgcaatgata ccgcgagacc cacgctcacc ggctccagat ttatcagcaa   9540
taaaccagcc agccggaagg gccgagcgca gaagtggtcc tgcaacttta tccgcctcca   9600
tccagtctat taattgttgc cgggaagcta gagtaagtag ttcgccagtt aatagtttgc   9660
gcaacgttgt tgccattgct acaggcatcg tggtgtcacg ctcgtcgttt ggtatggctt   9720
cattcagctc cggttcccaa cgatcaaggc gagttacatg atccccccatg ttgtgcaaaa   9780 aagcggttag ctccttcggt cctccgatcg ttgtcagaag taagttggcc gcagtgttat   9840
cactcatggt tatggcagca ctgcataatt ctcttactgt catgccatcc gtaagatgct   9900
tttctgtgac tggtgagtac tcaaccaagt cattctgaga atagtgtatg cggcgaccga   9960
gttgctcttg cccggcgtca atacgggata ataccgcgcc acatagcaga actttaaaag  10020
tgctcatcat tggaaaacgt tcttcggggc gaaaactctc aaggatctta ccgctgttga  10080
gatccagttc gatgtaaccc actcgtgcac ccaactgatc ttcagcatct tttactttca  10140
ccagcgtttc tgggtgagca aaaacaggaa ggcaaaatgc cgcaaaaaag gaataaggg   10200 cgacacggaa atgttgaata ctcatactct ccttttca atattattga agcatttatc   10260
agggttattg tctcatgagc ggatacatat ttgaatgtat ttagaaaaat aaacaaatag  10320
gggttccgcg cacatttccc cgaaaagtgc cacctgac                          10358
```

<210> SEQ ID NO 48
<211> LENGTH: 126
<212> TYPE: PRT
<213> ORGANISM: Artificial Sequence
<220> FEATURE:
<223> OTHER INFORMATION: Synthetic Sequence dFP 1.0

<400> SEQUENCE: 48

```
Glu Ile Trp Lys Ser His Glu Asp Ala Leu Gln Lys Phe Glu Glu Ala
1               5                   10                  15
```

```
Leu Asn Gln Phe Glu Asp Leu Lys Gln Leu Gly Gly Ser Gly Lys Gly
         20                  25                  30

Ser Gly Gly Glu Ile Lys Gln Arg His Glu Asp Ala Leu Arg Lys Phe
     35                  40                  45

Glu Glu Ala Leu Lys Arg Phe Glu Asp Leu Lys Gln Lys Gly Gly Cys
 50                  55                  60

Gly Arg Ile Trp Lys Glu His Glu Asp Ala His Gln Lys Phe Glu Glu
 65                  70                  75                  80

Ala Leu Asn Gln Phe Glu Asp Leu Lys Gln Leu Gly Gly Ser Gly Lys
             85                  90                  95

Gly Ser Gly Gly Glu Ile Lys Gln Arg His Glu Asp Ala Leu Arg Lys
             100                 105                 110

Phe Glu Glu Ala Leu Lys Arg His Glu Asp Arg Val Gln Lys
         115                 120                 125

<210> SEQ ID NO 49
<211> LENGTH: 5999
<212> TYPE: DNA
<213> ORGANISM: Artificial Sequence
<220> FEATURE:
<223> OTHER INFORMATION: Synthetic Sequence Mini dfP (E. Coli)

<400> SEQUENCE: 49
ttcttgaaga cgaaagggcc tcgtgatacg cctatttta taggttaatg tcatgataat     60 aatggttct tagacgtcag gtggcacttt cggggaaat gtgcgcggaa cccctatttg    120
tttatttttc taaatacatt caaatatgta tccgctcatg agacaataac cctgataaat   180
gcttcaataa tattgaaaaa ggaagagtat gagtattcaa catttccgtg tcgcccttat   240
tccctttttt gcggcatttt gccttcctgt ttttgctcac ccagaaacgc tggtgaaagt   300
aaaagatgct gaagatcagt tgggtgcacg agtgggttac atcgaactgg atctcaacag   360
cggtaagatc cttgagagtt tcgccccga gaacgtttt ccaatgatga gcactttaa     420 agttctgcta tgtggcgcgg tattatcccg tgttgacgcc gggcaagagc aactcggtcg   480
ccgcatacac tattctcaga atgacttggt tgagtactca ccagtcacag aaaagcatct   540
tacggatggc atgacagtaa gagaattatg cagtgctgcc ataaccatga gtgataacac   600
tgcggccaac ttacttctga caacgatcgg aggaccgaag gagctaaccg cttttttgca   660
caacatgggg gatcatgtaa ctcgccttga tcgttgggaa ccggagctga atgaagccat   720
accaaacgac gagcgtgaca ccacgatgcc tgcagcaatg gcaacaacgt tgcgcaaact   780
attaactggc gaactactta ctctagcttc ccggcaacaa ttaatagact ggatggaggc   840
ggataaagtt gcaggaccac ttctgcgctc ggcccttccg gctggctggt ttattgctga   900
taaatctgga gccggtgagc gtgggtctcg cggtatcatt gcagcactgg ggccagatgg   960
taagccctcc cgtatcgtag ttatctacac gacgggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct aacgtgagt ttcgttcca    1200 ctgagcgtca gaccccgtag aaaagatcaa aggatcttct tgagatcctt ttttctgcg   1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
```

```
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggccttt tacggttcct   1860 ggcctttgc tggccttttg ctcacatgtt ctttcctgcg ttatccctg attctgtgga   1920 taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta gagccgcga gcgatccttg aagctgtccc tgatggtcgt catctacctg   3300
cctggacagc atggcctgca acgcgggcat cccgatgccg ccggaagcga agaatcat   3360 aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag gcatcggtc gagatcccgg   3720 tgcctaatga gtgagctaac ttacattaat tgcgttgcgc tcactgcccg ctttccagtc   3780
```

```
gggaaacctg tcgtgccagc tgcattaatg aatcggccaa cgcgcgggga gaggcggttt    3840
gcgtattggg cgccaggtg gttttcttt tcaccagtga cacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt aatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc actttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc agtagtagg    4980 ttgaggccgt tgagcaccgc cgccgcaagg aatggtgcat gcaaggagat ggcgcccaac    5040 agtccccgg ccacggggcc tgccaccata cccacgccga aacaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actataggg aattgtgagc ggataacaat tcccctctag    5280
aaataatttt gtttaacttt aagaaggaga tataccatgg gcagcagcca tcatcatcat    5340
catcacggcg cgacggcga gaacttgtat tttcaagcta gcggatccat gggggaaatc    5400
tggaagtcac atgaagatgc tttgcagaag tttgaggaag ccttgaacca aggggggtcc    5460
ggcggcgatg cgttacgcaa gttcgaggag gccttgaaac gttttgaaga tttgaaacag    5520
aagggtggct gtggacgtat ctggaaagag catgaagatg cgcatcaaaa gtttgaggag    5580
gctcttaatc aaggaggttc tggtggcgat gcccttcgta aatttgagga agcattgaag    5640
cgtcacgagg atcgcgtgca aagtgataa gaattcctcg aggctgctaa caaagcccga    5700
aaggaagctg agttggctgc tgccaccgct gagcaataac tagcataacc ccttggggcc    5760
tctaaacggg tcttgagggg ttttttgctg aaaggaggaa ctatatccgg atatcccgca    5820
agaggcccgg cagtaccggc ataaccaagc ctatgcctac agcatccagg gtgacggtgc    5880
cgaggatgac gatgagcgca ttgttagatt tcatacacgg tgcctgactg cgttagcaat    5940
ttaactgtga taaactaccg cattaaagct tatcgatgat aagctgtcaa acatgagaa    5999
```

<210> SEQ ID NO 50
<211> LENGTH: 10244
<212> TYPE: DNA
<213> ORGANISM: Artificial Sequence
<220> FEATURE:
<223> OTHER INFORMATION: Synthetic Sequence Mini dfp (FCK mam)

<400> SEQUENCE: 50

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| accccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc aggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctggggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |

```
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccaggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggaggt aggaagagcg atgatcactt gtggactaag    3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg caacgggaa    3720 cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggatcc    3900 atggggaaa tctggaagtc acatgaagat gcttttgcaga agttgagga agccttgaac    3960 caagggggt ccggcggcga tgcgttacgc aagttcgagg aggccttgaa acgttttgaa    4020
gatttgaaac agaagggtgg ctgtggacgt atctggaaag agcatgaaga tgcgcatcaa    4080
aagtttgagg aggctcttaa tcaaggaggt tctggtggcg atgcccttcg taaatttgag    4140
gaagcattga agcgtcacga ggatcgcgtg caaaaggcgg caccggtagt agcagtgagc    4200
aagggcgagg agctgttcac cggggtggtg cccatcctgg tcgagctgga cggcgacgta    4260
aacggccaca gttcagcgt gtccggcgag ggcgagggcg atgccaccta cggcaagctg    4320
accctgaagt tcatttgcac caccggcaag ctgcccgtgc cctggcccac cctcgtgacc    4380
accctgacct acggcgtgca gtgcttcagc cgctaccccg accacatgaa gcagcacgac    4440
ttcttcaagt ccgccatgcc cgaaggctac gtccaggagc gcaccatctt cttcaaggac    4500
gacggcaact acaagacccg cgccgaggtg aagttcgagg gcgacaccct ggtgaaccgc    4560
atcgagctga agggcatcga cttcaaggag gacggcaaca tcctggggca caagctggag    4620
```

```
tacaactaca acagccacaa cgtctatatc atggccgaca agcagaagaa cggcatcaag    4680
gtgaacttca agatccgcca caacatcgag gacggcagcg tgcagctcgc cgaccactac    4740
cagcagaaca ccccatcgg cgacggcccc gtgctgctgc ccgacaacca ctacctgagc    4800
acccagtccg ccctgagcaa agaccccaac gagaagcgcg atcacatggt cctgctggag    4860
ttcgtgaccg ccgccgggat cactctcggc atggacgagc tgtacaagta agaattcgat    4920
atcaagctta tcgataatca acctctggat tacaaaattt gtgaaagatt gactggtatt    4980
cttaactatg ttgctccttt tacgctatgt ggatacgctg ctttaatgcc tttgtatcat    5040
gctattgctt cccgtatggc tttcattttc tcctccttgt ataaatcctg gttgctgtct    5100
ctttatgagg agttgtggcc cgttgtcagg caacgtggcg tggtgtgcac tgtgtttgct    5160
gacgcaaccc ccactggttg ggcattgcca ccacctgtc agctcctttc cgggactttc    5220
gctttccccc tccctattgc cacggcggaa ctcatcgccg cctgccttgc ccgctgctgg    5280 acagggctc ggctgttggg cactgacaat tccgtggtgt tgtcgggaa atcatcgtcc    5340 tttccttggc tgctcgcctg tgttgccacc tggattctgc gcgggacgtc cttctgctac    5400
gtcccttcgg ccctcaatcc agcggacctt ccttcccgcg gcctgctgcc ggctctgcgg    5460
cctcttccgc gtcttcgcct cgccctcag acgagtcgga tctccctttg gccgcctcc    5520 ccgcatcgat accgtcgacc tcgagaccta gaaaacatg gagcaatcac aagtagcaat    5580
acagcagcta ccaatgctga ttgtgcctgg ctagaagcac aagaggagga ggaggtgggt    5640
tttccagtca cacctcaggt acctttaaga ccaatgactt acaaggcagc tgtagatctt    5700
agccactttt taaagaaaaa ggggggactg gaagggctaa ttcactccca acgaagacaa    5760
gatatccttg atctgtggat ctaccacaca caaggctact ccctgattg cagaactac    5820 acaccagggc cagggatcag atatccactg acctttggat ggtgctacaa gctagtacca    5880
gttgagcaag agaaggtaga agaagccaat gaagggagaga acaccgctt gttacccct    5940 gtgagcctgc atgggatgga tgacccggag agagaagtat agagtggag gtttgacagc    6000 cgcctagcat ttcatcacat ggcccgagag ctgcatccgg actgtactgg gtctctctgg    6060
ttagaccaga tctgagcctg ggagctctct ggctaactag gaacccact gcttaagcct    6120 caataaagct tgccttgagt gcttcaagta gtgtgtgccc gtctgttgtg tgactctggt    6180
aactagagat ccctcagacc cttttagtca gtgtggaaaa tctctagcag ggcccgttta    6240
aacccgctga tcagcctcga ctgtgccttc tagttgccag ccatctgttg tttgcccctc    6300
ccccgtgcct tccttgaccc tggaaggtgc cactcccact gtcctttcct aataaaatga    6360
ggaaattgca tcgcattgtc tgagtaggtg tcattctatt ctggggggtg ggtggggca    6420 ggacagcaag ggggaggatt gggaagacaa tagcaggcat gctggggatg cggtgggctc    6480
tatggcttct gaggcggaaa gaaccagctg gggctctagg gggtatcccc acgcgccctg    6540
tagcggcgca ttaagcgcgg cgggtgtggt ggttacgcgc agcgtgaccg ctacacttgc    6600
cagcgcccta gcgcccgctc ctttcgcttt cttcccttcc tttctcgcca cgttcgccgg    6660
ctttccccgt caagctctaa atcggggct ccctttaggg ttccgattta gtgctttacg    6720
gcacctcgac cccaaaaaac ttgattaggg tgatggttca cgtagtgggc catcgccctg    6780
atagacggtt tttcgccctt tgacgttgga gtccacgttc tttaatagtg gactcttgtt    6840
ccaaactgga acaacactca acctatctc ggtctattct tttgatttat aagggatttt    6900
gccgatttcg gcctattggt taaaaaatga gctgatttaa caaaaattta acgcgaatta    6960
```

```
attctgtgga atgtgtgtca gttagggtgt ggaaagtccc caggctcccc agcaggcaga    7020
agtatgcaaa gcatgcatct caattagtca gcaaccaggt gtggaaagtc ccaggctcc    7080 ccagcaggca gaagtatgca aagcatgcat ctcaattagt cagcaaccat agtcccgccc    7140
ctaactccgc ccatcccgcc cctaactccg cccagttccg cccattctcc gccccatggc    7200
tgactaattt ttttttattta tgcagaggcc gaggccgcct ctgcctctga gctattccag    7260
aagtagtgag gaggcttttt tggaggccta ggcttttgca aaaagctccc gggagcttgt    7320
atatccattt tcggatctga tcagcacgtg ttgacaatta atcatcggca tagtatatcg    7380
gcatagtata atacgacaag gtgaggaact aaaccatggc caagttgacc agtgccgttc    7440
cggtgctcac cgcgcgcgac gtcgccggag cggtcgagtt ctggaccgac cggctcgggt    7500
tctcccggga cttcgtggag gacgacttcg ccggtgtggt ccgggacgac gtgaccctgt    7560
tcatcagcgc ggtccaggac caggtggtgc cggacaacac cctggcctgg gtgtgggtgc    7620
gcggcctgga cgagctgtac gccgagtggt cggaggtcgt gtccacgaac ttccgggacg    7680
cctccgggcc ggccatgacc gagatcgcg agcagccgtg ggggcgggag ttcgccctgc    7740
gcgacccggc cggcaactgc gtgcacttcg tggccgagga gcaggactga cacgtgctac    7800
gagatttcga ttccaccgcc gccttctatg aaaggttggg cttcggaatc gttttccggg    7860
acgccggctg gatgatcctc cagcgcgggg atctcatgct ggagttcttc gcccaccccca    7920 acttgtttat tgcagcttat aatggttaca aataaagcaa tagcatcaca aatttcacaa    7980
ataaagcatt ttttttcactg cattctagtt gtggtttgtc caaactcatc aatgtatctt    8040
atcatgtctg tataccgtcg acctctagct agagcttggc gtaatcatgg tcatagctgt    8100
ttcctgtgtg aaattgttat ccgctcacaa ttccacacaa catacgagcc ggaagcataa    8160
agtgtaaagc ctggggtgcc taatgagtga gctaactcac attaattgcg ttgcgctcac    8220
tgcccgcttt ccagtcggga aacctgtcgt gccagctgca ttaatgaatc ggccaacgcg    8280
cggggagagg cggtttgcgt attgggcgct cttccgcttc ctcgctcact gactcgctgc    8340
gctcggtcgt tcggctgcgg cgagcggtat cagctcactc aaaggcggta atacggttat    8400
ccacagaatc aggggataac gcaggaaaga acatgtgagc aaaaggccag caaaaggcca    8460
ggaaccgtaa aaaggccgcg ttgctggcgt ttttccatag gctccgcccc cctgacgagc    8520
atcacaaaaa tcgacgctca agtcagaggt ggcgaaaccc gacaggacta taaagatacc    8580
aggcgtttcc ccctggaagc tccctcgtgc gctctcctgt tccgaccctg ccgcttaccg    8640
gatacctgtc cgcctttctc ccttcgggaa gcgtggcgct ttctcatagc tcacgctgta    8700
ggtatctcag ttcggtgtag tcgttcgct ccaagctggg ctgtgtgcac gaaccccccg    8760
ttcagcccga ccgctgcgcc ttatccggta actatcgtct tgagtccaac ccggtaagac    8820
acgacttatc gccactggca gcagccactg gtaacaggat tagcagagcg aggtatgtag    8880
gcggtgctac agagttcttg aagtggtggc ctaactacgg ctacactaga agaacagtat    8940
ttggtatctg cgctctgctg aagccagtta ccttcggaaa aagagttggt agctcttgat    9000
ccggcaaaca aaccaccgct ggtagcggtg gtttttttgt ttgcaagcag cagattacgc    9060
gcagaaaaaa aggatctcaa gaagatcctt tgatcttttc tacggggtct gacgctcagt    9120
ggaacgaaaa ctcacgttaa gggattttgg tcatgagatt atcaaaaagg atcttcacct    9180
agatcctttt aaattaaaaa tgaagtttta aatcaatcta agtatatat gagtaaactt    9240 ggtctgacag ttaccaatgc ttaatcagtg aggcacctat ctcagcgatc tgtctatttc    9300
gttcatccat agttgcctga ctccccgtcg tgtagataac tacgatacgg gagggcttac    9360
```

```
catctggccc cagtgctgca atgataccgc gagacccacg ctcaccggct ccagatttat      9420
cagcaataaa ccagccagcc ggaagggccg agcgcagaag tggtcctgca actttatccg      9480
cctccatcca gtctattaat tgttgccggg aagctagagt aagtagttcg ccagttaata      9540
gtttgcgcaa cgttgttgcc attgctacag gcatcgtggt gtcacgctcg tcgtttggta      9600
tggcttcatt cagctccggt tcccaacgat caaggcgagt tacatgatcc cccatgttgt      9660
gcaaaaaagc ggttagctcc ttcggtcctc cgatcgttgt cagaagtaag ttggccgcag      9720
tgttatcact catggttatg gcagcactgc ataattctct tactgtcatg ccatccgtaa      9780
gatgcttttc tgtgactggt gagtactcaa ccaagtcatt ctgagaatag tgtatgcggc      9840
gaccgagttg ctcttgcccg gcgtcaatac gggataatac cgcgccacat agcagaactt      9900
taaaagtgct catcattgga aaacgttctt cggggcgaaa actctcaagg atcttaccgc      9960
tgttgagatc cagttcgatg taacccactc gtgcacccaa ctgatcttca gcatctttta     10020
ctttcaccag cgtttctggg tgagcaaaaa caggaaggca aaatgccgca aaaaagggaa     10080
taagggcgac acggaaatgt tgaatactca tactcttcct ttttcaatat tattgaagca     10140
tttatcaggg ttattgtctc atgagcggat acatatttga atgtatttag aaaaataaac     10200
aaataggggt tccgcgcaca tttccccgaa aagtgccacc tgac                      10244

<210> SEQ ID NO 51
<211> LENGTH: 90
<212> TYPE: PRT
<213> ORGANISM: Artificial Sequence
<220> FEATURE:
<223> OTHER INFORMATION: Synthetic Sequence Mini dfp

<400> SEQUENCE: 51

Glu Ile Trp Lys Ser His Glu Asp Ala Leu Gln Lys Phe Glu Glu Ala
1               5                   10                  15

Leu Asn Gln Gly Gly Ser Gly Gly Asp Ala Leu Arg Lys Phe Glu Glu
            20                  25                  30

Ala Leu Lys Arg Phe Glu Asp Leu Lys Gln Lys Gly Gly Cys Gly Arg
        35                  40                  45

Ile Trp Lys Glu His Glu Asp Ala His Gln Lys Phe Glu Glu Ala Leu
    50                  55                  60

Asn Gln Gly Gly Ser Gly Gly Asp Ala Leu Arg Lys Phe Glu Glu Ala
65                  70                  75                  80

Leu Lys Arg His Glu Asp Arg Val Gln Lys
            85                  90

<210> SEQ ID NO 52
<211> LENGTH: 5951
<212> TYPE: DNA
<213> ORGANISM: Artificial Sequence
<220> FEATURE:
<223> OTHER INFORMATION: Synthetic Sequence Nano dfp (E. Coli)

<400> SEQUENCE: 52
ttcttgaaga cgaaagggcc tcgtgatacg cctattttta taggttaatg tcatgataat        60
aatggtttct tagacgtcag gtggcacttt tcggggaaat gtgcgcggaa cccctatttg       120
tttatttttc taaatacatt caaatatgta tccgctcatg agacaataac cctgataaat       180
gcttcaataa tattgaaaaa ggaagagtat gagtattcaa catttccgtg tcgcccttat       240
tccctttttt gcggcatttt gccttcctgt ttttgctcac ccagaaacgc tggtgaaagt       300
```

```
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg    1020
aaatagacag atcgctgaga taggtgcctc actgattaag cattggtaac tgtcagacca    1080
agtttactca tatatacttt agattgattt aaaacttcat ttttaattta aaaggatcta    1140
ggtgaagatc ctttttgata atctcatgac caaaatccct taacgtgagt tttcgttcca    1200
ctgagcgtca gaccccgtag aaaagatcaa aggatcttct tgagatcctt ttttctgcg    1260 cgtaatctgc tgcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag gcgcagcggt cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggcctttt tacggttcct    1860
ggccttttgc tggccttttg ctcacatgtt ctttcctgcg ttatccctg attctgtgga    1920 taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460 tgtaagggggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
```

```
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360 aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
```

| | |
|---|---:|
| agtcccccgg ccacggggcc tgccaccata cccacgccga acaagcgct catgagcccg | 5100 |
| aagtggcgag cccgatcttc cccatcggtg atgtcggcga tataggcgcc agcaaccgca | 5160 |
| cctgtggcgc cggtgatgcc ggccacgatg cgtccggcgt agaggatcga gatctcgatc | 5220 |
| ccgcgaaatt aatacgactc actataggg aattgtgagc ggataacaat tcccctctag | 5280 |
| aaataatttt gtttaacttt aagaaggaga tataccatgg gcagcagcca tcatcatcat | 5340 |
| catcacggcg cgacggcga gaacttgtat tttcaagcta gcggatccat gggggaaatc | 5400 |
| tggaagtcac atgaagatgc tttgcagaag tttgaggaag ggggtccgg cggccgcttc | 5460 |
| gaggaggcct tgaaacgttt tgaagatttg aaacagaagg gtggctgtgg acgtatctgg | 5520 |
| aaagagcatg aagatgcgca tcaaaagttt gaggagggag gttctggtgg ccgttttgag | 5580 |
| gaagcattga agcgtcacga ggatcgcgtg caaaagtgat aagaattcct cgaggctgct | 5640 |
| aacaaagccc gaaaggaagc tgagttggct gctgccaccg ctgagcaata actagcataa | 5700 |
| cccccttgggg cctctaaacg ggtcttgagg ggttttttgc tgaaaggagg aactatatcc | 5760 |
| ggatatcccg caagaggccc ggcagtaccg gcataaccaa gcctatgcct acagcatcca | 5820 |
| gggtgacggt gccgaggatg acgatgagcg cattgttaga tttcatacac ggtgcctgac | 5880 |
| tgcgttagca atttaactgt gataaactac cgcattaaag cttatcgatg ataagctgtc | 5940 |
| aaacatgaga a | 5951 |

<210> SEQ ID NO 53
<211> LENGTH: 10196
<212> TYPE: DNA
<213> ORGANISM: Artificial Sequence
<220> FEATURE:
<223> OTHER INFORMATION: Synthetic Sequence Nano dfp (FCK mam)

<400> SEQUENCE: 53

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg cccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt tgtttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |

```
ttttgactag cggaggctag aaggagagag atgggtgcga gagcgtcagt attaagcggg    1200
ggagaattag atcgcgatgg gaaaaaattc ggttaaggcc aggggaaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgaaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
```

```
aagggcccta tagttggagg tgggggaggt aggaagagcg atgatcactt gtggactaag      3540
tttgttcaca tccccttctc caaccccctc agtacatcac cctgggagaa caaggtccac      3600
ttgcttctgg gcccacacag tcctgcagta ttgtgtatat aaggccaggg caacggagga      3660
gcaggttttg aagtgaaagg caggcaggtg ttggggaggc agttaccggg caacgggaa       3720 cagggcgttt cggaggtggt tgccatgggg acctggatgc tgacgaaggc tcgcgaggct      3780
gtgagcagcc acagtgccct gctcagaagc cccaagctcg tcaatcaagc tggttctcca      3840
tttgcactca ggagcacggg caggcgagtg gcccctagtt ctgggggcag cggggatcc       3900 atggggaaa tctggaagtc acatgaagat gctttgcaga agtttgagga agggggtcc        3960 ggcggccgct tcgaggaggc cttgaaacgt tttgaagatt tgaaacagaa gggtggctgt      4020
ggacgtatct ggaaagagca tgaagatgcg catcaaaagt ttgaggaggg aggttctggt      4080
ggccgttttg aggaagcatt gaagcgtcac gaggatcgcg tgcaaaaggc ggcaccggta      4140
gtagcagtga gcaagggcga ggagctgttc accggggtgg tgcccatcct ggtcgagctg      4200 gacgcgacg taaacggcca caagttcagc gtgtccggcg agggcgaggg cgatgccacc       4260
tacggcaagc tgaccctgaa gttcatttgc accaccggca agctgcccgt gccctggccc      4320
accctcgtga ccaccctgac ctacggcgtg cagtgcttca gccgctaccc cgaccacatg      4380
aagcagcacg acttcttcaa gtccgccatg cccgaaggct acgtccagga gcgcaccatc      4440
ttcttcaagg acgacggcaa ctacaagacc cgcgccgagg tgaagttcga gggcgacacc      4500
ctggtgaacc gcatcgagct gaagggcatc gacttcaagg aggacggcaa catcctgggg      4560
cacaagctgg agtacaacta caacagccac aacgtctata tcatggccga caagcagaag      4620
aacggcatca aggtgaactt caagatccgc cacaacatcg aggacggcag cgtgcagctc      4680
gccgaccact accagcagaa cacccccatc ggcgacggcc ccgtgctgct gcccgacaac      4740
cactacctga gcacccagtc cgccctgagc aaagaccccc acgagaagcg cgatcacatg      4800
gtcctgctgg agttcgtgac cgccgccggg atcactctcg gcatggacga gctgtacaag      4860
taagaattcg atatcaagct tatcgataat caacctctgg attacaaaat ttgtgaaaga      4920
ttgactggta ttcttaacta tgttgctcct tttacgctat gtggatacgc tgctttaatg      4980
cctttgtatc atgctattgc ttcccgtatg gctttcattt tctcctcctt gtataaatcc      5040
tggttgctgt ctctttatga ggagttgtgg cccgttgtca gcaacgtggc gtggtgtgc       5100 actgtgtttg ctgacgcaac ccccactggt tgggcattg ccaccacctg tcagctcctt      5160
tccgggactt tcgctttccc cctccctatt gccacggcgg aactcatcgc cgcctgcctt      5220
gcccgctgct ggacaggggc tcggctgttg gcactgaca attccgtggt gttgtcgggg      5280
aaatcatcgt cctttccttg gctgctcgcc tgtgttgcca cctggattct gcgcgggacg      5340
tccttctgct acgtcccttc ggccctcaat ccagcggacc ttccttcccg cggcctgctg      5400
ccggctctgc ggcctcttcc gcgtcttcgc cttcgccctc agacgagtcg atctccctt      5460 tgggccgcct ccccgcatcg ataccgtcga cctcgagacc tagaaaaaca tggagcaatc      5520
acaagtagca atacagcagc taccaatgct gattgtgcct ggctagaagc acaagaggag      5580
gaggaggtgg ttttccagt cacacctcag gtacctttaa gaccaatgac ttacaaggca      5640
gctgtagatc ttagccactt tttaaaagaa aagggggggac tggaagggct aattcactcc      5700
caacgaagac aagatatcct tgatctgtgg atctaccaca cacaaggcta cttccctgat      5760
tggcagaact acacaccagg gccagggatc agatatccac tgacctttgg atggtgctac      5820
aagctagtac cagttgagca agagaaggta gaagaagcca atgaaggaga gaacacccgc      5880
```

```
ttgttacacc ctgtgagcct gcatgggatg gatgacccgg agagagaagt attagagtgg    5940
aggtttgaca gccgcctagc atttcatcac atggcccgag agctgcatcc ggactgtact    6000
gggtctctct ggttagacca gatctgagcc tgggagctct ctggctaact agggaaccca    6060
ctgcttaagc ctcaataaag cttgccttga gtgcttcaag tagtgtgtgc ccgtctgttg    6120
tgtgactctg gtaactagag atccctcaga ccctttagt cagtgtggaa atctctagc     6180
agggcccgtt taaacccgct gatcagcctc gactgtgcct tctagttgcc agccatctgt    6240
tgtttgcccc tcccccgtgc cttccttgac cctggaaggt gccactccca ctgtcctttc    6300
ctaataaaat gaggaaattg catcgcattg tctgagtagg tgtcattcta ttctgggggg    6360
tggggtgggg caggacagca aggggagga ttgggaagac aatagcaggc atgctgggga    6420
tgcggtgggc tctatggctt ctgaggcgga agaaccagc tggggctcta ggggtatcc     6480
ccacgcgccc tgtagcggcg cattaagcgc ggcgggtgtg gtggttacgc gcagcgtgac    6540
cgctacactt gccagcgccc tagcgcccgc tcctttcgct ttcttccctt cctttctcgc    6600
cacgttcgcc ggctttcccc gtcaagctct aaatcggggg ctccctttag ggttccgatt    6660
tagtgcttta cggcacctcg accccaaaaa acttgattag ggtgatggtt cacgtagtgg    6720
gccatcgccc tgatagacgg ttttcgccc tttgacgttg gagtccacgt tctttaatag    6780
tggactcttg ttccaaactg gaacaacact caaccctatc tcggtctatt cttttgattt    6840
ataagggatt ttgccgattt cggcctattg gttaaaaaat gagctgattt aacaaaaatt    6900
taacgcgaat taattctgtg gaatgtgtgt cagttagggt gtggaaagtc cccaggctcc    6960
ccagcaggca gaagtatgca aagcatgcat ctcaattagt cagcaaccag gtgtggaaag    7020
tccccaggct ccccagcagg cagaagtatg caaagcatgc atctcaatta gtcagcaacc    7080
atagtcccgc ccctaactcc gcccatcccg cccctaactc cgcccagttc cgcccattct    7140
ccgccccatg gctgactaat ttttttatt tatgcagagg ccgaggccgc ctctgcctct    7200
gagctattcc agaagtagtg aggaggcttt tttggaggcc taggcttttg caaaaagctc    7260
ccgggagctt gtatatccat tttcggatct gatcagcacg tgttgacaat taatcatcgg    7320
catagtatat cggcatagta taatacgaca aggtgaggaa ctaaaccatg gccaagttga    7380
ccagtgccgt tccggtgctc accgcgcgcg acgtcgccgg agcggtcgag ttctggaccg    7440
accggctcgg gttctcccgg gacttcgtgg aggacgactt cgccggtgtg gtccgggacg    7500
acgtgaccct gttcatcagc gcggtccagg accaggtggt gccggacaac accctggcct    7560
gggtgtgggt gcgcggcctg gacgagtcgt acgccgagtg gtcggaggtc gtgtccacga    7620
acttccggga cgcctccggg ccggccatga ccgagatcgg cgagcagccg tggggcggg    7680
agttcgccct gcgcgacccg gccggcaact gcgtgcactt cgtggccgag gagcaggact    7740
gacacgtgct acgagatttc gattccaccg ccgccttcta tgaaaggttg gcttcggaa    7800
tcgtttccg gacgccggc tggatgatcc tccagcgcgg ggatctcatg ctggagttct    7860
tcgcccaccc caacttgttt attgcagctt ataatggtta caaataaagc aatagcatca    7920
caaatttcac aaataaagca tttttttcac tgcattctag ttgtggtttg tccaaactca    7980
tcaatgtatc ttatcatgtc tgtataccgt cgacctctag ctagagcttg gcgtaatcat    8040
ggtcatagct gtttcctgtg tgaaattgtt atccgctcac aattccacac aacatacgag    8100
ccggaagcat aaagtgtaaa gcctggggtg cctaatgagt gagctaactc acattaattg    8160
cgttgcgctc actgcccgct ttccagtcgg gaaacctgtc gtgccagctg cattaatgaa    8220
```

| | |
|---|---|
| tcggccaacg cgcggggaga ggcggtttgc gtattgggcg ctcttccgct tcctcgctca | 8280 |
| ctgactcgct gcgctcggtc gttcggctgc ggcgagcgt atcagctcac tcaaaggcgg | 8340 |
| taatacggtt atccacagaa tcaggggata acgcaggaaa gaacatgtga gcaaaaggcc | 8400 |
| agcaaaaggc caggaaccgt aaaaaggccg cgttgctggc gttttccat aggctccgcc | 8460 |
| cccctgacga gcatcacaaa aatcgacgct caagtcagag gtggcgaaac ccgacaggac | 8520 |
| tataaagata ccaggcgttt ccccctggaa gctccctcgt gcgctctcct gttccgaccc | 8580 |
| tgccgcttac cggatacctg tccgcctttc tcccttcggg aagcgtggcg ctttctcata | 8640 |
| gctcacgctg taggtatctc agttcggtgt aggtcgttcg ctccaagctg gctgtgtgc | 8700 |
| acgaaccccc cgttcagccc gaccgctgcg ccttatccgg taactatcgt cttgagtcca | 8760 |
| acccggtaag acacgactta tcgccactgg cagcagccac tggtaacagg attagcagag | 8820 |
| cgaggtatgt aggcggtgct acagagttct tgaagtggtg gcctaactac ggctacacta | 8880 |
| gaagaacagt atttggtatc tgcgctctgc tgaagccagt taccttcgga aaaagagttg | 8940 |
| gtagctcttg atccggcaaa caaaccaccg ctggtagcgg tggttttttt gtttgcaagc | 9000 |
| agcagattac gcgcagaaaa aaaggatctc aagaagatcc tttgatcttt tctacggggt | 9060 |
| ctgacgctca gtgaacgaa aactcacgtt aagggatttt ggtcatgaga ttatcaaaaa | 9120 |
| ggatcttcac ctagatcctt ttaaattaaa aatgaagttt taaatcaatc taaagtatat | 9180 |
| atgagtaaac ttggtctgac agttaccaat gcttaatcag tgaggcacct atctcagcga | 9240 |
| tctgtctatt tcgttcatcc atagttgcct gactccccgt cgtgtagata actacgatac | 9300 |
| gggagggctt accatctggc cccagtgctg caatgatacc gcgagaccca cgctcaccgg | 9360 |
| ctccagattt atcagcaata aaccagccag ccggaagggc cgagcgcaga agtggtcctg | 9420 |
| caactttatc cgcctccatc cagtctatta attgttgccg ggaagctaga gtaagtagtt | 9480 |
| cgccagttaa tagtttgcgc aacgttgttg ccattgctac aggcatcgtg gtgtcacgct | 9540 |
| cgtcgtttgg tatggcttca ttcagctccg gttcccaacg atcaaggcga gttacatgat | 9600 |
| cccccatgtt gtgcaaaaaa gcggttagct ccttcggtcc tccgatcgtt gtcagaagta | 9660 |
| agttggccgc agtgttatca ctcatggtta tggcagcact gcataattct cttactgtca | 9720 |
| tgccatccgt aagatgcttt tctgtgactg gtgagtactc aaccaagtca ttctgagaat | 9780 |
| agtgtatgcg gcgaccgagt tgctcttgcc cggcgtcaat acgggataat accgcgccac | 9840 |
| atagcagaac tttaaaagtg ctcatcattg gaaaacgttc ttcggggcga aaactctcaa | 9900 |
| ggatcttacc gctgttgaga tccagttcga tgtaacccac tcgtgcaccc aactgatctt | 9960 |
| cagcatcttt tactttcacc agcgtttctg ggtgagcaaa aacaggaagg caaaatgccg | 10020 |
| caaaaaaggg aataagggcg acacggaaat gttgaatact catactcttc ctttttcaat | 10080 |
| attattgaag catttatcag ggttattgtc tcatgagcgg atacatattt gaatgtattt | 10140 |
| agaaaaataa acaaataggg gttccgcgca catttccccg aaaagtgcca cctgac | 10196 |

<210> SEQ ID NO 54
<211> LENGTH: 74
<212> TYPE: PRT
<213> ORGANISM: Artificial Sequence
<220> FEATURE:
<223> OTHER INFORMATION: Synthetic Sequence Nano dfp

<400> SEQUENCE: 54

Glu Ile Trp Lys Ser His Glu Asp Ala Leu Gln Lys Phe Glu Glu Gly
1               5                   10                  15

Gly Ser Gly Gly Arg Phe Glu Glu Ala Leu Lys Arg Phe Glu Asp Leu
              20                  25                  30

Lys Gln Lys Gly Gly Cys Gly Arg Ile Trp Lys Glu His Glu Asp Ala
          35                  40                  45

His Gln Lys Phe Glu Glu Gly Gly Ser Gly Gly Arg Phe Glu Glu Ala
      50                  55                  60

Leu Lys Arg His Glu Asp Arg Val Gln Lys
65                  70

<210> SEQ ID NO 55
<211> LENGTH: 6131
<212> TYPE: DNA
<213> ORGANISM: Artificial Sequence
<220> FEATURE:
<223> OTHER INFORMATION: Synthetic Sequence 528-GL (E. Coli)

<400> SEQUENCE: 55

| | | |
|---|---|---|
| ttcttgaaga cgaaagggcc tcgtgatacg cctattttta taggttaatg tcatgataat | 60 |
| aatggtttct tagacgtcag gtggcacttt tcggggaaat gtgcgcggaa ccccctatttg | 120 |
| tttattttc taaatacatt caaatatgta tccgctcatg agacaataac cctgataaat | 180 |
| gcttcaataa tattgaaaaa ggaagagtat gagtattcaa catttccgtg tcgcccttat | 240 |
| tccctttttt gcggcatttt gccttcctgt ttttgctcac ccagaaacgc tggtgaaagt | 300 |
| aaaagatgct gaagatcagt tgggtgcacg agtgggttac atcgaactgg atctcaacag | 360 |
| cggtaagatc cttgagagtt ttcgccccga agaacgtttt ccaatgatga gcacttttaa | 420 |
| agttctgcta tgtggcgcgg tattatcccg tgttgacgcc gggcaagagc aactcggtcg | 480 |
| ccgcatacac tattctcaga atgacttggt tgagtactca ccagtcacag aaaagcatct | 540 |
| tacgatggc atgacagtaa gagaattatg cagtgctgcc ataaccatga gtgataacac | 600 |
| tgcggccaac ttacttctga caacgatcgg aggaccgaag gagctaaccg cttttttgca | 660 |
| caacatgggg gatcatgtaa ctcgccttga tcgttgggaa ccggagctga atgaagccat | 720 |
| accaaacgac gagcgtgaca ccacgatgcc tgcagcaatg gcaacaacgt tgcgcaaact | 780 |
| attaactggc gaactactta ctctagcttc ccggcaacaa ttaatagact ggatggaggc | 840 |
| ggataaagtt gcaggaccac ttctgcgctc ggcccttccg gctggctggt ttattgctga | 900 |
| taaatctgga gccggtgagc gtgggtctcg cggtatcatt gcagcactgg ggccagatgg | 960 |
| taagccctcc cgtatcgtag ttatctacac gacggggagt caggcaacta tggatgaacg | 1020 |
| aaatagacag atcgctgaga taggtgcctc actgattaag cattggtaac tgtcagacca | 1080 |
| agtttactca tatatacttt agattgattt aaaacttcat ttttaattta aaaggatcta | 1140 |
| ggtgaagatc cttttttgata atctcatgac caaaatccct taacgtgagt tttcgttcca | 1200 |
| ctgagcgtca gaccccgtag aaaagatcaa aggatcttct tgagatcctt ttttttctgcg | 1260 |
| cgtaatctgc tgcttgcaaa caaaaaaacc accgctacca gcggtggttt gtttgccgga | 1320 |
| tcaagagcta ccaactcttt ttccgaaggt aactggcttc agcagagcgc agataccaaa | 1380 |
| tactgtcctt ctagtgtagc cgtagttagg ccaccacttc aagaactctg tagcaccgcc | 1440 |
| tacatacctc gctctgctaa tcctgttacc agtggctgct gccagtggcg ataagtcgtg | 1500 |
| tcttaccggg ttggactcaa gacgatagtt accggataag gcgcagcggt cgggctgaac | 1560 |
| ggggggttcg tgcacacagc ccagcttgga gcgaacgacc tacaccgaac tgagatacct | 1620 |
| acagcgtgag ctatgagaaa gcgccacgct tcccgaaggg agaaaggcgg acaggtatcc | 1680 |
| ggtaagcggc agggtcggaa caggagagcg cacgagggag cttccagggg gaaacgcctg | 1740 |

```
gtatctttat agtcctgtcg ggtttcgcca cctctgactt gagcgtcgat ttttgtgatg   1800
ctcgtcaggg gggcggagcc tatggaaaaa cgccagcaac gcggccttTT tacggttcct   1860
ggccttttgc tggccttttg ctcacatgtt ctttcctgcg ttatccctg attctgtgga    1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccggagct gcatgtgtca gaggttttca ccgtcatcac    2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga aagaatcat    3360
aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag gcatcggtc gagatcccgg    3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg ttttttcttt tcaccagtga cgggcaac agctgattgc     3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
```

```
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100
aagtggcgag cccgatcttc cccatcggtg atgtcggcga tataggcgcc agcaaccgca    5160
cctgtggcgc cggtgatgcc ggccacgatg cgtccgcgt agaggatcga gatctcgatc    5220
ccgcgaaatt aatacgactc actatagggg aattgtgagc ggataacaat tcccctctag    5280
aaataatttt gtttaactt aagaaggaga tataccatgg gcgaaggcga tattcatatg    5340
ggtaaaggtg gcatcacca tcatcaccac ggaggcgatg gtgaaaacct gtatttttcag    5400
ggatccggca tgggcgagat ttggaagcaa cacgaggacg ctctgcagaa gtttgaggaa    5460
gcactgaacc aatttgagga cctgaagcaa ctgggtggca gcggcaaggg cagcggcggt    5520
gagatctgga acagtgcga agacgcgctg cgtaagttcg aagaggcgct gaagcgtttc    5580
gaggatctga agcagaaagg cggtagcggc gagatctgga agcagcacga agacgctctg    5640
cagaaattcg aagaggcgct gaaccagttt gaggatctga agcagctggg cggtagcggt    5700
aaaggcagcg gcggtgaaat ctggaagcag cacgaagatg ccctgcgtaa gtttgaagaa    5760
gccctgaagc gttttgagga cctgaagcag aagaccggtt gactcgagga tccggctgct    5820
aacaaagccc gaaaggaagc tgagttggct gctgccaccg ctgagcaata actagcataa    5880
ccccttgggg cctctaaacg ggtcttgagg gttttttgc tgaaaggagg aactatatcc    5940
ggatatcccg caagaggccc ggcagtaccg gcataaccaa gcctatgcct acagcatcca    6000
gggtgacggt gccgaggatg acgatgagcg cattgttaga tttcatacac ggtgcctgac    6060
tgcgttagca atttaactgt gataaactac cgcattaaag cttatcgatg ataagctgtc    6120
aaacatgaga a                                                       6131
```

<210> SEQ ID NO 56
<211> LENGTH: 10350
<212> TYPE: DNA
<213> ORGANISM: Artificial Sequence
<220> FEATURE:
<223> OTHER INFORMATION: Synthetic Sequence 528-GL (FCK mam)

<400> SEQUENCE: 56

-continued

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt gcgctgcttc gcgatgtacg ggccagatat acgcgttgac   240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca tagggactt    420 tccattgacg tcaatgggtg gagtatttac ggtaaactgc ccacttggca gtacatcaag   480
tgtatcatat gccaagtacg cccctattg acgtcaatga cggtaaatgg cccgcctggc    540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc  1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
```

```
gaaggtggag agagagacag agacagatcc attcgattag tgaacggatc ggcactgcgt    2400
gcgccaattc tgcagacaaa tggcagtatt catccacaat tttaaaagaa aaggggggat    2460 tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggaggt aggaagagcg atgatcactt gtggactaag    3540
tttgttcaca tcccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg caacgggaa    3720 cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggatcc    3900 ggcatgggcg agatttggaa gcaacacgag gacgctctgc agaagtttga ggaagcactg    3960
aaccaatttg aggacctgaa gcaactgggt ggcagcggca agggcagcgg cggtgagatc    4020
tggaaacagt gcgaagacgc gctgcgtaag ttcgaagagg cgctgaagcg tttcgaggat    4080
ctgaagcaga aaggcggtag cggcgagatc tggaagcagc acgaagacgc tctgcagaaa    4140
ttcgaagagg cgctgaacca gtttgaggat ctgaagcagc tggcggtag cggtaaaggc    4200 agcggcggtg aaatctggaa gcagcacgaa gatgccctgc gtaagtttga agaagccctg    4260 aagcgtttg aggacctgaa gcagaagacc ggtagtagca gtgagcaagg gcgaggagct    4320
gttcaccggg gtggtgccca tcctggtcga gctggacggc gacgtaaacg ccacaagtt    4380 cagcgtgtcc ggcgagggcg agggcgatgc cacctacggc aagctgaccc tgaagttcat    4440
ttgcaccacc ggcaagctgc ccgtgccctg gcccaccctc gtgaccaccc tgacctacgg    4500
cgtgcagtgc ttcagccgct accccgacca catgaagcag cacgacttct tcaagtccgc    4560
catgcccgaa ggctacgtcc aggagcgcac catcttcttc aaggacgacg gcaactacaa    4620
gacccgcgcc gaggtgaagt tcgagggcga caccctggtg aaccgcatcg agctgaaggg    4680
catcgacttc aaggaggacg gcaacatcct ggggcacaag ctggagtaca actacaacag    4740
```

```
ccacaacgtc tatatcatgg ccgacaagca gaagaacggc atcaaggtga acttcaagat    4800
ccgccacaac atcgaggacg gcagcgtgca gctcgccgac cactaccagc agaacacccc    4860
catcggcgac ggccccgtgc tgctgcccga caaccactac ctgagcaccc agtccgccct    4920
gagcaaagac cccaacgaga gcgcgatca catggtcctg ctggagttcg tgaccgccgc    4980
cgggatcact ctcggcatgg acgagctgta caagtaagaa ttcgatatca agcttatcga    5040
taatcaacct ctggattaca aaatttgtga agattgact ggtattctta actatgttgc     5100
tccttttacg ctatgtggat acgctgcttt aatgcctttg tatcatgcta ttgcttcccg    5160
tatggctttc attttctcct ccttgtataa atcctggttg ctgtctcttt atgaggagtt    5220
gtggcccgtt gtcaggcaac gtggcgtggt gtgcactgtg tttgctgacg caacccccac    5280
tggttggggc attgccacca cctgtcagct cctttccggg actttcgctt tccccctccc    5340
tattgccacg gcggaactca tcgccgcctg ccttgcccgc tgctggacag gggctcggct    5400
gttgggcact gacaattccg tggtgttgtc ggggaaatca tcgtcctttc cttggctgct    5460
cgcctgtgtt gccacctgga ttctgcgcgg gacgtccttc tgctacgtcc cttcggccct    5520
caatccagcg gaccttcctt cccgcggcct gctgccggct ctgcggcctc ttccgcgtct    5580
tcgccttcgc cctcagacga gtcggatctc cctttgggcc gcctcccgc atcgataccg     5640 tcgacctcga gacctagaaa aacatggagc aatcacaagt agcaatacag cagctaccaa    5700
tgctgattgt gcctggctag aagcacaaga ggaggaggag gtgggttttc cagtcacacc    5760
tcaggtacct ttaagaccaa tgacttacaa ggcagctgta gatcttagcc acttttttaaa    5820 agaaaagggg ggactggaag ggctaattca ctcccaacga agacaagata tccttgatct    5880
gtggatctac cacacacaag gctacttccc tgattggcag aactacacac cagggccagg    5940
gatcagatat ccactgacct ttggatggtg ctacaagcta gtaccagttg agcaagagaa    6000
ggtagaagaa gccaatgaag gagagaacac ccgcttgtta cacctgtga gcctgcatgg     6060 gatggatgac ccggagagag aagtattaga gtggaggttt gacagccgcc tagcatttca    6120
tcacatggcc cgagagctgc atccggactg tactgggtct ctctggttag accagatctg    6180
agcctgggag ctctctggct aactagggaa cccactgctt aagcctcaat aaagcttgcc    6240
ttgagtgctt caagtagtgt gtgcccgtct gttgtgtgac tctggtaact agagatccct    6300
cagacccttt tagtcagtgt ggaaaatctc tagcagggcc cgtttaaacc cgctgatcag    6360
cctcgactgt gccttctagt tgccagccat ctgttgtttg ccctcccccc gtgccttcct    6420
tgaccctgga aggtgccact cccactgtcc tttcctaata aaatgaggaa attgcatcgc    6480
attgtctgag taggtgtcat tctattctgg ggggtgggt ggggcaggac agcaaggggg     6540
aggattggga agacaaatagc aggcatgctg gggatgcggt gggctctatg gcttctgagg    6600
cggaaagaac cagctggggc tctagggggt atccccacgc gccctgtagc ggcgcattaa    6660
gcgcggcggt gtggtggtt acgcgcagcg tgaccgctac acttgccagc gccctagcgc    6720
ccgctccttt cgctttcttc ccttcctttc tcgccacgtt cgccggcttt ccccgtcaag    6780
ctctaaatcg gggcatccct ttagggttcc gatttagtgc tttacggcac ctcgacccca    6840
aaaaacttga ttagggtgat ggttcacgta gtgggccatc gccctgatag acggtttttc    6900
gccctttgac gttggagtcc acgttcttta atagtggact cttgttccaa actggaacaa    6960
cactcaaccc tatctcggtc tattcttttg atttataagg gattttgccg atttcggcct    7020
attggttaaa aaatgagctg atttaacaaa aatttaacgc gaattaattc tgtggaatgt    7080
```

```
gtgtcagtta gggtgtggaa agtccccagg ctccccagca ggcagaagta tgcaaagcat    7140
gcatctcaat tagtcagcaa ccaggtgtgg aaagtcccca ggctcccag caggcagaag     7200
tatgcaaagc atgcatctca attagtcagc aaccatagtc ccgcccctaa ctccgcccat    7260
cccgcccta actccgccca gttccgccca ttctccgccc catggctgac taatttttt      7320
tatttatgca gaggccgagg ccgcctctgc ctctgagcta ttccagaagt agtgaggagg    7380
cttttttgga ggcctaggct tttgcaaaaa gctcccggga gcttgtatat ccattttcgg    7440
atctgatcag cacgtgttga caattaatca tcggcatagt atatcggcat agtataatac    7500
gacaaggtga ggaactaaac catgccaag ttgaccagtg ccgttccggt gctcaccgcg      7560
cgcgacgtcg ccggagcggt cgagttctgg accgaccggc tcgggttctc ccgggacttc    7620
gtggaggacg acttcgccgg tgtggtccgg gacgacgtga ccctgttcat cagcgcggtc    7680
caggaccagg tggtgccgga caacaccctg gcctgggtgt gggtgcgcgg cctggacgag    7740
ctgtacgccg agtggtcgga ggtcgtgtcc acgaacttcc gggacgcctc cgggccggcc    7800
atgaccgaga tcggcgagca gccgtggggg cgggagttcg ccctgcgcga cccggccggc    7860
aactgcgtgc acttcgtggc cgaggagcag gactgacacg tgctacgaga tttcgattcc    7920
accgccgcct tctatgaaag gttgggcttc ggaatcgttt ccgggacgc cggctggatg      7980
atcctccagc gcgggatct catgctggag ttcttcgccc accccaactt gtttattgca     8040
gcttataatg gttacaaata aagcaatagc atcacaaatt tcacaaataa agcattttt      8100
tcactgcatt ctagttgtgg tttgtccaaa ctcatcaatg tatcttatca tgtctgtata    8160
ccgtcgacct ctagctagag cttggcgtaa tcatggtcat agctgtttcc tgtgtgaaat    8220
tgttatccgc tcacaattcc acacaacata cgagccggaa gcataaagtg taaagcctgg    8280
ggtgcctaat gagtgagcta actcacatta attgcgttgc gctcactgcc cgcttccag    8340
tcgggaaacc tgtcgtgcca gctgcattaa tgaatcggcc aacgcgcggg gagaggcggt    8400
ttgcgtattg ggcgctcttc cgcttcctcg ctcactgact cgctgcgctc ggtcgttcgg    8460
ctgcggcgag cggtatcagc tcactcaaag gcggtaatac ggttatccac agaatcaggg    8520
gataacgcag gaaagaacat gtgagcaaaa ggccagcaaa aggccaggaa ccgtaaaaag    8580
gccgcgttgc tggcgttttt ccataggctc cgcccccctg acgagcatca aaaaatcga    8640
cgctcaagtc agaggtggcg aaacccgaca ggactataaa gataccaggc gtttccccct    8700
ggaagctccc tcgtgcgctc tcctgttccg accctgccgc ttaccggata cctgtccgcc    8760
tttctccctt cgggaagcgt ggcgctttct catagctcac gctgtaggta tctcagttcg    8820
gtgtaggtcg ttcgctccaa gctgggctgt gtgcacgaac cccccgttca gcccgaccgc    8880
tgcgccttat ccggtaacta tcgtcttgag tccaacccgg taagacacga cttatcgcca    8940
ctggcagcag ccactggtaa caggattagc agagcgaggt atgtaggcgg tgctacagag    9000
ttcttgaagt ggtggcctaa ctacggctac actagaagaa cagtatttgg tatctgcgct    9060
ctgctgaagc cagttacctt cggaaaaaga gttggtagct cttgatccgg caaacaaacc    9120
accgctggta gcggtggttt ttttgtttgc aagcagcaga ttacgcgcag aaaaaaagga    9180
tctcaagaag atcctttgat cttttctacg ggtctgacg ctcagtggaa cgaaaactca     9240
cgttaaggga ttttggtcat gagattatca aaaaggatct tcacctagat ccttttaaat    9300
taaaaatgaa gttttaaatc aatctaaagt atatatgagt aaacttggtc tgacagttac    9360
caatgcttaa tcagtgaggc acctatctca gcgatctgtc tatttcgttc atccatagtt    9420
gcctgactcc ccgtcgtgta gataactacg atacgggagg gcttaccatc tggccccagt    9480
```

```
gctgcaatga taccgcgaga cccacgctca ccggctccag atttatcagc aataaaccag    9540
ccagccggaa gggccgagcg cagaagtggt cctgcaactt tatccgcctc catccagtct    9600
attaattgtt gccgggaagc tagagtaagt agttcgccag ttaatagttt gcgcaacgtt    9660
gttgccattg ctacaggcat cgtggtgtca cgctcgtcgt ttggtatggc ttcattcagc    9720
tccggttccc aacgatcaag gcgagttaca tgatccccca tgttgtgcaa aaaagcggtt    9780
agctccttcg gtcctccgat cgttgtcaga agtaagttgg ccgcagtgtt atcactcatg    9840
gttatggcag cactgcataa ttctcttact gtcatgccat ccgtaagatg cttttctgtg    9900
actggtgagt actcaaccaa gtcattctga aatagtgta  tgcggcgacc gagttgctct    9960
tgcccggcgt caatacggga taataccgcg ccacatagca gaactttaaa agtgctcatc   10020
attggaaaac gttcttcggg gcgaaaactc tcaaggatct taccgctgtt gagatccagt   10080
tcgatgtaac ccactcgtgc acccaactga tcttcagcat ctttactttt caccagcgtt   10140
tctgggtgag caaaaacagg aaggcaaaat gccgcaaaaa agggaataag ggcgacacgg   10200
aaatgttgaa tactcatact cttcctttt caatattatt gaagcattta tcagggttat   10260
tgtctcatga gcggatacat atttgaatgt atttagaaaa ataaacaaat aggggttccg   10320
cgcacatttc cccgaaaagt gccacctgac                                    10350

<210> SEQ ID NO 57
<211> LENGTH: 126
<212> TYPE: PRT
<213> ORGANISM: Artificial Sequence
<220> FEATURE:
<223> OTHER INFORMATION: Synthetic Sequence 528-GL

<400> SEQUENCE: 57

Glu Ile Trp Lys Gln His Glu Asp Ala Leu Gln Lys Phe Glu Glu Ala
1               5                  10                  15

Leu Asn Gln Phe Glu Asp Leu Lys Gln Leu Gly Gly Ser Gly Lys Gly
            20                  25                  30

Ser Gly Gly Glu Ile Trp Lys Gln Cys Glu Asp Ala Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Trp Lys Gln His Glu Asp Ala Leu Arg Lys
            100                 105                 110

Phe Glu Glu Ala Leu Lys Arg Phe Glu Asp Leu Lys Gln Lys
        115                 120                 125

<210> SEQ ID NO 58
<211> LENGTH: 4442
<212> TYPE: DNA
<213> ORGANISM: Artificial Sequence
<220> FEATURE:
<223> OTHER INFORMATION: Synthetic Sequence MM3 FC (E. Coli)

<400> SEQUENCE: 58
cccgtagaaa agatcaaagg atcttcttga gatccttttt ttctgcgcgt aatctgctgc     60
ttgcaaacaa aaaaaccacc gctaccagcg gtggtttgtt tgccggatca agagctacca    120
```

```
actcttttc cgaaggtaac tggcttcagc agagcgcaga taccaaatac tgttcttcta   180
gtgtagccgt agttagccca ccacttcaag aactctgtag caccgcctac atacctcgct   240
ctgctaatcc tgttaccagt ggctgctgcc agtggcgata agtcgtgtct taccggttg    300
gactcaagac gatagttacc ggataaggcg cagcggtcgg gctgaacggg gggttcgtgc   360
acacagccca gcttggagcg aacgacctac accgaactga gatacctaca gcgtgagcta   420
tgagaaagcg ccacgcttcc cgaagggaga aggcggaca ggtatccggt aagcggcagg    480
gtcggaacag gagagcgcac gagggagctt ccagggggaa acgcctggta tctttatagt   540
cctgtcgggt ttcgccacct ctgacttgag cgtcgatttt tgtgatgctc gtcagggggg   600
cggagcctat ggaaaaacgc cagcaacgcg gccttttac ggttcctggc cttttgctgg    660
ccttttgctc acatgttctt tcctgcgtta tcccctgatt ctgtggataa ccgtattacc   720
gcctttgagt gagctgatac cgctcgccgc agccgaacga ccgagcgcag cgagtcagtg   780
agcgaggaag cggaaggcga gagtagggaa ctgccaggca tcaaactaag cagaaggccc   840
ctgacggatg gccttttgc gtttctacaa actctttctg tgttgtaaaa cgacggccag    900
tcttaagctc gggccccctg gcggttctg ataacgagta atcgttaatc gcaaataac    960
gtaaaaccc gcttcggcgg gttttttat gggggggagt tagggaaaga gcatttgtca    1020
gaatatttaa gggcgcctgt cactttgctt gatatatgag aattatttaa ccttataaat   1080
gagaaaaag caacgcactt taaataagat acgttgcttt ttcgattgat gaacacctat   1140
aattaaacta ttcatctatt atttatgatt ttttgtatat acaatatttc tagtttgtta   1200
aagagaatta agaaaataaa tctcgaaaat aataaaggga aaatcagttt ttgatatcaa   1260
aattatacat gtcaacgata atacaaaata taatacaaac tataagatgt tatcagtatt   1320
tattatcatt tagaataaat tttgtgtcgc ccttccgcga aattaatacg actcactata   1380
ggggaattgt gagcggataa caattcccct ctagaaataa ttttgtttaa cttttaggag   1440
gtaaaacata tgcatcatca tcatcaccac ggcggcggtg gcgaaaatct ttattttcaa   1500
ggtgaactac taaaaaaaca tgaagaagct ctcaagaagt ttgaagaact cctgaagaaa   1560
ttcgaggaag agctaaagaa aggtggctct gggtcgggaa gcggggtga  attactgaaa   1620
aagcacgaag aggcacttaa gaagttcgag gagttactaa agaagtttga ggaggaactc   1680
aaaaagggtg gctccggttg ggggtctggt ggcgagctgc ttaaaaagca tgaggaggcg   1740
ttgaagaaat ttgaagaact actgaagaag ttcgaagagt tgctaaagaa gggagggtca   1800
ggcagcggtt caggaggaga gcttttaaag aaacacgaag aagcccttaa aaattcgag    1860
gaattgctca aaaaatttga ggaacttttg aaaaatgac tcgagccccc tagcataacc   1920
ccttggggcc tctaaacggg tcttgagggg tttttttgccc ctgagacgcg tcaatcgagt   1980
tcgtacctaa gggcgacacc ccctaattag cccgggcgaa aggcccagtc tttcgactga   2040
gcctttcgtt ttatttgatg cctggcagtt ccctactctc gcatgggag tccccacact    2100
accatcggcg ctacggcgtt tcacttctga gttcggcatg gggtcaggtg gaccaccgc    2160
gctactgccg ccaggcaaac aagggtgtt atgagccata ttcaggtata aatgggctcg    2220
cgataatgtt cagaattggt taattggttg taacactgac ccctattgt ttatttttct    2280
aaatacattc aaatatgtat ccgctcatga acaataacc ctgataaatg cttcaataat    2340
attgaaaaag gaagaatatg agtattcaac atttccgtgt cgcccttatt ccctttttg    2400
cggcattttg ccttcctgtt tttgctcacc cagaaacgct ggtgaaagta aaagatgctg   2460
aagatcagtt gggtgcacga gtgggttaca tcgaactgga tctcaacagc ggtaagatcc   2520
```

```
ttgagagttt tcgccccgaa gaacgttttc caatgatgag cacttttaaa gttctgctat   2580
gtggcgcggt attatcccgt attgacgccg ggcaagagca actcggtcgc cgcatacact   2640
attctcagaa tgacttggtt gagtactcac cagtcacaga aaagcatctt acggatggca   2700
tgacagtaag agaattatgc agtgctgcca taaccatgag tgataacact gcggccaact   2760
tacttctgac aacgatcgga ggaccgaagg agctaaccgc ttttttgcac aacatggggg   2820
atcatgtaac tcgccttgat cgttgggaac cggagctgaa tgaagccata ccaaacgacg   2880
agcgtgacac cacgatgcct gtagcgatgg caacaacgtt gcgcaaacta ttaactggcg   2940
aactacttac tctagcttcc cggcaacaat taatagactg gatggaggcg gataaagttg   3000
caggaccact tctgcgctcg gcccttccgg ctggctggtt tattgctgat aaatccggag   3060
ccggtgagcg tggttctcgc ggtatcatcg cagcgctggg gccagatggt aagccctccc   3120
gtatcgtagt tatctacacg acggggagtc aggcaactat ggatgaacga aatagacaga   3180
tcgctgagat aggtgcctca ctgattaagc attggtaagc ggcgcgccat cgaatggcgc   3240
aaaacctttc gcggtatggc atgatagcgc ccggaagaga gtcaattcag gtggtgaat   3300 atgaaaccag taacgttata cgatgtcgca gagtatgccg gtgtctctta tcagaccgtt   3360
tcccgcgtgg tgaaccaggc cagccacgtt tctgcgaaaa cgcgggaaaa agtggaagcg   3420
gcgatggcgg agctgaatta cattcccaac cgcgtggcac aacaactggc gggcaaacag   3480
tcgttgctga ttggcgttgc cacctccagt ctggccctgc acgcgccgtc gcaaattgtc   3540
gcggcgatta aatctcgcgc cgatcaactg ggtgccagcg tggtggtgtc gatggtagaa   3600
cgaagcggcg tcgaagcctg taaagcggcg gtgcacaatc ttctcgcgca acgcgtcagt   3660
gggctgatca ttaactatcc gctggatgac caggatgcca ttgctgtgga agctgcctgc   3720
actaatgttc cggcgttatt tcttgatgtc tctgaccaga cacccatcaa cagtattatt   3780
ttctcccatg aggacggtac gcgactgggc gtggagcatc tggtcgcatt gggtcaccag   3840
caaatcgcgc tgttagcggg cccattaagt tctgtctcgg cgcgtctgcg tctggctggc   3900
tggcataaat atctcactcg caatcaaatt cagccgatag cggaacggga aggcgactgg   3960
agtgccatgt ccggttttca acaaaccatg caaatgctga atgagggcat cgttcccact   4020
gcgatgctgg ttgccaacga tcagatggcg ctgggcgcaa tgcgcgccat taccgagtcc   4080
gggctgcgcg ttggtgcgga tatctcggta gtgggatacg acgataccga agatagctca   4140
tgttatatcc cgccgttaac caccatcaaa caggattttc gcctgctggg gcaaaccagc   4200
gtggaccgct tgctgcaact ctctcagggc caggcggtga agggcaatca gctgttgcca   4260
gtctcactgg tgaaaagaaa aaccaccctg gcgcccaata cgcaaaccgc ctctccccgc   4320
gcgttggccg attcattaat gcagctggca cgacaggttt cccgactgga aagcgggcag   4380
tgactcatga ccaaaatccc ttaacgtgag ttacgcgcgc gtcgttccac tgagcgtcag   4440
ac                                                                 4442

<210> SEQ ID NO 59
<211> LENGTH: 10367
<212> TYPE: DNA
<213> ORGANISM: Artificial Sequence
<220> FEATURE:
<223> OTHER INFORMATION: Synthetic Sequence MM3 FC (FCK mam)

<400> SEQUENCE: 59
gtcgacggat cgggagatct cccgatcccc tatggtgcac tctcagtaca atctgctctg     60
```

| | |
|---|---|
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc aggggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctgggggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |
| agaatagttt ttgctgtact ttctatagtg aatagagtta ggcagggata ttcaccatta | 2280 |
| tcgtttcaga cccacctccc aaccccgagg ggacccgaca ggcccgaagg aatagaagaa | 2340 |
| gaaggtggag agagacag agacagatcc attcgattag tgaacggatc ggcactgcgt | 2400 |
| gcgccaattc tgcagacaaa tggcagtatt catccacaat tttaaaagaa aaggggggat | 2460 |

| | |
|---|---|
| tgggggtac agtgcagggg aaagaatagt agacataata gcaacagaca tacaaactaa | 2520 |
| agaattacaa aaacaaatta caaaaattca aaattttcgg gtttattaca gggacagcag | 2580 |
| agatccagtt tggttaatta acattatggc cttaggtcac ttcatctcca tggggttctt | 2640 |
| cttctgattt tctagaaaat gagatggggg tgcagagagc ttcctcagtg acctgcccag | 2700 |
| ggtcacatca gaaatgtcag agctagaact tgaactcaga ttactaatct taaattccat | 2760 |
| gccttggggg catgcaagta cgatatacag aaggagtgaa ctcattaggg cagatgacca | 2820 |
| atgagtttag gaagaagag tccagggcag ggtacatcta caccacccgc ccagccctgg | 2880 |
| gtgagtccag ccacgttcac ctcattatag ttgcctctct ccagtcctac cttgacggga | 2940 |
| agcacaagca gaaactggga caggagcccc aggagaccaa atcttcatgg tccctctggg | 3000 |
| aggatgggtg gggagagctg tggcagaggc ctcaggaggg gccctgctgc tcagtggtga | 3060 |
| cagatagggg tgagaaagca gacagagtca ttccgtcagc attctgggtc tgtttggtac | 3120 |
| ttcttctcac gctaaggtgg cggtgtgata tgcacaatgg ctaaaaagca gggagagctg | 3180 |
| gaaagaaaca aggacagaga cagaggccaa gtcaaccaga ccaattccca gaggaagcaa | 3240 |
| agaaaccatt acagagacta caaggggaa gggaaggaga gatgaattag cttcccctgt | 3300 |
| aaaccttaga acccagctgt tgccagggca acggggcaat acctgtctct tcagaggaga | 3360 |
| tgaagttgcc agggtaacta catcctgtct ttctcaagga ccatcccaga atgtggcacc | 3420 |
| cactagccgt taccatagca actgcctctt tgccccactt aatcccatcc cgtctgttaa | 3480 |
| aagggcccta tagttggagg tgggggaggt aggaagagcg atgatcactt gtggactaag | 3540 |
| tttgttcaca tccccttctc caacccctc agtacatcac cctgggagaa caaggtccac | 3600 |
| ttgcttctgg gcccacacag tcctgcagta ttgtgtatat aaggccaggg caacggagga | 3660 |
| gcaggttttg aagtgaaagg caggcaggtg ttggggaggc agttaccggg gcaacgggaa | 3720 |
| cagggcgttt cggaggtggt tgccatgggg acctggatgc tgacgaaggc tcgcgaggct | 3780 |
| gtgagcagcc acagtgccct gctcagaagc cccaagctcg tcaatcaagc tggttctcca | 3840 |
| tttgcactca ggagcacggg caggcgagtg gcccctagtt ctggggcag cggggatcc | 3900 |
| atgggtgaac tactaaaaaa acatgaagaa gctctcaaga agttgtgaaga actcctgaag | 3960 |
| aaattcgagg aagagctaaa gaaaggtggc tctgggtcgg gaagcggggg tgaattactg | 4020 |
| aaaagcacg aagaggcact taagaagttc gaggagttac taaagaagtt tgaggaggaa | 4080 |
| ctcaaaaagg gtggctccgg ttgggggtct ggtggcgagc tgcttaaaaa gcatgaggag | 4140 |
| gcgttgaaga aatttgaaga actactgaag aagttcgaag agttgctaaa gaagggaggg | 4200 |
| tcaggcagcg gttcaggagg agagcttta aagaaacacg aagaagccct taaaaaattc | 4260 |
| gaggaattgc tcaaaaaatt tgaggaactt ttgaaaaaag cggcaccggt agtagcagtg | 4320 |
| agcaagggcg aggagctgtt caccggggtg gtgcccatcc tggtcgagct ggacggcgac | 4380 |
| gtaaacggcc acaagttcag cgtgtccggc gagggcgagg gcgatgccac ctacggcaag | 4440 |
| ctgaccctga agttcatttg caccaccggc aagctgcccg tgcctggcc cacctcgtg | 4500 |
| accacccctga cctacggcgt gcagtgcttc agccgctacc ccgaccacat gaagcagcac | 4560 |
| gacttcttca gtccgccat gcccgaaggc tacgtccagg agcgcaccat cttcttcaag | 4620 |
| gacgacggca actacaagac ccgcgccgag gtgaagttcg agggcgacac cctggtgaac | 4680 |
| cgcatcgagc tgaagggcat cgacttcaag gaggacggca acatcctggg gcacaagctg | 4740 |
| gagtacaact acaacagcca caacgtctat atcatggccg acaagcagaa gaacggcatc | 4800 |

-continued

```
aaggtgaact tcaagatccg ccacaacatc gaggacggca gcgtgcagct cgccgaccac    4860
taccagcaga acaccccat cggcgacggc cccgtgctgc tgcccgacaa ccactacctg     4920
agcacccagt ccgccctgag caaagacccc aacgagaagc gcgatcacat ggtcctgctg    4980
gagttcgtga ccgccgccgg gatcactctc ggcatggacg agctgtacaa gtaagaattc    5040
gatatcaagc ttatcgataa tcaacctctg gattacaaaa tttgtgaaag attgactggt    5100
attcttaact atgttgctcc ttttacgcta tgtggatacg ctgctttaat gcctttgtat    5160
catgctattg cttcccgtat ggctttcatt ttctcctcct tgtataaatc ctggttgctg    5220
tctctttatg aggagttgtg gcccgttgtc aggcaacgtg gcgtggtgtg cactgtgttt    5280
gctgacgcaa cccccactgg ttggggcatt gccaccacct gtcagctcct ttccgggact    5340
ttcgctttcc ccctccctat tgccacggcg gaactcatcg ccgcctgcct tgcccgctgc    5400
tggacagggg ctcggctgtt gggcactgac aattccgtgg tgttgtcggg gaaatcatcg    5460
tcctttcctt ggctgctcgc ctgtgttgcc acctggattc tgcgcgggac gtccttctgc    5520
tacgtccctt cggccctcaa tccagcggac cttccttccc gcggcctgct gccggctctg    5580
cggcctcttc cgcgtcttcg ccttcgccct cagacgagtc ggatctccct ttgggccgcc    5640
tccccgcatc gataccgtcg acctcgagac ctagaaaaac atggagcaat cacaagtagc    5700
aatacagcag ctaccaatgc tgattgtgcc tggctagaag cacaagagga ggaggaggtg    5760
ggttttccag tcacacctca ggtacccttta agaccaatga cttacaaggc agctgtagat    5820
cttagccact ttttaaaaga aaagggggga ctggaagggc taattcactc ccaacgaaga    5880
caagatatcc ttgatctgtg gatctaccac acacaaggct acttccctga ttggcagaac    5940
tacacaccag ggccagggat cagatatcca ctgacctttg gatggtgcta caagctagta    6000
ccagttgagc aagagaaggt agaagaagcc aatgaaggag agaacacccg cttgttacac    6060
cctgtgagcc tgcatgggat ggatgacccg gagagagaag tattagagtg gaggtttgac    6120
agccgcctag catttcatca catggcccga gagctgcatc cggactgtac tgggtctctc    6180
tggttagacc agatctgagc ctgggagctc tctggctaac tagggaaccc actgcttaag    6240
cctcaataaa gcttgccttg agtgcttcaa gtagtgtgtg cccgtctgtt gtgtgactct    6300
ggtaactaga gatccctcag acccttttag tcagtgtgga aaatctctag cagggcccgt    6360
ttaaacccgc tgatcagcct cgactgtgcc ttctagttgc cagccatctg ttgtttgccc    6420
ctcccccgtg ccttccttga ccctggaagg tgccactccc actgtccttt cctaataaaa    6480
tgaggaaatt gcatcgcatt gtctgagtag gtgtcattct attctggggg gtggggtggg    6540
gcaggacagc aagggggagg attgggaaga caatagcagg catgctgggg atgcggtggg    6600
ctctatggct tctgaggcgg aaagaaccag ctggggctct agggggtatc cccacgcgcc    6660
ctgtagcggc gcattaagcg cggcgggtgt ggtggttacg cgcagcgtga ccgctacact    6720
tgccagcgcc ctagcgcccg ctcctttcgc tttcttccct ccttctcg ccacgttcgc     6780 cggctttccc cgtcaagctc taaatcgggg ctccctttta gggttccgat ttagtgcttt    6840
acggcacctc gaccccaaaa aacttgatta gggtgatggt tcacgtagtg gccatcgcc     6900 ctgatagacg gttttcgcc ctttgacgtt ggagtccacg ttctttaata gtggactctt     6960
gttccaaact ggaacaacac tcaaccctat ctcggtctat tcttttgatt tataagggat    7020
tttgccgatt tcggcctatt ggttaaaaaa tgagctgatt taacaaaaat ttaacgcgaa    7080
ttaattctgt ggaatgtgtg tcagttaggg tgtggaaagt ccccaggctc cccagcaggc    7140
agaagtatgc aaagcatgca tctcaattag tcagcaacca ggtgtggaaa gtccccaggc    7200
```

```
tccccagcag gcagaagtat gcaaagcatg catctcaatt agtcagcaac catagtcccg    7260
cccctaactc cgcccatccc gcccctaact ccgcccagtt ccgcccattc tccgcccat     7320 ggctgactaa ttttttttat ttatgcagag gccgaggccg cctctgcctc tgagctattc    7380
cagaagtagt gaggaggctt ttttggaggc ctaggctttt gcaaaaagct cccgggagct    7440
tgtatatcca ttttcggatc tgatcagcac gtgttgacaa ttaatcatcg gcatagtata    7500
tcggcatagt ataatacgac aaggtgagga actaaaccat ggccaagttg accagtgccg    7560
ttccggtgct caccgcgcgc gacgtcgccg agcggtcga gttctggacc gaccggctcg      7620
ggttctcccg ggacttcgtg gaggacgact tcgccggtgt ggtccgggac gacgtgaccc    7680
tgttcatcag cgcggtccag gaccaggtgg tgccggacaa caccctggcc tgggtgtggg    7740
tgcgcggcct ggacgagctg tacgccgagt ggtcggaggt cgtgtccacg aacttccggg    7800
acgcctccgg gccggccatg accgagatcg gcgagcagcc gtgggggcgg gagttcgccc    7860
tgcgcgaccc ggccggcaac tgcgtgcact tcgtggccga ggagcaggac tgacacgtgc    7920
tacgagattt cgattccacc gccgccttct atgaaaggtt gggcttcgga atcgttttcc    7980
gggacgccgg ctggatgatc ctccagcgcg ggatctcat gctggagttc ttcgcccacc     8040
ccaacttgtt tattgcagct tataatggtt acaaataaag caatagcatc acaaatttca    8100
caaataaagc attttttca ctgcattcta gttgtggttt gtccaaactc atcaatgtat     8160
cttatcatgt ctgtataccg tcgacctcta gctagagctt ggcgtaatca tggtcatagc    8220
tgtttcctgt gtgaaattgt tatccgctca caattccaca caacatacga gccggaagca    8280
taaagtgtaa agcctggggt gcctaatgag tgagctaact cacattaatt gcgttgcgct    8340
cactgcccgc tttccagtcg ggaaacctgt cgtgccagct gcattaatga atcggccaac    8400
gcgcggggag aggcggtttg cgtattgggc gctcttccgc ttcctcgctc actgactcgc    8460
tgcgctcggt cgttcggctg cggcgagcgg tatcagctca ctcaaaggcg gtaatacggt    8520
tatccacaga atcaggggat aacgcaggaa agaacatgtg agcaaaaggc cagcaaaagg    8580
ccaggaaccg taaaaaggcc gcgttgctgg cgtttttcca taggctccgc cccctgacg    8640 agcatcacaa aaatcgacgc tcaagtcaga ggtggcgaaa cccgacagga ctataaagat    8700
accaggcgtt tcccctggaa agctccctcg tgcgctctcc tgttccgacc ctgccgctta    8760
ccggatacct gtccgccttt ctcccttcgg gaagcgtggc gctttctcat agctcacgct    8820
gtaggtatct cagttcggtg taggtcgttc gctccaagct gggctgtgtg cacgaacccc    8880
ccgttcagcc cgaccgctgc gccttatccg gtaactatcg tcttgagtcc aacccggtaa    8940
gacacgactt atcgccactg gcagcagcca ctggtaacag gattagcaga gcgaggtatg    9000
taggcggtgc tacagagttc ttgaagtggt ggcctaacta cggctacact agaagaacag    9060
tatttggtat ctgcgctctg ctgaagccag ttaccttcgg aaaaagagtt ggtagctctt    9120
gatccggcaa acaaaccacc gctggtagcg gtggtttttt tgtttgcaag cagcagatta    9180
cgcgcagaaa aaaaggatct caagaagatc ctttgatctt ttctacgggg tctgacgctc    9240
agtggaacga aaactcacgt taagggattt tggtcatgag attatcaaaa aggatcttca    9300
cctagatcct tttaaattaa aaatgaagtt ttaaatcaat ctaaagtata tatgagtaaa    9360
cttggtctga cagttaccaa tgcttaatca gtgaggcacc tatctcagcg atctgtctat    9420
ttcgttcatc catagttgcc tgactccccg tcgtgtagat aactacgata cgggagggct    9480
taccatctgg ccccagtgct gcaatgatac cgcgagaccc acgctcaccg gctccagatt    9540
```

-continued

```
tatcagcaat aaaccagcca gccggaaggg ccgagcgcag aagtggtcct gcaactttat      9600
ccgcctccat ccagtctatt aattgttgcc gggaagctag agtaagtagt tcgccagtta      9660
atagtttgcg caacgttgtt gccattgcta caggcatcgt ggtgtcacgc tcgtcgtttg      9720
gtatggcttc attcagctcc ggttcccaac gatcaaggcg agttacatga tcccccatgt      9780
tgtgcaaaaa agcggttagc tccttcggtc ctccgatcgt tgtcagaagt aagttggccg      9840
cagtgttatc actcatggtt atggcagcac tgcataattc tcttactgtc atgccatccg      9900
taagatgctt ttctgtgact ggtgagtact caaccaagtc attctgagaa tagtgtatgc      9960
ggcgaccgag ttgctcttgc ccggcgtcaa tacgggataa taccgcgcca catagcagaa     10020
ctttaaaagt gctcatcatt ggaaaacgtt cttcggggcg aaaactctca aggatcttac     10080
cgctgttgag atccagttcg atgtaaccca ctcgtgcacc caactgatct tcagcatctt     10140
ttactttcac cagcgtttct gggtgagcaa aaacaggaag gcaaaatgcc gcaaaaaagg     10200
gaataagggc gacacggaaa tgttgaatac tcatactctt ccttttcaa tattattgaa      10260
gcatttatca gggttattgt ctcatgagcg gatacatatt tgaatgtatt tagaaaaata    10320
aacaaatagg ggttccgcgc acatttcccc gaaaagtgcc acctgac                  10367
```

<210> SEQ ID NO 60
<211> LENGTH: 131
<212> TYPE: PRT
<213> ORGANISM: Artificial Sequence
<220> FEATURE:
<223> OTHER INFORMATION: Synthetic Sequence MM3 FC

<400> SEQUENCE: 60

```
Glu Leu Leu Lys Lys His Glu Glu Ala Leu Lys Lys Phe Glu Glu Leu
1               5                   10                  15
Leu Lys Lys Phe Glu Glu Glu Leu Lys Lys Gly Gly Ser Gly Ser Gly
            20                  25                  30
Ser Gly Gly Glu Leu Leu Lys Lys Phe Glu Glu Ala Leu Lys Lys Phe
        35                  40                  45
Glu Glu Leu Leu Lys Lys Phe Glu Glu Glu Leu Lys Lys Gly Gly Ser
    50                  55                  60
Gly Trp Gly Ser Gly Gly Glu Leu Leu Lys Lys His Glu Glu Ala Leu
65                  70                  75                  80
Lys Lys Phe Glu Glu Leu Leu Lys Lys Phe Glu Glu Leu Leu Lys Lys
                85                  90                  95
Gly Gly Ser Gly Ser Gly Ser Gly Gly Glu Leu Leu Lys Lys Cys Glu
            100                 105                 110
Glu Ala Leu Lys Lys Phe Glu Glu Leu Leu Lys Lys Phe Glu Glu Leu
        115                 120                 125
Leu Lys Lys
    130
```

<210> SEQ ID NO 61
<211> LENGTH: 6345
<212> TYPE: DNA
<213> ORGANISM: Artificial Sequence
<220> FEATURE:
<223> OTHER INFORMATION: Synthetic Sequence AM-528-C4 (E. Coli)

<400> SEQUENCE: 61

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
```

-continued

```
ctttctcgcc acgttcgccg gctttccccg tcaagctcta atcgggggc tccctttagg      180 gttccgattt agtgctttac ggcacctcga ccccaaaaaa cttgattagg gtgatggttc      240
acgtagtggg ccatcgccct gatagacggt ttttcgccct ttgacgttgg agtccacgtt      300
ctttaatagt ggactcttgt tccaaactgg aacaacactc aacccatatct cggtctattc      360 ttttgattta aagggatttt tgccgatttc ggcctattgg ttaaaaaatg agctgattta      420
acaaaaattt aacgcgaatt ttaacaaaat attaacgttt acaatttcag gtggcactt       480 tcggggaaat gtgcgcggaa ccctattttg tttatttttc taaatacatt caaatatgta      540
tccgctcatg agacaataac cctgataaat gcttcaataa tattgaaaaa ggaagagtat      600
gagtattcaa catttccgtg tcgcccttat cccttttttg cggcatttt gccttcctgt       660 ttttgctcac ccagaaacgc tggtgaaagt aaaagatgct gaagatcagt tgggtgcacg      720
agtgggttac atcgaactgg atctcaacag cggtaagatc cttgagagtt ttcgccccga      780
agaacgtttt ccaatgatga gcacttttaa agttctgcta tgtggcgcgg tattatcccg      840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga caacgatcgg     1020
aggaccgaag gagctaaccg cttttttgca acatggggg atcatgtaa ctcgccttga       1080 tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380
gacggggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttctgcg cgtaatctgc tgcttgcaaa caaaaaaacc      1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agctgccagt ggcgataagt cgtgtcttac cgggttggac tcaagacgat agttaccgga     1920
taaggcgcag cggtcgggct gaacggggg ttcgtgcaca cagcccagct tggagcgaac      1980
gacctacacc gaactgagat acctacagcg tgagctatga gaaagcgcca cgcttcccga     2040
agggagaaag gcggacaggt atccggtaag cggcagggtc ggaacaggag agcgcacgag     2100
ggagcttcca gggggaaacg cctggtatct ttatagtcct gtcgggtttc gccacctctg     2160
acttgagcgt cgatttttgt gatgctcgtc agggggcgg agcctatgga aaaacgccag      2220
caacgcggcc ttttacggt tcctggcctt tgctggcct tttgctcaca tgttctttcc       2280
tgcgttatcc cctgattctg tggataaccg tattaccgcc tttgagtgag ctgataccgc     2340
tcgccgcagc cgaacgaccg agcgcagcga gtcagtgagc gaggaagcgg aagagcgcct     2400
gatgcggtat tttctcctta cgcatctgtg cggtatttca caccgcatat atggtgcact     2460
ctcagtacaa tctgctctga tgccgcatag ttaagccagt atacactccg ctatcgctac     2520
```

```
gtgactgggt catggctgcg ccccgacacc cgccaacacc cgctgacgcg ccctgacggg    2580
cttgtctgct cccggcatcc gcttacagac aagctgtgac cgtctccggg agctgcatgt    2640
gtcagaggtt ttcaccgtca tcaccgaaac gcgcgaggca gctgcggtaa agctcatcag    2700
cgtggtcgtg aagcgattca cagatgtctg cctgttcatc cgcgtccagc tcgttgagtt    2760
tctccagaag cgttaatgtc tggcttctga taaagcgggc catgttaagg gcggtttttt    2820
cctgtttggt cactgatgcc tccgtgtaag ggggatttct gttcatgggg gtaatgatac    2880
cgatgaaacg agagaggatg ctcacgatac gggttactga tgatgaacat gcccggttac    2940
tggaacgttg tgagggtaaa caactggcgg tatggatgcg gcgggaccag agaaaaatca    3000
ctcagggtca atgccagcgc ttcgttaata cagatgtagg tgttccacag ggtagccagc    3060
agcatcctgc gatgcagatc cggaacataa tggtgcaggg cgctgacttc gcgtttcca    3120 gactttacga aacacggaaa ccgaagacca ttcatgttgt tgctcaggtc gcagacgttt    3180
tgcagcagca gtcgcttcac gttcgctcgc gtatcggtga ttcattctgc taaccagtaa    3240
ggcaaccccg ccagcctagc cgggtcctca acgacaggag cacgatcatg cgcacccgtg    3300
gggccgccat gccggcgata atggcctgct tctcgccgaa acgtttggtg gcgggaccag    3360
tgacgaaggc ttgagcgagg gcgtgcaaga ttccgaatac cgcaagcgac aggccgatca    3420
tcgtcgcgct ccagcgaaag cggtcctcgc cgaaaatgac ccagagcgct gccggcacct    3480
gtcctacgag ttgcatgata agaagacag tcataagtgc ggcgacgata gtcatgcccc    3540
gcgcccaccg gaaggagctg actgggttga aggctctcaa gggcatcggt cgagatcccg    3600
gtgcctaatg agtgagctaa cttacattaa ttgcgttgcg ctcactgccc gctttccagt    3660
cgggaaacct gtcgtgccag ctgcattaat gaatcggcca acgcgcgggg agaggcggtt    3720
tgcgtattgg gcgccagggt ggttttctt ttcaccagtg agacgggcaa cagctgattg    3780
cccttcaccg cctggccctg agagagttgc agcaagcggt ccacgctggt ttgccccagc    3840
aggcgaaaat cctgtttgat ggtggttaac ggcgggatat aacatgagct gtcttcggta    3900
tcgtcgtatc ccactaccga gatatccgca ccaacgcgca gcccggactc ggtaatggcg    3960
cgcattgcgc ccagcgccat ctgatcgttg caaccagca tcgcagtggg aacgatgccc    4020
tcattcagca tttgcatggt ttgttgaaaa ccggacatgg cactccagtc gccttcccgt    4080
tccgctatcg gctgaatttg attgcgagtg agatatttat gccagccagc cagacgcaga    4140
cgcgccgaga cagaacttaa tgggcccgct aacagcgcga tttgctggtg acccaatgcg    4200
accagatgct ccacgcccag tcgcgtaccg tcttcatggg agaaaataat actgttgatg    4260
ggtgtctggt cagagacatc aagaaataac gccggaacat tagtgcaggc agcttccaca    4320
gcaatggcat cctggtcatc cagcggatag ttaatgatca gcccactgac gcgttgcgcg    4380
agaagattgt gcaccgccgc tttacaggct tcgacgccgc ttcgttctac catcgacacc    4440
accacgctgg cacccagttg atcggcgcga gatttaatcg ccgcgacaat ttgcgacggc    4500
gcgtgcaggg ccagactgga ggtggcaacg ccaatcagca acgactgttt gcccgccagt    4560
tgttgtgcca cgcggttggg aatgtaattc agctccgcca tcgccgcttc cacttttcc    4620 cgcgttttcg cagaaacgtg gctggcctgg ttcaccacgc gggaaacggt ctgataagag    4680
acaccggcat actctgcgac atcgtataac gttactggtt tcacattcac caccctgaat    4740
tgactctctt ccgggcgcta tcatgccata ccgcgaaagg ttttgcgcca ttcgatggtg    4800
tccgggatct cgacgctctc ccttatgcga ctcctgcatt aggaagcagc ccagtagtag    4860
```

```
gttgaggccg ttgagcaccg ccgccgcaag gaatggtgca tgcaaggaga tggcgcccaa    4920
cagtcccccg gccacggggc ctgccaccat acccacgccg aaacaagcgc tcatgagccc    4980
gaagtggcga gcccgatctt ccccatcggt gatgtcggcg atataggcgc cagcaaccgc    5040
acctgtggcg ccggtgatgc cggccacgat gcgtccggcg tagaggatcg agatctcgat    5100
cccgcgaaat taatacgact cactataggg gaattgtgag cggataacaa ttcccctcta    5160
gaaataattt tgtttaactt taagaaggag atatacatat gcataccccca gaacacatca    5220 ccgccgtggt acagcgcttt gtggctgcgc tcaatgccgg cgatctggac ggcatcgtcg    5280
cgctgtttgc cgatgacgcc acggtggaag accccgtggg ttccgagccc aggtccggta    5340
cggctgcgat tcgtgagttt tacgccaact cgctcaaact gcctttggcg gtggagctga    5400
cgcaggaggt acgcgcggtc gccaacgaag cggccttcgc tttcaccgtc agcttcgagt    5460
atcagggccg caagaccgta gttgcgccca tcgatcactt tcgcttcaat ggcgccggca    5520
aggtggtgag catccgcgcc ttgtttggcg agaagaatat tcacgcatgc cagatgctga    5580
atggtaccca tcatcatcat catcatggcg gcgacggcga gaacttgtat tttcaagcta    5640
gcggatccat gggagaaatc tggaaacaat tcgaggacgc actgcaaaag ttcttcgccc    5700
tgcacctgct gctggcactg ctgctgctgc tggctctgct gctgttcctg ctggcttttg    5760
agggcggtag cggcggtggc agcggtggca agttcctgtg cctgctggcg ctgctggccc    5820
tgttactgct ggccctgtta ctgttcctgc tggccttttg ggaggctctg aaccagttcg    5880
aagacctggc taagcagggt ggcagcggtg gcggtagcgg cggtgagatc tggaagcagt    5940
ttgaagatgc gctgcagaaa ttctttgctc tgcacctgct gctggcgctg ctgttactgc    6000
tggcgctgtt actgttcctg ctggcgttta agggcggtag cggcggtggc agcggtggcg    6060
aatttctgct gcacctggct ctgctggcgc tgctgctgct ggccctgctg ctgttcctgc    6120
tggctttctg ggaggcactg aaccaatttg aagacctggc taaacaaacc ggttaagaat    6180
tcctcgagca ccaccaccac caccactgag atccggctgc taacaaagcc cgaaaggaag    6240
ctgagttggc tgctgccacc gctgagcaat aactagcata ccccttggg gcctctaaac    6300 gggtcttgag gggttttttg ctgaaaggag gaactatatc cggat                   6345
```

<210> SEQ ID NO 62
<211> LENGTH: 521
<212> TYPE: DNA
<213> ORGANISM: Artificial Sequence
<220> FEATURE:
<223> OTHER INFORMATION: Synthetic Sequence AM-528-C4 (FCK mam)

<400> SEQUENCE: 62

```
ggatccgcca ccatggagat ctggaagagc cacgaagacg ctctgcagaa attctttgct     60
ctgctgctgc tgctggccct gctgctgctg ctggctctgc tgctgcacct gctggccttc    120
gagggcggta gcggcggtgg cagcggtggc aagtttctgc tgctgctggg gctgctggcc    180
ctgttactgc tggctctgtt attacacctg ctggccttct gggaggcgct gaagcgtttc    240
gaagacctga agcagaaagg tggctgcggc cgtatctgga aggagcacga agatgcgcac    300
cagaaattct tgcgttatt attactgctg gctctgttgt tactgctggc gctgttactg    360
cacctgctgg cgttcaaggg tggcagcggt ggcggtagcg cggtgaatt tctgttgctg    420 ctggctctgc tggcgctgct tctgctggcc ctgttgttac acctgctggc gttctgggag    480
gccctgaagc gtcacgaaga tcgtgtgcag aaagcaccgg t                         521
```

-continued

```
<210> SEQ ID NO 63
<211> LENGTH: 171
<212> TYPE: PRT
<213> ORGANISM: Artificial Sequence
<220> FEATURE:
<223> OTHER INFORMATION: Synthetic Sequence AM-528-C4

<400> SEQUENCE: 63

Glu Ile Trp Lys Gln Phe Glu Asp Ala Leu Gln Lys Phe Phe Ala Leu
1               5                   10                  15

His Leu Leu Leu Ala Leu Leu Leu Leu Ala Leu Leu Leu Phe Leu
            20                  25                  30

Leu Ala Phe Glu Gly Gly Ser Gly Gly Gly Ser Gly Gly Lys Phe Leu
        35                  40                  45

Cys Leu Leu Ala Leu Leu Ala Leu Leu Leu Ala Leu Leu Leu Phe
    50                  55                  60

Leu Leu Ala Phe Trp Glu Ala Leu Asn Gln Phe Glu Asp Leu Ala Lys
65                  70                  75                  80

Gln Gly Gly Ser Gly Gly Gly Ser Gly Gly Glu Ile Trp Lys Gln Phe
                85                  90                  95

Glu Asp Ala Leu Gln Lys Phe Phe Ala Leu His Leu Leu Leu Ala Leu
            100                 105                 110

Leu Leu Leu Leu Ala Leu Leu Leu Phe Leu Leu Ala Phe Lys Gly Gly
        115                 120                 125

Ser Gly Gly Gly Ser Gly Gly Glu Phe Leu Leu Leu His Leu Ala Leu Leu
    130                 135                 140

Ala Leu Leu Leu Ala Leu Leu Leu Phe Leu Leu Ala Phe Trp Glu
145                 150                 155                 160

Ala Leu Asn Gln Phe Glu Asp Leu Ala Lys Gln
                165                 170

<210> SEQ ID NO 64
<211> LENGTH: 6330
<212> TYPE: DNA
<213> ORGANISM: Artificial Sequence
<220> FEATURE:
<223> OTHER INFORMATION: Synthetic Sequence AM-1196 (EC)

<400> SEQUENCE: 64
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat tccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
```

-continued

```
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataaacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gaccccgtag aaaagatcaa   1620
aggatcttct tgagatcctt ttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agctgccagt ggcgataagt cgtgtcttac cgggttggac tcaagacgat agttaccgga   1920
taaggcgcag cggtcgggct gaacggggggg ttcgtgcaca gcccagct tggagcgaac   1980 gacctacacc gaactgagat acctacagcg tgagctatga gaaagcgcca cgcttcccga   2040
agggagaaag gcggacaggt atccggtaag cggcagggtc ggaacaggag agcgcacgag   2100
ggagcttcca gggggaaacg cctggtatct ttatagtcct gtcgggtttc gccacctctg   2160
acttgagcgt cgatttttgt gatgctcgtc aggggggcgg agcctatgga aaaacgccag   2220
caacgcggcc ttttacggt tcctggcctt ttgctggcct tttgctcaca tgttctttcc   2280
tgcgttatcc cctgattctg tggataaccg tattaccgcc tttgagtgag ctgataccgc   2340
tcgccgcagc cgaacgaccg agcgcagcga gtcagtgagc gaggaagcgg aagagcgcct   2400
gatgcggtat tttctcctta cgcatctgtg cggtatttca caccgcatat atggtgcact   2460
ctcagtacaa tctgctctga tgccgcatag ttaagccagt atacactccg ctatcgctac   2520
gtgactgggt catggctgcg ccccgacacc cgccaacacc cgctgacgcg ccctgacggg   2580
cttgtctgct cccggcatcc gcttacagac aagctgtgac cgtctccggg agctgcatgt   2640
gtcagaggtt ttcaccgtca tcaccgaaac gcgcgaggca gctgcggtaa agctcatcag   2700
cgtggtcgtg aagcgattca cagatgtctg cctgttcatc cgcgtccagc tcgttgagtt   2760
tctccagaag cgttaatgtc tggcttctga taaagcgggc catgttaagg gcggttttt   2820 cctgtttggt cactgatgcc tccgtgtaag ggggatttct gttcatgggg gtaatgatac   2880
cgatgaaacg agagaggatg ctcacgatac gggttactga tgatgaacat gcccggttac   2940
tggaacgttg tgagggtaaa caactggcgg tatggatgcg gcgggaccag agaaaaatca   3000
ctcagggtca atgccagcgc ttcgttaata cagatgtagg tgttccacag ggtagccagc   3060
agcatcctgc gatgcagatc cggaacataa tggtgcaggg cgctgacttc cgcgtttcca   3120
gactttacga aacacggaaa ccgaagacca ttcatgttgt tgctcaggtc gcagacgttt   3180
```

| | |
|---|---|
| tgcagcagca gtcgcttcac gttcgctcgc gtatcggtga ttcattctgc taaccagtaa | 3240 |
| ggcaaccccg ccagcctagc cgggtcctca acgacaggag cacgatcatg cgcacccgtg | 3300 |
| gggccgccat gccggcgata atggcctgct tctcgccgaa acgtttggtg gcgggaccag | 3360 |
| tgacgaaggc ttgagcgagg gcgtgcaaga ttccgaatac cgcaagcgac aggccgatca | 3420 |
| tcgtcgcgct ccagcgaaag cggtcctcgc cgaaaatgac ccagagcgct gccggcacct | 3480 |
| gtcctacgag ttgcatgata aagaagacag tcataagtgc ggcgacgata gtcatgcccc | 3540 |
| gcgcccaccg gaaggagctg actgggttga aggctctcaa gggcatcggt cgagatcccg | 3600 |
| gtgcctaatg agtgagctaa cttacattaa ttgcgttgcg ctcactgccc gctttccagt | 3660 |
| cgggaaacct gtcgtgccag ctgcattaat gaatcggcca acgcgcgggg agaggcggtt | 3720 |
| tgcgtattgg cgccagggt ggttttctt ttcaccagtg agacgggcaa cagctgattg | 3780 |
| cccttcaccg cctggccctg agagagttgc agcaagcggt ccacgctggt ttgccccagc | 3840 |
| aggcgaaaat cctgtttgat ggtggttaac ggcgggatat aacatgagct gtcttcggta | 3900 |
| tcgtcgtatc ccactaccga gatatccgca ccaacgcgca gcccggactc ggtaatggcg | 3960 |
| cgcattgcgc ccagcgccat ctgatcgttg gcaaccagca tcgcagtggg aacgatgccc | 4020 |
| tcattcagca tttgcatggt ttgttgaaaa ccggacatgg cactccagtc gccttcccgt | 4080 |
| tccgctatcg gctgaatttg attgcgagtg agatatttat gccagccagc cagacgcaga | 4140 |
| cgcgccgaga cagaacttaa tgggcccgct aacagcgcga tttgctggtg acccaatgcg | 4200 |
| accagatgct ccacgcccag tcgcgtaccg tcttcatggg agaaaataat actgttgatg | 4260 |
| ggtgtctggt cagagacatc aagaaataac gccggaacat tagtgcaggc agcttccaca | 4320 |
| gcaatggcat cctggtcatc cagcggatag ttaatgatca cccactgac gcgttgcgcg | 4380 |
| agaagattgt gcaccgccgc tttacaggct tcgacgccgc ttcgttctac catcgacacc | 4440 |
| accacgctgg cacccagttg atcggcgcga gatttaatcg ccgcgacaat tgcgacggc | 4500 |
| gcgtgcaggg ccagactgga ggtggcaacg ccaatcagca acgactgttt gcccgccagt | 4560 |
| tgttgtgcca cgcggttggg aatgtaattc agctccgcca tcgccgcttc cacttttcc | 4620 |
| cgcgttttcg cagaaacgtg gctggcctgg ttcaccacgc gggaaacggt ctgataagag | 4680 |
| acaccggcat actctgcgac atcgtataac gttactggtt tcacattcac caccctgaat | 4740 |
| tgactctctt ccgggcgcta tcatgccata ccgcgaaagg ttttgcgcca ttcgatggtg | 4800 |
| tccgggatct cgacgctctc ccttatgcga ctcctgcatt aggaagcagc ccagtagtag | 4860 |
| gttgaggccg ttgagcaccg ccgccgcaag gaatggtgca tgcaaggaga tggcgcccaa | 4920 |
| cagtcccccg gccacggggc ctgccaccat acccacgccg aaacaagcgc tcatgagccc | 4980 |
| gaagtggcga gcccgatctt ccccatcggt gatgtcggcg atataggcgc cagcaaccgc | 5040 |
| acctgtggcg ccggtgatgc cggccacgat gcgtccggcg tagaggatcg agatctcgat | 5100 |
| cccgcgaaat taatacgact cactataggg gaattgtgag cggataacaa ttcccctcta | 5160 |
| gaaataattt tgtttaactt taagaaggag atatacatat gcataccca gaacacatca | 5220 |
| ccgccgtggt acagcgcttt gtggctgcgc tcaatgccgg cgatctggac ggcatcgtcg | 5280 |
| cgctgtttgc cgatgacgcc acggtggaag acccgtggg ttcgagccc aggtccggta | 5340 |
| cggctgcgat tcgtgagttt tacgccaact cgctcaaact gcctttggcg gtggagctga | 5400 |
| cgcaggaggt acgcgcggtc gccaacgaag cggccttcgc tttcaccgtc agcttcgagt | 5460 |
| atcagggccg caagaccgta gttgcgccca tcgatcactt tcgcttcaat ggcgccggca | 5520 |
| aggtggtgag catccgcgcc ttgtttggcg agaagaatat tcacgcatgc cagatgctga | 5580 |

```
atggtaccca tcatcatcat catcatggcg gcgacggcga gaacttgtat tttcaagcta    5640
gcggatccat gggagagatc tggaagagcc acgaagacgc tctgcagaaa ttctttgctc    5700
tgctgctgct gctggccctg ctgctgctgc tggctctgct gctgcacctg ctggccttcg    5760
agggcggtag cggcggtggc agcggtggca agtttctgct gctgctggcg ctgctggccc    5820
tgttactgct ggctctgtta ttacacctgc tggccttctg ggaggcgctg aagcgtttcg    5880
aagacctgaa gcagaaaggt ggctgcggcc gtatctggaa ggagcacgaa gatgcgcacc    5940
agaaattctt tgcgttatta ttactgctgg ctctgttgtt actgctggcg ctgttactgc    6000
acctgctggc gttcaagggt ggcagcggtg gcggtagcgg cggtgaattt ctgttgctgc    6060
tggctctgct ggcgctgctt ctgctggccc tgttgttaca cctgctggcg ttctgggagg    6120
ccctgaagcg tcacgaagat cgtgtgcaga aaaccggtta agaattcctc gagcaccacc    6180
accaccacca ctgagatccg gctgctaaca aagcccgaaa ggaagctgag ttggctgctg    6240
ccaccgctga gcaataacta gcataacccc ttggggcctc taaacgggtc ttgaggggtt    6300
ttttgctgaa aggaggaact atatccggat                                      6330

<210> SEQ ID NO 65
<211> LENGTH: 521
<212> TYPE: DNA
<213> ORGANISM: Artificial Sequence
<220> FEATURE:
<223> OTHER INFORMATION: Synthetic Sequence AM-1196 (FCK mam)

<400> SEQUENCE: 65
ggatccgcca ccatggagat ctggaagagc cacgaagacg ctctgcagaa attctttgct     60
ctgctgctgc tgctggccct gctgctgctg ctggctctgc tgctgcacct gctggccttc    120
gagggcggta gcggcggtgg cagcggtggc aagtttctgc tgctgctggc gctgctggcc    180
ctgttactgc tggctctgtt attacacctg ctggccttct gggaggcgct gaagcgtttc    240
gaagacctga agcagaaagg tggctgcggc cgtatctgga aggagcacga agatgcgcac    300
cagaaattct ttgcgttatt attactgctg gctctgttgt tactgctggc gctgttactg    360
cacctgctgg cgttcaaggg tggcagcggt ggcggtagcg gcggtgaatt tctgttgctg    420
ctggctctgc tggcgctgct tctgctggcc ctgttgttac acctgctggc gttctgggag    480
gccctgaagc gtcacgaaga tcgtgtgcag aaagcaccgg t                        521

<210> SEQ ID NO 66
<211> LENGTH: 166
<212> TYPE: PRT
<213> ORGANISM: Artificial Sequence
<220> FEATURE:
<223> OTHER INFORMATION: Synthetic Sequence AM-1196

<400> SEQUENCE: 66

Glu Ile Trp Lys Ser His Glu Asp Ala Leu Gln Lys Phe Phe Ala Leu
1               5                   10                  15

Leu Leu Leu Leu Ala Leu Leu Leu Leu Ala Leu Leu Leu His Leu
            20                  25                  30

Leu Ala Phe Glu Gly Gly Ser Gly Gly Ser Gly Gly Lys Phe Leu
        35                  40                  45

Leu Leu Leu Ala Leu Leu Ala Leu Leu Leu Ala Leu Leu Leu His
    50                  55                  60

Leu Leu Ala Phe Trp Glu Ala Leu Lys Arg Phe Glu Asp Leu Lys Gln
65                  70                  75                  80
```

```
Lys Gly Gly Cys Gly Arg Ile Trp Lys Glu His Glu Asp Ala His Gln
            85                  90                  95

Lys Phe Phe Ala Leu Leu Leu Leu Ala Leu Leu Leu Leu Ala
            100                 105                 110

Leu Leu Leu His Leu Leu Ala Phe Lys Gly Ser Gly Gly Ser
        115                 120                 125

Gly Gly Glu Phe Leu Leu Leu Ala Leu Ala Leu Leu Leu
        130                 135                 140

Ala Leu Leu Leu His Leu Leu Ala Phe Trp Glu Ala Leu Lys Arg His
145                 150                 155                 160

Glu Asp Arg Val Gln Lys
                165

<210> SEQ ID NO 67
<211> LENGTH: 6345
<212> TYPE: DNA
<213> ORGANISM: Artificial Sequence
<220> FEATURE:
<223> OTHER INFORMATION: Synthetic Sequence AM-528 (E. Coli)

<400> SEQUENCE: 67
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttcccccg tcaagctcta atcgggggc tccctttagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta tagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat tccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca acatggggg atcatgtaa ctcgccttga    1080 tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
```

```
aaaacttcat ttttaatttta aaaggatcta ggtgaagatc ctttttgata atctcatgac    1560
caaaatccct taacgtgagt tttcgttcca ctgagcgtca gacccgtag  aaaagatcaa    1620 aggatcttct tgagatcctt tttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agctgccagt ggcgataagt cgtgtcttac cgggttggac tcaagacgat agttaccgga    1920
taaggcgcag cggtcgggct gaacggggggg ttcgtgcaca cagcccagct tggagcgaac    1980
gacctacacc gaactgagat acctacagcg tgagctatga gaaagcgcca cgcttcccga    2040
agggagaaag gcggacaggt atccggtaag cggcagggtc ggaacaggag agcgcacgag    2100
ggagcttcca gggggaaacg cctggtatct ttatagtcct gtcgggtttc gccacctctg    2160
acttgagcgt cgattttgt gatgctcgtc agggggggcgg agcctatgga aaaacgccag    2220
caacgcggcc tttttacggt tcctggcctt ttgctggcct tttgctcaca tgttctttcc    2280
tgcgttatcc cctgattctg tggataaccg tattaccgcc tttgagtgag ctgataccgc    2340
tcgccgcagc cgaacgaccg agcgcagcga gtcagtgagc gaggaagcgg aagagcgcct    2400
gatgcggtat tttctcctta cgcatctgtg cggtatttca caccgcatat atggtgcact    2460
ctcagtacaa tctgctctga tgccgcatag ttaagccagt atacactccg ctatcgctac    2520
gtgactgggt catggctgcg ccccgacacc cgccaacacc cgctgacgcg ccctgacggg    2580
cttgtctgct cccggcatcc gcttacagac aagctgtgac cgtctccggg agctgcatgt    2640
gtcagaggtt ttcaccgtca tcaccgaaac gcgcgaggca gctgcggtaa agctcatcag    2700
cgtggtcgtg aagcgattca cagatgtctg cctgttcatc cgcgtccagc tcgttgagtt    2760
tctccagaag cgttaatgtc tggcttctga taaagcgggc catgttaagg gcggtttttt    2820
cctgtttggt cactgatgcc tccgtgtaag ggggatttct gttcatgggg gtaatgatac    2880
cgatgaaacg agagaggatg ctcacgatac gggttactga tgatgaacat gcccggttac    2940
tggaacgttg tgagggtaaa caactggcgg tatggatgcg gcgggaccag agaaaaatca    3000
ctcagggtca atgccagcgc ttcgttaata cagatgtagg tgttccacag ggtagccagc    3060
agcatcctgc gatgcagatc cggaacataa tggtgcaggg cgctgacttc cgcgtttcca    3120
gactttacga aacacggaaa ccgaagacca ttcatgttgt tgctcaggtc gcagacgttt    3180
tgcagcagca gtcgcttcac gttcgctcgc gtatcggtga ttcattctgc taaccagtaa    3240
ggcaaccccg ccagcctagc cgggtcctca acgacaggag cacgatcatg cgcacccgtg    3300
gggccgccat gccggcgata atggcctgct tctcgccgaa acgtttggtg gcgggaccag    3360
tgacgaaggc ttgagcgagg gcgtgcaaga ttccgaatac cgcaagcgac aggccgatca    3420
tcgtcgcgct ccagcgaaag cggtcctcgc cgaaaatgac ccagagcgct gccggcacct    3480
gtcctacgag ttgcatgata agaagacag  tcataagtgc ggcgacgata gtcatgcccc    3540
gcgcccaccg gaaggagctg actgggttga aggctctcaa gggcatcggt cgagatcccg    3600
gtgcctaatg agtgagctaa cttacattaa ttgcgttgcg ctcactgccc gctttccagt    3660
cgggaaacct gtcgtgccag ctgcattaat gaatcggcca acgcgcgggg agaggcggtt    3720
tgcgtattgg gcgccagggt ggtttttctt ttcaccagtg agacgggcaa cagctgattg    3780
cccttcaccg cctggccctg agagagttgc agcaagcggt ccacgctggt ttgccccagc    3840
aggcgaaaat cctgtttgat ggtggttaac ggcgggatat aacatgagct gtcttcggta    3900
```

```
tcgtcgtatc ccactaccga gatatccgca ccaacgcgca gcccggactc ggtaatggcg    3960
cgcattgcgc ccagcgccat ctgatcgttg gcaaccagca tcgcagtggg aacgatgccc    4020
tcattcagca tttgcatggt ttgttgaaaa ccggacatgg cactccagtc gccttcccgt    4080
tccgctatcg gctgaatttg attgcgagtg agatatttat gccagccagc cagacgcaga    4140
cgcgccgaga cagaacttaa tgggcccgct aacagcgcga tttgctggtg acccaatgcg    4200
accagatgct ccacgcccag tcgcgtaccg tcttcatggg agaaataat actgttgatg     4260 ggtgtctggt cagagacatc aagaaataac gccggaacat tagtgcaggc agcttccaca    4320
gcaatggcat cctggtcatc cagcggatag ttaatgatca gcccactgac gcgttgcgcg    4380
agaagattgt gcaccgccgc tttacaggct tcgacgccgc ttcgttctac catcgacacc    4440
accacgctgg cacccagttg atcggcgcga gatttaatcg ccgcgacaat ttgcgacggc    4500
gcgtgcaggg ccagactgga ggtggcaacg ccaatcagca acgactgttt gcccgccagt    4560
tgttgtgcca cgcggttggg aatgtaattc agctccgcca tcgccgcttc cacttttttcc    4620 cgcgttttcg cagaaacgtg gctggcctgg ttcaccacgc gggaaacggt ctgataagag    4680
acaccggcat actctgcgac atcgtataac gttactggtt tcacattcac caccctgaat    4740
tgactctctt ccgggcgcta tcatgccata ccgcgaaagg ttttgcgcca ttcgatggtg    4800
tccgggatct cgacgctctc ccttatgcga ctcctgcatt aggaagcagc ccagtagtag    4860
gttgaggccg ttgagcaccg ccgccgcaag gaatggtgca tgcaaggaga tggcgcccaa    4920
cagtcccccg gccacggggc ctgccaccat acccacgccg aaacaagcgc tcatgagccc    4980
gaagtggcga gcccgatctt ccccatcggt gatgtcggcg atataggcgc cagcaaccgc    5040
acctgtggcg ccggtgatgc cggccacgat gcgtccggcg tagaggatcg agatctcgat    5100
cccgcgaaat taatacgact cactataggg gaattgtgag cggataacaa ttcccctcta    5160
gaaataattt tgtttaactt taagaaggag atatacatat gcataccca gaacacatca     5220 ccgccgtggt acagcgcttt gtggctgcgc tcaatgccgg cgatctggac ggcatcgtcg    5280
cgctgtttgc cgatgacgcc acggtggaag accccgtggg ttccgagccc aggtccggta    5340
cggctgcgat tcgtgagttt tacgccaact cgctcaaact gcctttggcg gtggagctga    5400
cgcaggaggt acgcgcggtc gccaacgaag cggccttcgc tttcaccgtc agcttcgagt    5460
atcagggccg caagaccgta gttgcgccca tcgatcactt tcgcttcaat ggcgccggca    5520
aggtggtgag catccgcgcc ttgtttggcg agaagaatat tcacgcatgc cagatgctga    5580
atggtaccca tcatcatcat catcatggcg gcgacgcga gaacttgtat tttcaagcta     5640
gcggatccat gggagaaatc tggaaacaat tcgaggacgc actgcaaaag ttcttcgccc    5700
tgcacctgct gctggcactg ctgctgctgc tggctctgct gctgttcctg ctggcttttg    5760
agggcggtag cggcggtggc agcggtggca agttcctgct gtgcctggcg ctgctggccc    5820
tgttactgct ggcccgtgta ctgttcctgc tggcctttttg ggaggctctg aaccagttcg    5880
aagacctggc taagcagggt ggcagcggtg gcggtagcgg cggtgagatc tggaagcagt    5940
ttgaagatgc gctgcagaaa ttctttgctc tgcacctgct gctggcgctg ctgttactgc    6000
tggcgctgtt actgttcctg ctggcgttta agggcggtag cggcggtggc agcggtggcg    6060
aatttctgct gcacctggct ctgctggcgc tgctgctgct ggccctgctg ctgttcctgc    6120
tggctttctg ggaggcactg aaccaatttg aagacctggc taaacaaacc ggttaagaat    6180
tcctcgagca ccaccaccac caccactgag atccggctgc taacaaagcc cgaaaggaag    6240
```

```
ctgagttggc tgctgccacc gctgagcaat aactagcata accccttggg gcctctaaac    6300
gggtcttgag gggttttttg ctgaaaggag gaactatatc cggat                    6345
```

<210> SEQ ID NO 68
<211> LENGTH: 1608
<212> TYPE: DNA
<213> ORGANISM: Artificial Sequence
<220> FEATURE:
<223> OTHER INFORMATION: Synthetic Sequence AM-528 (FCK mam)

<400> SEQUENCE: 68

```
ggatccgcca ccatggaaat ctggaaacaa ttcgaggacg cactgcaaaa gttcttcgcc      60
ctgcacctgc tgctggcact gctgctgctg ctggctctgc tgctgttcct gctggctttt     120
gagggcggta gcggcggtgg cagcggtggc aagttcctgc tgtgcctggc gctgctggcc     180
ctgttactgc tggccctgtt actgttcctg ctggcctttt gggaggctct gaaccagttc     240
gaagacctgg ctaagcaggg tggcagcggt ggcggtagcg gcggtgagat ctggaagcag     300
tttgaagatg cgctgcagaa attctttgct ctgcacctgc tgctggcgct gctgttactg     360
ctggcgctgt tactgttcct gctggcgttt aagggcggta gcggcggtgg cagcggtggc     420
gaatttctgc tgcacctggc tctgctgcg ctgctgctgc tggccctgct gctgttcctg      480
ctggctttct gggaggcact gaaccaattt gaagacctgg ctaaacaagc accggtggat     540
ccgccaccat ggaaatctgg aaacaattcg aggacgcact gcaaaagttc ttcgccctgc     600
acctgctgct ggcactgctg ctgctgctgg ctctgctgct gttcctgctg gcttttgagg     660
gcggtagcgg cggtggcagc ggtggcaagt tcctgctgtg cctggcgctg ctggccctgt     720
tactgctggc cctgttactg ttcctgctgg ccttttggga ggctctgaac cagttcgaag     780
acctggctaa gcagggtggc agcggtggcg gtagcggcgg tgagatctgg aagcagtttg     840
aagatgcgct gcagaaattc tttgctctgc acctgctgct ggcgctgctg ttactgctgg     900
cgctgttact gttcctgctg gcgtttaagg gcggtagcgg cggtggcagc ggtggcgaat     960
ttctgctgca cctggctctg ctggcgctgc tgctgctggc cctgctgctg ttcctgctgg    1020
ctttctggga ggcactgaac caatttgaag acctggctaa acaagcaccg gtggatccgc    1080
caccatggaa atctggaaac aattcgagga cgcactgcaa aagttcttcg ccctgcacct    1140
gctgctggca ctgctgctgc tgctggctct gctgctgttc ctgctggctt ttgagggcgg    1200
tagcggcggt ggcagcggtg gcaagttcct gctgtgcctg gcgctgctgg ccctgttact    1260
gctggccctg ttactgttcc tgctggcctt ttgggaggct ctgaaccagt tcgaagacct    1320
ggctaagcag ggtggcagcg gtggcggtag cggcggtgag atctggaagc agtttgaaga    1380
tgcgctgcag aaattctttg ctctgcacct gctgctggcg ctgctgttac tgctggcgct    1440
gttactgttc ctgctggcgt ttaagggcgg tagcggcggt ggcagcggtg gcgaatttct    1500
gctgcacctg gctctgctgg cgctgctgct gctggccctg ctgctgttcc tgctggcttt    1560
ctgggaggca ctgaaccaat ttgaagacct ggctaaacaa gcaccggt                 1608
```

<210> SEQ ID NO 69
<211> LENGTH: 170
<212> TYPE: PRT
<213> ORGANISM: Artificial Sequence
<220> FEATURE:
<223> OTHER INFORMATION: Synthetic Sequence AM-528

<400> SEQUENCE: 69

Glu Ile Trp Lys Gln Phe Glu Asp Ala Leu Gln Lys Phe Phe Ala Leu

```
1               5                   10                  15
His Leu Leu Leu Ala Leu Leu Leu Leu Ala Leu Leu Leu Phe Leu
            20                  25                  30
Leu Ala Phe Glu Gly Gly Ser Gly Gly Gly Gly Lys Phe Leu
            35                  40                  45
Leu Cys Leu Ala Leu Leu Ala Leu Leu Leu Ala Leu Leu Leu Phe
    50                  55                  60
Leu Leu Ala Phe Trp Glu Ala Leu Asn Gln Phe Glu Asp Leu Ala Lys
65                  70                  75                  80
Gln Gly Gly Ser Gly Gly Gly Ser Gly Gly Glu Ile Trp Lys Gln Phe
                85                  90                  95
Glu Asp Ala Leu Gln Lys Phe Phe Ala Leu His Leu Leu Ala Leu
            100                 105                 110
Leu Leu Leu Leu Ala Leu Leu Leu Phe Leu Leu Ala Phe Lys Gly Gly
            115                 120                 125
Ser Gly Gly Gly Gly Glu Phe Leu Leu His Leu Ala Leu Ala
    130                 135                 140
Leu Leu Leu Leu Ala Leu Leu Leu Phe Leu Leu Ala Phe Trp Glu Ala
145                 150                 155                 160
Leu Asn Gln Phe Glu Asp Leu Ala Lys Gln
                165                 170
```

<210> SEQ ID NO 70
<211> LENGTH: 887
<212> TYPE: DNA
<213> ORGANISM: Artificial Sequence
<220> FEATURE:
<223> OTHER INFORMATION: Synthetic Sequence GLSloop (E. Coli)

<400> SEQUENCE: 70

```
ggtaagttcc ctctagatat tttgtttaac ttttaggagg taaaacatat gggtaaaggc     60
ggtcaccatc atcaccacca cggcggcgac ggcgagaatt tgtattttca gggtgaaatt    120
tggaagcaac atgaggatgc actgcagaag tttgaagaag cgctgaacca attcgaggat    180
ctgaagcagt ggtggttc cggtaaaggc tctggtggtg aaatcaaaca acgtcatgag    240
gacgccctgc gcaaattcga gaggcgttg aaacgttttg aggacctgaa gcaaaaaggt    300
ggcagcggtg agatctggaa acagcacgag gatgctctgc agaaatttga agaggcactg    360
aaccagttcg aggacctgaa acaactgggc ggtagcggca agggcagcgg tggtgagatt    420
aagcagcgtc acgaggacgc gctgcgtaag ttcgaagaag ccctgaaacg cttcgaagat    480
cgtgtacaaa agtaactcga gccccctagc ataaccccct ggggcctcta acgggtctt    540
gaggggtttt tgccccctga cgcgtcaa tcgagttcgt acctaaggc gacacccat    600
aattagcccg ggcgaaaggc ccagtctttc gactgagcct ttcgttttat ttgatgcctg    660
gcagttccct actctcgcat ggggagtccc cacactacca tcggcgctac ggcgtttcac    720
ttctgagttc ggcatggggt caggtgggac caccgcgcta ctgccgccag gcaaacaagg    780
gtgttatgag ccatattcag gtataaatgg gctcgcgata atgttcagaa ttggttaatt    840
ggttgtaaca ctgaccccta tttgttattt ttctaataca ttcaaat              887
```

<210> SEQ ID NO 71
<211> LENGTH: 10358
<212> TYPE: DNA
<213> ORGANISM: Artificial Sequence
<220> FEATURE:
<223> OTHER INFORMATION: Synthetic Sequence GLSloop (FCK mam)

<400> SEQUENCE: 71

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt gcgctgcttc gcgatgtacg ggccagatat acgcgttgac   240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg cccctattg acgtcaatga cggtaaatgg cccgcctggc   540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc  1020
gcccgaacag ggacttgaaa gcgaaaggga accagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctgggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
```

```
tcgtttcaga cccacctccc aacccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggaggt aggaagagcg atgatcactt gtggactaag    3540
tttgttcaca tccccttctc caacccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg ccccctagtt ctgggggcag cggggggatcc   3900
gccaccatgg gtgaaatttg gaagcaacat gaggatgcac tgcagaagtt tgaagaagcg    3960
ctgaaccaat tcgaggatct gaagcagctg ggtggttccg gtaaaggctc tggtggtgaa    4020
atcaaacaac gtcatgagga cgccctgcgc aaattcgaag aggcgttgaa acgttttgag    4080
gacctgaagc aaaaaggtgg cagcggtgag atctggaaac agcacgagga tgctctgcag    4140
aaatttgaag aggcactgaa ccagttcgag gacctgaaac aactgggcgg tagcggcaag    4200
ggcagcggtg gtgagattaa gcagcgtcac gaggacgcgc tgcgtaagtt cgaagaagcc    4260
ctgaaacgct tcgaagatcg tgtacaaaag gcggcaccgg tagtagcagt gagcaagggc    4320
gaggagctgt tcaccggggt ggtgcccatc ctggtcgagc tggacggcga cgtaaacggc    4380
cacaagttca gcgtgtccgg cgagggcgag ggcgatgcca cctacggcaa gctgaccctg    4440
aagttcattt gcaccaccgg caagctgccc gtgccctggc ccaccctcgt gaccaccctg    4500
acctacggcg tgcagtgctt cagccgctac cccgaccaca tgaagcagca cgacttcttc    4560
aagtccgcca tgcccgaagg ctacgtccag gagcgcacca tcttcttcaa ggacgacggc    4620
aactacaaga cccgcgccga ggtgaagttc gagggcgaca ccctggtgaa ccgcatcgag    4680
```

```
ctgaagggca tcgacttcaa ggaggacggc aacatcctgg ggcacaagct ggagtacaac   4740
tacaacagcc acaacgtcta tatcatggcc gacaagcaga agaacggcat caaggtgaac   4800
ttcaagatcc gccacaacat cgaggacggc agcgtgcagc tcgccgacca ctaccagcag   4860
aacacccca tcggcgacgg ccccgtgctg ctgcccgaca accactacct gagcacccag   4920
tccgccctga gcaaagaccc caacgagaag cgcgatcaca tggtcctgct ggagttcgtg   4980
accgccgccg ggatcactct cggcatggac gagctgtaca agtaagaatt cgatatcaag   5040
cttatcgata atcaacctct ggattacaaa atttgtgaaa gattgactgg tattcttaac   5100
tatgttgctc cttttacgct atgtggatac gctgctttaa tgcctttgta tcatgctatt   5160
gcttcccgta tggctttcat tttctcctcc ttgtataaat cctggttgct gtctctttat   5220
gaggagttgt ggcccgttgt caggcaacgt ggcgtggtgt gcactgtgtt tgctgacgca   5280
acccccactg gttggggcat tgccaccacc tgtcagctcc tttccgggac tttcgctttc   5340
cccctcccta ttgccacggc ggaactcatc gccgcctgcc ttgcccgctg ctggacaggg   5400
gctcggctgt tgggcactga caattccgtg gtgttgtcgg ggaaatcatc gtcctttcct   5460
tggctgctcg cctgtgttgc cacctggatt ctgcgcggga cgtccttctg ctacgtccct   5520
tcggccctca atccagcgga ccttccttcc cgcggcctgc tgccggctct gcggcctctt   5580
ccgcgtcttc gccttcgccc tcagacgagt cggatctccc tttgggccgc ctccccgcat   5640
cgataccgtc gacctcgaga cctagaaaaa catggagcaa tcacaagtag caatacagca   5700
gctaccaatg ctgattgtgc ctggctagaa gcacaagagg aggaggaggt gggttttcca   5760
gtcacacctc aggtaccttt aagaccaatg acttacaagg cagctgtaga tcttagccac   5820
ttttaaaag aaaaggggg actgaagggg ctaattcact cccaacgaag acaagatatc   5880
cttgatctgt ggatctacca cacacaaggc tacttccctg attggcagaa ctacacacca   5940
gggccaggga tcagatatcc actgacctt ggatggtgct acaagctagt accagttgag   6000
caagagaagg tagaagaagc caatgaagga gagaacaccc gcttgttaca ccctgtgagc   6060
ctgcatggga tggatgaccc ggagagagaa gtattagagt ggaggtttga cagccgccta   6120
gcatttcatc acatggcccg agagctgcat ccggactgta ctgggtctct ctggttagac   6180
cagatctgag cctgggagct ctctggctaa ctagggaacc cactgcttaa gcctcaataa   6240
agcttgcctt gagtgcttca agtagtgtgt gcccgtctgt tgtgtgactc tggtaactag   6300
agatccctca gacccttta gtcagtgtgg aaaatctcta gcagggcccg tttaaacccg   6360
ctgatcagcc tcgactgtgc cttctagttg ccagccatct gttgtttgcc cctcccccgt   6420
gccttccttg accctggaag gtgccactcc cactgtcctt tcctaataaa atgaggaaat   6480
tgcatcgcat tgtctgagta ggtgtcattc tattctgggg ggtggggtgg ggcaggacag   6540
caagggggag gattgggaag acaatagcag gcatgctggg gatgcggtgg gctctatggc   6600
ttctgaggcg gaaagaacca gctggggctc taggggtat ccccacgcgc cctgtagcgg   6660
cgcattaagc gcggcgggtg tggtggttac gcgcagcgtg accgctacac ttgccagcgc   6720
cctagcgccc gctcctttcg ctttcttccc ttcctttctc gccacgttcg ccggctttcc   6780
ccgtcaagct ctaaatcggg ggctcccttt agggttccga tttagtgctt tacggcacct   6840
cgaccccaaa aaacttgatt agggtgatgg ttcacgtagt gggccatcgc cctgatagac   6900
ggttttcgc cctttgacgt tggagtccac gttctttaat agtggactct tgttccaaac   6960
tggaacaaca ctcaacccta tctcggtcta ttcttttgat ttataaggga ttttgccgat   7020
```

```
ttcggcctat tggttaaaaa atgagctgat ttaacaaaaa tttaacgcga attaattctg    7080
tggaatgtgt gtcagttagg gtgtggaaag tccccaggct ccccagcagg cagaagtatg    7140
caaagcatgc atctcaatta gtcagcaacc aggtgtggaa agtccccagg ctccccagca    7200
ggcagaagta tgcaaagcat gcatctcaat tagtcagcaa ccatagtccc gcccctaact    7260
ccgcccatcc cgcccctaac tccgcccagt tccgcccatt ctccgcccca tggctgacta    7320
atttttttta tttatgcaga ggccgaggcc gcctctgcct ctgagctatt ccagaagtag    7380
tgaggaggct ttttttggagg cctaggcttt tgcaaaaagc tcccgggagc ttgtatatcc    7440
attttcggat ctgatcagca cgtgttgaca attaatcatc ggcatagtat atcggcatag    7500
tataatacga caaggtgagg aactaaacca tggccaagtt gaccagtgcc gttccggtgc    7560
tcaccgcgcg cgacgtcgcc ggagcggtcg agttctggac cgaccggctc gggttctccc    7620
gggacttcgt ggaggacgac ttcgccggtg tggtccggga cgacgtgacc ctgttcatca    7680
gcgcggtcca ggaccaggtg gtgccggaca cacccctggc ctgggtgtgg gtgcgcggcc    7740
tggacgagct gtacgccgag tggtcggagg tcgtgtccac gaacttccgg gacgcctccg    7800 gccggccat gaccgagatc ggcgagcagc gtgggggcg ggagttcgcc ctgcgcgacc    7860
cggccggcaa ctgcgtgcac ttcgtggccg aggagcagga ctgacacgtg ctacgagatt    7920
tcgattccac cgccgccttc tatgaaaggt tgggcttcgg aatcgttttc cgggacgccg    7980
gctggatgat cctccagcgc ggggatctca tgctggagtt cttcgcccac ccaaccttgt    8040
ttattgcagc ttataatggt tacaaataaa gcaatagcat cacaaatttc acaaataaag    8100 cattttttc actgcattct agttgtggtt tgtccaaact catcaatgta tcttatcatg    8160
tctgtatacc gtcgacctct agctagagct tggcgtaatc atggtcatag ctgtttcctg    8220
tgtgaaattg ttatccgctc acaattccac acaacatacg agccggaagc ataaagtgta    8280
aagcctgggg tgcctaatga gtgagctaac tcacattaat tgcgttgcgc tcactgcccg    8340
ctttccagtc gggaaacctg tcgtgccagc tgcattaatg aatcggccaa cgcgcgggga    8400
gaggcggttt gcgtattggg cgctcttccg cttcctcgct cactgactcg ctgcgctcgg    8460
tcgttcggct gcggcgagcg gtatcagctc actcaaaggc ggtaatacgg ttatccacag    8520
aatcagggga taacgcagga aagaacatgt gagcaaaagg ccagcaaaag gccaggaacc    8580
gtaaaaaggc cgcgttgctg gcgtttttcc ataggctccg ccccctgac gagcatcaca    8640 aaaatcgacg ctcaagtcag aggtggcgaa acccgacagg actataaaga taccaggcgt    8700
ttccccctgg aagctccctc gtgcgctctc ctgttccgac cctgccgctt accggatacc    8760
tgtccgcctt tctcccttcg ggaagcgtgg cgctttctca tagctcacgc tgtaggtatc    8820
tcagttcggt gtaggtcgtt cgctccaagc tgggctgtgt gcacgaaccc cccgttcagc    8880
ccgaccgctg cgccttatcc ggtaactatc gtcttgagtc aacccggta agacacgact    8940 tatcgccact ggcagcagcc actggtaaca ggattagcag agcgaggtat gtaggcggtg    9000
ctacagagtt cttgaagtgg tggcctaact acggctacac tagaagaaca gtatttggta    9060
tctgcgctct gctgaagcca gttaccttcg gaaaagagt tggtagctct tgatccggca    9120
aacaaaccac cgctggtagc ggtggttttt tgtttgcaa gcagcagatt acgcgcagaa    9180 aaaaggatc tcaagaagat cctttgatct tttctacggg gtctgacgct cagtggaacg    9240
aaaactcacg ttaagggatt ttggtcatga gattatcaaa aaggatcttc acctagatcc    9300
ttttaaatta aaaatgaagt tttaaatcaa tctaaagtat atatgagtaa acttggtctg    9360
acagttacca atgcttaatc agtgaggcac ctatctcagc gatctgtcta tttcgttcat    9420
```

```
ccatagttgc ctgactcccc gtcgtgtaga taactacgat acgggagggc ttaccatctg    9480
gccccagtgc tgcaatgata ccgcgagacc cacgctcacc ggctccagat ttatcagcaa    9540
taaaccagcc agccggaagg gccgagcgca gaagtggtcc tgcaacttta tccgcctcca    9600
tccagtctat taattgttgc cgggaagcta gagtaagtag ttcgccagtt aatagtttgc    9660
gcaacgttgt tgccattgct acaggcatcg tggtgtcacg ctcgtcgttt ggtatggctt    9720
cattcagctc cggttcccaa cgatcaaggc gagttacatg atcccccatg ttgtgcaaaa    9780
aagcggttag ctccttcggt cctccgatcg ttgtcagaag taagttggcc gcagtgttat    9840
cactcatggt tatggcagca ctgcataatt ctcttactgt catgccatcc gtaagatgct    9900
tttctgtgac tggtgagtac tcaaccaagt cattctgaga atagtgtatg cggcgaccga    9960
gttgctcttg cccggcgtca atacgggata atccgcgcc acatagcaga actttaaaag    10020
tgctcatcat tggaaaacgt tcttcggggc gaaaactctc aaggatctta ccgctgttga    10080
gatccagttc gatgtaaccc actcgtgcac ccaactgatc ttcagcatct tttactttca    10140
ccagcgtttc tgggtgagca aaaacaggaa ggcaaaatgc cgcaaaaaag ggaataaggg    10200
cgacacggaa atgttgaata ctcatactct cctttttca atattattga agcatttatc    10260
agggttattg tctcatgagc ggatacatat ttgaatgtat ttagaaaaat aaacaaatag    10320
gggttccgcg cacatttccc cgaaaagtgc cacctgac                            10358
```

```
<210> SEQ ID NO 72
<211> LENGTH: 126
<212> TYPE: PRT
<213> ORGANISM: Artificial Sequence
<220> FEATURE:
<223> OTHER INFORMATION: Synthetic Sequence GLSloop

<400> SEQUENCE: 72
```

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Leu Lys Gln Lys
        115                 120                 125

```
<210> SEQ ID NO 73
<211> LENGTH: 126
<212> TYPE: PRT
<213> ORGANISM: Artificial Sequence
<220> FEATURE:
<223> OTHER INFORMATION: Synthetic Sequence PEB Mut B

<400> SEQUENCE: 73
```

Glu Ile Trp Lys Ser His Glu Asp Ala Leu Gln Lys Phe Glu Glu Ala
1               5                   10                  15

```
Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Ala Cys
    50                  55                  60

Gly Arg Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Arg Val Gln Lys
        115                 120                 125
```

<210> SEQ ID NO 74
<211> LENGTH: 126
<212> TYPE: PRT
<213> ORGANISM: Artificial Sequence
<220> FEATURE:
<223> OTHER INFORMATION: Synthetic Sequence PEB Mut C

<400> SEQUENCE: 74

```
Glu Ile Trp Lys Leu His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Glu His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Arg Val Gln Lys
        115                 120                 125
```

<210> SEQ ID NO 75
<211> LENGTH: 126
<212> TYPE: PRT
<213> ORGANISM: Artificial Sequence
<220> FEATURE:
<223> OTHER INFORMATION: Synthetic Sequence PEB Mut D

<400> SEQUENCE: 75

```
Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Gln His Glu Asp Ala Leu Gln Lys Phe Glu Glu
```

```
              65                  70                  75                  80
Ala Leu Asn Gln Phe Glu Asp Leu Lys Gln Leu Gly Gly Ser Gly Lys
                    85                  90                  95

Gly Ser Gly Gly Glu Ile Lys Gln Arg His Glu Asp Ala Leu Arg Lys
                100                 105                 110

Phe Glu Glu Ala Leu Lys Arg Phe Glu Asp Arg Val Gln Lys
                115                 120                 125
```

<210> SEQ ID NO 76
<211> LENGTH: 126
<212> TYPE: PRT
<213> ORGANISM: Artificial Sequence
<220> FEATURE:
<223> OTHER INFORMATION: Synthetic Sequence PEB Mut E

<400> SEQUENCE: 76

```
Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
                20                  25                  30

Ser Gly Gly Glu Ile Lys Gln Arg His Glu Asp Ala Leu Arg Lys Phe
            35                  40                  45

Glu Glu Ala Leu Lys Arg Phe Glu Asp Leu Lys Gln Lys Gly Gly Cys
        50                  55                  60

Gly Arg Asp Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
                100                 105                 110

Phe Glu Glu Ala Leu Lys Arg Phe Glu Asp Leu Lys Gln Lys
                115                 120                 125
```

<210> SEQ ID NO 77
<211> LENGTH: 116
<212> TYPE: PRT
<213> ORGANISM: Artificial Sequence
<220> FEATURE:
<223> OTHER INFORMATION: Synthetic Sequence PEB Mut F

<400> SEQUENCE: 77

```
Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Cys Gly Glu Ile
                20                  25                  30

Lys Gln Arg Ala Glu Asp Ala Leu Arg Lys Phe Glu Glu Ala Leu Lys
            35                  40                  45

Arg Phe Glu Asp Leu Lys Gln Lys Gly Gly Cys Gly Glu Ile Trp Lys
        50                  55                  60

Gln His Glu Asp Ala Leu Gln Lys Phe Glu Glu Ala Leu Asn Gln Phe
65                  70                  75                  80

Glu Asp Leu Lys Gln Leu Gly Gly Ser Gly Glu Ile Lys Gln Arg His
                85                  90                  95

Glu Asp Ala Leu Arg Lys Phe Glu Glu Ala Leu Lys Arg Phe Glu Asp
                100                 105                 110

Leu Lys Gln Lys
            115
```

<210> SEQ ID NO 78
<211> LENGTH: 126
<212> TYPE: PRT
<213> ORGANISM: Artificial Sequence
<220> FEATURE:
<223> OTHER INFORMATION: Synthetic Sequence PEB Mut G

<400> SEQUENCE: 78

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Glu Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Leu Lys Gln Lys
        115                 120                 125

<210> SEQ ID NO 79
<211> LENGTH: 131
<212> TYPE: PRT
<213> ORGANISM: Artificial Sequence
<220> FEATURE:
<223> OTHER INFORMATION: Synthetic Sequence Protein No. 35

<400> SEQUENCE: 79

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Cys Leu Arg Asp His Glu Asp Ala Leu Gln Lys Phe
        35                  40                  45

Glu Glu Ala Leu Asn Gln Phe Glu Asp Leu Lys Gln Leu Gly Gly Ser
    50                  55                  60

Gly Ser Gly Ser Gly Gly Glu Ile Trp Lys Gln His Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
            100                 105                 110

Asp Ala Leu Gln Lys Phe Glu Glu Ala Leu Asn Gln Phe Glu Asp Leu
        115                 120                 125

Lys Gln Leu
    130

<210> SEQ ID NO 80
<211> LENGTH: 131
<212> TYPE: PRT
<213> ORGANISM: Artificial Sequence
<220> FEATURE:
<223> OTHER INFORMATION: Synthetic Sequence Protein No. 36

-continued

```
<400> SEQUENCE: 80

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Cys Leu Arg Asp Glu Asp Ala Leu Gln Lys Phe
        35                  40                  45

Glu Glu Ala Leu Asn Gln Phe Glu Asp Leu Lys Gln Leu Gly Gly Ser
50                  55                  60

Gly Ser Gly Ser Gly Gly Glu Ile Trp Lys Gln His Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
            100                 105                 110

Asp Ala Leu Gln Lys Phe Glu Glu Ala Leu Asn Gln Phe Glu Asp Leu
        115                 120                 125

Lys Gln Leu
    130

<210> SEQ ID NO 81
<211> LENGTH: 131
<212> TYPE: PRT
<213> ORGANISM: Artificial Sequence
<220> FEATURE:
<223> OTHER INFORMATION: Synthetic Sequence Artificial Protein No. 37

<400> SEQUENCE: 81

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Trp Lys Gln His Glu Asp Ala Leu Gln Lys Phe
        35                  40                  45

Glu Glu Ala Leu Asn Gln Phe Glu Asp Cys Leu Arg Asp Gly Gly Ser
50                  55                  60

Gly Ser Gly Ser Gly Gly Glu Ile Trp Lys Gln His Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
            100                 105                 110

Asp Ala Leu Gln Lys Phe Glu Glu Ala Leu Asn Gln Phe Glu Asp Leu
        115                 120                 125

Lys Gln Leu
    130

<210> SEQ ID NO 82
<211> LENGTH: 131
<212> TYPE: PRT
<213> ORGANISM: Artificial Sequence
<220> FEATURE:
<223> OTHER INFORMATION: Synthetic Sequence Protein No. 38

<400> SEQUENCE: 82

Glu Ile Trp Lys Gln His Glu Asp Ala Leu Gln Lys Phe Glu Glu Ala
1               5                   10                  15
```

```
Leu Asn Gln Phe Glu Asp Leu Lys Gln Leu Gly Gly Ser Gly Ser Gly
            20                  25                  30

Ser Gly Gly Glu Ile Trp Lys Gln His Glu Asp Ala Leu Gln Lys Phe
        35                  40                  45

Glu Glu Ala Leu Asn Gln Phe Glu Asp Leu Cys Leu Arg Asp Gly Ser
    50                  55                  60

Gly Ser Gly Ser Gly Gly Glu Ile Trp Lys Gln His Glu Asp Ala Leu
 65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
            100                 105                 110

Asp Ala Leu Gln Lys Phe Glu Glu Ala Leu Asn Gln Phe Glu Asp Leu
            115                 120                 125

Lys Gln Leu
    130
```

<210> SEQ ID NO 83
<211> LENGTH: 131
<212> TYPE: PRT
<213> ORGANISM: Artificial Sequence
<220> FEATURE:
<223> OTHER INFORMATION: Synthetic Sequence Protein No. 39

<400> SEQUENCE: 83

```
Glu Ile Trp Lys Gln His Glu Asp Ala Leu Gln Lys Phe Glu Glu Ala
  1               5                  10                  15

Leu Asn Gln Phe Glu Asp Leu Lys Gln Leu Gly Gly Ser Gly Ser Gly
            20                  25                  30

Ser Gly Gly Glu Ile Trp Lys Gln His Glu Asp Ala Leu Gln Lys Phe
        35                  40                  45

Glu Glu Ala Leu Asn Gln Phe Glu Asp Leu Lys Cys Leu Arg Asp Ser
    50                  55                  60

Gly Ser Gly Ser Gly Gly Glu Ile Trp Lys Gln His Glu Asp Ala Leu
 65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
            100                 105                 110

Asp Ala Leu Gln Lys Phe Glu Glu Ala Leu Asn Gln Phe Glu Asp Leu
            115                 120                 125

Lys Gln Leu
    130
```

<210> SEQ ID NO 84
<211> LENGTH: 131
<212> TYPE: PRT
<213> ORGANISM: Artificial Sequence
<220> FEATURE:
<223> OTHER INFORMATION: Synthetic Sequence Protein No. 61

<400> SEQUENCE: 84

```
Glu Ile Trp Lys Gln Phe Glu Asp Ala Leu Gln Lys Phe Glu Glu Ala
  1               5                  10                  15

Leu Asn Gln Phe Glu Asp Leu Lys Gln Leu Gly Gly Ser Gly Ser Gly
            20                  25                  30

Ser Gly Gly Glu Ile Trp Lys Gln Cys Glu Asp Ala Leu Gln Lys Phe
        35                  40                  45
```

```
Glu Ala Leu Asn Gln Phe Glu Asp Leu Lys Gln Leu Gly Gly Ser
        50                  55                  60

Gly Ser Gly Ser Gly Gly Glu Ile Trp Lys Gln Phe Glu Asp Ala Leu
 65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Glu Ile Trp Lys Gln His Glu
            100                 105                 110

Asp Ala Leu Gln Lys Phe Glu Glu Ala Leu Asn Gln Phe Glu Asp Leu
        115                 120                 125

Lys Gln Leu
        130

<210> SEQ ID NO 85
<211> LENGTH: 129
<212> TYPE: PRT
<213> ORGANISM: Artificial Sequence
<220> FEATURE:
<223> OTHER INFORMATION: Synthetic Sequence Protein No. 214

<400> SEQUENCE: 85

Glu Ile Trp Lys Gln His Glu Asp Ala Leu Gln Lys Phe Glu Glu Ala
 1               5                  10                  15

Leu Asn Gln Phe Glu Asp Leu Lys Gln Leu Gly Gly Ser Gly Ser Gly
                20                  25                  30

Ser Gly Gly Glu Ile Trp Lys Gln Cys Glu Asp Ala Leu Gln Lys Phe
            35                  40                  45

Glu Glu Ala Leu Asn Gln Phe Glu Asp Leu Lys Gln Leu Gly Gly Ser
        50                  55                  60

Gly Ser Gly Ser Gly Gly Glu Ile Trp Lys Gln Phe Glu Asp Ala Leu
 65                  70                  75                  80

Gln Lys Phe Glu Glu Ala Leu Asn Gln Phe Glu Asp Ala Leu Gln Leu
                85                  90                  95

Gly Gly Ser Gly Ser Gly Ser Gly Glu Ile Trp Lys Gln Gly Glu Asp
            100                 105                 110

Ala Leu Gln Lys Phe Glu Glu Ala Leu Asn Gln Phe Glu Asp Leu Lys
        115                 120                 125

Gln

<210> SEQ ID NO 86
<211> LENGTH: 130
<212> TYPE: PRT
<213> ORGANISM: Artificial Sequence
<220> FEATURE:
<223> OTHER INFORMATION: Synthetic Sequence Protein No. 215

<400> SEQUENCE: 86

Glu Ile Trp Lys Gln Phe Glu Asp Ala Leu Gln Lys Phe Glu Glu Ala
 1               5                  10                  15

Leu Asn Gln Phe Glu Asp Leu Lys Gln Leu Gly Gly Ser Gly Ser Gly
                20                  25                  30

Ser Gly Gly Glu Ile Trp Lys Gln Cys Glu Asp Ala Leu Gln Lys Phe
            35                  40                  45

Glu Glu Ala Leu Asn Gln Phe Glu Asp Leu Lys Gln Leu Gly Gly Ser
        50                  55                  60

Gly Ser Gly Ser Gly Gly Glu Ile Trp Lys Gln Phe Glu Asp Ala Leu
 65                  70                  75                  80
```

```
Gln Lys Phe Glu Glu Ala Leu Asn Gln Phe Glu Asp Ala Leu Gln Leu
                85                  90                  95

Gly Gly Ser Gly Ser Gly Ser Gly Glu Ile Trp Lys Gln Gly Glu Asp
            100                 105                 110

Ala Leu Gln Lys Phe Glu Glu His Leu Asn Gln Phe Glu Asp Leu Lys
        115                 120                 125

Gln Leu
    130

<210> SEQ ID NO 87
<211> LENGTH: 144
<212> TYPE: PRT
<213> ORGANISM: Artificial Sequence
<220> FEATURE:
<223> OTHER INFORMATION: Synthetic Sequence Protein No. 216

<400> SEQUENCE: 87

Glu Ile Trp Lys Gln Phe Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Trp Lys Gln Cys Glu Asp Ala Leu Gln Lys Phe
        35                  40                  45

Glu Glu Ala Leu Asn Gln Phe Glu Asp Leu Lys Gln Leu Gly Gly Ser
50                  55                  60

Gly Ser Gly Ser Gly Gly Glu Ile Trp Lys Gln Phe Glu Asp Ala Leu
65                  70                  75                  80

Gln Lys His Glu Glu Ala Leu Asn Gln Phe Glu Asp Ala Leu Gln Lys
                85                  90                  95

His Glu Glu Ala Leu Asn Gln Phe Glu Asp Leu Lys Gln Leu Gly Gly
            100                 105                 110

Ser Gly Ser Gly Ser Gly Glu Ile Trp Lys Gln Gly Glu Asp Ala Leu
        115                 120                 125

Gln Lys Phe Glu Glu Ala Leu Asn Gln Phe Glu Asp Leu Lys Gln Leu
    130                 135                 140

<210> SEQ ID NO 88
<211> LENGTH: 131
<212> TYPE: PRT
<213> ORGANISM: Artificial Sequence
<220> FEATURE:
<223> OTHER INFORMATION: Synthetic Sequence Protein No. 528

<400> SEQUENCE: 88

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Trp Lys Gln Cys Glu Asp Ala Leu Gln Lys Phe
        35                  40                  45

Glu Glu Ala Leu Asn Gln Phe Glu Asp Leu Lys Gln Leu Gly Gly Ser
50                  55                  60

Gly Ser Gly Ser Gly Gly Glu Ile Trp Lys Gln His Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln His Glu
```

```
                       100                 105                 110
Asp Ala Leu Gln Lys Phe Glu Glu Ala Leu Asn Gln Phe Glu Asp Leu
        115                 120                 125

Lys Gln Leu
       130
```

<210> SEQ ID NO 89
<211> LENGTH: 6122
<212> TYPE: DNA
<213> ORGANISM: Artificial Sequence
<220> FEATURE:
<223> OTHER INFORMATION: Synthetic Sequence C-His Stab CGRD (E. Coli)

<400> SEQUENCE: 89

| | | | | | |
|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccgtactgcc | gggcctctt | 180 |
| gcgggatatc | cggatatagt | tcctcctttc | agcaaaaaac | ccctcaagac | ccgtttagag | 240 |
| gccccaaggg | gttatgctag | ttattgctca | gcggtggcag | cagccaactc | agcttccttt | 300 |
| cgggctttgt | tagcagccgg | atcctcgaga | ccggttcact | tttgcacacg | atcttcgtgg | 360 |
| cgcttcagcg | cttcctcaaa | tttgcgcagc | gcatcctcat | ggcgctgttt | aatctcgcca | 420 |
| ccgctgccct | tgccgctgcc | acccagttgt | ttcagatctt | caaattgatt | cagcgcttcc | 480 |
| tcaaactttt | ggtgcgcgtc | ttcgtgctcc | ttccaatcac | gaccgcagcc | acctttctgc | 540 |
| ttcagatcct | caaaacgttt | cagcgcttcc | tcgaacttac | gcagcgcgtc | ttcgtgacgt | 600 |
| tgcttgatct | cgccaccgct | gcctttaccg | ctgccaccca | gttgcttcag | atcctcaaac | 660 |
| tggttcagcc | cttcctcgaa | tttctgcagc | gcgtcttcgt | ggctcttcca | gatctcgccg | 720 |
| gatccctgaa | aatacaggtt | ttcaccatcg | cctccgtggt | gatgatggtg | atgcccacct | 780 |
| ttacccatat | gaatatcgcc | ttccatggta | tatctccttc | ttaaagttaa | acaaaattat | 840 |
| ttctagaggg | gaattgttat | ccgctcacaa | ttcccctata | gtgagtcgta | ttaatttcgc | 900 |
| gggatcgaga | tctcgatcct | ctacgccgga | cgcatcgtgg | ccggcatcac | cggcgccaca | 960 |
| ggtgcggttg | ctggcgccta | tcgccgacat | caccgatggg | gaagatcg | ggctcgccac | 1020 |
| ttcgggctca | tgagcgcttg | tttcggcgtg | ggtatggtgg | caggccccgt | ggccggggga | 1080 |
| ctgttgggcg | ccatctcctt | gcatgcacca | ttccttgcgg | cggcggtgct | caacggcctc | 1140 |
| aacctactac | tgggctgctt | cctaatgcag | gagtcgcata | agggagagcg | tcgagatccc | 1200 |
| ggacaccatc | gaatggcgca | aaacctttcg | cggtatggca | tgatagcgcc | cggaagagag | 1260 |
| tcaattcagg | gtggtgaatg | tgaaaccagt | aacgttatac | gatgtcgcag | agtatgccgg | 1320 |
| tgtctcttat | cagaccgttt | cccgcgtggt | gaaccaggcc | agccacgttt | ctgcgaaaac | 1380 |
| gcgggaaaaa | gtggaagcgg | cgatggcgga | gctgaattac | attcccaacc | gcgtggcaca | 1440 |
| acaactggcg | ggcaaacagt | cgttgctgat | tggcgttgcc | acctccagtc | tggccctgca | 1500 |
| cgcgccgtcg | caaattgtcg | cggcgattaa | atctcgcgcc | gatcaactgg | gtgccagcgt | 1560 |
| ggtggtgtcg | atggtagaac | gaagcggcgt | cgaagcctgt | aaagcggcgg | tgcacaatct | 1620 |
| tctcgcgcaa | cgcgtcagtg | ggctgatcat | taactatccg | ctggatgacc | aggatgccat | 1680 |
| tgctgtggaa | gctgcctgca | ctaatgttcc | ggcgttattt | cttgatgtct | ctgaccagac | 1740 |
| acccatcaac | agtattattt | tctcccatga | agacggtacg | cgactgggcg | tggagcatct | 1800 |
| ggtcgcattg | ggtcaccagc | aaatcgcgct | gttagcgggc | ccattaagtt | ctgtctcggc | 1860 |

```
gcgtctgcgt ctggctggct ggcataaata tctcactcgc aatcaaattc agccgatagc    1920
ggaacgggaa ggcgactgga gtgccatgtc cggttttcaa caaaccatgc aaatgctgaa    1980
tgagggcatc gttcccactg cgatgctggt tgccaacgat cagatggcgc tgggcgcaat    2040
gcgcgccatt accgagtccg ggctgcgcgt tggtgcggat atctcggtag tgggatacga    2100
cgataccgaa gacagctcat gttatatccc gccgttaacc accatcaaac aggattttcg    2160
cctgctgggg caaaccagcg tggaccgctt gctgcaactc tctcagggcc aggcggtgaa    2220
gggcaatcag ctgttgcccg tctcactggt gaaaagaaaa accaccctgg cgcccaatac    2280
gcaaaccgcc tctccccgcg cgttggccga ttcattaatg cagctggcac gacaggtttc    2340
ccgactggaa agcgggcagt gagcgcaacg caattaatgt aagttagctc actcattagg    2400
caccgggatc tcgaccgatg cccttgagag ccttcaaccc agtcagctcc ttccggtggg    2460
cgcggggcat gactatcgtc gccgcactta tgactgtctt ctttatcatg caactcgtag    2520
gacaggtgcc ggcagcgctc tgggtcattt tcggcgagga ccgctttcgc tggagcgcga    2580
cgatgatcgg cctgtcgctt gcggtattcg gaatcttgca cgccctcgct caagccttcg    2640
tcactggtcc cgccaccaaa cgtttcggcg agaagcaggc cattatcgcc ggcatggcgg    2700
ccgacgcgct gggctacgtc ttgctggcgt tcgcgacgcg aggctggatg ccttcccca    2760 ttatgattct tctcgcttcc ggcggcatcg ggatgcccgc gttgcaggcc atgctgtcca    2820
ggcaggtaga tgacgaccat cagggacagc ttcaaggatc gctcgcggct cttaccagcc    2880
taacttcgat cactgaccg ctgatcgtca cggcgattta tgccgcctcg gcgagcacat    2940
ggaacgggtt ggcatggatt gtaggcgccg ccctatacct tgtctgcctc cccgcgttgc    3000
gtcgcggtgc atggagccgg gccacctcga cctgaatgga agccggcggc acctcgctaa    3060
cggattcacc actccaagaa ttggagccaa tcaattcttg cggagaactg tgaatgcgca    3120
aaccaaccct tggcagaaca tatccatcgc gtccgccatc tccagcagcc gcacgcggcg    3180
catctcgggc agcgttgggt cctggccacg ggtgcgcatg atcgtgctcc tgtcgttgag    3240
gacccggcta ggctggcggg gttgccttac tggttagcag aatgaatcac cgatacgcga    3300
gcgaacgtga agcgactgct gctgcaaaac gtctgcgacc tgagcaacaa catgaatggt    3360
cttcggtttc cgtgtttcgt aaagtctgga aacgcggaag tcagcgccct gcaccattat    3420
gttccggatc tgcatcgcag gatgctgctg gctaccctgt ggaacaccta catctgtatt    3480
aacgaagcgc tggcattgac cctgagtgat ttttctctgg tcccgccgca tccataccgc    3540
cagttgttta ccctcacaac gttccagtaa ccgggcatgt tcatcatcag taacccgtat    3600
cgtgagcatc ctctctcgtt tcatcggtat cattacccccc atgaacagaa atccccctta    3660 cacgaggca tcagtgacca aacaggaaaa accgcccctt aacatggccc gctttatcag    3720
aagccagaca ttaacgcttc tggagaaact caacgagctg gacgcggatg aacaggcaga    3780
catctgtgaa tcgcttcacg accacgctga tgagctttac cgcagctgcc tcgcgcgttt    3840
cggtgatgac ggtgaaaacc tctgacacat gcagctcccg gagacggtca cagcttgtct    3900
gtaagcggat gccgggagca gacaagcccg tcagggcgcg tcagcgggtg ttggcgggtg    3960
tcggggcgca gccatgaccc agtcacgtag cgatagcgga gtgtatactg gcttaactat    4020
gcggcatcag agcagattgt actgagagtg caccatatat gcggtgtgaa ataccgcaca    4080
gatgcgtaag gagaaaatac cgcatcaggc gctcttccgc ttcctcgctc actgactcgc    4140
tgcgctcggt cgttcggctg cggcgagcgg tatcagctca ctcaaaggcg gtaatacggt    4200
```

| | | | | |
|---|---|---|---|---|
| tatccacaga | atcaggggat | aacgcaggaa | agaacatgtg | agcaaaaggc cagcaaaagg | 4260 |
| ccaggaaccg | taaaaaggcc | gcgttgctgg | cgttttttcca | taggctccgc cccctgacg | 4320 |
| agcatcacaa | aaatcgacgc | tcaagtcaga | ggtggcgaaa | cccgacagga ctataaagat | 4380 |
| accaggcgtt | tccccctgga | agctccctcg | tgcgctctcc | tgttccgacc ctgccgctta | 4440 |
| ccggatacct | gtccgccttt | ctcccttcgg | gaagcgtggc | gctttctcat agctcacgct | 4500 |
| gtaggtatct | cagttcggtg | taggtcgttc | gctccaagct | gggctgtgtg cacgaacccc | 4560 |
| ccgttcagcc | cgaccgctgc | gccttatccg | gtaactatcg | tcttgagtcc aacccggtaa | 4620 |
| gacacgactt | atcgccactg | gcagcagcca | ctggtaacag | gattagcaga gcgaggtatg | 4680 |
| taggcggtgc | tacagagttc | ttgaagtggt | ggcctaacta | cggctacact agaaggacag | 4740 |
| tatttggtat | ctgcgctctg | ctgaagccag | ttaccttcgg | aaaagagttg gtagctcttg | 4800 |
| atccggcaa | acaaaccacc | gctggtagcg | gtggtttttt | tgtttgcaag cagcagatta | 4860 |
| cgcgcagaaa | aaaggatct | caagaagatc | ctttgatctt | ttctacgggg tctgacgctc | 4920 |
| agtggaacga | aaactcacgt | taagggattt | tggtcatgag | attatcaaaa aggatcttca | 4980 |
| cctagatcct | tttaaattaa | aaatgaagtt | ttaaatcaat | ctaaagtata tatgagtaaa | 5040 |
| cttggtctga | cagttaccaa | tgcttaatca | gtgaggcacc | tatctcagcg atctgtctat | 5100 |
| ttcgttcatc | catagttgcc | tgactccccg | tcgtgtagat | aactacgata cgggagggct | 5160 |
| taccatctgg | ccccagtgct | gcaatgatac | cgcgagaccc | acgctcaccg gctccagatt | 5220 |
| tatcagcaat | aaaccagcca | gccggaaggg | ccgagcgcag | aagtggtcct gcaactttat | 5280 |
| ccgcctccat | ccagtctatt | aattgttgcc | gggaagctag | agtaagtagt tcgccagtta | 5340 |
| atagtttgcg | caacgttgtt | gccattgctg | caggcatcgt | ggtgtcacgc tcgtcgtttg | 5400 |
| gtatggcttc | attcagctcc | ggttcccaac | gatcaaggcg | agttacatga tcccccatgt | 5460 |
| tgtgcaaaaa | agcggttagc | tccttcggtc | ctccgatcgt | tgtcagaagt aagttggccg | 5520 |
| cagtgttatc | actcatggtt | atggcagcac | tgcataattc | tcttactgtc atgccatccg | 5580 |
| taagatgctt | ttctgtgact | ggtgagtact | caaccaagtc | attctgagaa tagtgtatgc | 5640 |
| ggcgaccgag | ttgctcttgc | ccggcgtcaa | cacgggataa | taccgcgcca catagcagaa | 5700 |
| ctttaaaagt | gctcatcatt | ggaaaacgtt | cttcggggcg | aaaactctca aggatcttac | 5760 |
| cgctgttgag | atccagttcg | atgtaaccca | ctcgtgcacc | caactgatct tcagcatctt | 5820 |
| ttactttcac | cagcgtttct | gggtgagcaa | aaacaggaag | gcaaaatgcc gcaaaaaagg | 5880 |
| gaataagggc | gacacggaaa | tgttaatac | tcatactctt | cctttttcaa tattattgaa | 5940 |
| gcatttatca | gggttattgt | ctcatgagcg | gatacatatt | tgaatgtatt tagaaaaata | 6000 |
| aacaaatagg | ggttccgcgc | acatttcccc | gaaaagtgcc | acctgacgtc taagaaacca | 6060 |
| ttattatcat | gacattaacc | tataaaaata | ggcgtatcac | gaggccctttt cgtcttcaag | 6120 |
| aa | | | | | 6122 |

<210> SEQ ID NO 90
<211> LENGTH: 10347
<212> TYPE: DNA
<213> ORGANISM: Artificial Sequence
<220> FEATURE:
<223> OTHER INFORMATION: Synthetic Sequence C-His Stab CGRD (FCK mam)

<400> SEQUENCE: 90

| | | | | | |
|---|---|---|---|---|---|
| gtcgacggat | cgggagatct | cccgatcccc | tatggtgcac | tctcagtaca atctgctctg | 60 |
| atgccgcata | gttaagccag | tatctgctcc | ctgcttgtgt | gttggaggtc gctgagtagt | 120 |

```
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360 accccgccc attgacgtca ataatgacgt atgttcccat agtaacgcca atagggactt     420
tccattgacg tcaatgggtg gagtatttac ggtaaactgc ccacttggca gtacatcaag    480
tgtatcatat gccaagtacg cccctattg acgtcaatga cggtaaatgg cccgcctggc     540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggaatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggat    2460
```

-continued

| | |
|---|---|
| tgggggtac agtgcagggg aaagaatagt agacataata gcaacagaca tacaaactaa | 2520 |
| agaattacaa aaacaaatta caaaaattca aaattttcgg gtttattaca gggacagcag | 2580 |
| agatccagtt tggttaatta acattatggc cttaggtcac ttcatctcca tggggttctt | 2640 |
| cttctgattt tctagaaaat gagatggggg tgcagagagc ttcctcagtg acctgcccag | 2700 |
| ggtcacatca gaaatgtcag agctagaact tgaactcaga ttactaatct taaattccat | 2760 |
| gccttggggg catgcaagta cgatatacag aaggagtgaa ctcattaggg cagatgacca | 2820 |
| atgagtttag gaaagaagag tccagggcag ggtacatcta caccacccgc ccagccctgg | 2880 |
| gtgagtccag ccacgttcac ctcattatag ttgcctctct ccagtcctac cttgacggga | 2940 |
| agcacaagca gaaactggga caggagcccc aggagaccaa atcttcatgg tccctctggg | 3000 |
| aggatgggtg gggagagctg tggcagaggc ctcaggaggg gccctgctgc tcagtggtga | 3060 |
| cagataggg tgagaaagca gacagagtca ttccgtcagc attctgggtc tgtttggtac | 3120 |
| ttcttctcac gctaaggtgg cggtgtgata tgcacaatgg ctaaaaagca gggagagctg | 3180 |
| gaaagaaaca aggacagaga cagaggccaa gtcaaccaga ccaattccca gaggaagcaa | 3240 |
| agaaaccatt acagagacta caaggggaa gggaaggaga gatgaattag cttcccctgt | 3300 |
| aaaccttaga acccagctgt tgccaggca acggggcaat acctgtctct tcagaggaga | 3360 |
| tgaagttgcc agggtaacta catcctgtct ttctcaagga ccatcccaga atgtggcacc | 3420 |
| cactagccgt taccatagca actgcctctt tgccccactt aatcccatcc cgtctgttaa | 3480 |
| aagggcccta tagttggagg tggggaggt aggaagagcg atgatcactt gtggactaag | 3540 |
| tttgttcaca tccccttctc caaccccctc agtacatcac cctgggagaa caaggtccac | 3600 |
| ttgcttctgg gcccacacag tcctgcagta ttgtgtatat aaggccaggg caacggagga | 3660 |
| gcaggttttg aagtgaaagg caggcaggtg ttggggaggc agttaccggg gcaacgggaa | 3720 |
| cagggcgttt cggaggtggt tgccatgggg acctggatgc tgacgaaggc tcgcgaggct | 3780 |
| gtgagcagcc acagtgccct gctcagaagc cccaagctcg tcaatcaagc tggttctcca | 3840 |
| tttgcactca ggagcacggg caggcgagtg gcccctagtt ctggggcag cgggggatcc | 3900 |
| ggcgagatct ggaagagcca cgaagacgcg ctgcagaaat tcgaggaagc gctgaaccag | 3960 |
| tttgaggatc tgaagcaact gggtggcagc ggtaaaggca gcggtggcga gatcaagcaa | 4020 |
| cgtcacgaag acgcgctgcg taagttcgag gaagcgctga acgttttga ggatctgaag | 4080 |
| cagaaaggtg gctgcggtcg tgattggaag gagcacgaag acgcgcacca aaagtttgag | 4140 |
| gaagcgctga tcaatttga agatctgaaa caactgggtg gcagcggcaa gggcagcggt | 4200 |
| ggcgagatta acagcgcca tgaggatgcg ctgcgcaaat ttgaggaagc gctgaagcgc | 4260 |
| cacgaagatc gtgtgcaaaa gtgaaccggt agtagcagtg agcaagggcg aggagctgtt | 4320 |
| caccggggtg gtgcccatcc tggtcgagct ggacggcgac gtaaacggcc acaagttcag | 4380 |
| cgtgtccggc gagggcgagg gcgatgccac ctacggcaag ctgaccctga agttcatttg | 4440 |
| cacaccggc aagctgcccg tgccctggcc caccctcgtg accaccctga cctacggcgt | 4500 |
| gcagtgcttc agccgctacc ccgaccacat gaagcagcac gacttcttca gtccgccat | 4560 |
| gcccgaaggc tacgtccagg agcgcaccat cttcttcaag gacgacggca actacaagac | 4620 |
| ccgcgccgag gtgaagttcg agggcgacac cctggtgaac cgcatcgagc tgaagggcat | 4680 |
| cgacttcaag gaggacggca acatcctggg gcacaagctg gagtacaact acaacagcca | 4740 |
| caacgtctat atcatggccg acaagcagaa gaacggcatc aaggtgaact tcaagatccg | 4800 |
| ccacaacatc gaggacggca gcgtgcagct cgccgaccac taccagcaga cacccccat | 4860 |

```
cggcgacggc cccgtgctgc tgcccgacaa ccactacctg agcacccagt ccgccctgag     4920
caaagacccc aacgagaagc gcgatcacat ggtcctgctg gagttcgtga ccgccgccgg     4980
gatcactctc ggcatggacg agctgtacaa gtaagaattc gatatcaagc ttatcgataa     5040
tcaacctctg gattacaaaa tttgtgaaag attgactggt attcttaact atgttgctcc     5100
ttttacgcta tgtggatacg ctgctttaat gcctttgtat catgctattg cttcccgtat     5160
ggctttcatt ttctcctcct tgtataaatc ctggttgctg tctctttatg aggagttgtg     5220
gcccgttgtc aggcaacgtg gcgtggtgtg cactgtgttt gctgacgcaa cccccactgg     5280
ttggggcatt gccaccacct gtcagctcct tccggggact ttcgctttcc cctcccctat     5340
tgccacggcg gaactcatcg ccgcctgcct gcccgctgc tggacagggg ctcggctgtt      5400
gggcactgac aattccgtgg tgttgtcggg gaaatcatcg tccttttcctt ggctgctcgc    5460
ctgtgttgcc acctggattc tgcgcgggac gtccttctgc tacgtcccctt cggccctcaa   5520
tccagcggac cttccttccc gcggcctgct gccggctctg cggcctcttc cgcgtcttcg     5580
ccttcgccct cagacgagtc ggatctcccct tgggccgcc tccccgcatc gataccgtcg     5640
acctcgagac ctagaaaaac atggagcaat cacaagtagc aatacagcag ctaccaatgc     5700
tgattgtgcc tggctagaag cacaagagga ggaggaggtg ggttttccag tcacacctca     5760
ggtacccttta agaccaatga cttacaaggc agctgtagat cttagccact ttttaaaaga    5820
aaagggggga ctggaagggc taattcactc ccaacgaaga caagatatcc ttgatctgtg     5880
gatctaccac acacaaggct acttccctga ttggcagaac tacacaccag gccaggggat     5940
cagatatcca ctgacctttg gatggtgcta caagctagta ccagttgagc aagagaaggt     6000
agaagaagcc aatgaaggag agaacacccg cttgttacac cctgtgagcc tgcatgggat     6060
ggatgacccg gagagagaag tattagagtg gaggtttgac agccgcctag catttcatca     6120
catggcccga gagctgcatc cggactgtac tgggtctctc tggttagacc agatctgagc     6180
ctgggagctc tctggctaac tagggaaccc actgcttaag cctcaataaa gcttgccttg     6240
agtgcttcaa gtagtgtgtg cccgtctgtt gtgtgactct ggtaactaga gatccctcag     6300
accctttttag tcagtgtgga aaatctctag cagggcccgt ttaaacccgc tgatcagcct    6360
cgactgtgcc ttctagttgc cagccatctg ttgtttgccc ctcccccgtg ccttccttga    6420
ccctggaagg tgccactccc actgtccttt cctaataaaa tgaggaaatt gcatcgcatt     6480
gtctgagtag gtgtcattct attctggggg gtgggtggg gcaggacagc aaggggagg      6540
attgggaaga caatagcagg catgctgggg atgcggtggg ctctatggct tctgaggcgg     6600
aaagaaccag ctggggctct aggggtatc cccacgcgcc ctgtagcggc gcattaagcg      6660
cggcgggtgt ggtggttacg cgcagcgtga ccgctacact tgccagcgcc ctagcgcccg    6720
ctccttttcgc tttcttccct tccttttctcg ccacgttcgc cggctttccc cgtcaagctc   6780
taaatcgggg gctcccttta gggttccgat ttagtgcttt acggcacctc gaccccaaaa     6840
aacttgatta gggtgatggt tcacgtagtg gccatcgcc ctgatagacg ttttttcgcc      6900
ctttgacgtt ggagtccacg ttctttaata gtggactctt gttccaaact ggaacaacac     6960
tcaaccctat ctcggtctat tcttttgatt tataagggat tttgccgatt tcggcctatt     7020
ggttaaaaaa tgagctgatt taacaaaaat ttaacgcgaa ttaattctgt ggaatgtgtg     7080
tcagttaggg tgtggaaagt ccccaggctc cccagcaggc agaagtatgc aaagcatgca     7140
tctcaattag tcagcaacca ggtgtggaaa gtccccaggc tccccagcag gcagaagtat     7200
```

-continued

```
gcaaagcatg catctcaatt agtcagcaac catagtcccg cccctaactc cgcccatccc    7260
gccCctaact ccgcccagtt ccgcccattc tccgcCccat ggctgactaa tttttttat    7320 ttatgcagag gccgaggccg cctctgcctc tgagctattc cagaagtagt gaggaggctt    7380
ttttggaggc ctaggctttt gcaaaaagct cccgggagct gtatatccat ttttcggatc    7440
tgatcagcac gtgttgacaa ttaatcatcg gcatagtata tcggcatagt ataatacgac    7500
aaggtgagga actaaaccat ggccaagttg accagtgccg ttccggtgct caccgcgcgc    7560
gacgtcgccg gagcggtcga gttctggacc gaccggctcg ggttctcccg ggacttcgtg    7620
gaggacgact cgccggtgt ggtccgggac gacgtgaccc tgttcatcag cgcggtccag    7680
gaccaggtgg tgccggacaa caccctggcc tgggtgtggg tgcgcggcct ggacgagctg    7740
tacgccgagt ggtcggaggt cgtgtccacg aacttccggg acgcctccgg gccggccatg    7800
accgagatcg gcgagcagcc gtgggggcgg gagttcgccc tgcgcgaccc ggccggcaac    7860
tgcgtgcact tcgtgccga ggagcaggac tgacacgtgc tacgagattt cgattccacc    7920
gccgccttct atgaaaggtt gggcttcgga atcgttttcc gggacgccgg ctggatgatc    7980
ctccagcgcg gggatctcat gctggagttc ttcgcccacc ccaacttgtt tattgcagct    8040
tataatggtt acaaataaag caatagcatc acaaatttca caaataaagc attttttca    8100 ctgcattcta gttgtggttt gtccaaactc atcaatgtat cttatcatgt ctgtataccg    8160
tcgacctcta gctagagctt ggcgtaatca tggtcatagc tgtttcctgt gtgaaattgt    8220
tatccgctca caattccaca acatacga gccggaagca taaagtgtaa agcctggggt    8280
gcctaatgag tgagctaact cacattaatt gcgttgcgct cactgcccgc tttccagtcg    8340
ggaaacctgt cgtgccagct gcattaatga atcggccaac gcgcggggag aggcggtttg    8400
cgtattgggc gctcttccgc ttcctcgctc actgactcgc tgcgctcggt cgttcggctg    8460
cggcgagcgg tatcagctca ctcaaaggcg gtaatacggt tatccacaga atcaggggat    8520
aacgcaggaa agaacatgtg agcaaaaggc cagcaaaagg ccaggaaccg taaaaaggcc    8580
gcgttgctgg cgtttttcca taggctccgc cccCctgacg agcatcacaa aaatcgacgc    8640
tcaagtcaga ggtggcgaaa cccgacagga ctataaagat accaggcgtt ccccctgga    8700 agctccctcg tgcgctctcc tgttccgacc ctgccgctta ccggatacct gtccgccttt    8760
ctcccttcgg gaagcgtggc gctttctcat agctcacgct gtaggtatct cagttcggtg    8820
taggtcgttc gctccaagct gggctgtgtg cacgaacccc ccgttcagcc cgaccgctgc    8880
gccttatccg gtaactatcg tcttgagtcc aacccggtaa gacacgactt atcgccactg    8940
gcagcagcca ctggtaacag gattagcaga gcgaggtatg taggcggtgc tacagagttc    9000
ttgaagtggt ggcctaacta cggctacact agaagaacag tatttggtat ctgcgctctg    9060
ctgaagccag ttaccttcgg aaaaagagtt ggtagctctt gatccggcaa acaaaccacc    9120
gctggtagcg gtggtttttt tgtttgcaag cagcagatta cgcgcagaaa aaaggatct    9180 caagaagatc ctttgatctt ttctacgggg tctgacgctc agtggaacga aaactcacgt    9240
taagggattt tggtcatgag attatcaaaa aggatcttca cctagatcct tttaaattaa    9300
aaatgaagtt ttaaatcaat ctaaagtata tatgagtaaa cttggtctga cagttaccaa    9360
tgcttaatca gtgaggcacc tatctcagcg atctgtctat ttcgttcatc catagttgcc    9420
tgactcCccg tcgtgtagat aactacgata cgggagggct taccatctgg ccccagtgct    9480
gcaatgatac cgcgagaccc acgctcaccg gctccagatt tatcagcaat aaaccagcca    9540
gccggaaggg ccgagcgcag aagtggtcct gcaactttat ccgcctccat ccagtctatt    9600
```

```
aattgttgcc gggaagctag agtaagtagt tcgccagtta atagtttgcg caacgttgtt    9660
gccattgcta caggcatcgt ggtgtcacgc tcgtcgtttg gtatggcttc attcagctcc    9720
ggttcccaac gatcaaggcg agttacatga tcccccatgt tgtgcaaaaa agcggttagc    9780
tccttcggtc ctccgatcgt tgtcagaagt aagttggccg cagtgttatc actcatggtt    9840
atggcagcac tgcataattc tcttactgtc atgccatccg taagatgctt ttctgtgact    9900
ggtgagtact caaccaagtc attctgagaa tagtgtatgc ggcgaccgag ttgctcttgc    9960
ccggcgtcaa tacgggataa taccgcgcca catagcagaa ctttaaaagt gctcatcatt   10020
ggaaaacgtt cttcggggcg aaaactctca aggatcttac cgctgttgag atccagttcg   10080
atgtaaccca ctcgtgcacc caactgatct tcagcatctt ttactttcac cagcgtttct   10140
gggtgagcaa aaacaggaag gcaaaatgcc gcaaaaaagg gaataagggc gacacgaaa    10200 tgttgaatac tcatactctt ccttttcaa tattattgaa gcatttatca gggttattgt    10260
ctcatgagcg gatacatatt tgaatgtatt tagaaaaata acaaatagg ggttccgcgc    10320 acatttcccc gaaaagtgcc acctgac                                       10347
```

<210> SEQ ID NO 91
<211> LENGTH: 126
<212> TYPE: PRT
<213> ORGANISM: Artificial Sequence
<220> FEATURE:
<223> OTHER INFORMATION: Synthetic Sequence C-His Stab CGRD

<400> SEQUENCE: 91

```
Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Asp Trp Lys Glu His Glu Asp Ala His Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg His Glu Asp Arg Val Gln Lys
        115                 120                 125
```

<210> SEQ ID NO 92
<211> LENGTH: 6122
<212> TYPE: DNA
<213> ORGANISM: Artificial Sequence
<220> FEATURE:
<223> OTHER INFORMATION: Synthetic Sequence C41 Stab Map (E. Coli)

<400> SEQUENCE: 92

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
```

```
gccccaaggg gttatgctag ttattgctca gcggtggcag cagccaactc agcttccttt    300
cgggctttgt tagcagccgg atcctcgaga ccggttcatt tttgcttcag atcctcaaag    360
cgcttcagcg cttcctcatg tttacgcagc gcgtcttcgt ggctctgctt aatctcgcca    420
ccgctgcctt taccgctgcc acccagctgt tcagatcttc gaactggttt cagcgcttcc    480
tcgtgctttt gcagcgcgtc ttcaaacagt tccaaatctc gccgctgcca cctttctgc    540 ttcagatcct cgaaacgttt cagcgcttcc tcaaacttac gcagcgcgtc cgcgcaacgt    600
tgtttgattt cgccaccgct gcccttgccg ctgccaccca gttgcacacg atcctcgaac    660
tggttcagtt cgtgctcaaa cttctgcagc gcgtcttcga acagtttcca gatctcgccg    720
gatccctgaa aatacaggtt ttcaccatcg cctccgtggt gatgatggtg atgcccacct    780
ttacccatat gaatatcgcc ttccatggta tatctccttc ttaaagttaa acaaaattat    840
ttctagaggg gaattgttat ccgctcacaa ttcccctata gtgagtcgta ttaatttcgc    900
gggatcgaga tctcgatcct ctacgccgga cgcatcgtgg ccggcatcac cggcgccaca    960
ggtgcggttg ctggcgccta tcgccgac atcaccgatg gggaagatcg ggctcgccac    1020
ttcgggctca tgagcgcttg tttcggcgtg ggtatggtgg caggccccgt ggccggggga    1080
ctgttgggcg ccatctcctt gcatgcacca ttccttgcgg cggcggtgct caacggcctc    1140
aacctactac tgggctgctt cctaatgcag gagtcgcata agggagagcg tcgagatccc    1200
ggacaccatc gaatggcgca aaacctttcg cggtatggca tgatagcgcc cggaagagag    1260
tcaattcagg gtggtgaatg tgaaaccagt aacgttatac gatgtcgcag agtatgccgg    1320
tgtctcttat cagaccgttt cccgcgtggt gaaccaggcc agccacgttt ctgcgaaaac    1380
gcgggaaaaa gtggaagcgg cgatggcgga gctgaattac attcccaacc gcgtggcaca    1440
acaactggcg ggcaaacagt cgttgctgat tggcgttgcc acctccagtc tggccctgca    1500
cgcgccgtcg caaattgtcg cggcgattaa atctcgcgcc gatcaactgg gtgccagcgt    1560
ggtggtgtca atggtagaac gaagcggcgt cgaagcctgt aaagcggcgg tgcacaatct    1620
tctcgcgcaa cgcgtcagtg ggctgatcat taactatccg ctggatgacc aggatgccat    1680
tgctgtggaa gctgcctgca ctaatgttcc ggcgttattt cttgatgtct ctgaccagac    1740
acccatcaac agtattattt tctcccatga agacggtacg cgactgggcg tggagcatct    1800
ggtcgcattg ggtcaccagc aaatcgcgct gttagcgggc ccattaagtt ctgtctcggc    1860
gcgtctgcgt ctggctggct ggcataaata tctcactcgc aatcaaattc agccgatagc    1920
ggaacgggaa ggcgactgga gtgccatgtc cggttttcaa caaaccatgc aaatgctgaa    1980
tgagggcatc gttcccactg cgatgctggt tgccaacgat cagatggcgc tgggcgcaat    2040
gcgcgccatt accgagtccg ggctgcgcgt tggtgcggat atctcggtag tgggatacga    2100
cgataccgaa gacagctcat gttatatccc gccgttaacc accatcaaac aggattttcg    2160
cctgctgggg caaaccagcg tggaccgctt gctgcaactc tctcagggcc aggcggtgaa    2220
gggcaatcag ctgttgcccg tctcactggt gaaaagaaaa accaccctgg cgcccaatac    2280
gcaaaccgcc tctccccgcg cgttggccga ttcattaatg cagctggcac gacaggtttc    2340
ccgactggaa agcgggcagt gagcgcaacg caattaatgt aagttagctc actcattagg    2400
caccgggatc tcgaccgatg cccttgagag ccttcaaccc agtcagctcc ttccggtggg    2460
cgcggggcat gactatcgtc gccgcactta tgactgtctt ctttatcatg caactcgtag    2520
gacaggtgcc ggcagcgctc tgggtcattt tcggcgagga ccgctttcgc tggagcgcga    2580
cgatgatcgg cctgtcgctt gcggtattcg gaatcttgca cgccctcgct caagccttcg    2640
```

```
tcactggtcc cgccaccaaa cgtttcggcg agaagcaggc cattatcgcc ggcatggcgg    2700
ccgacgcgct gggctacgtc ttgctggcgt tcgcgacgcg aggctggatg gccttcccca    2760
ttatgattct tctcgcttcc ggcggcatcg ggatgcccgc gttgcaggcc atgctgtcca    2820
ggcaggtaga tgacgaccat cagggacagc ttcaaggatc gctcgcggct cttaccagcc    2880
taacttcgat cactggaccg ctgatcgtca cggcgattta tgccgcctcg gcgagcacat    2940
ggaacgggtt ggcatggatt gtaggcgccg ccctatacct tgtctgcctc cccgcgttgc    3000
gtcgcggtgc atggagccgg gccacctcga cctgaatgga agccggcggc acctcgctaa    3060
cggattcacc actccaagaa ttggagccaa tcaattcttg cggagaactg tgaatgcgca    3120
aaccaaccct tggcagaaca tatccatcgc gtccgccatc tccagcagcc gcacgcggcg    3180
catctcgggc agcgttgggt cctggccacg ggtgcgcatg atcgtgctcc tgtcgttgag    3240
gacccggcta ggctggcggg gttgccttac tggttagcag aatgaatcac cgatacgcga    3300
gcgaacgtga agcgactgct gctgcaaaac gtctgcgacc tgagcaacaa catgaatggt    3360
cttcggtttc cgtgtttcgt aaagtctgga aacgcggaag tcagcgccct gcaccattat    3420
gttccggatc tgcatcgcag gatgctgctg gctaccctgt ggaacaccta catctgtatt    3480
aacgaagcgc tggcattgac cctgagtgat ttttctctgg tcccgccgca tccataccgc    3540
cagttgttta ccctcacaac gttccagtaa ccgggcatgt tcatcatcag taacccgtat    3600
cgtgagcatc ctctctcgtt tcatcggtat cattaccccc atgaacagaa atccccctta    3660 cacgaggca tcagtgacca aacaggaaaa aaccgccctt aacatggccc gctttatcag    3720
aagccagaca ttaacgcttc tggagaaact caacgagctg gacgcggatg aacaggcaga    3780
catctgtgaa tcgcttcacg accacgctga tgagctttac cgcagctgcc tcgcgcgttt    3840
cggtgatgac ggtgaaaacc tctgacacat gcagctcccg gagacggtca cagcttgtct    3900
gtaagcggat gccgggagca gacaagcccg tcagggcgcg tcagcgggtg ttggcgggtg    3960
tcggggcgca gccatgaccc agtcacgtag cgatagcgga gtgtatactg gcttaactat    4020
gcggcatcag agcagattgt actgagagtg caccatatat gcggtgtgaa ataccgcaca    4080
gatgcgtaag gagaaaatac cgcatcaggc gctcttccgc ttcctcgctc actgactcgc    4140
tgcgctcggt cgttcggctg cggcgagcgg tatcagctca ctcaaaggcg gtaatacggt    4200
tatccacaga atcaggggat aacgcaggaa agaacatgtg agcaaaaggc cagcaaaagg    4260
ccaggaaccg taaaaaggcc gcgttgctgg cgttttttcca taggctccgc cccctgacg    4320 agcatcacaa aaatcgacgc tcaagtcaga ggtggcgaaa cccgacagga ctataaagat    4380
accaggcgtt ccccctggaa gctccctcg tgcgctctcc tgttccgacc ctgccgctta    4440
ccggataccc gtccgccttt ctcccttcgg gaagcgtggc gctttctcat agctcacgct    4500
gtaggtatct cagttcggtg taggtcgttc gctccaagct gggctgtgtg cacgaacccc    4560
ccgttcagcc cgaccgctgc gccttatccg gtaactatcg tcttgagtcc aacccggtaa    4620
gacacgactt atcgccactg gcagcagcca ctggtaacag gattagcaga gcgaggtatg    4680
taggcggtgc tacagagttc ttgaagtggt ggcctaacta cggctacact agaaggacag    4740
tatttggtat ctgcgctctg ctgaagccag ttaccttcgg aaaaagagtt ggtagctctt    4800
gatccggcaa acaaaccacc gctggtagcg gtggtttttt tgtttgcaag cagcagatta    4860
cgcgcagaaa aaaaggatct caagaagatc ctttgatctt ttctacgggg tctgacgctc    4920
agtggaacga aaactcacgt taagggattt tggtcatgag attatcaaaa aggatcttca    4980
```

```
cctagatcct tttaaattaa aaatgaagtt ttaaatcaat ctaaagtata tatgagtaaa    5040
cttggtctga cagttaccaa tgcttaatca gtgaggcacc tatctcagcg atctgtctat    5100
ttcgttcatc catagttgcc tgactccccg tcgtgtagat aactacgata cgggagggct    5160
taccatctgg ccccagtgct gcaatgatac cgcgagaccc acgctcaccg gctccagatt    5220
tatcagcaat aaaccagcca gccggaaggg ccgagcgcag aagtggtcct gcaactttat    5280
ccgcctccat ccagtctatt aattgttgcc gggaagctag agtaagtagt tcgccagtta    5340
atagtttgcg caacgttgtt gccattgctg caggcatcgt ggtgtcacgc tcgtcgtttg    5400
gtatggcttc attcagctcc ggttcccaac gatcaaggcg agttacatga tcccccatgt    5460
tgtgcaaaaa agcggttagc tccttcggtc ctccgatcgt tgtcagaagt aagttggccg    5520
cagtgttatc actcatggtt atggcagcac tgcataattc tcttactgtc atgccatccg    5580
taagatgctt ttctgtgact ggtgagtact caaccaagtc attctgagaa tagtgtatgc    5640
ggcgaccgag ttgctcttgc ccggcgtcaa cacgggataa taccgcgcca catagcagaa    5700
ctttaaaagt gctcatcatt ggaaaacgtt cttcggggcg aaaactctca aggatcttac    5760
cgctgttgag atccagttcg atgtaaccca ctcgtgcacc caactgatct tcagcatctt    5820
ttactttcac cagcgtttct gggtgagcaa aaacaggaag gcaaaatgcc gcaaaaaagg    5880
gaataagggc gacacggaaa tgttgaatac tcatactctt cctttttcaa tattattgaa    5940
gcatttatca gggttattgt ctcatgagcg gatacatatt tgaatgtatt tagaaaaata    6000
aacaaatagg ggttccgcgc acatttcccc gaaaagtgcc acctgacgtc taagaaacca    6060
ttattatcat gacattaacc tataaaaata ggcgtatcac gaggccctt cgtcttcaag    6120 aa                                                                   6122
```

<210> SEQ ID NO 93
<211> LENGTH: 10347
<212> TYPE: DNA
<213> ORGANISM: Artificial Sequence
<220> FEATURE:
<223> OTHER INFORMATION: Synthetic Sequence C41 Stab Map (FCK mam)

<400> SEQUENCE: 93

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
```

```
aagcctcaat aaagcttgcc ttgagtgctt caagtagtgt gtgcccgtct gttgtgtgac    960
tctggtaact agagatccct cagaccctt tagtcagtgt ggaaaatctc tagcagtggc    1020
gcccgaacag ggacttgaaa gcgaagggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
```

```
agaaaccatt acagagacta caaggggggaa gggaaggaga gatgaattag cttccctgt    3300
aaaccttaga acccagctgt tgccaggca acggggcaat acctgtctct tcagaggaga     3360
tgaagttgcc agggtaacta catcctgtct ttctcaagga ccatcccaga atgtggcacc    3420
cactagccgt taccatagca actgcctctt tgcccactt aatcccatcc cgtctgttaa     3480
aagggccta tagttggagg tggggaggt aggaagagcg atgatcactt gtggactaag      3540
tttgttcaca tccccttctc caaccccctc agtacatcac cctgggagaa caaggtccac    3600
ttgcttctgg gcccacacag tcctgcagta ttgtgtatat aaggccaggg caacggagga   3660
gcaggttttg aagtgaaagg caggcaggtg ttggggaggc agttaccggg caacgggaa     3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca   3840
tttgcactca ggagcacggg caggcgagtg gcccctagtt ctgggggcag cggggatcc    3900
ggcgagatct ggaaactgtt cgaagacgcg ctgcagaagt ttgagcacga actgaaccag   3960
ttcgaggatc gtgtgcaact gggtggcagc ggcaagggca gcgtggcga aatcaaacaa    4020
cgttgcgcgg acgcgctgcg taagtttgag gaagcgctga aacgtttcga ggatctgaag   4080
cagaaaggtg gcagcggcga gatttggaaa ctgtttgaag acgcgctgca aaagcacgag   4140
gaagcgctga accagttcga agatctgaaa cagctgggtg gcagcggtaa aggcagcggt   4200
ggcgagatta gcagagcca cgaagacgcg ctgcgtaaac atgaggaagc gctgaagcgc    4260
tttgaggatc tgaagcaaaa atgaaccggt agtagcagtg agcaagggcg aggagctgtt   4320
caccggggtg gtgcccatcc tggtcgagct ggacggcgac gtaaacggcc acaagttcag   4380
cgtgtccggc gagggcgagg gcgatgccac ctacggcaag ctgaccctga agttcatttg   4440
caccaccggc aagctgcccg tgccctggcc cacccctgtg accacccga cctacgccgt    4500
gcagtgcttc agccgctacc ccgaccacat gaagcagcac gacttcttca agtccgccat   4560
gcccgaaggc tacgtccagg agcgcaccat cttcttcaag gacgacggca actacaagac   4620
ccgcgccgag gtgaagttcg agggcgacac cctggtgaac cgcatcgagc tgaagggcat   4680
cgacttcaag gaggacggca acatcctggg gcacaagctg gagtacaact acaacagcca   4740
caacgtctat atcatggccg acaagcagaa gaacggcatc aaggtgaact tcaagatccg   4800
ccacaacatc gaggacggca gcgtgcagct cgccgaccac taccagcaga caccccat     4860
cggcgacggc cccgtgctgc tgcccgacaa ccactacctg agcacccagt ccgccctgag   4920
caaagacccc aacgagaagc gcgatcacat ggtcctgctg gagttcgtga ccgccgccgg   4980
gatcactctc ggcatggacg agctgtacaa gtaagaattc gatatcaagc ttatcgataa   5040
tcaacctctg gattacaaaa tttgtgaaag attgactggt attcttaact atgttgctcc    5100
ttttacgcta tgtggatacg ctgctttaat gcctttgtat catgctattg cttcccgtat    5160
ggctttcatt ttctcctcct tgtataaatc ctggttgctg tctctttatg aggagttgtg    5220
gcccgttgtc aggcaacgtg gcgtggtgtg cactgtgttt gctgacgcaa ccccactgg     5280
ttggggcatt gccaccacct gtcagctcct ttccgggact ttcgctttcc cctccctat    5340
tgccacggcg gaactcatcg ccgcctgcct tgcccgctgc tggacagggg ctcggctgtt    5400
gggcactgac aattccgtgg tgttgtcggg gaaatcatcg tccttccctt ggctgctcgc   5460
ctgtgttgcc acctggattc tgcgcggac gtccttctgc tacgtccctt cggccctcaa    5520
tccagcggac cttccttccc gcggcctgct gccggctctg cggcctcttc cgcgtcttcg   5580
ccttcgccct cagacgagtc ggatctccct ttgggccgcc tccccgcatc gataccgtcg   5640
```

```
acctcgagac ctagaaaaac atggagcaat cacaagtagc aatacagcag ctaccaatgc    5700
tgattgtgcc tggctagaag cacaagagga ggaggaggtg ggttttccag tcacacctca    5760 ggtacccttta agaccaatga cttacaaggc agctgtagat cttagccact ttttaaaaga   5820 aaaggggga ctggaagggc taattcactc ccaacgaaga caagatatcc ttgatctgtg     5880
gatctaccac acacaaggct acttccctga ttggcagaac tacacaccag ggccagggat    5940
cagatatcca ctgacctttg gatggtgcta caagctagta ccagttgagc aagagaaggt    6000
agaagaagcc aatgaaggag agaacacccg cttgttacac cctgtgagcc tgcatgggat    6060
ggatgacccg gagagagaag tattagagtg gaggtttgac agccgcctag catttcatca    6120
catggcccga gagctgcatc cggactgtac tgggtctctc tggttagacc agatctgagc    6180
ctgggagctc tctggctaac tagggaaccc actgcttaag cctcaataaa gcttgccttg    6240
agtgcttcaa gtagtgtgtg cccgtctgtt gtgtgactct ggtaactaga gatccctcag    6300 accctttttag tcagtgtgga aaatctctag cagggcccgt ttaaacccgc tgatcagcct    6360
cgactgtgcc ttctagttgc cagccatctg ttgtttgccc ctcccccgtg ccttccttga    6420
ccctggaagg tgccactccc actgtccttt cctaataaaa tgaggaaatt gcatcgcatt    6480
gtctgagtag gtgtcattct attctggggg gtggggtggg gcaggacagc aaggggagg    6540 attgggaaga caatagcagg catgctgggg atgcggtggg ctctatggct tctgaggcgg    6600
aaagaaccag ctgggctct aggggtatc cccacgcgcc ctgtagcggc gcattaagcg     6660
cggcgggtgt ggtggttacg cgcagcgtga ccgctacact tgccagcgcc ctagcgcccg    6720
ctcctttcgc tttcttccct cctttctcg ccacgttcgc cggctttccc cgtcaagctc     6780
taaatcgggg gctcccttta gggttccgat ttagtgcttt acggcacctc gaccccaaaa    6840
aacttgatta gggtgatggt tcacgtagtg gccatcgcc ctgatagacg ttttttcgcc     6900
ctttgacgtt ggagtccacg ttctttaata gtggactctt gttccaaact ggaacaacac    6960
tcaaccctat ctcggtctat tcttttgatt tataagggat tttgccgatt tcggcctatt    7020
ggttaaaaaa tgagctgatt taacaaaaat ttaacgcgaa ttaattctgt ggaatgtgtg    7080
tcagttaggg tgtggaaagt ccccaggctc cccagcaggc agaagtatgc aaagcatgca    7140
tctcaattag tcagcaacca ggtgtggaaa gtccccaggc tccccagcag gcagaagtat    7200
gcaaagcatg catctcaatt agtcagcaac catagtcccg cccctaactc cgcccatccc    7260
gcccctaact ccgcccagtt ccgcccattc tccgccccat ggctgactaa ttttttttat    7320
ttatgcagag gccgaggccg cctctgcctc tgagctattc cagaagtagt gaggaggctt    7380
ttttggaggc ctaggctttt gcaaaaagct cccgggagct gtatatcca ttttcggatc     7440 tgatcagcac gtgttgacaa ttaatcatcg gcatagtata tcggcatagt ataatacgac    7500
aaggtgagga actaaaccat ggccaagttg accagtgccg ttccggtgct caccgcgcgc    7560
gacgtcgccg gagcggtcga gttctggacc gaccggctcg ggttctcccg ggacttcgtg    7620
gaggacgact tcgccggtgt ggtccgggac gacgtgaccc tgttcatcag cgcggtccag    7680
gaccaggtgg tgccggacaa caccctggcc tgggtgtggg tgcgcggcct ggacgagctg    7740
tacgccgagt ggtcggaggt cgtgtccacg aacttccggg acgcctccgg ccggccatg    7800 accgagatcg cgcagcagcc gtgggggcgg gagttcgccc tgcgcgaccc ggccggcaac    7860
tgcgtgcact tcgtggccga ggagcaggac tgacacgtgc tacgagattt cgattccacc    7920
gccgccttct atgaaaggtt gggcttcgga atcgttttcc gggacgccgg ctggatgatc    7980
```

```
ctccagcgcg gggatctcat gctggagttc ttcgcccacc ccaacttgtt tattgcagct    8040
tataatggtt acaaataaag caatagcatc acaaatttca caaataaagc attttttca     8100 ctgcattcta gttgtggttt gtccaaactc atcaatgtat cttatcatgt ctgtataccg    8160
tcgacctcta gctagagctt ggcgtaatca tggtcatagc tgtttcctgt gtgaaattgt    8220
tatccgctca caattccaca acatacga gccggaagca taaagtgtaa agcctggggt      8280
gcctaatgag tgagctaact cacattaatt gcgttgcgct cactgcccgc tttccagtcg    8340
ggaaacctgt cgtgccagct gcattaatga atcggccaac gcgcgggag aggcggtttg     8400 cgtattgggc gctcttccgc ttcctcgctc actgactcgc tgcgctcggt cgttcggctg    8460
cggcgagcgg tatcagctca ctcaaaggcg gtaatacggt tatccacaga atcaggggat    8520
aacgcaggaa agaacatgtg agcaaaaggc cagcaaaagg ccaggaaccg taaaaaggcc    8580
gcgttgctgg cgtttttcca taggctccgc cccctgacg agcatcacaa aaatcgacgc     8640
tcaagtcaga ggtggcgaaa cccgacagga ctataaagat accaggcgtt tcccctggaa    8700
agctccctcg tgcgctctcc tgttccgacc ctgccgctta ccggatacct gtccgccttt    8760
ctcccttcgg gaagcgtggc gctttctcat agctcacgct gtaggtatct cagttcggtg    8820
taggtcgttc gctccaagct gggctgtgtg cacgaacccc ccgttcagcc cgaccgctgc    8880
gccttatccg gtaactatcg tcttgagtcc aacccggtaa gacacgactt atcgccactg    8940
gcagcagcca ctggtaacag gattagcaga gcgaggtatg taggcggtgc tacagagttc    9000
ttgaagtggt ggcctaacta cggctacact agaagaacag tatttggtat ctgcgctctg    9060
ctgaagccag ttaccttcgg aaaaagagtt ggtagctctt gatccggcaa acaaaccacc    9120
gctggtagcg gtggtttttt tgtttgcaag cagcagatta cgcgcagaaa aaaggatct     9180 caagaagatc ctttgatctt ttctacgggg tctgacgctc agtggaacga aaactcacgt    9240
taagggattt tggtcatgag attatcaaaa aggatcttca cctagatcct tttaaattaa    9300
aaatgaagtt ttaaatcaat ctaaagtata tatgagtaaa cttggtctga cagttaccaa    9360
tgcttaatca gtgaggcacc tatctcagcg atctgtctat ttcgttcatc catagttgcc    9420
tgactccccg tcgtgtagat aactacgata cgggagggct taccatctgg ccccagtgct    9480
gcaatgatac cgcgagaccc acgctcaccg gctccagatt tatcagcaat aaaccagcca    9540
gccgaagggg ccgagcgcag aagtggtcct gcaactttat ccgcctccat ccagtctatt    9600
aattgttgcc gggaagctag agtaagtagt tcgccagtta atagtttgcg caacgttgtt    9660
gccattgcta caggcatcgt ggtgtcacgc tcgtcgtttg gtatggcttc attcagctcc    9720
ggttcccaac gatcaaggcg agttacatga tcccccatgt tgtgcaaaaa agcggttagc    9780
tccttcggtc ctccgatcgt tgtcagaagt aagttggccg cagtgttatc actcatggtt    9840
atggcagcac tgcataattc tcttactgtc atgccatccg taagatgctt ttctgtgact    9900
ggtgagtact caaccaagtc attctgagaa tagtgtatgc ggcgaccgag ttgctcttgc    9960
ccggcgtcaa tacgggataa taccgcgcca catagcagaa ctttaaaagt gctcatcatt   10020
ggaaaacgtt cttcggggcg aaaactctca aggatcttac cgctgttgag atccagttcg   10080
atgtaaccca ctcgtgcacc caactgatct tcagcatctt ttactttcac cagcgtttct   10140
gggtgagcaa aaacaggaag gcaaaatgcc gcaaaaaagg gaataagggc gacacggaaa   10200
tgttgaatac tcatactctt cctttttcaa tattattgaa gcatttatca gggttattgt   10260
ctcatgagcg gatacatatt tgaatgtatt tagaaaaata acaaataggg gttccgcgc    10320 acatttcccc gaaaagtgcc acctgac                                       10347
```

<210> SEQ ID NO 94
<211> LENGTH: 126
<212> TYPE: PRT
<213> ORGANISM: Artificial Sequence
<220> FEATURE:
<223> OTHER INFORMATION: Synthetic Sequence C41 Stab Map

<400> SEQUENCE: 94

```
Glu Ile Trp Lys Leu Phe Glu Asp Ala Leu Gln Lys Phe Glu His Glu
1               5                   10                  15

Leu Asn Gln Phe Glu Asp Arg Val Gln Leu Gly Gly Ser Gly Lys Gly
                20                  25                  30

Ser Gly Gly Glu Ile Lys Gln Arg Cys Ala Asp Ala Leu Arg Lys Phe
            35                  40                  45

Glu Glu Ala Leu Lys Arg Phe Glu Asp Leu Lys Gln Lys Gly Gly Ser
50                  55                  60

Gly Glu Ile Trp Lys Leu Phe Glu Asp Ala Leu Gln Lys His Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Ser His Glu Asp Ala Leu Arg Lys
            100                 105                 110

His Glu Glu Ala Leu Lys Arg Phe Glu Asp Leu Lys Gln Lys
            115                 120                 125
```

<210> SEQ ID NO 95
<211> LENGTH: 6122
<212> TYPE: DNA
<213> ORGANISM: Artificial Sequence
<220> FEATURE:
<223> OTHER INFORMATION: Synthetic Sequence C41 Stab Map CARD (E. Coli)

<400> SEQUENCE: 95

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atcctcgaga ccggttcatt tttgcttcag atcctcaaag     360
cgcttcagcg cttcctcatg tttacgcagc gcgtcttcgt ggctctgctt aatctcgcca     420
ccgctgcctt taccgctgcc acccagctgt tcagatcttc gaactggttc agcgcttcc     480
tcgtgctttt gcagcgcgtc ttcaaacagt tccaaatctc gccgctgcc acctttctgc     540
ttcagatcct cgaaacgttt cagcgcttcc tcaaacttac gcagatcacg cgcgcaacgt     600
tgtttgattt cgccaccgct gcccttgccg ctgccaccca gttgcacacg atcctcgaac     660
tggttcagtt cgtgctcaaa cttctgcagc gcgtcttcga acagtttcca gatctcgccg     720
gatccctgaa aatacaggtt tcaccatcg cctccgtggt gatgatggtg atgcccacct     780
ttacccatat gaatatcgcc ttccatggta tatctccttc ttaaagttaa acaaaattat     840
ttctagaggg gaattgttat ccgctcacaa ttcccctata gtgagtcgta ttaatttcgc     900
gggatcgaga tctcgatcct ctacgccgga cgcatcgtgg ccggcatcac cggcgccaca     960
ggtgcggttg ctggcgccta tcgccgac atcaccgatg gggaagatcg gctcgccac    1020
```

-continued

```
ttcgggctca tgagcgcttg tttcggcgtg ggtatggtgg caggccccgt ggccggggga      1080
ctgttgggcg ccatctcctt gcatgcacca ttccttgcgg cggcggtgct caacggcctc      1140
aacctactac tgggctgctt cctaatgcag gagtcgcata agggagagcg tcgagatccc      1200
ggacaccatc gaatggcgca aaacctttcg cggtatggca tgatagcgcc cggaagagag      1260
tcaattcagg gtggtgaatg tgaaaccagt aacgttatac gatgtcgcag agtatgccgg      1320
tgtctcttat cagaccgttt cccgcgtggt gaaccaggcc agccacgttt ctgcgaaaac      1380
gcgggaaaaa gtggaagcgg cgatggcgga gctgaattac attcccaacc gcgtggcaca      1440
acaactggcg ggcaaacagt cgttgctgat tggcgttgcc acctccagtc tggccctgca      1500
cgcgccgtcg caaattgtcg cggcgattaa atctcgcgcc gatcaactgg gtgccagcgt      1560
ggtggtgtcg atggtagaac gaagcggcgt cgaagcctgt aaagcggcgg tgcacaatct      1620
tctcgcgcaa cgcgtcagtg gctgatcat taactatccg ctggatgacc aggatgccat      1680
tgctgtggaa gctgcctgca ctaatgttcc ggcgttattt cttgatgtct ctgaccagac      1740
acccatcaac agtattattt ctcccatga agacggtacg cgactgggcg tggagcatct      1800
ggtcgcattg ggtcaccagc aaatcgcgct gttagcgggc ccattaagtt ctgtctcggc      1860
gcgtctgcgt ctggctggct ggcataaata tctcactcgc aatcaaattc agccgatagc      1920
ggaacgggaa ggcgactgga gtgccatgtc cggttttcaa caaaccatgc aaatgctgaa      1980
tgagggcatc gttcccactg cgatgctggt tgccaacgat cagatggcgc tgggcgcaat      2040
gcgcgccatt accgagtccg ggctgcgcgt tggtgcggat atctcggtag tgggatacga      2100
cgataccgaa gacagctcat gttatatccc gccgttaacc accatcaaac aggatttcg      2160 cctgctgggg caaaccagcg tggaccgctt gctgcaactc tctcagggcc aggcggtgaa      2220
gggcaatcag ctgttgcccg tctcactggt gaaaagaaaa accaccctgg cgcccaatac      2280
gcaaaccgcc tctccccgcg cgttggccga ttcattaatg cagctggcac gacaggtttc      2340
ccgactggaa agcgggcagt gagcgcaacg caattaatgt aagttagctc actcattagg      2400
caccgggatc tcgaccgatg cccttgagag ccttcaaccc agtcagctcc ttccggtggg      2460
cgcggggcat gactatcgtc gccgcactta tgactgtctt ctttatcatg caactcgtag      2520
gacaggtgcc ggcagcgctc tgggtcattt tcggcgagga ccgctttcgc tggagcgcga      2580
cgatgatcgg cctgtcgctt gcggtattcg gaatcttgca cgccctcgct caagccttcg      2640
tcactggtcc cgccaccaaa cgtttcggcg agaagcaggc cattatcgcc ggcatggcgg      2700
ccgacgcgct gggctacgtc ttgctggcgt tcgcgacgcg aggctggatg ccttccccca      2760
ttatgattct tctcgcttcc ggcggcatcg ggatgcccgc gttgcaggcc atgctgtcca      2820
ggcaggtaga tgacgaccat cagggacagc ttcaaggatc gctcgcggct cttaccagcc      2880
taacttcgat cactggaccg ctgatcgtca cggcgattta tgccgcctcg gcgagcacat      2940
ggaacgggtt ggcatggatt gtaggcgccg ccctatacct tgtctgcctc cccgcgttgc      3000
gtcgcggtgc atggagccgg gccacctcga cctgaatgga agccggcggc acctcgctaa      3060
cggattcacc actccaagaa ttggagccaa tcaattcttg cggagaactg tgaatgcgca      3120
aaccaaccct tggcagaaca tatccatcgc gtccgccatc tccagcagcc gcacgcggcg      3180
catctcgggc agcgttgggt cctggccacg ggtgcgcatg atcgtgctcc tgtcgttgag      3240
gacccggcta ggctggcggg gttgccttac tggttagcag aatgaatcac cgatacgcga      3300
gcgaacgtga agcgactgct gctgcaaaac gtctgcgacc tgagcaacaa catgaatggt      3360
cttcggtttc cgtgtttcgt aaagtctgga aacgcggaag tcagcgccct gcaccattat      3420
```

```
gttccggatc tgcatcgcag gatgctgctg gctaccctgt ggaacaccta catctgtatt    3480
aacgaagcgc tggcattgac cctgagtgat ttttctctgg tcccgccgca tccataccgc    3540
cagttgttta ccctcacaac gttccagtaa ccgggcatgt tcatcatcag taacccgtat    3600
cgtgagcatc ctctctcgtt tcatcggtat cattaccccc atgaacagaa atccccctta    3660
cacggaggca tcagtgacca aacaggaaaa aaccgccctt aacatggccc gctttatcag    3720
aagccagaca ttaacgcttc tggagaaact caacgagctg gacgcggatg aacaggcaga    3780
catctgtgaa tcgcttcacg accacgctga tgagctttac cgcagctgcc tcgcgcgttt    3840
cggtgatgac ggtgaaaacc tctgacacat gcagctcccg gagacggtca cagcttgtct    3900
gtaagcggat gccgggagca gacaagcccg tcagggcgcg tcagcgggtg ttggcgggtg    3960
tcggggcgca gccatgaccc agtcacgtag cgatagcgga gtgtatactg gcttaactat    4020
gcggcatcag agcagattgt actgagagtg caccatatat gcggtgtgaa ataccgcaca    4080
gatgcgtaag gagaaaatac cgcatcaggc gctcttccgc ttcctcgctc actgactcgc    4140
tgcgctcggt cgttcggctg cggcgagcgg tatcagctca ctcaaaggcg gtaatacggt    4200
tatccacaga atcaggggat aacgcaggaa agaacatgtg agcaaaaggc cagcaaaagg    4260
ccaggaaccg taaaaaggcc gcgttgctgg cgtttttcca taggctccgc ccccctgacg    4320
agcatcacaa aaatcgacgc tcaagtcaga ggtggcgaaa cccgacagga ctataaagat    4380
accaggcgtt tccccctgga agctccctcg tgcgctctcc tgttccgacc ctgccgctta    4440
ccggatacct gtccgccttt ctcccttcgg gaagcgtggc gctttctcat agctcacgct    4500
gtaggtatct cagttcggtg taggtcgttc gctccaagct gggctgtgtg cacgaaccccc   4560
ccgttcagcc cgaccgctgc gccttatccg gtaactatcg tcttgagtcc aacccggtaa    4620
gacacgactt atcgccactg gcagcagcca ctggtaacag gattagcaga gcgaggtatg    4680
taggcggtgc tacagagttc ttgaagtggt ggcctaacta cggctacact agaaggacag    4740
tatttggtat ctgcgctctg ctgaagccag ttaccttcgg aaaaagagtt ggtagctctt    4800
gatccggcaa acaaaccacc gctggtagcg gtggtttttt tgtttgcaag cagcagatta    4860
cgcgcagaaa aaaaggatct caagaagatc ctttgatctt ttctacgggg tctgacgctc    4920
agtggaacga aaactcacgt taagggattt tggtcatgag attatcaaaa aggatcttca    4980
cctagatcct tttaaattaa aaatgaagtt ttaaatcaat ctaaagtata tatgagtaaa    5040
cttggtctga cagttaccaa tgcttaatca gtgaggcacc tatctcagcg atctgtctat    5100
ttcgttcatc catagttgcc tgactccccg tcgtgtagat aactacgata cgggagggct    5160
taccatctgg ccccagtgct gcaatgatac cgcgagaccc acgctcaccg gctccagatt    5220
tatcagcaat aaaccagcca gccggaaggg ccgagcgcag aagtggtcct gcaactttat    5280
ccgcctccat ccagtctatt aattgttgcc gggaagctag agtaagtagt tcgccagtta    5340
atagtttgcg caacgttgtt gccattgctg caggcatcgt ggtgtcacgc tcgtcgtttg    5400
gtatggcttc attcagctcc ggttcccaac gatcaaggcg agttacatga tcccccatgt    5460
tgtgcaaaaa agcggttagc tccttcggtc ctccgatcgt tgtcagaagt aagttggccg    5520
cagtgttatc actcatggtt atggcagcac tgcataattc tcttactgtc atgccatccg    5580
taagatgctt ttctgtgact ggtgagtact caaccaagtc attctgagaa tagtgtatgc    5640
ggcgaccgag ttgctcttgc ccggcgtcaa cacgggataa taccgcgcca catagcagaa    5700
ctttaaaagt gctcatcatt ggaaaacgtt cttcggggcg aaaactctca aggatcttac    5760
```

```
cgctgttgag atccagttcg atgtaaccca ctcgtgcacc caactgatct tcagcatctt    5820
ttactttcac cagcgtttct gggtgagcaa aaacaggaag gcaaaatgcc gcaaaaaagg    5880
gaataagggc gacacggaaa tgttgaatac tcatactctt cctttttcaa tattattgaa    5940
gcatttatca gggttattgt ctcatgagcg gatacatatt tgaatgtatt tagaaaaata    6000
aacaaatagg ggttccgcgc acatttcccc gaaaagtgcc acctgacgtc taagaaacca    6060
ttattatcat gacattaacc tataaaaata ggcgtatcac gaggccctt  cgtcttcaag    6120 aa                                                                  6122

<210> SEQ ID NO 96
<211> LENGTH: 10347
<212> TYPE: DNA
<213> ORGANISM: Artificial Sequence
<220> FEATURE:
<223> OTHER INFORMATION: Synthetic Sequence C41 Stab Map CARD (FCK mam)

<400> SEQUENCE: 96
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360 accccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
```

-continued

```
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtgaaaga tacctaaagg atcaacagct cctgggatt      1920 tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagacagag acagatcc attcgattag tgaacggatc ggcactgcgt      2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt     3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggaggt aggaagagcg atgatcactt gtggactaag     3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggatcc     3900 ggcgagatct ggaaactgtt cgaagacgcg ctgcagaagt ttgagcacga actgaaccag    3960
ttcgaggatc gtgtgcaact gggtggcagc ggcaagggca gcggtggcga aatcaaacaa    4020
```

| | |
|---|---|
| cgttgcgcgc gtgatctgcg taagtttgag gaagcgctga acgtttcga ggatctgaag | 4080 |
| cagaaaggtg gcagcggcga gatttggaaa ctgtttgaag acgcgctgca aaagcacgag | 4140 |
| gaagcgctga accagttcga agatctgaaa cagctgggtg gcagcggtaa aggcagcggt | 4200 |
| ggcgagatta agcagagcca cgaagacgcg ctgcgtaaac atgaggaagc gctgaagcgc | 4260 |
| tttgaggatc tgaagcaaaa atgaaccggt agtagcagtg agcaagggcg aggagctgtt | 4320 |
| caccgggggtg gtgcccatcc tggtcgagct ggacggcgac gtaaacggcc acaagttcag | 4380 |
| cgtgtccggc gagggcgagg gcgatgccac ctacggcaag ctgaccctga agttcatttg | 4440 |
| caccaccggc aagctgcccg tgccctggcc caccctcgtg accaccctga cctacggcgt | 4500 |
| gcagtgcttc agccgctacc ccgaccacat gaagcagcac gacttcttca agtccgccat | 4560 |
| gcccgaaggc tacgtccagg agcgcaccat cttcttcaag gacgacggca actacaagac | 4620 |
| ccgcgccgag gtgaagttcg agggcgacac cctggtgaac cgcatcgagc tgaagggcat | 4680 |
| cgacttcaag gaggacggca acatcctggg gcacaagctg gagtacaact acaacagcca | 4740 |
| caacgtctat atcatggccg acaagcagaa gaacggcatc aaggtgaact tcaagatccg | 4800 |
| ccacaacatc gaggacggca gcgtgcagct cgccgaccac taccagcaga caccccccat | 4860 |
| cggcgacggc cccgtgctgc tgcccgacaa ccactacctg agcacccagt ccgccctgag | 4920 |
| caaagacccc aacgagaagc gcgatcacat ggtcctgctg gagttcgtga ccgccgccgg | 4980 |
| gatcactctc ggcatggacg agctgtacaa gtaagaattc gatatcaagc ttatcgataa | 5040 |
| tcaacctctg gattacaaaa tttgtgaaag attgactggt attcttaact atgttgctcc | 5100 |
| ttttacgcta tgtggatacg ctgctttaat gcctttgtat catgctattg cttcccgtat | 5160 |
| ggctttcatt ttctcctcct tgtataaatc ctggttgctg tctctttatg aggagttgtg | 5220 |
| gcccgttgtc aggcaacgtg gcgtggtgtg cactgtgttt gctgacgcaa ccccccactgg | 5280 |
| ttggggcatt gccaccacct gtcagctcct ttccgggact ttcgctttcc cctccctat | 5340 |
| tgccacggcg gaactcatcg ccgcctgcct tgcccgctgc tggacagggg ctcggctgtt | 5400 |
| gggcactgac aattccgtgg tgttgtcggg gaaatcatcg tccttttcctt ggctgctcgc | 5460 |
| ctgtgttgcc acctggattc tgcgcgggac gtccttctgc tacgtccctt cggccctcaa | 5520 |
| tccagcggac cttccttccc gcggcctgct gccggctctg cggcctcttc cgcgtcttcg | 5580 |
| ccttcgccct cagacgagtc ggatctccct ttgggccgcc tccccgcatc gataccgtcg | 5640 |
| acctcgagac ctagaaaaac atggagcaat cacaagtagc aatacagcag ctaccaatgc | 5700 |
| tgattgtgcc tggctagaag cacaagagga ggaggaggtg ggttttccag tcacacctca | 5760 |
| ggtacccttta agaccaatga cttacaaggc agctgtagat cttagccact tttaaaaga | 5820 |
| aaaggggggga ctggaagggc taattcactc ccaacgaaga caagatatcc ttgatctgtg | 5880 |
| gatctaccac acacaaggct acttccctga ttggcagaac tacacaccag ggccagggat | 5940 |
| cagatatcca ctgacctttg gatggtgcta agctagta ccagttgagc aagagaaggt | 6000 |
| agaagaagcc aatgaaggag agaacacccg cttgttacac cctgtgagcc tgcatgggat | 6060 |
| ggatgacccg gagagagaag tattagagtg gaggtttgac agccgcctag catttcatca | 6120 |
| catgcccga gagctgcatc cggactgtac tgggtctctc tggttagacc agatctgagc | 6180 |
| ctgggagctc tctggctaac tagggaaccc actgcttaag cctcaataaa gcttgccttg | 6240 |
| agtgcttcaa gtagtgtgtg cccgtctgtt gtgtgactct ggtaactaga gatccctcag | 6300 |
| accctttttag tcagtgtgga aaatctctag cagggcccgt ttaaacccgc tgatcagcct | 6360 |
| cgactgtgcc ttctagttgc cagccatctg ttgtttgccc ctcccccgtg ccttccttga | 6420 |

```
ccctggaagg tgccactccc actgtccttt cctaataaaa tgaggaaatt gcatcgcatt      6480
gtctgagtag gtgtcattct attctggggg gtggggtggg gcaggacagc aaggggaggg     6540
attgggaaga caatagcagg catgctgggg atgcggtggg ctctatggct tctgaggcgg     6600
aaagaaccag ctggggctct aggggggtatc cccacgcgcc ctgtagcggc gcattaagcg    6660
cggcgggtgt ggtggttacg cgcagcgtga ccgctacact tgccagcgcc ctagcgcccg     6720
ctcctttcgc tttcttccct tcctttctcg ccacgttcgc cggctttccc cgtcaagctc     6780
taaatcgggg gctccctta gggttccgat ttagtgcttt acggcacctc gaccccaaaa      6840
aacttgatta gggtgatggt tcacgtagtg ggccatcgcc ctgatagacg ttttttcgcc     6900
ctttgacgtt ggagtccacg ttctttaata gtggactctt gttccaaact ggaacaacac     6960
tcaaccctat ctcggtctat tctttgatt tataagggat tttgccgatt tcggcctatt      7020
ggttaaaaaa tgagctgatt taacaaaaat ttaacgcgaa ttaattctgt ggaatgtgtg     7080
tcagttaggg tgtggaaagt ccccaggctc cccagcaggc agaagtatgc aaagcatgca     7140
tctcaattag tcagcaacca ggtgtggaaa gtccccaggc tccccagcag gcagaagtat     7200
gcaaagcatg catctcaatt agtcagcaac catagtcccg cccctaactc cgcccatccc     7260
gcccctaact ccgcccagtt ccgcccattc tccgccccat ggctgactaa ttttttttat     7320
ttatgcagag gccgaggccg cctctgcctc tgagctattc cagaagtagt gaggaggctt     7380
ttttggaggc ctaggctttt gcaaaaagct cccgggagct tgtatatcca ttttcggatc     7440
tgatcagcac gtgttgacaa ttaatcatcg gcatagtata tcggcatagt ataatacgac     7500
aaggtgagga actaaaccat ggccaagttg accagtgccg ttccggtgct caccgcgcgc    7560
gacgtcgccg gagcggtcga gttctggacc gaccggctcg ggttctcccg ggacttcgtg    7620
gaggacgact tcgccggtgt ggtccgggac gacgtgaccc tgttcatcag cgcggtccag    7680
gaccaggtgg tgccggacaa caccctggcc tgggtgtggg tgcgcggcct ggacgagctg    7740
tacgccgagt ggtcggaggt cgtgtccacg aacttccggg acgcctccgg ccggccatg     7800 accgagatcg cgcagcagcc gtgggggcgg gagttcgccc tgcgcgaccc ggccggcaac    7860
tgcgtgcact tcgtggccga ggagcaggac tgacacgtgc tacgagattt cgattccacc    7920
gccgccttct atgaaaggtt gggcttcgga atcgttttcc gggacgccgg ctggatgatc    7980
ctccagcgcg ggatctcat gctggagttc ttcgcccacc ccaacttgtt tattgcagct     8040
tataatggtt acaaataaag caatagcatc acaaatttca caaataaagc atttttttca    8100
ctgcattcta gttgtggttt gtccaaactc atcaatgtat cttatcatgt ctgtataccg    8160
tcgacctcta gctagagctt ggcgtaatca tggtcatagc tgtttcctgt gtgaaattgt    8220
tatccgctca caattccaca acatacga gccgaagca taaagtgtaa agcctggggt       8280
gcctaatgag tgagctaact cacattaatt gcgttgcgct cactgcccgc tttccagtcg    8340
ggaaacctgt cgtgccagct gcattaatga atcggccaac gcgcggggag aggcggtttg    8400
cgtattgggc gctcttccgc ttcctcgctc actgactcgc tgcgctcggt cgttcggctg    8460
cggcgagcgg tatcagctca ctcaaaggcg gtaatacggt tatccacaga atcaggggat    8520
aacgcaggaa agaacatgtg agcaaaaggc cagcaaaagg ccaggaaccg taaaaaggcc    8580
gcgttgctgg cgtttttcca taggctccgc cccctgacg agcatcacaa aaatcgacgc     8640
tcaagtcaga ggtggcgaaa cccgacagga ctataaagat accaggcgtt tcccctggaa     8700
agctccctcg tgcgctctcc tgttccgacc ctgccgctta ccggatacct gtccgccttt    8760
```

```
ctcccttcgg gaagcgtggc gctttctcat agctcacgct gtaggtatct cagttcggtg    8820
taggtcgttc gctccaagct gggctgtgtg cacgaacccc ccgttcagcc cgaccgctgc    8880
gccttatccg gtaactatcg tcttgagtcc aacccggtaa gacacgactt atcgccactg    8940
gcagcagcca ctggtaacag gattagcaga gcgaggtatg taggcggtgc tacagagttc    9000
ttgaagtggt ggcctaacta cggctacact agaagaacag tatttggtat ctgcgctctg    9060
ctgaagccag ttccttcgg aaaaagagtt ggtagctctt gatccggcaa acaaaccacc    9120
gctggtagcg gtggttttttt tgtttgcaag cagcagatta cgcgcagaaa aaaggatct    9180 caagaagatc ctttgatctt ttctacgggg tctgacgctc agtggaacga aaactcacgt    9240
taagggattt tggtcatgag attatcaaaa aggatcttca cctagatcct tttaaattaa    9300
aaatgaagtt ttaaatcaat ctaaagtata tatgagtaaa cttggtctga cagttaccaa    9360
tgcttaatca gtgaggcacc tatctcagcg atctgtctat ttcgttcatc catagttgcc    9420 tgactcccg tcgtgtagat aactacgata cgggagggct taccatctgg ccccagtgct    9480
gcaatgatac cgcgagaccc acgctcaccg gctccagatt tatcagcaat aaaccagcca    9540
gccggaaggg ccgagcgcag aagtggtcct gcaactttat ccgcctccat ccagtctatt    9600
aattgttgcc gggaagctag agtaagtagt tcgccagtta atagtttgcg caacgttgtt    9660
gccattgcta caggcatcgt ggtgtcacgc tcgtcgtttg gtatggcttc attcagctcc    9720
ggttcccaac gatcaaggcg agttacatga tcccccatgt tgtgcaaaaa agcggttagc    9780
tccttcggtc ctccgatcgt tgtcagaagt aagttggccg cagtgttatc actcatggtt    9840
atggcagcac tgcataattc tcttactgtc atgccatccg taagatgctt ttctgtgact    9900
ggtgagtact caaccaagtc attctgagaa tagtgtatgc ggcgaccgag ttgctcttgc    9960
ccggcgtcaa tacgggataa taccgcgcca catagcagaa ctttaaaagt gctcatcatt    10020
ggaaaacgtt cttcggggcg aaaactctca aggatcttac cgctgttgag atccagttcg    10080
atgtaaccca ctcgtgcacc caactgatct tcagcatctt ttactttcac cagcgtttct    10140
gggtgagcaa aaacaggaag gcaaaatgcc gcaaaaaagg gaataagggc gacacggaaa    10200
tgttgaatac tcatactctt cctttttcaa tattattgaa gcatttatca gggttattgt    10260
ctcatgagcg gatacatatt tgaatgtatt tagaaaaata aacaaatagg ggttccgcgc    10320
acatttcccc gaaaagtgcc acctgac                                        10347
```

```
<210> SEQ ID NO 97
<211> LENGTH: 126
<212> TYPE: PRT
<213> ORGANISM: Artificial Sequence
<220> FEATURE:
<223> OTHER INFORMATION: Synthetic Sequence C41 Stab Map CARD

<400> SEQUENCE: 97

Glu Ile Trp Lys Leu Phe Glu Asp Ala Leu Gln Lys Phe Glu His Glu
1               5                   10                  15

Leu Asn Gln Phe Glu Asp Arg Val Gln Leu Gly Gly Ser Gly Lys Gly
                20                  25                  30

Ser Gly Gly Glu Ile Lys Gln Arg Cys Ala Arg Asp Leu Arg Lys Phe
            35                  40                  45

Glu Glu Ala Leu Lys Arg Phe Glu Asp Leu Lys Gln Lys Gly Gly Ser
        50                  55                  60

Gly Glu Ile Trp Lys Leu Phe Glu Asp Ala Leu Gln Lys His Glu Glu
65                  70                  75                  80
```

Ala Leu Asn Gln Phe Glu Asp Leu Lys Gln Leu Gly Gly Ser Gly Lys
            85                  90                  95

Gly Ser Gly Gly Glu Ile Lys Gln Ser His Glu Asp Ala Leu Arg Lys
        100                 105                 110

His Glu Glu Ala Leu Lys Arg Phe Glu Asp Leu Lys Gln Lys
        115                 120                 125

<210> SEQ ID NO 98
<211> LENGTH: 6122
<212> TYPE: DNA
<213> ORGANISM: Artificial Sequence
<220> FEATURE:
<223> OTHER INFORMATION: Synthetic Sequence C41 Py Stab (E. Coli)

<400> SEQUENCE: 98

| | | | | | | |
|---|---|---|---|---|---|---|
| ttctcatgtt | tgacagctta | tcatcgataa | gctttaatgc | ggtagtttat | cacagttaaa | 60 |
| ttgctaacgc | agtcaggcac | cgtgtatgaa | atctaacaat | gcgctcatcg | tcatcctcgg | 120 |
| caccgtcacc | ctggatgctg | taggcatagg | cttggttatg | ccgtactgcc | gggcctctt | 180 |
| gcgggatatc | cggatatagt | tcctcctttc | agcaaaaaac | ccctcaagac | ccgtttagag | 240 |
| gccccaaggg | gttatgctag | ttattgctca | gcggtggcag | cagccaactc | agcttccttt | 300 |
| cgggctttgt | tagcagccgg | atcctcgaga | ccggttcatt | tttgcttcag | atcctcaaag | 360 |
| cgcttcagcg | cttcctcatg | tttacgcagc | gcgtcttcgc | tacgctgctt | aatctcgcca | 420 |
| ccgctgcctt | taccgctgcc | acccagctgt | tgtgatctt | cgaactggtt | cagcgcttcc | 480 |
| tcgtgctttt | gcagcgcgtc | ttcaaacagt | tccaaatct | cgccgctgcc | acctttctgc | 540 |
| ttcagatcct | cgaaacgttt | cagcgcttcc | tcaaacttac | gcaggtcacg | cgcgcacagt | 600 |
| tgtttgattt | cgccaccgct | gcccttgccg | ctgccaccca | gttgcacacg | atcctcgaac | 660 |
| tggttcaggt | cttcctcaaa | cttctgcagc | gcgtcttcga | acagtttcca | gatctcgccg | 720 |
| gatccctgaa | aatacaggtt | tcaccatcg | cctccgtggt | gatgatggtg | atgcccacct | 780 |
| ttacccatat | gaatatcgcc | ttccatggta | tatctccttc | ttaaagttaa | acaaaattat | 840 |
| ttctagaggg | gaattgttat | ccgctcacaa | ttccccctata | gtgagtcgta | ttaatttcgc | 900 |
| gggatcgaga | tctcgatcct | ctacgccgga | cgcatcgtgg | ccggcatcac | cggcgccaca | 960 |
| ggtgcggttg | ctggcgccta | tatcgccgac | atcaccgatg | gggaagatcg | ggctcgccac | 1020 |
| ttcgggctca | tgagcgcttg | tttcggcgtg | ggtatggtgg | caggccccgt | ggccggggga | 1080 |
| ctgttgggcg | ccatctcctt | gcatgcacca | ttccttgcgg | cggcggtgct | caacggcctc | 1140 |
| aacctactac | tgggctgctt | cctaatgcag | gagtcgcata | agggagagcg | tcgagatccc | 1200 |
| ggacaccatc | gaatggcgca | aaacctttcg | cggtatggca | tgatagcgcc | cggaagagag | 1260 |
| tcaattcagg | gtggtgaatg | tgaaaccagt | aacgttatac | gatgtcgcag | agtatgccgg | 1320 |
| tgtctcttat | cagaccgttt | cccgcgtggt | gaaccaggcc | agccacgttt | ctgcgaaaac | 1380 |
| gcgggaaaaa | gtggaagcgg | cgatggcgga | gctgaattac | attcccaacc | gcgtggcaca | 1440 |
| acaactggcg | ggcaaacagt | cgttgctgat | tggcgttgcc | acctccagtc | tggccctgca | 1500 |
| cgcgccgtcg | caaattgtcg | cggcgattaa | atctcgcgcc | gatcaactgg | gtgccagcgt | 1560 |
| ggtggtgtcg | atggtagaac | gaagcggcgt | cgaagcctgt | aaagcggcgg | tgcacaatct | 1620 |
| tctcgcgcaa | cgcgtcagtg | ggctgatcat | taactatccg | ctggatgacc | aggatgccat | 1680 |
| tgctgtggaa | gctgcctgca | ctaatgttcc | ggcgttattt | cttgatgtct | ctgaccagac | 1740 |
| acccatcaac | agtattattt | tctcccatga | agacggtacg | cgactgggcg | tggagcatct | 1800 |

-continued

```
ggtcgcattg ggtcaccagc aaatcgcgct gttagcgggc ccattaagtt ctgtctcggc   1860
gcgtctgcgt ctggctggct ggcataaata tctcactcgc aatcaaattc agccgatagc   1920
ggaacgggaa ggcgactgga gtgccatgtc cggttttcaa caaaccatgc aaatgctgaa   1980
tgagggcatc gttcccactg cgatgctggt tgccaacgat cagatggcgc tgggcgcaat   2040
gcgcgccatt accgagtccg ggctgcgcgt tggtgcggat atctcggtag tgggatacga   2100
cgataccgaa gacagctcat gttatatccc gccgttaacc accatcaaac aggattttcg   2160
cctgctgggg caaaccagcg tggaccgctt gctgcaactc tctcagggcc aggcggtgaa   2220
gggcaatcag ctgttgcccg tctcactggt gaaaagaaaa accaccctgg cgcccaatac   2280
gcaaaccgcc tctccccgcg cgttggccga ttcattaatg cagctggcac gacaggtttc   2340
ccgactggaa agcgggcagt gagcgcaacg caattaatgt aagttagctc actcattagg   2400
cacccgggatc tcgaccgatg cccttgagag ccttcaaccc agtcagctcc ttccggtggg   2460
cgcggggcat gactatcgtc gccgcactta tgactgtctt ctttatcatg caactcgtag   2520
gacaggtgcc ggcagcgctc tgggtcattt tcggcgagga ccgctttcgc tggagcgcga   2580
cgatgatcgg cctgtcgctt gcggtattcg gaatcttgca cgccctcgct caagccttcg   2640
tcactggtcc cgccaccaaa cgtttcggcg agaagcaggc cattatcgcc ggcatggcgg   2700
ccgacgcgct gggctacgtc ttgctggcgt cgcgacgcg aggctggatg ccttcccca    2760
ttatgattct tctcgcttcc ggcggcatcg ggatgcccgc gttgcaggcc atgctgtcca   2820
ggcaggtaga tgacgaccat cagggacagc ttcaaggatc gctcgcggct cttaccagcc   2880
taacttcgat cactggaccg ctgatcgtca cggcgattta tgccgcctcg gcgagcacat   2940
ggaacgggtt ggcatggatt gtaggcgccg ccctatacct tgtctgcctc cccgcgttgc   3000
gtcgcggtgc atggagccgg gccacctcga cctgaatgga agccggcggc acctcgctaa   3060
cggattcacc actccaagaa ttggagccaa tcaattcttg cggagaactg tgaatgcgca   3120
aaccaaccct tggcagaaca tatccatcgc gtccgccatc tccagcagcc gcacgcggcg   3180
catctcgggc agcgttgggt cctggccacg ggtgcgcatg atcgtgctcc tgtcgttgag   3240
gacccggcta ggctggcggg gttgccttac tggttagcag aatgaatcac cgatacgcga   3300
gcgaacgtga agcgactgct gctgcaaaac gtctgcgacc tgagcaacaa catgaatggt   3360
cttcggtttc cgtgtttcgt aaagtctgga aacgcggaag tcagcgccct gcaccattat   3420
gttccggatc tgcatcgcag gatgctgctg gctaccctgt ggaacaccta catctgtatt   3480
aacgaagcgc tggcattgac cctgagtgat ttttctctgg tcccgccgca tccataccgc   3540
cagttgttta ccctcacaac gttccagtaa ccgggcatgt tcatcatcag taacccgtat   3600
cgtgagcatc ctctctcgtt tcatcggtat cattaccccc atgaacagaa atccccctta   3660
cacggaggca tcagtgacca aacaggaaaa aaccgccctt aacatggccc gctttatcag   3720
aagccagaca ttaacgcttc tggagaaact caacgagctg gacgcggatg aacaggcaga   3780
catctgtgaa tcgcttcacg accacgctga tgagctttac cgcagctgcc tcgcgcgttt   3840
cggtgatgac ggtgaaaacc tctgacacat gcagctcccg gagacggtca gcttgtct    3900
gtaagcggat gccgggagca gacaagcccg tcagggcgcg tcagcgggtg ttggcgggtg   3960
tcggggcgca gccatgaccc agtcacgtag cgatagcgga gtgtatactg gcttaactat   4020
gcggcatcag agcagattgt actgagagtg caccatatat gcggtgtgaa ataccgcaca   4080
gatgcgtaag gagaaaatac cgcatcaggc gctcttccgc ttcctcgctc actgactcgc   4140
tgcgctcggt cgttcggctg cggcgagcgg tatcagctca ctcaaaggcg gtaatacggt   4200
```

```
tatccacaga atcaggggat aacgcaggaa agaacatgtg agcaaaaggc cagcaaaagg    4260
ccaggaaccg taaaaaggcc gcgttgctgg cgttttttcca taggctccgc ccccctgacg    4320
agcatcacaa aaatcgacgc tcaagtcaga ggtggcgaaa cccgacagga ctataaagat    4380
accaggcgtt tccccctgga agctccctcg tgcgctctcc tgttccgacc ctgccgctta    4440
ccggatacct gtccgccttt ctcccttcgg gaagcgtggc gctttctcat agctcacgct    4500
gtaggtatct cagttcggtg taggtcgttc gctccaagct gggctgtgtg cacgaacccc    4560
ccgttcagcc cgaccgctgc gccttatccg gtaactatcg tcttgagtcc aacccggtaa    4620
gacacgactt atcgccactg gcagcagcca ctggtaacag gattagcaga gcgaggtatg    4680
taggcggtgc tacagagttc ttgaagtggt ggcctaacta cggctacact agaaggacag    4740
tatttggtat ctgcgctctg ctgaagccag ttaccttcgg aaaaagagtt ggtagctctt    4800
gatccggcaa acaaaccacc gctggtagcg gtggtttttt tgtttgcaag cagcagatta    4860
cgcgcagaaa aaaaggatct caagaagatc ctttgatctt ttctacgggg tctgacgctc    4920
agtggaacga aaactcacgt taagggattt tggtcatgag attatcaaaa aggatcttca    4980
cctagatcct tttaaattaa aaatgaagtt ttaaatcaat ctaaagtata tatgagtaaa    5040
cttggtctga cagttaccaa tgcttaatca gtgaggcacc tatctcagcg atctgtctat    5100
ttcgttcatc catagttgcc tgactccccg tcgtgtagat aactacgata cgggagggct    5160
taccatctgg ccccagtgct gcaatgatac cgcgagaccc acgctcaccg gctccagatt    5220
tatcagcaat aaaccagcca gccggaaggg ccgagcgcag aagtggtcct gcaactttat    5280
ccgcctccat ccagtctatt aattgttgcc gggaagctag agtaagtagt tcgccagtta    5340
atagtttgcg caacgttgtt gccattgctg caggcatcgt ggtgtcacgc tcgtcgtttg    5400
gtatggcttc attcagctcc ggttcccaac gatcaaggcg agttacatga tcccccatgt    5460
tgtgcaaaaa agcggttagc tccttcggtc ctccgatcgt tgtcagaagt aagttggccg    5520
cagtgttatc actcatggtt atggcagcac tgcataattc tcttactgtc atgccatccg    5580
taagatgctt ttctgtgact ggtgagtact caaccaagtc attctgagaa tagtgtatgc    5640
ggcgaccgag ttgctcttgc ccggcgtcaa cacgggataa taccgcgcca catagcagaa    5700
ctttaaaagt gctcatcatt ggaaaacgtt cttcggggcg aaaactctca aggatcttac    5760
cgctgttgag atccagttcg atgtaaccca ctcgtgcacc caactgatct tcagcatctt    5820
ttactttcac cagcgtttct gggtgagcaa aaacaggaag gcaaaatgcc gcaaaaaagg    5880
gaataagggc gacacggaaa tgttgaatac tcatactctt cctttttcaa tattattgaa    5940
gcatttatca gggttattgt ctcatgagcg gatacatatt tgaatgtatt tagaaaaata    6000
aacaaatagg ggttccgcgc acatttcccc gaaaagtgcc acctgacgtc taagaaacca    6060
ttattatcat gacattaacc tataaaaata ggcgtatcac gaggcccttt cgtcttcaag    6120
aa    6122
```

<210> SEQ ID NO 99
<211> LENGTH: 10347
<212> TYPE: DNA
<213> ORGANISM: Artificial Sequence
<220> FEATURE:
<223> OTHER INFORMATION: Synthetic Sequence C41 Py Stab (FCK mam)

<400> SEQUENCE: 99

```
gtcgacggat cgggagatct cccgatcccc tatggtgcac tctcagtaca atctgctctg    60
```

-continued

| | |
|---|---|
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca aacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg cccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg agggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctgggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |
| agaatagttt ttgctgtact ttctatagtg aatagagtta ggcagggata ttcaccatta | 2280 |
| tcgtttcaga cccacctccc aaccccgagg ggacccgaca ggcccgaagg aatagaagaa | 2340 |
| gaaggtggag agagacag agacagatcc attcgattag tgaacggatc ggcactgcgt | 2400 |
| gcgccaattc tgcagacaaa tggcagtatt catccacaat tttaaaagaa aagggggat | 2460 |

```
tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggcggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggggaggt aggaagagcg atgatcactt gtggactaag    3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg cccctagtt ctgggggcag cggggatcc     3900 ggcgagatct ggaaactgtt cgaagacgcg ctgcagaagt tgaggaaga cctgaaccag     3960 ttcgaggatc gtgtgcaact gggtggcagc ggcaagggca gcggtggcga aatcaaacaa    4020
ctgtgcgcgc gtgacctgcg taagtttgag gaagcgctga acgtttcga ggatctgaag     4080 cagaaaggtg gcagcggcga gatttggaaa ctgtttgaag acgcgctgca aaagcacgag    4140
gaagcgctga accagttcga agatcacaaa cagctgggtg gcagcggtaa aggcagcggt    4200
ggcgagatta gcagcgtag cgaagacgcg ctgcgtaaac atgaggaagc gctgaagcgc     4260
tttgaggatc tgaagcaaaa atgaaccggt agtagcagtg agcaagggcg aggagctgtt    4320
caccggggtg gtgcccatcc tggtcgagct ggacggcgac gtaaacggcc acaagttcag    4380
cgtgtccggc gagggcgagg gcgatgccac ctacggcaag ctgaccctga agttcatttg    4440
caccaccggc aagctgcccg tgccctggcc caccctcgtg accaccctga cctacggcgt    4500
gcagtgcttc agccgctacc ccgaccacat gaagcagcac gacttcttca gtccgccat     4560 gcccgaaggc tacgtccagg agcgcaccat cttcttcaag gacgacggca actacaagac    4620
ccgcgccgag gtgaagttcg agggcgacac cctggtgaac cgcatcgagc tgaagggcat    4680
cgacttcaag gaggacggca acatcctggg gcacaagctg gagtacaact acaacagcca    4740
caacgtctat atcatggccg acaagcagaa gaacggcatc aaggtgaact tcaagatccg    4800
```

```
ccacaacatc gaggacggca gcgtgcagct cgccgaccac taccagcaga acaccccat    4860 cggcgacggc cccgtgctgc tgcccgacaa ccactacctg agcacccagt ccgccctgag    4920
caaagacccc aacgagaagc gcgatcacat ggtcctgctg gagttcgtga ccgccgccgg    4980
gatcactctc ggcatggacg agctgtacaa gtaagaattc gatatcaagc ttatcgataa    5040
tcaacctctg gattacaaaa tttgtgaaag attgactggt attcttaact atgttgctcc    5100
ttttacgcta tgtggatacg ctgctttaat gcctttgtat catgctattg cttcccgtat    5160
ggctttcatt ttctcctcct tgtataaatc ctggttgctg tctctttatg aggagttgtg    5220
gcccgttgtc aggcaacgtg gcgtggtgtg cactgtgttt gctgacgcaa ccccactgg    5280 ttggggcatt gccaccacct gtcagctcct ttccgggact ttcgctttcc cctccctat    5340 tgccacggcg gaactcatcg ccgcctgcct tgcccgctgc tggacagggg ctcggctgtt    5400
gggcactgac aattccgtgg tgttgtcggg gaaatcatcg tccttt cctt ggctgctcgc    5460 ctgtgttgcc acctggattc tgcgcgggac gtccttctgc tacgtccctt cggccctcaa    5520
tccagcggac cttccttccc gcggcctgct gccggctctg cggcctcttc cgcgtcttcg    5580
ccttcgccct cagacgagtc ggatctccct ttgggccgcc tccccgcatc gataccgtcg    5640
acctcgagac ctagaaaaac atggagcaat cacaagtagc aatacagcag ctaccaatgc    5700
tgattgtgcc tggctagaag cacaagagga ggaggaggtg ggttttccag tcacacctca    5760
ggtaccttta agaccaatga cttacaaggc agctgtagat cttagccact ttttaaaaga    5820 aaaggggga ctggaagggc taattcactc ccaacgaaga caagatatcc ttgatctgtg    5880
gatctaccac acacaaggct acttccctga ttggcagaac tacacaccag gccagggat    5940 cagatatcca ctgacctttg gatggtgcta caagctagta ccagttgagc aagagaaggt    6000
agaagaagcc aatgaaggag agaacacccg cttgttacac cctgtgagcc tgcatgggat    6060
ggatgacccg gagagagaag tattagagtg gaggtttgac agccgcctag catttcatca    6120
catggcccga gagctgcatc cggactgtac tgggtctctc tggttagacc agatctgagc    6180
ctgggagctc tctggctaac tagggaaccc actgcttaag cctcaataaa gcttgccttg    6240
agtgcttcaa gtagtgtgtg cccgtctgtt gtgtgactct ggtaactaga tccctcag    6300 acccttttag tcagtgtgga aaatctctag caggcccgt ttaaacccgc tgatcagcct    6360
cgactgtgcc ttctagttgc cagccatctg ttgtttgccc ctcccccgtg ccttccttga    6420
ccctggaagg tgccactccc actgtccttt cctaataaaa tgaggaaatt gcatcgcatt    6480
gtctgagtag tgtcattct attctggggg gtggggtggg gcaggacagc aagggggagg    6540
attgggaaga caatagcagg catgctgggg atgcggtggg ctctatggct tctgaggcgg    6600
aaagaaccag ctgggggctct aggggggtatc cccacgcgcc ctgtagcggc gcattaagcg    6660
cggcgggtgt ggtggttacg cgcagcgtga ccgctacact tgccagcgcc ctagcgcccg    6720 ctccttcgc tttcttccct tcctttctcg ccacgttcgc cggctttccc cgtcaagctc    6780
taaatcgggg gctcccttta gggttccgat ttagtgcttt acggcacctc gacccccaaaa    6840 aacttgatta gggtgatggt tcacgtagtg gccatcgcc ctgatagacg gtttttcgcc    6900
ctttgacgtt ggagtccacg ttctttaata gtggactctt gttccaaact ggaacaacac    6960
tcaaccctat ctcggtctat tcttttgatt tataagggat tttgccgatt tcggcctatt    7020
ggttaaaaaa tgagctgatt taacaaaaat ttaacgcgaa ttaattctgt ggaatgtgtg    7080
tcagttaggg tgtggaaagt ccccaggctc cccagcaggc agaagtatgc aaagcatgca    7140
tctcaattag tcagcaacca ggtgtggaaa gtccccaggc tccccagcag gcagaagtat    7200
```

```
gcaaagcatg catctcaatt agtcagcaac catagtcccg ccectaactc cgeccatccc    7260 gccectaact ccgcccagtt ccgcccattc tccgecccat ggctgactaa tttttttat    7320 ttatgcagag gccgaggccg cctctgcctc tgagctattc cagaagtagt gaggaggctt    7380
ttttggaggc ctaggctttt gcaaaaagct cccgggagct tgtatatcca ttttcggatc    7440
tgatcagcac gtgttgacaa ttaatcatcg gcatagtata tcggcatagt ataatacgac    7500
aaggtgagga actaaaccat ggccaagttg accagtgccg ttccggtgct caccgcgcgc    7560
gacgtcgccg gagcggtcga gttctggacc gaccggctcg ggttctcccg ggacttcgtg    7620
gaggacgact tcgccggtgt ggtccgggac gacgtgaccc tgttcatcag cgcggtccag    7680
gaccaggtgg tgccggacaa caccctggcc tgggtgtggg tgcgcggcct ggacgagctg    7740
tacgccgagt ggtcggaggt cgtgtccacg aacttccggg acgcctccgg gccggccatg    7800
accgagatcg gcgagcagcc gtgggggcgg gagttcgccc tgcgcgaccc ggccggcaac    7860
tgcgtgcact tcgtggccga ggagcaggac tgacacgtgc tacgagattt cgattccacc    7920
gccgccttct atgaaaggtt gggcttcgga atcgttttcc gggacgccgg ctggatgatc    7980
ctccagcgcg gggatctcat gctggagttc ttcgcccacc ccaacttgtt tattgcagct    8040
tataatggtt acaaataaag caatagcatc acaaatttca caaataaagc atttttttca    8100
ctgcattcta gttgtggttt gtccaaactc atcaatgtat cttatcatgt ctgtataccg    8160
tcgacctcta gctagagctt ggcgtaatca tggtcatagc tgtttcctgt gtgaaattgt    8220
tatccgctca caattccaca acatacga gccggaagca taagtgtaa agcctggggt    8280 gcctaatgag tgagctaact cacattaatt gcgttgcgct cactgcccgc tttccagtcg    8340
ggaaacctgt cgtgccagct gcattaatga atcggccaac gcgcggggag aggcggtttg    8400
cgtattgggc gctcttccgc ttcctcgctc actgactcgc tgcgctcggt cgttcggctg    8460
cggcgagcgg tatcagctca ctcaaaggcg gtaatacggt tatccacaga atcaggggat    8520
aacgcaggaa agaacatgtg agcaaaaggc cagcaaaagg ccaggaaccg taaaaaggcc    8580
gcgttgctgg cgtttttcca taggctccgc cccctgacg agcatcacaa aaatcgacgc    8640
tcaagtcaga ggtggcgaaa cccgacagga ctataaagat accaggcgtt tccccctgga    8700
agctccctcg tgcgctctcc tgttccgacc ctgccgctta ccggatacct gtccgccttt    8760
ctcccttcgg aagcgtggc gctttctcat agctcacgct gtaggtatct cagttcggtg    8820
taggtcgttc gctccaagct gggctgtgtg cacgaacccc ccgttcagcc cgaccgctgc    8880
gccttatccg gtaactatcg tcttgagtcc aacccggtaa gacacgactt atcgccactg    8940
gcagcagcca ctggtaacag gattagcaga gcgaggtatg taggcggtgc tacagagttc    9000
ttgaagtggt ggcctaacta cggctacact agaagaacag tatttggtat ctgcgctctg    9060
ctgaagccag ttaccttcgg aaaaagagtt ggtagctctt gatccggcaa acaaaccacc    9120
gctggtagcg gtggtttttt tgtttgcaag cagcagatta cgcgcagaaa aaaggatct    9180 caagaagatc ctttgatctt ttctacgggg tctgacgctc agtggaacga aaactcacgt    9240
taagggattt tggtcatgag attatcaaaa aggatcttca cctagatcct ttaaattaa    9300 aaatgaagtt ttaaatcaat ctaaagtata tatgagtaaa cttggtctga cagttaccaa    9360
tgcttaatca gtgaggcacc tatctcagcg atctgtctat ttcgttcatc catagttgcc    9420
tgactccccg tcgtgtagat aactacgata cgggagggct taccatctgg ccccagtgct    9480
gcaatgatac cgcgagaccc acgctcaccg gctccagatt tatcagcaat aaaccagcca    9540
```

```
gccggaaggg ccgagcgcag aagtggtcct gcaactttat ccgcctccat ccagtctatt    9600
aattgttgcc gggaagctag agtaagtagt tcgccagtta atagtttgcg caacgttgtt    9660
gccattgcta caggcatcgt ggtgtcacgc tcgtcgtttg gtatggcttc attcagctcc    9720
ggttcccaac gatcaaggcg agttacatga tccccatgt tgtgcaaaaa agcggttagc    9780
tccttcggtc ctccgatcgt tgtcagaagt aagttggccg cagtgttatc actcatggtt    9840
atggcagcac tgcataattc tcttactgtc atgccatccg taagatgctt ttctgtgact    9900
ggtgagtact caaccaagtc attctgagaa tagtgtatgc ggcgaccgag ttgctcttgc    9960
ccggcgtcaa tacgggataa taccgcgcca catagcagaa ctttaaaagt gctcatcatt   10020
ggaaaacgtt cttcggggcg aaaactctca aggatcttac cgctgttgag atccagttcg   10080
atgtaaccca ctcgtgcacc caactgatct tcagcatctt ttactttcac cagcgtttct   10140
gggtgagcaa aaacaggaag gcaaaatgcc gcaaaaaagg gaataagggc gacacggaaa   10200
tgttgaatac tcatactctt ccttttcaa tattattgaa gcatttatca gggttattgt   10260
ctcatgagcg gatacatatt tgaatgtatt tagaaaaata acaaatagg ggttccgcgc   10320 acatttcccc gaaaagtgcc acctgac                                      10347
```

```
<210> SEQ ID NO 100
<211> LENGTH: 126
<212> TYPE: PRT
<213> ORGANISM: Artificial Sequence
<220> FEATURE:
<223> OTHER INFORMATION: Synthetic Sequence C41 Py Stab

<400> SEQUENCE: 100

Glu Ile Trp Lys Leu Phe Glu Asp Ala Leu Gln Lys Phe Glu Glu Asp
1               5                   10                  15

Leu Asn Gln Phe Glu Asp Arg Val Gln Leu Gly Gly Ser Gly Lys Gly
            20                  25                  30

Ser Gly Gly Glu Ile Lys Gln Leu Cys Ala Arg Asp Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Leu Phe Glu Asp Ala Leu Gln Lys His Glu Glu
65                  70                  75                  80

Ala Leu Asn Gln Phe Glu Asp His Lys Gln Leu Gly Gly Ser Gly Lys
                85                  90                  95

Gly Ser Gly Gly Glu Ile Lys Gln Arg Ser Glu Asp Ala Leu Arg Lys
            100                 105                 110

His Glu Glu Ala Leu Lys Arg Phe Glu Asp Leu Lys Gln Lys
        115                 120                 125
```

```
<210> SEQ ID NO 101
<211> LENGTH: 4455
<212> TYPE: DNA
<213> ORGANISM: Artificial Sequence
<220> FEATURE:
<223> OTHER INFORMATION: Synthetic Sequence BT6 CysAla (E. Coli)

<400> SEQUENCE: 101
cccgtagaaa agatcaaagg atcttcttga gatccttttt ttctgcgcgt aatctgctgc      60
ttgcaaacaa aaaaaccacc gctaccagcg gtggtttgtt tgccggatca agagctacca    120
actctttttc cgaaggtaac tggcttcagc agagcgcaga taccaaatac tgttcttcta    180
gtgtagccgt agttagccca ccacttcaag aactctgtag caccgcctac atacctcgct    240
```

-continued

```
ctgctaatcc tgttaccagt ggctgctgcc agtggcgata agtcgtgtct taccgggttg       300
gactcaagac gatagttacc ggataaggcg cagcggtcgg gctgaacggg gggttcgtgc       360
acacagccca gcttggagcg aacgacctac accgaactga gatacctaca gcgtgagcta       420
tgagaaagcg ccacgcttcc cgaagggaga aaggcggaca ggtatccggt aagcggcagg       480
gtcggaacag gagagcgcac gagggagctt ccaggggaa acgcctggta tctttatagt        540
cctgtcgggt ttcgccacct ctgacttgag cgtcgatttt tgtgatgctc gtcaggggg        600 cggagcctat ggaaaaacgc cagcaacgcg gcctttttac ggttcctggc cttttgctgg       660
ccttttgctc acatgttctt tcctgcgtta tcccctgatt ctgtggataa ccgtattacc       720
gcctttgagt gagctgatac cgctcgccgc agccgaacga ccgagcgcag cgagtcagtg       780
agcgaggaag cggaaggcga gagtagggaa ctgccaggca tcaaactaag cagaaggccc       840
ctgacggatg cctttttgc gtttctacaa actctttctg tgttgtaaaa cgacggccag        900
tcttaagctc gggccccctg gcggttctg ataacgagta atcgttaatc cgcaaataac        960
gtaaaaaccc gcttcggcgg gttttttat gggggagtt tagggaaaga gcatttgtca        1020
gaatatttaa gggcgcctgt cactttgctt gatatgag aattatttaa ccttataaat        1080
gagaaaaaag caacgcactt taaataagat acgttgcttt ttcgattgat gaacacctat      1140
aattaaacta ttcatctatt atttatgatt ttttgtatat acaatatttc tagtttgtta      1200
aagagaatta agaaaataaa tctcgaaaat aataagggga aaatcagttt ttgatatcaa      1260
aattatacat gtcaacgata atacaaaata taatacaaac tataagatgt tatcagtatt     1320
tattatcatt tagaataaat tttgtgtcgc ccttccgcga aattaatacg actcactata     1380
ggggaattgt gagcggataa caattcccct ctagaaataa ttttgtttaa ctttgaagg      1440 agatatacat atgggcaaag gcggccacca ccaccaccac cacggcggcg acggcgagaa     1500
tctgtacttt cagggcgaga tctgaaaaca acacgaggac gctctgcaga gtttgaaga     1560 agccctgaat cagtttgaag atctgaaaca actgggcggc agcggctccg gttcgggtgg     1620
tgagatctgg aagcagcacg aggatgcgct gcagaagttc gaagaggcgc tgaaccagtt    1680
cgaggacctg aagcagctgg gtggcagcgg ttccggcagc ggcggtgaga tttgaaaaca     1740
gcacgaagat gccctgcaga aattcgaaga ggcgctgaac cagtttgagg acttgaagca     1800
actgggtggt agcggctctg gtagcggtgg tgagatttgg aagcaacatg aagatgcact    1860
gcaaaagttc gaagaggcgc tgaaccaatt tgaagatctg aagcaattgt aactcgagcc    1920
ccctagcata cccccttggg gcctctaaac gggtcttgag gggttttttg ccctgagac     1980 gcgtcaatcg agttcgtacc taagggcgac accccctaat tagcccgggc gaaaggccca    2040
gtctttcgac tgagcctttc gttttatttg atgcctggca gttccctact ctcgcatggg    2100
gagtccccac actaccatcg gcgctacggc gtttcactt cgagttcggc atggggtcag     2160
gtgggaccac cgcgctactg ccgccaggca acaagggggt gttatgagcc atattcaggt    2220
ataaatgggc tcgcgataat gttcagaatt ggttaattgg ttgtaacact gaccccctat    2280
tgtttatttt tctaaataca ttcaaatatg tatccgctca tgagacaata accctgataa    2340
atgcttcaat aatattgaaa aaggaagaat atgagtattc aacatttccg tgtcgccctt    2400
attccctttt ttgcggcatt ttgccttcct gttttgctc acccagaaac gctggtgaaa    2460
gtaaaagatg ctgaagatca gttgggtgca cgagtgggtt acatcgaact ggatctcaac    2520
agcggtaaga tccttgagag ttttcgcccc gaagaacgtt ttccaatgat gagcactttt    2580
```

| | |
|---|---:|
| aaagttctgc tatgtggcgc ggtattatcc cgtattgacg ccgggcaaga gcaactcggt | 2640 |
| cgccgcatac actattctca gaatgacttg gttgagtact caccagtcac agaaaagcat | 2700 |
| cttacggatg gcatgacagt aagagaatta tgcagtgctg ccataaccat gagtgataac | 2760 |
| actgcggcca acttacttct gacaacgatc ggaggaccga aggagctaac cgcttttttg | 2820 |
| cacaacatgg gggatcatgt aactcgcctt gatcgttggg aaccggagct gaatgaagcc | 2880 |
| ataccaaacg acgagcgtga caccacgatg cctgtagcga tggcaacaac gttgcgcaaa | 2940 |
| ctattaactg gcgaactact tactctagct tcccggcaac aattaataga ctggatggag | 3000 |
| gcggataaag ttgcaggacc acttctgcgc tcggcccttc cggctggctg gtttattgct | 3060 |
| gataaatccg gagccggtga gcgtggttct cgcggtatca tcgcagcgct ggggccagat | 3120 |
| ggtaagccct cccgtatcgt agttatctac acgacgggga gtcaggcaac tatggatgaa | 3180 |
| cgaaatagac agatcgctga gataggtgcc tcactgatta agcattggta agcggcgcgc | 3240 |
| catcgaatgg cgcaaaacct ttcgcggtat ggcatgatag cgcccggaag agagtcaatt | 3300 |
| cagggtggtg aatatgaaac cagtaacgtt atacgatgtc gcagagtatg ccggtgtctc | 3360 |
| ttatcagacc gtttcccgcg tggtgaacca ggccagccac gtttctgcga aaacgcggga | 3420 |
| aaaagtggaa gcggcgatgg cggagctgaa ttacattccc aaccgcgtgg cacaacaact | 3480 |
| ggcgggcaaa cagtcgttgc tgattggcgt tgccacctcc agtctggccc tgcacgcgcc | 3540 |
| gtcgcaaatt gtcgcggcga ttaaatctcg cgccgatcaa ctgggtgcca gcgtggtggt | 3600 |
| gtcgatggta gaacgaagcg gcgtcgaagc ctgtaaagcg gcggtgcaca atcttctcgc | 3660 |
| gcaacgcgtc agtgggctga tcattaacta tccgctggat gaccaggatg ccattgctgt | 3720 |
| ggaagctgcc tgcactaatg ttccggcgtt atttcttgat gtctctgacc agacacccat | 3780 |
| caacagtatt attttctccc atgaggacgg tacgcgactg ggcgtggagc atctggtcgc | 3840 |
| attgggtcac cagcaaatcg cgctgttagc gggcccatta agttctgtct cggcgcgtct | 3900 |
| gcgtctggct ggctgcata aatatctcac tcgcaatcaa attcagccga tagcggaacg | 3960 |
| ggaaggcgac tggagtgcca tgtccggttt tcaacaaacc atgcaaatgc tgaatgaggg | 4020 |
| catcgttccc actgcgatgc tggttgccaa cgatcagatg gcgctgggcg caatgcgcgc | 4080 |
| cattaccgag tccgggctgc gcgttggtgc ggatatctcg gtagtgggat acgacgatac | 4140 |
| cgaagatagc tcatgttata tcccgccgtt aaccaccatc aaacaggatt ttcgcctgct | 4200 |
| ggggcaaacc agcgtggacc gcttgctgca actctctcag gccaggcgg tgaagggcaa | 4260 |
| tcagctgttg ccagtctcac tggtgaaaag aaaaaccacc ctggcgccca atacgcaaac | 4320 |
| cgcctctccc cgcgcgttgg ccgattcatt aatgcagctg gcacgacagg tttcccgact | 4380 |
| ggaaagcggg cagtgactca tgaccaaaat cccttaacgt gagttacgcg cgcgtcgttc | 4440 |
| cactgagcgt cagac | 4455 |

<210> SEQ ID NO 102
<211> LENGTH: 10367
<212> TYPE: DNA
<213> ORGANISM: Artificial Sequence
<220> FEATURE:
<223> OTHER INFORMATION: Synthetic Sequence BT6 CysAla (FCK mam)

<400> SEQUENCE: 102

| | |
|---|---:|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |

```
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca tagggactt    420 tccattgacg tcaatgggtg gagtatttac ggtaaactgc ccacttggca gtacatcaag    480
tgtatcatat gccaagtacg cccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagaccctt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc aggggggaaag aaaaaatata   1260 aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt   1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggat   2460 tggggggtac agtgcagggg aaagaatagt agacataata gcaacagaca tacaaactaa   2520
```

```
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tgggggaggt aggaagagcg atgatcactt gtggactaag    3540
tttgttcaca tccccttctc caacccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg ccccctagtt ctgggggcag cggggggatcc    3900 atgggcgaga tctggaaaca acacgaggac gctctgcaga agtttgaaga agccctgaat    3960
cagtttgaag atctgaaaca actgggcggc agcggctccg gttcgggtgg tgagatctgg    4020
aagcagcacg aggatgcgct gcagaagttc gaagaggcgc tgaaccagtt cgaggacctg    4080
aagcagctgg gtgcagcgg ttccggcagc ggcggtgaga tttggaaaca gcacgaagat    4140
gccctgcaga aattcgaaga ggcgctgaac cagtttgagg acttgaagca actgggtggt    4200
agcggctctg gtagcggtgg tgagatttgg aagcaacatg aagatgcact gcaaaagttc    4260
gaagaggcgc tgaaccaatt tgaagatctg aagcaattgg cggcaccggt agtagcagtg    4320
agcaagggcg aggagctgtt caccggggtg gtgcccatcc tggtcgagct ggacggcgac    4380
gtaaacggcc acaagttcag cgtgtccggc gagggcgagg gcgatgccac ctacggcaag    4440
ctgaccctga agttcatttg caccaccggc aagctgcccg tgccctggcc cacccctgtg    4500
accaccctga cctacggcgt gcagtgcttc agccgctacc ccgaccacat gaagcagcac    4560
gacttcttca gtccgccat gcccgaaggc tacgtccagg agcgcaccat cttcttcaag    4620
gacgacggca actacaagac ccgcgccgag gtgaagttcg agggcgacac cctggtgaac    4680
cgcatcgagc tgaagggcat cgacttcaag gaggacggca acatcctggg gcacaagctg    4740
gagtacaact acaacagcca caacgtctat atcatggccg acaagcagaa gaacggcatc    4800
aaggtgaact tcaagatccg ccacaacatc gaggacggca gcgtgcagct cgccgaccac    4860
taccagcaga acaccccat cggcgacggc cccgtgctgc tgcccgacaa ccactacctg    4920
```

```
agcacccagt ccgccctgag caaagacccc aacgagaagc gcgatcacat ggtcctgctg    4980
gagttcgtga ccgccgccgg gatcactctc ggcatggacg agctgtacaa gtaagaattc    5040
gatatcaagc ttatcgataa tcaacctctg gattacaaaa tttgtgaaag attgactggt    5100
attcttaact atgttgctcc ttttacgcta tgtggatacg ctgctttaat gcctttgtat    5160
catgctattg cttcccgtat ggctttcatt ttctcctcct tgtataaatc ctggttgctg    5220
tctctttatg aggagttgtg gcccgttgtc aggcaacgtg gcgtggtgtg cactgtgttt    5280
gctgacgcaa cccccactgg ttggggcatt gccaccacct gtcagctcct tccgggact     5340 ttcgctttcc cctcccctat tgccacggcg gaactcatcg ccgcctgcct tgcccgctgc    5400
tggacagggg ctcggctgtt gggcactgac aattccgtgg tgttgtcggg gaaatcatcg    5460 tccttcctt ggctgctcgc ctgtgttgcc acctggattc tgcgcgggac gtccttctgc     5520
tacgtccctt cggccctcaa tccagcggac cttccttccc gcggcctgct gccggctctg    5580
cggcctcttc cgcgtcttcg ccttcgccct cagacgagtc ggatctccct ttgggccgcc    5640
tccccgcatc gataccgtcg acctcgagac ctagaaaaac atggagcaat cacaagtagc    5700
aatacagcag ctaccaatgc tgattgtgcc tggctagaag cacaagagga ggaggagtg    5760 ggttttccag tcacacctca ggtacctta agaccaatga cttacaaggc agctgtagat     5820
cttagccact ttttaaaaga aaaggggga ctggaagggc taattcactc ccaacgaaga     5880
caagatatcc ttgatctgtg gatctaccac acacaaggct acttccctga ttggcagaac    5940
tacacaccag ggccagggat cagatatcca ctgacctttg gatggtgcta caagctagta    6000
ccagttgagc aagagaaggt agaagaagcc aatgaaggag agaacacccg cttgttacac    6060
cctgtgagcc tgcatgggat ggatgacccg gagagagaag tattagagtg gaggtttgac    6120
agccgcctag catttcatca catggcccga gagctgcatc cggactgtac tgggtctctc    6180
tggttagacc agatctgagc ctgggagctc tctggctaac tagggaaccc actgcttaag    6240
cctcaataaa gcttgccttg agtgcttcaa gtagtgtgtg cccgtctgtt gtgtgactct    6300
ggtaactaga gatccctcag acccttttag tcagtgtgga aaatctctag cagggcccgt    6360
ttaaacccgc tgatcagcct cgactgtgcc ttctagttgc cagccatctg ttgtttgccc    6420
ctcccccgtg ccttccttga ccctggaagg tgccactccc actgtccttt cctaataaaa    6480
tgaggaaatt gcatcgcatt gtctgagtag gtgtcattct attctggggg gtggggtggg    6540
gcaggacagc aagggggagg attgggaaga caatagcagg catgctgggg atgcggtggg    6600
ctctatggct tctgaggcgg aaagaaccag ctggggctct agggggtatc cccacgcgcc    6660
ctgtagcggc gcattaagcg cggcgggtgt ggtggttacg cgcagcgtga ccgctacact    6720
tgccagcgcc ctagcgcccg ctcctttcgc tttcttccct cctttctcg ccacgttcgc     6780 cggctttccc cgtcaagctc taaatcgggg ctcccttta gggttccgat ttagtgcttt     6840
acggcacctc gaccccaaaa aacttgatta gggtgatggt tcacgtagtg gccatcgcc     6900 ctgatagacg gttttcgcc ctttgacgtt ggagtccacg ttctttaata gtggactctt     6960
gttccaaact ggaacaacac tcaacccta ctcggtctat tcttttgatt tataagggat     7020
tttgccgatt tcggcctatt ggttaaaaaa tgagctgatt taacaaaaat ttaacgcgaa    7080
ttaattctgt ggaatgtgtg tcagttaggg tgtggaaagt ccccaggctc cccagcaggc    7140
agaagtatgc aaagcatgca tctcaattag tcagcaacca ggtgtggaaa gtccccaggc    7200
tccccagcag gcagaagtat gcaaagcatg catctcaatt agtcagcaac catagtcccg    7260
```

| | | | | |
|---|---|---|---|---|
| cccctaactc | cgcccatccc | gcccctaact | ccgcccagtt | ccgcccattc | tccgcccat | 7320 |
| ggctgactaa | ttttttttat | ttatgcagag | gccgaggccg | cctctgcctc | tgagctattc | 7380 |
| cagaagtagt | gaggaggctt | ttttggaggc | ctaggctttt | gcaaaaagct | cccgggagct | 7440 |
| tgtatatcca | ttttcggatc | tgatcagcac | gtgttgacaa | ttaatcatcg | gcatagtata | 7500 |
| tcggcatagt | ataatacgac | aaggtgagga | actaaaccat | ggccaagttg | accagtgccg | 7560 |
| ttccggtgct | caccgcgcgc | gacgtcgccg | gagcggtcga | gttctggacc | gaccggctcg | 7620 |
| ggttctcccg | ggacttcgtg | gaggacgact | tcgccggtgt | ggtccgggac | gacgtgaccc | 7680 |
| tgttcatcag | cgcggtccag | gaccaggtgg | tgccggacaa | caccctggcc | tgggtgtggg | 7740 |
| tgcgcggcct | ggacgagctg | tacgccgagt | ggtcggaggt | cgtgtccacg | aacttccggg | 7800 |
| acgcctccgg | gccggccatg | accgagatcg | gcgagcagcc | gtggggcgg | gagttcgccc | 7860 |
| tgcgcgaccc | ggccggcaac | tgcgtgcact | tcgtggccga | ggagcaggac | tgacacgtgc | 7920 |
| tacgagattt | cgattccacc | gccgccttct | atgaaaggtt | gggcttcgga | atcgttttcc | 7980 |
| gggacgccgg | ctggatgatc | ctccagcgcg | gggatctcat | gctggagttc | ttcgcccacc | 8040 |
| ccaacttgtt | tattgcagct | tataatggtt | acaaataaag | caatagcatc | acaaatttca | 8100 |
| caaataaagc | atttttttca | ctgcattcta | gttgtggttt | gtccaaactc | atcaatgtat | 8160 |
| cttatcatgt | ctgtataccg | tcgacctcta | gctagagctt | ggcgtaatca | tggtcatagc | 8220 |
| tgtttcctgt | gtgaaattgt | tatccgctca | caattccaca | caacatacga | gccggaagca | 8280 |
| taaagtgtaa | agcctggggt | gcctaatgag | tgagctaact | cacattaatt | gcgttgcgct | 8340 |
| cactgcccgc | tttccagtcg | ggaaacctgt | cgtgccagct | gcattaatga | atcggccaac | 8400 |
| gcgcggggag | aggcggtttg | cgtattgggc | gctcttccgc | ttcctcgctc | actgactcgc | 8460 |
| tgcgctcggt | cgttcggctg | cggcgagcgg | tatcagctca | ctcaaaggcg | gtaatacggt | 8520 |
| tatccacaga | atcaggggat | aacgcaggaa | agaacatgtg | agcaaaaggc | cagcaaaagg | 8580 |
| ccaggaaccg | taaaaaggcc | gcgttgctgg | cgttttttcca | taggctccgc | cccccctgacg | 8640 |
| agcatcacaa | aaatcgacgc | tcaagtcaga | ggtggcgaaa | cccgacagga | ctataaagat | 8700 |
| accaggcgtt | tccccctgga | agctccctcg | tgcgctctcc | tgttccgacc | ctgccgctta | 8760 |
| ccggatacct | gtccgccttt | ctcccttcgg | gaagcgtggc | gctttctcat | agctcacgct | 8820 |
| gtaggtatct | cagttcggtg | taggtcgttc | gctccaagct | gggctgtgtg | cacgaacccc | 8880 |
| ccgttcagcc | cgaccgctgc | gccttatccg | gtaactatcg | tcttgagtcc | aacccggtaa | 8940 |
| gacacgactt | atcgccactg | gcagcagcca | ctggtaacag | gattagcaga | gcgaggtatg | 9000 |
| taggcggtgc | tacagagttc | ttgaagtggt | ggcctaacta | cggctacact | agaagaacag | 9060 |
| tatttggtat | ctgcgctctg | ctgaagccag | ttaccttcgg | aaaaagagtt | ggtagctctt | 9120 |
| gatccggcaa | acaaaccacc | gctggtagcg | gtggtttttt | tgtttgcaag | cagcagatta | 9180 |
| cgcgcagaaa | aaaaggatct | caagaagatc | ctttgatctt | ttctacgggg | tctgacgctc | 9240 |
| agtggaacga | aaactcacgt | taagggattt | tggtcatgag | attatcaaaa | aggatcttca | 9300 |
| cctagatcct | tttaaattaa | aaatgaagtt | ttaaatcaat | ctaaagtata | tatgagtaaa | 9360 |
| cttggtctga | cagttaccaa | tgcttaatca | gtgaggcacc | tatctcagcg | atctgtctat | 9420 |
| ttcgttcatc | catagttgcc | tgactccccg | tcgtgtagat | aactacgata | cgggagggct | 9480 |
| taccatctgg | ccccagtgct | gcaatgatac | cgcgagaccc | acgctcaccg | gctccagatt | 9540 |
| tatcagcaat | aaaccagcca | gccggaaggg | ccgagcgcag | aagtggtcct | gcaactttat | 9600 |
| ccgcctccat | ccagtctatt | aattgttgcc | gggaagctag | agtaagtagt | tcgccagtta | 9660 |

```
atagtttgcg caacgttgtt gccattgcta caggcatcgt ggtgtcacgc tcgtcgtttg   9720
gtatggcttc attcagctcc ggttcccaac gatcaaggcg agttacatga tcccccatgt   9780
tgtgcaaaaa agcggttagc tccttcggtc ctccgatcgt tgtcagaagt aagttggccg   9840
cagtgttatc actcatggtt atggcagcac tgcataattc tcttactgtc atgccatccg   9900
taagatgctt ttctgtgact ggtgagtact caaccaagtc attctgagaa tagtgtatgc   9960
ggcgaccgag ttgctcttgc ccggcgtcaa tacgggataa taccgcgcca catagcagaa  10020
ctttaaaagt gctcatcatt ggaaaacgtt cttcggggcg aaaactctca aggatcttac  10080
cgctgttgag atccagttcg atgtaaccca ctcgtgcacc caactgatct tcagcatctt  10140
ttactttcac cagcgtttct gggtgagcaa aaacaggaag gcaaatgccc gcaaaaaggg  10200
gaataagggc gacacggaaa tgttaatac tcatactctt ccttttcaa tattattgaa  10260
gcatttatca gggttattgt ctcatgagcg gatacatatt tgaatgtatt tagaaaaata  10320
aacaaatagg ggttccgcgc acatttcccc gaaaagtgcc acctgac            10367
```

<210> SEQ ID NO 103
<211> LENGTH: 131
<212> TYPE: PRT
<213> ORGANISM: Artificial Sequence
<220> FEATURE:
<223> OTHER INFORMATION: Synthetic Sequence BT6 CysAla

<400> SEQUENCE: 103

```
Glu Ile Trp Lys Gln Phe Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Trp Lys Gln Cys Glu Asp Ala Leu Gln Lys Phe
        35                  40                  45

Glu Glu Ala Leu Asn Gln Phe Glu Asp Leu Lys Gln Leu Gly Gly Ser
    50                  55                  60

Gly Ser Gly Ser Gly Gly Glu Ile Trp Lys Gln Phe Glu Asp Ala Leu
65                  70                  75                  80

Gln Lys Phe Glu Glu Ala Leu Asn Gln Phe Glu Asp Leu Lys Gln Leu
                85                  90                  95

Gly Gly Ser Gly Ser Gly Ser Gly Gly Glu Ile Trp Lys Gln Ala Glu
            100                 105                 110

Asp Ala Leu Gln Lys Phe Glu Glu Ala Leu Asn Gln Phe Glu Asp Leu
        115                 120                 125

Lys Gln Leu
    130
```

<210> SEQ ID NO 104
<211> LENGTH: 131
<212> TYPE: PRT
<213> ORGANISM: Artificial Sequence
<220> FEATURE:
<223> OTHER INFORMATION: Synthetic Sequence MM3 FC H6F H76F

<400> SEQUENCE: 104

```
Glu Leu Leu Lys Lys Phe Glu Glu Ala Leu Lys Lys Phe Glu Glu Leu
1               5                   10                  15

Leu Lys Lys Phe Glu Glu Glu Leu Lys Lys Gly Gly Ser Gly Ser Gly
            20                  25                  30

Ser Gly Gly Glu Leu Leu Lys Lys Phe Glu Glu Ala Leu Lys Lys Phe
```

```
                    35                  40                  45

Glu Leu Leu Lys Lys Phe Glu Glu Leu Lys Lys Gly Gly Ser
            50                  55                  60

Gly Trp Gly Ser Gly Gly Glu Leu Leu Lys Lys Phe Glu Ala Leu
65                  70                  75                  80

Lys Lys Phe Glu Glu Leu Leu Lys Lys Phe Glu Glu Leu Leu Lys
                    85                  90                  95

Gly Gly Ser Gly Ser Gly Ser Gly Gly Glu Leu Leu Lys Cys Glu
                100                 105                 110

Glu Ala Leu Lys Lys Phe Glu Glu Leu Leu Lys Lys Phe Glu Glu Leu
            115                 120                 125

Leu Lys Lys
    130

<210> SEQ ID NO 105
<211> LENGTH: 131
<212> TYPE: PRT
<213> ORGANISM: Artificial Sequence
<220> FEATURE:
<223> OTHER INFORMATION: Synthetic Sequence MM3 FC H6F H76F F90D

<400> SEQUENCE: 105

Glu Leu Leu Lys Lys Phe Glu Glu Ala Leu Lys Lys Phe Glu Glu Leu
1               5                   10                  15

Leu Lys Lys Phe Glu Glu Glu Leu Lys Lys Gly Gly Ser Gly Ser Gly
                20                  25                  30

Ser Gly Gly Glu Leu Leu Lys Lys Phe Glu Glu Ala Leu Lys Lys Phe
            35                  40                  45

Glu Glu Leu Leu Lys Lys Phe Glu Glu Leu Lys Lys Gly Gly Ser
            50                  55                  60

Gly Trp Gly Ser Gly Gly Glu Leu Leu Lys Lys Phe Glu Ala Leu
65                  70                  75                  80

Lys Lys Phe Glu Glu Leu Leu Lys Asp Glu Glu Leu Leu Lys Lys
                    85                  90                  95

Gly Gly Ser Gly Ser Gly Ser Gly Gly Glu Leu Leu Lys Cys Glu
                100                 105                 110

Glu Ala Leu Lys Lys Phe Glu Glu Leu Leu Lys Lys Phe Glu Glu Leu
            115                 120                 125

Leu Lys Lys
    130

<210> SEQ ID NO 106
<211> LENGTH: 5195
<212> TYPE: DNA
<213> ORGANISM: Artificial Sequence
<220> FEATURE:
<223> OTHER INFORMATION: Synthetic Sequence Positive (E. Coli)

<400> SEQUENCE: 106
agcagacaag cccgtcaggg cgcgtcagcg ggtgttggcg ggtgtcgggg ctggcttaac      60
tatgcggcat cagagcagat tgtactgaga gtgcaccata tgcggtgtga ataccgcac     120 agatgcgtaa ggagaaaata ccgcatcagg cgccattcgc cattcaggct gcgcaactgt    180
tgggaagggc gatcggtgcg ggcctcttcg ctattacgcc agctggcgaa aggggatgt     240 gctgcaaggc gattaagttg ggtaacgcca gggttttccc agtcacgacg ttgtaaaacg    300
acggccagtg ccaagcttaa ttaatctttc tgcgaattga gatgacgcca ctggctgggc    360
```

```
gtcatcccgg tttcccgggt aaacaccacc gaaaaatagt tactatcttc aaagccacat    420
tcggtcgaaa tatcactgat taacaggcgg ctatgctgga gaagatattg cgcatgacac    480
actctgacct gtcgcagata ttgattgatg gtcattccag tctgctggcg aaattgctga    540
cgcaaaacgc gctcactgca cgatgcctca tcacaaaatt tatccagcgc aaagggactt    600
ttcaggctag ccgccagccg ggtaatcagc ttatccagca acgtttcgct ggatgttggc    660
ggcaacgaat cactggtgta acgatggcga ttcagcaaca tcaccaactg cccgaacagc    720
aactcagcca tttcgttagc aaacggcaca tgctgactac tttcatgctc aagctgacca    780
ataacctgcc gcgcctgcgc catccccatg ctacctaagc gccagtgtgg ttgccctgcg    840
ctggcgttaa tcccggaat cgcccctgc cagtcaagat tcagcttcag acgctccggg    900
caataaataa tattctgcaa aaccagatcg ttaacggaag cgtaggagtg tttatcatca    960
gcatgaatgt aaaagagatc gccacgggta atgcgataag ggcgatcgtt gagtacatgc   1020
aggccattac cgcgccagac aatcaccagc tcacaaaaat catgtgtatg ttcagcaaag   1080
acatcttgcg gataacggtc agccacagcg actgcctgct ggtcgctggc aaaaaaatca   1140
tctttgagaa gttttaactg atgcgccacc gtggctacct cggccagaga acgaagttga   1200
ttattcgcaa tatggcgtac aaatacgttg agaagattcg cgttattgca gaaagccatc   1260
ccgtccctgg cgaatatcac gcggtgacca gttaaactct cggcgaaaaa gcgtcgaaaa   1320
gtggttactg tcgctgaatc cacagcgata ggcgatgtca gtaacgctgg cctcgctgtg   1380
gcgtagcaga tgtcgggctt tcatcagtcg caggcggttc aggtatcgct gaggcgtcag   1440
tcccgtttgc tgcttaagct gccgatgtag cgtacgcagt gaaagagaaa attgatccgc   1500
cacggcatcc caattcacct catcggcaaa atggtcctcc agccaggcca gaagcaagtt   1560
gagacgtgat gcgctgtttt ccaggttctc ctgcaaactg cttttacgca gcaagagcag   1620
taattgcata aacaagatct cgcgactggc ggtcgagggt aaatcatttt ccccttcctg   1680
ctgttccatc tgtgcaacca gctgtcgcac ctgctgcaat acgctgtggt taacgcgcca   1740
gtgagacgga tactgcccat ccagctcttg tggcagcaac tgattcagcc cggcgagaaa   1800
ctgaaatcga tccggcgagc gatacagcac attggtcaga cacagattat cggtatgttc   1860
atacagatgc cgatcatgat cgcgtacgaa acagaccgtg ccaccggtga tggtataggg   1920
ctgcccatta aacacatgaa tacccgtgcc atgttcgaca atcacaattt catgaaaatc   1980
atgatgatgt tcaggaaaat ccgcctgcgg gagccggggt tctatcgcca cggacgcgtt   2040
accagacgga aaaaatcca cactatgtaa tacggtcata ctggcctcct gatgtcgtca   2100
acacggcgaa atagtaatca cgaggtcagg ttcttaccct aaattttcga cggaaaacca   2160
cgtaaaaaac gtcgattttt caagatacag cgtgaatttt caggaaatgc ggtgagcatc   2220
acatcaccac aattcagcaa attgtgaaca tcatcacgtt catctttccc tggttgccaa   2280
tggcccattt tcctgtcagt aacgagaagg tcgcgaattc aggcgctttt tagactggtc   2340
gtaatgaaat tctttaagga gataaaacat atgggcggcg acggtcatca tcatcaccac   2400
cacggcggca aaggcgagaa cttgtatttc caaggtgaga ttaagcgtca gcatgaggac   2460
gcgctgcgca agttcgaaga agcgctgaag cgcttcgagg acaagaaaca aaagggtggt   2520
agcggtaaag gttccggcgg tgagatttgg aagcgtcacg aagatgcctt gcgtaagttt   2580
gaagaggcgc tgaaacgttt cgaggataag aagcagaaag gtggttctgg taaaggtagc   2640
ggtggtgaaa tctggaaacg ccacgaggac gctctgcgca aatttgaaga agcactgaag   2700
cgttttgagg acaaaaagca gaagggcggc agcggtaagg gcagcggtgg cgagatcaaa   2760
```

```
caacgtcacg aggatgcgct gcgtaaattc gaagaggcac tgaaacgctt tgaagataag    2820
aaacagaaat aactcgagcc cctcatccga aagggcgtat tggtaccgag ctcgaattcg    2880
taatcatgtc atagctgttt cctgtgtgaa attgttatcc gctcacaatt ccacacaaca    2940
tacgagccgg aagcataaag tgtaaagcct ggggtgccta atgagtgagc taactcacat    3000
taattgcgtt gcgctcactg cccgctttcc agtcgggaaa cctgtcgtgc cagctgcatt    3060
aatgaatcgg ccaacgcgcg gggagaggcg gtttgcgtat tgggcgctct tccgcttcct    3120
cgctcactga ctcgctgcgc tcggtcgttc ggctgcggcg agcggtatca gctcactcaa    3180
aggcggtaat acgttatcc acagaatcag gggataacgc aggaaagaac atgtgagcaa    3240
aaggccagca aaaggccagg aaccgtaaaa aggccgcgtt gctggcgttt ttccataggc    3300
tccgcccccc tgacgagcat cacaaaaatc gacgctcaag tcagaggtgg cgaaacccga    3360
caggactata aagataccag gcgtttcccc ctggaagctc cctcgtgcgc tctcctgttc    3420
cgaccctgcc gcttaccgga tacctgtccg ccttttctccc ttcgggaagc gtggcgcttt    3480
ctcatagctc acgctgtagg tatctcagtt cggtgtaggt cgttcgctcc aagctgggct    3540
gtgtgcacga accccccgtt cagcccgacc gctgcgcctt atccggtaac tatcgtcttg    3600
agtccaaccc ggtaagacac gacttatcgc cactggcagc agccactggt aacaggatta    3660
gcagagcgag gtatgtaggc ggtgctacag agttcttgaa gtggtggcct aactacggct    3720
acactagaag gacagtattt ggtatctgcg ctctgctgaa gccagttacc ttcggaaaaa    3780
gagttggtag ctcttgatcc ggcaaacaaa ccaccgctgg tagcggtggt ttttttgttt    3840
gcaagcagca gattacgcgc agaaaaaaag gatctcaaga agatcctttg atcttttcta    3900
cggggtctga cgctcagtgg aacgaaaact cacgttaagg gattttggtc atgagattat    3960
caaaaaggat cttcacctag atccttttaa attaaaaatg aagttttaaa tcaatctaaa    4020
gtatatatga gtaaacttgg tctgacagtt accaatgctt aatcagtgag gcacctatct    4080
cagcgatctg tctatttcgt tcatccatag ttgcctgact ccccgtcgtg tagataacta    4140
cgatacggga gggcttacca tctggcccca gtgctgcaat gataccgcgg cacccacgct    4200
caccggctcc agatttatca gcaataaacc agccagccgg aagggccgag cgcagaagtg    4260
gtcctgcaac tttatccgcc tccatccagt ctattaattg ttgccgggaa gctagagtaa    4320
gtagttcgcc agttaatagt ttgcgcaacg ttgttgccat tgctacaggc atcgtggtgt    4380
cacgctcgtc gtttggtatg gcttcattca gctccggttc ccaacgatca aggcgagtta    4440
catgatcccc catgttgtgc aaaaaagcgg ttagctcctt cggtcctccg atcgttgtca    4500
gaagtaagtt ggccgcagtg ttatcactca tggttatggc agcactgcat aattctctta    4560
ctgtcatgcc atccgtaaga tgcttttctg tgactggtga gtactcaacc aagtcattct    4620
gagaatagtg tatgcggcga ccgagttgct cttgcccggc gtcaatacgg gataataccg    4680
cgccacatag cagaacttta aaagtgctca tcattggaaa acgttcttcg ggcgaaaac    4740 tctcaaggat cttaccgctg ttgagatcca gttcgatgta acccactcgt gcacccaact    4800
gatcttcagc atcttttact ttcaccagcg tttctgggtg agcaaaaaca ggaaggcaaa    4860
atgccgcaaa aaagggaata agggcgacac ggaaatgttg aatactcata ctcttccttt    4920
ttcaatatta ttgaagcatt tatcagggtt attgtctcat gagcggatac atatttgaat    4980
gtatttagaa aaataaacaa ataggggttc cgcgcacatt tccccgaaaa gtgccacctg    5040
acgtctaaga aaccattatt atcatgacat taacctataa aaataggcgt atcacgaggc    5100
```

```
cctttcgtct cgcgcgtttc ggtgatgacg gtgaaaacct ctgacacatg cagctcccgg   5160
agacggtcac agcttgtctg taagcggatg ccggg                              5195

<210> SEQ ID NO 107
<211> LENGTH: 10367
<212> TYPE: DNA
<213> ORGANISM: Artificial Sequence
<220> FEATURE:
<223> OTHER INFORMATION: Synthetic Sequence Positive (FCK mam)

<400> SEQUENCE: 107
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt cgcgctgcttc gcgatgtacg ggccagatat acgcgttgac   240
attgattatt gactagttat taatagtaat caattacggg gtcattagtt catagcccat    300
atatggagtt ccgcgttaca taacttacgg taaatggccc gcctggctga ccgcccaacg    360 accccccgccc attgacgtca ataatgacgt atgttcccat agtaacgcca tagggactt    420 tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
```

```
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggat    2460 tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tggggggaggt aggaagagcg atgatcactt gtggactaag    3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggatcc    3900 atgggtgaga ttaagcgtca gcatgaggac gcgctgcgca agttcgaaga agcgctgaag    3960
cgcttcgagg acaagaaaca aaagggtggt agcggtaaag gttccggcgg tgagatttgg    4020
aagcgtcacg aagatgcctt gcgtaagttt gaagaggcgc tgaaacgttt cgaggataag    4080
aagcagaaag gtggttctgg taaaggtagc ggtggtgaaa tctggaaacg ccacgaggac    4140
gctctgcgca aatttgaaga agcactgaag cgttttgagg acaaaaagca gaagggcggc    4200
agcggtaagg gcagcggtgg cgagatcaaa caacgtcacg aggatgcgct gcgtaaattc    4260
gaagaggcac tgaaacgctt tgaagataag aaacagaaag cggcaccggt agtagcagtg    4320
```

-continued

```
agcaagggcg aggagctgtt caccggggtg gtgcccatcc tggtcgagct ggacggcgac   4380
gtaaacggcc acaagttcag cgtgtccggc gagggcgagg gcgatgccac ctacggcaag   4440
ctgaccctga agttcatttg caccaccggc aagctgcccg tgccctggcc caccctcgtg   4500
accaccctga cctacggcgt gcagtgcttc agccgctacc ccgaccacat gaagcagcac   4560
gacttcttca agtccgccat gcccgaaggc tacgtccagg agcgcaccat cttcttcaag   4620
gacgacggca actacaagac ccgcgccgag gtgaagttcg agggcgacac cctggtgaac   4680
cgcatcgagc tgaagggcat cgacttcaag gaggacggca acatcctggg gcacaagctg   4740
gagtacaact acaacagcca caacgtctat atcatggccg acaagcagaa gaacggcatc   4800
aaggtgaact tcaagatccg ccacaacatc gaggacggca gcgtgcagct cgccgaccac   4860
taccagcaga cacccccat cggcgacggc cccgtgctgc tgcccgacaa ccactacctg   4920
agcacccagt ccgccctgag caaagacccc aacgagaagc gcgatcacat ggtcctgctg   4980
gagttcgtga ccgccgccgg gatcactctc ggcatggacg agctgtacaa gtaagaattc   5040
gatatcaagc ttatcgataa tcaacctctg gattacaaaa tttgtgaaag attgactggt   5100
attcttaact atgttgctcc ttttacgcta tgtggatacg ctgctttaat gcctttgtat   5160
catgctattg cttcccgtat ggctttcatt ttctcctcct tgtataaatc ctggttgctg   5220
tctctttatg aggagttgtg gcccgttgtc aggcaacgtg gcgtggtgtg cactgtgttt   5280
gctgacgcaa ccccccactgg ttggggcatt gccaccacct gtcagctcct ttccgggact   5340
ttcgctttcc ccctccctat gccacggcg gaactcatcg ccgcctgcct tgcccgctgc   5400
tggacagggg ctcggctgtt gggcactgac aattccgtgg tgttgtcggg gaaatcatcg   5460
tccttttcctt ggctgctcgc ctgtgttgcc acctggattc tgcgcgggac gtccttctgc   5520
tacgtcccctt cggccctcaa tccagcggac cttccttccc gcggcctgct gccggctctg   5580
cggcctcttc cgcgtcttcg ccttcgccct cagacgagtc ggatctccct ttgggccgcc   5640
tccccgcatc gataccgtcg acctcgagac ctagaaaaac atggagcaat cacaagtagc   5700
aatacagcag ctaccaatgc tgattgtgcc tggctagaag cacaagagga ggaggaggtg   5760
ggttttccag tcacacctca ggtaccttta agaccaatga cttacaaggc agctgtagat   5820
cttagccact ttttaaaaga aaaggggggga ctggaagggc taattcactc ccaacgaaga   5880
caagatatcc ttgatctgtg gatctaccac acacaaggct acttccctga ttggcagaac   5940
tacacaccag ggccagggat cagatatcca ctgacctttg gatggtgcta caagctagta   6000
ccagttgagc aagagaaggt agaagaagcc aatgaaggag agaacacccg cttgttacac   6060
cctgtgagcc tgcatgggat ggatgacccg gagagagaag tattagagtg gaggtttgac   6120
agccgcctag catttcatca catggcccga gagctgcatc cggactgtac tgggtctctc   6180
tggttagacc agatctgagc ctgggagctc tctggctaac tagggaaccc actgcttaag   6240
cctcaataaa gcttgccttg agtgcttcaa gtagtgtgtg cccgtctgtt gtgtgactct   6300
ggtaactaga gatccctcag acccttttag tcagtgtgga aaatctctag cagggcccgt   6360
ttaaacccgc tgatcagcct cgactgtgcc ttctagttgc cagccatctg ttgtttgccc   6420
ctccccgtg ccttccttga ccctggaagg tgccactccc actgtccttt cctaataaaa   6480
tgaggaaatt gcatcgcatt gtctgagtag gtgtcattct attctggggg gtggggtggg   6540
gcaggacagc aagggggagg attgggaaga caatagcagg catgctgggg atgcggtggg   6600
ctctatggct tctgaggcgg aaagaaccag ctggggctct aggggtatc cccacgcgcc   6660
ctgtagcggc gcattaagcg cggcgggtgt ggtggttacg cgcagcgtga ccgctacact   6720
```

| | |
|---|---|
| tgccagcgcc ctagcgcccg ctcctttcgc tttcttccct tcctttctcg ccacgttcgc | 6780 |
| cggctttccc cgtcaagctc taaatcgggg gctccctta gggttccgat ttagtgcttt | 6840 |
| acggcacctc gaccccaaaa aacttgatta gggtgatggt tcacgtagtg ggccatcgcc | 6900 |
| ctgatagacg gttttcgcc ctttgacgtt ggagtccacg ttctttaata gtggactctt | 6960 |
| gttccaaact ggaacaacac tcaaccctat ctcggtctat tcttttgatt tataagggat | 7020 |
| tttgccgatt tcggcctatt ggttaaaaaa tgagctgatt taacaaaaat ttaacgcgaa | 7080 |
| ttaattctgt ggaatgtgtg tcagttaggg tgtggaaagt ccccaggctc cccagcaggc | 7140 |
| agaagtatgc aaagcatgca tctcaattag tcagcaacca ggtgtggaaa gtccccaggc | 7200 |
| tccccagcag gcagaagtat gcaaagcatg catctcaatt agtcagcaac catagtcccg | 7260 |
| cccctaactc cgcccatccc gcccctaact ccgcccagtt ccgcccattc tccgccccat | 7320 |
| ggctgactaa ttttttttat ttatgcagag gccgaggccg cctctgcctc tgagctattc | 7380 |
| cagaagtagt gaggaggctt ttttggaggc ctaggctttt gcaaaaagct cccgggagct | 7440 |
| tgtatatcca ttttcggatc tgatcagcac gtgttgacaa ttaatcatcg gcatagtata | 7500 |
| tcggcatagt ataatacgac aaggtgagga actaaaccat ggccaagttg accagtgccg | 7560 |
| ttccggtgct caccgcgcgc gacgtcgccg gagcggtcga ttctggacc gaccggctcg | 7620 |
| ggttctcccg ggacttcgtg gaggacgact tcgccggtgt ggtccgggac gacgtgaccc | 7680 |
| tgttcatcag cgcggtccag gaccaggtgg tgccggacaa caccctggcc tgggtgtggg | 7740 |
| tgcgcggcct ggacgagctg tacgccgagt ggtcggaggt cgtgtccacg aacttccggg | 7800 |
| acgcctccgg gccggccatg accgagatcg gcgagcagcc gtggggggcg gagttcgccc | 7860 |
| tgcgcgaccc ggccggcaac tgcgtgcact tcgtggccga ggagcaggac tgacacgtgc | 7920 |
| tacgagattt cgattccacc gccgccttct atgaaaggtt gggcttcgga atcgttttcc | 7980 |
| gggacgccgg ctggatgatc ctccagcgcg ggatctcat gctggagttc ttcgcccacc | 8040 |
| ccaacttgtt tattgcagct tataatggtt acaaataaag caatagcatc acaaatttca | 8100 |
| caaataaagc atttttttca ctgcattcta gttgtggttt gtccaaactc atcaatgtat | 8160 |
| cttatcatgt ctgtataccg tcgacctcta gctagagctt ggcgtaatca tggtcatagc | 8220 |
| tgtttcctgt gtgaaattgt tatccgctca caattccaca acatacga gccggaagca | 8280 |
| taaagtgtaa agcctgggt gcctaatgag tgagctaact cacattaatt gcgttgcgct | 8340 |
| cactgcccgc tttccagtcg ggaaacctgt cgtgccagct gcattaatga atcggccaac | 8400 |
| gcgcggggag aggcggtttg cgtattgggc gctcttccgc ttcctcgctc actgactcgc | 8460 |
| tgcgctcggt cgttcggctg cggcgagcgg tatcagctca ctcaaaggcg gtaatacggt | 8520 |
| tatccacaga atcaggggat aacgcaggaa agaacatgtg agcaaaaggc cagcaaaagg | 8580 |
| ccaggaaccg taaaaaggcc gcgttgctgg cgttttccca taggctccgc cccctgacg | 8640 |
| agcatcacaa aaatcgacgc tcaagtcaga ggtggcgaaa cccgacagga ctataaagat | 8700 |
| accaggcgtt tcccctgga agctccctcg tgcgctctcc tgttccgacc ctgccgctta | 8760 |
| ccggatacct gtccgccttt ctcccttcgg aagcgtggc gctttctcat agctcacgct | 8820 |
| gtaggtatct cagttcggtg taggtcgttc gctccaagct gggctgtgtg cacgaacccc | 8880 |
| ccgttcagcc cgaccgctgc gccttatccg gtaactatcg tcttgagtcc aacccggtaa | 8940 |
| gacacgactt atcgccactg gcagcagcca ctggtaacag gattagcaga gcgaggtatg | 9000 |
| taggcggtgc tacagagttc ttgaagtggt ggcctaacta cggctacact agaagaacag | 9060 |

```
tatttggtat ctgcgctctg ctgaagccag ttaccttcgg aaaaagagtt ggtagctctt    9120
gatccggcaa acaaaccacc gctggtagcg gtggttttt  tgtttgcaag cagcagatta   9180
cgcgcagaaa aaaggatct  caagaagatc ctttgatctt ttctacgggg tctgacgctc   9240
agtggaacga aaactcacgt taagggattt tggtcatgag attatcaaaa aggatcttca   9300
cctagatcct tttaaattaa aaatgaagtt ttaaatcaat ctaaagtata tatgagtaaa   9360
cttggtctga cagttaccaa tgcttaatca gtgaggcacc tatctcagcg atctgtctat   9420
ttcgttcatc catagttgcc tgactccccg tcgtgtagat aactacgata cgggagggct   9480
taccatctgg ccccagtgct gcaatgatac cgcgagaccc acgctcaccg gctccagatt   9540
tatcagcaat aaaccagcca gccggaaggg ccgagcgcag aagtggtcct gcaactttat   9600
ccgcctccat ccagtctatt aattgttgcc gggaagctag agtaagtagt tcgccagtta   9660
atagtttgcg caacgttgtt gccattgcta caggcatcgt ggtgtcacgc tcgtcgtttg   9720
gtatggcttc attcagctcc ggttcccaac gatcaaggcg agttacatga tcccccatgt   9780
tgtgcaaaaa agcggttagc tccttcggtc tccgatcgt  tgtcagaagt aagttggccg   9840
cagtgttatc actcatggtt atggcagcac tgcataattc tcttactgtc atgccatccg   9900
taagatgctt ttctgtgact ggtgagtact caaccaagtc attctgagaa tagtgtatgc   9960
ggcgaccgag ttgctcttgc ccggcgtcaa tacgggataa taccgcgcca catagcagaa  10020
ctttaaaagt gctcatcatt ggaaaacgtt cttcggggcg aaaactctca aggatcttac  10080
cgctgttgag atccagttcg atgtaaccca ctcgtgcacc caactgatct tcagcatctt  10140
ttactttcac cagcgtttct gggtgagcaa aacaggaag  gcaaaatgcc gcaaaaaagg  10200
gaataagggc gacacggaaa tgttgaatac tcatactctt cctttttcaa tattattgaa  10260
gcatttatca gggttattgt ctcatgagcg gatacatatt tgaatgtatt tagaaaaata  10320
aacaaatagg ggttccgcgc acatttcccc gaaaagtgcc acctgac               10367
```

<210> SEQ ID NO 108
<211> LENGTH: 131
<212> TYPE: PRT
<213> ORGANISM: Artificial Sequence
<220> FEATURE:
<223> OTHER INFORMATION: Synthetic Sequence Positive

<400> SEQUENCE: 108

```
Glu Ile Lys Arg Gln His Glu Asp Ala Leu Arg Lys Phe Glu Glu Ala
1               5                   10                  15

Leu Lys Arg Phe Glu Asp Lys Lys Gln Lys Gly Gly Ser Gly Lys Gly
                20                  25                  30

Ser Gly Gly Glu Ile Trp Lys Arg His Glu Asp Ala Leu Arg Lys Phe
            35                  40                  45

Glu Glu Ala Leu Lys Arg Phe Glu Asp Lys Lys Gln Lys Gly Gly Ser
        50                  55                  60

Gly Lys Gly Ser Gly Gly Glu Ile Trp Lys Arg His Glu Asp Ala Leu
65                  70                  75                  80

Arg Lys Phe Glu Glu Ala Leu Lys Arg Phe Glu Asp Lys Lys Gln Lys
                85                  90                  95

Gly Gly Ser Gly Lys Gly Ser Gly Gly Glu Ile Lys Gln Arg His Glu
                100                 105                 110

Asp Ala Leu Arg Lys Phe Glu Glu Ala Leu Lys Arg Phe Glu Asp Lys
            115                 120                 125

Lys Gln Lys
```

<210> SEQ ID NO 109
<211> LENGTH: 6318
<212> TYPE: DNA
<213> ORGANISM: Artificial Sequence
<220> FEATURE:
<223> OTHER INFORMATION: Synthetic Sequence AM1 (E. Coli)

<400> SEQUENCE: 109

| | | | | | |
|---|---|---|---|---|---|
| atccggatat | agttcctcct | ttcagcaaaa | aacccctcaa | gacccgttta | gaggccccaa | 60 |
| ggggttatgc | tagttattgc | tcagcggtgg | cagcagccaa | ctcagcttcc | tttcgggctt | 120 |
| tgttagcagc | cggatctcag | tggtggtggt | ggtggtgctc | gagttactgt | ttcgccaggt | 180 |
| cctcaaattg | gttcagtgct | tcccagaacg | ccagcaggtg | cagcaacaga | gccagcaaca | 240 |
| gcaaggccag | cagcgccaac | aacaacagaa | actcaccacc | ggaaccacca | ccgctaccac | 300 |
| ctttgaaggc | caacaaatgc | aacagcagag | ccaacagcag | caacaatgcc | aacaacagca | 360 |
| acaacgcgaa | gaatttctgc | agcgcatcct | catgctgttt | ccaaatctca | ccgccgctac | 420 |
| cgccaccgct | gccaccctgc | ttcgccagat | cttcgaactg | attcagcgct | tcccaaaaag | 480 |
| ccagcagatg | caacaacagc | gccagcagca | gcagggccag | caacgccaac | agcagcaaga | 540 |
| acttaccgcc | gctgccgcca | ccagaaccac | cttcaaatgc | cagcaagtgc | agcagcagtg | 600 |
| ccagcagcag | caacagggcc | aacagcaaca | gcaatgcaaa | gaacttttgc | agtgcgtcct | 660 |
| catgttgctt | ccagatttcg | ccttgaaaat | acaagttctc | gccgtcgccg | ccatgatgat | 720 |
| gatgatgatg | ggtaccattc | agcatctggc | ctgcgtgaat | attcttctcg | ccaaacaagg | 780 |
| cgcggatgct | caccaccttg | ccggcgccat | tgaagcgaaa | gtgatcgatg | gcgcaacta | 840 |
| cggtcttgcg | gccctgatac | tcgaagctga | cggtgaaagc | gaaggccgct | tcgttggcga | 900 |
| ccgcgcgtac | ctcctgcgtc | agctccaccg | ccaaaggcag | tttgagcgag | ttggcgtaaa | 960 |
| actcacgaat | cgcagccgta | ccggacctgg | gctcggaacc | cacggggtct | tccaccgtgg | 1020 |
| cgtcatcggc | aaacagcgcg | acgatgccgt | ccagatcgcc | ggcattgagc | gcagccacaa | 1080 |
| agcgctgtac | cacggcggtg | atgtgttctg | gggtatgcat | atgtatatct | ccttcttaaa | 1140 |
| gttaaacaaa | attatttcta | gaggggaatt | gttatccgct | cacaattccc | ctatagtgag | 1200 |
| tcgtattaat | ttcgcgggat | cgagatctcg | atcctacg | ccggacgcat | cgtggccggc | 1260 |
| atcaccggcg | ccacaggtgc | ggttgctggc | gcctatatcg | ccgacatcac | cgatggggaa | 1320 |
| gatcgggctc | gccacttcgg | gctcatgagc | gcttgtttcg | gcgtgggtat | ggtgcaggc | 1380 |
| cccgtggccg | ggggactgtt | gggcgccatc | tccttgcatg | caccattcct | gcggcggcg | 1440 |
| gtgctcaacg | gcctcaacct | actactgggc | tgcttcctaa | tgcaggagtc | gcataaggga | 1500 |
| gagcgtcgag | atcccggaca | ccatcgaatg | gcgcaaaacc | tttcgcggta | tggcatgata | 1560 |
| gcgcccggaa | gagagtcaat | tcagggtggt | gaatgtgaaa | ccagtaacgt | tatacgatgt | 1620 |
| cgcagagtat | gccggtgtct | cttatcagac | cgtttcccgc | gtggtgaacc | aggccagcca | 1680 |
| cgtttctgcg | aaaacgcggg | aaaaagtgga | agcggcgatg | gcggagctga | attacattcc | 1740 |
| caaccgcgtg | gcacaacaac | tggcgggcaa | acagtcgttg | ctgattggcg | ttgccacctc | 1800 |
| cagtctggcc | ctgcacgcgc | cgtcgcaaat | tgtcgcggcg | attaaatctc | gcgccgatca | 1860 |
| actgggtgcc | agcgtggtgg | tgtcgatggt | agaacgaagc | ggcgtcgaag | cctgtaaagc | 1920 |
| ggcggtgcac | aatcttctcg | cgcaacgcgt | cagtgggctg | atcattaact | atccgctgga | 1980 |
| tgaccaggat | gccattgctg | tggaagctgc | ctgcactaat | gttccggcgt | tatttcttga | 2040 |

-continued

```
tgtctctgac cagacaccca tcaacagtat tattttctcc catgaagacg gtacgcgact    2100
gggcgtggag catctggtcg cattgggtca ccagcaaatc gcgctgttag cgggcccatt    2160
aagttctgtc tcggcgcgtc tgcgtctggc tggctggcat aaatatctca ctcgcaatca    2220
aattcagccg atagcggaac gggaaggcga ctggagtgcc atgtccggtt ttcaacaaac    2280
catgcaaatg ctgaatgagg gcatcgttcc cactgcgatg ctggttgcca acgatcagat    2340
ggcgctgggc gcaatgcgcg ccattaccga gtccgggctg cgcgttggtg cggatatctc    2400
ggtagtggga tacgacgata ccgaagacag ctcatgttat atcccgccgt taaccaccat    2460
caaacaggat tttcgcctgc tggggcaaac cagcgtggac cgcttgctgc aactctctca    2520
gggccaggcg gtgaagggca atcagctgtt gcccgtctca ctggtgaaaa gaaaaaccac    2580
cctggcgccc aatacgcaaa ccgcctctcc ccgcgcgttg gccgattcat taatgcagct    2640
ggcacgacag gtttccgac tggaaagcgg gcagtgagcg caacgcaatt aatgtaagtt     2700
agctcactca ttaggcaccg ggatctcgac cgatgccctt gagagccttc aacccagtca    2760
gctccttccg gtgggcgcgg gcatgactac tcgtcgccgc acttatgact gtcttcttta    2820
tcatgcaact cgtaggacag gtgccggcag cgctctgggt cattttcggc gaggaccgct    2880
ttcgctggag cgcgacgatg atcggcctgt cgcttgcggt attcggaatc ttgcacgccc    2940
tcgctcaagc cttcgtcact ggtcccgcca ccaaacgttt cggcgagaag caggccatta    3000
tcgccggcat ggcggcccca cgggtgcgca tgatcgtgct cctgtcgttg aggacccggc    3060
taggctggcg gggttgcctt actggttagc agaatgaatc accgatacgc gagcgaacgt    3120
gaagcgactg ctgctgcaaa acgtctgcga cctgagcaac aacatgaatg gtcttcggtt    3180
tccgtgtttc gtaaagtctg gaaacgcgga agtcagcgcc ctgcaccatt atgttccgga    3240
tctgcatcgc aggatgctgc tggctaccct gtggaacacc tacatctgta ttaacgaagc    3300
gctggcattg accctgagtg atttttctct ggtcccgccg catccatacc gccagttgtt    3360
taccctcaca cgttccagt aaccgggcat gttcatcatc agtaacccgt atcgtgagca     3420
tcctctctcg tttcatcggt atcattaccc ccatgaacag aaatcccct tacacggagg     3480 catcagtgac caaacaggaa aaaaccgccc ttaacatggc ccgctttatc agaagccaga    3540
cattaacgct tctggagaaa ctcaacgagc tggacgcgga tgaacaggca gacatctgtg    3600
aatcgcttca cgaccacgct gatgagcttt accgcagctg cctcgcgcgt ttcggtgatg    3660
acggtgaaaa cctctgacac atgcagctcc cggagacggt cacagcttgt ctgtaagcgg    3720
atgccgggag cagacaagcc cgtcagggcg cgtcagcggg tgttggcggg tgtcggggcg    3780
cagccatgac ccagtcacgt agcgatagcg gagtgtatac tggcttaact atgcggcatc    3840
agagcagatt gtactgagag tgcaccatat atgcggtgtg aaataccgca cagatgcgta    3900
aggagaaaat accgcatcag gcgctcttcc gcttcctcgc tcactgactc gctgcgctcg    3960
gtcgttcggc tgcggcgagc ggtatcagct cactcaaagg cggtaatacg gttatccaca    4020
gaatcagggg ataacgcagg aaagaacatg tgagcaaaag gccagcaaaa ggccaggaac    4080
cgtaaaaagg ccgcgttgct ggcgtttttc cataggctcc gcccccctga cgagcatcac    4140
aaaaatcgac gctcaagtca gaggtggcga acccgacag gactataaag ataccaggcg     4200
tttccccctg gaagctccct cgtgcgctct cctgttccga ccctgccgct taccggatac    4260
ctgtccgcct ttctcccttc gggaagcgtg gcgctttctc atagctcacg ctgtaggtat    4320
ctcagttcgg tgtaggtcgt tcgctccaag ctgggctgtg tgcacgaacc cccgttcag    4380
```

```
cccgaccgct gcgccttatc cggtaactat cgtcttgagt ccaacccggt aagacacgac    4440
ttatcgccac tggcagctgg taacaggatt agcagagcga ggtatgtagg cggtgctaca    4500
gagttcttga agtggtggcc taactacggc tacactagaa ggacagtatt tggtatctgc    4560
gctctgctga agccagttac cttcggaaaa agagttggta gctcttgatc cggcaaacaa    4620
accaccgctg gtagcggtgg ttttttttgtt tgcaagcagc agattacgcg cagaaaaaaa    4680
ggatctcaag aagatccttt gatcttttct acggggtctg acgctcagtg gaacgaaaac    4740
tcacgttaag ggattttggt catgagatta tcaaaaagga tcttcaccta gatccttttta    4800 aattaaaaat gaagttttaa atcaatctaa agtatatatg agtaaacttg gtctgacagt    4860
taccaatgct taatcagtga ggcacctatc tcagcgatct gtctatttcg ttcatccata    4920
gttgcctgac tccccgtcgt gtagataact acgatacggg agggcttacc atctggcccc    4980
agtgctgcaa tgataccgcg agacccacgc tcaccggctc cagatttatc agcaataaac    5040
cagccagccg aagggccgag cgcagaagt ggtcctgcaa ctttatccgc ctccatccag    5100
tctattaatt gttgccggga agctagagta agtagttcgc cagttaatag tttgcgcaac    5160
gttgttgcca ttgctgcagg catcgtggtg tcacgctcgt cgtttggtat ggcttcattc    5220
agctccggtt cccaacgatc aaggcagtt acatgatccc ccatgttgtg caaaaaagcg    5280
gttagctcct tcggtcctcc gatcgttgtc agaagtaagt tggccgcagt gttatcactc    5340
atggttatgg cagcactgca taattctctt actgtcatgc catccgtaag atgcttttct    5400
gtgactggtg agtactcaac caagtcattc tgagaatagt gtatgcggcg accgagttgc    5460
tcttgcccgg cgtcaatacg ggataatacc gcgccacata gcagaacttt aaaagtgctc    5520
atcattggaa aacgttcttc ggggcgaaaa ctctcaagga tcttaccgct gttgagatcc    5580
agttcgatgt aacccactcg tgcacccaac tgatcttcag catctttac tttcaccagc    5640 gtttctgggt gagcaaaaac aggaaggcaa aatgccgcaa aaaagggaat aagggcgaca    5700
cggaaatgtt gaatactcat actcttcctt tttcaatatt attgaagcat ttatcagggt    5760
tattgtctca tgagcggata catatttgaa tgtatttaga aaaataaaca ataggggtt    5820 ccgcgcacat ttccccgaaa agtgccacct gaaattgtaa acgttaatat tttgttaaaa    5880
ttcgcgttaa attttttgtta atcagctca ttttttaacc aataggccga atcggcaaa    5940 atcccttata aatcaaaga atagaccgag atagggttga gtgttgttcc agtttggaac    6000
aagagtccac tattaaagaa cgtggactcc aacgtcaaag ggcgaaaaac cgtctatcag    6060
ggcgatggcc cactacgtga accatcaccc taatcaagtt ttttggggtc gaggtgccgt    6120
aaagcactaa atcggaaccc taagggagc ccccgattta gagcttgacg gggaaagccg    6180
gcgaacgtgg cgagaaagga agggaagaaa gcgaaaggag cgggcgctag gcgctggca    6240 agtgtagcgg tcacgctgcg cgtaaccacc acacccgccg cgcttaatgc gccgctacag    6300
ggcgcgtccc attcgcca                                                 6318
```

<210> SEQ ID NO 110
<211> LENGTH: 10493
<212> TYPE: DNA
<213> ORGANISM: Artificial Sequence
<220> FEATURE:
<223> OTHER INFORMATION: Synthetic Sequence AM1 (FCK mam)

<400> SEQUENCE: 110

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
```

```
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga gaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt   1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagacag agacagatcc attcgattag tgaacggatc ggcactgcgt   2400
gcgccaattc tgcagacaaa tggcagtatt catccacaat tttaaaagaa aagggggat   2460
```

```
tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760 gccttgggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttcccctgt    3300
aaaccttaga acccagctgt tgccaggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tgggggaggt aggaagagcg atgatcactt gtggactaag    3540
tttgttcaca tcccctttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctggggcag cggggatcc    3900 gccaccatgg gcgaaatctg gaagcaacat gaggacgcac tgcaaaagtt ctttgcattg    3960
ctgttgctgt tggccctgtt gctgctgctg gcactgctgc tgcacttgct ggcatttgaa    4020 ggtggtctg gtggcggcag cggcggtaag ttcttgctgc tgttggcgtt gctgccctg    4080 ctgctgctgg cgctgttgtt gcatctgctg gcttttggg aagcgctgaa tcagttcgaa    4140
gatctggcga agcaggtgg cagcggtggc ggtagcggcg gtgagatttg gaaacagcat    4200
gaggatgcgc tgcagaaatt cttcgcgttg ttgctgttgt tggcattgtt gctgctgttg    4260
gctctgctgt tgcatttgtt ggccttcaaa ggtggtagcg gtggtggttc cggtggtgag    4320
tttctgttgt tgttggcgct gctggccttg ctgttgctgg ctctgttgct gcacctgctg    4380
gcgttctggg aagcactgaa ccaatttgag gacctggcga acaggcggc accggtagta    4440 gcagtgagca agggcgagga gctgttcacc gggtggtgc ccatcctggt cgagctggac    4500
ggcgacgtaa acggccacaa gttcagcgtg tccggcgagg gcgagggcga tgccacctac    4560
ggcaagctga ccctgaagtt catttgcacc accggcaagc tgcccgtgcc ctggcccacc    4620
ctcgtgacca ccctgaccta cggcgtgcag tgcttcagcc gctaccccga ccacatgaag    4680
cagcacgact tcttcaagtc cgccatgccc gaaggctacg tccaggagcg caccatcttc    4740
ttcaaggacg acggcaacta caagacccgc gccgaggtga agttcgaggg cgacaccctg    4800
gtgaaccgca tcgagctgaa gggcatcgac ttcaaggagg acggcaacat cctggggcac    4860
```

```
aagctggagt acaactacaa cagccacaac gtctatatca tggccgacaa gcagaagaac    4920
ggcatcaagg tgaacttcaa gatccgccac aacatcgagg acggcagcgt gcagctcgcc    4980
gaccactacc agcagaacac ccccatcggc gacggccccg tgctgctgcc cgacaaccac    5040
tacctgagca cccagtccgc cctgagcaaa gaccccaacg agaagcgcga tcacatggtc    5100
ctgctggagt tcgtgaccgc cgccgggatc actctcggca tggacgagct gtacaagtaa    5160
gaattcgata tcaagcttat cgataatcaa cctctggatt acaaaatttg tgaaagattg    5220
actggtattc ttaactatgt tgctcctttt acgctatgtg gatacgctgc tttaatgcct    5280
ttgtatcatg ctattgcttc ccgtatggct ttcattttct cctccttgta taaatcctgg    5340
ttgctgtctc tttatgagga gttgtggccc gttgtcaggc aacgtggcgt ggtgtgcact    5400
gtgtttgctg acgcaacccc cactggttgg ggcattgcca ccacctgtca gctccttttcc   5460 gggactttcg ctttccccct ccctattgcc acggcggaac tcatcgccgc ctgccttgcc    5520
cgctgctgga caggggctcg gctgttgggc actgacaatt ccgtggtgtt gtcggggaaa    5580
tcatcgtcct ttccttggct gctcgcctgt gttgccacct ggattctgcg cgggacgtcc    5640
ttctgctacg tcccttcggc cctcaatcca gcggaccttc cttcccgcgg cctgctgccg    5700
gctctgcggc ctcttccgcg tcttcgcctt cgccctcaga cgagtcggat ctcccttttgg   5760 gccgcctccc cgcatcgata ccgtcgacct cgagacctag aaaaacatgg agcaatcaca    5820
agtagcaata cagcagctac caatgctgat tgtgcctggc tagaagcaca agaggaggag    5880 gaggtggggtt ttccagtcac acctcaggta cctttaagac caatgactta caaggcagct   5940
gtagatctta gccactttttt aaaagaaaag gggggactgg aagggctaat tcactcccaa    6000
cgaagacaag atatccttga tctgtggatc taccacacac aaggctactt ccctgattgg    6060
cagaactaca caccagggcc aggatcaga tatccactga cctttggatg gtgctacaag    6120
ctagtaccag ttgagcaaga aaggtagaa gaagccaatg aaggagagaa caccgcttg     6180 ttacaccctg tgagcctgca tgggatggat gacccggaga gagaagtatt agagtggagg    6240
tttgacagcc gcctagcatt tcatcacatg gcccgagagc tgcatccgga ctgtactggg    6300
tctctctggt tagaccagat ctgagcctgg gagctctctg gctaactagg gaacccactg    6360
cttaagcctc aataaagctt gccttgagtg cttcaagtag tgtgtgcccg tctgttgtgt    6420
gactctggta actagagatc cctcagaccc ttttagtcag tgtggaaaat ctctagcagg    6480
gcccgtttaa accgctgatc agcctcgac tgtgccttct agttgccagc catctgttgt     6540
ttgcccctcc cccgtgcctt ccttgaccct ggaaggtgcc actcccactg tccttttccta    6600 ataaaatgag gaaattgcat cgcattgtct gagtaggtgt cattctattc tggggggtgg    6660 ggtgggcag acagcaagg gggaggattg ggaagacaat agcaggcatg ctggggatgc      6720
ggtgggctct atggcttctg aggcggaaag aaccagctgg ggctctaggg ggtatcccca    6780
cgcgccctgt agcggcgcat taagcgcggc gggtgtggtg gttacgcgca gcgtgaccgc    6840
tacacttgcc agcgccctag cgcccgctcc tttcgctttc ttcccttcct ttctcgccac    6900
gttcgccggc tttccccgtc aagctctaaa tcggggggctc cctttagggt tccgatttag    6960
tgctttacgg cacctcgacc ccaaaaaact tgattagggt gatggttcac gtagtgggcc    7020
atcgccctga tagacggttt ttcgcccttt gacgttggag tccacgttct ttaatagtgg    7080
actcttgttc caaactggaa caacactcaa cccctatctcg gtctattctt ttgatttata    7140
agggattttg ccgatttcgg cctattggtt aaaaaatgag ctgatttaac aaaaatttaa    7200
```

```
cgcgaattaa ttctgtggaa tgtgtgtcag ttagggtgtg aaagtcccc  aggctcccca    7260 gcaggcagaa gtatgcaaag catgcatctc aattagtcag caaccaggtg tggaaagtcc    7320
ccaggctccc cagcaggcag aagtatgcaa agcatgcatc tcaattagtc agcaaccata    7380
gtcccgcccc taactccgcc catcccgccc ctaactccgc ccagttccgc ccattctccg    7440
ccccatggct gactaatttt ttttatttat gcagaggccg aggccgcctc tgcctctgag    7500
ctattccaga agtagtgagg aggcttttt  ggaggcctag gcttttgcaa aaagctcccg    7560
ggagcttgta tatccatttt cggatctgat cagcacgtgt tgacaattaa tcatcggcat    7620
agtatatcgg catagtataa tacgacaagg tgaggaacta aaccatggcc aagttgacca    7680
gtgccgttcc ggtgctcacc gcgcgcgacg tcgccggagc ggtcgagttc tggaccgacc    7740
ggctcgggtt ctcccgggac ttcgtggagg acgacttcgc cggtgtggtc cgggacgacg    7800
tgaccctgtt catcagcgcg gtccaggacc aggtggtgcc ggacaacacc ctggcctggg    7860
tgtgggtgcg cggcctggac gagctgtacg ccgagtggtc ggaggtcgtg tccacgaact    7920
tccgggacgc ctccgggccg gccatgaccg agatcggcga gcagccgtgg gggcgggagt    7980
tcgccctgcg cgaccggccc ggcaactgcg tgcacttcgt ggccgaggag caggactgac    8040
acgtgctacg agatttcgat tccaccgccg ccttctatga aggttgggc  ttcggaatcg    8100 ttttccggga cgccggctgg atgatcctcc agcgcgggga tctcatgctg gagttcttcg    8160 cccacccca  cttgtttatt gcagcttata atggttacaa ataaagcaat agcatcacaa    8220
atttcacaaa taaagcattt ttttcactgc attctagttg tggtttgtcc aaactcatca    8280
atgtatctta tcatgtctgt ataccgtcga cctctagcta gagcttggcg taatcatggt    8340
catagctgtt tcctgtgtga aattgttatc cgctcacaat tccacacaac atacgagccg    8400
gaagcataaa gtgtaaagcc tggggtgcct aatgagtgag ctaactcaca ttaattgcgt    8460
tgcgctcact gcccgctttc cagtcgggaa acctgtcgtg ccagctgcat taatgaatcg    8520
gccaacgcgc ggggagaggc ggtttgcgta ttgggcgctc ttccgcttcc tcgctcactg    8580
actcgctgcg ctcggtcgtt cggctgcggc gagcggtatc agctcactca aaggcggtaa    8640
tacggttatc cacagaatca ggggataacg caggaaagaa catgtgagca aaaggccagc    8700
aaaaggccag gaaccgtaaa aaggccgcgt tgctggcgtt tttccatagg ctccgccccc    8760
ctgacgagca tcacaaaaat cgacgctcaa gtcagaggtg cgaaacccg  acaggactat    8820 aaagatacca ggcgtttccc cctggaagct ccctcgtgcg ctctcctgtt ccgaccctgc    8880
cgcttaccgg atacctgtcc gcctttctcc cttcgggaag cgtggcgctt tctcatagct    8940
cacgctgtag gtatctcagt tcggtgtagg tcgttcgctc caagctgggc tgtgtgcacg    9000
aaccccccgt tcagcccgac cgctgcgcct tatccggtaa ctatcgtctt gagtccaacc    9060
cggtaagaca cgacttatcg ccactggcag cagccactgg taacaggatt agcagagcga    9120
ggtatgtagg cggtgctaca gagttcttga agtggtggcc taactacggc tacactagaa    9180
gaacagtatt tggtatctgc gctctgctga agccagttac cttcggaaaa agagttggta    9240
gctcttgatc cggcaaacaa accaccgctg gtagcggtgg ttttttttgtt tgcaagcagc    9300 agattacgcg cagaaaaaaa ggatctcaag aagatccttt gatcttttct acggggtctg    9360
acgctcagtg gaacgaaaac tcacgttaag ggattttggt catgagatta tcaaaaagga    9420
tcttcaccta gatcctttta aattaaaaat gaagttttaa atcaatctaa agtatatatg    9480
agtaaacttg gtctgacagt taccaatgct taatcagtga ggcacctatc tcagcgatct    9540
gtctatttcg ttcatccata gttgcctgac tccccgtcgt gtagataact acgatacggg    9600
```

```
agggcttacc atctggcccc agtgctgcaa tgataccgcg agacccacgc tcaccggctc    9660
cagatttatc agcaataaac cagccagccg gaagggccga gcgcagaagt ggtcctgcaa    9720
ctttatccgc ctccatccag tctattaatt gttgccggga agctagagta agtagttcgc    9780
cagttaatag tttgcgcaac gttgttgcca ttgctacagg catcgtggtg tcacgctcgt    9840
cgtttggtat ggcttcattc agctccggtt cccaacgatc aaggcgagtt acatgatccc    9900
ccatgttgtg caaaaagcg gttagctcct tcggtcctcc gatcgttgtc agaagtaagt    9960
tggccgcagt gttatcactc atggttatgg cagcactgca taattctctt actgtcatgc   10020
catccgtaag atgctttct gtgactggtg agtactcaac caagtcattc tgagaatagt   10080
gtatgcggcg accgagttgc tcttgcccgg cgtcaatacg gataatacc gcgccacata    10140 gcagaacttt aaaagtgctc atcattggaa aacgttcttc ggggcgaaaa ctctcaagga   10200
tcttaccgct gttgagatcc agttcgatgt aacccactcg tgcacccaac tgatcttcag   10260
catcttttac tttcaccagc gtttctgggt gagcaaaaac aggaaggcaa aatgccgcaa   10320 aaagggaat aagggcgaca cggaaatgtt gaatactcat actcttcctt tttcaatatt    10380
attgaagcat ttatcagggt tattgtctca tgagcggata catatttgaa tgtatttaga   10440
aaaataaaca aatagggtt ccgcgcacat ttccccgaaa agtgccacct gac            10493
```

<210> SEQ ID NO 111
<211> LENGTH: 171
<212> TYPE: PRT
<213> ORGANISM: Artificial Sequence
<220> FEATURE:
<223> OTHER INFORMATION: Synthetic Sequence AM1

<400> SEQUENCE: 111

```
Glu Ile Trp Lys Gln His Glu Asp Ala Leu Gln Lys Phe Phe Ala Leu
1               5                   10                  15

Leu Leu Leu Leu Ala Leu Leu Leu Leu Ala Leu Leu Leu His Leu
            20                  25                  30

Leu Ala Phe Glu Gly Gly Ser Gly Gly Gly Ser Gly Gly Lys Phe Leu
        35                  40                  45

Leu Leu Leu Ala Leu Leu Ala Leu Leu Leu Ala Leu Leu Leu His
    50                  55                  60

Leu Leu Ala Phe Trp Glu Ala Leu Asn Gln Phe Glu Asp Leu Ala Lys
65                  70                  75                  80

Gln Gly Gly Ser Gly Gly Ser Gly Gly Glu Ile Trp Lys Gln His
                85                  90                  95

Glu Asp Ala Leu Gln Lys Phe Phe Ala Leu Leu Leu Leu Ala Leu
            100                 105                 110

Leu Leu Leu Ala Leu Leu Leu His Leu Leu Ala Phe Lys Gly Gly
        115                 120                 125

Ser Gly Gly Gly Ser Gly Gly Glu Phe Leu Leu Leu Ala Leu Leu
    130                 135                 140

Ala Leu Leu Leu Ala Leu Leu Leu His Leu Leu Ala Phe Trp Glu
145                 150                 155                 160

Ala Leu Asn Gln Phe Glu Asp Leu Ala Lys Gln
                165                 170
```

<210> SEQ ID NO 112
<211> LENGTH: 126
<212> TYPE: PRT
<213> ORGANISM: Artificial Sequence

```
<220> FEATURE:
<223> OTHER INFORMATION: Synthetic Sequence GLSloop Q5L

<400> SEQUENCE: 112

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Arg Val Gln Lys
        115                 120                 125

<210> SEQ ID NO 113
<211> LENGTH: 126
<212> TYPE: PRT
<213> ORGANISM: Artificial Sequence
<220> FEATURE:
<223> OTHER INFORMATION: Synthetic Sequence C L5S

<400> SEQUENCE: 113

Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys Gly Gly Cys
    50                  55                  60

Gly Arg Ile Trp Lys Glu His Glu Asp Ala Leu Gln Lys Phe Glu Glu
65                  70                  75                  80

Ala Leu Asn Gln Phe Glu Asp Leu Lys Gln Leu Gly Gly Ser Gly Lys
                85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Arg Val Gln Lys
        115                 120                 125

<210> SEQ ID NO 114
<211> LENGTH: 126
<212> TYPE: PRT
<213> ORGANISM: Artificial Sequence
<220> FEATURE:
<223> OTHER INFORMATION: Synthetic Sequence C V124K

<400> SEQUENCE: 114

Glu Ile Trp Lys Leu His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30
```

Ser Gly Gly Glu Ile Lys Gln Arg His Glu Asp Ala Leu Arg Lys Phe
            35                  40                  45

Glu Glu Ala Leu Lys Arg Phe Glu Asp Leu Lys Gln Lys Gly Gly Cys
 50                  55                  60

Gly Arg Ile Trp Lys Glu His Glu Asp Ala Leu Gln Lys Phe Glu Glu
 65                  70                  75                  80

Ala Leu Asn Gln Phe Glu Asp Leu Lys Gln Leu Gly Gly Ser Gly Lys
                 85                  90                  95

Gly Ser Gly Gly Glu Ile Lys Gln Arg His Glu Asp Ala Leu Arg Lys
            100                 105                 110

Phe Glu Glu Ala Leu Lys Arg Phe Glu Asp Arg Lys Gln Lys
            115                 120                 125

<210> SEQ ID NO 115
<211> LENGTH: 6113
<212> TYPE: DNA
<213> ORGANISM: Artificial Sequence
<220> FEATURE:
<223> OTHER INFORMATION: Synthetic Sequence 1191min15 (E. Coli)

<400> SEQUENCE: 115

| | |
|---|---|
| ttcttgaaga cgaaagggcc tcgtgatacg cctattttta taggttaatg tcatgataat | 60 |
| aatggtttct tagacgtcag gtggcacttt tcggggaaat gtgcgcggaa cccctatttg | 120 |
| tttattttc taaatacatt caaatatgta tccgctcatg agacaataac cctgataaat | 180 |
| gcttcaataa tattgaaaaa ggaagagtat gagtattcaa catttccgtg tcgcccttat | 240 |
| tccctttttt gcggcatttt gccttcctgt ttttgctcac ccagaaacgc tggtgaaagt | 300 |
| aaaagatgct gaagatcagt tgggtgcacg agtgggttac atcgaactgg atctcaacag | 360 |
| cggtaagatc cttgagagtt ttcgccccga agaacgtttt ccaatgatga gcacttttaa | 420 |
| agttctgcta tgtggcgcgg tattatcccg tgttgacgcc gggcaagagc aactcggtcg | 480 |
| ccgcatacac tattctcaga atgacttggt tgagtactca ccagtcacag aaaagcatct | 540 |
| tacggatggc atgacagtaa gagaattatg cagtgctgcc ataaccatga gtgataacac | 600 |
| tgcggccaac ttacttctga caacgatcgg aggaccgaag gagctaaccg cttttttgca | 660 |
| caacatgggg gatcatgtaa ctcgccttga tcgttgggaa ccggagctga atgaagccat | 720 |
| accaaacgac gagcgtgaca ccacgatgcc tgcagcaatg gcaacaacgt tgcgcaaact | 780 |
| attaactggc gaactactta ctctagcttc ccggcaacaa ttaatagact ggatggaggc | 840 |
| ggataaagtt gcaggaccac ttctgcgctc ggcccttccg gctggctggt ttattgctga | 900 |
| taaatctgga gccggtgagc gtgggtctcg cggtatcatt gcagcactgg ggccagatgg | 960 |
| taagccctcc cgtatcgtag ttatctacac gacgggagt caggcaacta tggatgaacg | 1020 |
| aaatagacag atcgctgaga taggtgcctc actgattaag cattggtaac tgtcagacca | 1080 |
| agtttactca tatatacttt agattgattt aaaacttcat ttttaattta aaaggatcta | 1140 |
| ggtgaagatc ctttttgata atctcatgac caaaatccct taacgtgagt tttcgttcca | 1200 |
| ctgagcgtca gaccccgtag aaaagatcaa aggatcttct tgagatcctt ttttctgcg | 1260 |
| cgtaatctgc tgcttgcaaa caaaaaaacc accgctacca gcggtggttt gtttgccgga | 1320 |
| tcaagagcta ccaactcttt ttccgaaggt aactggcttc agcagagcgc agataccaaa | 1380 |
| tactgtcctt ctagtgtagc cgtagttagg ccaccacttc aagaactctg tagcaccgcc | 1440 |
| tacatacctc gctctgctaa tcctgttacc agtggctgct gccagtggcg ataagtcgtg | 1500 |
| tcttaccggg ttggactcaa gacgatagtt accggataag gcgcagcggt cgggctgaac | 1560 |

-continued

```
gggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttt tacggttcct     1860 ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctt ttcatccgcg tccagctcgt tgagtttctc cagaagcgtt aatgtctggc    2400
ttctgataaa gcgggccatg ttaagggcgg ttttttcctg tttggtcact gatgcctccg    2460 tgtaagggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg ggaggcagac aaggtatag gcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat     3360 aatgggaag ccatccagc ctcgcgtcgc gaacgccagc aagacgtagc ccagcgcgtc     3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag gcatcggtc gagatcccgg     3720 tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg gttttttctt tcaccagtga gacgggcaac agctgattgc    3900
```

```
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaataata ctgttgatgg    4380 gtgtctggtc agagacatca agaaataacg ccggaacatt agtgcaggca gcttccacag    4440
caatggcatc ctggtcatcc agcggatagt aatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga aacaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actataggg aattgtgagc ggataacaat tcccctctag    5280
aaataatttt gtttaacttt aagaaggaga tataccatgg gcagcagcca tcatcatcat    5340
catcacggcg cgacggcga gaacttgtat tttcaagcta gcggatccat gggagagatc    5400
tggaagagcc acgaagacgc gctgcagaaa ttcgaggaag ccctgaacca gtttgaggat    5460
ctgaagcagc tgggcggtag cgtgaaggt agcggcggtg aaatctggaa gcagcacgag    5520
gacgctctgc agaaattcga gaggcgctg aaccgtttcg aagatctgaa caactgggc    5580 ggttgcggcc gtatctggaa ggagcacgaa gacgcccacc agaaattcga ggaagctctg    5640
aaccaattcg aggatctgaa acagctgggc ggtagcggtg aaggtagcgg cggtgaaata    5700
tggaaacaac acgaggatgc tctgcaaaag tttgaggaag ccctgaaccg tcacgaagat    5760
cgtgtgcagc tggcaccggt ttaagaattc ctcgaggctg ctaacaaagc ccgaaggaa    5820 gctgagttgg ctgctgccac cgctgagcaa taactagcat aacccccttgg ggcctctaaa    5880 cgggtcttga ggggttttt gctgaaagga ggaactatat ccggatatcc cgcaagaggc    5940
ccggcagtac cggcataacc aagcctatgc ctacagcatc cagggtgacg gtgccgagga    6000
tgacgatgag cgcattgtta gatttcatac acggtgcctg actgcgttag caatttaact    6060
gtgataaact accgcattaa agcttatcga tgataagctg tcaaacatga gaa          6113
```

<210> SEQ ID NO 116
<211> LENGTH: 1891
<212> TYPE: DNA
<213> ORGANISM: Artificial Sequence
<220> FEATURE:
<223> OTHER INFORMATION: Synthetic Sequence 1191min15 (FCK mam)

<400> SEQUENCE: 116

```
gctgcggcga gcggtatcag ctcactcaaa ggcggtaata cggttatcca cagaatcagg    60
ggataacgca ggaaagaaca tgtgagcaaa aggccagcaa aaggccagga accgtaaaaa   120
ggccgcgttg ctggcgtttt tccataggct ccgcccccct gacgagcatc acaaaaatcg   180
acgctcaagt cagaggtggc gaaacccgac aggactataa agataccagg cgtttccccc   240
tggaagctcc ctcgtgcgct ctcctgttcc gaccctgccg cttaccggat acctgtccgc   300
ctttctccct tcgggaagcg tggcgctttc tcatagctca cgctgtaggt atctcagttc   360
ggtgtaggtc gttcgctcca agctgggctg tgtgcacgaa ccccccgttc agcccgaccg   420
ctgcgcctta tccggtaact atcgtcttga gtccaacccg gtaagacacg acttatcgcc   480
actggcagca gccactggta acaggattag cagagcgagg tatgtaggcg gtgctacaga   540
gttcttgaag tggtggccta actacggcta cactagaaga acagtatttg gtatctgcgc   600
tctgctgaag ccagttacct tcggaaaaag agttggtagc tcttgatccg gcaaacaaac   660
caccgctggt agcggtggtt tttttgtttg caagcagcag attacgcgca gaaaaaaagg   720
atctcaagaa gatcctttga tcttttctac ggggtctgac gctcagtgga acgaaaactc   780
acgttaaggg attttggtca tgagattatc aaaaaggatc ttcacctaga tccttttaaa   840
ttaaaaatga agttttaaat caatctaaag tatatatgag taaacttggt ctgacagtta   900
ccaatgctta atcagtgagg cacctatctc agcgatctgt ctatttcgtt catccatagt   960
tgcctgactc cccgtcgtgt agataactac gatacgggag ggcttaccat ctggccccag  1020
tgctgcaatg ataccgcgag acccacgctc accggctcca gatttatcag caataaacca  1080
gccagccgga agggccgagc gcagaagtgg tcctgcaact ttatccgcct ccatccagtc  1140
tattaattgt tgccgggaag ctagagtaag tagttcgcca gttaatagtt tgcgcaacgt  1200
tgttgccatt gctacaggca tcgtggtgtc acgctcgtcg tttggtatgg cttcattcag  1260
ctccggttcc caacgatcaa ggcgagttac atgatccccc atgttgtgca aaaaagcggt  1320
tagctccttc ggtcctccga tcgttgtcag aagtaagttg gccgcagtgt tatcactcat  1380
ggttatggca gcactgcata attctcttac tgtcatgcca tccgtaagat gcttttctgt  1440
gactggtgag tactcaacca agtcattctg agaatagtgt atgcggcgac cgagttgctc  1500
ttgcccggcg tcaatacggg ataataccgc gccacatagc agaactttaa aagtgctcat  1560
cattggaaaa cgttcttcgg ggcgaaaact ctcaaggatc ttaccgctgt tgagatccag  1620
ttcgatgtaa cccactcgtg cacccaactg atcttcagca tcttttactt tcaccagcgt  1680
ttctgggtga gcaaaaacag gaaggcaaaa tgccgcaaaa aagggaataa gggcgacacg  1740
gaaatgttga atactcatac tcttcctttt tcaatattat tgaagcattt atcagggtta  1800
ttgtctcatg agcggataca tatttgaatg tatttagaaa aataaacaaa tagggggttcc  1860
gcgcacattt ccccgaaaag tgccacctga c                                 1891
```

<210> SEQ ID NO 117
<211> LENGTH: 126
<212> TYPE: PRT
<213> ORGANISM: Artificial Sequence
<220> FEATURE:
<223> OTHER INFORMATION: Synthetic Sequence 1191min15

<400> SEQUENCE: 117

```
Glu Ile Trp Lys Ser His Glu Asp Ala Leu Gln Lys Phe Glu Ala
1               5                   10                  15

Leu Asn Gln Phe Glu Asp Leu Lys Gln Leu Gly Gly Ser Gly Glu Gly
            20                  25                  30

Ser Gly Gly Glu Ile Trp Lys Gln His Glu Asp Ala Leu Gln Lys Phe
        35                  40                  45

Glu Glu Ala Leu Asn Arg Phe Glu Asp Leu Lys Gln Leu Gly Gly Cys
    50                  55                  60

Gly Arg Ile Trp Lys Glu His Glu Asp Ala His Gln Lys Phe Glu Glu
65              70                  75                  80

Ala Leu Asn Gln Phe Glu Asp Leu Lys Gln Leu Gly Gly Ser Gly Glu
                85                  90                  95

Gly Ser Gly Gly Glu Ile Trp Lys Gln His Glu Asp Ala Leu Gln Lys
            100                 105                 110

Phe Glu Glu Ala Leu Asn Arg His Glu Asp Arg Val Gln Leu
            115                 120                 125
```

<210> SEQ ID NO 118
<211> LENGTH: 6113
<212> TYPE: DNA
<213> ORGANISM: Artificial Sequence
<220> FEATURE:
<223> OTHER INFORMATION: Synthetic Sequence GL Van Core (E. Coli)

<400> SEQUENCE: 118

```
ttcttgaaga cgaaagggcc tcgtgatacg cctatttta taggttaatg tcatgataat    60
aatggtttct tagacgtcag gtggcacttt tcggggaaat gtgcgcggaa cccctatttg   120
tttattttc taaatacatt caaatatgta tccgctcatg agacaataac cctgataaat   180
gcttcaataa tattgaaaaa ggaagagtat gagtattcaa catttccgtg tcgcccttat   240
tcccttttt gcggcatttt gccttcctgt ttttgctcac ccagaaacgc tggtgaaagt   300
aaaagatgct gaagatcagt tgggtgcacg agtgggttac atcgaactgg atctcaacag   360
cggtaagatc cttgagagtt ttcgccccga agaacgtttt ccaatgatga gcacttttaa   420
agttctgcta tgtggcgcgg tattatcccg tgttgacgcc gggcaagagc aactcggtcg   480
ccgcatacac tattctcaga atgacttggt tgagtactca ccagtcacag aaaagcatct   540
tacggatggc atgacagtaa gagaattatg cagtgctgcc ataaccatga gtgataacac   600
tgcggccaac ttacttctga caacgatcgg aggaccgaag gagctaaccg cttttttgca   660
caacatgggg gatcatgtaa ctcgccttga tcgttgggaa ccggagctga atgaagccat   720
accaaacgac gagcgtgaca ccacgatgcc tgcagcaatg gcaacaacgt tgcgcaaact   780
attaactggc gaactactta ctctagcttc ccggcaacaa ttaatagact ggatggaggc   840
ggataaagtt gcaggaccac ttctgcgctc ggcccttccg gctggctggt ttattgctga   900
taaatctgga gccggtgagc gtgggtctcg cggtatcatt gcagcactgg ggccagatgg   960
taagccctcc cgtatcgtag ttatctacac gacgggagt caggcaacta tggatgaacg  1020
aaatagacag atcgctgaga taggtgcctc actgattaag cattggtaac tgtcagacca  1080
agttactca tatatacttt agattgattt aaaacttcat ttttaattta aaaggatcta  1140
ggtgaagatc ctttttgata atctcatgac caaaatccct aacgtgagt tttcgttcca  1200
ctgagcgtca gaccccgtag aaaagatcaa aggatcttct tgagatcctt ttttctgcg  1260
cgtaatctgc tgcttgcaaa caaaaaaacc accgctacca gcggtggttt gtttgccgga  1320
tcaagagcta ccaactcttt ttccgaaggt aactggcttc agcagagcgc agataccaaa  1380
```

```
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag gcgcagcggt cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggcctttt tacggttcct    1860
ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460
tgtaaggggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag gcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga agaatcat    3360 aatgggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag gcatcggtc gagatcccgg    3720
```

-continued

```
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga cgggcaac agctgattgc      3900 ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg       5100 aagtggcgag cccgatcttc cccatcggtg atgtcggcga tataggcgcc agcaaccgca    5160
cctgtggcgc cggtgatgcc ggccacgatg cgtccgcgt agaggatcga gatctcgatc     5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg gcgacggcga gaacttgtat tttcaagcta gcggatccat gggagagctg    5400
ctgaagcagc tggaagacct gctgcagaaa ctggaggaac tgctgaacca gctgaggat    5460 ctgaagcagc tgggcggtag cggcaaaggt agcggcggtg agctgaagca gcgtctggaa    5520
gacctgctgc gtaagctgga ggaactgctg aaacgtctgg aggatctgaa acaaaaaggc    5580
ggttgcggcc gtctgctgaa ggaactggaa gacctgctgc aaaagctgga ggagctgctg    5640
aaccagctgg aagatctgaa acaactgggc ggtagcggca agggtagcgg cggtgagctg    5700
aaacagcgtc tggaagacct gctgagaaag ttcgaagagc tgctgaaacg tctggaggat    5760
ctgaagcaaa aagcaccggt ttaagaattc ctcgaggctg ctaacaaagc ccgaaggaa     5820 gctgagttgg ctgctgccac cgctgagcaa taactagcat aaccccttgg ggcctctaaa    5880
cgggtcttga ggggttttt gctgaaagga ggaactatat ccggatatcc cgcaagaggc     5940
ccggcagtac cggcataacc aagcctatgc ctacagcatc cagggtgacg gtgccgagga    6000
tgacgatgag cgcattgtta gatttcatac acgtgcctg actgcgttag caatttaact    6060
gtgataaact accgcattaa agcttatcga tgataagctg tcaaacatga gaa           6113
```

<210> SEQ ID NO 119
<211> LENGTH: 10349
<212> TYPE: DNA
<213> ORGANISM: Artificial Sequence
<220> FEATURE:
<223> OTHER INFORMATION: Synthetic Sequence GL Van Core (FCK mam)

<400> SEQUENCE: 119

| | | | | | |
|---|---|---|---|---|---|
| gtcgacggat | cgggagatct | cccgatcccc | tatggtgcac | tctcagtaca | atctgctctg | 60 |
| atgccgcata | gttaagccag | tatctgctcc | ctgcttgtgt | gttggaggtc | gctgagtagt | 120 |
| gcgcgagcaa | aatttaagct | acaacaaggc | aaggcttgac | cgacaattgc | atgaagaatc | 180 |
| tgcttagggt | taggcgtttt | gcgctgcttc | gcgatgtacg | ggccagatat | acgcgttgac | 240 |
| attgattatt | gactagttat | taatagtaat | caattacggg | gtcattagtt | catagcccat | 300 |
| atatggagtt | ccgcgttaca | taacttacgg | taaatggccc | gcctggctga | ccgcccaacg | 360 |
| acccccgccc | attgacgtca | ataatgacgt | atgttcccat | agtaacgcca | atagggactt | 420 |
| tccattgacg | tcaatgggtg | gagtatttac | ggtaaactgc | ccacttggca | gtacatcaag | 480 |
| tgtatcatat | gccaagtacg | ccccctattg | acgtcaatga | cggtaaatgg | cccgcctggc | 540 |
| attatgccca | gtacatgacc | ttatgggact | ttcctacttg | gcagtacatc | tacgtattag | 600 |
| tcatcgctat | taccatggtg | atgcggtttt | ggcagtacat | caatgggcgt | ggatagcggt | 660 |
| ttgactcacg | gggatttcca | agtctccacc | ccattgacgt | caatgggagt | ttgttttggc | 720 |
| accaaaatca | acgggacttt | ccaaaatgtc | gtaacaactc | cgccccattg | acgcaaatgg | 780 |
| gcggtaggcg | tgtacggtgg | gaggtctata | taagcagcgc | gttttgcctg | tactgggtct | 840 |
| ctctggttag | accagatctg | agcctgggag | ctctctggct | aactagggaa | cccactgctt | 900 |
| aagcctcaat | aaagcttgcc | ttgagtgctt | caagtagtgt | gtgcccgtct | gttgtgtgac | 960 |
| tctggtaact | agagatccct | cagacccttt | tagtcagtgt | ggaaaatctc | tagcagtggc | 1020 |
| gcccgaacag | ggacttgaaa | gcgaaaggga | aaccagagga | gctctctcga | cgcaggactc | 1080 |
| ggcttgctga | agcgcgcacg | gcaagaggcg | aggggcggcg | actggtgagt | acgccaaaaa | 1140 |
| ttttgactag | cggaggctag | aaggagagag | atgggtgcga | gagcgtcagt | attaagcggg | 1200 |
| ggagaattag | atcgcgatgg | gaaaaaattc | ggttaaggcc | aggggaaag | aaaaaatata | 1260 |
| aattaaaaca | tatagtatgg | gcaagcaggg | agctagaacg | attcgcagtt | aatcctggcc | 1320 |
| tgttagaaac | atcagaaggc | tgtagacaaa | tactgggaca | gctacaacca | tcccttcaga | 1380 |
| caggatcaga | agaacttaga | tcattatata | atacagtagc | aaccctctat | tgtgtgcatc | 1440 |
| aaaggataga | gataaaagac | accaaggaag | ctttagacaa | gatagaggaa | gagcaaaaca | 1500 |
| aaagtaagac | caccgcacag | caagcggccg | ctgatcttca | gacctggagg | aggagatatg | 1560 |
| agggacaatt | ggagaagtga | attatataaa | tataaagtag | taaaaattga | accattagga | 1620 |
| gtagcaccca | ccaaggcaaa | gagaagagtg | gtgcagagag | aaaaaagagc | agtgggaata | 1680 |
| ggagctttgt | tccttgggtt | cttgggagca | gcaggaagca | ctatgggcgc | agcgtcaatg | 1740 |
| acgctgacgg | tacaggccag | acaattattg | tctggtatag | tgcagcagca | gaacaatttg | 1800 |
| ctgagggcta | ttgaggcgca | acagcatctg | ttgcaactca | cagtctgggg | catcaagcag | 1860 |
| ctccaggcaa | gaatcctggc | tgtggaaaga | tacctaaagg | atcaacagct | cctggggatt | 1920 |
| tggggttgct | ctggaaaact | catttgcacc | actgctgtgc | cttggaatgc | tagttggagt | 1980 |
| aataaatctc | tggaacagat | ttggaatcac | acgacctgga | tggagtggga | cagagaaatt | 2040 |

```
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta acattatggc cttaggtcac ttcatctcca tggggttctt   2640
cttctgattt tctagaaaat gagatggggg tgcagagagc ttcctcagtg acctgcccag   2700
ggtcacatca gaaatgtcag agctagaact tgaactcaga ttactaatct taaattccat   2760
gccttggggg catgcaagta cgatatacag aaggagtgaa ctcattaggg cagatgacca   2820
atgagtttag gaaagaagag tccagggcag ggtacatcta caccaccgc ccagccctgg    2880
gtgagtccag ccacgttcac ctcattatag ttgcctctct ccagtcctac cttgacggga   2940
agcacaagca gaaactggga caggagcccc aggagaccaa atcttcatgg tccctctggg   3000
aggatgggtg gggagagctg tggcagaggc ctcaggaggg gccctgctgc tcagtggtga   3060
cagataggg tgagaaagca gacagagtca ttccgtcagc attctgggtc tgtttggtac    3120
ttcttctcac gctaaggtgg cggtgtgata tgcacaatgg ctaaaaagca gggagagctg   3180
gaaagaaaca aggacagaga cagaggccaa gtcaaccaga ccaattccca gaggaagcaa   3240
agaaaccatt acagagacta caaggggaa gggaaggaga gatgaattag cttcccctgt    3300
aaaccttaga acccagctgt tgccagggca acggggcaat acctgtctct tcagaggaga   3360
tgaagttgcc agggtaacta catcctgtct ttctcaagga ccatcccaga atgtggcacc   3420
cactagccgt taccatagca actgcctctt tgccccactt aatcccatcc cgtctgttaa   3480
aagggcccta tagttggagg tgggggaggt aggaagagcg atgatcactt gtggactaag   3540
tttgttcaca tccccttctc caaccccctc agtacatcac cctgggagaa caaggtccac   3600
ttgcttctgg gccacacag tcctgcagta ttgtgtatat aaggccaggg caacggagga    3660
gcaggttttg aagtgaaagg caggcaggtg ttggggaggc agttaccggg gcaacgggaa   3720
cagggcgttt cggaggtggt tgccatgggg acctggatgc tgacgaaggc tcgcgaggct   3780
gtgagcagcc acagtgccct gctcagaagc cccaagctcg tcagtcaagc cggttctccg   3840
tttgcactca ggagcacggg caggcgagtg gcccctagtt ctgggggcag cgggggatcc   3900
atgggagagc tgctgaagca gctggaagac ctgctgcaga aactggagga actgctgaac   3960
cagctggagg atctgaagca gctgggcggt agcggcaaag gtagcggcgg tgagctgaag   4020
cagcgtctgg aagacctgct gcgtaagctg gaggaactgc tgaaacgtct ggaggatctg   4080
aaacaaaaag gcggttgcgg ccgtctgctg aaggaactgg aagacctgct gcaaaagctg   4140
gaggagctgc tgaaccagct ggaagatctg aaacaactgg gcgtagcgg caagggtagc    4200
ggcggtgagc tgaaacagcg tctggaagac ctgctgagaa agttcgaaga gctgctgaaa   4260
cgtctggagg atctgaagca aaaagcaccg gtagtagcag tgagcaaggg cgaggagctg   4320
ttcaccgggg tggtgcccat cctggtcgag ctggacggcg acgtaaacgg ccacaagttc   4380
agcgtgtccg gcgagggcga gggcgatgcc acctacggca agctgaccct gaagttcatt   4440
```

```
tgcaccaccg gcaagctgcc cgtgccctgg cccaccctcg tgaccaccct gacctacggc    4500
gtgcagtgct tcagccgcta ccccgaccac atgaagcagc acgacttctt caagtccgcc    4560
atgcccgaag gctacgtcca ggagcgcacc atcttcttca aggacgacgg caactacaag    4620
acccgcgccg aggtgaagtt cgagggcgac accctggtga accgcatcga gctgaagggc    4680
atcgacttca aggaggacgg caacatcctg ggcacaagc tggagtacaa ctacaacagc    4740
cacaacgtct atatcatggc cgacaagcag aagaacggca tcaaggtgaa cttcaagatc    4800
cgccacaaca tcgaggacgg cagcgtgcag ctcgccgacc actaccagca gaacacccc    4860 atcggcgacg gccccgtgct gctgcccgac aaccactacc tgagcaccca gtccgccctg    4920
agcaaagacc ccaacgagaa gcgcgatcac atggtcctgc tggagttcgt gaccgccgcc    4980
gggatcactc tcggcatgga cgagctgtac aagtaagaat tcgatatcaa gcttatcgat    5040
aatcaacctc tggattacaa aatttgtgaa agattgactg gtattcttaa ctatgttgct    5100
ccttttacgc tatgtggata cgctgcttta atgcctttgt atcatgctat tgcttcccgt    5160
atggctttca ttttctcctc cttgtataaa tcctggttgc tgtctcttta tgaggagttg    5220
tggcccgttg tcaggcaacg tggcgtggtg tgcactgtgt ttgctgacgc aaccccact    5280 ggttggggca ttgccaccac ctgtcagctc ctttccggga ctttcgcttt cccctccct    5340 attgccacgg cggaactcat cgccgcctgc cttgcccgct gctggacagg ggctcggctg    5400
ttgggcactg acaattccgt ggtgttgtcg gggaaatcat cgtccttcc ttggctgctc    5460 gcctgtgttg ccacctggat tctgcgcggg acgtccttct gctacgtccc ttcggccctc    5520
aatccagcgg accttccttc ccgcggcctg ctgccggctc tgcggcctct tccgcgtctt    5580
cgccttcgcc ctcagacgag tcggatctcc ctttgggccg cctccccgca tcgataccgt    5640
cgacctcgag acctagaaaa acatggagca atcacaagta gcaatacagc agctaccaat    5700
gctgattgtg cctggctaga agcacaagag gaggaggagg tgggttttcc agtcacacct    5760 caggtaccttt aagaccaat gacttacaag gcagctgtag atcttagcca cttttaaaa    5820 gaaaagggg gactgaagg gctaattcac tcccaacgaa gacaagatat ccttgatctg    5880
tggatctacc acacacaagg ctacttccct gattggcaga actacacacc agggccaggg    5940
atcagatatc cactgacctt tggatggtgc tacaagctag taccagttga gcaagagaag    6000
gtagaagaag ccaatgaagg agagaacacc cgcttgttac accctgtgag cctgcatggg    6060
atggatgacc cggagagaga agtattagag tggaggtttg acagccgcct agcatttcat    6120
cacatggccc gagagctgca tccggactgt actgggtctc tctggttaga ccagatctga    6180
gcctgggagc tctctggcta actagggaac ccactgctta agcctcaata aagcttgcct    6240
tgagtgcttc aagtagtgtg tgcccgtctg ttgtgtgact ctggtaacta gagatccctc    6300 agacctttt agtcagtgtg gaaaatctct agcagggccc gtttaaaccc gctgatcagc    6360
ctcgactgtg ccttctagtt gccagccatc tgttgtttgc ccctccccg tgccttcctt    6420 gaccctggaa ggtgccactc ccactgtcct ttcctaataa aatgaggaaa ttgcatcgca    6480
ttgtctgagt aggtgtcatt ctattctggg gggtggggtg gggcaggaca gcaagggga    6540 ggattgggaa gacaatagca ggcatgctgg ggatgcggtg ggctctatgg cttctgaggc    6600
ggaaagaacc agctggggct ctaggggta tccccacgcg ccctgtagcg gcgcattaag    6660
cgcggcgggt gtggtggtta cgcgcagcgt gaccgctaca cttgccagcg ccctagcgcc    6720
cgctcctttc gctttcttcc cttcctttct cgccacgttc gccggctttc cccgtcaagc    6780
```

```
tctaaatcgg gggctcccctt tagggttccg atttagtgct ttacggcacc tcgaccccaa    6840
aaaacttgat tagggtgatg gttcacgtag tgggccatcg ccctgataga cggttttttcg    6900 cccctttgacg ttggagtcca cgttctttaa tagtggactc ttgttccaaa ctggaacaac    6960
actcaaccct atctcggtct attcttttga tttataaggg attttgccga tttcggccta    7020
ttggttaaaa aatgagctga tttaacaaaa atttaacgcg aattaattct gtggaatgtg    7080
tgtcagttag ggtgtggaaa gtccccaggc tccccagcag gcagaagtat gcaaagcatg    7140
catctcaatt agtcagcaac caggtgtgga aagtccccag gctccccagc aggcagaagt    7200
atgcaaagca tgcatctcaa ttagtcagca accatagtcc cgcccctaac tccgcccatc    7260
ccgcccctaa ctccgcccag ttccgcccat tctccgcccc atggctgact aattttttttt    7320 atttatgcag aggccgaggc cgcctctgcc tctgagctat tccagaagta gtgaggaggc    7380
ttttttggag gcctaggctt ttgcaaaaag ctcccgggag cttgtatatc cattttcgga    7440
tctgatcagc acgtgttgac aattaatcat cggcatagta tatcggcata gtataatacg    7500
acaaggtgag gaactaaacc atggccaagt tgaccagtgc cgttccggtg ctcaccgcgc    7560
gcgacgtcgc cggagcggtc gagttctgga ccgaccggct cgggttctcc cgggacttcg    7620
tggaggacga cttcgccggt gtggtccggg acgacgtgac cctgttcatc agcgcggtcc    7680
aggaccaggt ggtgccggac aacaccctgg cctgggtgtg ggtgcgcggc ctggacgagc    7740
tgtacgccga gtggtcggag gtcgtgtcca cgaacttccg gacgcctcc gggccggcca    7800 tgaccgagat cggcgagcag ccgtgggggc gggagttcgc cctgcgcgac ccggccggca    7860
actgcgtgca cttcgtggcc gaggagcagg actgacacgt gctacgagat ttcgattcca    7920
ccgccgcctt ctatgaaagg ttgggcttcg gaatcgtttt ccgggacgcc ggctggatga    7980
tcctccagcg cggggatctc atgctggagt tcttcgccca ccccaacttg tttattgcag    8040
cttataatgg ttacaaataa agcaatagca tcacaaattt cacaaataaa gcatttttttt    8100 cactgcattc tagttgtggt ttgtccaaac tcatcaatgt atcttatcat gtctgtatac    8160
cgtcgacctc tagctagagc ttggcgtaat catggtcata gctgtttcct gtgtgaaatt    8220
gttatccgct cacaattcca cacaacatac gagccggaag cataaagtgt aaagcctggg    8280
gtgcctaatg agtgagctaa ctcacattaa ttgcgttgcg ctcactgccc gctttccagt    8340
cgggaaacct gtcgtgccag ctgcattaat gaatcggcca acgcgcgggg agaggcggtt    8400
tgcgtattgg gcgctcttcc gcttcctcgc tcactgactc gctgcgctcg tcgttcggc    8460 tgcggcgagc ggtatcagct cactcaaagg cggtaatacg ttatccaca gaatcagggg    8520 ataacgcagg aaagaacatg tgagcaaaag gccagcaaaa ggccaggaac cgtaaaaagg    8580
ccgcgttgct ggcgtttttc cataggctcc gccccctga cgagcatcac aaaaatcgac    8640
gctcaagtca gaggtggcga aacccgacag gactataaag ataccaggcg tttccccctg    8700
gaagctccct cgtgcgctct cctgttccga ccctgccgct taccggatac ctgtccgcct    8760
ttctcccttc gggaagcgtg gcgctttctc atagctcacg ctgtaggtat ctcagttcgg    8820
tgtaggtcgt tcgctccaag ctgggctgtg tgcacgaacc ccccgttcag cccgaccgct    8880
gcgccttatc cggtaactat cgtcttgagt ccaacccggt aagacacgac ttatcgccac    8940
tggcagcagc cactggtaac aggattagca gagcgaggta tgtaggcggt gctacagagt    9000
tcttgaagtg gtggcctaac tacggctaca ctagaagaac agtatttggt atctgcgctc    9060
tgctgaagcc agttaccttc ggaaaaagag ttggtagctc ttgatccggc aaacaaacca    9120
ccgctggtag cggtggtttt tttgtttgca agcagcagat tacgcgcaga aaaaaaggat    9180
```

```
ctcaagaaga tcctttgatc ttttctacgg ggtctgacgc tcagtggaac gaaaactcac   9240
gttaagggat tttggtcatg agattatcaa aaaggatctt cacctagatc cttttaaatt   9300
aaaaatgaag ttttaaatca atctaaagta tatatgagta aacttggtct gacagttacc   9360
aatgcttaat cagtgaggca cctatctcag cgatctgtct atttcgttca tccatagttg   9420
cctgactccc cgtcgtgtag ataactacga tacgggaggg cttaccatct ggccccagtg   9480
ctgcaatgat accgcgagac ccacgctcac cggctccaga tttatcagca ataaccagc    9540
cagccggaag ggccgagcgc agaagtggtc ctgcaacttt atccgcctcc atccagtcta   9600
ttaattgttg ccgggaagct agagtaagta gttcgccagt taatagtttg cgcaacgttg   9660
ttgccattgc tacaggcatc gtggtgtcac gctcgtcgtt tggtatggct tcattcagct   9720
ccggttccca acgatcaagg cgagttacat gatcccccat gttgtgcaaa aaagcggtta   9780
gctccttcgg tcctccgatc gttgtcagaa gtaagttggc cgcagtgtta tcactcatgg   9840
ttatggcagc actgcataat tctcttactg tcatgccatc cgtaagatgc ttttctgtga   9900
ctggtgagta ctcaaccaag tcattctgag aatagtgtat gcggcgaccg agttgctctt   9960
gcccggcgtc aatacgggat aataccgcgc cacatagcag aactttaaaa gtgctcatca  10020
ttggaaaacg ttcttcgggg cgaaaactct caaggatctt accgctgttg agatccagtt  10080
cgatgtaacc cactcgtgca cccaactgat cttcagcatc ttttactttc accagcgttt  10140
ctgggtgagc aaaaacagga aggcaaaatg ccgcaaaaaa gggaataagg gcgacacgga  10200
aatgttgaat actcatactc ttcctttttc aatattattg aagcatttat cagggttatt  10260
gtctcatgag cggatacata tttgaatgta tttagaaaaa taaacaaata ggggttccgc  10320
gcacatttcc ccgaaaagtg ccacctgac                                    10349

<210> SEQ ID NO 120
<211> LENGTH: 126
<212> TYPE: PRT
<213> ORGANISM: Artificial Sequence
<220> FEATURE:
<223> OTHER INFORMATION: Synthetic Sequence GL Van Core

<400> SEQUENCE: 120

Glu Leu Leu Lys Gln Leu Glu Asp Leu Leu Gln Lys Leu Glu Glu Leu
1               5                   10                  15
Leu Asn Gln Leu Glu Asp Leu Lys Gln Leu Gly Gly Ser Gly Lys Gly
                20                  25                  30
Ser Gly Gly Glu Leu Lys Gln Arg Leu Glu Asp Leu Leu Arg Lys Leu
            35                  40                  45
Glu Glu Leu Leu Lys Arg Leu Glu Asp Leu Lys Gln Lys Gly Gly Cys
        50                  55                  60
Gly Arg Leu Leu Lys Glu Leu Glu Asp Leu Leu Gln Lys Leu Glu Glu
65                  70                  75                  80
Leu Leu Asn Gln Leu Glu Asp Leu Lys Gln Leu Gly Gly Ser Gly Lys
                85                  90                  95
Gly Ser Gly Gly Glu Leu Lys Gln Arg Leu Glu Asp Leu Leu Arg Lys
            100                 105                 110
Phe Glu Glu Leu Leu Lys Arg Leu Glu Asp Leu Lys Gln Lys
        115                 120                 125

<210> SEQ ID NO 121
<211> LENGTH: 6116
<212> TYPE: DNA
```

<213> ORGANISM: Artificial Sequence
<220> FEATURE:
<223> OTHER INFORMATION: Synthetic Sequence minus8maquette (E. Coli)

<400> SEQUENCE: 121

```
ttcttgaaga cgaaagggcc tcgtgatacg cctatttta taggttaatg tcatgataat      60
aatggtttct tagacgtcag gtggcacttt tcggggaaat gtgcgcggaa cccctatttg     120
tttattttc  taaatacatt caaatatgta tccgctcatg agacaataac cctgataaat     180
gcttcaataa tattgaaaaa ggaagagtat gagtattcaa catttccgtg tcgcccttat     240
tccctttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg cttttttgca     660
caacatgggg gatcatgtaa ctcgccttga tcgttgggaa ccggagctga atgaagccat     720
accaaacgac gagcgtgaca ccacgatgcc tgcagcaatg gcaacaacgt tgcgcaaact     780
attaactggc gaactactta ctctagcttc ccggcaacaa ttaatagact ggatggaggc     840
ggataaagtt gcaggaccac ttctgcgctc ggcccttccg gctggctggt ttattgctga     900
taaatctgga gccggtgagc gtgggtctcg cggtatcatt gcagcactgg ggccagatgg     960
taagccctcc cgtatcgtag ttatctacac gacgggagt caggcaacta tggatgaacg    1020
aaatagacag atcgctgaga taggtgcctc actgattaag cattggtaac tgtcagacca    1080
agtttactca tatatacttt agattgattt aaaacttcat ttttaattta aaaggatcta    1140
ggtgaagatc ctttttgata atctcatgac caaaatccct taacgtgagt tttcgttcca    1200
ctgagcgtca gaccccgtag aaaagatcaa aggatcttct tgagatcctt ttttttctgcg    1260
cgtaatctgc tgcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag cgcagcggt  cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttt  tacggttcct    1860
ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
```

| | |
|---|---|
| acagacaagc tgtgaccgtc tccgggagct gcatgtgtca gaggttttca ccgtcatcac | 2280 |
| cgaaacgcgc gaggcagctg cggtaaagct catcagcgtg gtcgtgaagc gattcacaga | 2340 |
| tgtctgcctg ttcatccgcg tccagctcgt tgagtttctc cagaagcgtt aatgtctggc | 2400 |
| ttctgataaa gcgggccatg ttaagggcgg ttttttcctg tttggtcact gatgcctccg | 2460 |
| tgtaagggggg atttctgttc atggggtaa tgataccgat gaaacgagag aggatgctca | 2520 |
| cgatacgggt tactgatgat gaacatgccc ggttactgga acgttgtgag ggtaaacaac | 2580 |
| tggcggtatg gatgcggcgg gaccagagaa aaatcactca gggtcaatgc cagcgcttcg | 2640 |
| ttaatacaga tgtaggtgtt ccacaggta gccagcagca tcctgcgatg cagatccgga | 2700 |
| acataatggt gcagggcgct gacttccgcg tttccagact ttacgaaaca cggaaaccga | 2760 |
| agaccattca tgttgttgct caggtcgcag acgttttgca gcagcagtcg cttcacgttc | 2820 |
| gctcgcgtat cggtgattca ttctgctaac cagtaaggca accccgccag cctagccggg | 2880 |
| tcctcaacga caggagcacg atcatgcgca cccgtggcca ggacccaacg ctgcccgaga | 2940 |
| tgcgccgcgt gcggctgctg gagatggcgg acgcgatgga tatgttctgc caagggttgg | 3000 |
| tttgcgcatt cacagttctc cgcaagaatt gattggctcc aattcttgga gtggtgaatc | 3060 |
| cgttagcgag gtgccgccgg cttccattca ggtcgaggtg gcccggctcc atgcaccgcg | 3120 |
| acgcaacgcg gggaggcaga caaggtatag ggcggcgcct acaatccatg ccaacccgtt | 3180 |
| ccatgtgctc gccgaggcgg cataaatcgc cgtgacgatc agcggtccag tgatcgaagt | 3240 |
| taggctggta agagccgcga gcgatccttg aagctgtccc tgatggtcgt catctacctg | 3300 |
| cctggacagc atggcctgca acgcgggcat cccgatgccg ccggaagcga aagaatcat | 3360 |
| aatggggaag gccatccagc ctcgcgtcgc gaacgccagc aagacgtagc ccagcgcgtc | 3420 |
| ggccgccatg ccggcgataa tggcctgctt ctcgccgaaa cgtttggtgg cgggaccagt | 3480 |
| gacgaaggct tgagcgaggg cgtgcaagat tccgaatacc gcaagcgaca ggccgatcat | 3540 |
| cgtcgcgctc cagcgaaagc ggtcctcgcc gaaaatgacc cagagcgctg ccggcacctg | 3600 |
| tcctacgagt tgcatgataa agaagacagt cataagtgcg gcgacgatag tcatgccccg | 3660 |
| cgcccaccgg aaggagctga ctgggttgaa ggctctcaag gcatcggtc gagatcccgg | 3720 |
| tgcctaatga gtgagctaac ttacattaat tgcgttgcgc tcactgcccg ctttccagtc | 3780 |
| gggaaacctg tcgtgccagc tgcattaatg aatcggccaa cgcgcgggga gaggcggttt | 3840 |
| gcgtattggg cgccagggtg gttttctttt tcaccagtga cgggcaac agctgattgc | 3900 |
| ccttcaccgc ctggccctga gagagttgca gcaagcggtc cacgctggtt tgccccagca | 3960 |
| ggcgaaaatc ctgtttgatg gtggttaacg gcgggatata acatgagctg tcttcggtat | 4020 |
| cgtcgtatcc cactaccgag atatccgcac caacgcgcag cccggactcg gtaatggcgc | 4080 |
| gcattgcgcc cagcgccatc tgatcgttgg caaccagcat cgcagtggga acgatgccct | 4140 |
| cattcagcat ttgcatggtt tgttgaaaac cggacatggc actccagtcg ccttcccgtt | 4200 |
| ccgctatcgg ctgaatttga ttgcgagtga gatatttatg ccagccagcc agacgcagac | 4260 |
| gcgccgagac agaacttaat gggcccgcta acagcgcgat ttgctggtga cccaatgcga | 4320 |
| ccagatgctc cacgcccagt cgcgtaccgt cttcatggga gaaaataata ctgttgatgg | 4380 |
| gtgtctggtc agagacatca agaaataacg ccggaacatt agtgcaggca gcttccacag | 4440 |
| caatggcatc ctggtcatcc agcggatagt taatgatcag cccactgacg cgttgcgcga | 4500 |
| gaagattgtg caccgccgct ttacaggctt cgacgccgct tcgttctacc atcgacacca | 4560 |

```
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg gcgacggcga gaacttgtat tttcaagcta gcggatccat gggagagatc    5400
tggaagcagc acgaagacgc gctgcagaaa ttcgaggaag ccctgaacca gtttgaggat    5460
ctgaagcagc tgggcggtag cggcagcggt agcggcggtg agatctggaa acagtgcgaa    5520
gacgctctgc gtaagttcga agaggcgctg aagcaattcg aggatctgaa gcagaaaggc    5580
ggtagcggcg aaatttggaa acaacacgaa gacgccctgc aaaagttcga ggaagctctg    5640
aaccagtttg aagatctgaa acaactgggc ggtagcggca gcggtagcgg cggtgagata    5700
tggaaacagc atgaggacgc gctgcgtaag ttcgaggaag ccctgaaaca attcgaagat    5760
ctgaagcaga aaaccggtta agaattcctc gaggatccgg ctgctaacaa agcccgaaag    5820
gaagctgagt tggctgctgc caccgctgag caataactag cataaccct tggggcctct    5880
aaacgggtct tgagggggtt tttgctgaaa ggaggaacta tatccggata tcccgcaaga    5940
ggcccggcag taccggcata accaagccta tgcctacagc atccagggtg acggtgccga    6000
ggatgacgat gagcgcattg ttagatttca tacacggtgc ctgactgcgt tagcaattta    6060
actgtgataa actaccgcat taaagcttat cgatgataag ctgtcaaaca tgagaa        6116
```

<210> SEQ ID NO 122
<211> LENGTH: 126
<212> TYPE: PRT
<213> ORGANISM: Artificial Sequence
<220> FEATURE:
<223> OTHER INFORMATION: Synthetic Sequence minus8maquette

<400> SEQUENCE: 122

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

Ser Gly Gly Glu Ile Trp Lys Gln Cys Glu Asp Ala Leu Arg Lys Phe
        35                  40                  45

Glu Glu Ala Leu Lys Gln Phe Glu Asp Leu Lys Gln Lys Gly Gly Ser
    50                  55                  60

Gly Glu Ile Trp Lys Gln His Glu Asp Ala Leu Gln Lys Phe Glu Glu
65                  70                  75                  80

Ala Leu Asn Gln Phe Glu Asp Leu Lys Gln Leu Gly Gly Ser Gly Ser
                85                  90                  95

Gly Ser Gly Gly Glu Ile Trp Lys Gln His Glu Asp Ala Leu Arg Lys
            100                 105                 110

Phe Glu Glu Ala Leu Lys Gln Phe Glu Asp Leu Lys Gln Lys
            115                 120                 125

<210> SEQ ID NO 123
<211> LENGTH: 6116
<212> TYPE: DNA
<213> ORGANISM: Artificial Sequence
<220> FEATURE:
<223> OTHER INFORMATION: Synthetic Sequence minus12maquette (E. Coli)

<400> SEQUENCE: 123

| | | | | | |
|---|---|---|---|---|---|
| ttcttgaaga | cgaaagggcc | tcgtgatacg | cctatttta | taggttaatg | tcatgataat | 60 |
| aatggtttct | tagacgtcag | gtggcactt | tcggggaaat | gtgcgcggaa | ccccctatttg | 120 |
| tttatttttc | taaatacatt | caaatatgta | tccgctcatg | agacaataac | cctgataaat | 180 |
| gcttcaataa | tattgaaaaa | ggaagagtat | gagtattcaa | catttccgtg | tcgcccttat | 240 |
| tcccttttt | gcggcatttt | gccttcctgt | ttttgctcac | ccagaaacgc | tggtgaaagt | 300 |
| aaaagatgct | gaagatcagt | tgggtgcacg | agtgggttac | atcgaactgg | atctcaacag | 360 |
| cggtaagatc | cttgagagtt | ttcgccccga | agaacgtttt | ccaatgatga | gcacttttaa | 420 |
| agttctgcta | tgtggcgcgg | tattatcccg | tgttgacgcc | gggcaagagc | aactcggtcg | 480 |
| ccgcatacac | tattctcaga | atgacttggt | tgagtactca | ccagtcacag | aaaagcatct | 540 |
| tacggatggc | atgacagtaa | gagaattatg | cagtgctgcc | ataaccatga | gtgataacac | 600 |
| tgcggccaac | ttacttctga | caacgatcgg | aggaccgaag | gagctaaccg | ctttttttgca | 660 |
| caacatgggg | gatcatgtaa | ctcgccttga | tcgttgggaa | ccggagctga | atgaagccat | 720 |
| accaaacgac | gagcgtgaca | ccacgatgcc | tgcagcaatg | gcaacaacgt | tgcgcaaact | 780 |
| attaactggc | gaactactta | ctctagcttc | ccggcaacaa | ttaatagact | ggatggaggc | 840 |
| ggataaagtt | gcaggaccac | ttctgcgctc | ggcccttccg | gctggctggt | ttattgctga | 900 |
| taaatctgga | gccggtgagc | gtgggtctcg | cggtatcatt | gcagcactgg | ggccagatgg | 960 |
| taagccctcc | cgtatcgtag | ttatctacac | gacggggagt | caggcaacta | tggatgaacg | 1020 |
| aaatagacag | atcgctgaga | taggtgcctc | actgattaag | cattggtaac | tgtcagacca | 1080 |
| agtttactca | tatatacttt | agattgattt | aaaacttcat | ttttaattta | aaaggatcta | 1140 |
| ggtgaagatc | cttttttgata | atctcatgac | caaaatccct | taacgtgagt | ttcgttcca | 1200 |
| ctgagcgtca | gaccccgtag | aaaagatcaa | aggatcttct | tgagatcctt | tttttctgcg | 1260 |
| cgtaatctgc | tgcttgcaaa | caaaaaaacc | accgctacca | gcggtggttt | gtttgccgga | 1320 |
| tcaagagcta | ccaactcttt | ttccgaaggt | aactggcttc | agcagagcgc | agataccaaa | 1380 |
| tactgtcctt | ctagtgtagc | cgtagttagg | ccaccacttc | aagaactctg | tagcaccgcc | 1440 |
| tacatacctc | gctctgctaa | tcctgttacc | agtggctgct | gccagtggcg | ataagtcgtg | 1500 |
| tcttaccggg | ttggactcaa | gacgatagtt | accggataag | gcgcagcggt | cgggctgaac | 1560 |
| ggggggttcg | tgcacacagc | ccagcttgga | gcgaacgacc | tacaccgaac | tgagatacct | 1620 |
| acagcgtgag | ctatgagaaa | gcgccacgct | tcccgaaggg | agaaaggcgg | acaggtatcc | 1680 |
| ggtaagcggc | agggtcggaa | caggagagcg | cacgagggag | cttccagggg | gaaacgcctg | 1740 |
| gtatctttat | agtcctgtcg | ggtttcgcca | cctctgactt | gagcgtcgat | ttttgtgatg | 1800 |
| ctcgtcaggg | gggcggagcc | tatggaaaaa | cgccagcaac | gcggcctttt | tacggttcct | 1860 |

-continued

```
ggccttttgc tggcctttg ctcacatgtt cttcctgcg ttatccctg attctgtgga      1920
taaccgtatt accgcttg agtgagctga taccgctcgc cgcagccgaa cgaccgagcg      1980
cagcgagtca gtgagcgagg aagcggaaga gcgcctgatg cggtatttc tccttacgca    2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag gcggcgcct acaatccatg ccaacccgtt    3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacaga atggcctgca acgcgggcat cccgatgccg ccggaagcga aagaatcat    3360
aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag gcatcggtc gagatcccgg    3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg ttttttcttt tcaccagtga gacgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
```

```
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt gcgacggcg    4620 cgtgcagggc cagactggag gtggcaacgc caatcagcaa cgactgtttg cccgccagtt    4680
gttgtgccac gcggttggga atgtaattca gctccgccat cgccgcttcc acttttcc     4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat cgatggtgt    4920 ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100 aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg gcgacggcga gaacttgtat tttcaagcta gcggatccat gggagagatc    5400
tggaagcagc acgaagacgc gctgcagaaa ttcgaggaag ccctgaacca gtttgaggat    5460
ctgaagcagc tgggcggtag cggcagcggt agcggcggtg agatctggaa acagtgcgaa    5520
gacgctctgc agaagttcga agaggcgctg aagcaattcg aagatctgaa caactgggc    5580 ggtagcggtg aaatttggaa acaacacgaa gacgccctgc aaaagttcga ggaagctctg    5640
aaccagtttg aagatctgaa acagctgggc ggtagcggca gcggtagcgg cggtgagata    5700
tggaaacagc atgaggatgc tctgcaaaag tttgaggaag ccctgaagca gtttgaggat    5760
ctgaaacagc tgaccggtta agaattcctc gaggatccgg ctgctaacaa agcccgaaag    5820
gaagctgagt tggctgctgc caccgctgag caataactag cataacccct ggggcctct    5880 aaacgggtct tgaggggttt tttgctgaaa ggaggaacta tatccggata tcccgcaaga    5940
ggcccggcag taccggcata accaagccta tgcctacagc atccagggtg acggtgccga    6000
ggatgacgat gagcgcattg ttagatttca tacacggtgc ctgactgcgt tagcaattta    6060
actgtgataa actaccgcat taagcttat cgatgataag ctgtcaaaca tgagaa        6116
```

<210> SEQ ID NO 124
<211> LENGTH: 126
<212> TYPE: PRT
<213> ORGANISM: Artificial Sequence
<220> FEATURE:
<223> OTHER INFORMATION: Synthetic Sequence minus12maquette

<400> SEQUENCE: 124

Glu Ile Trp Lys Gln His Glu Asp Ala Leu Gln Lys Phe Glu Glu Ala
1               5                   10                  15

Leu Asn Gln Phe Glu Asp Leu Lys Gln Leu Gly Gly Ser Gly Ser Gly
            20                  25                  30

```
Ser Gly Gly Glu Ile Trp Lys Gln Cys Glu Asp Ala Leu Gln Lys Phe
         35                  40                  45

Glu Glu Ala Leu Lys Gln Phe Glu Asp Leu Lys Gln Leu Gly Gly Ser
 50                  55                  60

Gly Glu Ile Trp Lys Gln His Glu Asp Ala Leu Gln Lys Phe Glu Glu
 65                  70                  75                  80

Ala Leu Asn Gln Phe Glu Asp Leu Lys Gln Leu Gly Gly Ser Gly Ser
             85                  90                  95

Gly Ser Gly Gly Glu Ile Trp Lys Gln His Glu Asp Ala Leu Gln Lys
             100                 105                 110

Phe Glu Glu Ala Leu Lys Gln Phe Glu Asp Leu Lys Gln Leu
             115                 120                 125

<210> SEQ ID NO 125
<211> LENGTH: 6113
<212> TYPE: DNA
<213> ORGANISM: Artificial Sequence
<220> FEATURE:
<223> OTHER INFORMATION: Synthetic Sequence plus4maquette (E. Coli)

<400> SEQUENCE: 125
```

| | | | | | |
|---|---|---|---|---|---|
| ttcttgaaga | cgaaagggcc | tcgtgatacg | cctattttta | taggttaatg | tcatgataat | 60 |
| aatggtttct | tagacgtcag | gtggcacttt | tcggggaaat | gtgcgcggaa | ccccctatttg | 120 |
| tttattttc | taaatacatt | caaatatgta | tccgctcatg | agacaataac | cctgataaat | 180 |
| gcttcaataa | tattgaaaaa | ggaagagtat | gagtattcaa | catttccgtg | tcgcccttat | 240 |
| tcccttttt | gcggcatttt | gccttcctgt | ttttgctcac | ccagaaacgc | tggtgaaagt | 300 |
| aaaagatgct | gaagatcagt | tgggtgcacg | agtgggttac | atcgaactgg | atctcaacag | 360 |
| cggtaagatc | cttgagagtt | ttcgccccga | agaacgtttt | ccaatgatga | gcacttttaa | 420 |
| agttctgcta | tgtggcgcgg | tattatcccg | tgttgacgcc | gggcaagagc | aactcggtcg | 480 |
| ccgcatacac | tattctcaga | atgacttggt | tgagtactca | ccagtcacag | aaaagcatct | 540 |
| tacggatggc | atgacagtaa | gagaattatg | cagtgctgcc | ataaccatga | gtgataacac | 600 |
| tgcggccaac | ttacttctga | caacgatcgg | aggaccgaag | gagctaaccg | cttttttgca | 660 |
| caacatgggg | gatcatgtaa | ctcgccttga | tcgttgggaa | ccggagctga | atgaagccat | 720 |
| accaaacgac | gagcgtgaca | ccacgatgcc | tgcagcaatg | gcaacaacgt | tgcgcaaact | 780 |
| attaactggc | gaactactta | ctctagcttc | ccggcaacaa | ttaatagact | ggatggaggc | 840 |
| ggataaagtt | gcaggaccac | ttctgcgctc | ggcccttccg | gctggctggt | ttattgctga | 900 |
| taaatctgga | gccggtgagc | gtgggtctcg | cggtatcatt | gcagcactgg | ggccagatgg | 960 |
| taagccctcc | cgtatcgtag | ttatctacac | gacggggagt | caggcaacta | tggatgaacg | 1020 |
| aaatagacag | atcgctgaga | taggtgcctc | actgattaag | cattggtaac | tgtcagacca | 1080 |
| agtttactca | tatatacttt | agattgattt | aaaacttcat | ttttaattta | aaaggatcta | 1140 |
| ggtgaagatc | ctttttgata | atctcatgac | caaaatccct | taacgtgagt | tttcgttcca | 1200 |
| ctgagcgtca | gaccccgtag | aaaagatcaa | aggatcttct | tgagatcctt | ttttctgcg | 1260 |
| cgtaatctgc | tgcttgcaaa | caaaaaaacc | accgctacca | gcggtggttt | gtttgccgga | 1320 |
| tcaagagcta | ccaactcttt | ttccgaaggt | aactggcttc | agcagagcgc | agataccaaa | 1380 |
| tactgtcctt | ctagtgtagc | cgtagttagg | ccaccacttc | aagaactctg | tagcaccgcc | 1440 |
| tacatacctc | gctctgctaa | tcctgttacc | agtggctgct | gccagtggcg | ataagtcgtg | 1500 |
| tcttaccggg | ttggactcaa | gacgatagtt | accggataag | gcgcagcggt | cgggctgaac | 1560 |

```
gggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggccttttt tacggttcct   1860
ggcctttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctt ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga agaatcat    3360
aatgggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag gcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg ttttttcttt tcaccagtga gacgggcaac agctgattgc   3900
```

```
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat cgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga aacaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg cgacggcga gaacttgtat tttcaagcta gcggatccat gggagagatc    5400
tggaagcagc acgaagacgc gctgcgtaag ttcgaggaag cgctgaaacg ttttgaggat    5460
ctgaagcaga aaggtggcag cggcaagggt agcggtggcg agatctggaa acaatgcgag    5520
gatgcgctgc gcaaatttga ggaagcgctg aagcgcttcg aagacctgaa acaaaaaggt    5580
ggcagcggcg agatttggaa acaacatgag gatgcgctgc gcaagtttga ggaagcgctg    5640
cgtaaatttg aagacctgaa acagaaaggt ggcagcggca aggtagcgg tggcgagatt    5700
tggaagcagc atgaggatgc gctgcgtaaa ttcgaggaag cgctgaagcg ttttgaagat    5760
ctgaagcaaa agcaccggt ttaagaattc ctcgaggctg ctaacaaagc ccgaaggaa    5820
gctgagttgg ctgctgccac cgctgagcaa taactagcat aacccctggg ggcctctaaa    5880
cgggtcttga ggggttttt gctgaaagga ggaactatat ccggatatcc cgcaagaggc    5940
ccggcagtac cggcataacc aagcctatgc ctacagcatc cagggtgacg gtgccgagga    6000
tgacgatgag cgcattgtta gatttcatac acggtgcctg actgcgttag caatttaact    6060
gtgataaact accgcattaa agcttatcga tgataagctg tcaaacatga gaa           6113
```

<210> SEQ ID NO 126
<211> LENGTH: 10349
<212> TYPE: DNA
<213> ORGANISM: Artificial Sequence
<220> FEATURE:
<223> OTHER INFORMATION: Synthetic Sequence plus4maquette (FCK mam)

<400> SEQUENCE: 126

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc aggggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctggggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |

```
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggggat   2460 tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tggcagaggc ctcaggaggg gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggggaa gggaaggaga gatgaattag cttcccctgt    3300
aaaccttaga acccagctgt tgccaggggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatccatcc cgtctgttaa     3480 aagggcccta tagttggagg tggggggaggt aggaagagcg atgatcactt gtggactaag   3540
tttgttcaca tccccttctc caaccccctc agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggggatcc   3900 atgggagaga tctggaagca gcacgaagac gcgctgcgta agttcgagga agcgctgaaa    3960
cgttttgagg atctgaagca gaaaggtggc agcggcaagg gtagcggtgg cgagatctgg    4020
aaacaatgcg aggatgcgct gcgcaaattt gaggaagcgc tgaagcgctt cgaagacctg    4080
aaacaaaaag gtggcagcgg cgagatttgg aaacaacatg gaggatgcgct gcgcaagttt    4140 gaggaagcgc tgcgtaaatt tgaagacctg aaacagaaag gtggcagcgg caaaggtagc    4200
ggtggcgaga tttggaagca gcatgaggat gcgctgcgta aattcgagga agcgctgaag    4260
cgttttgaag atctgaagca aaaagcaccg gtagtagcag tgagcaaggg cgaggagctg    4320
ttcaccgggg tggtgcccat cctggtcgag ctggacggcg acgtaaacgg ccacaagttc    4380
agcgtgtccg gcgagggcga gggcgatgcc acctacggca agctgaccct gaagttcatt    4440
tgcaccaccg gcaagctgcc cgtgccctgg cccaccctcg tgaccaccct gacctacggc    4500
gtgcagtgct tcagccgcta ccccgaccac atgaagcagc acgacttctt caagtccgcc    4560
atgcccgaag gctacgtcca ggagcgcacc atcttcttca aggacgacgg caactacaag    4620
```

```
acccgcgccg aggtgaagtt cgagggcgac accctggtga accgcatcga gctgaagggc    4680
atcgacttca aggaggacgg caacatcctg gggcacaagc tggagtacaa ctacaacagc    4740
cacaacgtct atatcatggc cgacaagcag aagaacggca tcaaggtgaa cttcaagatc    4800
cgccacaaca tcgaggacgg cagcgtgcag ctcgccgacc actaccagca gaacacccccc   4860
atcggcgacg gccccgtgct gctgcccgac aaccactacc tgagcaccca gtccgccctg    4920
agcaaagacc ccaacgagaa gcgcgatcac atggtcctgc tggagttcgt gaccgccgcc    4980
gggatcactc tcggcatgga cgagctgtac aagtaagaat tcgatatcaa gcttatcgat    5040
aatcaacctc tggattacaa aatttgtgaa agattgactg gtattcttaa ctatgttgct    5100
ccttttacgc tatgtggata cgctgcttta atgcctttgt atcatgctat tgcttcccgt    5160
atggctttca ttttctcctc cttgtataaa tcctggttgc tgtctcttta tgaggagttg    5220
tggcccgttg tcaggcaacg tggcgtggtg tgcactgtgt ttgctgacgc aacccccact    5280
ggttgggca ttgccaccac ctgtcagctc ctttccggga cttcgctttcccctccct        5340
attgccacgg cggaactcat cgccgcctgc cttgcccgct gctggacagg ggctcggctg    5400
ttggcactg acaattccgt ggtgttgtcg gggaaatcat cgtcctttcc ttggctgctc     5460
gcctgtgttg ccacctggat tctgcgcggg acgtccttct gctacgtccc ttcggccctc    5520
aatccagcgg accttccttc ccgcggcctg ctgccggctc tgcggcctct tccgcgtctt    5580
cgccttcgcc ctcagacgag tcggatctcc ctttgggccg cctccccgca tcgataccgt    5640
cgacctcgag acctagaaaa acatggagca atcacaagta gcaatacagc agctaccaat    5700
gctgattgtg cctggctaga agcacaagag gaggaggagg tgggttttcc agtcacacct    5760
caggtacctt taagaccaat gacttacaag gcagctgtag atcttagcca cttttttaaaa    5820
gaaaaggggg gactggaagg gctaattcac tcccaacgaa gacaagatat ccttgatctg     5880
tggatctacc acacacaagg ctacttccct gattggcaga actacacacc agggccaggg    5940
atcagatatc cactgacctt tggatggtgc tacaagctag taccagttga gcaagagaag    6000
gtagaagaag ccaatgaagg agagaacacc cgcttgttac accctgtgag cctgcatggg    6060
atggatgacc cggagagaga agtattagag tggaggtttg acagccgcct agcatttcat    6120
cacatggccc gagagctgca tccggactgt actgggtctc tctggttaga ccagatctga    6180
gcctgggagc tctctggcta actagggaac ccactgctta agcctcaata aagcttgcct    6240
tgagtgcttc aagtagtgtg tgcccgtctg ttgtgtgact ctggtaacta gagatccctc    6300
agacccttt agtcagtgtg gaaaatctct agcaggccc gtttaaaccc gctgatcagc       6360
ctcgactgtg ccttctagtt gccagccatc tgttgtttgc ccctcccccg tgccttcctt    6420
gaccctggaa ggtgccactc ccactgtcct ttcctaataa aatgaggaaa ttgcatcgca    6480
ttgtctgagt aggtgtcatt ctattctggg gggtgggggtg gggcaggaca gcaagggga    6540
ggattgggaa gacaatagca ggcatgctgg ggatgcggtg ggctctatgg cttctgaggc    6600
ggaaagaacc agctggggct ctagggggta tccccacgcg ccctgtagcg gcgcattaag    6660
cgcggcgggt gtggtggtta cgcgcagcgt gaccgctaca cttgccagcg ccctagcgcc    6720
cgctcctttc gctttcttcc cttcctttct cgccacgttc gccggctttc cccgtcaagc    6780
tctaaatcgg gggctccctt tagggttccg atttagtgct ttacggcacc tcgaccccaa    6840
aaaacttgat tagggtgatg gttcacgtag tgggccatcg cccctgataga cggttttttcg   6900
ccctttgacg ttggagtcca cgttctttaa tagtggactc ttgttccaaa ctggaacaac    6960
```

```
actcaaccct atctcggtct attcttttga tttataaggg attttgccga tttcggccta    7020
ttggttaaaa aatgagctga tttaacaaaa atttaacgcg aattaattct gtggaatgtg    7080
tgtcagttag ggtgtggaaa gtccccaggc tccccagcag gcagaagtat gcaaagcatg    7140
catctcaatt agtcagcaac caggtgtgga aagtccccag gctccccagc aggcagaagt    7200
atgcaaagca tgcatctcaa ttagtcagca accatagtcc cgcccctaac tccgcccatc    7260
ccgcccctaa ctccgcccag ttccgcccat tctccgcccc atggctgact aattttttt    7320 atttatgcag aggccgaggc cgcctctgcc tctgagctat tccagaagta gtgaggaggc    7380
ttttttggag gcctaggctt ttgcaaaaag ctcccgggag cttgtatatc cattttcgga    7440
tctgatcagc acgtgttgac aattaatcat cggcatagta tatcggcata gtataatacg    7500
acaaggtgag gaactaaacc atggccaagt tgaccagtgc cgttccggtg ctcaccgcgc    7560
gcgacgtcgc cggagcggtc gagttctgga ccgaccggct cgggttctcc cgggacttcg    7620
tggaggacga cttcgccggt gtggtccggg acgacgtgac cctgttcatc agcgcggtcc    7680
aggaccaggt ggtgccggac aacaccctgg cctgggtgtg ggtgcgcggc ctggacgagc    7740
tgtacgccga gtggtcggag gtcgtgtcca cgaacttccg ggacgcctcc gggccggcca    7800
tgaccgagat cggcgagcag ccgtgggggc gggagttcgc cctgcgcgac ccggccggca    7860
actgcgtgca cttcgtggcc gaggagcagg actgacacgt gctacgagat ttcgattcca    7920
ccgccgcctt ctatgaaagg ttgggcttcg gaatcgtttt ccgggacgcc ggctggatga    7980
tcctccagcg cggggatctc atgctggagt tcttcgccca ccccaacttg tttattgcag    8040
cttataatgg ttacaaataa agcaatagca tcacaaattt cacaaataaa gcatttttt    8100 cactgcattc tagttgtggt ttgtccaaac tcatcaatgt atcttatcat gtctgtatac    8160
cgtcgacctc tagctagagc ttggcgtaat catggtcata gctgtttcct gtgtgaaatt    8220
gttatccgct cacaattcca cacaacatac gagccggaag cataaagtgt aaagcctggg    8280
gtgcctaatg agtgagctaa ctcacattaa ttgcgttgcg ctcactgccc gctttccagt    8340
cgggaaacct gtcgtgccag ctgcattaat gaatcggcca acgcgcgggg agaggcggtt    8400
tgcgtattgg gcgctcttcc gcttcctcgc tcactgactc gctgcgctcg tcgttcggc    8460 tgcggcgagc ggtatcagct cactcaaagg cggtaatacg ttatccaca gaatcagggg    8520 ataacgcagg aaagaacatg tgagcaaaag gccagcaaaa ggccaggaac cgtaaaaagg    8580
ccgcgttgct ggcgttttc cataggctcc gcccccctga cgagcatcac aaaaatcgac    8640
gctcaagtca gaggtggcga aacccgacag gactataaag ataccaggcg tttccccctg    8700
gaagctccct cgtgcgctct cctgttccga ccctgccgct taccggatac ctgtccgcct    8760
ttctcccttc gggaagcgtg gcgctttctc atagctcacg ctgtaggtat ctcagttcgg    8820
tgtaggtcgt tcgctccaag ctgggctgtg tgcacgaacc ccccgttcag cccgaccgct    8880
gcgccttatc cggtaactat cgtcttgagt ccaacccggt aagacacgac ttatcgccac    8940
tggcagcagc cactggtaac aggattagca gagcgaggta tgtaggcggt gctacagagt    9000
tcttgaagtg gtggcctaac tacggctaca ctagaagaac agtatttggt atctgcgctc    9060
tgctgaagcc agttaccttc ggaaaaagag ttggtagctc ttgatccggc aaacaaacca    9120
ccgctggtag cggtggtttt tttgtttgca agcagcagat tacgcgcaga aaaaaggat    9180 ctcaagaaga tcctttgatc ttttctacgg ggtctgacgc tcagtggaac gaaaactcac    9240
gttaagggat tttggtcatg agattatcaa aaaggatctt cacctagatc cttttaaatt    9300
aaaaatgaag ttttaaatca atctaaagta tatatgagta aacttggtct gacagttacc    9360
```

-continued

```
aatgcttaat cagtgaggca cctatctcag cgatctgtct atttcgttca tccatagttg   9420
cctgactccc cgtcgtgtag ataactacga tacgggaggg cttaccatct ggccccagtg   9480
ctgcaatgat accgcgagac ccacgctcac cggctccaga tttatcagca ataaaccagc   9540
cagccggaag ggccgagcgc agaagtggtc ctgcaacttt atccgcctcc atccagtcta   9600
ttaattgttg ccgggaagct agagtaagta gttcgccagt taatagtttg cgcaacgttg   9660
ttgccattgc tacaggcatc gtggtgtcac gctcgtcgtt tggtatggct tcattcagct   9720
ccggttccca acgatcaagg cgagttacat gatcccccat gttgtgcaaa aaagcggtta   9780
gctccttcgg tcctccgatc gttgtcagaa gtaagttggc cgcagtgtta tcactcatgg   9840
ttatggcagc actgcataat tctcttactg tcatgccatc cgtaagatgc ttttctgtga   9900
ctggtgagta ctcaaccaag tcattctgag aatagtgtat gcggcgaccg agttgctctt   9960
gcccggcgtc aatacgggat aataccgcgc cacatagcag aactttaaaa gtgctcatca  10020
ttggaaaacg ttcttcgggg cgaaaactct caaggatctt accgctgttg agatccagtt  10080
cgatgtaacc cactcgtgca cccaactgat cttcagcatc ttttactttc accagcgttt  10140
ctgggtgagc aaaaacagga aggcaaaatg ccgcaaaaaa gggaataagg gcgacacgga  10200
aatgttgaat actcatactc ttcctttttc aatattattg aagcatttat cagggttatt  10260
gtctcatgag cggatacata tttgaatgta tttagaaaaa taaacaaata ggggttccgc  10320
gcacatttcc ccgaaaagtg ccacctgac                                    10349
```

<210> SEQ ID NO 127
<211> LENGTH: 126
<212> TYPE: PRT
<213> ORGANISM: Artificial Sequence
<220> FEATURE:
<223> OTHER INFORMATION: Synthetic Sequence plus4maquette

<400> SEQUENCE: 127

```
Glu Ile Trp Lys Gln His Glu Asp Ala Leu Arg Lys Phe Glu Glu Ala
 1               5                  10                  15

Leu Lys Arg Phe Glu Asp Leu Lys Gln Lys Gly Gly Ser Gly Lys Gly
            20                  25                  30

Ser Gly Gly Glu Ile Trp Lys Gln Cys Glu Asp Ala Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Gln His Glu Asp Ala Leu Arg Lys Phe Glu Glu
65                  70                  75                  80

Ala Leu Arg Lys Phe Glu Asp Leu Lys Gln Lys Gly Gly Ser Gly Lys
                85                  90                  95

Gly Ser Gly Gly Glu Ile Trp Lys Gln His Glu Asp Ala Leu Arg Lys
            100                 105                 110

Phe Glu Glu Ala Leu Lys Arg Phe Glu Asp Leu Lys Gln Lys
        115                 120                 125
```

<210> SEQ ID NO 128
<211> LENGTH: 6113
<212> TYPE: DNA
<213> ORGANISM: Artificial Sequence
<220> FEATURE:
<223> OTHER INFORMATION: Synthetic Sequence plus8maquette (E. Coli)

<400> SEQUENCE: 128

-continued

| | | | | | |
|---|---|---|---|---|---|
| ttcttgaaga | cgaaagggcc | tcgtgatacg | cctattttta | taggttaatg | tcatgataat | 60 |
| aatggtttct | tagacgtcag | gtggcacttt | tcggggaaat | gtgcgcggaa | ccccctatttg | 120 |
| tttattttc | taaatacatt | caaatatgta | tccgctcatg | agacaataac | cctgataaat | 180 |
| gcttcaataa | tattgaaaaa | ggaagagtat | gagtattcaa | catttccgtg | tcgcccttat | 240 |
| tcccttttt | gcggcatttt | gccttcctgt | ttttgctcac | ccagaaacgc | tggtgaaagt | 300 |
| aaaagatgct | gaagatcagt | tgggtgcacg | agtgggttac | atcgaactgg | atctcaacag | 360 |
| cggtaagatc | cttgagagtt | ttcgccccga | agaacgtttt | ccaatgatga | gcacttttaa | 420 |
| agttctgcta | tgtggcgcgg | tattatcccg | tgttgacgcc | gggcaagagc | aactcggtcg | 480 |
| ccgcatacac | tattctcaga | atgacttggt | tgagtactca | ccagtcacag | aaaagcatct | 540 |
| tacggatggc | atgacagtaa | gagaattatg | cagtgctgcc | ataaccatga | gtgataacac | 600 |
| tgcggccaac | ttacttctga | caacgatcgg | aggaccgaag | gagctaaccg | cttttttgca | 660 |
| caacatgggg | gatcatgtaa | ctcgccttga | tcgttgggaa | ccggagctga | atgaagccat | 720 |
| accaaacgac | gagcgtgaca | ccacgatgcc | tgcagcaatg | gcaacaacgt | tgcgcaaact | 780 |
| attaactggc | gaactactta | ctctagcttc | ccggcaacaa | ttaatagact | ggatggaggc | 840 |
| ggataaagtt | gcaggaccac | ttctgcgctc | ggcccttccg | gctggctggt | ttattgctga | 900 |
| taaatctgga | gccggtgagc | gtgggtctcg | cggtatcatt | gcagcactgg | ggccagatgg | 960 |
| taagccctcc | cgtatcgtag | ttatctacac | gacggggagt | caggcaacta | tggatgaacg | 1020 |
| aaatagacag | atcgctgaga | taggtgcctc | actgattaag | cattggtaac | tgtcagacca | 1080 |
| agtttactca | tatatacttt | agattgattt | aaaacttcat | ttttaattta | aaaggatcta | 1140 |
| ggtgaagatc | ctttttgata | atctcatgac | caaaatccct | taacgtgagt | tttcgttcca | 1200 |
| ctgagcgtca | gaccccgtag | aaaagatcaa | aggatcttct | tgagatcctt | ttttctgcg | 1260 |
| cgtaatctgc | tgcttgcaaa | caaaaaaacc | accgctacca | gcggtggttt | gtttgccgga | 1320 |
| tcaagagcta | ccaactcttt | ttccgaaggt | aactggcttc | agcagagcgc | agataccaaa | 1380 |
| tactgtcctt | ctagtgtagc | cgtagttagg | ccaccacttc | aagaactctg | tagcaccgcc | 1440 |
| tacatacctc | gctctgctaa | tcctgttacc | agtggctgct | gccagtggcg | ataagtcgtg | 1500 |
| tcttaccggg | ttggactcaa | gacgatagtt | accggataag | gcgcagcggt | cgggctgaac | 1560 |
| ggggggttcg | tgcacacagc | ccagcttgga | gcgaacgacc | tacaccgaac | tgagatacct | 1620 |
| acagcgtgag | ctatgagaaa | gcgccacgct | tcccgaaggg | agaaaggcgg | acaggtatcc | 1680 |
| ggtaagcggc | agggtcggaa | caggagagcg | cacgagggag | cttccagggg | gaaacgcctg | 1740 |
| gtatctttat | agtcctgtcg | ggtttcgcca | cctctgactt | gagcgtcgat | ttttgtgatg | 1800 |
| ctcgtcaggg | gggcggagcc | tatggaaaaa | cgccagcaac | gcggccttt | tacggttcct | 1860 |
| ggccttttgc | tggccttttg | ctcacatgtt | ctttcctgcg | ttatcccctg | attctgtgga | 1920 |
| taaccgtatt | accgcctttg | agtgagctga | taccgctcgc | cgcagccgaa | cgaccgagcg | 1980 |
| cagcgagtca | gtgagcgagg | aagcggaaga | gcgcctgatg | cggtattttc | tccttacgca | 2040 |
| tctgtgcggt | atttcacacc | gcatatatgg | tgcactctca | gtacaatctg | ctctgatgcc | 2100 |
| gcatagttaa | gccagtatac | actccgctat | cgctacgtga | ctgggtcatg | gctgcgcccc | 2160 |
| gacacccgcc | aacacccgct | gacgcgccct | gacgggcttg | tctgctcccg | gcatccgctt | 2220 |
| acagacaagc | tgtgaccgtc | tccgggagct | gcatgtgtca | gaggttttca | ccgtcatcac | 2280 |
| cgaaacgcgc | gaggcagctg | cggtaaagct | catcagcgtg | gtcgtgaagc | gattcacaga | 2340 |
| tgtctgcctg | ttcatccgcg | tccagctcgt | tgagtttctc | cagaagcgtt | aatgtctggc | 2400 |

```
ttctgataaa gcgggccatg ttaagggcgg ttttttcctg tttggtcact gatgcctccg    2460
tgtaaggggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag gcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat     3360 aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740
```

```
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg     5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg gcgacggcga gaacttgtat tttcaagcta gcggatccat gggagagatc    5400
tggaagcagc acgaagacgc gctgcgtaag ttcgaggaag cgctgaaacg ttttgaggat    5460
aagaaacaga agggtggcag cggtaaaggc agcggtggcg agatctggaa gcaatgcgag    5520
gatgcgctgc gcaaatttga ggaagcgctg aagcgttttg aggatctgaa gcagaaaggt    5580
ggcagcggcg agatttggaa acgtcatgag gatgcgctgc gcaagtttga ggaagcgctg    5640
cgtaaatttg aagataagaa acaaaagggt ggcagcggca agggcagcgg tggcgagatt    5700
tggaagcgcc atgaggatgc gctgcgtaaa ttcgaggaag cgctgaagcg ctttgaagat    5760
ctgaagcaaa aagcaccggt ttaagaattc ctcgaggctg ctaacaaagc ccgaaaggaa    5820
gctgagttgg ctgctgccac cgctgagcaa taactagcat aacccccttgg ggcctctaaa    5880
cgggtcttga ggggttttt gctgaaagga ggaactatat ccggatatcc cgcaagaggc    5940
ccggcagtac cggcataacc aagcctatgc ctacagcatc cagggtgacg gtgccgagga    6000
tgacgatgag cgcattgtta gatttcatac acggtgcctg actgcgttag caatttaact    6060
gtgataaact accgcattaa agcttatcga tgataagctg tcaaacatga gaa          6113
```

<210> SEQ ID NO 129
<211> LENGTH: 10349
<212> TYPE: DNA
<213> ORGANISM: Artificial Sequence
<220> FEATURE:
<223> OTHER INFORMATION: Synthetic Sequence plus8maquette (FCK mam)

<400> SEQUENCE: 129

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
accccgccc attgacgtca ataatgacgt atgttcccat agtaacgcca atagggactt     420
tccattgacg tcaatgggtg gagtattac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
```

```
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggaatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta acattatggc cttaggtcac ttcatctcca tggggttctt   2640
cttctgattt tctagaaaat gagatggggg tgcagagagc ttcctcagtg acctgcccag   2700
ggtcacatca gaaatgtcag agctagaact tgaactcaga ttactaatct taaattccat   2760
gccttggggg catgcaagta cgatatacag aaggagtgaa ctcattaggg cagatgacca   2820
atgagtttag gaaagaagag tccagggcag ggtcacatcta caccacccgc ccagccctgg   2880
gtgagtccag ccacgttcac ctcattatag ttgcctctct ccagtcctac cttgacggga   2940
agcacaagca gaaactggga caggagcccc aggagaccaa atcttcatgg tccctctggg   3000
aggatgggtg gggagagctg tggcagaggc ctcaggaggg gccctgctgc tcagtggtga   3060
```

```
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggaa gggaaggaga gatgaattag cttccctgt     3300 aaaccttaga acccagctgt tgccagggca acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatcccatcc cgtctgttaa    3480
aagggcccta tagttggagg tgggggaggt aggaagagcg atgatcactt gtggactaag    3540
tttgttcaca tccccttctc caacccctc agtacatcac cctgggagaa caaggtccac     3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggatcc     3900 atgggagaga tctggaagca gcacgaagac gcgctgcgta agttcgagga agcgctgaaa    3960
cgttttgagg ataagaaaca aagggtggc agcggtaaag gcagcggtgg cgagatctgg     4020
aagcaatgcg aggatgcgct gcgcaaattt gaggaagcgc tgaagcgttt tgaggatctg    4080
aagcagaaag gtggcagcgg cgagatttgg aaacgtcatg aggatgcgct gcgcaagttt    4140
gaggaagcgc tgcgtaaatt tgaagataag aaacaaaagg gtggcagcgg caagggcagc    4200
ggtggcgaga tttggaagcg ccatgaggat gcgctgcgta aattcgagga agcgctgaag    4260
cgctttgaag atctgaagca aaaagcaccg gtagtagcag tgagcaaggg cgaggagctg    4320
ttcaccgggg tggtgcccat cctggtcgag ctggacggcg acgtaaacgg ccacaagttc    4380
agcgtgtccg gcgagggcga gggcgatgcc acctacggca agctgaccct gaagttcatt    4440
tgcaccaccg gcaagctgcc cgtgccctgg cccacccctcg tgaccaccct gacctacggc    4500
gtgcagtgct tcagccgcta ccccgaccac atgaagcagc acgacttctt caagtccgcc    4560
atgcccgaag gctacgtcca ggagcgcacc atcttcttca aggacgacgg caactacaag    4620
acccgcgccg aggtgaagtt cgagggcgac accctggtga accgcatcga gctgaagggc    4680
atcgacttca aggaggacgg caacatcctg ggcacaagc tggagtacaa ctacaacagc    4740
cacaacgtct atatcatggc cgacaagcag aagaacggca tcaaggtgaa cttcaagatc    4800
cgccacaaca tcgaggacgg cagcgtgcag ctcgccgacc actaccagca gaacacccc     4860 atcggcgacg gccccgtgct gctgcccgac aaccactacc tgagcaccca gtccgccctg    4920
agcaaagacc ccaacgagaa gcgcgatcac atggtcctgc tggagttcgt gaccgccgcc    4980
gggatcactc tcggcatgga cgagctgtac aagtaagaat tcgatatcaa gcttatcgat    5040
aatcaacctc tggattacaa aatttgtgaa agattgactg gtattcttaa ctatgttgct    5100
ccttttacgc tatgtggata cgctgcttta atgcctttgt atcatgctat tgcttcccgt    5160
atggctttca ttttctcctc cttgtataaa tcctggttgc tgtctcttta tgaggagttg    5220
tggcccgttg tcaggcaacg tggcgtggtg tgcactgtgt ttgctgacgc aacccccact    5280
ggttggggca ttgccaccac ctgtcagctc ctttccggga cttttgcttt tcccctccct    5340
attgccacgc cggaactcat cgccgcctgc cttgcccgct gctggacagg gctcggctg     5400 ttgggcactg acaattccgt ggtgttgtcg gggaaatcat cgtcctttcc ttggctgctc    5460
```

```
gcctgtgttg ccacctggat tctgcgcggg acgtccttct gctacgtccc ttcggccctc  5520
aatccagcgg accttccttc ccgcggcctg ctgccggctc tgcggcctct tccgcgtctt  5580
cgccttcgcc ctcagacgag tcggatctcc ctttgggccg cctccccgca tcgataccgt  5640
cgacctcgag acctagaaaa acatggagca atcacaagta gcaatacagc agctaccaat  5700
gctgattgtg cctggctaga agcacaagag gaggaggagg tgggttttcc agtcacacct  5760
caggtacctt taagaccaat gacttacaag gcagctgtag atcttagcca cttttttaaaa  5820
gaaaaggggg gactggaagg gctaattcac tcccaacgaa gacaagatat ccttgatctg  5880
tggatctacc acacaaagg ctacttccct gattggcaga actacacacc agggccaggg  5940
atcagatatc cactgacctt tggatggtgc tacaagctag taccagttga gcaagagaag  6000
gtagaagaag ccaatgaagg agagaacacc cgcttgttac accctgtgag cctgcatggg  6060
atggatgacc cggagagaga agtattagag tggaggtttg acagccgcct agcatttcat  6120
cacatggccc gagagctgca tccggactgt actgggtctc tctggttaga ccagatctga  6180
gcctgggagc tctctggcta actagggaac ccactgctta agcctcaata aagcttgcct  6240
tgagtgcttc aagtagtgtg tgcccgtctg ttgtgtgact ctggtaacta gagatccctc  6300
agaccctttt agtcagtgtg gaaaatctct agcagggccc gtttaaaccc gctgatcagc  6360
ctcgactgtg ccttctagtt gccagccatc tgttgtttgc ccctccccg tgccttcctt  6420
gaccctggaa ggtgccactc ccactgtcct ttcctaataa aatgaggaaa ttgcatcgca  6480
ttgtctgagt aggtgtcatt ctattctggg gggtggggtg gggcaggaca gcaaggggga  6540
ggattgggaa gacaatagca ggcatgctgg ggatgcggtg ggctctatgg cttctgaggc  6600
ggaaagaacc agctgggct ctaggggta tccccacgcg ccctgtagcg gcgcattaag  6660
cgcggcgggt gtggtggtta cgcgcagcgt gaccgctaca cttgccagcg ccctagcgcc  6720
cgctcctttc gctttcttcc cttcctttct cgccacgttc gccggctttc cccgtcaagc  6780
tctaaatcgg gggctccctt tagggttccg atttagtgct ttacggcacc tcgaccccaa  6840
aaaacttgat tagggtgatg gttcacgtag tgggccatcg ccctgataga cggtttttcg  6900
cccctttgacg ttggagtcca cgttctttaa tagtggactc ttgttccaaa ctggaacaac  6960
actcaaccct atctcggtct attcttttga tttataaggg attttgccga tttcggccta  7020
ttggttaaaa aatgagctga tttaacaaaa atttaacgcg aattaattct gtggaatgtg  7080
tgtcagttag ggtgtggaaa gtccccaggc tccccagcag gcagaagtat gcaaagcatg  7140
catctcaatt agtcagcaac caggtgtgga aagtccccag gctccccagc aggcagaagt  7200
atgcaaagca tgcatctcaa ttagtcagca accatagtcc cgcccctaac tccgcccatc  7260
ccgcccctaa ctccgcccag ttccgcccat tctccgcccc atggctgact aattttttt  7320
atttatgcag aggccgaggc cgcctctgcc tctgagctat tccagaagta gtgaggaggc  7380
ttttttggag gcctaggctt ttgcaaaaag ctcccgggag cttgtatatc cattttcgga  7440
tctgatcagc acgtgttgac aattaatcat cggcatagta tatcggcata gtataatacg  7500
acaaggtgag gaactaaacc atggccaagt tgaccagtgc cgttccggtg ctcaccgcgc  7560
gcgacgtcgc cggagcggtc gagttctgga ccgaccggct cgggttctcc cgggacttcg  7620
tggaggacga cttcgccggt gtggtccggg acgacgtgac cctgttcatc agcgcggtcc  7680
aggaccaggt ggtgccggac aacacccctgg cctgggtgtg gtgcgcggc ctggacgagc  7740
tgtacgccga gtggtcggag gtcgtgtcca cgaacttccg ggacgcctcc gggccggcca  7800
```

```
tgaccgagat cggcgagcag ccgtgggggc gggagttcgc cctgcgcgac ccggccggca   7860
actgcgtgca cttcgtggcc gaggagcagg actgacacgt gctacgagat ttcgattcca   7920
ccgccgcctt ctatgaaagg ttgggcttcg gaatcgtttt ccgggacgcc ggctggatga   7980
tcctccagcg cggggatctc atgctggagt tcttcgccca ccccaacttg tttattgcag   8040
cttataatgg ttacaaataa agcaatagca tcacaaattt cacaaataaa gcattttttt   8100
cactgcattc tagttgtggt ttgtccaaac tcatcaatgt atcttatcat gtctgtatac   8160
cgtcgacctc tagctagagc ttggcgtaat catggtcata gctgtttcct gtgtgaaatt   8220
gttatccgct cacaattcca cacaacatac gagccggaag cataaagtgt aaagcctggg   8280
gtgcctaatg agtgagctaa ctcacattaa ttgcgttgcg ctcactgccc gctttccagt   8340
cgggaaacct gtcgtgccag ctgcattaat gaatcggcca acgcgcgggg agaggcggtt   8400
tgcgtattgg gcgctcttcc gcttcctcgc tcactgactc gctgcgctcg tcgttcggc    8460
tgcggcgagc ggtatcagct cactcaaagg cggtaatacg ttatccaca gaatcagggg    8520
ataacgcagg aaagaacatg tgagcaaaag gccagcaaaa ggccaggaac cgtaaaaagg   8580
ccgcgttgct ggcgtttttc cataggctcc gcccccctga cgagcatcac aaaaatcgac   8640
gctcaagtca gaggtggcga aacccgacag gactataaag ataccaggcg ttccccctg    8700
gaagctccct cgtgcgctct cctgttccga ccctgccgct taccggatac ctgtccgcct   8760
ttctcccttc gggaagcgtg cgctttctc atagctcacg ctgtaggtat ctcagttcgg    8820
tgtaggtcgt tcgctccaag ctgggctgtg tgcacgaacc ccccgttcag cccgaccgct   8880
gcgccttatc cggtaactat cgtcttgagt ccaacccggt aagacacgac ttatcgccac   8940
tggcagcagc cactggtaac aggattagca gagcgaggta tgtaggcggt gctacagagt   9000
tcttgaagtg gtggcctaac tacggctaca ctagaagaac agtatttggt atctgcgctc   9060
tgctgaagcc agttaccttc ggaaaaagag ttggtagctc ttgatccggc aaacaaacca   9120
ccgctggtag cggtggtttt tttgtttgca agcagcagat tacgcgcaga aaaaaaggat   9180
ctcaagaaga tccttttgatc ttttctacgg ggtctgacgc tcagtggaac gaaaactcac   9240
gttaagggat tttggtcatg agattatcaa aaaggatctt cacctagatc ctttttaaatt   9300
aaaaatgaag ttttaaatca atctaaagta tatatgagta acttggtct gacagttacc    9360
aatgcttaat cagtgaggca cctatctcag cgatctgtct atttcgttca tccatagttg    9420
cctgactccc cgtcgtgtag ataactacga tacgggaggg cttaccatct ggccccagtg    9480
ctgcaatgat accgcgagac ccacgctcac cggctccaga tttatcagca ataaaccagc    9540
cagccggaag ggccgagcgc agaagtggtc ctgcaacttt atccgcctcc atccagtcta    9600
ttaattgttg ccgggaagct agagtaagta gttcgccagt taatagtttg cgcaacgttg    9660
ttgccattgc tacaggcatc gtggtgtcac gctcgtcgtt tggtatggct tcattcagct    9720
ccggttccca acgatcaagg cgagttacat gatcccccat gttgtgcaaa aaagcggtta    9780
gctccttcgg tcctccgatc gttgtcagaa gtaagttggc cgcagtgtta tcactcatgg    9840
ttatggcagc actgcataat tctcttactg tcatgccatc cgtaagatgc ttttctgtga    9900
ctggtgagta ctcaaccaag tcattctgag aatagtgtat gcggcgaccg agttgctctt    9960
gcccggcgtc aatacgggat aataccgcgc cacatagcag aactttaaaa gtgctcatca   10020
ttggaaaacg ttcttcgggg cgaaaactct caaggatctt accgctgttg agatccagtt   10080
cgatgtaacc cactcgtgca cccaactgat cttcagcatc ttttactttc accagcgttt   10140
ctgggtgagc aaaaacagga aggcaaaatg ccgcaaaaaa gggaataagg gcgacacgga   10200
```

```
aatgttgaat actcatactc ttccttttc aatattattg aagcatttat cagggttatt    10260
gtctcatgag cggatacata tttgaatgta tttagaaaaa taaacaaata ggggttccgc    10320
gcacatttcc ccgaaaagtg ccacctgac                                     10349
```

<210> SEQ ID NO 130
<211> LENGTH: 126
<212> TYPE: PRT
<213> ORGANISM: Artificial Sequence
<220> FEATURE:
<223> OTHER INFORMATION: Synthetic Sequence plus8maquette

<400> SEQUENCE: 130

```
Glu Ile Trp Lys Gln His Glu Asp Ala Leu Arg Lys Phe Glu Glu Ala
1               5                   10                  15

Leu Lys Arg Phe Glu Asp Lys Lys Gln Lys Gly Gly Ser Gly Lys Gly
            20                  25                  30

Ser Gly Gly Glu Ile Trp Lys Gln Cys Glu Asp Ala Leu Arg Lys Phe
        35                  40                  45

Glu Glu Ala Leu Lys Arg Phe Glu Asp Leu Lys Gln Lys Gly Gly Ser
    50                  55                  60

Gly Glu Ile Trp Lys Arg His Glu Asp Ala Leu Arg Lys Phe Glu Glu
65                  70                  75                  80

Ala Leu Arg Lys Phe Glu Asp Lys Lys Gln Lys Gly Gly Ser Gly Lys
                85                  90                  95

Gly Ser Gly Gly Glu Ile Trp Lys Arg His Glu Asp Ala Leu Arg Lys
            100                 105                 110

Phe Glu Glu Ala Leu Lys Arg Phe Glu Asp Leu Lys Gln Lys
        115                 120                 125
```

<210> SEQ ID NO 131
<211> LENGTH: 6113
<212> TYPE: DNA
<213> ORGANISM: Artificial Sequence
<220> FEATURE:
<223> OTHER INFORMATION: Synthetic Sequence MMmin4 (E. Coli)

<400> SEQUENCE: 131

```
ttcttgaaga cgaaagggcc tcgtgatacg cctatttta taggttaatg tcatgataat      60
aatggtttct tagacgtcag gtggcacttt tcggggaaat gtgcgcggaa ccccatttg     120 tttattttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
```

```
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttttgata atctcatgac caaaatccct taacgtgagt tttcgttcca   1200
ctgagcgtca gaccccgtag aaaagatcaa aggatcttct tgagatcctt ttttctgcg    1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacataccct gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacgttcct    1860
ggcctttgc tggccttttg ctcacatgtt ctttcctgcg ttatcccctg attctgtgga    1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgaa tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg ggaggcagac aaggtatagg gcggcgccta caatccatg ccaacccgtt    3180
ccatgtgctc gccgaggcgg cataaatcgc cgtgacgatc agcggtccag tgatcgaagt   3240
```

```
taggctggta agagccgcga gcgatccttg aagctgtccc tgatggtcgt catctacctg    3300
cctggacagc atggcctgca acgcgggcat cccgatgccg ccggaagcga agaagaatcat   3360
aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg gttttctt tcaccagtga cgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg cgacggcga gaacttgtat tttcaagcta gcggatccat gggagagctg    5400
tggaagaaac acgaggaagc gctgaagaaa ttcgaggaac tgctgaagaa atttgaggaa    5460
gagctgaaac tgggtggcag cggcgaggt agcggtggcg aactgctgaa gaaatgcgaa    5520
gaggcgctga agaaattcga agagctgctg aagaaatttg aagaggaact gaagctgggt    5580
```

| | |
|---|---|
| ggcagcggtg aactgctgaa gaaacatgag gaagcgctga agaaatttga ggagttactg | 5640 |
| aagaaattcg aggagctgtt aaagctgggt ggcagcggcg aaggcagcgg tggcgaatta | 5700 |
| ctgaagaaac acgaggaagc gctgaagaaa ttcgaggaat tactgaagaa atttgaagag | 5760 |
| ctgctgaaac tggcaccggt ttaagaattc ctcgaggctg ctaacaaagc ccgaaaggaa | 5820 |
| gctgagttgg ctgctgccac cgctgagcaa taactagcat aacccottgg ggcctctaaa | 5880 |
| cgggtcttga gggggttttttt gctgaaagga ggaactatat ccggatatcc cgcaagaggc | 5940 |
| ccggcagtac cggcataacc aagcctatgc ctacagcatc cagggtgacg gtgccgagga | 6000 |
| tgacgatgag cgcattgtta gatttcatac acggtgcctg actgcgttag caatttaact | 6060 |
| gtgataaact accgcattaa agcttatcga tgataagctg tcaaacatga gaa | 6113 |

<210> SEQ ID NO 132
<211> LENGTH: 10349
<212> TYPE: DNA
<213> ORGANISM: Artificial Sequence
<220> FEATURE:
<223> OTHER INFORMATION: Synthetic Sequence MMmin4 (FCK mam)

<400> SEQUENCE: 132

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgcgctgctt cgcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |

```
agggacaatt ggagaagtga attatataaa tataaagtag taaaaattga accattagga      1620
gtagcaccca ccaaggcaaa gagaagagtg gtgcagagag aaaaaagagc agtgggaata      1680
ggagctttgt tccttgggtt cttgggagca gcaggaagca ctatgggcgc agcgtcaatg      1740
acgctgacgg tacaggccag acaattattg tctggtatag tgcagcagca gaacaatttg      1800
ctgagggcta ttgaggcgca acagcatctg ttgcaactca cagtctgggg catcaagcag      1860
ctccaggcaa gaatcctggc tgtgaaaga tacctaaagg atcaacagct cctgggatt        1920
tggggttgct ctggaaaact catttgcacc actgctgtgc cttggaatgc tagttggagt      1980
aataaatctc tggaacagat ttggaatcac acgacctgga tggagtggga cagagaaatt      2040
aacaattaca caagcttaat acactcctta attgaagaat cgcaaaacca gcaagaaaag      2100
aatgaacaag aattattgga attagataaa tgggcaagtt tgtggaattg gtttaacata      2160
acaaattggc tgtggtatat aaaattattc ataatgatag taggaggctt ggtaggttta      2220
agaatagttt ttgctgtact ttctatagtg aatagagtta ggcagggata ttcaccatta      2280
tcgtttcaga cccacctccc aaccccgagg ggacccgaca ggcccgaagg aatagaagaa      2340
gaaggtggag agagacag agacagatcc attcgattag tgaacggatc ggcactgcgt        2400
gcgccaattc tgcagacaaa tggcagtatt catccacaat tttaaaagaa aaggggggat      2460
tggggggtac agtgcagggg aaagaatagt agacataata gcaacagaca tacaaactaa      2520
agaattacaa aaacaaatta caaaaattca aaattttcgg gtttattaca gggacagcag      2580
agatccagtt tggttaatta acattatggc cttaggtcac ttcatctcca tggggttctt      2640
cttctgattt tctagaaaat gagatggggg tgcagagagc ttcctcagtg acctgcccag      2700
ggtcacatca gaaatgtcag agctagaact tgaactcaga ttactaatct taaattccat      2760
gccttggggg catgcaagta cgatatacag aaggagtgaa ctcattaggg cagatgacca      2820
atgagtttag gaaagaagag tccagggcag ggtacatcta caccacccgc ccagccctgg      2880
gtgagtccag ccacgttcac ctcattatag ttgcctctct ccagtcctac cttgacggga      2940
agcacaagca gaaactggga caggagcccc aggagaccaa atcttcatgg tccctctggg      3000
aggatgggtg gggagagctg tggcagaggc ctcaggaggg gccctgctgc tcagtggtga      3060
cagatagggg tgagaaagca gacagagtca ttccgtcagc attctgggtc tgtttggtac      3120
ttcttctcac gctaaggtgg cggtgtgata tgcacaatgg ctaaaaagca gggagagctg      3180
gaaagaaaca aggacagaga cagaggccaa gtcaaccaga ccaattccca gaggaagcaa      3240
agaaaccatt acagagacta caaggggaa gggaaggaga gatgaattag cttcccctgt       3300
aaaccttaga acccagctgt tgccagggca acggggcaat acctgtctct tcagaggaga      3360
tgaagttgcc agggtaacta catcctgtct ttctcaagga ccatcccaga atgtggcacc      3420
cactagccgt taccatagca actgcctctt tgccccactt aatcccatcc cgtctgttaa      3480
aagggcccta tagttggagg tggggaggt aggaagagcg atgatcactt gtggactaag       3540
tttgttcaca tccccttctc caacccctc agtacatcac cctgggagaa caaggtccac       3600
ttgcttctgg gcccacacag tcctgcagta ttgtgtatat aaggccaggg caacggagga     3660
gcaggttttg aagtgaaagg caggcaggtg ttggggaggc agttaccggg gcaacgggaa      3720
cagggcgttt cggaggtggt tgccatgggg acctggatgc tgacgaaggc tcgcgaggct      3780
gtgagcagcc acagtgccct gctcagaagc cccaagctcg tcaatcaagc tggttctcca      3840
tttgcactca ggagcacggg caggcgagtg gcccctagtt ctgggggcag cggggggatcc     3900
```

-continued

```
atgggagagc tgtggaagaa acacgaggaa gcgctgaaga aattcgagga actgctgaag    3960
aaatttgagg aagagctgaa actgggtggc agcggcgagg gtagcggtgg cgaactgctg    4020
aagaaatgcg aagaggcgct gaagaaattc gaagagctgc tgaagaaatt tgaagaggaa    4080
ctgaagctgg gtggcagcgg tgaactgctg aagaaacatg aggaagcgct gaagaaattt    4140
gaggagttac tgaagaaatt cgaggagctg ttaaagctgg gtggcagcgg cgaaggcagc    4200
ggtggcgaat tactgaagaa acacgaggaa gcgctgaaga aattcgagga attactgaag    4260
aaatttgaag agctgctgaa actggcaccg gtagtagcag tgagcaaggg cgaggagctg    4320
ttcaccgggg tggtgcccat cctggtcgag ctggacggcg acgtaaacgg ccacaagttc    4380
agcgtgtccg gcgagggcga gggcgatgcc acctacggca agctgaccct gaagttcatt    4440
tgcaccaccg gcaagctgcc cgtgccctgg cccacccctcg tgaccaccct gacctacggc    4500
gtgcagtgct tcagccgcta ccccgaccac atgaagcagc acgacttctt caagtccgcc    4560
atgcccgaag gctacgtcca ggagcgcacc atcttcttca aggacgacgg caactacaag    4620
acccgcgccg aggtgaagtt cgaggggcgac accctggtga accgcatcga gctgaagggc    4680
atcgacttca aggaggacgg caacatcctg ggcacaagc tggagtacaa ctacaacagc    4740
cacaacgtct atatcatggc cgacaagcag aagaacggca tcaaggtgaa cttcaagatc    4800
cgccacaaca tcgaggacgg cagcgtgcag ctcgccgacc actaccagca gaacacccccc   4860 atcggcgacg gccccgtgct gctgcccgac aaccactacc tgagcaccca gtccgccctg    4920
agcaaagacc ccaacgagaa gcgcgatcac atggtcctgc tggagttcgt gaccgccgcc    4980
gggatcactc tcggcatgga cgagctgtac aagtaagaat tcgatatcaa gcttatcgat    5040
aatcaacctc tggattacaa aatttgtgaa agattgactg gtattcttaa ctatgttgct    5100
ccttttacgc tatgtggata cgctgcttta atgcctttgt atcatgctat tgcttcccgt    5160
atggctttca ttttctcctc cttgtataaa tcctggttgc tgtctcttta tgaggagttg    5220
tggcccgttg tcaggcaacg tggcgtggtg tgcactgtgt ttgctgacgc aaccccccact   5280 ggttggggca ttgccaccac ctgtcagctc ctttccggga ctttcgcttt ccccctcccct   5340 attgccacgg cggaactcat cgccgcctgc cttgcccgct gctggacagg gctcggctg     5400 ttgggcactg acaattccgt ggtgttgtcg gggaaatcat cgtcctttcc ttggctgctc    5460
gcctgtgttg ccacctggat tctgcgcggg acgtccttct gctacgtccc ttcggccctc    5520
aatccagcgg accttccttc ccgcggcctg ctgccggctc tgcggcctct tccgcgtctt    5580
cgccttcgcc ctcagacgag tcggatctcc ctttgggccg cctccccgca tcgataccgt    5640
cgacctcgag acctagaaaa acatggagca atcacaagta gcaatacagc agctaccaat    5700
gctgattgtg cctggctaga agcacaagag gaggaggagg tgggttttcc agtcacacct    5760
caggtacctt taagaccaat gacttacaag gcagctgtag atcttagcca cttttttaaaa   5820 gaaaagggg gactgaagg gctaattcac tcccaacgaa gacaagatat ccttgatctg     5880
tggatctacc acacacaagg ctacttccct gattggcaga actacacacc agggccaggg    5940
atcagatatc cactgacctt tggatggtgc tacaagctag taccagttga gcaagagaag    6000
gtagaagaag ccaatgaagg agagaacacc cgcttgttac accctgtgag cctgcatggg    6060
atggatgacc cggagagaga agtattagag tggaggtttg acagccgcct agcatttcat    6120
cacatggccc gagagctgca tccggactgt actgggtctc tctggttaga ccagatctga    6180
gcctgggagc tctctggcta actagggaac ccactgctta agcctcaata aagcttgcct    6240
tgagtgcttc aagtagtgtg tgcccgtctg ttgtgtgact ctggtaacta gagatccctc    6300
```

```
agacccttttt agtcagtgtg gaaaatctct agcagggccc gtttaaaccc gctgatcagc   6360
ctcgactgtg ccttctagtt gccagccatc tgttgtttgc ccctcccccg tgccttcctt   6420
gaccctggaa ggtgccactc ccactgtcct ttcctaataa aatgaggaaa ttgcatcgca   6480
ttgtctgagt aggtgtcatt ctattctggg gggtggggtg gggcaggaca gcaaggggga   6540
ggattgggaa gacaatagca ggcatgctgg ggatgcggtg ggctctatgg cttctgaggc   6600
ggaaagaacc agctggggct ctaggggta  tccccacgcg ccctgtagcg gcgcattaag   6660
cgcggcgggt gtggtggtta cgcgcagcgt gaccgctaca cttgccagcg ccctagcgcc   6720
cgctcctttc gctttcttcc cttcctttct cgccacgttc gccggctttc ccgtcaagc    6780
tctaaatcgg gggctcccctt tagggttccg atttagtgct ttacggcacc tcgaccccaa  6840
aaaacttgat tagggtgatg gttcacgtag tgggccatcg ccctgataga cggttttttcg 6900
cccctttgacg ttggagtcca cgttctttaa tagtggactc ttgttccaaa ctggaacaac  6960
actcaaccct atctcggtct attcttttga tttataaggg attttgccga tttcggccta   7020
ttggttaaaa aatgagctga tttaacaaaa atttaacgcg aattaattct gtggaatgtg   7080
tgtcagttag ggtgtggaaa gtccccaggc tccccagcag gcagaagtat gcaaagcatg   7140
catctcaatt agtcagcaac caggtgtgga aagtccccag gctccccagc aggcagaagt   7200
atgcaaagca tgcatctcaa ttagtcagca accatagtcc cgcccctaac tccgcccatc   7260
ccgcccctaa ctccgcccag ttccgcccat tctccgcccc atggctgact aattttttttt 7320
atttatgcag aggccgaggc cgcctctgcc tctgagctat tccagaagta gtgaggaggc   7380
tttttttggag gcctaggctt ttgcaaaaag ctcccgggag cttgtatatc cattttcgga  7440
tctgatcagc acgtgttgac aattaatcat cggcatagta tatcggcata gtataatacg   7500
acaaggtgag gaactaaacc atggccaagt tgaccagtgc cgttccggtg ctcaccgcgc   7560
gcgacgtcgc cggagcggtc gagttctgga ccgaccggct cgggttctcc cgggacttcg   7620
tggaggacga cttcgccggt gtggtccggg acgacgtgac cctgttcatc agcgcggtcc   7680
aggaccaggt ggtgccggac aacacccctg gcctgggtgtg ggtgcgcggc ctggacgagc  7740
tgtacgccga gtggtcggag gtcgtgtcca cgaacttccg gacgcctcc gggccggcca   7800
tgaccgagat cggcgagcag ccgtggggggc gggagttcgc cctgcgcgac ccggccggca  7860
actgcgtgca cttcgtggcc gaggagcagg actgacacgt gctacgagat ttcgattcca   7920
ccgccgcctt ctatgaaagg ttgggcttcg gaatcgtttt ccgggacgcc ggctggatga   7980
tcctccagcg cggggatctc atgctggagt tcttcgccca ccccaacttg tttattgcag   8040
cttataatgg ttacaaataa agcaatagca tcacaaattt cacaaataaa gcatttttt    8100
cactgcattc tagttgtggt ttgtccaaac tcatcaatgt atcttatcat gtctgtatac   8160
cgtcgacctc tagctagagc ttggcgtaat catggtcata gctgtttcct gtgtgaaatt   8220
gttatccgct cacaattcca cacaacatac gagccggaag cataaagtgt aaagcctggg   8280
gtgcctaatg agtgagctaa ctcacattaa ttgcgttgcg ctcactgccc gctttccagt   8340
cgggaaacct gtcgtgccag ctgcattaat gaatcggcca acgcgcgggg agaggcggtt   8400
tgcgtattgg gcgctcttcc gcttcctcgc tcactgactc gctgcgctcg gtcgttcggc   8460
tgcggcgagc ggtatcagct cactcaaagg cggtaatacg ttatccaca  gaatcagggg   8520
ataacgcagg aaagaacatg tgagcaaaag gccagcaaaa ggccaggaac cgtaaaaagg   8580
ccgcgttgct ggcgtttttc cataggctcc gcccccctga cgagcatcac aaaaatcgac   8640
```

-continued

```
gctcaagtca gaggtggcga aacccgacag gactataaag ataccaggcg tttccccctg   8700
gaagctccct cgtgcgctct cctgttccga ccctgccgct taccggatac ctgtccgcct   8760
ttctcccttc gggaagcgtg gcgctttctc atagctcacg ctgtaggtat ctcagttcgg   8820
tgtaggtcgt tcgctccaag ctgggctgtg tgcacgaacc ccccgttcag cccgaccgct   8880
gcgccttatc cggtaactat cgtcttgagt ccaacccggt aagacacgac ttatcgccac   8940
tggcagcagc cactggtaac aggattagca gagcgaggta tgtaggcggt gctacagagt   9000
tcttgaagtg gtggcctaac tacggctaca ctagaagaac agtatttggt atctgcgctc   9060
tgctgaagcc agttaccttc ggaaaaagag ttggtagctc ttgatccggc aaacaaacca   9120
ccgctggtag cggtggtttt tttgtttgca agcagcagat tacgcgcaga aaaaaggat   9180
ctcaagaaga tcctttgatc ttttctacgg ggtctgacgc tcagtggaac gaaaactcac   9240
gttaagggat tttggtcatg agattatcaa aaaggatctt cacctagatc cttttaaatt   9300
aaaaatgaag ttttaaatca atctaaagta tatatgagta aacttggtct gacagttacc   9360
aatgcttaat cagtgaggca cctatctcag cgatctgtct atttcgttca tccatagttg   9420
cctgactccc cgtcgtgtag ataactacga tacgggaggg cttaccatct ggccccagtg   9480
ctgcaatgat accgcgagac ccacgctcac cggctccaga tttatcagca ataaaccagc   9540
cagccggaag ggccgagcgc agaagtggtc ctgcaacttt atccgcctcc atccagtcta   9600
ttaattgttg ccgggaagct agagtaagta gttcgccagt taatagtttg cgcaacgttg   9660
ttgccattgc tacaggcatc gtggtgtcac gctcgtcgtt tggtatggct tcattcagct   9720
ccggttccca acgatcaagg cgagttacat gatcccccat gttgtgcaaa aaagcggtta   9780
gctccttcgg tcctccgatc gttgtcagaa gtaagttggc cgcagtgtta tcactcatgg   9840
ttatggcagc actgcataat tctcttactg tcatgccatc cgtaagatgc ttttctgtga   9900
ctggtgagta ctcaaccaag tcattctgag aatagtgtat gcggcgaccg agttgctctt   9960
gcccggcgtc aatacgggat aataccgcgc cacatagcag aactttaaaa gtgctcatca  10020
ttggaaaacg ttcttcgggg cgaaaactct caaggatctt accgctgttg agatccagtt  10080
cgatgtaacc cactcgtgca cccaactgat cttcagcatc ttttactttc accagcgttt  10140
ctgggtgagc aaaaacagga aggcaaaatg ccgcaaaaaa gggaataagg gcgacacgga  10200
aatgttgaat actcatactc ttcctttttc aatattattg aagcatttat cagggttatt  10260
gtctcatgag cggatacata tttgaatgta tttagaaaaa taaacaaata ggggttccgc  10320
gcacatttcc ccgaaaagtg ccacctgac                                    10349
```

<210> SEQ ID NO 133  
<211> LENGTH: 126  
<212> TYPE: PRT  
<213> ORGANISM: Artificial Sequence  
<220> FEATURE:  
<223> OTHER INFORMATION: Synthetic Sequence MMmin4

<400> SEQUENCE: 133

```
Glu Leu Trp Lys Lys His Glu Glu Ala Leu Lys Lys Phe Glu Glu Leu
1               5                   10                  15

Leu Lys Lys Phe Glu Glu Glu Leu Lys Leu Gly Gly Ser Gly Glu Gly
            20                  25                  30

Ser Gly Gly Glu Leu Leu Lys Lys Cys Glu Glu Ala Leu Lys Lys Phe
        35                  40                  45

Glu Glu Leu Leu Lys Lys Phe Glu Glu Glu Leu Lys Leu Gly Gly Ser
    50                  55                  60
```

Gly Glu Leu Leu Lys Lys His Glu Glu Ala Leu Lys Lys Phe Glu Glu
65                  70                  75                  80

Leu Leu Lys Lys Phe Glu Glu Leu Leu Lys Leu Gly Gly Ser Gly Glu
                85                  90                  95

Gly Ser Gly Gly Glu Leu Leu Lys Lys His Glu Glu Ala Leu Lys Lys
            100                 105                 110

Phe Glu Glu Leu Leu Lys Lys Phe Glu Glu Leu Leu Lys Leu
            115                 120                 125

<210> SEQ ID NO 134
<211> LENGTH: 6113
<212> TYPE: DNA
<213> ORGANISM: Artificial Sequence
<220> FEATURE:
<223> OTHER INFORMATION: Synthetic Sequence GL-MM (E. Coli)

<400> SEQUENCE: 134

| | |
|---|---:|
| ttcttgaaga cgaaagggcc tcgtgatacg cctatttttta taggttaatg tcatgataat | 60 |
| aatggtttct tagacgtcag gtggcacttt tcggggaaat gtgcgcggaa ccccctatttg | 120 |
| tttatttttc taaatacatt caaatatgta tccgctcatg agacaataac cctgataaat | 180 |
| gcttcaataa tattgaaaaa ggaagagtat gagtattcaa catttccgtg tcgcccttat | 240 |
| tccctttttt gcggcatttt gccttcctgt ttttgctcac ccagaaacgc tggtgaaagt | 300 |
| aaaagatgct gaagatcagt tgggtgcacg agtgggttac atcgaactgg atctcaacag | 360 |
| cggtaagatc cttgagagtt ttcgccccga agaacgtttt ccaatgatga gcacttttaa | 420 |
| agttctgcta tgtggcgcgg tattatcccg tgttgacgcc gggcaagagc aactcggtcg | 480 |
| ccgcatacac tattctcaga atgacttggt tgagtactca ccagtcacag aaaagcatct | 540 |
| tacggatggc atgacagtaa gagaattatg cagtgctgcc ataaccatga gtgataacac | 600 |
| tgcggccaac ttacttctga acgatcgg aggaccgaag gagctaaccg cttttttgca | 660 |
| caacatgggg gatcatgtaa ctcgccttga tcgttgggaa ccggagctga atgaagccat | 720 |
| accaaacgac gagcgtgaca ccacgatgcc tgcagcaatg gcaacaacgt tgcgcaaact | 780 |
| attaactggc gaactactta ctctagcttc ccggcaacaa ttaatagact ggatggaggc | 840 |
| ggataaagtt gcaggaccac ttctgcgctc ggcccttccg gctggctggt ttattgctga | 900 |
| taaatctgga gccggtgagc gtgggtctcg cggtatcatt gcagcactgg ggccagatgg | 960 |
| taagccctcc cgtatcgtag ttatctacac gacggggagt caggcaacta tggatgaacg | 1020 |
| aaatagacag atcgctgaga taggtgcctc actgattaag cattggtaac tgtcagacca | 1080 |
| agtttactca tatatacttt agattgattt aaaacttcat ttttaattta aaaggatcta | 1140 |
| ggtgaagatc ctttttgata atctcatgac caaaatccct taacgtgagt tttcgttcca | 1200 |
| ctgagcgtca gaccccgtag aaaagatcaa aggatcttct tgagatcctt ttttctgcg | 1260 |
| cgtaatctgc tgcttgcaaa caaaaaaacc accgctacca gcggtggttt gtttgccgga | 1320 |
| tcaagagcta ccaactcttt ttccgaaggt aactggcttc agcagagcgc agataccaaa | 1380 |
| tactgtcctt ctagtgtagc cgtagttagg ccaccacttc aagaactctg tagcaccgcc | 1440 |
| tacatacctc gctctgctaa tcctgttacc agtggctgct gccagtggcg ataagtcgtg | 1500 |
| tcttaccggg ttggactcaa gacgatagtt accggataag gcgcagcggt cgggctgaac | 1560 |
| ggggggttcg tgcacacagc ccagcttgga gcgaacgacc tacaccgaac tgagatacct | 1620 |
| acagcgtgag ctatgagaaa gcgccacgct tcccgaaggg agaaaggcgg acaggtatcc | 1680 |

```
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttt tacggttcct    1860 ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460
tgtaaggggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag gcggcgccct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360 aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag gcatcggtc gagatcccgg    3720 tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg gtttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
```

```
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttccc    4740
gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtccccgg ccacggggcc tgccaccata cccacgccga acaagcgct catgagcccg    5100
aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacggcg cgacggcga gaacttgtat tttcaagcta gcggatccat gggagagatc    5400
tggaagcagc acgaggaagc gctgaagaaa ttcgaggaac tgctgaaaca atttgaggaa    5460
gagctgaaga aaggtggcag cggtagcggt agcggtggcg agatctggaa gcagtgcgaa    5520
gaggcgctga agaaattcga agagctgctg aagaaatttg aagaggaact gaagaaaggt    5580
ggcagcgggg aaatttggaa acaacatgag gaagcgctga agaaatttga ggagctgctg    5640
aagcaatttg aggaacttct gaagaaaggt ggcagcggca gcggtagcgg tggcgaaatt    5700
tggaaacaac acgaggaagc gctgaagaaa ttcgaggagt tactgaagaa attcgaggag    5760
ctgctgaaga aagcaccggt ttaagaattc ctcgaggctc taacaaagc ccgaaaggaa    5820
gctgagttgg ctgctgccac cgctgagcaa taactagcat aaccccttgg ggcctctaaa    5880
cgggtcttga ggggtttttt gctgaaagga ggaactatat ccggatatcc cgcaagaggc    5940
ccggcagtac cggcataacc aagcctatgc ctacagcatc agggtgacg gtgccgagga    6000
tgacgatgag cgcattgtta gatttcatac acggtgcctg actgcgttag caatttaact    6060
gtgataaact accgcattaa agcttatcga tgataagctg tcaaacatga gaa           6113
```

<210> SEQ ID NO 135
<211> LENGTH: 10349
<212> TYPE: DNA
<213> ORGANISM: Artificial Sequence
<220> FEATURE:
<223> OTHER INFORMATION: Synthetic Sequence GL-MM (FCK mam)

<400> SEQUENCE: 135

-continued

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt cgcgctgctt cgcgatgtacg ggccagatat acgcgttgac   240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg ccccctattg acgtcaatga cggtaaatgg cccgcctggc   540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc  1020
gcccgaacag ggacttgaaa gcgaaaggga accagagga gctctctcga cgcaggactc  1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaaagac accaaggaag ctttagacaa gatagaggaa gagcaaaaca  1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gagaagagtg gtgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga taccaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
acaaattggc tgtggtatat aaaattattc ataatgatag taggaggctt ggtaggttta  2220
agaatagttt ttgctgtact ttctatagtg aatagagtta ggcagggata ttcaccatta  2280
tcgtttcaga cccacctccc aaccccgagg ggacccgaca ggcccgaagg aatagaagaa  2340
gaaggtggag agagagacag agacagatcc attcgattag tgaacggatc ggcactgcgt  2400
```

```
gcgccaattc tgcagacaaa tggcagtatt catccacaat tttaaaagaa aaggggggat    2460 tgggggtac  agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta acattatggc cttaggtcac ttcatctcca tggggttctt    2640
cttctgattt tctagaaaat gagatggggg tgcagagagc ttcctcagtg acctgcccag    2700
ggtcacatca gaaatgtcag agctagaact tgaactcaga ttactaatct taaattccat    2760
gccttggggg catgcaagta cgatatacag aaggagtgaa ctcattaggg cagatgacca    2820
atgagtttag gaaagaagag tccagggcag ggtacatcta caccacccgc ccagccctgg    2880
gtgagtccag ccacgttcac ctcattatag ttgcctctct ccagtcctac cttgacggga    2940
agcacaagca gaaactggga caggagcccc aggagaccaa atcttcatgg tccctctggg    3000
aggatgggtg gggagagctg tgcagaggc  tcaggaggg  gccctgctgc tcagtggtga    3060
cagatagggg tgagaaagca gacagagtca ttccgtcagc attctgggtc tgtttggtac    3120
ttcttctcac gctaaggtgg cggtgtgata tgcacaatgg ctaaaaagca gggagagctg    3180
gaaagaaaca aggacagaga cagaggccaa gtcaaccaga ccaattccca gaggaagcaa    3240
agaaaccatt acagagacta caaggggggaa gggaaggaga gatgaattag cttcccctgt    3300
aaaccttaga acccagctgt tgccaggca  acggggcaat acctgtctct tcagaggaga    3360
tgaagttgcc agggtaacta catcctgtct ttctcaagga ccatcccaga atgtggcacc    3420
cactagccgt taccatagca actgcctctt tgccccactt aatccatcc  cgtctgttaa    3480 aagggcccta tagttggagg tggggaggt  aggaagagcg atgatcactt gtggactaag    3540
tttgttcaca tcccccttctc caacccctc  agtacatcac cctgggagaa caaggtccac    3600
ttgcttctgg gcccacacag tcctgcagta ttgtgtatat aaggccaggg caacggagga    3660
gcaggttttg aagtgaaagg caggcaggtg ttggggaggc agttaccggg gcaacgggaa    3720
cagggcgttt cggaggtggt tgccatgggg acctggatgc tgacgaaggc tcgcgaggct    3780
gtgagcagcc acagtgccct gctcagaagc cccaagctcg tcaatcaagc tggttctcca    3840
tttgcactca ggagcacggg caggcgagtg gcccctagtt ctgggggcag cggggggatcc    3900 atgggagaga tctggaagca gcacgaggaa gcgctgaaga aattcgagga actgctgaaa    3960
caatttgagg aagagctgaa gaaggtggc  agcggtagcg gtagcggtgg cgagatctgg    4020
aagcagtgcg aagaggcgct gaagaaattc gaagagctgc tgaagaaatt gaagaggaa    4080 ctgaagaaag gtggcagcgg ggaaatttgg aaacaacatg aggaagcgct gaagaaattt    4140
gaggagctgc tgaagcaatt tgaggaactt ctgaagaaag gtggcagcgg cagcggtagc    4200
ggtggcgaaa tttggaaaca acacgaggaa gcgctgaaga aattcgagga gttactgaag    4260
aaattcgagg agctgctgaa gaaagcaccg gtagtagcag tgagcaaggg cgaggagctg    4320
ttcaccgggg tggtgcccat cctggtcgag ctggacggcg acgtaaacgg ccacaagttc    4380
agcgtgtccg gcgagggcga gggcgatgcc acctacggca agctgaccct gaagttcatt    4440
tgcaccaccg gcaagctgcc cgtgccctgg cccaccctcg tgaccaccct gacctacggc    4500
gtgcagtgct tcagccgcta ccccgaccac atgaagcagc acgacttctt caagtccgcc    4560
atgcccgaag gctacgtcca ggagcgcacc atcttcttca aggacgacgg caactacaag    4620
acccgcgccg aggtgaagtt cgagggcgac accctggtga accgcatcga gctgaagggc    4680
atcgacttca aggaggacgg caacatcctg gggcacaagc tggagtacaa ctacaacagc    4740
```

```
cacaacgtct atatcatggc cgacaagcag aagaacggca tcaaggtgaa cttcaagatc    4800
cgccacaaca tcgaggacgg cagcgtgcag ctcgccgacc actaccagca gaacaccccc    4860
atcggcgacg gccccgtgct gctgcccgac aaccactacc tgagcaccca gtccgccctg    4920
agcaaagacc ccaacgagaa cgcgatcac atggtcctgc tggagttcgt gaccgccgcc     4980
gggatcactc tcggcatgga cgagctgtac aagtaagaat tcgatatcaa gcttatcgat    5040
aatcaacctc tggattacaa aatttgtgaa agattgactg gtattcttaa ctatgttgct    5100
ccttttacgc tatgtggata cgctgcttta atgcctttgt atcatgctat tgcttcccgt    5160
atggctttca ttttctcctc cttgtataaa tcctggttgc tgtctcttta tgaggagttg    5220
tggcccgttg tcaggcaacg tggcgtggtg tgcactgtgt ttgctgacgc aacccccact    5280
ggttggggca ttgccaccac ctgtcagctc ctttccggga ctttcgcttt ccccctccct    5340
attgccacgg cggaactcat cgccgcctgc cttgcccgct gctggacagg ggctcggctg    5400
ttgggcactg acaattccgt ggtgttgtcg gggaaatcat cgtccttcc ttggctgctc      5460 gcctgtgttg ccacctggat tctgcgcggg acgtccttct gctacgtccc ttcggccctc    5520
aatccagcgg accttccttc ccgcggcctg ctgccggctc tgcggcctct tccgcgtctt    5580
cgccttcgcc ctcagacgag tcggatctcc ctttgggccg cctccccgca tcgataccgt    5640
cgacctcgag acctagaaaa acatggagca atcacaagta gcaatacagc agctaccaat    5700
gctgattgtg cctggctaga agcacaagag gaggaggagg tgggttttcc agtcacacct    5760
caggtacctt taagaccaat gacttacaag gcagctgtag atcttagcca ctttttaaaa    5820
gaaaaggggg gactggaagg gctaattcac tcccaacgaa gacaagatat ccttgatctg    5880
tggatctacc acacacaagg ctacttccct gattggcaga actacacacc agggccaggg    5940
atcagatatc cactgacctt tggatggtgc tacaagctag taccagttga gcaagagaag    6000
gtagaagaag ccaatgaagg agagaacacc cgcttgttac accctgtgag cctgcatggg    6060
atggatgacc cggagagaga agtattagag tggaggtttg acagccgcct agcatttcat    6120
cacatggccc gagagctgca tccggactgt actgggtctc tctggttaga ccagatctga    6180
gcctgggagc tctctggcta actagggaac ccactgctta agcctcaata aagcttgcct    6240
tgagtgcttc aagtagtgtg tgcccgtctg ttgtgtgact ctggtaacta gagatccctc    6300
agaccctttt agtcagtgtg gaaaatctct agcagggccc gtttaaaccc gctgatcagc    6360
ctcgactgtg ccttctagtt gccagccatc tgttgtttgc ccctccccg tgccttcctt    6420 gaccctggaa ggtgccactc ccactgtcct ttcctaataa aatgaggaaa ttgcatcgca    6480
ttgtctgagt aggtgtcatt ctattctggg gggtggggtg gggcaggaca gcaagggga    6540 ggattgggaa gacaatagca ggcatgctgg ggatgcggtg ggctctatgg cttctgaggc    6600
ggaaagaacc agctggggct ctagggggta tccccacgcg ccctgtagcg gcgcattaag    6660
cgcggcgggt gtggtggtta cgcgcagcgt gaccgctaca cttgccagcg ccctagcgcc    6720
cgctcctttc gctttcttcc cttcctttct cgccacgttc gccggctttc cccgtcaagc    6780
tctaaatcgg gggctccctt tagggttccg atttagtgct ttacggcacc tcgaccccaa    6840
aaaacttgat tagggtgatg gttcacgtag tgggccatcg ccctgataga cggttttcg    6900 ccctttgacg ttggagtcca cgttctttaa tagtggactc ttgttccaaa ctggaacaac    6960
actcaaccct atctcggtct attcttttga tttataaggg attttgccga tttcggccta    7020
ttggttaaaa aatgagctga tttaacaaaa atttaacgcg aattaattct gtggaatgtg    7080
tgtcagttag ggtgtggaaa gtccccaggc tccccagcag gcagaagtat gcaaagcatg    7140
```

```
catctcaatt agtcagcaac caggtgtgga aagtccccag gctccccagc aggcagaagt   7200
atgcaaagca tgcatctcaa ttagtcagca accatagtcc cgcccctaac tccgcccatc   7260
ccgcccctaa ctccgcccag ttccgcccat tctccgcccc atggctgact aattttttt    7320 atttatgcag aggccgaggc cgcctctgcc tctgagctat tccagaagta gtgaggaggc   7380
ttttttggag gcctaggctt ttgcaaaaag ctcccgggag cttgtatatc cattttcgga   7440
tctgatcagc acgtgttgac aattaatcat cggcatagta tatcggcata gtataatacg   7500
acaaggtgag gaactaaacc atggccaagt tgaccagtgc cgttccggtg ctcaccgcgc   7560
gcgacgtcgc cggagcggtc gagttctgga ccgaccggct cgggttctcc cgggacttcg   7620
tggaggacga cttcgccggt gtggtccggg acgacgtgac cctgttcatc agcgcggtcc   7680
aggaccaggt ggtgccggac aacaccctgg cctgggtgtg ggtgcgcggc ctggacgagc   7740
tgtacgccga gtggtcggag gtcgtgtcca cgaacttccg ggacgcctcc gggccggcca   7800
tgaccgagat cggcgagcag ccgtgggggc gggagttcgc cctgcgcgac ccggccggca   7860
actgcgtgca cttcgtggcc gaggagcagg actgacacgt gctacgagat ttcgattcca   7920
ccgccgcctt ctatgaaagg ttgggcttcg gaatcgtttt ccgggacgcc ggctggatga   7980
tcctccagcg cggggatctc atgctggagt tcttcgccca ccccaacttg tttattgcag   8040
cttataatgg ttacaaataa agcaatagca tcacaaattt cacaaataaa gcatttttt    8100 cactgcattc tagttgtggt ttgtccaaac tcatcaatgt atcttatcat gtctgtatac   8160
cgtcgacctc tagctagagc ttggcgtaat catggtcata gctgtttcct gtgtgaaatt   8220
gttatccgct cacaattcca cacaacatac gagccggaag cataaagtgt aaagcctggg   8280
gtgcctaatg agtgagctaa ctcacattaa ttgcgttgcg ctcactgccc gctttccagt   8340
cgggaaacct gtcgtgccag ctgcattaat gaatcggcca acgcgcgggg agaggcggtt   8400
tgcgtattgg gcgctcttcc gcttcctcgc tcactgactc gctgcgctcg gtcgttcggc   8460
tgcggcgagc ggtatcagct cactcaaagg cggtaatacg ttatccaca gaatcagggg    8520 ataacgcagg aaagaacatg tgagcaaaag gccagcaaaa ggccaggaac cgtaaaaagg   8580
ccgcgttgct ggcgtttttc cataggctcc gcccccctga cgagcatcac aaaaatcgac   8640
gctcaagtca gaggtggcga aacccgacag gactataaag ataccaggcg tttccccctg   8700
gaagctccct cgtgcgctct cctgttccga ccctgccgct taccggatac ctgtccgcct   8760
ttctcccttc gggaagcgtg gcgctttctc atagctcacg ctgtaggtat ctcagttcgg   8820
tgtaggtcgt tcgctccaag ctgggctgtg tgcacgaacc ccccgttcag cccgaccgct   8880
gcgccttatc cggtaactat cgtcttgagt ccaacccggt aagacacgac ttatcgccac   8940
tggcagcagc cactggtaac aggattagca gagcgaggta tgtaggcggt gctacagagt   9000
tcttgaagtg gtggcctaac tacggctaca ctagaagaac agtatttggt atctgcgctc   9060
tgctgaagcc agttaccttc ggaaaaagag ttggtagctc ttgatccggc aaacaaacca   9120
ccgctggtag cggtggtttt tttgtttgca agcagcagat tacgcgcaga aaaaaggat    9180 ctcaagaaga tcctttgatc ttttctacgg ggtctgacgc tcagtggaac gaaaactcac   9240
gttaagggat tttggtcatg agattatcaa aaaggatctt cacctagatc cttttaaatt   9300
aaaaatgaag ttttaaatca atctaaagta tatatgagta aacttggtct gacagttacc   9360
aatgcttaat cagtgaggca cctatctcag cgatctgtct atttcgttca tccatagttg   9420
cctgactccc cgtcgtgtag ataactacga tacgggaggg cttaccatct ggccccagtg   9480
```

```
ctgcaatgat accgcgagac ccacgctcac cggctccaga tttatcagca ataaaccagc   9540
cagccggaag ggccgagcgc agaagtggtc ctgcaacttt atccgcctcc atccagtcta   9600
ttaattgttg ccgggaagct agagtaagta gttcgccagt aatagtttgc gcaacgttg    9660 ttgccattgc tacaggcatc gtggtgtcac gctcgtcgtt tggtatggct tcattcagct   9720
ccggttccca acgatcaagg cgagttacat gatcccccat gttgtgcaaa aaagcggtta   9780
gctccttcgg tcctccgatc gttgtcagaa gtaagttggc cgcagtgtta tcactcatgg   9840
ttatggcagc actgcataat tctcttactg tcatgccatc cgtaagatgc ttttctgtga   9900
ctggtgagta ctcaaccaag tcattctgag aatagtgtat gcggcgaccg agttgctctt   9960
gcccggcgtc aatacgggat aataccgcgc cacatagcag aactttaaaa gtgctcatca  10020
ttggaaaacg ttcttcgggg cgaaaactct caaggatctt accgctgttg agatccagtt  10080
cgatgtaacc cactcgtgca cccaactgat cttcagcatc ttttactttc accagcgttt  10140
ctgggtgagc aaaaacagga aggcaaaatg ccgcaaaaaa gggaataagg gcgacacgga  10200
aatgttgaat actcatactc ttcctttttc aatattattg aagcatttat cagggttatt  10260
gtctcatgag cggatacata tttgaatgta tttagaaaaa taaacaaata ggggttccgc  10320
gcacatttcc ccgaaaagtg ccacctgac                                    10349
```

<210> SEQ ID NO 136
<211> LENGTH: 126
<212> TYPE: PRT
<213> ORGANISM: Artificial Sequence
<220> FEATURE:
<223> OTHER INFORMATION: Synthetic Sequence GL-MM

<400> SEQUENCE: 136

```
Glu Ile Trp Lys Gln His Glu Glu Ala Leu Lys Lys Phe Glu Leu
1               5                   10                  15

Leu Lys Gln Phe Glu Glu Leu Lys Lys Gly Gly Ser Gly Ser Gly
                20                  25                  30

Ser Gly Gly Glu Ile Trp Lys Gln Cys Glu Glu Ala Leu Lys Lys Phe
            35                  40                  45

Glu Glu Leu Leu Lys Lys Phe Glu Glu Leu Lys Lys Gly Gly Ser
    50                  55                  60

Gly Glu Ile Trp Lys Gln His Glu Glu Ala Leu Lys Lys Phe Glu Glu
65                  70                  75                  80

Leu Leu Lys Gln Phe Glu Glu Leu Leu Lys Lys Gly Gly Ser Gly Ser
                85                  90                  95

Gly Ser Gly Gly Glu Ile Trp Lys Gln His Glu Glu Ala Leu Lys Lys
            100                 105                 110

Phe Glu Glu Leu Leu Lys Lys Phe Glu Glu Leu Leu Lys Lys
        115                 120                 125
```

<210> SEQ ID NO 137
<211> LENGTH: 4646
<212> TYPE: DNA
<213> ORGANISM: Artificial Sequence
<220> FEATURE:
<223> OTHER INFORMATION: Synthetic Sequence MZH3 (E. Coli)

<400> SEQUENCE: 137

```
ctcatgacca aaatcccttta acgtgagtta cgcgcgcgtc gttccactga gcgtcagacc     60
ccgtagaaaa gatcaaagga tcttcttgag atccttttttt tctgcgcgta atctgctgct    120
tgcaaacaaa aaaaccaccg ctaccagcgg tggtttgttt gccggatcaa gagctaccaa    180
```

```
ctcttttttcc gaaggtaact ggcttcagca gagcgcagat accaaatact gttcttctag    240
tgtagccgta gttagcccac cacttcaaga actctgtagc accgcctaca tacctcgctc    300
tgctaatcct gttaccagtg gctgctgcca gtggcgataa gtcgtgtctt accgggttgg    360
actcaagacg atagttaccg gataaggcgc agcggtcggg ctgaacgggg ggttcgtgca    420
cacagcccag cttggagcga acgacctaca ccgaactgag atacctacag cgtgagctat    480
gagaaagcgc cacgcttccc gaagggagaa aggcggacag tatccggta gcggcaggg     540 tcggaacagg agagcgcacg agggagcttc caggggaaa cgcctggtat ctttatagtc    600
ctgtcgggtt tcgccacctc tgacttgagc gtcgattttt gtgatgctcg tcagggggc    660 ggagcctatg gaaaaacgcc agcaacgcgg ccttttacg gttcctggcc ttttgctggc    720
cttttgctca catgttcttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg ccttttttgcg tttctacaaa ctctttctgt gttgtaaaac gacggccagt    960
cttaagctcg ggccccctgg gcggttctga taacgagtaa tcgttaatcc gcaaataacg   1020
taaaaacccg cttcggcggg tttttttatg gggggagttt agggaaagag catttgtcag   1080
aatatttaag ggcgcctgtc actttgcttg atatatgaga attatttaac cttataaatg   1140 agaaaaagc aacgcacttt aaataagata cgttgctttt tcgattgatg aacacctata   1200
attaaactat tcatctatta tttatgattt tttgtatata caatatttct agtttgttaa   1260
agagaattaa gaaaataaat ctcgaaaata ataaagggaa aatcagtttt tgatatcaaa   1320
attatacatg tcaacgataa tacaaaatat aatacaaact ataagatgtt atcagtattt   1380
attatcattt agaataaatt ttgtgtcgcc cttccgcgaa attaatacga ctcactatag   1440
gggaattgtg agcggataac aattcccctc tagaaataat tttgtttaac ttttaggagg   1500 taaacatat gggtaagggc ggtcatcatc atcaccatca tggcggcgac ggcgagaatt   1560
tgtattttca gggcagcccg gagttgcgc aagagcacca gcagctggca caagagttcc   1620
aacaactgtt gcaggagatt caacaactgg gccgtgagct gttgaaaggt gagctgcagg   1680
gcattaaaca gctgcgtgag gcgagcgaga aagcgcgtaa cccggagaag aaatctgtgt   1740
tgcagaagat cctggaagat gaagagaaac acattgagct gctggaaacc ctgcaacaga   1800
cgggtcaaga ggcgcaacag ctgctgcaag agttgcagca gaccggtcaa gaactgtggc   1860
aactgggcgt tccggtggc ccggagctgc gccagaaaca ccaacagctg cccagaaga   1920 ttcagcaact gctgcagaag caccaacagt gggtgcaaa atcttggaa gatgaagaaa   1980 aacacatcga actgctggag actatcctgg gtggcagcgg cggtgacgaa ctgcgtgaac   2040
tgctgaaggg tgaactgcag ggtatcaagc aataccgcga actgcagcaa ctgggtcaaa   2100
aagctcagca attggttcaa aagctgcagc aaaccggtca gaagctgtgg cagctgggtt   2160
aactcgagcc ccctagcata accccttggg gcctctaaac gggtcttgag ggttttttg   2220 cccctgagac gcgtcaatcg agttcgtacc taagggcgac accccctaat tagcccgggc   2280
gaaaggccca gtctttcgac tgagcctttc gttttatttg atgcctggca gttccctact   2340
ctcgcatggg gagtccccac actaccatcg cgctacggc gtttcacttc tgagttcggc   2400
atggggtcag gtgggaccac cgcgctactg ccgccaggca acaaggggt gttatgagcc   2460 atattcaggt ataaatgggc tcgcgataat gttcagaatt ggttaattgg ttgtaacact   2520
```

```
gaccccctatt tgtttatttt tctaaataca ttcaaatatg tatccgctca tgagacaata    2580
accctgataa atgcttcaat aatattgaaa aaggaagaat atgagtattc aacatttccg    2640
tgtcgccctt attccttttt tgcggcatt  ttgccttcct gttttgctc  acccagaaac    2700
gctggtgaaa gtaaaagatg ctgaagatca gttgggtgca cgagtgggtt acatcgaact    2760
ggatctcaac agcggtaaga tccttgagag ttttcgcccc gaagaacgtt ttccaatgat    2820
gagcactttt aaagttctgc tatgtggcgc ggtattatcc cgtattgacg ccgggcaaga    2880
gcaactcggt cgccgcatac actattctca gaatgacttg gttgagtact caccagtcac    2940
agaaaagcat cttacggatg gcatgacagt aagagaatta tgcagtgctg ccataaccat    3000
gagtgataac actgcggcca acttacttct gacaacgatc ggaggaccga aggagctaac    3060
cgcttttttg cacaacatgg ggatcatgt  aactcgcctt gatcgttggg aaccggagct    3120
gaatgaagcc ataccaaacg acgagcgtga caccacgatg cctgtagcga tggcaacaac    3180
gttgcgcaaa ctattaactg gcgaactact tactctagct tcccggcaac aattaataga    3240
ctggatggag gcggataaag ttgcaggacc acttctgcgc tcggcccttc cggctggctg    3300
gtttattgct gataaatccg gagccggtga gcgtggttct cgcggtatca tcgcagcgct    3360
ggggccagat ggtaagccct cccgtatcgt agttatctac acgacgggga gtcaggcaac    3420
tatggatgaa cgaaatagac agatcgctga gataggtgcc tcactgatta agcattggta    3480
agcggcgcgc catcgaatgg cgcaaaacct ttcgcggtat ggcatgatag cgcccggaag    3540
agagtcaatt cagggtggtg aatatgaaac cagtaacgtt atacgatgtc gcagagtatg    3600
ccggtgtctc ttatcagacc gtttcccgcg tggtgaacca ggccagccac gtttctgcga    3660
aaacgcggga aaaagtggaa gcggcgatgg cggagctgaa ttacattccc aaccgcgtgg    3720
cacaacaact ggcgggcaaa cagtcgttgc tgattggcgt tgccacctcc agtctggccc    3780
tgcacgcgcc gtcgcaaatt gtcgcggcga ttaaatctcg cgccgatcaa ctgggtgcca    3840
gcgtggtggt gtcgatggta gaacgaagcg cgtcgaagc  ctgtaaagcg gcggtgcaca    3900
atcttctcgc gcaacgcgtc agtgggctga tcattaacta tccgctggat gaccaggatg    3960
ccattgctgt ggaagctgcc tgcactaatg ttccggcgtt atttcttgat gtctctgacc    4020
agacacccat caacagtatt attttctccc atgaagacgg tacgcgactg ggcgtggagc    4080
atctggtcgc attgggtcac cagcaaatcg cgctgttagc gggcccatta agttctgtct    4140
cggcgcgtct gcgtctggct ggctggcata atatctcac  tcgcaatcaa attcagccga    4200
tagcggaacg ggaaggcgac tggagtgcca tgtccggttt tcaacaaacc atgcaaatgc    4260
tgaatgaggg catcgttccc actgcgatgc tggttgccaa cgatcagatg cgctgggcg    4320
caatgcgcgc cattaccgag tccgggctgc gcgttggtgc ggatatctcg gtagtgggat    4380
acgacgatac cgaagatagc tcatgttata tcccgccgtt aaccaccatc aaacaggatt    4440
ttcgcctgct ggggcaaacc agcgtggacc gcttgctgca actctctcag gccaggcgg    4500
tgaagggcaa tcagctgttg ccagtctcac tggtgaaaag aaaaaccacc ctggcgccca    4560
atacgcaaac cgcctctccc cgcgcgttgg ccgattcatt aatgcagctg gcacgacagg    4620
tttcccgact ggaaagcggg cagtga                                         4646
```

<210> SEQ ID NO 138
<211> LENGTH: 196
<212> TYPE: PRT
<213> ORGANISM: Artificial Sequence
<220> FEATURE:
<223> OTHER INFORMATION: Synthetic Sequence MZH3

<400> SEQUENCE: 138

```
Gly Ser Pro Glu Leu Arg Gln Glu His Gln Gln Leu Ala Gln Glu Phe
1               5                   10                  15
Gln Gln Leu Leu Gln Glu Ile Gln Gln Leu Gly Arg Glu Leu Leu Lys
                20                  25                  30
Gly Glu Leu Gln Gly Ile Lys Gln Leu Arg Glu Ala Ser Glu Lys Ala
            35                  40                  45
Arg Asn Pro Glu Lys Lys Ser Val Leu Gln Lys Ile Leu Glu Asp Glu
        50                  55                  60
Glu Lys His Ile Glu Leu Leu Glu Thr Leu Gln Gln Thr Gly Gln Glu
65                  70                  75                  80
Ala Gln Gln Leu Leu Gln Glu Leu Gln Gln Thr Gly Gln Glu Leu Trp
                85                  90                  95
Gln Leu Gly Gly Ser Gly Gly Pro Glu Leu Arg Gln Lys His Gln Gln
            100                 105                 110
Leu Ala Gln Lys Ile Gln Gln Leu Leu Gln Lys His Gln Gln Leu Gly
        115                 120                 125
Ala Lys Ile Leu Glu Asp Glu Glu Lys His Ile Glu Leu Leu Glu Thr
    130                 135                 140
Ile Leu Gly Gly Ser Gly Gly Asp Glu Leu Arg Glu Leu Leu Lys Gly
145                 150                 155                 160
Glu Leu Gln Gly Ile Lys Gln Tyr Arg Glu Leu Gln Glu Leu Gly Gln
                165                 170                 175
Lys Ala Gln Gln Leu Val Gln Lys Leu Gln Gln Thr Gly Gln Lys Leu
            180                 185                 190
Trp Gln Leu Gly
        195
```

<210> SEQ ID NO 139
<211> LENGTH: 196
<212> TYPE: PRT
<213> ORGANISM: Artificial Sequence
<220> FEATURE:
<223> OTHER INFORMATION: Synthetic Sequence MZH3 H138D

<400> SEQUENCE: 139

```
Gly Ser Pro Glu Leu Arg Gln Glu His Gln Gln Leu Ala Gln Glu Phe
1               5                   10                  15
Gln Gln Leu Leu Gln Glu Ile Gln Gln Leu Gly Arg Glu Leu Leu Lys
                20                  25                  30
Gly Glu Leu Gln Gly Ile Lys Gln Leu Arg Glu Ala Ser Glu Lys Ala
            35                  40                  45
Arg Asn Pro Glu Lys Lys Ser Val Leu Gln Lys Ile Leu Glu Asp Glu
        50                  55                  60
Glu Lys His Ile Glu Leu Leu Glu Thr Leu Gln Gln Thr Gly Gln Glu
65                  70                  75                  80
Ala Gln Gln Leu Leu Gln Glu Leu Gln Gln Thr Gly Gln Glu Leu Trp
                85                  90                  95
Gln Leu Gly Gly Ser Gly Gly Pro Glu Leu Arg Gln Lys His Gln Gln
            100                 105                 110
Leu Ala Gln Lys Ile Gln Gln Leu Leu Gln Lys His Gln Gln Leu Gly
        115                 120                 125
Ala Lys Ile Leu Glu Asp Glu Glu Lys Asp Ile Glu Leu Leu Glu Thr
    130                 135                 140
```

```
Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 140
<211> LENGTH: 196
<212> TYPE: PRT
<213> ORGANISM: Artificial Sequence
<220> FEATURE:
<223> OTHER INFORMATION: Synthetic Sequence MZH3 H138N

<400> SEQUENCE: 140

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys His Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
        115                 120                 125

Ala Lys Ile Leu Glu Asp Glu Glu Lys Asn Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 141
<211> LENGTH: 196
<212> TYPE: PRT
<213> ORGANISM: Artificial Sequence
<220> FEATURE:
<223> OTHER INFORMATION: Synthetic Sequence MZH3 H67D

<400> SEQUENCE: 141

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45
```

```
Arg Asn Pro Glu Lys Lys Ser Val Leu Gln Lys Ile Leu Glu Asp Glu
 50                  55                  60

Glu Lys Asp Ile Glu Leu Leu Glu Thr Leu Gln Gln Thr Gly Gln Glu
 65                  70                  75                  80

Ala Gln Gln Leu Leu Gln Glu Leu Gln Gln Thr Gly Gln Glu Leu Trp
                 85                  90                  95

Gln Leu Gly Gly Ser Gly Gly Pro Glu Leu Arg Gln Lys His Gln Gln
                100                 105                 110

Leu Ala Gln Lys Ile Gln Gln Leu Leu Gln Lys His Gln Gln Leu Gly
            115                 120                 125

Ala Lys Ile Leu Glu Asp Glu Lys His Ile Glu Leu Leu Glu Thr
        130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 142
<211> LENGTH: 196
<212> TYPE: PRT
<213> ORGANISM: Artificial Sequence
<220> FEATURE:
<223> OTHER INFORMATION: Synthetic Sequence MZH3 H67N

<400> SEQUENCE: 142

Gly Ser Pro Glu Leu Arg Gln Glu His Gln Gln Leu Ala Gln Glu Phe
  1               5                  10                  15

Gln Gln Leu Leu Gln Glu Ile Gln Gln Leu Gly Arg Glu Leu Leu Lys
                 20                  25                  30

Gly Glu Leu Gln Gly Ile Lys Gln Leu Arg Glu Ala Ser Glu Lys Ala
             35                  40                  45

Arg Asn Pro Glu Lys Lys Ser Val Leu Gln Lys Ile Leu Glu Asp Glu
 50                  55                  60

Glu Lys Asn Ile Glu Leu Leu Glu Thr Leu Gln Gln Thr Gly Gln Glu
 65                  70                  75                  80

Ala Gln Gln Leu Leu Gln Glu Leu Gln Gln Thr Gly Gln Glu Leu Trp
                 85                  90                  95

Gln Leu Gly Gly Ser Gly Gly Pro Glu Leu Arg Gln Lys His Gln Gln
                100                 105                 110

Leu Ala Gln Lys Ile Gln Gln Leu Leu Gln Lys His Gln Gln Leu Gly
            115                 120                 125

Ala Lys Ile Leu Glu Asp Glu Lys His Ile Glu Leu Leu Glu Thr
        130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195
```

<210> SEQ ID NO 143
<211> LENGTH: 196
<212> TYPE: PRT
<213> ORGANISM: Artificial Sequence
<220> FEATURE:
<223> OTHER INFORMATION: Synthetic Sequence MZH3 H67D, H138D

<400> SEQUENCE: 143

```
Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
50                  55                  60

Glu Lys Asp Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
        115                 120                 125

Ala Lys Ile Leu Glu Asp Glu Lys Asp Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195
```

<210> SEQ ID NO 144
<211> LENGTH: 196
<212> TYPE: PRT
<213> ORGANISM: Artificial Sequence
<220> FEATURE:
<223> OTHER INFORMATION: Synthetic Sequence MZH3 H67D, H138N

<400> SEQUENCE: 144

```
Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
50                  55                  60

Glu Lys Asp Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
```

```
                    100                 105                 110

Leu Ala Gln Lys Ile Gln Gln Leu Leu Gln Lys His Gln Gln Leu Gly
            115                 120                 125

Ala Lys Ile Leu Glu Asp Glu Glu Lys Asn Ile Glu Leu Leu Glu Thr
        130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 145
<211> LENGTH: 196
<212> TYPE: PRT
<213> ORGANISM: Artificial Sequence
<220> FEATURE:
<223> OTHER INFORMATION: Synthetic Sequence MZH3 H67N, H138D

<400> SEQUENCE: 145

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys Asn Ile Glu Leu Leu Glu Thr Leu Gln Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
            115                 120                 125

Ala Lys Ile Leu Glu Asp Glu Glu Lys Asp Ile Glu Leu Leu Glu Thr
        130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Leu Gln Gln Thr Gly Gln Lys Leu
            180                 185                 190

Trp Gln Leu Gly
        195

<210> SEQ ID NO 146
<211> LENGTH: 196
<212> TYPE: PRT
<213> ORGANISM: Artificial Sequence
<220> FEATURE:
<223> OTHER INFORMATION: Synthetic Sequence MZH3 H67N, H138N

<400> SEQUENCE: 146
```

Gly Ser Pro Glu Leu Arg Gln Glu His Gln Gln Leu Ala Gln Glu Phe
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys Asn Ile Glu Leu Glu Thr Leu Gln Thr Gly Gln Glu
65                  70                  75                  80

Ala Gln Gln Leu Leu Gln Glu Leu Gln Gln Thr Gly Gln Glu Leu Trp
                85                  90                  95

Gln Leu Gly Gly Ser Gly Gly Pro Glu Leu Arg Gln Lys His Gln Gln
            100                 105                 110

Leu Ala Gln Lys Ile Gln Gln Leu Leu Gln Lys His Gln Gln Leu Gly
        115                 120                 125

Ala Lys Ile Leu Glu Asp Glu Glu Lys Asn Ile Glu Leu Leu Glu Thr
    130                 135                 140

Ile Leu Gly Gly Ser Gly Gly Asp Glu Leu Arg Glu Leu Leu Lys Gly
145                 150                 155                 160

Glu Leu Gln Gly Ile Lys Gln Tyr Arg Glu Leu Gln Gln Leu Gly Gln
                165                 170                 175

Lys Ala Gln Gln Leu Val Gln Lys Gln Gln Thr Gly Gln Lys Leu
            180                 185                 190

Trp Gln Leu Gly
        195

<210> SEQ ID NO 147
<211> LENGTH: 196
<212> TYPE: PRT
<213> ORGANISM: Artificial Sequence
<220> FEATURE:
<223> OTHER INFORMATION: Synthetic Sequence MZH3 P3G H9A Q10D L12I A13R
      F16L T91R G92E L95G G100N P105T L106R R107L Q108E H110I A114G
      Q115R Q118R V182M Q183E L185C Q186G T188R G189A Q190M L192R W193N

<400> SEQUENCE: 147

Gly Ser Gly Glu Leu Arg Gln Glu Ala Asp Gln Ile Arg Gln Glu Leu
1               5                   10                  15

Gln Gln Leu Leu Gln Glu Ile Gln Gln Leu Gly Arg Glu Leu Leu Lys
            20                  25                  30

Gly Glu Leu Gln Gly Ile Lys Gln Leu Arg Glu Ala Ser Glu Lys Ala
        35                  40                  45

Arg Asn Pro Glu Lys Lys Ser Val Leu Gln Lys Ile Leu Glu Asp Glu
    50                  55                  60

Glu Lys His Ile Glu Leu Leu Glu Thr Leu Gln Gln Thr Gly Gln Glu
65                  70                  75                  80

Ala Gln Gln Leu Leu Gln Glu Leu Gln Gln Arg Glu Gln Glu Gly Trp
                85                  90                  95

Gln Leu Gly Asn Ser Gly Gly Thr Glu Arg Leu Glu Lys Ile Gln Gln
            100                 105                 110

Leu Gly Arg Lys Ile Arg Gln Leu Gln Lys His Gln Gln Leu Gly
        115                 120                 125

Ala Lys Ile Leu Glu Asp Glu Glu Lys His Ile Glu Leu Leu Glu Thr
    130                 135                 140

Ile Leu Gly Gly Ser Gly Gly Asp Glu Leu Arg Glu Leu Leu Lys Gly

```
145                 150                 155                 160
Glu Leu Gln Gly Ile Lys Gln Tyr Arg Glu Leu Gln Gln Leu Gly Gln
                165                 170                 175
Lys Ala Gln Gln Leu Met Glu Lys Cys Gly Gln Arg Ala Met Lys Arg
            180                 185                 190
Asn Gln Leu Gly
        195
```

<210> SEQ ID NO 148
<211> LENGTH: 7
<212> TYPE: PRT
<213> ORGANISM: Artificial Sequence
<220> FEATURE:
<223> OTHER INFORMATION: Synthetic Sequence Heptad repeats

<400> SEQUENCE: 148

```
Glu Leu Leu Lys Lys Phe Glu
1               5
```

<210> SEQ ID NO 149
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 149

```
Glu Ile Trp Lys Gln His Glu Asp Ala Leu Gln Lys Phe Glu Glu Ala
1               5                   10                  15
Leu Asn Gln Phe Glu Asp Leu Lys Gln Leu Gly Gly Ser Gly Ser Gly
            20                  25                  30
Ser Gly Gly Glu Ile Trp Lys Gln Cys Glu Asp Ala Leu Gln Lys Phe
        35                  40                  45
Glu Glu Ala Leu Asn Gln Phe Glu Asp Leu Lys Gln Leu
    50                  55                  60
```

<210> SEQ ID NO 150
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 150

```
Glu Ile Trp Lys Gln His Glu Asp Ala Leu Gln Lys Phe Glu Glu Ala
1               5                   10                  15
Leu Asn Gln Phe Glu Asp Leu Lys Gln Leu Gly Gly Ser Gly Ser Gly
            20                  25                  30
Ser Gly Gly Glu Ile Trp Lys Gln Cys Glu Asp Ala Leu Gln Lys Phe
        35                  40                  45
Glu Glu Ala Leu Lys Gln Phe Glu Asp Leu Lys Gln Leu
    50                  55                  60
```

<210> SEQ ID NO 151
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 151

```
Glu Ile Trp Lys Gln His Glu Asp Ala Leu Gln Lys Phe Glu Glu Ala
```

```
                1               5                  10                 15
Leu Asn Gln Phe Glu Asp Leu Lys Gln Leu Gly Gly Ser Gly Lys Gly
                    20                  25                  30

Ser Gly Gly Glu Ile Trp Lys Gln Cys Glu Asp Ala Leu Arg Lys Phe
            35                  40                  45

Glu Glu Ala Leu Lys Arg Phe Glu Asp Leu Lys Gln Lys
    50                  55                  60
```

<210> SEQ ID NO 152
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 152

```
Glu Ile Trp Lys Gln His Glu Asp Ala Leu Arg Lys Phe Glu Glu Ala
1               5                  10                  15

Leu Asn Arg Phe Glu Asp Leu Lys Gln Lys Gly Gly Ser Gly Lys Gly
                    20                  25                  30

Ser Gly Gly Glu Ile Trp Lys Gln Cys Glu Asp Ala Leu Arg Lys Phe
            35                  40                  45

Glu Glu Ala Leu Lys Arg Phe Glu Asp Leu Lys Gln Lys
    50                  55                  60
```

<210> SEQ ID NO 153
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 153

```
Glu Ile Trp Lys Gln His Glu Asp Ala Leu Arg Lys Phe Glu Glu Ala
1               5                  10                  15

Leu Lys Arg Phe Glu Asp Lys Lys Gln Leu Gly Gly Ser Gly Lys Gly
                    20                  25                  30

Ser Gly Gly Glu Ile Trp Lys Gln Cys Glu Asp Ala Leu Arg Lys Phe
            35                  40                  45

Glu Glu Ala Leu Lys Arg Phe Glu Asp Leu Lys Gln Lys
    50                  55                  60
```

<210> SEQ ID NO 154
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 154

```
Glu Ile Lys Arg Gln His Glu Asp Ala Leu Arg Lys Phe Glu Glu Ala
1               5                  10                  15

Leu Lys Arg Phe Glu Asp Lys Lys Gln Leu Gly Gly Ser Gly Lys Gly
                    20                  25                  30

Ser Gly Gly Glu Ile Trp Lys Arg His Glu Asp Ala Leu Arg Lys Phe
            35                  40                  45

Glu Glu Ala Leu Lys Arg Phe Glu Asp Lys Lys Gln Lys
    50                  55                  60
```

<210> SEQ ID NO 155

```
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 155

Glu Ile Trp Lys Leu His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys
    50                  55                  60

<210> SEQ ID NO 156
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 156

Glu Ile Trp Lys Ser His Glu Asp Ala Leu Gln Lys Phe Glu Glu Ala
1               5                   10                  15

Leu Asn Gln Phe Glu Asp Leu Lys Gln Leu Gly Gly Ser Gly Lys Gly
            20                  25                  30

Ser Gly Gly Glu Ile Lys Gln Arg His Glu Asp Ala Leu Arg Lys Phe
        35                  40                  45

Glu Glu Ala Leu Lys Arg Phe Glu Asp Leu Lys Gln Lys
    50                  55                  60

<210> SEQ ID NO 157
<211> LENGTH: 61
<212> TYPE: PRT
<213> ORGANISM: Artificial Sequence
<220> FEATURE:
<223> OTHER INFORMATION: Synthetic Sequence

<400> SEQUENCE: 157

Arg Ile Gln Lys Glu His Glu Asp Ala His Gln Lys Phe Glu Glu Ala
1               5                   10                  15

Leu Asn Gln Phe Glu Asp Leu Lys Gln Leu Gly Gly Ser Gly Glu Gly
            20                  25                  30

Ser Gly Gly Glu Ile Trp Lys Gln His Glu Asp Ala Leu Gln Lys Phe
        35                  40                  45

Glu Glu Ala Leu Asn Arg His Glu Asp Arg Val Gln Leu
    50                  55                  60
```